United States Patent
Collingwood et al.

(10) Patent No.: US 12,377,105 B2
(45) Date of Patent: Aug. 5, 2025

(54) COMPOUNDS

(71) Applicant: TMEM16A Limited, Brighton (GB)

(72) Inventors: Stephen Collingwood, Hayward's Heath (GB); Clive McCarthy, Wantage (GB); Jonathan David Hargrave, Bath (GB); Duncan Alexander Hay, Wallingford (GB); Thomas Beauregard Schofield, Oxford (GB); Sarah Ellam, Didcot (GB); Craig Stephen Buxton, Didcot (GB); Matthew Habgood, Abingdon (GB); Peter Neville Ingram, Abingdon (GB); Chun Yan Ma, Reading (GB); Spencer Charles Robert Napier, Didcot (GB); Abdul Kadar Shaikh, Camberley (GB); Matthew Raymond Smith, Didcot (GB); Christopher Charles Stimson, Oxford (GB); Edward Richard Walker, Didcot (GB)

(73) Assignee: TMEM16A Limited, Welwyn Garden City (GB)

( * ) Notice: Subject to any disclaimer, the term of this patent is extended or adjusted under 35 U.S.C. 154(b) by 600 days.

(21) Appl. No.: 17/663,716

(22) Filed: May 17, 2022

(65) Prior Publication Data

US 2022/0395512 A1 Dec. 15, 2022

Related U.S. Application Data

(60) Division of application No. 16/501,493, filed on Nov. 22, 2019, now Pat. No. 11,364,246, which is a (Continued)

(30) Foreign Application Priority Data

Jan. 26, 2018 (GB) .................................... 1801355

(51) Int. Cl.
*A61K 31/5377* (2006.01)
*A61K 31/167* (2006.01)
(Continued)

(52) U.S. Cl.
CPC ........ *A61K 31/5377* (2013.01); *A61K 31/167* (2013.01); *A61K 31/351* (2013.01); *A61K 31/4025* (2013.01); *A61K 31/4045* (2013.01); *A61K 31/416* (2013.01); *A61K 31/44* (2013.01); *A61K 31/443* (2013.01); (Continued)

(58) Field of Classification Search
CPC ............. A61K 31/5377; A61K 31/167; A61K 31/351; A61K 31/4025; A61K 31/4045; A61K 31/416; A61K 31/44; A61K 31/443; A61K 31/4439; A61K 31/444; A61K 31/498; A61K 45/06; C07C 233/76; C07C 2061/04; C07C 2601/14; C07C 2603/74; C07C 233/00; C07C 237/42; C07C 1/00; A61P 11/00; C07D 209/18; C07D 213/18; C07D 231/56; C07D 309/14; C07D 401/12; C07D 405/12; C07D 409/12; C07D 413/12; C07D 309/10; C07D 417/12; C07D 213/72; C07D 233/00
See application file for complete search history.

(56) References Cited

U.S. PATENT DOCUMENTS

| | | |
|---|---|---|
| 11,364,246 B2 | 6/2022 | Collingwood et al. |
| 2006/0069132 A1 | 3/2006 | Armel et al. |

(Continued)

FOREIGN PATENT DOCUMENTS

| | | | |
|---|---|---|---|
| CN | 1580056 A | * | 2/2005 |
| EP | 1403235 A1 | | 3/2004 |

(Continued)

OTHER PUBLICATIONS

Accurso, et al., Tiger-1 Investigator Study Group, Denufosol tetrasodium in patients with cystic fibrosis and normal to mildly impaired lung function, Am J Respir Crit Care Med, 2011, pp. 627-634, vol. 183, No. 5.

(Continued)

*Primary Examiner* — Joseph K McKane
*Assistant Examiner* — Anna Grace Kuckla
(74) *Attorney, Agent, or Firm* — Robert C. Hall

(57) ABSTRACT

Compounds of general formula (I): wherein $R^1$, $R^2$, $R^3$, $R^4$, $R^{5a}$, $R^{5b}$ $X^1$, $X^2$, Z and Y are as defined herein are positive modulators of the calcium-activated chloride channel (CaCC), TMEM16A. The compounds are useful for treating diseases and conditions affected by modulation of TMEM16A, particularly respiratory diseases and conditions.

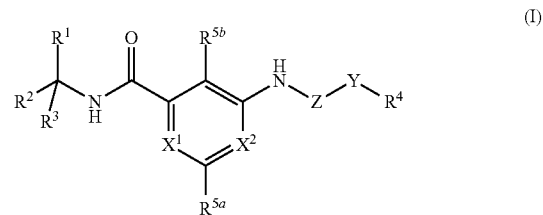

14 Claims, 1 Drawing Sheet

Related U.S. Application Data continuation of application No. PCT/GB2019/050209, filed on Jan. 25, 2019.

(51) Int. Cl.

| | | |
|---|---|---|
| *A61K 31/351* | (2006.01) | |
| *A61K 31/4025* | (2006.01) | |
| *A61K 31/4045* | (2006.01) | |
| *A61K 31/416* | (2006.01) | |
| *A61K 31/44* | (2006.01) | |
| *A61K 31/443* | (2006.01) | |
| *A61K 31/4439* | (2006.01) | |
| *A61K 31/444* | (2006.01) | |
| *A61K 31/498* | (2006.01) | |
| *A61K 45/06* | (2006.01) | |
| *C07C 233/76* | (2006.01) | |
| *C07D 209/18* | (2006.01) | |
| *C07D 213/81* | (2006.01) | |
| *C07D 231/56* | (2006.01) | |
| *C07D 309/14* | (2006.01) | |
| *C07D 401/12* | (2006.01) | |
| *C07D 405/12* | (2006.01) | |
| *C07D 409/12* | (2006.01) | |
| *C07D 413/12* | (2006.01) | |

(52) U.S. Cl.
CPC ........ *A61K 31/4439* (2013.01); *A61K 31/444* (2013.01); *A61K 31/498* (2013.01); *A61K 45/06* (2013.01); *C07C 233/76* (2013.01); *C07D 209/18* (2013.01); *C07D 213/81* (2013.01); *C07D 231/56* (2013.01); *C07D 309/14* (2013.01); *C07D 401/12* (2013.01); *C07D 405/12* (2013.01); *C07D 409/12* (2013.01); *C07D 413/12* (2013.01)

(56) References Cited

U.S. PATENT DOCUMENTS

| | | |
|---|---|---|
| 2007/0072862 A1 | 3/2007 | Dimauro et al. |
| 2009/0163545 A1 | 6/2009 | Goldfarb |
| 2016/0272577 A1 | 9/2016 | Schaefer et al. |
| 2020/0361871 A1 | 11/2020 | Collingwood et al. |
| 2020/0383988 A1 | 12/2020 | Collingwood et al. |

FOREIGN PATENT DOCUMENTS

| | | |
|---|---|---|
| JP | 2011525193 A | 9/2011 |
| JP | 2012507482 A | 3/2012 |
| KR | 20110082181 A | 7/2011 |
| TW | 201833111 A | 9/2018 |
| WO | WO-2002064545 A1 | 8/2002 |
| WO | WO-2002100819 A1 | 12/2002 |
| WO | WO-2004011430 A1 | 2/2004 |
| WO | WO-2004106324 A1 | 12/2004 |
| WO | WO-2006115374 A1 | 11/2006 |
| WO | WO-2008002671 A2 | 1/2008 |
| WO | WO-2009080203 A2 | 7/2009 |
| WO | WO-2009135590 A1 | 11/2009 |
| WO | WO-2010036316 A1 | 4/2010 |
| WO | WO-2013030802 A1 | 3/2013 |
| WO | WO-2013033620 A1 | 3/2013 |
| WO | WO-2013165606 A1 | 11/2013 |
| WO | WO-2014181287 A1 | 11/2014 |
| WO | WO-2016029136 A1 | 2/2016 |
| WO | WO-2017083971 A1 | 5/2017 |
| WO | WO-2019145726 A1 | 8/2019 |
| WO | WO-2021014168 A1 | 1/2021 |

OTHER PUBLICATIONS

Boucher, Evidence for airway surface dehydration as the initiating event in CF airway disease, J Intern Med., 2007, pp. 5-16, vol. 261, No. 1.

Caputo, et al., TMEM16A, a membrane protein associated with calcium-dependent chloride channel activity, Science, 2008, pp. 590-594, vol. 322, No. 5901.

Database CAS STN Registry No. 791802-37-4, entered Dec. 3, 2004.

Database CAS STN Registry No. 723736-17-2, entered Aug. 8, 2004.

Database CAS STN Registry No. 723736-15-0, entered Aug. 8, 2004.

Database CAS STN Registry No. 355403-27-9, entered Sep. 10, 2001.

De La Fuente, Small molecule screen identifies inhibitors of a human intestinal calcium-activated chloride channel, Mol Pharmacol, 2008, pp. 758-768, vol. 73, No. 3.

European Patent Office, International Search Report and Written Opinion for PCT/GB2019/050209, Jul. 30, 2019, 11 pages.

Gray, et al., Tetrahedron Letters, 2000, pp. 6237-6240, vol. 41, No. 32.

Kellerman, et al., Denufosol: a review of studies with inhaled P2Y(2) agonists that led to Phase 2, Pulm Pharmacol Ther, 2008, pp. 600-607, vol. 21, No. 4.

Kubinyi, 3D QSAR in Drug Design: Ligand-Protein Interactions and Molecular Similarity, Springer, 1998, vol. 2-3, pp. 243-244.

Kunzelmann, et al., Pharmacotherapy of the ion transport defect in cystic fibrosis: role of purinergic receptor agonists and other potential therapeutics, Am J Respir Med, 2003, pp. 299-309, vol. 2, No. 4.

Matsui, et al., Evidence for periciliary liquid layer depletion, not abnormal ion composition, in the pathogenesis of cystic fibrosis airways disease, Cell, 1998, pp. 1005-1015, vol. 95, No. 7.

Morwick, et al., Hit to lead account of the discovery of bisbenzamide and related ureidobenzamide inhibitors of rho kinase, J. of Medicinal Chemistry, Jan. 28, 2010, pp. 759-777, vol. 53, No. 2.

Moss, Pitfalls of drug development: lessons learned from trials of denufosol in cystic fibrosis. J Pediatr, 2013, pp. 676-680, vol. 162, No. 4.

Namkung et al., Small-molecule activators of TMEM16A, a calcium-activated chloridechannel, stimulate epithelial chloride secretion and intestinal contraction, the FASEB Journal, Nov. 2011, vol. 25, pp. 4048-4062.

Pedemonte, et al., Structure and function of TMEM16 proteins (anoctamins), Physiol Rev, 2014, pp. 419-459, vol. 94, No. 2.

Pezullo, et al., Reduced airway surface pH impairs bacterial killing in the porcine cystic fibrosis lung, Nature, 2012, pp. 109-113, vol. 487, No. 7405.

Veryser, et al., Low-cost instant CO generation at room temperature using formic acid, mesyl chloride and trimethylamine, React. Chem. Eng., 2016, pp. 142-146.

Wermuth, The Practice of Medicinal Chemistry, 2d ed., 2003, 78 pages, Chs. 9-10.

Willardsen, et al., Design synthesis and biological activity of potent and selective inhibitors of blood coagulation factor Xa, Journal of Medicinal Chemistry, 2004, pp. 4089-4099, vol. 47, No. 16.

Yang, et al., TMEM16A confers receptor-activated calcium-dependent chloride conductance, 2008, pp. 1210-1215, vol. 455, No. 7217.

\* cited by examiner

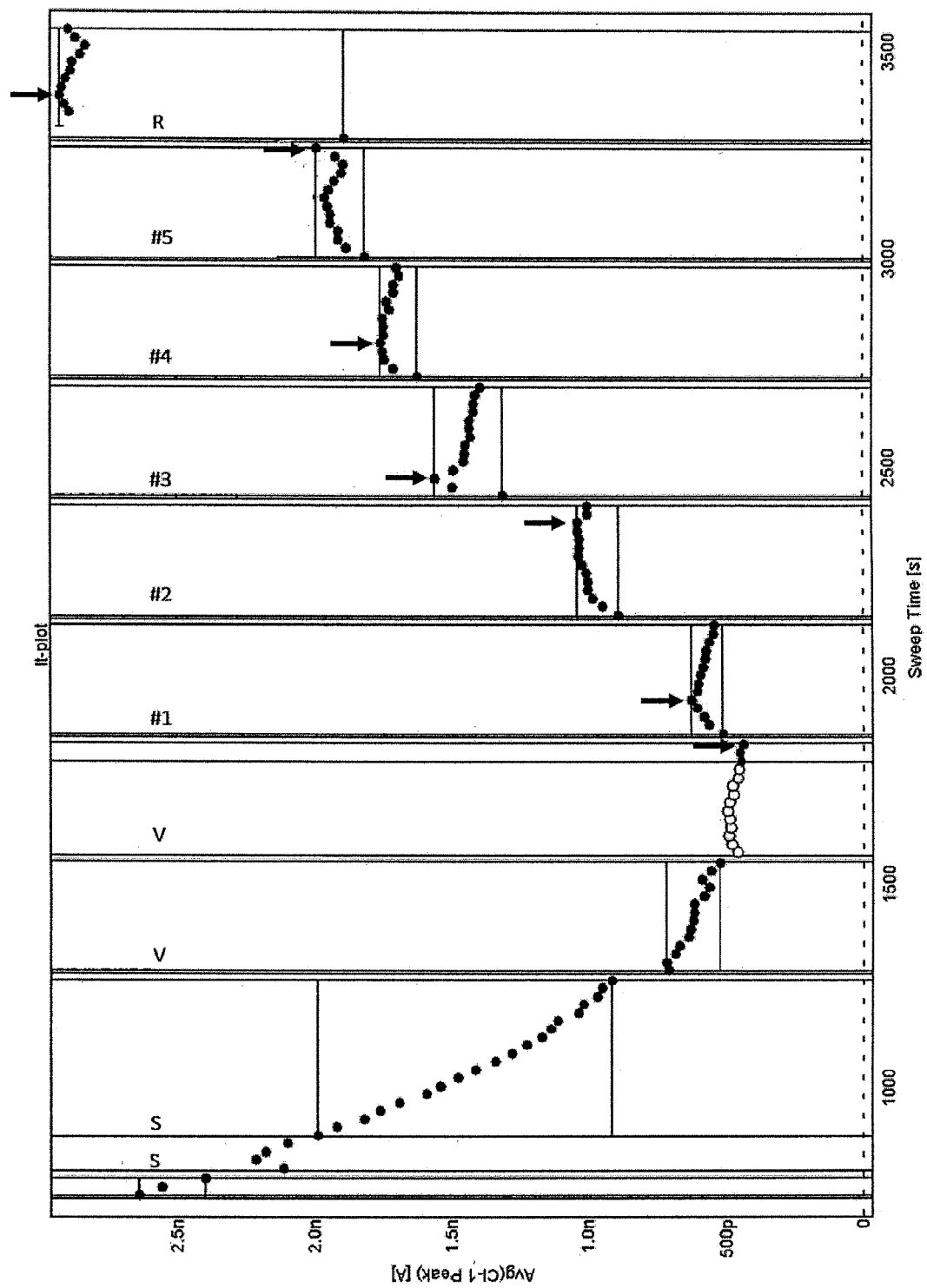

COMPOUNDS

This application is a divisional of U.S. patent application Ser. No. 16/501,493, filed Nov. 22, 2019, which is a continuation of International Application No. PCT/GB2019/050209, filed Jan. 25, 2019, which claims the benefit of GB Application No. 1801355.7, filed Jan. 26, 2018, each of which is incorporated by reference herein in its entirety.

The present invention relates to novel compounds which have activity as positive modulators of the calcium-activated chloride channel (CaCC), TMEM16A. The invention also relates to methods of preparing the compounds and pharmaceutical compositions containing them as well as to the use of these compounds in treating diseases and conditions modulated by TMEM16A, particularly respiratory diseases and conditions.

Humans can inhale up to 12,000 L of air each day and with it comes the potential for airborne pathogens (such as bacteria, viruses and fungal spores) to enter the airways. To protect against these airborne pathogens, the lung has evolved innate defence mechanisms to minimise the potential for infection and colonisation of the airways. One such mechanism is the mucus clearance system, whereby secreted mucus is propelled up and out of the airways by the coordinated beating of cilia together with cough clearance. This ongoing 'cleansing' of the lung constantly removes inhaled particles and microbes thereby reducing the risk of infection.

In recent years it has become clear that the hydration of the mucus gel is critical to enable mucus clearance (Boucher 2007; Matsui et al, 1998). In a normal, healthy airway, the mucus gel is typically 97% water and 3% w/v solids under which conditions the mucus is cleared by mucociliary action. The hydration of the airway mucosa is regulated by the coordinated activity of a number of ion channels and transporters. The balance of anion ($Cl^-/HCO_3^-$) secretion mediated via the Cystic Fibrosis Transmembrane Conductance Regulator (CFTR) and the Calcium Activated Chloride Conductance (CaCC; TMEM16A) and $Na^+$ absorption through the epithelial $Na^+$ channel (ENaC) determine the hydration status of the airway mucosa. As ions are transported across the epithelium, water is osmotically obliged to follow and thus fluid is either secreted or absorbed.

In respiratory diseases such as chronic bronchitis and cystic fibrosis, the % solids of the mucus gel is increased as the hydration is reduced and mucus clearance is reduced (Boucher, 2007). In cystic fibrosis, where loss of function mutations in CFTR attenuates ability of the airway to secrete fluid, the % solids can be increased to 15% which is believed to contribute towards the plugging of small airways and failure of mucus clearance. Strategies to increase the hydration of the airway mucus include either the stimulation of anion and thereby fluid secretion or the inhibition of $Na^+$ absorption. To this end, stimulating the activity of TMEM16A channels will increase anion secretion and therefore increase fluid accumulation in the airway mucosa, hydrate mucus and enhance mucus clearance mechanisms.

TMEM16A, also referred to as Anoctamin-1 (Ano1), is the molecular identity of calcium-activated chloride channels (Caputo et al, 2008; Yang et al, 2008). TMEM16A channels open in response to elevation of intracellular calcium levels and allow the bidirectional flux of chloride, bicarbonate and other anions across the cell membrane. Functionally TMEM16A channels have been proposed to modulate transepithelial ion transport, gastrointestinal peristalsis, nociception and cell migration/proliferation (Pedemonte & Galietta, 2014).

TMEM16A channels are expressed by the epithelial cells of different organs including the lungs, liver, kidney, pancreas and salivary glands. In the airway epithelium TMEM16A is expressed at high levels in mucus producing goblet cells, ciliated cells and in submucosal glands. Physiologically TMEM16A is activated by stimuli which mobilise intracellular calcium, particularly purinergic agonists (ATP, UTP), which are released by the respiratory epithelium in response to cyclical shear stress caused by breathing and other mechanical stimuli such as cough. In addition to increasing anion secretion leading to enhanced hydration of the airways, activation of TMEM16A plays an important role in bicarbonate secretion. Bicarbonate secretion is reported to be an important regulator of mucus properties and in controlling airway lumen pH and hence the activity of native antimicrobials such as defensins (Pezzulo et al, 2012).

Indirect modulation of TMEM16A, via elevation of intracellular calcium, has been clinically explored eg. denufosol (Kunzelmann & Mall, 2003). Although encouraging initial results were observed in small patient cohorts this approach did not deliver clinical benefit in larger patient cohorts (Accurso et al 2011; Kellerman et al 2008). This lack of clinical effect was ascribed to only a transient elevation in anion secretion, the result of a short half-life of denufosol on the surface of the epithelium and receptor/pathway desensitisation, and unwanted effects of elevating intracellular calcium such as increased release of mucus from goblet cells (Moss, 2013). Compounds which act directly upon TMEM16A to enhance channel opening at low levels of calcium elevation are expected to durably enhance anion secretion and mucociliary clearance in patients and improve innate defence. As TMEM16A activity is independent of CFTR function, TMEM16A positive modulators have the potential to deliver clinical benefit to all CF patients and non-CF respiratory diseases characterised by mucus congestion including chronic bronchitis and severe asthma.

TMEM16A modulation has been implicated as a therapy for dry mouth (xerostomia), resultant from salivary gland dysfunction in Sjorgen's syndrome and radiation therapy, dry eye, cholestasis and gastrointestinal motility disorders.

The present inventors have developed novel compounds which are positive modulators of TMEM16A and which are therefore of use in the treatment of diseases and conditions in which modulation of TMEM16A plays a role, particularly respiratory diseases and conditions.

In a first aspect of the present invention there is provided a compound of general formula (I) including all tautomeric forms all enantiomers and isotopic variants and salts and solvates thereof:

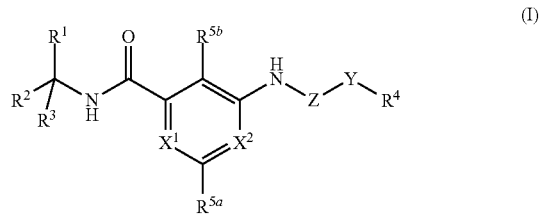

wherein:
$R^1$ is H, CN, C(O)OR$^{12}$, $C_{1-3}$ alkyl, $C_{2-3}$ alkenyl or $C_{2-3}$ alkynyl, any of which alkyl, alkenyl or alkynyl groups are optionally substituted with one or more substituents, suitably one substituent, selected from fluoro, $OR^{12}$, $N(R^{12})_2$, $C(O)OR^{12}$, $C(O)N(R^{12})_2$, $C(O)R^{12}$ and $N(R^{13})C(O)R^{12}$;
  wherein each $R^{12}$ and $R^{13}$ is independently selected from H, $C_{1-6}$ alkyl and $C_{1-6}$ fluoroalkyl
$R^2$ is H or $C_{1-6}$ alkyl optionally substituted with $OR^{12}$;
$R^3$ is:
$C_{1-10}$ alkyl, $C_{2-10}$ alkenyl or $C_{2-10}$ alkynyl, any of which is optionally substituted with one or more substituents, suitably one substituent, selected from fluoro, CN, $R^{14}$ $OR^{14}$, $OR^{15}$, $N(R^{15})_2$, $C(O)OR^{15}$, $C(O)N(R^{15})_2$, $N(R^{16})C(O)R^{15}$, $N(R^{15})S(O)_2R^{14}$, $N(R^{15})S(O)_2R^{16}$ and $N(R^{15})C(O)OR^{16}$; or
a 3- to 7-membered carbocyclic or heterocyclic ring system or a 6- to 10 membered aryl or 5- to 10-membered heteroaryl ring system, either of which is optionally substituted with one or more substituents selected from halo, CN, $C_{1-4}$ alkyl, $C_{1-4}$ haloalkyl, $OR^{17}$ and $N(R^{17})_2$;
  wherein $R^{14}$ is a 6- to 10-membered aryl or 5- to 10-membered heteroaryl ring system or a 3- to 7-membered carbocyclic or heterocyclic ring system, any of which is optionally substituted with one or more substituents selected from halo, $C_{1-4}$ alkyl, $C_{1-4}$ haloalkyl, $OR^{17}$ and $N(R^{17})_2$; wherein each $R^{17}$ is independently H, $C_{1-4}$ alkyl or $C_{1-4}$ haloalkyl;
  each $R^{15}$ and $R^{16}$ is independently H, $C_{1-6}$ alkyl or $C_{1-6}$ haloalkyl; or
$R^2$ and $R^3$ together with the carbon atom to which they are attached combine to form a 3- to 10-membered carbocyclic or heterocyclic ring system optionally substituted with one or more substituents selected from halo, CN, $OR^9$, $N(R^9)_2$, $C(O)OR^9$, $C(O)N(R^9)_2$, $C(O)R^9$, $N(R^9)C(O)R^9$ and $C_{1-4}$ alkyl optionally substituted with halo, $OR^9$ or $N(R^9)_2$; or
$R^1$, $R^2$ and $R^3$ together with the carbon atom to which they are attached combine to form a bridged 5- to 10-membered carbocyclic or heterocyclic ring system or phenyl, any of which is optionally substituted with one or more substituents selected from halo, CN, $OR^9$, $N(R^9)_2$, $C(O)OR^9$, $C(O)N(R^9)_2$, $C(O)R^9$, $N(R^9)C(O)R^9$ and $C_{1-4}$ alkyl optionally substituted with halo, $OR^9$ or $N(R^9)_2$;
  each $R^9$ is independently selected from H, $C_{1-6}$ alkyl or $C_{1-6}$ haloalkyl;
each of $X^1$ and $X^2$ is independently N or $CR^8$;
$R^8$ is H, halo, OH, $O(C_{1-4}$ alkyl), CN or $NH_2$;
Y is a bond or a straight $C_{1-6}$ alkylene chain which is optionally substituted with one or more substituents $R^{18}$, wherein two substituents $R^{18}$ may be attached to the same or to different carbon atoms;
  wherein each $R^{18}$ is independently $C_{1-3}$ alkyl or $C_{1-3}$ haloalkyl in which a —$CH_2$— is optionally replaced with —NH— or —O— and wherein two $R^{18}$ groups may combine with the atom or atoms to which they are attached to form a 3- to 6-membered carbocyclic or heterocyclic ring system;
Z is —C(O)— or —C(O)NH—;
$R^4$ is a 6- to 14-membered aryl, 5- to 14-membered heteroaryl or a 5- to 10-membered carbocyclic ring system, any of which is optionally substituted with one or more substituents selected from:
halo, CN, nitro, $R^{19}$, $OR^{19}$, $OR^6$, $SR^6$, $NR^6R^7$, $C(O)R^6$, $C(O)R^{19}$, $C(O)OR^6$, $C(O)N(R^6)(R^7)$, $N(R^7)C(O)R^6$; $C_{1-6}$ alkyl or $O(C_{1-6}$ alkyl) either of which is optionally substituted with one or more substituents selected from halo, CN, nitro, $R^{19}$, $OR^6$, $SR^6$, $NR^6R^7$, $C(O)R^6$ $C(O)OR^6$, $C(O)N(R^6)(R^7)$ and $N(R^7)C(O)R^6$; and
when $R^4$ is not fully aromatic in character, oxo;
  wherein $R^{19}$ is 5- or 6-membered aryl or heteroaryl ring system or a 3- to 7-membered carbocyclic or heterocyclic ring system, any of which is optionally substituted with one or more substituents selected from halo, $C_{1-4}$ alkyl, $C_{1-4}$ haloalkyl, OH, $O(C_{1-4}$ alkyl), $O(C_{1-4}$ haloalkyl);
  $R^6$ is H, $C_{1-6}$ alkyl, $C_{1-6}$ haloalkyl, benzyl, 3- to 7-membered carbocyclyl or 3- to 7-membered heterocyclyl;
  $R^7$ is H, $C_{1-6}$ alkyl or $C_{1-6}$ haloalkyl; or
  $R^6$ and $R^7$ together with the nitrogen atom to which they are attached may form a 4 to 7-membered heterocyclic ring optionally containing one or more further heteroatoms and optionally substituted with one or more substituents selected from oxo and halo; and
each of $R^{5a}$ and $R^{5b}$ is independently H, $C_{1-4}$ alkyl or halo; for use in medicine.

In the present specification, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

In the present specification, references to "pharmaceutical use" refer to use for administration to a human or an animal, in particular a human or a mammal, for example a domesticated or livestock mammal, for the treatment or prophylaxis of a disease or medical condition. The term "pharmaceutical composition" refers to a composition which is suitable for pharmaceutical use and "pharmaceutically acceptable" refers to an agent which is suitable for use in a pharmaceutical composition. Other similar terms should be construed accordingly.

In the present specification, the term "$C_{1-6}$" alkyl refers to a straight or branched fully saturated hydrocarbon group having from 1 to 6 carbon atoms. The term encompasses methyl, ethyl, n-propyl, isopropyl, n-butyl, isobutyl and t-butyl. Other alkyl groups, for example $C_{1-10}$ alkyl are as defined above but contain different numbers of carbon atoms.

The term "$C_{2-6}$" alkenyl refers to a straight or branched hydrocarbon group having from 1 to 6 carbon atoms and at least one carbon-carbon double bond. The term encompasses ethenyl, propen-1-yl, propen-2-yl, buten-1-yl and buten-2-yl. Other alkenyl groups, for example $C_{2-10}$ alkenyl are as defined above but contain different numbers of carbon atoms.

The term "$C_{2-6}$" alkynyl refers to a straight or branched hydrocarbon group having from 1 to 6 carbon atoms and at least one carbon-carbon triple bond. The term encompasses ethynyl, propyn-1-yl, propyn-2-yl, butyn-1-yl and butyn-2-yl. Other alkynyl groups, for example $C_{2-10}$ alkynyl are as defined above but contain different numbers of carbon atoms.

The term "$C_{1-6}$ alkylene" refers to a straight or branched fully saturated hydrocarbon chain having from 1 to 6 carbon atoms. Examples of alkylene groups include —$CH_2$—, —$CH_2CH_2$—, $CH(CH_3)$—$CH_2$—, $CH_2CH(CH_3)$—, —$CH_2CH_2CH_2$—, —$CH_2CH(CH_2CH_3)$— and —$CH_2CH(CH_2CH_3)CH_2$—. Other alkylene groups, for example $C_{1-3}$ alkylene are as defined above except that they contain the specified number (e.g. 1 to 3) carbon atoms.

The terms "carbocyclic" and "carbocyclyl" refer to a non-aromatic hydrocarbon ring system containing from 3 to 10 ring carbon atoms, unless otherwise indicated, and optionally one or more double bond. The carbocyclic group may be a single ring or may contain two or three rings which may be fused or bridged, where carbon atoms in a bridge are included in the number of ring carbon atoms. Examples include cyclopropyl, cyclobutyl, cyclopentyl, cyclohexyl, cyclopentenyl and cyclohexenyl as well as bridged systems such as bicyclo[1.1.1]pentyl, bicyclo-[2.2.1]heptyl, bicyclo-[2.2.2]octyl and adamantyl.

In the context of the present specification, the terms "heterocyclic" and "heterocyclyl" refer to a non-aromatic ring system containing 3 to 10 ring atoms including at least one heteroatom selected from N, O and S. The heterocyclic group may be a single ring or may contain two or three rings which may be fused or bridged, where bridge atoms are included in the number of ring atoms. Examples include tetrahydrofuranyl, tetrahydropyranyl, pyrrolidinyl, piperidinyl, morpholinyl, piperazinyl and thiomorpholinyl, as well as fused systems such as cyclopropyl-fused pyrrolidine.

The terms "aryl" and "aromatic" in the context of the present specification refer to a ring system with aromatic character having from 5 to 14 ring carbon atoms and containing up to three rings. Where an aryl group contains more than one ring, not all rings must be fully aromatic in character. Examples of aromatic moieties are benzene, naphthalene, fluorene, tetrahydronaphthalene, indane and indene.

The terms "heteroaryl" and "heteroaromatic" in the context of the specification refer to a ring system with aromatic character having from 5 to 14 ring atoms, at least one of which is a heteroatom selected from N, O and S, and containing up to three rings. Where a heteroaryl group contains more than one ring, not all rings must be aromatic in character. Examples of heteroaryl groups include pyridine, pyrimidine, indole, indazole, thiophene, benzothiophene, benzoxazole, benzofuran, dihydrobenzofuran, tetrahydrobenzofuran, benzimidazole, benzimidazoline, quinoline and indolene.

The term "oxo" refers to a C=O substituent, where the carbon atom is a ring atom of a carbocyclyl, heterocyclyl group or a ring of an aryl or heteroaryl group which is not aromatic in character.

The term "halogen" refers to fluorine, chlorine, bromine or iodine and the term "halo" to fluoro, chloro, bromo or iodo groups. Similarly, "halide" refers to fluoride, chloride, bromide or iodide.

The term "$C_{1-6}$ haloalkyl" as used herein refers to a $C_{1-6}$ alkyl group as defined above in which one or more of the hydrogen atoms is replaced by a halo group. Any number of hydrogen atoms may be replaced, up to perhalo substitution. Examples include trifluoromethyl, chloroethyl and 1,1-difluoroethyl. A fluoroalkyl group is a haloalkyl group in which halo is fluoro.

The term "isotopic variant" refers to isotopically-labelled compounds which are identical to those recited in formula (I) but for the fact that one or more atoms are replaced by an atom having an atomic mass or mass number different from the atomic mass or mass number most commonly found in nature, or in which the proportion of an atom having an atomic mass or mass number found less commonly in nature has been increased (the latter concept being referred to as "isotopic enrichment"). Examples of isotopes that can be incorporated into compounds of the invention include isotopes of hydrogen, carbon, nitrogen, oxygen, fluorine, iodine and chlorine such as 2H (deuterium), 3H, 11C, 13C, 14C, 18F, 123I or 125I (e.g. 3H, 11C, 14C, 18F, 123I or 125I), which may be naturally occurring or non-naturally occurring isotopes.

The compounds of general formula (I) are modulators of TMEM16A and therefore, in a further aspect of the invention, there is provided a compound of general formula (I) as defined above for use in the treatment or prophylaxis of diseases and conditions affected by modulation of TMEM16A.

There is also provided the use of a compound of general formula (I) in the manufacture of a medicament for the treatment or prophylaxis of diseases and conditions affected by modulation of TMEM16A.

There is also provided a method for the treatment or prophylaxis of diseases and conditions affected by modulation of TMEM16A, the method comprising administering to a patient in need of such treatment an effective amount of a compound of general formula (I).

The diseases and conditions affected by modulation of TMEM16A include respiratory diseases and conditions, dry mouth (xerostomia), intestinal hypermobility, cholestasis and ocular conditions.

There is also provided:

A compound of general formula (I) for use in the treatment or prophylaxis of respiratory diseases and conditions.

A compound of general formula (I) for use in the treatment or prophylaxis of dry mouth (xerostomia).

A compound of general formula (I) for use in the treatment or prophylaxis of intestinal hypermobility.

A compound of general formula (I) for use in the treatment or prophylaxis of cholestasis.

A compound of general formula (I) for use in the treatment or prophylaxis of ocular conditions.

The invention also provides:

The use of a compound of general formula (I) in the manufacture of a medicament for the treatment or prophylaxis of respiratory diseases and conditions.

The use of a compound of general formula (I) in the manufacture of a medicament for the treatment or prophylaxis of dry mouth (xerostomia).

The use of a compound of general formula (I) in the manufacture of a medicament for the treatment or prophylaxis of intestinal hypermobility.

The use of a compound of general formula (I) in the manufacture of a medicament for the treatment or prophylaxis of cholestasis.

The use of a compound of general formula (I) in the manufacture of a medicament for the treatment or prophylaxis of ocular conditions.

There is further provided:

A method for the treatment or prophylaxis of respiratory diseases and conditions, the method comprising administering to a patient in need of such treatment an effective amount of a compound of general formula (I).

A method for the treatment or prophylaxis of dry mouth (xerostomia), the method comprising administering to a patient in need of such treatment an effective amount of a compound of general formula (I).

A method for the treatment or prophylaxis of intestinal hypermobility, the method comprising administering to a patient in need of such treatment an effective amount of a compound of general formula (I).

A method for the treatment or prophylaxis of cholestasis, the method comprising administering to a patient in need of such treatment an effective amount of a compound of general formula (I).

A method for the treatment or prophylaxis of ocular conditions, the method comprising administering to a patient in need of such treatment an effective amount of a compound of general formula (I).

Respiratory diseases and conditions which may be treated or prevented by the compounds of general formula (I) include cystic fibrosis, chronic obstructive pulmonary disease (COPD), chronic bronchitis, emphysema, bronchiectasis, including non-cystic fibrosis bronchiectasis, asthma and primary ciliary dyskinesia.

Dry mouth (xerostomia) which may be treated or prevented by the compounds of general formula (I) may result from Sjorgens syndrome, radiotherapy treatment and xerogenic drugs.

Intestinal hypermobility which may be treated or prevented by the compounds of general formula (I) may be associated with gastric dyspepsia, gastroparesis, chronic constipation and irritable bowel syndrome.

Ocular conditions which may be treated or prevented by the compounds of by the compounds of general formula (I) include dry eye disease.

In some cases, in the compound of general formula (I), Z is —C(O)— and $R^{5b}$ is H, such that the compound is of formula (Iz):

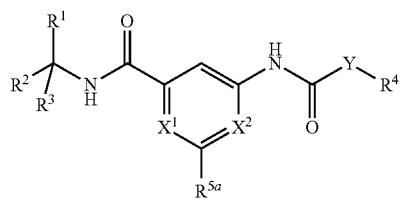

(Iz)

wherein $R^1$, $R^2$, $R^3$, $R^4$, $R^{5a}$ and Y are as defined for general formula (I).

In some cases, in the compound of general formula (I), Z is —C(O)NH—, and $R^{5b}$ is H such that the compound is of general formula (Iy):

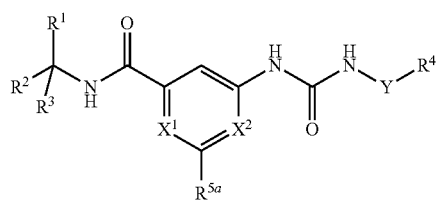

(Iy)

wherein $R^1$, $R^2$, $R^3$, $R^4$, $R^{5a}$ and Y are as defined for general formula (I).

In some compounds of general formula (Iz), Y is not a bond.

In some cases, the compound of general formula (I) is a compound of general formula (Ix) including all tautomeric forms all enantiomers and isotopic variants and salts and solvates thereof:

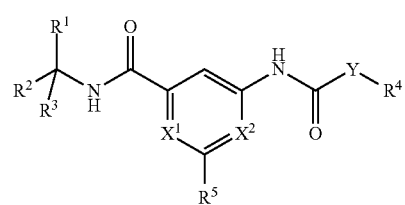

(Ix)

wherein:
$R^1$ is H, CN or $C_{1-3}$ alkyl optionally substituted with one or more substituents selected from
halo, $OR^{12}$, $N(R^{12})_2$, $C(O)OR^{12}$, $C(O)N(R^{12})_2$, $C(O)R^{12}$ and $N(R^{13})C(O)R^{12}$;
wherein each $R^{12}$ and $R^{13}$ is independently selected from H, $C_{1-6}$ alkyl or $C_{1-6}$ haloalkyl;
$R^2$ is $C_{1-6}$ alkyl;
$R^3$ is $C_{1-6}$ alkyl optionally substituted with one or more substituents selected from halo, OH, O($C_{1-6}$ alkyl), C(O)O—($C_{1-6}$ alkyl) and N(H)C(O)O—($C_{1-6}$ alkyl); or
$R^2$ and $R^3$ together with the carbon atom to which they are attached combine to form a 3- to 10-membered carbocyclic or heterocyclic ring system optionally substituted with one or more substituents selected from halo, $OR^9$, $N(R^9)_2$, $C(O)OR^9$, $C(O)N(R^9)_2$, $C(O)R^9$ and $N(R^9)C(O)R^9$; or
$R^1$, $R^2$ and $R^3$ together with the carbon atom to which they are attached combine to form a bridged 5- to 10-membered carbocyclic or heterocyclic ring system optionally substituted with one or more substituents selected from halo, $OR^9$, $N(R^9)_2$, $C(O)OR^9$, $C(O)N(R^9)_2$, $C(O)R^9$, $N(R^9)C(O)R^9$;
each $R^9$ is independently selected from H, $C_{1-6}$ alkyl or $C_{1-6}$ haloalkyl;
each of $X^1$ and $X^2$ is independently N or $CR^8$
$R^8$ is H, halo, OH, CN or $NH_2$;
Y is a bond or $C_{1-6}$ alkylene;
$R^4$ is 6-10-membered aryl, 5- to 10-membered heteroaryl or a 5- to 10-membered carbocyclic or heterocyclic ring system, any of which is optionally substituted with one or more substituents selected from:
halo, CN, nitro;
$OR^6$, $SR^6$, $NR^6R^7$, $C(O)R^6$ $C(O)OR^6$, $C(O)N(R^6)(R^7)$, $N(R^7)C(O)R^6$;
$C_{1-6}$ alkyl optionally substituted with one or more substituents selected from halo, CN, nitro, $OR^6$, $SR^6$, $NR^6R^7$, $C(O)R^6$ $C(O)OR^6$, $C(O)N(R^6)(R^7)$ and $N(R^7)C(O)R^6$; and
when $R^4$ is not fully aromatic in character, oxo;
wherein $R^6$ is H, $C_{1-6}$ alkyl, $C_{1-6}$ haloalkyl, 3-7 membered carbocyclyl or 3-7 membered heterocyclyl;
$R^7$ is H, $C_{1-6}$ alkyl or $C_{1-6}$ haloalkyl; or
$R^6$ and $R^7$ together with the nitrogen atom to which they are attached may form a 4 to 7-membered heterocyclic ring optionally containing one or more further heteroatoms and optionally substituted with one or more oxo substituents;
$R^5$ is H, $C_{1-4}$ alkyl or halo.
In some suitable compounds of the present invention, $R^1$ is H, CN, $C(O)OR^{12}$ or methyl, ethyl or ethynyl optionally substituted with one or more substituents selected from fluoro, $OR^{12}$, $N(R^{12})_2$, $C(O)OR^{12}$, $C(O)N(R^{12})_2$, $C(O)R^{12}$ and $N(R^{13})C(O)R^{12}$;
wherein each $R^{12}$ and $R^{13}$ is independently as defined above but is more suitably H or $C_{1-4}$ alkyl.

More suitably, $R^1$ is H, CN, C(O)OH, C(O)OMe or methyl, ethyl or ethynyl any of which may be unsubstituted or substituted with one or more substituents selected from fluoro, OH, methoxy, C(O)OC$_{1-4}$ alkyl, NHC(O)C$_{1-4}$ alkyl, C(O)NHC$_{1-4}$ alkyl, NHC$_{1-4}$ alkyl and NHC$_{1-4}$ fluoroalkyl.

In some more suitable compounds, $R^1$ is H, CN, ethynyl or methyl either of which may be unsubstituted or substituted with OH; especially H, CN or methyl.

In some suitable compounds of the present invention:
$R^2$ is methyl or ethyl, particularly methyl; and
$R^3$ is $C_{1-4}$ alkyl, or more suitably $C_{1-3}$ alkyl, for example methyl, ethyl or isopropyl; any of which is optionally substituted with one or more substituents selected from hydroxyl, methoxy, ethoxy, —C(O)O—(C$_{1-4}$ alkyl) and —N(H)C(O)O—(C$_{1-4}$ alkyl).

More suitably in this case, $R^3$ is unsubstituted or substituted with a single substituent selected from methoxy, ethoxy and —N(H)C(O)O—(C$_{1-4}$ alkyl), particularly methoxy or and —N(H)C(O)O—(C$_{1-4}$ alkyl).

In these compounds, $R^1$ is suitably methyl.

In other suitable compounds of the present invention, $R^2$ is H or $C_{1-4}$ alkyl, more suitably H, methyl or ethyl, especially H or methyl.

In some suitable compounds of the present invention, $R^3$ is $C_{1-10}$ alkyl, more suitably $C_{1-6}$ alkyl, $C_{2-6}$ alkenyl or $C_{2-6}$ alkynyl, any of which is optionally substituted as described above.

More suitably, $R^3$ is $C_{1-10}$ alkyl, more suitably $C_{1-6}$ alkyl, or $C_{2-3}$ alkynyl.

More suitably, when $R^3$ is an alkyl, alkenyl or alkynyl group, it is unsubstituted or substituted with a single substituent selected from fluoro, $R^{14}$ OR$^{14}$, OR$^{15}$, C(O)OR$^{15}$, N(R$^{16}$)S(O)$_2$R$^{15}$ and N(R$^{16}$)C(O)OR$^{15}$; wherein $R^{14}$, $R^{15}$ and $R^{16}$ are as described above.

In these compounds, it is still more suitable for $R^{14}$ to be selected from phenyl, pyridyl and a 5- or 6-membered heterocyclic ring, especially a nitrogen containing ring and more especially a 6-membered nitrogen containing ring such as morpholine, piperidine or piperazine. More suitably, $R^{15}$ is selected from H, or $C_{1-4}$ alkyl. $R^{16}$ is suitably H.

Examples of such $R^3$ groups include:
methyl or ethyl optionally substituted with OH, F, phenyl, O-phenyl, morpholine, NHS(O)$_2$C$_{1-4}$ alkyl or NHC(O)C$_{1-4}$ alkyl;
propynyl, for example prop-1-ynyl, and ethynyl.

In other suitable compounds, $R^3$ is a 3- to 7-membered carbocyclic or heterocyclic ring system, in particular a $C_{3-7}$ cycloalkyl group, for example cyclopropyl, which may be substituted as defined above but is more suitably unsubstituted.

In still other suitable compounds of general formula (I), $R^3$ is a 6- to 10 membered aryl or 5- to 10-membered heteroaryl ring system, either of which is optionally substituted as defined above.

More suitably in this case, $R^3$ is phenyl or a 5- or 6-membered heteroaryl group optionally substituted as defined above, in particular phenyl or pyridyl.

Such $R^3$ groups may be unsubstituted or substituted as defined above, with particularly suitable substituents being selected from OR$^{17}$ and N(R$^{17}$)$_2$, wherein each $R^{17}$ is independently as defined above but is more suitably H or methyl.

In some particularly suitable compounds of the present invention, $R^1$ is methyl or CN and $R^2$ and $R^3$ are both methyl.

In some suitable compounds of the present invention, $R^2$ and $R^3$ combine with the carbon atom to which they are attached to form a carbocyclic or heterocyclic ring system.

Suitable carbocyclic rings formed by $R^2$ and $R^3$ include: cyclopropyl, cyclobutyl, cyclopentyl, cyclohexyl; and bridged systems such as bicyclo[1.1.1]pentyl, bicyclo-[2.2.1]heptyl, bicyclo-[2.2.2]octyl and adamantyl, (provided that the atom to which $R^2$ and $R^3$ are attached is not a bridge atom).

More suitable carbocyclic rings formed by $R^2$ and $R^3$ include cyclopropyl, cyclobutyl, cyclopentyl and cyclohexyl.

Suitable heterocyclic rings formed by $R^2$ and $R^3$ include; tetrahydropyran-yl, for example tetrahydropyran-4-yl; tetrahydrofuranyl, for example tetrahydrofuran-3-yl; oxetanyl, for example oxetan-3-yl; piperidinyl, for example piperidin-2-yl and piperidin-4-yl; morpholinyl, piperazinyl and cyclopropyl-fused pyrrolidine.

More suitable heterocyclic rings formed by $R^2$ and $R^3$ include; tetrahydropyran-yl, for example tetrahydropyran-4-yl; tetrahydrofuranyl, for example tetrahydrofuran-3-yl; oxetanyl, for example oxetan-3-yl; piperidinyl, for example piperidin-2-yl and piperidin-4-yl; and cyclopropyl-fused pyrrolidine.

Any of the ring systems formed by $R^2$ and $R^3$ may be substituted as described above. In some cases, the ring system is unsubstituted or are substituted with a single substituent selected from OR$^9$ and C(O)OR$^9$, where $R^9$ is as defined above but is suitably $C_{1-4}$ alkyl, for example tert-butyl.

In alternative suitable compounds, the carbocyclic or heterocyclic ring system formed by $R^2$ and $R^3$ may be unsubstituted or substituted with one or more substituents, for example 1 or 2 substituents, selected from halo, OR$^9$, C(O)OR$^9$, unsubstituted C$_{1-4}$ alkyl and C$_{1-4}$ alkyl substituted with halo or OR$^9$, more suitably with 1 or 2 substituents selected from fluoro, OR$^9$, C(O)OR$^9$, unsubstituted C$_{1-4}$ alkyl and C$_{1-4}$ alkyl substituted with fluoro or OR$^9$.

In particular, the carbocyclic or heterocyclic ring system formed by $R^2$ and $R^3$ may be unsubstituted or substituted with one or more substituents, for example 1 or 2 substituents, selected from fluoro, OH, C(O)O(C$_{1-4}$ alkyl), unsubstituted C$_{1-4}$ alkyl or C$_{1-4}$ alkyl substituted with OH.

In some compounds where $R^2$ and $R^3$ form a carbocyclic or heterocyclic ring system, $R^1$ is H;
In other such compounds, $R^1$ is methyl.
In other such compounds, $R^1$ is methyl substituted with OH.
In still other such compounds, $R^1$ is CN.
In still other such compounds, $R^1$ is ethynyl.
In still other such compounds, $R^1$ is C(O)OR$^{12}$, for example C(O)OCH$_3$.

In particularly suitable compounds where $R^2$ and $R^3$ form a carbocyclic or heterocyclic ring system:
$R^1$ is H or cyano and $R^2$ and $R^3$ form a 5- or 6-membered carbocyclic or heterocyclic ring system, particularly a 6-membered ring system, for example cyclohexyl or tetrahydropyranyl, such as tetrahydropyran-4yl.

In still other suitable compounds of the present invention, $R^1$, $R^2$ and $R^3$ combine with the carbon atom to which they are attached to form a bridged carbocyclic or heterocyclic ring system, especially a carbocyclic system such as bicyclo [1.1.1]pentanyl, bicyclo[2.1.1]hexanyl, bicyclo-[2.2.1]heptanyl, bicyclo-[2.2.2]octanyl or adamantyl.

In some cases, the carbocyclic system may be selected from 3-bicyclo[1.1.1]pentanyl, bicyclo-[2.2.1]heptanyl, bicyclo-[2.2.2]octanyl and 1-adamantyl.

In other cases, the carbocyclic ring system may be selected from bicyclo[1.1.1]pentanyl, bicyclo[2.1.1]hexanyl and adamantyl, especially, 3-bicyclo[1.1.1]pentanyl, 1-bicyclo[2.1.1]hexanyl and 1-adamantyl, Suitably, the ring system is unsubstituted or substituted with a single substituent selected from $OR^9$ and $C(O)OR^9$, where $R^9$ is as defined above but is suitably H, methyl or ethyl, especially H or methyl and more particularly methyl. More suitably, the ring system is unsubstituted.

Alternatively, the ring system may be unsubstituted or substituted with one or more substituents, suitably one or two substituents and more suitably with a single substituent selected from fluoro, cyano, $C_{1-4}$ alkyl, $OR^9$ and $C(O)OR^9$, where $R^9$ is as defined above but is suitably H, methyl or ethyl, especially H or methyl and more particularly methyl.

In still other suitable compounds of the present invention, $R^1$, $R^2$ and $R^3$ combine with the carbon atom to which they are attached to form a phenyl group which may be substituted as defined above but is more suitably unsubstituted.

In some suitable compounds of general formula (I), $X^1$ is N and $X^2$ is $CR^8$, where $R^8$ is as defined above. In particular, $X^1$ is N and $X^2$ is CH.

Suitably in such compounds, when —Z is C(O)— and Y is a bond, $R^4$ is not a 5- to 10-membered heteroaryl ring system which is attached to the linker Y via a ring nitrogen atom. In other suitable compounds of general formula (I), both $X^1$ and $X^2$ are $CR^8$, where each $R^8$ is independently as defined above.

In such compounds, $R^4$ is suitably phenyl having an OH substituent at the 2- or 3-position and optionally one or more further substituents as defined above.

More suitably, $R^4$ is phenyl having an OH substituent at the 2-position and optionally one or more further substituents as defined above.

In other suitable compounds of general formula (I), $X^1$ is $CR^8$, where $R^8$ is as defined above, and $X^2$ is N.

In some suitable compounds of this type, Z is —C(O)— and Y is not a bond. Thus, Y may be a straight $C_{1-6}$ alkylene chain optionally substituted with one or more substituents $R^{18}$ as defined above.

In other compounds in which $X^1$ is $CR^8$, $X^2$ is N, Z is —C(O)NH— and Y is a bond, $R^4$ is suitably not a 12-membered heteroaryl ring system.

In other suitable compounds of general formula (I) in which $X^1$ is $CR^8$, where $R^8$ is as defined above, and $X^2$ is N:
when $R^1$ and $R^2$ are both H, $R^3$ is not a 5- or 6-membered aryl or heteroaryl ring system optionally substituted as described above; and when $R^1$ is H, $R^2$ and $R^3$ do not combine to form a cyclohexyl ring.

In still other suitable compounds of general formula (I), both $X^1$ and $X^2$ are N.

In these compounds, suitably when one of $R^1$ and $R^2$ is H and the other of $R^1$ and $R^2$ is H or methyl, $R^3$ is not substituted or unsubstituted phenyl.

In the compounds of the present invention, when $X^1$ and/or $X^2$ is $CR^8$, $R^8$ is suitably H or halo, for example H or fluoro. In alternative suitable compounds, $R^8$ is H, halo, OH, methoxy or ethoxy, especially H, fluoro, chloro, OH or methoxy.

As described above, in more suitable compounds of the present invention, Z is —C(O)— or C(O)NH and that the compound is of general formula (Iz), (Iy) or (Ix).

In some more suitable compounds of the present invention, Y is $C_{1-3}$ alkylene, still more suitably —$CH_2$—, —CH($CH_3$)$CH_2$— or —$CH_2CH_2$—. More suitably, Y is —$CH_2$— or —$CH_2CH_2$— and in particularly suitable compounds, Y is —$CH_2$—.

In other suitable compounds of the invention, Y is a bond.

In other suitable compounds of the present invention, Y is a straight $C_{1-3}$ alkylene optionally substituted with one or more substituents $R^{18}$, wherein $R^{18}$ is as defined above and wherein two substituents $R^{18}$ may be attached to the same or to different carbon atoms.

Suitably in such compounds, each $R^{18}$ is independently methyl or ethyl or two $R^{18}$ groups attached to the same carbon atom combine to form a cyclopropyl, cyclobutyl or cyclopentyl ring.

Still more suitably, Y is a bond or —$C_{1-3}$ alkylene-.

Examples of linkers Y include a bond, —$CH_2$—, —CH($CH_3$)—, —$CH_2CH_2$— and

In other suitable compounds of general formula (I), Y is —$CH_2$—, —$CH_2CH_2$—, —CH($CH_3$)$CH_2$—, —$CH_2$CH($CH_3$)— or —$CH_2CH_2CH_2$—, especially —$CH_2$— or —$CH_2CH_2$— and more especially —$CH_2$—.

In some suitable compounds of general formulae (I), $R^{5b}$ is H or halo, for example fluoro.

More usually, $R^{5b}$ is H such that the compound is a compound of general formula (Iz), (Iy) or (Ix) above.

In some suitable compounds of general formulae (I), (Iz) and (Iy), $R^{5a}$ is H, $C_{1-4}$ alkyl or halo, for example fluoro.

In some suitable compounds of general formulae (I), (Iz) and (Iy), $R^{5a}$ is methyl or ethyl, especially methyl.

In other suitable compounds of general formula (I), (Iz) and (Iy), $R^{5a}$ is halo, especially fluoro More usually in compounds of general formulae (I), (Iz), and (Iy), $R^{5a}$ is H.

In some suitable compounds of general formula (Ix), $R^5$ is H.

In other suitable compounds of general formula (Ix), $R^5$ is $C_{1-4}$ alkyl, more usually methyl or ethyl and especially methyl.

In still other suitable compounds of the invention, $R^5$ is halo, especially fluoro.

In typical compounds of general formula (I), both $R^{5a}$ and $R^{5b}$ are H.

In the compounds of the present invention $R^4$ is a 6-14-membered aryl, 5-14-membered heteroaryl or a 5- to 10-membered carbocyclic ring system, any of which is optionally substituted as defined above. More suitably, $R^4$ is 6-10-membered aryl, 5- to 10-membered heteroaryl or a 5- to 10-membered carbocyclic or heterocyclic ring system, any of which is optionally substituted with one or more substituents as described above.

In some more suitable compounds of general formula (I), $R^4$ is a 6- to 11-membered aryl group, for example a group selected from phenyl, naphthyl, indanyl, 1,2,3,4-tetrahydronaphthyl and benzocycloheptanyl, any of which is optionally substituted as described above.

In other more suitable compounds of general formula (I), $R^4$ is a 5- to 10-membered heteroaryl group, for example a group selected from pyridyl, quinolinyl, quinoxalinyl, indazolyl, indolyl, benzoxazolyl, dihydrobenzofuranyl, furyl and thienyl, any of which is optionally substituted as described above.

In other more suitable compounds of general formula (I), $R^4$ is a carbocyclyl group, for example a group selected from cyclohexyl and adamantyl, any of which is unsubstituted or substituted as described above.

In some suitable compounds of the present invention, $R^4$ is phenyl optionally substituted with one or more substituents as described above.

Alternatively, $R^4$ is 5-10-membered heteroaryl optionally substituted with one or more substituents as described above. More suitably in this case $R^4$ is pyridyl, pyrrolyl, thienyl, furyl, benzoxazolyl, imidazolyl, indolyl or indazolyl.

In some suitable compounds, $R^4$ is substituted with one or more substituents selected from:

halo, CN;

$OR^6$, $NR^6R^7$, $C(O)OR^6$, $C(O)N(R^6)(R^7)$;

$C_{1-6}$ alkyl optionally substituted with one or more substituents selected from halo, CN, $OR^6$, $NR^6R^7$, $C(O)OR^6$ and $C(O)N(R^6)(R^7)$;

wherein $R^6$ is H, $C_{1-6}$ alkyl, $C_{1-6}$ haloalkyl, 3-7 membered carbocyclyl or 3-7 membered heterocyclyl;

$R^7$ is H, $C_{1-6}$ alkyl or $C_{1-6}$ haloalkyl; or $R^6$ and $R^7$ together with the nitrogen atom to which they are attached may form a 5- or 6-membered heterocyclic ring optionally containing one or more further heteroatoms and optionally substituted with one or more oxo substituents.

In other suitable compounds, wherein $R^4$ is an aryl group, it is more suitably unsubstituted or substituted with one or more substituents selected from:

halo, CN, $R^{19}$, $OR^{19}$;

$OR^6$, $C(O)OR^6$;

$C_{1-4}$ alkyl or $O(C_{1-4}$ alkyl) optionally substituted with one or more substituents selected from halo, CN, $R^{19}$, $OR^{19}$, $OR^6$ and $NR^6R^7$;

wherein $R^6$, $R^7$ and $R^{19}$ are as defined above.

More suitably, however, $R^6$ is H, $C_{1-4}$ alkyl or $C_{1-4}$ haloalkyl or, for a moiety $NR^6R^7$, $R^6$ and $R^7$ combine with the nitrogen atom to which they are attached to form a 5- or 6-membered heterocyclic ring, optionally containing one or more further heteroatoms and optionally substituted with one or more halo substituents.

$R^{19}$ is more suitably a 3- to 6-membered carbocyclyl group or phenyl, either or which is optionally substituted with one or more substituents selected from halo, methyl and methoxy.

In particularly suitable compounds, $R^4$ is phenyl substituted with an OH group at either the 2- or the 3-position and optionally with one or more further substituents as defined for general formula (I), more suitably with one or more further substituents, for example one further substituent, selected from those defined immediately above.

When $R^4$ is a bicyclic aryl group it is more suitably unsubstituted or substituted with one or two substituents selected from OH and halo.

When $R^4$ is a heteroaryl group, it is more suitably unsubstituted or substituted with one or more substituents selected from OH and halo.

When $R^4$ is a carbocyclic group it is more suitably unsubstituted or substituted with one or more substituents selected from OH and halo. Still more suitably, it is unsubstituted.

In particularly suitable compounds of the present invention, Y is $-CH_2-$, $R^4$ is phenyl and the compound is a compound of general formula (Ia):

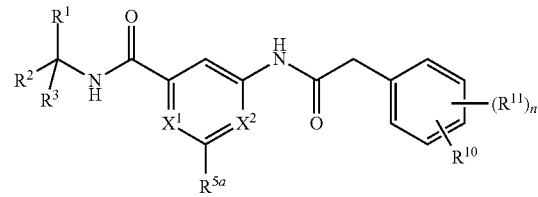

(Ia)

wherein $R^1$, $R^2$, $R^3$, $R^{5a}$, $X^1$ and $X^2$ are as defined for general formula (I);

$R^{10}$ is H, OH, halo, $C_{1-6}$ alkyl, $-O(C_{1-6}$ alkyl);

each $R^{11}$ is independently H, halo, OH, CN, $C_{1-6}$ alkyl, $C_{1-6}$ haloalkyl, $-O(C_{1-6}$ alkyl) or $C(O)O-(C_{1-6}$ alkyl); and n is 1 or 2.

Still more suitably, the compound is a compound of general formula (Ib) or (Ic):

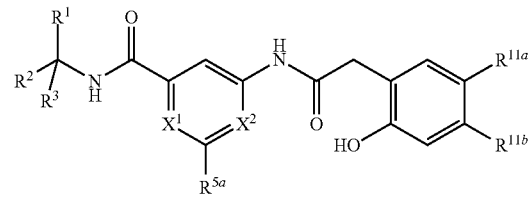

(Ib)

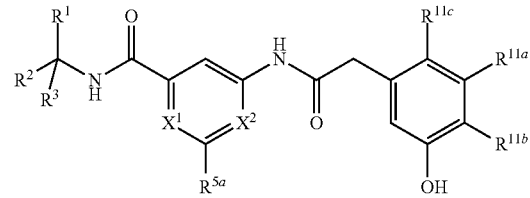

(Ic)

wherein $R^1$, $R^2$, $R^3$, $R^{5a}$, $X^1$ and $X^2$ are as defined for general formula (I);

$R^{11a}$ is H, halo, $C_{1-4}$ alkyl, $C_{1-4}$ haloalkyl or $C(O)O(C_{1-4}$ alkyl);

$R^{11b}$ is H, halo, $C_{1-4}$ alkyl or $C_{1-4}$ haloalkyl; and $R^{11c}$ is H, halo, CN, $C_{1-4}$ alkyl or $C_{1-4}$ haloalkyl.

In particularly suitable compounds of general formula (Ib), one or both of $R^{11a}$ and $R^{11b}$ is H.

In some such compounds of general formula (Ib), $R^{11a}$ is H, halo, $C_{1-4}$ alkyl or $C(O)O(C_{1-4}$ alkyl) and $R^{11b}$ is H.

More suitably, $R^{11a}$ is H, chloro, $C_{1-4}$ alkyl or $C(O)OCH_3$ and $R^{11b}$ is H.

In some compounds of general formula (Ib) $R^{11a}$ is chloro and $R^{11b}$ is H.

In other such compounds of general formula (Ib), $R^{11a}$ is H and $R^{11b}$ is H, halo or $C_{1-6}$ haloalkyl.

More suitably, $R^{11a}$ is H and $R^{11b}$ is H, chloro, bromo or trifluoromethyl.

Alternatively, in other particularly suitable compounds of general formula (Ib) both $R^{11a}$ and $R^{11b}$ are halo, particularly chloro or bromo.

In some particularly suitable compounds of general formula (Ic), $R^{11a}$ is H.

More suitably in compounds of general formula (Ic), $R^{11b}$ is $C_{1-4}$ alkyl or $C_{1-4}$ halo alkyl, for example t-butyl.

In the compounds of general formulae (Ia) and (Ib) suitable $R^1$, $R^2$, $R^3$, $R^5$, $X^1$ and $X^2$ groups are as set out above for the compounds of general formula (I). However, still more suitably, $X^1$ is N, $X^2$ is CH and $R^{5b}$ is H such that the compounds is of general formula (Id) or (Ie):

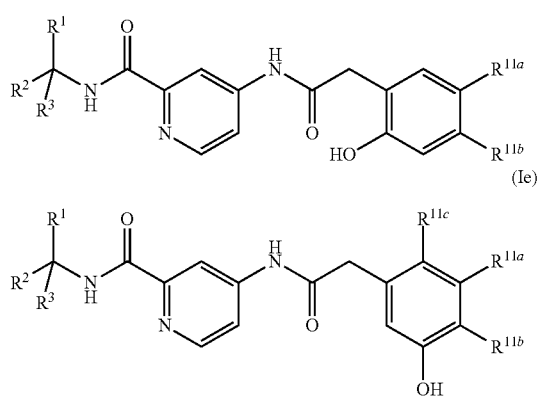

wherein $R^1$, $R^2$, $R^3$, $R^{11a}$, $R^{11b}$ and $R^{11c}$ are as defined above for compounds of general formulae (Ib) and (Ic).

Particularly suitable groups $R^{11a}$ and $R^{11b}$ for general formula (Id) are as described above for general formula (Ib) and particularly suitable groups $R^{11a}$ and $R^{11b}$ for general formula (Ie) are as described above for general formula (Ic).

Suitable compounds of general formula (I) include:
Specific examples of compounds of general formula (I) include the following:
N-tert-Butyl-4-[[2-(2-hydroxyphenyl)acetyl]amino]pyridine-2-carboxamide (Compound 1);
N-(1,1-Dimethylpropyl)-3-[[2-(2-hydroxyphenyl)acetyl]amino]benzamide (Compound 1.1);
N-(1-Adamantyl)-3-[[2-(5-chloro-2-hydroxy-phenyl)acetyl]amino]benzamide (Compound 1.2);
N-(1-Adamantyl)-4-[[2-(5-chloro-2-hydroxy-phenyl)acetyl]amino]pyridine-2-carboxamide (Compound 1.3);
4-[[2-(5-Chloro-2-hydroxy-phenyl)acetyl]amino]-N-(3-methoxy-1,1-dimethyl-propyl)pyridine-2-carboxamide (Compound 1.4);
3-[[2-(5-Chloro-2-hydroxy-phenyl)acetyl]amino]-N-(1,1-dimethyl propyl)benzamide (Compound 1.5);
4-[[2-(5-Chloro-2-hydroxy-phenyl)acetyl]amino]-N-(1-methylcyclobutyl)pyridine-2-carboxamide (Compound 1.6);
4-[[2-(5-Chloro-2-hydroxy-phenyl)acetyl]amino]-N-(1-methylcyclohexyl)pyridine-2-carboxamide (Compound 1.7);
tert-Butyl N-[3-[[4-[[2-(5-chloro-2-hydroxy-phenyl)acetyl]amino]pyridine-2-carbonyl]amino]-3-methyl-butyl]carbamate (Compound 1.8);
3-[[2-(2-Hydroxyphenyl)acetyl]amino]-N-(2-methoxy-1,1-dimethyl-ethyl)benzamide (Compound 1.9);
4-[[2-(5-Chloro-2-hydroxy-phenyl)acetyl]amino]-N-cyclohexyl-pyridine-2-carboxamide (Compound 1.10);
N-tert-Butyl-3-[[2-(5-chloro-2-hydroxy-phenyl)acetyl]amino]benzamide (Compound 2);
N-tert-Butyl-3-[[2-(5-fluoro-2-hydroxy-phenyl)acetyl]amino]benzamide (Compound 2.1);
N-tert-Butyl-3-[[2-(3-fluoro-2-hydroxy-phenyl)acetyl]amino]benzamide (Compound 2.2);
N-tert-Butyl-3-[[2-(4-fluoro-2-hydroxy-phenyl)acetyl]amino]benzamide (Compound 2.3);
N-tert-Butyl-3-[[2-(2,6-dihydroxy phenyl)acetyl]amino]benzamide (Compound 2.4);
N-tert-Butyl-3-[3-(2-hydroxyphenyl)propanamido]benzamide (Compound 2.5);
N-tert-Butyl-3-[[2-(2-hydroxy-6-methoxy-phenyl)acetyl]amino]benzamide (Compound 2.6);
N-tert-Butyl-3-[2-(2-hydroxyphenyl)propanamido]benzamide (Compound 2.7);
N-tert-Butyl-3-[[2-(2-hydroxy-3-methoxy-phenyl)acetyl]amino]benzamide (Compound 2.8);
N-tert-Butyl-3-[[2-(3,5-difluoro-2-hydroxy-phenyl)acetyl]amino]benzamide (Compound 2.9);
3-[[2-(5-Bromo-2-hydroxy-phenyl) acetyl]amino]-N-tert-butyl-benzamide (Compound 2.10);
N-tert-Butyl-3-[[2-(2,3-difluoro-6-hydroxy-phenyl)acetyl]amino]benzamide (Compound 2.11);
N-tert-Butyl-3-[[2-(4,5-difluoro-2-hydroxy-phenyl)acetyl]amino]benzamide (Compound 2.12);
N-(1,1-Dimethylpropyl)-3-[[2-(4-fluoro-2-hydroxy-phenyl)acetyl]amino]benzamide (Compound 2.13);
N-tert-Butyl-3-[[2-(2-hydroxy-4-methoxy-phenyl)acetyl]amino]benzamide (Compound 2.14);
N-tert-Butyl-3-[[2-(2-fluoro-6-hydroxy-phenyl)acetyl]amino]benzamide (Compound 2.15);
N-tert-Butyl-3-[[2-(2,3-dihydroxyphenyl) acetyl]amino]benzamide (Compound 2.16);
N-tert-Butyl-3-[[2-[2-hydroxy-5-(trifluoro methyl)phenyl]acetyl]amino]benzamide (Compound 2.17);
Methyl 3-[2-[3-(tert-butylcarbamoyl)anilino]-2-oxo-ethyl]-4-hydroxy-benzoate (Compound 2.18);
N-tert-Butyl-3-[[2-[2-hydroxy-4-(trifluoro methyl)phenyl]acetyl]amino]benzamide (Compound 2.19);
N-tert-Butyl-4-[[2-(5-chloro-2-hydroxy-phenyl)acetyl]amino]pyridine-2-carboxamide (Compound 3);
N-(1,1-Dimethylpropyl)-4-[[2-(4-fluoro-2-hydroxy-phenyl)acetyl]amino]pyridine-2-carboxamide (Compound 3.1a);
N-tert-Butyl-4-[[2-(4-fluoro-2-hydroxy-phenyl)acetyl]amino]pyridine-2-carboxamide (Compound 3.2a);
N-tert-Butyl-4-[[2-(2-chloro-6-hydroxy-phenyl)acetyl]amino]pyridine-2-carboxamide (Compound 3.3a);
4-[[2-(4-Bromo-5-chloro-2-hydroxy-phenyl)acetyl]amino]-N-tert-butyl-pyridine-2-carboxamide (Compound 3.4a);
4-[[2-(5-tert-Butyl-2-hydroxy-phenyl)acetyl]amino]-N-(1-cyanocyclobutyl)pyridine-2-carboxamide (Compound 3.5a);
4-[[2-(5-tert-Butyl-2-hydroxy-phenyl)acetyl]amino]-N-(1-methyl cyclobutyl)pyridine-2-carboxamide (Compound 3.6a);
N-tert-butyl-4-[2-(2,5-dibromo-3-fluoro-6-hydroxyphenyl) acetamido]pyridine-2-carboxamide (Compound 3.7a);
N-tert-Butyl-4-[[2-[2-hydroxy-5-(trifluoromethyl)phenyl]acetyl]amino]pyridine-2-carboxamide (Compound 3.5b);
N-tert-Butyl-4-[[2-(4-chloro-2-hydroxy-phenyl)acetyl]amino]pyridine-2-carboxamide (Compound 3.6b);
N-tert-Butyl-4-[[2-[2-hydroxy-4-(trifluoro methyl)phenyl]acetyl]amino]pyridine-2-carboxamide (Compound 3.7b);
N-tert-Butyl-4-[[2-(2-hydroxy-5-methoxy-phenyl)acetyl]amino]pyridine-2-carboxamide (Compound 3.8b);
N-tert-Butyl-4-[(6-hydroxyindane-1-carbonyl)amino]pyridine-2-carboxamide (Compound 3.9b);
N-tert-Butyl-4-[(7-hydroxyindane-1-carbonyl)amino]pyridine-2-carboxamide (Compound 3.10b);

N-tert-Butyl-4-[[2-(2,5-dibromo-3-chloro-6-hydroxy-phenyl)acetyl]amino]pyridine-2-carboxamide (Compound 3.11b);

N-tert-Butyl-4-[[2-(3-hydroxyphenyl) acetyl]amino]pyridine-2-carboxamide (Compound 3.12b);

N-tert-Butyl-4-[[2-(2-fluoro-5-hydroxy-phenyl) acetyl]amino]pyridine-2-carboxamide (Compound 3.13b);

N-tert-Butyl-4-[[2-(4-chloro-3-hydroxy-phenyl)acetyl]amino]pyridine-2-carboxamide (Compound 3.14b);

N-tert-Butyl-4-[[2-(2-chloro-3-hydroxy-phenyl)acetyl]amino]pyridine-2-carboxamide (Compound 3.15b);

N-tert-Butyl-4-[[2-(2-chloro-5-hydroxy-phenyl) acetyl]amino]pyridine-2-carboxamide (Compound 3.16b);

N-tert-Butyl-4-[[2-(3-chloro-5-hydroxy-phenyl)acetyl]amino]pyridine-2-carboxamide (Compound 3.17b);

N-tert-Butyl-3-[[2-(3-hydroxyphenyl)acetyl]amino]benzamide (Compound 4);

N-tert-Butyl-3-[[2-(1H-indazol-3-yl)acetyl]amino]benzamide (Compound 4.1);

N-tert-Butyl-3-[[2-(5-fluoro-1H-indol-3-yl)acetyl]amino]benzamide (Compound 4.2);

N-tert-Butyl-3-[[2-(2-hydroxyphenyl)acetyl]amino]benzamide (Compound 4.3);

N-tert-Butyl-3-[[2-(7-fluoro-2-methyl-1H-indol-3-yl)acetyl]amino]benzamide (Compound 4.4);

N-tert-Butyl-3-[[2-(1H-indol-3-yl)acetyl]amino]benzamide (Compound 4.5);

N-tert-Butyl-3-[(2-phenylacetyl)amino]benzamide (Compound 4.6);

N-tert-Butyl-3-[[2-(2-fluoro-6-methoxy-phenyl)acetyl]amino]benzamide (Compound 4.7);

N-tert-Butyl-3-[[2-(2,3-difluoro-6-methoxy-phenyl)acetyl]amino]benzamide (Compound 4.8);

N-tert-Butyl-3-[[2-[2-methoxy-4-(trifluoro methyl)phenyl]acetyl]amino]benzamide (Compound 4.9);

N-tert-Butyl-4-[[2-(2-thienyl)acetyl]amino]pyridine-2-carboxamide (Compound 5);

4-[[2-(2-Adamantyl)acetyl]amino]-N-tert-butyl-pyridine-2-carboxamide (Compound 5.1);

N-tert-Butyl-4-[[2-(4-fluoro-2-methoxy-phenyl)acetyl]amino]pyridine-2-carboxamide (Compound 5.2);

N-tert-Butyl-4-[[2-(5-chloro-2-fluoro-phenyl)acetyl]amino]pyridine-2-carboxamide (Compound 5.3);

N-tert-Butyl-4-[[2-(2-furyl)acetyl]amino]pyridine-2-carboxamide (Compound 5.4);

N-tert-Butyl-4-[[2-(3-chlorophenyl) acetyl]amino]pyridine-2-carboxamide (Compound 5.5);

N-tert-Butyl-4-[[2-(1H-indol-3-yl)acetyl]amino]pyridine-2-carboxamide (Compound 5.6);

N-tert-Butyl-4-[[2-(o-tolyl)acetyl]amino]pyridine-2-carboxamide (Compound 5.7);

N-tert-Butyl-4-[[2-(3,4-dichlorophenyl) acetyl]amino]pyridine-2-carboxamide (Compound 5.8);

N-tert-Butyl-4-[[2-(3-fluorophenyl)acetyl]amino]pyridine-2-carboxamide (Compound 5.9);

N-tert-Butyl-4-[[2-(5-chloro-2-methoxy-phenyl)acetyl]amino]pyridine-2-carboxamide (Compound 5.10);

N-tert-Butyl-4-[[2-(p-tolyl)acetyl]amino]pyridine-2-carboxamide (Compound 5.11);

N-tert-Butyl-4-[[2-(2-fluorophenyl) acetyl]amino]pyridine-2-carboxamide (Compound 5.12);

N-tert-Butyl-4-[[2-(4-fluorophenyl) acetyl]amino]pyridine-2-carboxamide (Compound 5.13);

N-tert-Butyl-4-[[2-(m-tolyl)acetyl]amino]pyridine-2-carboxamide (Compound 5.14);

4-[[2-(1,3-Benzoxazol-6-yl)acetyl]amino]-N-tert-butyl-pyridine-2-carboxamide (Compound 5.15);

N-tert-Butyl-4-[[2-(2-chloro-3-pyridyl) acetyl]amino]pyridine-2-carboxamide (Compound 5.16);

N-tert-Butyl-4-[[2-(2,6-dichlorophenyl) acetyl]amino]pyridine-2-carboxamide (Compound 5.17);

N-tert-Butyl-4-[[2-(4-chloro-3-fluoro-phenyl)acetyl]amino]pyridine-2-carboxamide (Compound 5.18);

N-tert-Butyl-4-[[2-(3,5-dichloro phenyl)acetyl]amino]pyridine-2-carboxamide (Compound 5.19);

N-tert-Butyl-4-[[2-(2-chlorophenyl) acetyl]amino]pyridine-2-carboxamide (Compound 5.20);

N-tert-Butyl-4-[[2-(3-chloro-4-hydroxy-phenyl)acetyl]amino]pyridine-2-carboxamide (Compound 5.21);

N-tert-Butyl-4-(indane-1-carbonyl amino)pyridine-2-carboxamide (Compound 5.22);

N-tert-Butyl-4-[(2-quinoxalin-6-ylacetyl)amino]pyridine-2-carboxamide (Compound 5.23);

N-tert-Butyl-4-[[2-(2-naphthyl) acetyl]amino]pyridine-2-carboxamide (Compound 5.24);

N-tert-Butyl-4-(2,3-dihydrobenzofuran-3-carbonylamino)pyridine-2-carboxamide (Compound 5.25);

N-tert-Butyl-4-(6,7,8,9-tetrahydro-5H-benzo[7]annulene-5-carbonylamino)pyridine-2-carboxamide (Compound 5.26);

N-tert-Butyl-4-(tetralin-1-carbonylamino)pyridine-2-carboxamide (Compound 5.27);

N-tert-Butyl-4-[[2-(6-quinolyl)acetyl]amino]pyridine-2-carboxamide (Compound 5.29);

N-tert-butyl-4-[[1-(3-chlorophenyl)cyclopropanecarbonyl]amino]pyridine-2-carboxamide (Compound 5.31);

N-tert-Butyl-4-[[2-(2,3-dihydro-1,4-benzodioxin-6-yl)acetyl]amino]pyridine-2-carboxamide (Compound 5.32);

N-(1,1-Dimethylprop-2-ynyl)-4-[(2-isochroman-1-ylacetyl)amino]pyridine-2-carboxamide (Compound 5.33);

4-[[2-(4,4-Difluorocyclohexyl)acetyl]amino]-N-(1,1-dimethylprop-2-ynyl)pyridine-2-carboxamide (Compound 5.34);

N-(1,1-Dimethylprop-2-ynyl)-4-[[2-[4-(trifluoromethyl)phenyl]acetyl]amino]pyridine-2-carboxamide (Compound 5.35);

N-(1,1-Dimethylprop-2-ynyl)-4-[[2-[3-(trifluoromethyl)-1H-pyrazol-4-yl]acetyl]amino]pyridine-2-carboxamide (Compound 5.36);

N-(1,1-Dimethylprop-2-ynyl)-4-[[2-[3-(trifluoromethyl)phenyl]acetyl]amino]pyridine-2-carboxamide (Compound 5.37);

N-(1,1-Dimethylprop-2-ynyl)-4-[[2-[2-(trifluoromethyl)phenyl]acetyl]amino]pyridine-2-carboxamide (Compound 5.38);

4-[[2-(2,3-Dihydro-1,4-benzoxazin-4-yl)acetyl]amino]-N-(1,1-dimethylprop-2-ynyl)pyridine-2-carboxamide (Compound 5.39);

N-tert-Butyl-4-[[2-(5-cyano-2-hydroxy-phenyl)acetyl]amino]pyridine-2-carboxamide (Compound 6);

3-[[2-(5-Chloro-2-hydroxy-phenyl)acetyl]amino]-N-(1,1,2,2-tetramethylpropyl)benzamide (Compound 7);

3-[[2-(5-Chloro-2-hydroxy-phenyl)acetyl]amino]-N-(1,1-dimethylbutyl)benzamide (Compound 7.1);

4-[[2-(5-Chloro-2-hydroxy-phenyl)acetyl]amino]-N-(1,1-dimethylbutyl)pyridine-2-carboxamide (Compound 7.2);

3-[[2-(5-Chloro-2-hydroxy-phenyl)acetyl]amino]-N-cyclohexyl-benzamide (Compound 7.3);

3-[[2-(5-Chloro-2-hydroxy-phenyl)acetyl]amino]-N-tetrahydropyran-4-yl-benzamide (Compound 7.4);

3-[[2-(5-Chloro-2-hydroxy-phenyl)acetyl]amino]-N-(1,1,2-trimethylpropyl)benzamide (Compound 7.5);

4-[[2-(5-Chloro-2-hydroxy-phenyl)acetyl]amino]-N-(1,1,2-trimethylpropyl)pyridine-2-carboxamide (Compound 7.6);
4-[[2-(5-Chloro-2-hydroxy-phenyl)acetyl]amino]-N-isopropyl-pyridine-2-carboxamide (Compound 7.7);
3-[[2-(5-Chloro-2-hydroxy-phenyl)acetyl]amino]-N-(4-methyltetrahydropyran-4-yl)benzamide (Compound 7.8);
4-[[2-(5-Chloro-2-hydroxy-phenyl)acetyl]amino]-N-(4-methyltetrahydropyran-4-yl)pyridine-2-carboxamide (Compound 7.9);
3-[[2-(5-Chloro-2-hydroxy-phenyl)acetyl]amino]-N-(1-methylcyclobutyl)benzamide (Compound 7.10);
4-[[2-(5-Chloro-2-hydroxy-phenyl)acetyl]amino]-N-tetrahydropyran-4-yl-pyridine-2-carboxamide (Compound 7.11);
4-[2-(5-Chloro-2-hydroxyphenyl)acetamido]-N-[(1s,4s)-4-hydroxycyclohexyl]pyridine-2-carboxamide (Compound 7.12);
4-[[2-(5-Chloro-2-hydroxy-phenyl)acetyl]amino]-N-sec-butyl-pyridine-2-carboxamide (Compound 7.13);
4-[[2-(5-Chloro-2-hydroxy-phenyl)acetyl]amino]-N-(2-hydroxy-1,1,2-trimethyl-propyl)pyridine-2-carboxamide (Compound 7.14);
N-(3-Bicyclo[1.1.1]pentanyl)-4-[[2-(5-chloro-2-hydroxy-phenyl)acetyl]amino]pyridine-2-carboxamide (Compound 7.15);
4-[[2-(5-Chloro-2-hydroxy-phenyl)acetyl]amino]-N-(1-cyanocyclobutyl)pyridine-2-carboxamide (Compound 7.16);
tert-Butyl-3-[[3-[[2-(5-chloro-2-hydroxy-phenyl)acetyl]amino]benzoyl]amino]piperidine-1-carboxylate (Compound 8);
tert-Butyl-3-[[4-[[2-(5-chloro-2-hydroxy-phenyl)acetyl]amino]pyridine-2-carbonyl]amino]piperidine-1-carboxylate (Compound 8.1);
tert-Butyl 4-[[3-[[2-(5-chloro-2-hydroxy-phenyl) acetyl]amino]benzoyl]amino]-4-methyl-piperidine-1-carboxylate (Compound 8.2);
tert-Butyl (1r,5s,6s)-6-{4-[2-(5-chloro-2-hydroxyphenyl)acetamido]pyridine-2-amido}-3-azabicyclo[3.1.0]hexane-3-carboxylate (Compound 8.3);
N-tert-Butyl-3-[[2-(5-chloro-2-hydroxy-phenyl)acetyl]amino]-4-fluoro-benzamide (Compound 9);
N-tert-Butyl-3-[[2-(5-chloro-2-hydroxy-phenyl)acetyl]amino]-5-methyl-benzamide (Compound 9.1);
4-[[2-(5-Chloro-2-hydroxy-phenyl)acetyl]amino]-N-(1,1-dimethylpropyl)pyridine-2-carboxamide (Compound 9.2);
N-tert-Butyl-4-[[2-(5-tert-butyl-2-hydroxy-phenyl)acetyl]amino]pyridine-2-carboxamide (Compound 10);
N-tert-Butyl-5-[[2-(5-chloro-2-hydroxy-phenyl)acetyl]amino]-2-hydroxy-benzamide (Compound 11);
N-tert-Butyl-3-[[2-(5-cyano-2-hydroxy-phenyl)acetyl]amino]benzamide (Compound 12);
Methyl 3-[2-[[2-(tert-butylcarbamoyl)-4-pyridyl]amino]-2-oxo-ethyl]-4-hydroxy-benzoate (Compound 13);
N-tert-Butyl-3-[[2-(5-chloro-2-hydroxy-phenyl)acetyl]amino]-4-hydroxy-benzamide (Compound 14);
N-tert-Butyl-4-[[2-(2-hydroxy-5-methyl-phenyl)acetyl]amino]pyridine-2-carboxamide (Compound 15);
N-tert-Butyl-3-[[2-(5-chloro-2-hydroxy-phenyl)acetyl]amino]-4-methoxy-benzamide (Compound 16);
N-tert-Butyl-5-[[2-(5-chloro-2-hydroxy-phenyl)acetyl]amino]-2-fluoro-benzamide (Compound 17);
N-tert-Butyl-3-[[2-(5-chloro-2-hydroxy-phenyl)acetyl]amino]-5-fluoro-benzamide (Compound 18);
N-tert-Butyl-4-[[2-(3-hydroxy-2-pyridyl)acetyl]amino]pyridine-2-carboxamide (Compound 19);
N-tert-Butyl-4-[[2-(5-fluoro-2-hydroxy-phenyl)acetyl]amino]pyridine-2-carboxamide (Compound 20);
N-tert-Butyl-4-[[(1R) or (1S)-indane-1-carbonyl]amino]pyridine-2-carboxamide (Compound 21a);
N-tert-Butyl-4-[[(1R) or (1S)-indane-1-carbonyl]amino]pyridine-2-carboxamide (Compound 21b);
N-tert-Butyl-4-[(2-phenylacetyl)amino]pyridine-2-carboxamide (Compound 22);
4-(3,3-Dimethylbutanoylamino)-N-(1,1-dimethylprop-2-ynyl)pyridine-2-carboxamide (Compound 22.1);
4-[(2-Cyclopentylacetyl)amino]-N-(1,1-dimethylprop-2-ynyl)pyridine-2-carboxamide (Compound 22.2);
4-[[2-(3-Chloro-4-pyridyl)acetyl]amino]-N-(1,1-dimethylprop-2-ynyl)pyridine-2-carboxamide (Compound 22.3);
4-[[2-(4-Chlorophenyl)acetyl]amino]-N-(1-cyanocyclopropyl)pyridine-2-carboxamide (Compound 23);
4-[[2-(3-Chlorophenyl)acetyl]amino]-N-(1-cyanocyclo propyl)pyridine-2-carboxamide (Compound 23.1);
4-[[2-(2-Chloro-5-fluoro-phenyl) acetyl]amino]-N-(1-cyanocyclo propyl)pyridine-2-carboxamide (Compound 23.2);
N-tert-Butyl-4-(indane-2-carbonyl amino)pyridine-2-carboxamide (Compound 23.3);
N-tert-Butyl-4-[[2-[2-(difluoromethoxy)phenyl]acetyl]amino]pyridine-2-carboxamide (Compound 23.4);
N-tert-Butyl-4-[[2-[2-(difluoromethyl)phenyl]acetyl]amino]pyridine-2-carboxamide (Compound 23.5);
N-tert-Butyl-4-[[2-(3,4-difluorophenyl) acetyl]amino]pyridine-2-carboxamide (Compound 23.6);
N-tert-Butyl-4-[[2-(3,5-difluorophenyl) acetyl]amino]pyridine-2-carboxamide (Compound 23.7);
N-tert-Butyl-4-[[2-(2,3-difluorophenyl) acetyl]amino]pyridine-2-carboxamide (Compound 23.8);
4-[[2-(2-Chlorophenyl)acetyl]amino]-N-tetrahydropyran-4-yl-pyridine-2-carboxamide (Compound 23.9);
N-(1-Cyanocyclobutyl)-4-[[2-(6-quinolyl) acetyl]amino]pyridine-2-carboxamide (Compound 23.11);
N-tert-Butyl-4-[[2-[2-(trifluoromethyl)phenyl]acetyl]amino]pyridine-2-carboxamide (Compound 23.12);
4-[[2-(2-Bromophenyl)acetyl]amino]-N-tert-butyl-pyridine-2-carboxamide (Compound 23.13);
N-tert-Butyl-4-[[2-(2-cyanophenyl) acetyl]amino]pyridine-2-carboxamide (Compound 23.14);
4-[[2-(2-Chlorophenyl)acetyl]amino]-N-(4-cyanotetrahydropyran-4-yl)pyridine-2-carboxamide (Compound 23.15);
N-(4-Cyanotetrahydropyran-4-yl)-4-[[2-(6-quinolyl)acetyl]amino]pyridine-2-carboxamide (Compound 23.16);
4-[[2-(2-Chloro-5-methoxy-phenyl)acetyl]amino]-N-(1-cyanocyclopropyl)pyridine-2-carboxamide (Compound 24);
N-(3-Bicyclo[1.1.1]pentanyl)-4-[[2-(5-tert-butyl-2-hydroxy-phenyl)acetyl]amino]pyridine-2-carboxamide (Compound 25);
-[[2-(5-tert-Butyl-2-hydroxy-phenyl)acetyl]amino]-N-(4-cyanotetrahydropyran-4-yl)pyridine-2-carboxamide (Compound 25.1);
N-tert-Butyl-4-[[2-(2-hydroxy-5-phenyl-phenyl)acetyl]amino]pyridine-2-carboxamide (Compound 26);
N-tert-Butyl-4-[[2-[5-chloro-2-hydroxy-4-(pyrrolidin-1-ylmethyl)phenyl]acetyl]amino]pyridine-2-carboxamide (Compound 27);
N-tert-Butyl-4-[[2-[4-[(tert-butylamino)methyl]-5-chloro-2-hydroxy-phenyl]acetyl]amino]pyridine-2-carboxamide (Compound 27.1);

N-tert-Butyl-4-[[2-[5-chloro-2-hydroxy-4-(morpholinomethyl)phenyl]acetyl]amino]pyridine-2-carboxamide (Compound 27.2);

N-tert-Butyl-4-[[2-[5-chloro-4-[(3,3-difluoropyrrolidin-1-yl)methyl]-2-hydroxy-phenyl]acetyl]amino]pyridine-2-carboxamide (Compound 27.3);

N-tert-butyl-4-[[2-(5-chloro-2-hydroxy-phenyl)acetyl]amino]-5-fluoro-pyridine-2-carboxamide (Compound 28);

N-tert-Butyl-4-[[2-(5-chloro-2-hydroxy-phenyl)acetyl]amino]-3-fluoro-pyridine-2-carboxamide (Compound 28.1);

4-[[2-(2-Chlorophenyl)acetyl]amino]-N-(1-cyanocyclobutyl)pyridine-2-carboxamide (Compound 30);

4-[[2-(2-Chlorophenyl)acetyl]amino]-N-(1,1-dimethylprop-2-ynyl)pyridine-2-carboxamide (Compound 30.1);

4-[[2-(2-Chlorophenyl)acetyl]amino]-N-(4-fluoro-1-bicyclo[2.1.1]hexanyl)pyridine-2-carboxamide (Compound 30.2);

4-[[2-(2-Chlorophenyl)acetyl]amino]-N-(1-cyclopropyl-1-methyl-ethyl)pyridine-2-carboxamide (Compound 30.3);

4-[[2-(2-Chlorophenyl)acetyl]amino]-N-(1-cyano-1-methyl-ethyl)pyridine-2-carboxamide (Compound 30.3a);

4-[[2-(2-Chlorophenyl)acetyl]amino]-N-(1-methyl-3-bicyclo[1.1.1]pentanyl)pyridine-2-carboxamide (Compound 30.4);

4-[[2-(2-Chlorophenyl)acetyl]amino]-N-(1-cyano-3-bicyclo[1.1.1]pentanyl)pyridine-2-carboxamide (Compound 30.5);

4-[[2-(2-Chlorophenyl)acetyl]amino]-N-(2,2-difluorocyclopropyl)pyridine-2-carboxamide (Compound 30.6);

4-[[2-(2-Chlorophenyl)acetyl]amino]-N-(1-cyanocyclopropyl)pyridine-2-carboxamide (Compound 30.7);

4-[[2-(2-Chlorophenyl)acetyl]amino]-N-(1-methylcyclopropyl)pyridine-2-carboxamide (Compound 30.8);

4-[[2-(2-Chlorophenyl)acetyl]amino]-N-(3-fluoro-1-bicyclo[1.1.1]pentanyl)pyridine-2-carboxamide (Compound 30.9);

4-[[2-(2-Chlorophenyl)acetyl]amino]-N-(2-fluoro-1,1-dimethyl-ethyl)pyridine-2-carboxamide (Compound 30.10);

4-[[2-(2-Chlorophenyl)acetyl]amino]-N-(4-ethynyltetrahydropyran-4-yl)pyridine-2-carboxamide (Compound 30.11);

4-[[2-(2-Chlorophenyl)acetyl]amino]-N-(1-cyanocyclopentyl)pyridine-2-carboxamide (Compound 30.12);

4-[[2-(2-Chlorophenyl)acetyl]amino]-N-(2,2-difluoro-1,1-dimethyl-ethyl)pyridine-2-carboxamide (Compound 30.13);

4-[[2-(5-Chloro-2-hydroxy-phenyl)acetyl]amino]-N-(4-cyanotetrahydropyran-4-yl)pyridine-2-carboxamide (Compound 31);

4-[[2-(5-Chloro-2-hydroxy-phenyl)acetyl]amino]-N-(1-ethynylcyclopentyl)pyridine-2-carboxamide (Compound 31.2);

4-[2-(5-Chloro-2-hydroxyphenyl)acetamido]-N-[(1s,2s)-2-hydroxycyclohexyl]pyridine-2-carboxamide (Compound 31.3);

4-[[2-(5-Chloro-2-hydroxy-phenyl)acetyl]amino]-N-[(1S,2S)-2-hydroxycyclohexyl]pyridine-2-carboxamide or 4-[[2-(5-Chloro-2-hydroxy-phenyl)acetyl]amino]-N-[(1R,2R)-2-hydroxycyclohexyl]pyridine-2-carboxamide (Compound 31.3a);

4-[[2-(5-Chloro-2-hydroxy-phenyl)acetyl]amino]-N-(4-ethynyltetrahydropyran-4-yl)pyridine-2-carboxamide (Compound 31.4);

N-[(6-Amino-2-pyridyl)methyl]-4-[[2-(5-chloro-2-hydroxy-phenyl)acetyl]amino]pyridine-2-carboxamide (Compound 32);

12-[[4-[[2-(5-Chloro-2-hydroxy-phenyl)acetyl]amino]pyridine-2-carbonyl]amino]dodecanoic acid (Compound 32.1);

4-[[2-(5-Chloro-2-hydroxy-phenyl) acetyl]amino]-N-(3-pyridylmethyl)pyridine-2-carboxamide (Compound 32.2);

4-[[2-(5-Chloro-2-hydroxy-phenyl)acetyl]amino]-N-(2-pyridylmethyl)pyridine-2-carboxamide (Compound 32.3);

4-[[2-(5-Chloro-2-hydroxy-phenyl) acetyl]amino]-N-(4-pyridylmethyl)pyridine-2-carboxamide (Compound 32.4);

4-[[2-(5-Chloro-2-hydroxy-phenyl) acetyl]amino]-N-[(2-hydroxyphenyl)methyl]pyridine-2-carboxamide (Compound 32.5);

4-[[2-(5-Chloro-2-hydroxy-phenyl)acetyl]amino]-N-(1,1-dimethyl-2-morpholino-ethyl)pyridine-2-carboxamide (Compound 32.6);

4-[[2-(5-Chloro-2-hydroxy-phenyl) acetyl]amino]-N-(2-hydroxy-1,1-dimethyl-ethyl)pyridine-2-carboxamide (Compound 32.7);

4-[[2-(5-Chloro-2-hydroxy-phenyl) acetyl]amino]-N-(3,3-difluoro-4-piperidyl)pyridine-2-carboxamide (Compound 32.8);

4-[[2-(5-Chloro-2-hydroxy-phenyl) acetyl]amino]-N-(1H-imidazol-2-yl)pyridine-2-carboxamide (Compound 32.9);

4-[[2-(5-Chloro-2-hydroxy-phenyl)acetyl]amino]-N-[(1R,2R)-2-hydroxycyclopentyl]pyridine-2-carboxamide (Compound 33);

4-[[2-(5-Chloro-2-hydroxy-phenyl)acetyl]amino]-N-(1-cyano-1-methyl-ethyl)pyridine-2-carboxamide (Compound 34);

4-[[2-(5-Chloro-2-hydroxy-phenyl)acetyl]amino]-N-[3-(hydroxymethyl)tetrahydrofuran-3-yl]pyridine-2-carboxamide (Compound 35);

4-[[2-(5-Chloro-2-hydroxy-phenyl)acetyl]amino]-N-[(3R)-3-(hydroxymethyl)tetrahydro furan-3-yl]pyridine-2-carboxamide or 4-[[2-(5-chloro-2-hydroxy-phenyl)acetyl]amino]-N-[(3S)-3-(hydroxymethyl)tetrahydrofuran-3-yl]pyridine-2-carboxamide (Compound 35a);

-[[2-(5-Chloro-2-hydroxy-phenyl)acetyl]amino]-N-[(3R)-3-(hydroxymethyl)tetrahydro furan-3-yl]pyridine-2-carboxamide or 4-[[2-(5-chloro-2-hydroxy-phenyl)acetyl]amino]-N-[(3S)-3-(hydroxymethyl)tetrahydrofuran-3-yl]pyridine-2-carboxamide (Compound 35b);

4-[[2-(5-Chloro-2-hydroxy-phenyl)acetyl]amino]-N-(4-hydroxy-4-methyl-cyclohexyl)pyridine-2-carboxamide as a 6:4 mixture of stereoisomers (Compound 35.1);

4-[[2-(5-Chloro-2-hydroxy-phenyl) acetyl]amino]-N-[(1s,2r)-2-(hydroxy methyl)cyclohexyl]pyridine-2-carboxamide (Compound 35.2);

4-[[2-(5-Chloro-2-hydroxy-phenyl)acetyl]amino]-N-[(1s,3r)-3-hydroxycyclopentyl]pyridine-2-carboxamide (Compound 35.3);

4-[[2-(5-Chloro-2-hydroxy-phenyl)acetyl]amino]-N-[2-hydroxy-1-(hydroxy methyl)-1-methyl-ethyl]pyridine-2-carboxamide (Compound 35.4);

4-[[2-(5-Chloro-2-hydroxy-phenyl)acetyl]amino]-N-(3-hydroxycyclohexyl)pyridine-2-carboxamide as a mixture of stereoisomers (Compound 35.6);

4-[[2-(5-Chloro-2-hydroxy-phenyl)acetyl]amino]-N-(3-phenoxypropyl)pyridine-2-carboxamide (Compound 35.7);

4-[[2-(5-Chloro-2-hydroxy-phenyl)acetyl]amino]-N-(1-methylcyclo propyl)pyridine-2-carboxamide (Compound 35.8);

4-[[2-(5-Chloro-2-hydroxy-phenyl)acetyl]amino]-N-[1-methyl-1-(2-pyridyl)ethyl]pyridine-2-carboxamide (Compound 35.9);

4-[[2-(5-Chloro-2-hydroxy-phenyl)acetyl]amino]-N-(3-phenylpropyl)pyridine-2-carboxamide (Compound 35.10);

4-[[2-(5-Chloro-2-hydroxy-phenyl)acetyl]amino]-N-[2-hydroxy-1-(2-pyridyl)ethyl]pyridine-2-carboxamide (Compound 35.11);

4-[[2-(5-Chloro-2-hydroxy-phenyl) acetyl]amino]-N-[(5-methoxy-2-pyridyl)methyl]pyridine-2-carboxamide (Compound 35.12);

Ethyl 3-[[4-[[2-(5-chloro-2-hydroxy-phenyl) acetyl]amino]pyridine-2-carbonyl]amino]-3-methyl-butanoate (Compound 35.13);

4-[[2-(5-Chloro-2-hydroxy-phenyl) acetyl]amino]-N-(3-hydroxy-1,1-dimethyl-propyl)pyridine-2-carboxamide (Compound 35.14);

N-Benzyl-4-[[2-(5-chloro-2-hydroxy-phenyl) acetyl]amino]pyridine-2-carboxamide (Compound 35.15);

4-[[2-(5-Chloro-2-hydroxy-phenyl) acetyl]amino]-N-phenyl-pyridine-2-carboxamide (Compound 35.16);

4-[[2-(5-Chloro-2-hydroxy-phenyl)acetyl]amino]-N-[(1S,2S)-2-hydroxycyclopentyl]pyridine-2-carboxamide (Compound 35.17);

4-[[2-(5-Chloro-2-hydroxy-phenyl) acetyl]amino]-N-[(1R,2S)-2-hydroxy cyclopentyl]pyridine-2-carboxamide (Compound 35.18);

4-[[2-(5-Chloro-2-hydroxy-phenyl)acetyl]amino]-N-[(1S,2R)-2-hydroxy cyclopentyl]pyridine-2-carboxamide (Compound 35.19);

3-[[2-(5-Fluoro-2-hydroxy-phenyl)acetyl]amino]-N-(1-methylcyclohexyl)benzamide (Compound 35.20);

N-(1,1-Dimethylprop-2-ynyl)-3-[[2-(5-fluoro-2-hydroxy-phenyl)acetyl]amino]benzamide (Compound 35.21);

N-Cyclohexyl-3-[[2-(5-fluoro-2-hydroxy-phenyl)acetyl]amino]benzamide (Compound 35.22);

3-[[2-(5-Fluoro-2-hydroxy-phenyl)acetyl]amino]-N-[3-(hydroxymethyl)tetrahydrofuran-3-yl]benzamide (Compound 35.23);

4-[[2-(5-Chloro-2-hydroxy-phenyl)acetyl]amino]-N-(1-ethynylcyclohexyl)pyridine-2-carboxamide (Compound 35.24);

4-[[2-(5-Chloro-2-hydroxy-phenyl)acetyl]amino]-N-[1-(hydroxymethyl)cyclobutyl]pyridine-2-carboxamide (Compound 35.25);

4-[[2-(5-Chloro-2-hydroxy-phenyl)acetyl]amino]-N-[3-(hydroxymethyl)oxetan-3-yl]pyridine-2-carboxamide (Compound 35.26);

4-[[2-(5-Chloro-2-hydroxy-phenyl)acetyl]amino]-N-(1-cyano-2-methoxy-1-methyl-ethyl)pyridine-2-carboxamide (Compound 35.27);

4-[[2-(5-Chloro-2-hydroxy-phenyl)acetyl]amino]-N-[(1-hydroxycyclobutyl)methyl]pyridine-2-carboxamide (Compound 35.28);

4-[[2-(5-Chloro-2-hydroxy-phenyl)acetyl]amino]-N-(1,1-dimethylprop-2-ynyl)pyridine-2-carboxamide (Compound 36);

4-[[2-(5-Chloro-2-hydroxy-phenyl)acetyl]amino]-N-(1-cyano-1,2-dimethyl-propyl)pyridine-2-carboxamide (Compound 37);

4-[[2-(5-Chloro-2-hydroxy-phenyl)acetyl]amino]-N-(1-methylcyclopentyl)pyridine-2-carboxamide (Compound 38);

N-(4-tert-Butylcyclohexyl)-4-[[2-(5-chloro-2-hydroxy-phenyl)acetyl]amino]pyridine-2-carboxamide (Compound 39);

N-tert-Butyl-4-[[2-(2-chloro-3-fluoro-phenyl)acetyl]amino]pyridine-2-carboxamide (Compound 40);

N-tert-Butyl-4-[[2-(2-chloro-5-fluoro-phenyl)acetyl]amino]pyridine-2-carboxamide (Compound 40.1);

N-(4-Cyanotetrahydropyran-4-yl)-3-[[2-(5-fluoro-2-hydroxy-phenyl)acetyl]amino]benzamide (Compound 41);

4-[[2-(5-Chloro-2-hydroxy-phenyl)acetyl]amino]-N-[4-(2-hydroxyethyl)tetrahydropyran-4-yl]pyridine-2-carboxamide (Compound 42);

4-[[2-(5-Chloro-2-hydroxy-phenyl)acetyl]amino]-N-[1,1-dimethyl-3-(2,2,2-trifluoro ethylamino)propyl]pyridine-2-carboxamide (Compound 43);

4-[[2-(5-Chloro-2-hydroxy-phenyl)acetyl]amino]-N-(4-fluoro-1-bicyclo[2.1.1]hexanyl)pyridine-2-carboxamide (Compound 44);

4-[[2-(5-Chloro-2-hydroxy-phenyl)acetyl]amino]-N-[3-(2,2-dimethylpropanoyl amino)-1,1-dimethyl-propyl]pyridine-2-carboxamide (Compound 45);

4-[[2-(5-Chloro-2-hydroxy-phenyl)acetyl]amino]-N-(1-cyano-2-hydroxy-1-methyl-ethyl)pyridine-2-carboxamide (Compound 46);

4-[[2-(5-Chloro-2-hydroxy-phenyl)acetyl]amino]-N-[(1S)-1-cyano-2-hydroxy-1-methyl-ethyl]pyridine-2-carboxamide or 4-[[2-(5-chloro-2-hydroxy-phenyl)acetyl]amino]-N-[(1R)-1-cyano-2-hydroxy-1-methyl-ethyl]pyridine-2-carboxamide (Compound 46a);

4-[[2-(5-Chloro-2-hydroxy-phenyl)acetyl]amino]-N-[(1S)-1-cyano-2-hydroxy-1-methyl-ethyl]pyridine-2-carboxamide or 4-[[2-(5-chloro-2-hydroxy-phenyl)acetyl]amino]-N-[(1R)-1-cyano-2-hydroxy-1-methyl-ethyl]pyridine-2-carboxamide (Compound 46b);

4-[[2-(5-Chloro-2-hydroxy-phenyl)acetyl]amino]-N-(3-cyanotetrahydrofuran-3-yl)pyridine-2-carboxamide (Compound 47);

Methyl 2-[4-[[4-[[2-(5-chloro-2-hydroxy-phenyl) acetyl]amino]pyridine-2-carbonyl]amino]tetrahydropyran-4-yl]acetate (Compound 47.1);

Methyl 4-[[4-[[2-(5-chloro-2-hydroxy-phenyl)acetyl]amino]pyridine-2-carbonyl]amino]tetrahydropyran-4-carboxylate (Compound 47.2);

4-[[2-(5-Chloro-2-hydroxy-phenyl)acetyl]amino]-N-(3-cyanooxetan-3-yl)pyridine-2-carboxamide (Compound 47.3);

4-[[2-(5-Fluoro-2-hydroxy-phenyl)acetyl]amino]-N-(1-methylcyclobutyl)pyridine-2-carboxamide (Compound 48);

N-(4-Cyanotetrahydropyran-4-yl)-4-[[2-(5-fluoro-2-hydroxy-phenyl)acetyl]amino]pyridine-2-carboxamide (Compound 48.1);

N-[3-(tert-Butylamino)-1,1-dimethyl-3-oxo-propyl]-4-[[2-(5-chloro-2-hydroxy-phenyl) acetyl]amino]pyridine-2-carboxamide (Compound 49);

4-[[2-(5-Chloro-2-hydroxy-phenyl)acetyl]amino]-N-[3-(methanesulfonamido)-1,1-dimethyl-propyl]pyridine-2-carboxamide (Compound 50);

N-(3-Acetamido-1,1-dimethyl-propyl)-4-[[2-(5-chloro-2-hydroxy-phenyl)acetyl]amino]pyridine-2-carboxamide (Compound 51);

4-[[2-(5-Chloro-2-hydroxy-phenyl)acetyl]amino]-N-[4-(hydroxymethyl)tetrahydro pyran-4-yl]pyridine-2-carboxamide (Compound 53);

N-tert-Butyl-4-[[2-[3-(1-hydroxyethyl)phenyl]acetyl]amino]pyridine-2-carboxamide (Compound 54);

N-tert-Butyl-5-chloro-4-[[2-(5-chloro-2-hydroxy-phenyl) acetyl]amino]pyridine-2-carboxamide (Compound 55);

N-tert-Butyl-4-[[2-[5-chloro-2-[(4-methoxyphenyl) methoxy]phenyl]acetyl]amino]pyridine-2-carboxamide (Compound 56);

N-tert-butyl-4-[[(1S) or (1R)-4-chloro-7-hydroxy-indane-1-carbonyl]amino]pyridine-2-carboxamide and Example 57b: N-tert-butyl-4-[[(1S) or (1R)-4-chloro-7-hydroxy-indane-1-carbonyl]amino]pyridine-2-carboxamide (Compound 57a);

N-tert-butyl-4-[[(1S) or (1R)-4-chloro-7-hydroxy-indane-1-carbonyl]amino]pyridine-2-carboxamide and Example 57b: N-tert-butyl-4-[[(1S) or (1R)-4-chloro-7-hydroxy-indane-1-carbonyl]amino]pyridine-2-carboxamide (Compound 57b);

N-tert-Butyl-4-[[2-(2-cyclopropylphenyl)acetyl]amino] pyridine-2-carboxamide (Compound 58);

4-[[2-(3-Bromo-5-chloro-2-hydroxy-phenyl)acetyl]amino]-N-tert-butyl-pyridine-2-carboxamide (Compound 59);

N-(4-Fluoro-1-bicyclo[2.1.1]hexanyl)-4-[[2-(2-fluorophenyl)acetyl]amino]pyridine-2-carboxamide (Compound 60);

N-(1-Cyano-2-hydroxy-1-methyl-ethyl)-4-[[2-(2-fluorophenyl)acetyl]amino]pyridine-2-carboxamide (Compound 60.1);

N-(1,1-Dimethylprop-2-ynyl)-4-[[2-(2-fluorophenyl)acetyl] amino]pyridine-2-carboxamide (Compound 60.2);

N-tert-Butyl-4-[[2-(5-chloro-2-hydroxy-3-isopropyl-phenyl)acetyl]amino]pyridine-2-carboxamide (Compound 61);

N-tert-Butyl-4-[[2-[5-chloro-2-hydroxy-3-(1-methoxyethyl) phenyl]acetyl]amino]pyridine-2-carboxamide (Compound 62);

4-[[2-(6-Quinolyl)acetyl]amino]-N-tetrahydropyran-4-yl-pyridine-2-carboxamide (Compound 63);

4-(Benzylcarbamoylamino)-N-tert-butyl-pyridine-2-carboxamide (Compound 64);

N-tert-Butyl-4-(cyclohexylmethylcarbamoyl amino)pyridine-2-carboxamide (Compound 64.1);

N-tert-Butyl-4-(2-phenylethylcarbamoyl amino)pyridine-2-carboxamide (Compound 64.2);

N-tert-Butyl-4-[[(1R)-1-phenylethyl]carbamoyl amino] pyridine-2-carboxamide (Compound 64.3);

N-tert-Butyl-4-[[(1S)-1-phenylethyl]carbamoylamino]pyridine-2-carboxamide (Compound 64.4);

N-tert-Butyl-4-[(2-chlorophenyl)methylcarbamoylamino] pyridine-2-carboxamide (Compound 64.5);

N-tert-butyl-4-(1H-indol-3-ylcarbamoyl amino)pyridine-2-carboxamide (Compound 64.6);

N-tert-Butyl-4-[(3-chlorophenyl)methyl carbamoylamino] pyridine-2-carboxamide (Compound 64.7);

N-tert-butyl-4-[(4-chlorophenyl)methyl carbamoylamino] pyridine-2-carboxamide (Compound 64.8);

N-tert-Butyl-4-[(2-hydroxyphenyl)carbamoylamino]pyridine-2-carboxamide (Compound 65);

N-tert-Butyl-4-[(2-methoxyphenyl)methylcarbamoylamino] pyridine-2-carboxamide (Compound 65.1);

N-tert-Butyl-4-[(2-hydroxyphenyl)methylcarbamoylamino] pyridine-2-carboxamide (Compound 65.2);

N-tert-Butyl-4-[(3-hydroxyphenyl)methylcarbamoylamino] pyridine-2-carboxamide (Compound 65.3);

N-tert-Butyl-4-[(4-hydroxyphenyl)methylcarbamoylamino] pyridine-2-carboxamide (Compound 65.4);

N-tert-Butyl-4-[[2-[2-hydroxy-5-(1-hydroxyethyl)phenyl] acetyl]amino]pyridine-2-carboxamide (Compound 66);

N-tert-Butyl-4-[[2-[2-hydroxy-5-[1-(2,2,2-trifluoroethylamino)ethyl]phenyl]acetyl]amino]pyridine-2-carboxamide (Compound 67);

N-tert-Butyl-4-[[2-[3-(cyanomethyl)phenyl]acetyl]amino] pyridine-2-carboxamide (Compound 68);

N-tert-Butyl-4-[[2-[3-(methoxymethyl)phenyl]acetyl] amino]pyridine-2-carboxamide (Compound 69);

N-tert-Butyl-4-[[2-[2-hydroxy-5-(morpholinomethyl)phenyl]acetyl]amino]pyridine-2-carboxamide (Compound 70);

3-[[2-(5-Chloro-2-hydroxy-phenyl)acetyl]amino]-N-(3-cyanotetrahydrofuran-3-yl)benzamide (Compound 71);

3-[[2-(5-Chloro-2-hydroxy-phenyl)acetyl]amino]-N-(1-methylcyclohexyl)benzamide (Compound 71.1);

4-[[2-(5-Fluoro-2-hydroxy-phenyl)acetyl]amino]-N-[3-(hydroxymethyl)tetrahydrofuran-3-yl]pyridine-2-carboxamide (Compound 72);

4-[[2-(5-Chloro-2-hydroxy-phenyl)acetyl]amino]-N-[1-(hydroxymethyl)-2-methoxy-1-methyl-ethyl]pyridine-2-carboxamide (Compound 73);

4-[[2-(5-Chloro-2-hydroxy-phenyl)acetyl]amino]-N-(1,1-dimethylbut-2-ynyl)pyridine-2-carboxamide (Compound 73.1);

3-[[2-(5-Chloro-2-hydroxy-phenyl)acetyl]amino]-N-(1,1-dimethylprop-2-ynyl)benzamide (Compound 74);

3-[[2-(5-Chloro-2-hydroxy-phenyl)acetyl]amino]-N-[3-(hydroxymethyl)tetra hydrofuran-3-yl]benzamide (Compound 74.1);

N-tert-Butyl-4-[[2-[2-hydroxy-5-(3-hydroxypropyl)phenyl] acetyl]amino]pyridine-2-carboxamide (Compound 75);

4-[[2-(5-Chloro-4-fluoro-2-hydroxy-phenyl)acetyl]amino]-N-(1-methylcyclo butyl)pyridine-2-carboxamide (Compound 76);

4-[[2-(2,5-Difluorophenyl)acetyl]amino]-N-(1,1-dimethylprop-2-ynyl)pyridine-2-carboxamide (Compound 77);

4-[[2-(2,5-Difluorophenyl)acetyl]amino]-N-(4-fluoro-1-bicyclo[2.1.1]hexanyl)pyridine-2-carboxamide (Compound 77.1);

4-[[2-(4-Chloro-2-hydroxy-phenyl)acetyl]amino]-N-(1,1-dimethylprop-2-ynyl)pyridine-2-carboxamide (Compound 78);

N-(1,1-Dimethylprop-2-ynyl)-4-[[2-[2-hydroxy-4-(trifluoromethyl)phenyl]acetyl]amino]pyridine-2-carboxamide (Compound 78.1);

N-(1,1-Dimethylprop-2-ynyl)-4-[[2-[2-hydroxy-5-(trifluoromethyl)phenyl]acetyl]amino]pyridine-2-carboxamide (Compound 78.2);

4-[(2-Chroman-4-ylacetyl)amino]-N-(1,1-dimethylprop-2-ynyl)pyridine-2-carboxamide (Compound 79);

N-(1,1-Dimethylprop-2-ynyl)-4-[[2-(1-isopropyl-3,5-dimethyl-pyrazol-4-yl)acetyl]amino]pyridine-2-carboxamide (Compound 79.1);

N-(1,1-Dimethylprop-2-ynyl)-4-[[2-(1H-indazol-4-yl) acetyl]amino]pyridine-2-carboxamide (Compound 79.2);

N-(1,1-Dimethylprop-2-ynyl)-4-[[2-(1H-indol-7-yl)acetyl] amino]pyridine-2-carboxamide (Compound 79.3);

3-[[2-(5-Chloro-2-hydroxy-phenyl)acetyl]amino]-N-(4-cyanotetrahydropyran-4-yl)benzamide (Compound 80);

N-(1-Cyano-1-methyl-ethyl)-4-[[2-(5-fluoro-2-hydroxy-phenyl)acetyl]amino]pyridine-2-carboxamide (Compound 81);

N-(1-Cyano-2-hydroxy-1-methyl-ethyl)-4-[[2-(5-fluoro-2-hydroxy-phenyl)acetyl]amino]pyridine-2-carboxamide (Compound 81.1);

4-[[2-(5-Fluoro-2-hydroxy-phenyl)acetyl]amino]-N-isopropyl-pyridine-2-carboxamide (Compound 81.2);

N-(1,1-Dimethylprop-2-ynyl)-4-[[2-(5-fluoro-2-hydroxy-phenyl)acetyl]amino]pyridine-2-carboxamide (Compound 81.3);
N-(4-Fluoro-1-bicyclo[2.1.1]hexanyl)-4-[[2-(5-fluoro-2-hydroxy-phenyl)acetyl]amino]pyridine-2-carboxamide (Compound 81.4);
4-[[2-(5-Fluoro-2-hydroxy-phenyl)acetyl]amino]-N-[1-(hydroxymethyl)cyclobutyl]pyridine-2-carboxamide (Compound 81.5);
N-tert-Butyl-6-[[2-(5-chloro-2-methoxy-phenyl)acetyl]amino]pyrimidine-4-carboxamide (Compound 82);
N-(1-Cyano-1-methyl-ethyl)-4-(thiophene-3-carbonylamino)pyridine-2-carboxamide (Compound 83);
N-(1-Cyano-1-methyl-ethyl)-4-[(2-cyclohexylacetyl)amino]pyridine-2-carboxamide (Compound 83.1);
N-(1-Cyano-1-methyl-ethyl)-4-(cyclohexane carbonylamino)pyridine-2-carboxamide (Compound 83.2);
N-(1-Cyano-1-methyl-ethyl)-4-[(3,3-difluorocyclo pentanecarbonyl)amino]pyridine-2-carboxamide (Compound 83.3);
N-(1-Cyano-1-methyl-ethyl)-4-[(1-methylcyclo pentanecarbonyl)amino]pyridine-2-carboxamide (Compound 83.4);
N-(1-Cyano-1-methyl-ethyl)-4-(3-cyclohexyl propanoylamino)pyridine-2-carboxamide (Compound 83.5);
4-(2-{Bicyclo[2.2.1]heptan-2-yl}acetamido)-N-(1-cyano-1-methylethyl)pyridine-2-carboxamide (Compound 83.6);
N-(1-Cyano-1-methyl-ethyl)-4-[[2-(1-methylcyclo hexyl)acetyl]amino]pyridine-2-carboxamide (Compound 83.7);
N-[2-[(1-Cyano-1-methyl-ethyl)carbamoyl]-4-pyridyl]-2-cyclopropyl-pyrimidine-5-carboxamide (Compound 83.8);
N-[2-[(1-Cyano-1-methyl-ethyl)carbamoyl]-4-pyridyl]-3-isobutyl-isoxazole-5-carboxamide (Compound 83.9);
N-(1-Cyano-1-methyl-ethyl)-4-[[2-(4,4-difluorocyclo hexyl)acetyl]amino]pyridine-2-carboxamide (Compound 83.10);
4-[(1-Benzylcyclopropanecarbonyl)amino]-N-(1-cyano-1-methyl-ethyl)pyridine-2-carboxamide (Compound 83.11);
N-(1-Cyano-1-methyl-ethyl)-4-[3-(2-methoxy-4-pyridyl)propanoylamino]pyridine-2-carboxamide (Compound 83.13);
4-[(5-tert-Butyl-2-methyl-pyrazole-3-carbonyl)amino]-N-(1-cyano-1-methyl-ethyl)pyridine-2-carboxamide (Compound 83.14);
N-(1-Cyano-1-methyl-ethyl)-4-[(2-pyrazol-1-ylbenzoyl)amino]pyridine-2-carboxamide (Compound 83.15);
N-[2-[(1-Cyano-1-methyl-ethyl)carbamoyl]-4-pyridyl]-6-(trifluoromethyl)pyridine-2-carboxamide (Compound 83.16);
N-[2-[(1-Cyano-1-methyl-ethyl)carbamoyl]-4-pyridyl]-3-oxo-4H-1,4-benzoxazine-7-carboxamide (Compound 83.17);
N-[2-[(1-Cyano-1-methyl-ethyl)carbamoyl]-4-pyridyl]-1-ethyl-indole-2-carboxamide (Compound 83.18);
N-(1-Cyano-1-methyl-ethyl)-4-[[2-(2,2,2-trifluoroethyl)pyrazole-3-carbonyl]amino]pyridine-2-carboxamide (Compound 83.19);
N-[2-[(1-Cyano-1-methyl-ethyl)carbamoyl]-4-pyridyl]-3-phenyl-isoxazole-4-carboxamide (Compound 83.20);
4-[(1-Benzylpyrazole-4-carbonyl)amino]-N-(1-cyano-1-methyl-ethyl)pyridine-2-carboxamide (Compound 83.21);
N-(1-Cyano-1-methyl-ethyl)-4-[(2-methyl-5-phenyl-pyrazole-3-carbonyl)amino]pyridine-2-carboxamide (Compound 83.22);

N-(1-Cyano-1-methyl-ethyl)-4-[[2-(3-methyl-1,2,4-oxadiazol-5-yl)benzoyl]amino]pyridine-2-carboxamide (Compound 83.23);
N-(1-Cyano-1-methyl-ethyl)-4-[(3-methyl-1-phenyl-pyrazole-4-carbonyl)amino]pyridine-2-carboxamide (Compound 83.24);
N-[2-[(1-Cyano-1-methyl-ethyl)carbamoyl]-4-pyridyl]-2-phenoxy-pyridine-3-carboxamide (Compound 83.25);
N-(1-Cyano-1-methyl-ethyl)-4-[[2,5-dimethyl-1-(2-thienylmethyl)pyrrole-3-carbonyl]amino]pyridine-2-carboxamide (Compound 83.26);
N-[2-[(1-Cyano-1-methyl-ethyl)carbamoyl]-4-pyridyl]-5-(2-methoxyphenyl)isoxazole-3-carboxamide (Compound 83.27);
N-[2-[(1-Cyano-1-methyl-ethyl)carbamoyl]-4-pyridyl]-4-methyl-2-phenyl-thiazole-5-carboxamide (Compound 83.28);
4-[(4-Acetamidobenzoyl)amino]-N-(1-cyano-1-methyl-ethyl)pyridine-2-carboxamide (Compound 83.29);
N-[2-[(1-Cyano-1-methyl-ethyl)carbamoyl]-4-pyridyl]-1,3-benzothiazole-7-carboxamide (Compound 83.30);
N-(1-Cyano-1-methyl-ethyl)-4-[3-(4-fluorophenyl)butanoylamino]pyridine-2-carboxamide (Compound 83.31);
N-[2-[(1-Cyano-1-methyl-ethyl)carbamoyl]-4-pyridyl]-1-methyl-2-oxo-quinoline-3-carboxamide (Compound 83.32);
N-tert-Butyl-3-[[2-(2-hydroxycyclohexyl)acetyl]amino]benzamide (Compound 84);
N-tert-Butyl-6-[[2-(5-chloro-2-hydroxy-phenyl)acetyl]amino]pyrimidine-4-carboxamide (Compound 85);
4-[[2-(5-Chloro-2-hydroxy-phenyl)acetyl]amino]-N-[1-cyano-2-methoxy-1-(methoxy methyl)ethyl]pyridine-2-carboxamide (Compound 86);
4-[[2-(3-Amino-4-tert-butyl-phenyl)acetyl]amino]-N-tert-butyl-pyridine-2-carboxamide (Compound 87);
4-[[2-(2-Amino-4-tert-butyl-phenyl)acetyl]amino]-N-tert-butyl-pyridine-2-carboxamide (Compound 88);
N-tert-Butyl-4-[[2-(4-tert-butyl-3-hydroxy-phenyl)acetyl]amino]pyridine-2-carboxamide (Compound 89);
N-tert-Butyl-4-[[2-(4-tert-butyl-2-hydroxy-phenyl)acetyl]amino]pyridine-2-carboxamide (Compound 90);
N-tert-Butyl-4-[[2-(4-tert-butyl-2-fluoro-5-hydroxy-phenyl)acetyl]amino]pyridine-2-carboxamide (Compound 91);
4-[[2-(4-Chloro-3-hydroxy-phenyl)acetyl]amino]-N-(4-cyanotetrahydropyran-4-yl)pyridine-2-carboxamide (Compound 92);
4-[[2-(4-Chloro-3-hydroxy-phenyl)acetyl]amino]-N-(1-cyano-1-methyl-ethyl)pyridine-2-carboxamide (Compound 92.1);
4-[[2-(4-Chloro-3-hydroxy-phenyl)acetyl]amino]-N-(1,1-dimethylprop-2-ynyl)pyridine-2-carboxamide (Compound 92.2);
4-[[2-(4-Chloro-3-hydroxy-phenyl)acetyl]amino]-N-[(1s,2s)-2-hydroxycyclopentyl]pyridine-2-carboxamide (Compound 92.3);
4-[[2-(4-tert-Butyl-3-hydroxy-phenyl)acetyl]amino]-N-[3-(hydroxymethyl)tetrahydrofuran-3-yl]pyridine-2-carboxamide (Compound 93);
4-[[2-(4-tert-Butyl-3-hydroxy-phenyl)acetyl]amino]-N-[(2S)-2-hydroxycyclohexyl]pyridine-2-carboxamide (Compound 93.1);
4-[[2-(4-tert-Butyl-3-hydroxy-phenyl)acetyl]amino]-N-[(2S)-2-hydroxycyclopentyl]pyridine-2-carboxamide (Compound 93.2);

4-[[2-(4-tert-Butyl-3-hydroxy-phenyl)acetyl]amino]-N-(4-cyanotetrahydropyran-4-yl)pyridine-2-carboxamide (Compound 93.3);
4-[[2-(4-tert-Butyl-3-hydroxy-phenyl)acetyl]amino]-N-(1-cyano-1-methyl-ethyl)pyridine-2-carboxamide (Compound 93.4);
4-[[2-(4-tert-Butyl-3-hydroxy-phenyl)acetyl]amino]-N-(1,1-dimethylprop-2-ynyl)pyridine-2-carboxamide (Compound 93.5);
4-[[2-(5-Chloro-2-hydroxy-phenyl)acetyl]amino]-N-(1-methyl-1-phenyl-ethyl)pyridine-2-carboxamide (Compound 94); and salts and solvates of any of the above.

Some compounds of general formula (I) are new and therefore in a further aspect of the present invention there is provided a compound of general formula (I) as defined above, provided that:
when $X^1$ is N and $X^2$ is $CR^8$, especially when $X^1$ is N and $X^2$ is CH, Z is —C(O)— and Y is a bond, $R^4$ is not a 5- to 10-membered heteroaryl or heterocyclic ring linked to Y via a nitrogen atom; and
when $X^1$ and $X^2$ are both $CR^8$, and especially when $X^1$ and $X^2$ are both CH, $R^4$ is phenyl having an OH at the 2- or 3-position and optionally one or more further substituents as defined above; and
when $X^1$ is $CR^8$ and $X^2$ is N, especially when $X^1$ is CH and $X^2$ is N:
when Z is —C(O)—, Y is not a bond; and
when Z is —C(O)NH— and Y is a bond, $R^4$ is not a 12-membered heteroaryl ring system; and
when $X^1$ and $X^2$ are both N and when one of $R^1$ and $R^2$ is H and the other of $R^1$ and $R^2$ is H or methyl, $R^3$ is not substituted or unsubstituted phenyl.

Suitable values for $R^1$, $R^2$, $R^3$, $R^4$, $R^5$, $X^1$, $X^2$, Y and Z are as defined above.

In some particularly suitable novel compounds of the invention, $X^1$ is N and $X^2$ is $CR^8$, especially CH.

Examples of novel compounds according to the invention are:
N-tert-Butyl-4-[[2-(2-hydroxyphenyl)acetyl]amino]pyridine-2-carboxamide (Compound 1);
N-(1,1-Dimethylpropyl)-3-[[2-(2-hydroxyphenyl)acetyl]amino]benzamide (Compound 1.1);
N-(1-Adamantyl)-3-[[2-(5-chloro-2-hydroxy-phenyl)acetyl]amino]benzamide (Compound 1.2);
N-(1-Adamantyl)-4-[[2-(5-chloro-2-hydroxy-phenyl)acetyl]amino]pyridine-2-carboxamide (Compound 1.3);
4-[[2-(5-Chloro-2-hydroxy-phenyl)acetyl]amino]-N-(3-methoxy-1,1-dimethyl-propyl)pyridine-2-carboxamide (Compound 1.4);
3-[[2-(5-Chloro-2-hydroxy-phenyl)acetyl]amino]-N-(1,1-dimethyl propyl)benzamide (Compound 1.5);
4-[[2-(5-Chloro-2-hydroxy-phenyl)acetyl]amino]-N-(1-methylcyclobutyl)pyridine-2-carboxamide (Compound 1.6);
4-[[2-(5-Chloro-2-hydroxy-phenyl)acetyl]amino]-N-(1-methylcyclohexyl)pyridine-2-carboxamide (Compound 1.7);
tert-Butyl N-[3-[[4-[[2-(5-chloro-2-hydroxy-phenyl)acetyl]amino]pyridine-2-carbonyl]amino]-3-methyl-butyl]carbamate (Compound 1.8);
3-[[2-(2-Hydroxyphenyl)acetyl]amino]-N-(2-methoxy-1,1-dimethyl-ethyl)benzamide (Compound 1.9);
4-[[2-(5-Chloro-2-hydroxy-phenyl)acetyl]amino]-N-cyclohexyl-pyridine-2-carboxamide (Compound 1.10);
N-tert-Butyl-3-[[2-(5-chloro-2-hydroxy-phenyl)acetyl]amino]benzamide (Compound 2);
N-tert-Butyl-3-[[2-(5-fluoro-2-hydroxy-phenyl)acetyl]amino]benzamide (Compound 2.1);
N-tert-Butyl-3-[[2-(3-fluoro-2-hydroxy-phenyl)acetyl]amino]benzamide (Compound 2.2);
N-tert-Butyl-3-[[2-(4-fluoro-2-hydroxy-phenyl)acetyl]amino]benzamide (Compound 2.3);
N-tert-Butyl-3-[[2-(2,6-dihydroxy phenyl)acetyl]amino]benzamide (Compound 2.4);
N-tert-Butyl-3-[3-(2-hydroxyphenyl)propanamido]benzamide (Compound 2.5);
N-tert-Butyl-3-[[2-(2-hydroxy-6-methoxy-phenyl)acetyl]amino]benzamide (Compound 2.6);
N-tert-Butyl-3-[2-(2-hydroxyphenyl)propanamido]benzamide (Compound 2.7);
N-tert-Butyl-3-[[2-(2-hydroxy-3-methoxy-phenyl)acetyl]amino]benzamide (Compound 2.8);
N-tert-Butyl-3-[[2-(3,5-difluoro-2-hydroxy-phenyl)acetyl]amino]benzamide (Compound 2.9);
3-[[2-(5-Bromo-2-hydroxy-phenyl) acetyl]amino]-N-tert-butyl-benzamide (Compound 2.10);
N-tert-Butyl-3-[[2-(2,3-difluoro-6-hydroxy-phenyl)acetyl]amino]benzamide (Compound 2.11);
N-tert-Butyl-3-[[2-(4,5-difluoro-2-hydroxy-phenyl)acetyl]amino]benzamide (Compound 2.12);
N-(1,1-Dimethylpropyl)-3-[[2-(4-fluoro-2-hydroxy-phenyl)acetyl]amino]benzamide (Compound 2.13);
N-tert-Butyl-3-[[2-(2-hydroxy-4-methoxy-phenyl)acetyl]amino]benzamide (Compound 2.14);
N-tert-Butyl-3-[[2-(2-fluoro-6-hydroxy-phenyl)acetyl]amino]benzamide (Compound 2.15);
N-tert-Butyl-3-[[2-(2,3-dihydroxyphenyl) acetyl]amino]benzamide (Compound 2.16);
N-tert-Butyl-3-[[2-[2-hydroxy-5-(trifluoro methyl)phenyl]acetyl]amino]benzamide (Compound 2.17);
Methyl 3-[2-[3-(tert-butylcarbamoyl)anilino]-2-oxo-ethyl]-4-hydroxy-benzoate (Compound 2.18);
N-tert-Butyl-3-[[2-[2-hydroxy-4-(trifluoro methyl)phenyl]acetyl]amino]benzamide (Compound 2.19);
N-tert-Butyl-4-[[2-(5-chloro-2-hydroxy-phenyl)acetyl]amino]pyridine-2-carboxamide (Compound 3);
N-(1,1-Dimethylpropyl)-4-[[2-(4-fluoro-2-hydroxy-phenyl)acetyl]amino]pyridine-2-carboxamide (Compound 3.1a);
N-tert-Butyl-4-[[2-(4-fluoro-2-hydroxy-phenyl)acetyl]amino]pyridine-2-carboxamide (Compound 3.2a);
N-tert-Butyl-4-[[2-(2-chloro-6-hydroxy-phenyl)acetyl]amino]pyridine-2-carboxamide (Compound 3.3a);
4-[[2-(4-Bromo-5-chloro-2-hydroxy-phenyl)acetyl]amino]-N-tert-butyl-pyridine-2-carboxamide (Compound 3.4a);
4-[[2-(5-tert-Butyl-2-hydroxy-phenyl)acetyl]amino]-N-(1-cyanocyclobutyl)pyridine-2-carboxamide (Compound 3.5a);
4-[[2-(5-tert-Butyl-2-hydroxy-phenyl)acetyl]amino]-N-(1-methyl cyclobutyl)pyridine-2-carboxamide (Compound 3.6a);
N-tert-butyl-4-[2-(2,5-dibromo-3-fluoro-6-hydroxyphenyl)acetamido]pyridine-2-carboxamide (Compound 3.7a);
N-tert-Butyl-4-[[2-[2-hydroxy-5-(trifluoromethyl)phenyl]acetyl]amino]pyridine-2-carboxamide (Compound 3.5b);
N-tert-Butyl-4-[[2-(4-chloro-2-hydroxy-phenyl)acetyl]amino]pyridine-2-carboxamide (Compound 3.6b);
N-tert-Butyl-4-[[2-[2-hydroxy-4-(trifluoro methyl)phenyl]acetyl]amino]pyridine-2-carboxamide (Compound 3.7b);
N-tert-Butyl-4-[[2-(2-hydroxy-5-methoxy-phenyl)acetyl]amino]pyridine-2-carboxamide (Compound 3.8b);
N-tert-Butyl-4-[(6-hydroxyindane-1-carbonyl)amino]pyridine-2-carboxamide (Compound 3.9b);

N-tert-Butyl-4-[(7-hydroxyindane-1-carbonyl)amino]pyridine-2-carboxamide (Compound 3.10b);
N-tert-Butyl-4-[[2-(2,5-dibromo-3-chloro-6-hydroxy-phenyl)acetyl]amino]pyridine-2-carboxamide (Compound 3.11b);
N-tert-Butyl-4-[[2-(3-hydroxyphenyl) acetyl]amino]pyridine-2-carboxamide (Compound 3.12b);
N-tert-Butyl-4-[[2-(2-fluoro-5-hydroxy-phenyl) acetyl]amino]pyridine-2-carboxamide (Compound 3.13b);
N-tert-Butyl-4-[[2-(4-chloro-3-hydroxy-phenyl)acetyl]amino]pyridine-2-carboxamide (Compound 3.14b);
N-tert-Butyl-4-[[2-(2-chloro-3-hydroxy-phenyl)acetyl]amino]pyridine-2-carboxamide (Compound 3.15b);
N-tert-Butyl-4-[[2-(2-chloro-5-hydroxy-phenyl) acetyl]amino]pyridine-2-carboxamide (Compound 3.16b);
N-tert-Butyl-4-[[2-(3-chloro-5-hydroxy-phenyl)acetyl]amino]pyridine-2-carboxamide (Compound 3.17b);
N-tert-Butyl-3-[[2-(3-hydroxyphenyl)acetyl]amino]benzamide (Compound 4);
N-tert-Butyl-3-[[2-(1H-indazol-3-yl)acetyl]amino]benzamide (Compound 4.1);
N-tert-Butyl-3-[[2-(5-fluoro-1H-indol-3-yl)acetyl]amino]benzamide (Compound 4.2);
N-tert-Butyl-3-[[2-(2-hydroxyphenyl)acetyl]amino]benzamide (Compound 4.3);
N-tert-Butyl-4-[[2-(2-thienyl)acetyl]amino]pyridine-2-carboxamide (Compound 5);
4-[[2-(2-Adamantyl)acetyl]amino]-N-tert-butyl-pyridine-2-carboxamide (Compound 5.1);
N-tert-Butyl-4-[[2-(4-fluoro-2-methoxy-phenyl)acetyl]amino]pyridine-2-carboxamide (Compound 5.2);
N-tert-Butyl-4-[[2-(5-chloro-2-fluoro-phenyl)acetyl]amino]pyridine-2-carboxamide (Compound 5.3);
N-tert-Butyl-4-[[2-(2-furyl)acetyl]amino]pyridine-2-carboxamide (Compound 5.4);
N-tert-Butyl-4-[[2-(3-chlorophenyl) acetyl]amino]pyridine-2-carboxamide (Compound 5.5);
N-tert-Butyl-4-[[2-(1H-indol-3-yl)acetyl]amino]pyridine-2-carboxamide (Compound 5.6);
N-tert-Butyl-4-[[2-(o-tolyl)acetyl]amino]pyridine-2-carboxamide (Compound 5.7);
N-tert-Butyl-4-[[2-(3,4-dichlorophenyl) acetyl]amino]pyridine-2-carboxamide (Compound 5.8);
N-tert-Butyl-4-[[2-(3-fluorophenyl)acetyl]amino]pyridine-2-carboxamide (Compound 5.9);
N-tert-Butyl-4-[[2-(5-chloro-2-methoxy-phenyl)acetyl]amino]pyridine-2-carboxamide (Compound 5.10);
N-tert-Butyl-4-[[2-(p-tolyl)acetyl]amino]pyridine-2-carboxamide (Compound 5.11);
N-tert-Butyl-4-[[2-(2-fluorophenyl) acetyl]amino]pyridine-2-carboxamide (Compound 5.12);
N-tert-Butyl-4-[[2-(4-fluorophenyl) acetyl]amino]pyridine-2-carboxamide (Compound 5.13);
N-tert-Butyl-4-[[2-(m-tolyl)acetyl]amino]pyridine-2-carboxamide (Compound 5.14);
4-[[2-(1,3-Benzoxazol-6-yl)acetyl]amino]-N-tert-butyl-pyridine-2-carboxamide (Compound 5.15);
N-tert-Butyl-4-[[2-(2-chloro-3-pyridyl) acetyl]amino]pyridine-2-carboxamide (Compound 5.16);
N-tert-Butyl-4-[[2-(2,6-dichlorophenyl) acetyl]amino]pyridine-2-carboxamide (Compound 5.17);
N-tert-Butyl-4-[[2-(4-chloro-3-fluoro-phenyl)acetyl]amino]pyridine-2-carboxamide (Compound 5.18);
N-tert-Butyl-4-[[2-(3,5-dichloro phenyl)acetyl]amino]pyridine-2-carboxamide (Compound 5.19);
N-tert-Butyl-4-[[2-(2-chlorophenyl) acetyl]amino]pyridine-2-carboxamide (Compound 5.20);
N-tert-Butyl-4-[[2-(3-chloro-4-hydroxy-phenyl)acetyl]amino]pyridine-2-carboxamide (Compound 5.21);
N-tert-Butyl-4-(indane-1-carbonyl amino)pyridine-2-carboxamide (Compound 5.22);
N-tert-Butyl-4-[(2-quinoxalin-6-ylacetyl]amino]pyridine-2-carboxamide (Compound 5.23);
N-tert-Butyl-4-[[2-(2-naphthyl) acetyl]amino]pyridine-2-carboxamide (Compound 5.24);
N-tert-Butyl-4-(2,3-dihydrobenzofuran-3-carbonylamino) pyridine-2-carboxamide (Compound 5.25);
N-tert-Butyl-4-(6,7,8,9-tetrahydro-5H-benzo[7]annulene-5-carbonylamino)pyridine-2-carboxamide (Compound 5.26);
N-tert-Butyl-4-(tetralin-1-carbonylamino)pyridine-2-carboxamide (Compound 5.27);
N-tert-Butyl-4-[[2-(6-quinolyl)acetyl]amino]pyridine-2-carboxamide (Compound 5.29);
N-tert-butyl-4-[[1-(3-chlorophenyl)cyclopropanecarbonyl]amino]pyridine-2-carboxamide (Compound 5.31);
N-tert-Butyl-4-[[2-(2,3-dihydro-1,4-benzodioxin-6-yl) acetyl]amino]pyridine-2-carboxamide (Compound 5.32);
N-(1,1-Dimethylprop-2-ynyl)-4-[(2-isochroman-1-ylacetyl) amino]pyridine-2-carboxamide (Compound 5.33);
4-[[2-(4,4-Difluorocyclohexyl)acetyl]amino]-N-(1,1-dimethylprop-2-ynyl)pyridine-2-carboxamide (Compound 5.34);
N-(1,1-Dimethylprop-2-ynyl)-4-[[2-[4-(trifluoromethyl) phenyl]acetyl]amino]pyridine-2-carboxamide (Compound 5.35);
N-(1,1-Dimethylprop-2-ynyl)-4-[[2-[3-(trifluoromethyl)-1H-pyrazol-4-yl]acetyl]amino]pyridine-2-carboxamide (Compound 5.36);
N-(1,1-Dimethylprop-2-ynyl)-4-[[2-[3-(trifluoromethyl) phenyl]acetyl]amino]pyridine-2-carboxamide (Compound 5.37);
N-(1,1-Dimethylprop-2-ynyl)-4-[[2-[2-(trifluoromethyl) phenyl]acetyl]amino]pyridine-2-carboxamide (Compound 5.38);
4-[[2-(2,3-Dihydro-1,4-benzoxazin-4-yl)acetyl]amino]-N-(1,1-dimethylprop-2-ynyl)pyridine-2-carboxamide (Compound 5.39);
N-tert-Butyl-4-[[2-(5-cyano-2-hydroxy-phenyl)acetyl]amino]pyridine-2-carboxamide (Compound 6);
3-[[2-(5-Chloro-2-hydroxy-phenyl)acetyl]amino]-N-(1,1,2,2-tetramethylpropyl)benzamide (Compound 7);
3-[[2-(5-Chloro-2-hydroxy-phenyl)acetyl]amino]-N-(1,1-dimethylbutyl)benzamide (Compound 7.1);
4-[[2-(5-Chloro-2-hydroxy-phenyl)acetyl]amino]-N-(1,1-dimethylbutyl)pyridine-2-carboxamide (Compound 7.2);
3-[[2-(5-Chloro-2-hydroxy-phenyl)acetyl]amino]-N-cyclohexyl-benzamide (Compound 7.3);
3-[[2-(5-Chloro-2-hydroxy-phenyl)acetyl]amino]-N-tetrahydropyran-4-yl-benzamide (Compound 7.4);
3-[[2-(5-Chloro-2-hydroxy-phenyl)acetyl]amino]-N-(1,1,2-trimethylpropyl)benzamide (Compound 7.5);
4-[[2-(5-Chloro-2-hydroxy-phenyl)acetyl]amino]-N-(1,1,2-trimethylpropyl)pyridine-2-carboxamide (Compound 7.6);
4-[[2-(5-Chloro-2-hydroxy-phenyl)acetyl]amino]-N-isopropyl-pyridine-2-carboxamide (Compound 7.7);
3-[[2-(5-Chloro-2-hydroxy-phenyl)acetyl]amino]-N-(4-methyltetrahydropyran-4-yl)benzamide (Compound 7.8);
4-[[2-(5-Chloro-2-hydroxy-phenyl)acetyl]amino]-N-(4-methyltetrahydropyran-4-yl)pyridine-2-carboxamide (Compound 7.9);
3-[[2-(5-Chloro-2-hydroxy-phenyl)acetyl]amino]-N-(1-methylcyclobutyl)benzamide (Compound 7.10);

4-[[2-(5-Chloro-2-hydroxy-phenyl)acetyl]amino]-N-tetrahydropyran-4-yl-pyridine-2-carboxamide (Compound 7.11);

4-[2-(5-Chloro-2-hydroxyphenyl)acetamido]-N-[(1s,4s)-4-hydroxycyclohexyl]pyridine-2-carboxamide (Compound 7.12);

4-[[2-(5-Chloro-2-hydroxy-phenyl)acetyl]amino]-N-sec-butyl-pyridine-2-carboxamide (Compound 7.13);

4-[[2-(5-Chloro-2-hydroxy-phenyl)acetyl]amino]-N-(2-hydroxy-1,1,2-trimethyl-propyl)pyridine-2-carboxamide (Compound 7.14);

N-(3-Bicyclo[1.1.1]pentanyl)-4-[[2-(5-chloro-2-hydroxyphenyl)acetyl]amino]pyridine-2-carboxamide (Compound 7.15);

4-[[2-(5-Chloro-2-hydroxy-phenyl)acetyl]amino]-N-(1-cyanocyclobutyl)pyridine-2-carboxamide (Compound 7.16);

tert-Butyl-3-[[3-[[2-(5-chloro-2-hydroxy-phenyl)acetyl]amino]benzoyl]amino]piperidine-1-carboxylate (Compound 8);

tert-Butyl-3-[[4-[[2-(5-chloro-2-hydroxy-phenyl)acetyl]amino]pyridine-2-carbonyl]amino]piperidine-1-carboxylate (Compound 8.1);

tert-Butyl 4-[[3-[[2-(5-chloro-2-hydroxy-phenyl) acetyl]amino]benzoyl]amino]-4-methyl-piperidine-1-carboxylate (Compound 8.2);

tert-Butyl (1r,5s,6s)-6-{4-[2-(5-chloro-2-hydroxyphenyl)acetamido]pyridine-2-amido}-3-azabicyclo[3.1.0]hexane-3-carboxylate (Compound 8.3);

N-tert-Butyl-3-[[2-(5-chloro-2-hydroxy-phenyl)acetyl]amino]-4-fluoro-benzamide (Compound 9);

N-tert-Butyl-3-[[2-(5-chloro-2-hydroxy-phenyl)acetyl]amino]-5-methyl-benzamide (Compound 9.1);

4-[[2-(5-Chloro-2-hydroxy-phenyl)acetyl]amino]-N-(1,1-dimethylpropyl)pyridine-2-carboxamide (Compound 9.2);

N-tert-Butyl-4-[[2-(5-tert-butyl-2-hydroxy-phenyl)acetyl]amino]pyridine-2-carboxamide (Compound 10);

N-tert-Butyl-5-[[2-(5-chloro-2-hydroxy-phenyl)acetyl]amino]-2-hydroxy-benzamide (Compound 11);

N-tert-Butyl-3-[[2-(5-cyano-2-hydroxy-phenyl)acetyl]amino]benzamide (Compound 12);

Methyl 3-[2-[[2-(tert-butylcarbamoyl)-4-pyridyl]amino]-2-oxo-ethyl]-4-hydroxy-benzoate (Compound 13);

N-tert-Butyl-3-[[2-(5-chloro-2-hydroxy-phenyl)acetyl]amino]-4-hydroxy-benzamide (Compound 14);

N-tert-Butyl-4-[[2-(2-hydroxy-5-methyl-phenyl)acetyl]amino]pyridine-2-carboxamide (Compound 15);

N-tert-Butyl-3-[[2-(5-chloro-2-hydroxy-phenyl)acetyl]amino]-4-methoxy-benzamide (Compound 16);

N-tert-Butyl-5-[[2-(5-chloro-2-hydroxy-phenyl)acetyl]amino]-2-fluoro-benzamide (Compound 17);

N-tert-Butyl-3-[[2-(5-chloro-2-hydroxy-phenyl)acetyl]amino]-5-fluoro-benzamide (Compound 18);

N-tert-Butyl-4-[[2-(3-hydroxy-2-pyridyl)acetyl]amino]pyridine-2-carboxamide (Compound 19);

N-tert-Butyl-4-[[2-(5-fluoro-2-hydroxy-phenyl)acetyl]amino]pyridine-2-carboxamide (Compound 20);

N-tert-Butyl-4-[[(1R) or (1S)-indane-1-carbonyl]amino]pyridine-2-carboxamide (Compound 21a);

N-tert-Butyl-4-[[(1R) or (1S)-indane-1-carbonyl]amino]pyridine-2-carboxamide (Compound 21b);

N-tert-Butyl-4-[(2-phenylacetyl)amino]pyridine-2-carboxamide (Compound 22);

4-(3,3-Dimethylbutanoylamino)-N-(1,1-dimethylprop-2-ynyl)pyridine-2-carboxamide (Compound 22.1);

4-[(2-Cyclopentylacetyl)amino]-N-(1,1-dimethylprop-2-ynyl)pyridine-2-carboxamide (Compound 22.2);

4-[[2-(3-Chloro-4-pyridyl)acetyl]amino]-N-(1,1-dimethylprop-2-ynyl)pyridine-2-carboxamide (Compound 22.3);

4-[[2-(4-Chlorophenyl)acetyl]amino]-N-(1-cyanocyclopropyl)pyridine-2-carboxamide (Compound 23);

4-[[2-(3-Chlorophenyl)acetyl]amino]-N-(1-cyanocyclo propyl)pyridine-2-carboxamide (Compound 23.1);

4-[[2-(2-Chloro-5-fluoro-phenyl) acetyl]amino]-N-(1-cyanocyclo propyl)pyridine-2-carboxamide (Compound 23.2);

N-tert-Butyl-4-(indane-2-carbonyl amino)pyridine-2-carboxamide (Compound 23.3);

N-tert-Butyl-4-[[2-[2-(difluoromethoxy)phenyl]acetyl]amino]pyridine-2-carboxamide (Compound 23.4);

N-tert-Butyl-4-[[2-[2-(difluoromethyl)phenyl]acetyl]amino]pyridine-2-carboxamide (Compound 23.5);

N-tert-Butyl-4-[[2-(3,4-difluorophenyl) acetyl]amino]pyridine-2-carboxamide (Compound 23.6);

N-tert-Butyl-4-[[2-(3,5-difluorophenyl) acetyl]amino]pyridine-2-carboxamide (Compound 23.7);

N-tert-Butyl-4-[[2-(2,3-difluorophenyl) acetyl]amino]pyridine-2-carboxamide (Compound 23.8);

4-[[2-(2-Chlorophenyl)acetyl]amino]-N-tetrahydropyran-4-yl-pyridine-2-carboxamide (Compound 23.9);

N-(1-Cyanocyclobutyl)-4-[[2-(6-quinolyl) acetyl]amino] pyridine-2-carboxamide (Compound 23.11);

N-tert-Butyl-4-[[2-[2-(trifluoromethyl)phenyl]acetyl]amino]pyridine-2-carboxamide (Compound 23.12);

4-[[2-(2-Bromophenyl)acetyl]amino]-N-tert-butyl-pyridine-2-carboxamide (Compound 23.13);

N-tert-Butyl-4-[[2-(2-cyanophenyl) acetyl]amino]pyridine-2-carboxamide (Compound 23.14);

4-[[2-(2-Chlorophenyl)acetyl]amino]-N-(4-cyanotetrahydropyran-4-yl)pyridine-2-carboxamide (Compound 23.15);

N-(4-Cyanotetrahydropyran-4-yl)-4-[[2-(6-quinolyl)acetyl]amino]pyridine-2-carboxamide (Compound 23.16);

4-[[2-(2-Chloro-5-methoxy-phenyl)acetyl]amino]-N-(1-cyanocyclopropyl)pyridine-2-carboxamide (Compound 24);

N-(3-Bicyclo[1.1.1]pentanyl)-4-[[2-(5-tert-butyl-2-hydroxy-phenyl)acetyl]amino]pyridine-2-carboxamide (Compound 25);

-[[2-(5-tert-Butyl-2-hydroxy-phenyl)acetyl]amino]-N-(4-cyanotetrahydropyran-4-yl)pyridine-2-carboxamide (Compound 25.1);

N-tert-Butyl-4-[[2-(2-hydroxy-5-phenyl-phenyl)acetyl]amino]pyridine-2-carboxamide (Compound 26);

N-tert-Butyl-4-[[2-[5-chloro-2-hydroxy-4-(pyrrolidin-1-ylmethyl)phenyl]acetyl]amino]pyridine-2-carboxamide (Compound 27);

N-tert-Butyl-4-[[2-[4-[(tert-butylamino)methyl]-5-chloro-2-hydroxy-phenyl]acetyl]amino]pyridine-2-carboxamide (Compound 27.1);

N-tert-Butyl-4-[[2-[5-chloro-2-hydroxy-4-(morpholinomethyl)phenyl]acetyl]amino]pyridine-2-carboxamide (Compound 27.2);

N-tert-Butyl-4-[[2-[5-chloro-4-[(3,3-difluoropyrrolidin-1-yl)methyl]-2-hydroxy-phenyl]acetyl]amino]pyridine-2-carboxamide (Compound 27.3);

N-tert-butyl-4-[[2-(5-chloro-2-hydroxy-phenyl)acetyl]amino]-5-fluoro-pyridine-2-carboxamide (Compound 28);

N-tert-Butyl-4-[[2-(5-chloro-2-hydroxy-phenyl)acetyl]amino]-3-fluoro-pyridine-2-carboxamide (Compound 28.1);

4-[[2-(2-Chlorophenyl)acetyl]amino]-N-(1-cyanocyclobutyl)pyridine-2-carboxamide (Compound 30);

4-[[2-(2-Chlorophenyl)acetyl]amino]-N-(1,1-dimethylprop-2-ynyl)pyridine-2-carboxamide (Compound 30.1);
4-[[2-(2-Chlorophenyl)acetyl]amino]-N-(4-fluoro-1-bicyclo[2.1.1]hexanyl)pyridine-2-carboxamide (Compound 30.2);
4-[[2-(2-Chlorophenyl)acetyl]amino]-N-(1-cyclopropyl-1-methyl-ethyl)pyridine-2-carboxamide (Compound 30.3);
4-[[2-(2-Chlorophenyl)acetyl]amino]-N-(1-cyano-1-methyl-ethyl)pyridine-2-carboxamide (Compound 30.3a);
4-[[2-(2-Chlorophenyl)acetyl]amino]-N-(1-methyl-3-bicyclo[1.1.1]pentanyl)pyridine-2-carboxamide (Compound 30.4);
4-[[2-(2-Chlorophenyl)acetyl]amino]-N-(1-cyano-3-bicyclo[1.1.1]pentanyl)pyridine-2-carboxamide (Compound 30.5);
4-[[2-(2-Chlorophenyl)acetyl]amino]-N-(2,2-difluorocyclopropyl)pyridine-2-carboxamide (Compound 30.6);
4-[[2-(2-Chlorophenyl)acetyl]amino]-N-(1-cyanocyclopropyl)pyridine-2-carboxamide (Compound 30.7);
4-[[2-(2-Chlorophenyl)acetyl]amino]-N-(1-methylcyclopropyl)pyridine-2-carboxamide (Compound 30.8);
4-[[2-(2-Chlorophenyl)acetyl]amino]-N-(3-fluoro-1-bicyclo[1.1.1]pentanyl)pyridine-2-carboxamide (Compound 30.9);
4-[[2-(2-Chlorophenyl)acetyl]amino]-N-(2-fluoro-1,1-dimethyl-ethyl)pyridine-2-carboxamide (Compound 30.10);
4-[[2-(2-Chlorophenyl)acetyl]amino]-N-(4-ethynyltetrahydropyran-4-yl)pyridine-2-carboxamide (Compound 30.11);
4-[[2-(2-Chlorophenyl)acetyl]amino]-N-(1-cyanocyclopentyl)pyridine-2-carboxamide (Compound 30.12);
4-[[2-(2-Chlorophenyl)acetyl]amino]-N-(2,2-difluoro-1,1-dimethyl-ethyl)pyridine-2-carboxamide (Compound 30.13);
4-[[2-(5-Chloro-2-hydroxy-phenyl)acetyl]amino]-N-(4-cyanotetrahydropyran-4-yl)pyridine-2-carboxamide (Compound 31);
4-[[2-(5-Chloro-2-hydroxy-phenyl)acetyl]amino]-N-(1-ethynylcyclopentyl)pyridine-2-carboxamide (Compound 31.2);
4-[2-(5-Chloro-2-hydroxyphenyl)acetamido]-N-[(1s,2s)-2-hydroxycyclohexyl]pyridine-2-carboxamide (Compound 31.3);
4-[[2-(5-Chloro-2-hydroxy-phenyl)acetyl]amino]-N-[(1S,2S)-2-hydroxycyclo hexyl]pyridine-2-carboxamide or 4-[[2-(5-Chloro-2-hydroxy-phenyl)acetyl]amino]-N-[(1R,2R)-2-hydroxycyclohexyl]pyridine-2-carboxamide (Compound 31.3a);
4-[[2-(5-Chloro-2-hydroxy-phenyl)acetyl]amino]-N-(4-ethynyltetrahydropyran-4-yl)pyridine-2-carboxamide (Compound 31.4);
N-[(6-Amino-2-pyridyl)methyl]-4-[[2-(5-chloro-2-hydroxy-phenyl)acetyl]amino]pyridine-2-carboxamide (Compound 32);
12-[[4-[[2-(5-Chloro-2-hydroxy-phenyl)acetyl]amino]pyridine-2-carbonyl]amino]dodecanoic acid (Compound 32.1);
4-[[2-(5-Chloro-2-hydroxy-phenyl) acetyl]amino]-N-(3-pyridylmethyl)pyridine-2-carboxamide (Compound 32.2);
4-[[2-(5-Chloro-2-hydroxy-phenyl)acetyl]amino]-N-(2-pyridylmethyl)pyridine-2-carboxamide (Compound 32.3);
4-[[2-(5-Chloro-2-hydroxy-phenyl) acetyl]amino]-N-(4-pyridylmethyl)pyridine-2-carboxamide (Compound 32.4);
4-[[2-(5-Chloro-2-hydroxy-phenyl) acetyl]amino]-N-[(2-hydroxyphenyl)methyl]pyridine-2-carboxamide (Compound 32.5);
4-[[2-(5-Chloro-2-hydroxy-phenyl)acetyl]amino]-N-(1,1-dimethyl-2-morpholino-ethyl)pyridine-2-carboxamide (Compound 32.6);
4-[[2-(5-Chloro-2-hydroxy-phenyl) acetyl]amino]-N-(2-hydroxy-1,1-dimethyl-ethyl)pyridine-2-carboxamide (Compound 32.7);
4-[[2-(5-Chloro-2-hydroxy-phenyl) acetyl]amino]-N-(3,3-difluoro-4-piperidyl)pyridine-2-carboxamide (Compound 32.8);
4-[[2-(5-Chloro-2-hydroxy-phenyl) acetyl]amino]-N-(1H-imidazol-2-yl)pyridine-2-carboxamide (Compound 32.9);
4-[[2-(5-Chloro-2-hydroxy-phenyl)acetyl]amino]-N-[(1R,2R)-2-hydroxycyclopentyl]pyridine-2-carboxamide (Compound 33);
4-[[2-(5-Chloro-2-hydroxy-phenyl)acetyl]amino]-N-(1-cyano-1-methyl-ethyl)pyridine-2-carboxamide (Compound 34);
4-[[2-(5-Chloro-2-hydroxy-phenyl)acetyl]amino]-N-[3-(hydroxymethyl)tetrahydrofuran-3-yl]pyridine-2-carboxamide (Compound 35);
4-[[2-(5-Chloro-2-hydroxy-phenyl)acetyl]amino]-N-[(3R)-3-(hydroxymethyl)tetrahydro furan-3-yl]pyridine-2-carboxamide or 4-[[2-(5-chloro-2-hydroxy-phenyl)acetyl]amino]-N-[(3S)-3-(hydroxymethyl)tetrahydrofuran-3-yl]pyridine-2-carboxamide (Compound 35a);
-[[2-(5-Chloro-2-hydroxy-phenyl)acetyl]amino]-N-[(3R)-3-(hydroxymethyl)tetrahydro furan-3-yl]pyridine-2-carboxamide or 4-[[2-(5-chloro-2-hydroxy-phenyl)acetyl]amino]-N-[(3S)-3-(hydroxymethyl)tetrahydrofuran-3-yl]pyridine-2-carboxamide (Compound 35b);
4-[[2-(5-Chloro-2-hydroxy-phenyl)acetyl]amino]-N-(4-hydroxy-4-methyl-cyclohexyl)pyridine-2-carboxamide as a 6:4 mixture of stereoisomers (Compound 35.1);
4-[[2-(5-Chloro-2-hydroxy-phenyl) acetyl]amino]-N-[(1s,2r)-2-(hydroxy methyl)cyclohexyl]pyridine-2-carboxamide (Compound 35.2);
4-[[2-(5-Chloro-2-hydroxy-phenyl)acetyl]amino]-N-[(1s,3r)-3-hydroxycyclopentyl]pyridine-2-carboxamide (Compound 35.3);
4-[[2-(5-Chloro-2-hydroxy-phenyl)acetyl]amino]-N-[2-hydroxy-1-(hydroxy methyl)-1-methyl-ethyl]pyridine-2-carboxamide (Compound 35.4);
4-[[2-(5-Chloro-2-hydroxy-phenyl)acetyl]amino]-N-(3-hydroxycyclohexyl)pyridine-2-carboxamide as a mixture of stereoisomers (Compound 35.6);
4-[[2-(5-Chloro-2-hydroxy-phenyl)acetyl]amino]-N-(3-phenoxypropyl)pyridine-2-carboxamide (Compound 35.7);
4-[[2-(5-Chloro-2-hydroxy-phenyl)acetyl]amino]-N-(1-methylcyclo propyl)pyridine-2-carboxamide (Compound 35.8);
4-[[2-(5-Chloro-2-hydroxy-phenyl)acetyl]amino]-N-[1-methyl-1-(2-pyridyl)ethyl]pyridine-2-carboxamide (Compound 35.9);
4-[[2-(5-Chloro-2-hydroxy-phenyl)acetyl]amino]-N-(3-phenylpropyl)pyridine-2-carboxamide (Compound 35.10);
4-[[2-(5-Chloro-2-hydroxy-phenyl)acetyl]amino]-N-[2-hydroxy-1-(2-pyridyl)ethyl]pyridine-2-carboxamide (Compound 35.11);
4-[[2-(5-Chloro-2-hydroxy-phenyl) acetyl]amino]-N-[(5-methoxy-2-pyridyl)methyl]pyridine-2-carboxamide (Compound 35.12);

Ethyl 3-[[4-[[2-(5-chloro-2-hydroxy-phenyl) acetyl]amino]pyridine-2-carbonyl]amino]-3-methyl-butanoate (Compound 35.13);

4-[[2-(5-Chloro-2-hydroxy-phenyl) acetyl]amino]-N-(3-hydroxy-1,1-dimethyl-propyl)pyridine-2-carboxamide (Compound 35.14);

N-Benzyl-4-[[2-(5-chloro-2-hydroxy-phenyl) acetyl]amino] pyridine-2-carboxamide (Compound 35.15);

4-[[2-(5-Chloro-2-hydroxy-phenyl) acetyl]amino]-N-phenyl-pyridine-2-carboxamide (Compound 35.16);

4-[[2-(5-Chloro-2-hydroxy-phenyl)acetyl]amino]-N-[(1S,2S)-2-hydroxycyclopentyl]pyridine-2-carboxamide (Compound 35.17);

4-[[2-(5-Chloro-2-hydroxy-phenyl) acetyl]amino]-N-[(1R,2S)-2-hydroxy cyclopentyl]pyridine-2-carboxamide (Compound 35.18);

4-[[2-(5-Chloro-2-hydroxy-phenyl)acetyl]amino]-N-[(1S,2R)-2-hydroxy cyclopentyl]pyridine-2-carboxamide (Compound 35.19);

3-[[2-(5-Fluoro-2-hydroxy-phenyl)acetyl]amino]-N-(1-methylcyclohexyl)benzamide (Compound 35.20);

N-(1,1-Dimethylprop-2-ynyl)-3-[[2-(5-fluoro-2-hydroxyphenyl)acetyl]amino]benzamide (Compound 35.21);

N-Cyclohexyl-3-[[2-(5-fluoro-2-hydroxy-phenyl)acetyl] amino]benzamide (Compound 35.22);

3-[[2-(5-Fluoro-2-hydroxy-phenyl)acetyl]amino]-N-[3-(hydroxymethyl)tetrahydrofuran-3-yl]benzamide (Compound 35.23);

4-[[2-(5-Chloro-2-hydroxy-phenyl)acetyl]amino]-N-(1-ethynylcyclohexyl)pyridine-2-carboxamide (Compound 35.24);

4-[[2-(5-Chloro-2-hydroxy-phenyl)acetyl]amino]-N-[1-(hydroxymethyl)cyclobutyl]pyridine-2-carboxamide (Compound 35.25);

4-[[2-(5-Chloro-2-hydroxy-phenyl)acetyl]amino]-N-[3-(hydroxymethyl)oxetan-3-yl]pyridine-2-carboxamide (Compound 35.26);

4-[[2-(5-Chloro-2-hydroxy-phenyl)acetyl]amino]-N-(1-cyano-2-methoxy-1-methyl-ethyl)pyridine-2-carboxamide (Compound 35.27);

4-[[2-(5-Chloro-2-hydroxy-phenyl)acetyl]amino]-N-[(1-hydroxycyclobutyl)methyl]pyridine-2-carboxamide (Compound 35.28);

4-[[2-(5-Chloro-2-hydroxy-phenyl)acetyl]amino]-N-(1,1-dimethylprop-2-ynyl)pyridine-2-carboxamide (Compound 36);

4-[[2-(5-Chloro-2-hydroxy-phenyl)acetyl]amino]-N-(1-cyano-1,2-dimethyl-propyl)pyridine-2-carboxamide (Compound 37);

4-[[2-(5-Chloro-2-hydroxy-phenyl)acetyl]amino]-N-(1-methylcyclopentyl)pyridine-2-carboxamide (Compound 38);

N-(4-tert-Butylcyclohexyl)-4-[[2-(5-chloro-2-hydroxy-phenyl)acetyl]amino]pyridine-2-carboxamide (Compound 39);

N-tert-Butyl-4-[[2-(2-chloro-3-fluoro-phenyl)acetyl]amino] pyridine-2-carboxamide (Compound 40);

N-tert-Butyl-4-[[2-(2-chloro-5-fluoro-phenyl)acetyl]amino] pyridine-2-carboxamide (Compound 40.1);

N-(4-Cyanotetrahydropyran-4-yl)-3-[[2-(5-fluoro-2-hydroxy-phenyl)acetyl]amino]benzamide (Compound 41);

4-[[2-(5-Chloro-2-hydroxy-phenyl)acetyl]amino]-N-[4-(2-hydroxyethyl)tetrahydropyran-4-yl]pyridine-2-carboxamide (Compound 42);

4-[[2-(5-Chloro-2-hydroxy-phenyl)acetyl]amino]-N-[1,1-dimethyl-3-(2,2,2-trifluoro ethylamino)propyl]pyridine-2-carboxamide (Compound 43);

4-[[2-(5-Chloro-2-hydroxy-phenyl)acetyl]amino]-N-(4-fluoro-1-bicyclo[2.1.1]hexanyl)pyridine-2-carboxamide (Compound 44);

4-[[2-(5-Chloro-2-hydroxy-phenyl)acetyl]amino]-N-[3-(2,2-dimethylpropanoyl amino)-1,1-dimethyl-propyl]pyridine-2-carboxamide (Compound 45);

4-[[2-(5-Chloro-2-hydroxy-phenyl)acetyl]amino]-N-(1-cyano-2-hydroxy-1-methyl-ethyl)pyridine-2-carboxamide (Compound 46);

4-[[2-(5-Chloro-2-hydroxy-phenyl)acetyl]amino]-N-[(1S)-1-cyano-2-hydroxy-1-methyl-ethyl]pyridine-2-carboxamide or 4-[[2-(5-chloro-2-hydroxy-phenyl)acetyl] amino]-N-[(1R)-1-cyano-2-hydroxy-1-methyl-ethyl] pyridine-2-carboxamide (Compound 46a);

4-[[2-(5-Chloro-2-hydroxy-phenyl)acetyl]amino]-N-[(1S)-1-cyano-2-hydroxy-1-methyl-ethyl]pyridine-2-carboxamide or 4-[[2-(5-chloro-2-hydroxy-phenyl)acetyl] amino]-N-[(1R)-1-cyano-2-hydroxy-1-methyl-ethyl] pyridine-2-carboxamide (Compound 46b);

4-[[2-(5-Chloro-2-hydroxy-phenyl)acetyl]amino]-N-(3-cyanotetrahydrofuran-3-yl)pyridine-2-carboxamide (Compound 47);

Methyl2-[4-[[4-[[2-(5-chloro-2-hydroxy-phenyl) acetyl] amino]pyridine-2-carbonyl]amino]tetrahydropyran-4-yl] acetate (Compound 47.1);

Methyl 4-[[4-[[2-(5-chloro-2-hydroxy-phenyl)acetyl] amino]pyridine-2-carbonyl]amino]tetrahydropyran-4-carboxylate (Compound 47.2);

4-[[2-(5-Chloro-2-hydroxy-phenyl)acetyl]amino]-N-(3-cyanooxetan-3-yl)pyridine-2-carboxamide (Compound 47.3);

4-[[2-(5-Fluoro-2-hydroxy-phenyl)acetyl]amino]-N-(1-methylcyclobutyl)pyridine-2-carboxamide (Compound 48);

N-(4-Cyanotetrahydropyran-4-yl)-4-[[2-(5-fluoro-2-hydroxy-phenyl)acetyl]amino]pyridine-2-carboxamide (Compound 48.1);

N-[3-(tert-Butylamino)-1,1-dimethyl-3-oxo-propyl]-4-[[2-(5-chloro-2-hydroxy-phenyl) acetyl]amino]pyridine-2-carboxamide (Compound 49);

4-[[2-(5-Chloro-2-hydroxy-phenyl)acetyl]amino]-N-[3-(methanesulfonamido)-1,1-dimethyl-propyl]pyridine-2-carboxamide (Compound 50);

N-(3-Acetamido-1,1-dimethyl-propyl)-4-[[2-(5-chloro-2-hydroxy-phenyl)acetyl]amino]pyridine-2-carboxamide (Compound 51);

4-[[2-(5-Chloro-2-hydroxy-phenyl)acetyl]amino]-N-[4-(hydroxymethyl)tetrahydro pyran-4-yl]pyridine-2-carboxamide (Compound 53);

N-tert-Butyl-4-[[2-[3-(1-hydroxyethyl)phenyl]acetyl] amino]pyridine-2-carboxamide (Compound 54);

N-tert-Butyl-5-chloro-4-[[2-(5-chloro-2-hydroxy-phenyl) acetyl]amino]pyridine-2-carboxamide (Compound 55);

N-tert-Butyl-4-[[2-[5-chloro-2-[(4-methoxyphenyl) methoxy]phenyl]acetyl]amino]pyridine-2-carboxamide (Compound 56);

N-tert-butyl-4-[[(1S) or (1R)-4-chloro-7-hydroxy-indane-1-carbonyl]amino]pyridine-2-carboxamide and Example 57b: N-tert-butyl-4-[[(1S) or (1R)-4-chloro-7-hydroxy-indane-1-carbonyl]amino]pyridine-2-carboxamide (Compound 57a);

N-tert-butyl-4-[[(1S) or (1R)-4-chloro-7-hydroxy-indane-1-carbonyl]amino]pyridine-2-carboxamide and Example 57b: N-tert-butyl-4-[[(1S) or (1R)-4-chloro-7-hydroxy-indane-1-carbonyl]amino]pyridine-2-carboxamide (Compound 57b);

N-tert-Butyl-4-[[2-(2-cyclopropylphenyl)acetyl]amino]pyridine-2-carboxamide (Compound 58);
4-[[2-(3-Bromo-5-chloro-2-hydroxy-phenyl)acetyl]amino]-N-tert-butyl-pyridine-2-carboxamide (Compound 59);
N-(4-Fluoro-1-bicyclo[2.1.1]hexanyl)-4-[[2-(2-fluorophenyl)acetyl]amino]pyridine-2-carboxamide (Compound 60);
N-(1-Cyano-2-hydroxy-1-methyl-ethyl)-4-[[2-(2-fluorophenyl)acetyl]amino]pyridine-2-carboxamide (Compound 60.1);
N-(1,1-Dimethylprop-2-ynyl)-4-[[2-(2-fluorophenyl)acetyl]amino]pyridine-2-carboxamide (Compound 60.2);
N-tert-Butyl-4-[[2-(5-chloro-2-hydroxy-3-isopropyl-phenyl)acetyl]amino]pyridine-2-carboxamide (Compound 61);
N-tert-Butyl-4-[[2-[5-chloro-2-hydroxy-3-(1-methoxyethyl)phenyl]acetyl]amino]pyridine-2-carboxamide (Compound 62);
4-[[2-(6-Quinolyl)acetyl]amino]-N-tetrahydropyran-4-yl-pyridine-2-carboxamide (Compound 63);
4-(Benzylcarbamoylamino)-N-tert-butyl-pyridine-2-carboxamide (Compound 64);
N-tert-Butyl-4-(cyclohexylmethylcarbamoyl amino)pyridine-2-carboxamide (Compound 64.1);
N-tert-Butyl-4-(2-phenylethylcarbamoyl amino)pyridine-2-carboxamide (Compound 64.2);
N-tert-Butyl-4-[[(1R)-1-phenylethyl]carbamoyl amino]pyridine-2-carboxamide (Compound 64.3);
N-tert-Butyl-4-[[(1S)-1-phenylethyl]carbamoylamino]pyridine-2-carboxamide (Compound 64.4);
N-tert-Butyl-4-[(2-chlorophenyl)methylcarbamoylamino]pyridine-2-carboxamide (Compound 64.5);
N-tert-butyl-4-(1H-indol-3-ylcarbamoyl amino)pyridine-2-carboxamide (Compound 64.6);
N-tert-Butyl-4-[(3-chlorophenyl)methyl carbamoylamino]pyridine-2-carboxamide (Compound 64.7);
N-tert-butyl-4-[(4-chlorophenyl)methyl carbamoylamino]pyridine-2-carboxamide (Compound 64.8);
N-tert-Butyl-4-[(2-hydroxyphenyl)carbamoylamino]pyridine-2-carboxamide (Compound 65);
N-tert-Butyl-4-[(2-methoxyphenyl)methylcarbamoylamino]pyridine-2-carboxamide (Compound 65.1);
N-tert-Butyl-4-[(2-hydroxyphenyl)methylcarbamoylamino]pyridine-2-carboxamide (Compound 65.2);
N-tert-Butyl-4-[(3-hydroxyphenyl)methylcarbamoylamino]pyridine-2-carboxamide (Compound 65.3);
N-tert-Butyl-4-[(4-hydroxyphenyl)methylcarbamoylamino]pyridine-2-carboxamide (Compound 65.4);
N-tert-Butyl-4-[[2-[2-hydroxy-5-(1-hydroxyethyl)phenyl]acetyl]amino]pyridine-2-carboxamide (Compound 66);
N-tert-Butyl-4-[[2-[2-hydroxy-5-[1-(2,2,2-trifluoroethylamino)ethyl]phenyl]acetyl]amino]pyridine-2-carboxamide (Compound 67);
N-tert-Butyl-4-[[2-[3-(cyanomethyl)phenyl]acetyl]amino]pyridine-2-carboxamide (Compound 68);
N-tert-Butyl-4-[[2-[3-(methoxymethyl)phenyl]acetyl]amino]pyridine-2-carboxamide (Compound 69);
N-tert-Butyl-4-[[2-[2-hydroxy-5-(morpholinomethyl)phenyl]acetyl]amino]pyridine-2-carboxamide (Compound 70);
3-[[2-(5-Chloro-2-hydroxy-phenyl)acetyl]amino]-N-(3-cyanotetrahydrofuran-3-yl)benzamide (Compound 71);
3-[[2-(5-Chloro-2-hydroxy-phenyl)acetyl]amino]-N-(1-methylcyclohexyl)benzamide (Compound 71.1);
4-[[2-(5-Fluoro-2-hydroxy-phenyl)acetyl]amino]-N-[3-(hydroxymethyl)tetrahydrofuran-3-yl]pyridine-2-carboxamide (Compound 72);
4-[[2-(5-Chloro-2-hydroxy-phenyl)acetyl]amino]-N-[1-(hydroxymethyl)-2-methoxy-1-methyl-ethyl]pyridine-2-carboxamide (Compound 73);
4-[[2-(5-Chloro-2-hydroxy-phenyl)acetyl]amino]-N-(1,1-dimethylbut-2-ynyl)pyridine-2-carboxamide (Compound 73.1);
3-[[2-(5-Chloro-2-hydroxy-phenyl)acetyl]amino]-N-(1,1-dimethylprop-2-ynyl)benzamide (Compound 74);
3-[[2-(5-Chloro-2-hydroxy-phenyl)acetyl]amino]-N-[3-(hydroxymethyl)tetra hydrofuran-3-yl]benzamide (Compound 74.1);
N-tert-Butyl-4-[[2-[2-hydroxy-5-(3-hydroxypropyl)phenyl]acetyl]amino]pyridine-2-carboxamide (Compound 75);
4-[[2-(5-Chloro-4-fluoro-2-hydroxy-phenyl)acetyl]amino]-N-(1-methylcyclo butyl)pyridine-2-carboxamide (Compound 76);
4-[[2-(2,5-Difluorophenyl)acetyl]amino]-N-(1,1-dimethylprop-2-ynyl)pyridine-2-carboxamide (Compound 77);
4-[[2-(2,5-Difluorophenyl)acetyl]amino]-N-(4-fluoro-1-bicyclo[2.1.1]hexanyl)pyridine-2-carboxamide (Compound 77.1);
4-[[2-(4-Chloro-2-hydroxy-phenyl)acetyl]amino]-N-(1,1-dimethylprop-2-ynyl)pyridine-2-carboxamide (Compound 78);
N-(1,1-Dimethylprop-2-ynyl)-4-[[2-[2-hydroxy-4-(trifluoromethyl)phenyl]acetyl]amino]pyridine-2-carboxamide (Compound 78.1);
N-(1,1-Dimethylprop-2-ynyl)-4-[[2-[2-hydroxy-5-(trifluoromethyl)phenyl]acetyl]amino]pyridine-2-carboxamide (Compound 78.2);
4-[(2-Chroman-4-ylacetyl)amino]-N-(1,1-dimethylprop-2-ynyl)pyridine-2-carboxamide (Compound 79);
N-(1,1-Dimethylprop-2-ynyl)-4-[[2-(1-isopropyl-3,5-dimethyl-pyrazol-4-yl)acetyl]amino]pyridine-2-carboxamide (Compound 79.1);
N-(1,1-Dimethylprop-2-ynyl)-4-[[2-(1H-indazol-4-yl)acetyl]amino]pyridine-2-carboxamide (Compound 79.2);
N-(1,1-Dimethylprop-2-ynyl)-4-[[2-(1H-indol-7-yl)acetyl]amino]pyridine-2-carboxamide (Compound 79.3);
3-[[2-(5-Chloro-2-hydroxy-phenyl)acetyl]amino]-N-(4-cyanotetrahydropyran-4-yl)benzamide (Compound 80);
N-(1-Cyano-1-methyl-ethyl)-4-[[2-(5-fluoro-2-hydroxyphenyl)acetyl]amino]pyridine-2-carboxamide (Compound 81);
N-(1-Cyano-2-hydroxy-1-methyl-ethyl)-4-[[2-(5-fluoro-2-hydroxy-phenyl)acetyl]amino]pyridine-2-carboxamide (Compound 81.1);
4-[[2-(5-Fluoro-2-hydroxy-phenyl)acetyl]amino]-N-isopropyl-pyridine-2-carboxamide (Compound 81.2);
N-(1,1-Dimethylprop-2-ynyl)-4-[[2-(5-fluoro-2-hydroxyphenyl)acetyl]amino]pyridine-2-carboxamide (Compound 81.3);
N-(4-Fluoro-1-bicyclo[2.1.1]hexanyl)-4-[[2-(5-fluoro-2-hydroxy-phenyl)acetyl]amino]pyridine-2-carboxamide (Compound 81.4);
4-[[2-(5-Fluoro-2-hydroxy-phenyl)acetyl]amino]-N-[1-(hydroxymethyl)cyclobutyl]pyridine-2-carboxamide (Compound 81.5);
N-tert-Butyl-6-[[2-(5-chloro-2-methoxy-phenyl)acetyl]amino]pyrimidine-4-carboxamide (Compound 82);
N-(1-Cyano-1-methyl-ethyl)-4-(thiophene-3-carbonylamino)pyridine-2-carboxamide (Compound 83);
N-(1-Cyano-1-methyl-ethyl)-4-[(2-cyclohexylacetyl)amino]pyridine-2-carboxamide (Compound 83.1);
N-(1-Cyano-1-methyl-ethyl)-4-(cyclohexane carbonylamino)pyridine-2-carboxamide (Compound 83.2);

N-(1-Cyano-1-methyl-ethyl)-4-[(3,3-difluorocyclo pentanecarbonyl)amino]pyridine-2-carboxamide (Compound 83.3);

N-(1-Cyano-1-methyl-ethyl)-4-[(1-methylcyclo pentanecarbonyl)amino]pyridine-2-carboxamide (Compound 83.4);

N-(1-Cyano-1-methyl-ethyl)-4-(3-cyclohexyl propanoylamino)pyridine-2-carboxamide (Compound 83.5);

4-(2-{Bicyclo[2.2.1]heptan-2-yl}acetamido)-N-(1-cyano-1-methylethyl)pyridine-2-carboxamide (Compound 83.6);

N-(1-Cyano-1-methyl-ethyl)-4-[[2-(1-methylcyclo hexyl)acetyl]amino]pyridine-2-carboxamide (Compound 83.7);

N-[2-[(1-Cyano-1-methyl-ethyl)carbamoyl]-4-pyridyl]-2-cyclopropyl-pyrimidine-5-carboxamide (Compound 83.8);

N-[2-[(1-Cyano-1-methyl-ethyl)carbamoyl]-4-pyridyl]-3-isobutyl-isoxazole-5-carboxamide (Compound 83.9);

N-(1-Cyano-1-methyl-ethyl)-4-[[2-(4,4-difluorocyclo hexyl)acetyl]amino]pyridine-2-carboxamide (Compound 83.10);

4-[(1-Benzylcyclopropanecarbonyl)amino]-N-(1-cyano-1-methyl-ethyl)pyridine-2-carboxamide (Compound 83.11);

N-(1-Cyano-1-methyl-ethyl)-4-[3-(2-methoxy-4-pyridyl)propanoylamino]pyridine-2-carboxamide (Compound 83.13);

4-[(5-tert-Butyl-2-methyl-pyrazole-3-carbonyl)amino]-N-(1-cyano-1-methyl-ethyl)pyridine-2-carboxamide (Compound 83.14);

N-(1-Cyano-1-methyl-ethyl)-4-[(2-pyrazol-1-ylbenzoyl)amino]pyridine-2-carboxamide (Compound 83.15);

N-[2-[(1-Cyano-1-methyl-ethyl)carbamoyl]-4-pyridyl]-6-(trifluoromethyl)pyridine-2-carboxamide (Compound 83.16);

N-[2-[(1-Cyano-1-methyl-ethyl)carbamoyl]-4-pyridyl]-3-oxo-4H-1,4-benzoxazine-7-carboxamide (Compound 83.17);

N-[2-[(1-Cyano-1-methyl-ethyl)carbamoyl]-4-pyridyl]-1-ethyl-indole-2-carboxamide (Compound 83.18);

N-(1-Cyano-1-methyl-ethyl)-4-[[2-(2,2,2-trifluoroethyl)pyrazole-3-carbonyl]amino]pyridine-2-carboxamide (Compound 83.19);

N-[2-[(1-Cyano-1-methyl-ethyl)carbamoyl]-4-pyridyl]-3-phenyl-isoxazole-4-carboxamide (Compound 83.20);

4-[(1-Benzylpyrazole-4-carbonyl)amino]-N-(1-cyano-1-methyl-ethyl)pyridine-2-carboxamide (Compound 83.21);

N-(1-Cyano-1-methyl-ethyl)-4-[(2-methyl-5-phenyl-pyrazole-3-carbonyl)amino]pyridine-2-carboxamide (Compound 83.22);

N-(1-Cyano-1-methyl-ethyl)-4-[[2-(3-methyl-1,2,4-oxadiazol-5-yl)benzoyl]amino]pyridine-2-carboxamide (Compound 83.23);

N-(1-Cyano-1-methyl-ethyl)-4-[(3-methyl-1-phenyl-pyrazole-4-carbonyl)amino]pyridine-2-carboxamide (Compound 83.24);

N-[2-[(1-Cyano-1-methyl-ethyl)carbamoyl]-4-pyridyl]-2-phenoxy-pyridine-3-carboxamide (Compound 83.25);

N-(1-Cyano-1-methyl-ethyl)-4-[[2,5-dimethyl-1-(2-thienylmethyl)pyrrole-3-carbonyl]amino]pyridine-2-carboxamide (Compound 83.26);

N-[2-[(1-Cyano-1-methyl-ethyl)carbamoyl]-4-pyridyl]-5-(2-methoxyphenyl)isoxazole-3-carboxamide (Compound 83.27);

N-[2-[(1-Cyano-1-methyl-ethyl)carbamoyl]-4-pyridyl]-4-methyl-2-phenyl-thiazole-5-carboxamide (Compound 83.28);

4-[(4-Acetamidobenzoyl)amino]-N-(1-cyano-1-methyl-ethyl)pyridine-2-carboxamide (Compound 83.29);

N-[2-[(1-Cyano-1-methyl-ethyl)carbamoyl]-4-pyridyl]-1,3-benzothiazole-7-carboxamide (Compound 83.30);

N-(1-Cyano-1-methyl-ethyl)-4-[3-(4-fluorophenyl)butanoylamino]pyridine-2-carboxamide (Compound 83.31);

N-[2-[(1-Cyano-1-methyl-ethyl)carbamoyl]-4-pyridyl]-1-methyl-2-oxo-quinoline-3-carboxamide (Compound 83.32);

N-tert-Butyl-3-[[2-(2-hydroxycyclohexyl)acetyl]amino]benzamide (Compound 84);

N-tert-Butyl-6-[[2-(5-chloro-2-hydroxy-phenyl)acetyl]amino]pyrimidine-4-carboxamide (Compound 85);

4-[[2-(5-Chloro-2-hydroxy-phenyl)acetyl]amino]-N-[1-cyano-2-methoxy-1-(methoxy methyl)ethyl]pyridine-2-carboxamide (Compound 86);

4-[[2-(3-Amino-4-tert-butyl-phenyl)acetyl]amino]-N-tert-butyl-pyridine-2-carboxamide (Compound 87);

4-[[2-(2-Amino-4-tert-butyl-phenyl)acetyl]amino]-N-tert-butyl-pyridine-2-carboxamide (Compound 88);

N-tert-Butyl-4-[[2-(4-tert-butyl-3-hydroxy-phenyl)acetyl]amino]pyridine-2-carboxamide (Compound 89);

N-tert-Butyl-4-[[2-(4-tert-butyl-2-hydroxy-phenyl)acetyl]amino]pyridine-2-carboxamide (Compound 90);

N-tert-Butyl-4-[[2-(4-tert-butyl-2-fluoro-5-hydroxy-phenyl)acetyl]amino]pyridine-2-carboxamide (Compound 91);

4-[[2-(4-Chloro-3-hydroxy-phenyl)acetyl]amino]-N-(4-cyanotetrahydropyran-4-yl)pyridine-2-carboxamide (Compound 92);

4-[[2-(4-Chloro-3-hydroxy-phenyl)acetyl]amino]-N-(1-cyano-1-methyl-ethyl)pyridine-2-carboxamide (Compound 92.1);

4-[[2-(4-Chloro-3-hydroxy-phenyl)acetyl]amino]-N-(1,1-dimethylprop-2-ynyl)pyridine-2-carboxamide (Compound 92.2);

4-[[2-(4-Chloro-3-hydroxy-phenyl)acetyl]amino]-N-[(1s,2s)-2-hydroxycyclopentyl]pyridine-2-carboxamide (Compound 92.3);

4-[[2-(4-tert-Butyl-3-hydroxy-phenyl)acetyl]amino]-N-[3-(hydroxymethyl)tetrahydrofuran-3-yl]pyridine-2-carboxamide (Compound 93);

4-[[2-(4-tert-Butyl-3-hydroxy-phenyl)acetyl]amino]-N-[(2S)-2-hydroxycyclohexyl]pyridine-2-carboxamide (Compound 93.1);

4-[[2-(4-tert-Butyl-3-hydroxy-phenyl)acetyl]amino]-N-[(2S)-2-hydroxycyclopentyl]pyridine-2-carboxamide (Compound 93.2);

4-[[2-(4-tert-Butyl-3-hydroxy-phenyl)acetyl]amino]-N-(4-cyanotetrahydropyran-4-yl)pyridine-2-carboxamide (Compound 93.3);

4-[[2-(4-tert-Butyl-3-hydroxy-phenyl)acetyl]amino]-N-(1-cyano-1-methyl-ethyl)pyridine-2-carboxamide (Compound 93.4);

4-[[2-(4-tert-Butyl-3-hydroxy-phenyl)acetyl]amino]-N-(1,1-dimethylprop-2-ynyl)pyridine-2-carboxamide (Compound 93.5);

4-[[2-(5-Chloro-2-hydroxy-phenyl)acetyl]amino]-N-(1-methyl-1-phenyl-ethyl)pyridine-2-carboxamide (Compound 94); and salts and solvates of any of the above.

The compound of general formula (I) may be prepared as described below and the processes for its preparation form a further aspect of the invention.

A compound of general formula (I) in which Z is —C(O)— may be prepared from a compound of general formula (II):

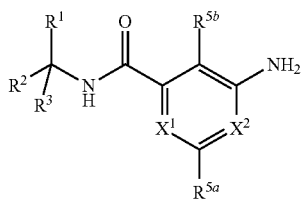

(II)

wherein $R^1$, $R^2$, $R^3$, $R^{5a}$ and $R^{5b}$, $X^1$ and $X^2$ are as defined for general formula (I); by reaction with a compound of general formula (III):

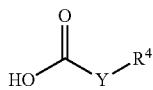

(III)

wherein $R^4$ and Y are as defined for general formula (I).

The reaction is suitably conducted in the presence of a coupling reagent and this method is particularly suitable for compounds of general formula (I) in which $X^1$ and $X^2$ are each independently N or $CR^8$, wherein $R^8$ is halo, and Y is a bond or alkylene.

One example of a suitable coupling reagent is a carbodiimide such as 1-ethyl-3-(3-dimethylaminopropyl)carbodiimide (EDCI) and a triazole such as 1-hydroxy-7-azabenzotriazole (HOAt) or hydroxybenzotriazole (HOBt). Suitably, the reaction is conducted under basic conditions, for example in the presence of an amine such as diisopropylethylamine (DIPEA) and in an organic solvent such as DMF.

Alternatively, the coupling reagent may be propylphosphonic anhydride (T3P). When T3P is used as the coupling reagent, the reaction may be conducted under basic conditions, for example in the presence of an amine such as diisopropylethylamine (DIPEA) or triethylamine (TEA) and in an organic solvent such as dioxane.

Other known peptide coupling agents such as O-(Benzotriazol-1-yl)-N,N,N',N'-tetramethyluronium hexafluorophosphate (HBTU), O-(Benzotriazol-1-yl)-N,N,N',N'-tetramethyluronium tetrafluoroborate (TBTU), O-(7-Azabenzotriazol-1-yl)-N,N,N',N'-tetramethyluronium hexafluorophosphate (HATU), O-(7-Azabenzotriazol-1-yl)-N,N,N',N'-tetramethyluronium tetrafluoroborate (TATU), (Benzotriazol-1-yloxy)tris(dimethylamino)phosphonium hexafluorophosphate (BOP), (Benzotriazol-1-yloxy)tripyrrolidinophosphonium hexafluorophosphate (PyBOP) etc may also be used.

Compounds of general formula (III) are commercially available or may be prepared by methods known to those of skill in the art. For example, compounds of general formula (III) in which Y is —CH$_2$— may be synthesised from nitriles of general formula (XXIII):

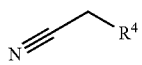

(XXIII)

wherein $R^4$ is as defined for general formula (I);
by reaction with an aqueous base, for example a metal hydroxide such as lithium hydroxide, followed by acidification, for example with hydrochloric acid.

The reaction is suitably carried out in an aqueous solution and is heated to reflux temperature.

A nitrile of general formula (XXIII) may be prepared from a compound of general formula (XXIV):

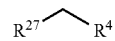

(XXIV)

wherein $R^4$ is as defined for general formula (I) and $R^{27}$ is halo, for example fluoro, chloro or bromo, especially chloro;
by reaction with a cyanide salt such as sodium cyanide.

The reaction may be carried out at a temperature of about 15 to 25° C., typically at room temperature, in an organic solvent such as N,N-dimethylformamide.

A compound of general formula (XXIV) can be prepared by halogenation a compound of general formula (XXV):

(XXV)

wherein $R^4$ is as defined for general formula (I).
by reaction with a halogenating agent.

Suitable halogenating agents for use in the reaction will depend upon which halo group $R^{27}$ is required. For example, when $R^{27}$ is chloro, the halogenating agent may be thionyl chloride. The reaction may be carried out at a temperature of about 15 to 25° C., typically at room temperature, in an organic solvent such as dichloromethane.

A compound of general formula (XXV) may be obtained by reduction of a compound of general formula (III) in which Y is a bond, ie which has the formula:

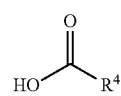

(XXV)

wherein $R^4$ is as defined for general formula (I).

The reduction may be carried out using any suitable reducing agent, for example borane-THF and is suitably conducted at elevated temperature, for example 30-60° C., typically about 50° C.

In an alternative method for the preparation of a compound of general formula (I), a compound of general formula (II) as defined above may be reacted with an acid chloride of general formula (IV):

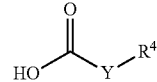

(IV)

wherein $R^4$ and Y are as defined for general formula (I).

The reaction is suitably conducted under basic conditions, for example in the presence of an amine such as DIPEA.

This method is particularly suitable for compounds in which Y is a bond or alkylene.

The acid chloride of general formula (IV) may be commercially available or may be obtained from the carboxylic acid of general formula (III) by reaction with a chlorinating agent, for example thionyl chloride.

Compounds of general formula (III) are known and are either commercially available or may be prepared by methods known to those of skill in the art.

Alternatively, for compounds of general formula (I) in which Z is —C(O)NH—, the compound of general formula (II) may be reacted with a compound of general formula (XIV):

O=C=N—Y—R⁴      (XIV)

wherein $R^4$ and Y are as defined for general formula (I).

Suitably, the reaction is carried out in an anhydrous organic solvent such as N,N-dimethylformamide at elevated temperature, for example about 70 to 85° C.

An alternative method for the preparation of a compound of general formula (Ia) or (Ib) is by reacting a compound of general formula (II) with a compound of general formula (XIII):

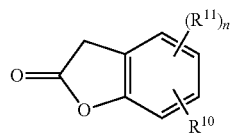

wherein $R^{10}$, $R^{11}$ and n are as defined for a compound of general formula (Ia).

For example, to prepare a compound of general formula (Ib) in which $R^{11a}$ is Cl and $R^{11b}$ is H, the compound of general formula (XIII) may be 5-chloro-2(3H)-benzofuranone, which has the structure:

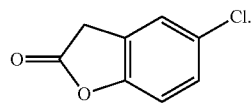

The reaction may be carried out in an organic solvent such as toluene, typically at elevated temperature, for example about 90 to 120° C., for example about 100 to 110° C. and under pressurised conditions such as in a sealed tube.

Compounds of general formulae (XIII) and (XIV) are known and are either commercially available or may be prepared by methods known to those of skill in the art.

The compound of general formula (II) may be formed by the reaction of a compound of general formula (VIII):

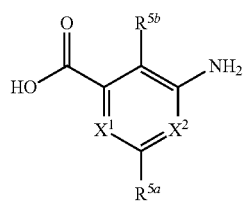

wherein $R^{5a}$, $R^{5b}$, $X^1$ and $X^2$ are as defined for general formula (I);

with a compound of general formula (VII):

wherein $R^1$, $R^2$ and $R^3$ are as defined for general formula (I).

Suitably the reaction is conducted in the presence of a coupling agent as described above for the reaction between the compounds of general formulae (II) and (III). TBTU is a particularly suitable coupling agent for this reaction, although EDCI and HOAt or HOBt may also be used.

In some cases, the compound of general formula (VIII) may be protected as a carbamate ester of general formula (VI):

wherein $R^{5a}$, $R^{5b}$, $X^1$ and $X^2$ are as defined for general formula (I); and $R^{20}$ is $C_{1-8}$ alkyl or benzyl.

In this case, the reaction with the compound of general formula (VII) produces a carbamate ester of general formula (V):

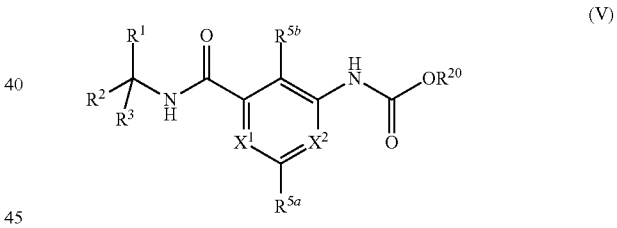

wherein $R^1$, $R^2$, $R^3$, $R^{5a}$, $R^{5b}$, $X^1$ and $X^2$ are as defined for general formula (I); and $R^{20}$ is as defined for general formula (VI).

The carbamate protecting group may be removed by hydrolysis, suitably acid hydrolysis, for example using hydrochloric acid and may be conducted in an organic solvent such as dichloromethane.

Compounds of general formulae (VI), (VII) and (VIII) are known and are commercially available or may be prepared by methods known to those of skill in the art.

For example, a compound of general formula (VIII) in which $X^2$ is C—Cl may be prepared from a compound of general formula (VIII) in which $X^2$ is CH by reaction with a chlorinating agent such as N-chlorosuccinimide. Suitably, the reaction takes place in an organic solvent such as N,N-dimethylformamide at elevated temperature, for example about 50 to 70° C.

Also, a compound of general formula (VII) in which $R^1$ is ethynyl and $R^2$ and $R^2$ together form a carbocyclic or heterocyclic ring may be prepared by reacting a compound of general formula (XVII):

(XVII)

wherein $R^2$ and $R^3$ form a carbocyclic or heterocyclic ring and $R^{21}$ is $C_{3-8}$ alkyl, for example t-butyl;

with a compound of general formula (XVIII):

(XVIII)

wherein each $R^{23}$ is independently $C_{1-3}$ alkyl, suitably in the presence of an aluminium catalyst and a base; followed by deprotection using an acid.

Suitable bases include strong bases such as n-butyl lithium and a suitable acid for the deprotection step is hydrochloric acid, suitably in an organic solvent such as dioxane.

The compound of general formula (XVII) may be prepared by reaction of a compound of general formula (XIX):

(XIX)

wherein $R^{21}$ is as defined for general formula (XVII);
with a compound of general formula (XX):

(XX)

wherein $R^2$ and $R^3$ form a carbocyclic or heterocyclic ring.

Suitably, the reaction is catalysed with titanium (IV) catalyst, for example titanium (IV) ethoxide.

Compounds of general formulae (XIX) and (XX) are known and are readily available.

An Alternative method for the preparation of a compound of general formula (II) is by reduction of a compound of general formula (IX):

(IX)

wherein $R^1$, $R^2$, $R^3$, $R^{5a}$, $R^{5b}$, $X^1$ and $X^2$ are as defined for general formula (I); for example by hydrogenation over a palladium catalyst.

The hydrogenation is typically carried out in an alcoholic solvent such as ethanol at a temperature of about 15 to 25° C., for example at room temperature.

Compounds of general formula (IX) may be obtained by reaction of a compound of general formula (VIIIa):

(VIIIa)

wherein $R^{5a}$, $R^{5b}$, $X^1$ and $X^2$ are as defined for general formula (I);

with an amine of general formula (VII)

The reaction may be carried out in the presence of a coupling agent, for example one of the coupling agents described above for the reaction between the compounds of general formulae (II) and (III).

An alternative method for the preparation of a compound of general formula (I) is by reacting a compound of general formula (X):

(X)

wherein $X^1$, $X^2$, Y, $R^4$, $R^{5a}$ and $R^{5b}$ are as defined for general formula (I);

with a compound of general formula (VII) as defined above.

This method is particularly suitable for compounds in which $X^1$ is N or $CR^8$, wherein $R^8$ is H or halo and/or $X^2$ is N or $CR^8$, wherein $R^8$ is H, OH or $O(C_{1-4}$ alkyl) and/or $R^{5a}$ is H or F.

Suitably the reaction is conducted under basic conditions, for example in the presence of an amine such as DIPEA or TEA, and in the presence of a coupling agent as described above for the reaction between the compounds of general formulae (II) and (III). EDCI and HOAt or HOBt is a suitable coupling agent for this reaction, as are HATU TBTU and HBTU.

A compound of general formula (X) may be prepared by deprotecting a compound of general formula (XI):

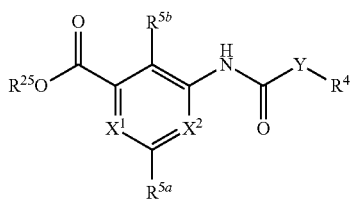

wherein $X^1$, $X^2$, Y, $R^4$, $R^{5a}$ and $R^{5b}$ are as defined for general formula (I); and $R^{25}$ is $C_{1-8}$ alkyl or benzyl.

One example of a suitable deprotecting agent is boron tribromide, although other methods of deprotecting carboxylic acid are known in the art and/or are discussed below.

This method using boron tribromide for deprotection is particularly suitable when the target compound is a compound of general formula (I) in which $R^4$ is substituted with OH, for example a compound of general formula (Ib), (Ic), (d) or (Ie) or a compound of general formula (Ia) in which $R^{10}$ and/or one or more $R^{11}$ groups is/are OH. In such compounds, the OH group on the $R^4$ moiety in the compound of general formula (XI) may be protected as a group $OR^{26}$, where $R^{21}$ is $C_{1-8}$ alkyl or benzyl. This protecting group can also be removed using boron tribromide. Similarly, boron tribromide deprotection is also suitable for the preparation of a compound of general formula (X) in which $X^1$ and/or $X^2$ is $CR^8$, wherein $R^8$ is OH.

On the other hand, if in the required compound of general formula (I) is a compound comprising an alkoxy group, for example a compound in which $R^4$ is substituted with a group such as $O(C_{1-6}$ alkyl) or in which $X^1$ and/or $X^2$ is $C(OC_{1-4}$ alkyl), it is preferable that the deprotection is carried out by hydrolysis, particularly base hydrolysis, for example using an alkali metal hydroxide such as lithium hydroxide. This ensures that the $C(O)OR^{25}$ group is hydrolysed to C(O)OH without effecting alkoxy substituents in other parts of the molecule.

A compound of general formula (XI) may be prepared from a compound of general formula (XII):

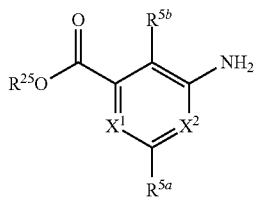

wherein $X^1$ and $X^2$, $R^{5a}$ and $R^{5b}$ are as defined for general formula (I); and $R^{25}$ is as defined for general formula (XI);
by reaction with a compound of general formula (III) as defined above or by reaction with a compound of general formula (IV) as defined above or by reaction with a compound of general formula (XIII), for example 5-chloro-2(3H)-benzofuranone, which gives a compound of general formula (Ib) in which $R^{11a}$ is chloro and $R^{11b}$ is H.

The reaction with the compound of general formula (III) is suitably carried out under basic conditions, for example in the presence of an amine such as DIPEA or TEA and a coupling agent is used as described above for the reaction between the compounds of general formulae (II) and (III). EDCI with HOAt or HOBt is a particularly suitable coupling agent.

The reaction with the compound of general formula (IV) will usually be conducted in an organic solvent such as dichloromethane. The compound of general formula (IV) may be generated in situ by reacting a compound of general formula (III) with thionyl chloride.

The reaction with the compound of general formula (XIII) may be carried out in an organic solvent such as toluene, typically at elevated temperature, for example about 90 to 120° C., for example about 100 to 110° C. and under pressurised conditions such as in a sealed tube.

Compounds of general formula (XII) are known and are either commercially available or may be prepared by methods known to those of skill in the art.

In a further alternative method, a compound of general formula (I) may be prepared by the reaction of a compound of general formula (XV):

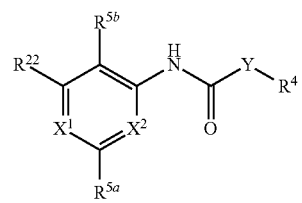

wherein $X^1$, $X^2$, Y, $R^4$, $R^{5a}$ and $R^{5b}$ are as defined for general formula (I) and $R^{22}$ is halo, suitably chloro or bromo;
with an amine of general formula (VII) as defined above and carbon monoxide in the presence of a phosphorus ligand such as XantPhos and a palladium catalyst.

A compound of general formula (XV) may be prepared by reacting a compound of general formula (XVI):

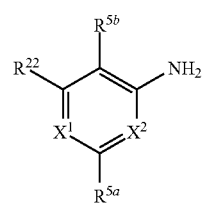

wherein $X^1$, $X^2$, $R^{5a}$ and $R^{5b}$ are as defined for general formula (I) and $R^{22}$ is as defined for general formula (XV);
with a compound of general formula (IV) as defined above or with a compound of general formula (III) above in the presence of a coupling agent such as HATU.

The reaction may be carried out under an inert atmosphere in an organic solvent such as N,N-dimethylformamide at a temperature of about 15 to 25° C., suitably at room temperature.

When a compound of general formula (IV) is used, it may be produced in situ by reaction of a compound of general formula (III) with thionyl chloride.

Alternatively, the compound of general formula (XVI) may be reacted with a lactone of general formula (XIII).

Compounds of general formula (XVI) are well known and are either commercially available or may be prepared by methods familiar to those of skill in the art.

Compounds of general formula (I) may be prepared in as protected derivatives. For example, a compound of general formula (I) in which $R^4$ has an OH substituent may be prepared from an equivalent compound of general formula (I) in which the OH is protected, for example as a $C_{1-6}$ alkoxy, benzyloxy or substituted benzyloxy group, wherein the benzyloxy group may be substituted with $C_{1-6}$ alkoxy or halo. The protecting group may be present in the precursors of general formulae (III), (IV), (X), (XI), (XIII), (XIV) and (XV) and may be removed using aqueous acid, for example aqueous hydrochloric acid or by hydrogenation, for example under a hydrogen atmosphere in the presence of a metal catalyst such as palladium on carbon.

Compounds of general formula (I) may also be converted to other compounds of general formula (I).

A compound of general formula (I) or (Ia) in which $R^4$ is an aryl or heteroaryl ring system substituted with one or more —O($C_{1-6}$ alkyl) substituents may be converted to a compound of general formula (I) or (Ia) in which the —O($C_{1-6}$ alkyl) substituents are replaced by OH substituents by reaction with boron tribromide. This method is useful for preparing a compounds of general formulae (Ib), (Ic), (Id) and (Ie).

A compound of general formula (I) or (Ia) in which $R^4$ is an aryl or heteroaryl ring system substituted with OH may also be prepared by reaction of an equivalent compound of general formula (I) in which $R^4$ is an aryl or heteroaryl ring system substituted with $NH_2$ by a diazotisation reaction with nitrous acid, generated in situ from sodium nitrite and a strong acid such as sulfuric acid. The resulting diazonium salt reacts with water to form an OH substituent on the $R^4$ group in a reaction which is suitably catalysed by copper (I), for example in the form of copper (I) oxide.

A compound of general formula (I) or (Ia) in which $R^4$ is an aryl or heteroaryl ring system substituted with $NH_2$ may be prepared by the reduction of an equivalent compound of general formula (I) in which $R^4$ is an aryl or heteroaryl ring system substituted with nitro. Typically, the reduction is achieved by hydrogenation, suitably catalysed with palladium.

A compound of general formula (I) or (Ia) in which $R^4$ is an aryl or heteroaryl ring system substituted with nitro may be prepared by nitration of equivalent compound of general formula (I), for example using concentrated nitric acid mixed with sulfuric acid. Alternatively, nitration may be carried out at an earlier stage of the process. For example, nitration may be carried out on a compound of general formula (III) or general formula (IV) and these nitrated derivatives may then be converted to compounds of general formula (I). A compound of general formula (I) in which $R^4$ is an aryl or heteroaryl group with a halide substituent may be converted to a compound of general formula (I) in which the halide substituent is replaced with CN, C(O)$R^6$, C(O)O$R^6$, C(O)N($R^6$)($R^7$), N($R^7$)C(O)$R^6$, $R^{19}$ or $C_{1-6}$ alkyl optionally substituted with one or more substituents selected from halo, CN, nitro, cycloalkyl, O$R^6$, S$R^6$, N$R^6R^7$, C(O)$R^6$ C(O)O$R^6$, C(O)N($R^6$)($R^7$) and N($R^7$)C(O)$R^6$, wherein $R^6$ and $R^7$ are as defined above for general formula (I) by using a palladium catalysed carbon-carbon coupling reaction, for example a Heck, Suzuki-Miyaura, Stille, Hiyama or Songoshira reaction. This may be followed, if required, by a further process, for example hydrogenation to reduce alkenyl to alkyl groups.

For example, a compound of general formula (I) in which $R^4$ has a halo substituent can be converted to an analogue in which $R^4$ has a cyano substituent by reaction with a metal cyanide salt, for example zinc cyanide. The reaction is suitably catalysed by a palladium/phosphine complex such as tetrakis(triphenylphosphine)palladium(0).

A compound of general formula (I) in which $R^4$ has a C(O)$R^6$ substituent may be prepared from the equivalent halo substituted compound by a palladium/phosphine catalysed reaction with a 1-vinyloxyalkane or a vinyloxysilane. Suitably, the reaction with the vinyloxyalkane is carried out in the presence of a base such as triethylamine and is conducted at elevated temperature, for example about 90 to 120° C., under pressurised conditions, for example in a sealed tube. Reaction with a vinyloxysilane may be carried out in the presence of zinc fluoride and in an anhydrous solvent such as N,N-dimethylformamide at elevated temperature, for example about 60 to 80° C., under pressurised conditions such as in a sealed tube. If required, the carbonyl group can be reduced to an OH group, for example using a hydride reducing agent such as sodium borohydride.

Similarly, compounds of general formula (I) in which $R^4$ has a halo substituent can be converted to compounds in which $R^4$ is substituted with $CH_2CH_2$—C(O)O$R^6$ by a palladium/phosphine catalysed reaction with a compound of general formula (XXII):

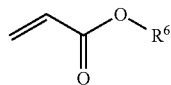

(XXII)

wherein $R^6$ is as defined for general formula (I) but is more suitably not hydrogen; followed by catalytic hydrogenation.

The reaction with the compound of general formula (XXII) may be conducted under a nitrogen atmosphere in the presence of a base such as triethylamine and at elevated temperature, for example about 60 to 80° C.

Hydrogenation may be catalysed by palladium or palladium/carbon.

The resultant compounds in $R^6$ is other than hydrogen can be converted to compounds in which $R^6$ is hydrogen by hydrolysis, typically base hydrolysis, for example using an aqueous alkali metal hydroxide such as lithium hydroxide.

The product of general formula (I) in which $R^4$ is substituted with $CH_2CH_2$—C(O)OH can be reduced to give compounds of general formula (I) in which $R^4$ is substituted with $CH_2CH_2$—$CH_2OH$. Suitably, the acid can be first converted into a mixed anhydride with an appropriate alkyl chloroformate regent such as methyl chloroformate followed by in situ reduction to the desired alcohol with an appropriate reducing agent such as sodium borohydride. The reaction may be conducted in the presence of a base such as triethylamine.

Compounds of general formula (I) in which $R^4$ has a C(O)O$R^6$ substituent, where $R^6$ is not H, may be prepared from compounds of general formula (I) in which $R^4$ is substituted with halo in a palladium/phosphine catalysed reaction with carbon monoxide and an appropriate alcohol. The catalyst may be generated from a pre-catalyst, suitably a third generation Buchwald precatalyst such as XantPhos. The carbon monoxide may be prepared by reacting formic acid with an agent such as methane sulfonyl chloride and a base such as triethylamine. The C(O)O$R^6$ group can be converted to C(O)OH by hydrolysis, for example base hydrolysis using an alkali metal hydroxide such as lithium hydroxide Compounds of general formula (I) in which $R^4$ has a halo substituent can be converted to compounds of general formula (I) in which $R^4$ is substituted with $C_{1-6}$ alkyl substituted with $OR^6$ or $NR^6R^7$ where $R^6$ and $R^7$ are as defined for general formula (I) in a palladium catalysed reaction with a compound of formula (XXa) or (XXb):

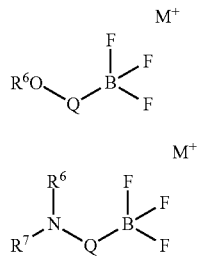

(XXa)

(XXb)

wherein $R^6$ and $R^7$ are as defined for general formula (I), $M^+$ is a metal ion, suitably a potassium ion, and Q is $C_{1-6}$ alkylene, suitably —$CH_2$—.

Suitably, the reaction is conducted under mildly basic conditions, for example in the presence of sodium carbonate at elevated temperature, for example about 70 to 90° C.

Compounds of general formula (I) where $R^4$ is aryl substituted with halo can be converted to compounds of general formula (I) where $R^4$ is aryl substituted with aryl by reaction with the appropriate aryl boronic acid. The reaction is suitably catalysed by a palladium/phosphine catalyst such as 1,1'-Bis(diphenylphosphino)ferrocenedichloropalladium (II). Suitably, the reaction is carried out in an organic solvent such as 1,4-dioxane and is conducted at elevated temperature, for example about 90 to 120° C. under pressurised conditions, for example in a sealed tube.

Compounds of general formula (I) in which $R^4$ is phenyl can be alkylated using a Friedel Crafts type alkylation by reaction with the appropriate alcohol or alkyl halide in the presence of a strong Lewis acid catalyst, for example sulfuric acid. The position of alkylation will depend upon the position of other substituents in the ring. For example, when $R^4$ is 2-fluoro-5-hydroxyphenyl, alkylation will occur at the 4-position as illustrated in Example 91.

In the compounds of general formula (I), replacement of a halo with a methyl group can be achieved via a Suzuki-Miyaura coupling (Grey, et al, *Tetrahedron Letters*, 41(32), 6237-6240; 2000); installation of nitrile can be achieved as described by Willardsen et al in *Journal of Medicinal Chemistry*, 47(16), 4089-4099; 2004. Installation of ester and amides may be via carbonylation as described by Veryser et al in *React. Chem. Eng.*, 2016, 1, 142-146.

The $R^4$ group of compounds of general formula (I) in which $R^4$ is an aryl or heteroaryl ring system substituted with a group $OR^6$ can be halogenated by reaction with halogenating agent, for example an N-halo succinimide or bromine.

The reaction with an N-halo succinimide may be conducted in a polar organic solvent such as acetonitrile and at elevated temperature, for example about 50 to 70° C. A reaction with bromine can take place in solution in a solvent such as acetic acid and at reduced temperature, for example about −5 to 5° C.

Compounds of general formula (I) in which $R^4$ is substituted with $C(O)R^{6'}$, where $R^{6'}$ is $C_{1-6}$ alkyl or haloalkyl can be converted to compounds of general formula (I) in which $R^4$ is substituted with $C(R^{6'})$—$NR^6R^7$, wherein $R^6$ and $R^7$ are as defined for general formula (I), by reaction with a compound of formula (XXI):

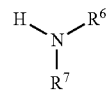

(XXI)

wherein $R^6$ and $R^7$ are as defined for general formula (I); under reducing conditions, for example in the presence of a borohydride such as sodium triacetoxyborohydride. The reaction may be carried out in an organic solvent, for example a halogenated solvent such as dichloroethane or dichloromethane, in the presence of an appropriate acid catalyst such as acetic acid and the reaction temperature may be about 15 to 25° C., typically room temperature.

A compound of general formula (I) in which $R^4$ is substituted with haloalkyl can be converted to an analogue in which $R^4$ is substituted with cyanoalkyl by reaction with a group I or group II metal cyanide salt, for example sodium cyanide in the presence of tetrabutylammonium bromide. The reaction is suitably conducted at a temperature of about 15 to 80° C. In some cases, the reaction may take a room temperature. The reaction solvent may be an aqueous solvent, typically a mixture of water and an organic solvent such as dichloromethane.

Reactions for interconverting the substituent groups on $R^4$ can also be carried out at an earlier stage of the process. For example, compounds of general formulae (III), (IV), (VI), (X), (XI) or (XV) can also be interconverted in the same way as compounds of general formula (I).

In compounds in which $R^1$ is C(O)OH or $R^1$ or $R^3$ is substituted with C(O)OH or in which $R^4$ has a substituent comprising a C(O)OH group, the C(O)OH group can be reduced to an OH group using any suitable method. Hydride reducing agents such as lithium aluminium hydride are particularly suitable.

In compounds of general formula (I) comprising an alkyl group substituted with a primary or secondary amino group $N(R)_2$, the amino group can be converted to a group —N(R)—C(O)-alkyl (where R is a group $R^6$, $R^{12}$ or $R^{15}$ depending on the position of the amino group in the molecule) a by reaction with a carboxylic acid in the presence of a coupling agent or with a base followed by an anhydride.

Primary and secondary amine groups in these compounds can be converted to a group —N(R)—C(O)O-alkyl by reaction with a carboxylic anhydride. The process can be reversed by treatment of the compound containing an alkyloxycarbonyl amino substituent with an acid or with boron tribromide to yield a primary or secondary amine.

Compounds of general formula (I) in which $R^3$ is $N(R^{15})S(O)_2R^{14}$ or $N(R^{15})S(O)_2R^{16}$ can be prepared from compounds of general formula (I) in which $R^3N(R^{15})_2$ by reaction with a sulfonyl halide W—$S(O)_2R^{14}$ or W—$S(O)_2R^{16}$, where W is halide, especially chloride and $R^{14}$, $R^{15}$ and $R^{16}$ are as defined above.

Compounds of general formula (I) in which $R^1$, $R^3$ or $R^4$ comprise a group C(O)OR', where R' is $R^6$, $R^7$, $R^{12}$ or $R^{15}$ as appropriate, can be converted to compounds containing a group $C(O)N(R')_2$ by reaction with appropriate amine in the presence of a coupling reagent.

Other interconversions of the various substituent groups can be carried out by methods familiar to those of skill in the art.

The compounds of the present invention will generally be administered as part of a pharmaceutical composition and therefore the invention further provides a pharmaceutical composition comprising a compound of general formula ((I), (Iz), (Iy), (Ix), (Ia), (Ib), (Ic), (Id) or (Ie) together with a pharmaceutically acceptable excipient.

The pharmaceutical composition may be formulated for oral, rectal, nasal, bronchial (inhaled), topical (including dermal, transdermal, eye drops, buccal and sublingual), vaginal or parenteral (including subcutaneous, intramuscular, intravenous and intradermal) administration and may be prepared by any methods well known in the art of pharmacy.

The composition may be prepared by bringing into association the above defined active agent with the excipient. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) in conjunction or association with a pharmaceutically acceptable carrier or vehicle.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate, stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

For topical application to the skin, compounds of general formula (I) may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40%-99.5% e.g. 40%-90% by weight of the total inhalation composition. The formulation may comprise excipients including co-solvents (e.g. ethanol) and surfactants (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Valois or 3M or alternatively by Aptar, Coster or Vari).

Topical administration to the lung may also be achieved by use of a non-pressurised formulation such as an aqueous solution or suspension. These may be administered by means of a nebuliser e.g. one that can be hand-held and portable or for home or hospital use (ie non-portable). The formulation may comprise excipients such as water, buffers, tonicity adjusting agents, pH adjusting agents, surfactants and co-solvents. Suspension liquid and aerosol formulations (whether pressurised or unpressurised) will typically contain the compound of the invention in finely divided form, for example with a $D_{50}$ of 0.5-10 µm e.g. around 1-5 µm. Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{90}$ values and refer to the particle size whereby 10% of the distribution lies below the $D_{10}$ value, and 90% of the distribution lies below the $D_{90}$ value, respectively.

Topical administration to the lung may also be achieved by use of a dry-powder formulation. A dry powder formulation will contain the compound of the disclosure in finely divided form, typically with a mass mean diameter (MMAD) of 1-10 µm or a $D_{50}$ of 0.5-10 µm e.g. around 1-5 µm. Powders of the compound of the invention in finely divided form may be prepared by a micronization process or similar size reduction process. Micronization may be performed using a jet mill such as those manufactured by Hosokawa Alpine. The resultant particle size distribution may be measured using laser diffraction (e.g. with a Malvern Mastersizer 2000S instrument). The formulation will typically contain a topically acceptable diluent such as lactose, glucose or mannitol (preferably lactose), usually of comparatively large particle size e.g. a mass mean diameter (MMAD) of 50 µm or more, e.g. 100 µm or more or a $D_{50}$ of 40-150 µm. As used herein, the term "lactose" refers to a lactose-containing component, including α-lactose monohydrate, β-lactose monohydrate, α-lactose anhydrous, β-lactose anhydrous and amorphous lactose. Lactose components may be processed by micronization, sieving, milling, compression, agglomeration or spray drying. Commercially available forms of lactose in various forms are also encompassed, for example Lactohale® (inhalation grade lactose; DFE Pharma), InhaLac®70 (sieved lactose for dry powder inhaler; Meggle), Pharmatose® (DFE Pharma) and Respitose® (sieved inhalation grade lactose; DFE Pharma) products. In one embodiment, the lactose component is selected from the group consisting of α-lactose monohydrate, α-lactose anhydrous and amorphous lactose. Preferably, the lactose is α-lactose monohydrate.

Dry powder formulations may also contain other excipients. Thus in one embodiment a dry powder formulation according the present disclosure comprises magnesium or calcium stearate. Such formulations may have superior chemical and/or physical stability especially when such formulations also contain lactose.

A dry powder formulation is typically delivered using a dry powder inhaler (DPI) device. Example dry powder delivery systems include SPINHALER®, DISKHALER®, TURBOHALER®, DISKUS®, SKYEHALER®, ACCUHALER® and CLICKHALER®. Further examples of dry powder delivery systems include ECLIPSE, NEXT, ROTAHALER, HANDIHALER, AEROLISER, CYCLOHALER, BREEZHALER/NEOHALER, MONODOSE, FLOWCAPS, TWINCAPS, X-CAPS, TURBOSPIN, ELPENHALER, MIATHALER, TWISTHALER, NOVOLIZER, PRESSAIR, ELLIPTA, ORIEL dry powder inhaler, MICRODOSE, PULVINAL, EASYHALER, ULTRAHALER, TAIFUN, PULMOJET, OMNIHALER, GYROHALER, TAPER, CONIX, XCELOVAIR and PROHALER.

In one embodiment a compound of general formula (I) is provided as a micronized dry powder formulation, for example comprising lactose of a suitable grade.

Thus, as an aspect of the invention there is provided a pharmaceutical composition comprising a compound of general formula (I) in particulate form in combination with particulate lactose, said composition optionally comprising magnesium stearate.

In one embodiment a compound of general formula (I) is provided as a micronized dry powder formulation, comprising lactose of a suitable grade and magnesium stearate, filled into a device such as DISKUS. Suitably, such a device is a multidose device, for example the formulation is filled into blisters for use in a multi-unit dose device such as DISKUS.

In another embodiment a compound of general formula (I) is provided as a micronized dry powder formulation, for example comprising lactose of a suitable grade, filled into hard shell capsules for use in a single dose device such as AEROLISER.

In another embodiment a compound of general formula (I) is provided as a micronized dry powder formulation, comprising lactose of a suitable grade and magnesium stearate, filled into hard shell capsules for use in a single dose device such as AEROLISER.

In another embodiment a compound of general formula (I) is provided as a fine powder for use in an inhalation dosage form wherein the powder is in fine particles with a $D_{50}$ of 0.5-10 μm e.g. around 1-5 μm, that have been produced by a size reduction process other than jet mill micronisation e.g. spray drying, spray freezing, microfluidisation, high pressure homogenisation, super critical fluid crystallisation, ultrasonic crystallisation or combinations of these methods thereof, or other suitable particle formation methods known in the art that are used to produce fine particles with an aerodynamic particle size of 0.5-10 μm. The resultant particle size distribution may be measured using laser diffraction (e.g. with a Malvern Mastersizer 2000S instrument). The particles may either comprise the compound alone or in combination with suitable other excipients that may aid the processing. The resultant fine particles may form the final formulation for delivery to humans or may optionally be further formulated with other suitable excipients to facilitate delivery in an acceptable dosage form.

The compound of the invention may also be administered rectally, for example in the form of suppositories or enemas, which include aqueous or oily solutions as well as suspensions and emulsions and foams. Such compositions are prepared following standard procedures, well known by those skilled in the art. For example, suppositories can be prepared by mixing the active ingredient with a conventional suppository base such as cocoa butter or other glycerides. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the compound of general formula (I) will be about 0.0001 to less than 4.0% (w/w).

Preferably, for topical ocular administration, the compositions administered according to general formula (I) will be formulated as solutions, suspensions, emulsions and other dosage forms. Aqueous solutions are generally preferred, based on ease of formulation, as well as a patient's ability to administer such compositions easily by means of instilling one to two drops of the solutions in the affected eyes. However, the compositions may also be suspensions, viscous or semi-viscous gels, or other types of solid or semi-solid compositions. Suspensions may be preferred for compounds that are sparingly soluble in water.

An alternative for administration to the eye is intravitreal injection of a solution or suspension of the compound of general formula (I). In addition, the compound of general formula (I) may also be introduced by means of ocular implants or inserts.

The compositions administered according to general formula (I) may also include various other ingredients, including, but not limited to, tonicity agents, buffers, surfactants, stabilizing polymer, preservatives, co-solvents and viscosity building agents. Suitable pharmaceutical compositions of general formula (I) include a compound of the invention formulated with a tonicity agent and a buffer. The pharmaceutical compositions of general formula (I) may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars such as dextrose, fructose, galactose, and/or simply polyols such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will be present in the range of 2 to 4% w/w. Preferred tonicity agents of the invention include the simple sugars or the sugar alcohols, such as D-mannitol.

An appropriate buffer system (e.g. sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7.

Surfactants may optionally be employed to deliver higher concentrations of compound of general formula (I). The surfactants function to solubilise the compound and stabilise colloid dispersion, such as micellar solution, microemulsion, emulsion and suspension. Examples of surfactants which may optionally be used include polysorbate, poloxamer, polyosyl 40 stearate, polyoxyl castor oil, tyloxapol, Triton, and sorbitan monolaurate. Preferred surfactants to be employed in the invention have a hydrophile/lipophile/ balance "HLB" in the range of 12.4 to 13.2 and are acceptable for ophthalmic use, such as TritonX114 and tyloxapol.

Additional agents that may be added to the ophthalmic compositions of compounds of general formula (I) are demulcents which function as a stabilising polymer. The stabilizing polymer should be an ionic/charged example with precedence for topical ocular use, more specifically, a polymer that carries negative charge on its surface that can exhibit a zeta-potential of (−)10-50 mV for physical stability and capable of making a dispersion in water (i.e. water soluble). A preferred stabilising polymer of the invention would be polyelectrolyte, or polyelectrolytes if more than one, from the family of cross-linked polyacrylates, such as carbomers and Pemulen®, specifically Carbomer 974p (polyacrylic acid), at 0.1-0.5% w/w.

Other compounds may also be added to the ophthalmic compositions of the compound of general formula (I) to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edentate disodium, sorbic acid, polyquaternium-1, or other agents known to those skilled in the art. Such preservatives are typically employed at a level of from 0.001 to 1.0% w/v. Unit dose compositions of general formula (I) will be sterile, but typically unpreserved. Such compositions, therefore, generally will not contain preservatives.

Parenteral formulations will generally be sterile.

The medical practitioner, or other skilled person, will be able to determine a suitable dosage for the compound of general formula (I), (Ia) or (Ib) and hence the amount of the compound of the invention that should be included in any particular pharmaceutical formulation (whether in unit dosage form or otherwise).

Compounds of general formula (I) may be used in combination with one or more other active agents which are useful in the treatment or prophylaxis of respiratory diseases and conditions.

An additional active agent of this type may be included in the pharmaceutical composition described above but alternatively it may be administered separately, either at the same time as the compound of general formula (I) or at an earlier or later time.

Therefore, in a further aspect of the present invention there is provided a product comprising a compound of general formula (I) and an additional agent useful in the treatment or prevention of respiratory conditions as a combined preparation for simultaneous, sequential or separate use in the treatment of a disease or condition affected by modulation of TMEM16A and especially a respiratory disease or condition, for example one of the diseases and conditions mentioned above.

There is also provided a compound of general formula (I) in combination with an additional agent useful in the treatment or prevention of respiratory conditions as a combined preparation for simultaneous, sequential or separate use in the treatment of a disease or condition affected by modulation of TMEM16A and especially a respiratory disease or condition, for example one of the diseases and conditions mentioned above.

Suitable additional active agents which may be included in a pharmaceutical composition or a combined preparation with the compounds of general formula (I) include:

$\beta 2$ adrenoreceptor agonists such as metaproterenol, isoproterenol, isoprenaline, albuterol, salbutamol, formoterol, salmeterol, indacaterol, terbutaline, orciprenaline, bitolterol mesylate, pirbuterol, olodaterol, vilanterol and abediterol;

antihistamines, for example histamine $H_1$ receptor antagonists such as loratadine, cetirizine, desloratadine, levocetirizine, fexofenadine, astemizole, azelastine and chlorpheniramine or $H_4$ receptor antagonists;

dornase alpha;

corticosteroids such as prednisone, prednisolone, flunisolide, triamcinolone acetonide, beclomethasone dipropionate, budesonide, fluticasone propionate mometasone furoate and fluticasone furoate;

Leukotriene antagonists such as montelukast and zafirlukast;

anticholinergic compounds, particularly muscarinic antagonists such as ipratropium, tiotropium, glycopyrrolate, aclidinium and umeclidinium;

CFTR repair therapies (e.g. CFTR potentiators, correctors or amplifiers) such as Ivacaftor, QBW251, VX659, VX445, VX561/CPT-656, VX152, VX440, GLP2737, GLP2222, GLP2451, PTI438, PTI801, PTI808, FDL-169 and FDL-176 and CFTR correctors such as Lumacaftor and Tezacaftor;

ENaC modulators, particularly ENaC inhibitors;

Antibiotics;

Airway hydrating agents (osmoloytes) such as hypertonic saline and mannitol (Bronchitol®); and Mucolytic agents eg. N-acetyl cytsteine.

When the additional active agent is an ENaC modulator, it may be an ENaC inhibitor such as amiloride, VX-371, AZD5634, QBW276, SPX-101, B1443651 and ETD001. Other suitable ENaC blockers are disclosed in our applications WO 2017/221008, WO 2018/096325, PCT/GB2018/052982 and GB 1808093.7 and any of the example compounds of those applications may be used in combination with the compounds of general formula (I). Particularly suitable compounds for use in combination with the compounds of general formula (I) include compounds having a cation selected from:

2-[({3-amino-5H-pyrrolo[2,3-b]pyrazin-2-yl}formamido)
ethyl]-6-(4-{bis[(2S,3R,4R,5R)-2,3,4,5,6-pentahydroxyhexyl]amino}piperidine-1-carbonyl)-1,3-diethyl-1H-1,3-benzodiazol-3-ium;

2-[({3-amino-5H-pyrrolo[2,3-b]pyrazin-2-yl}formamido)
methyl]-6-{[2-(4-{bis[(2S,3R,4R,5R)-2,3,4,5,6-pentahydroxyhexyl]amino}piperidin-1-yl)ethyl]carbamoyl}-1,3-diethyl-1H-1,3-benzodiazol-3-ium;

2-[({3-amino-5H-pyrrolo[2,3-b]pyrazin-2-yl}formamido)
methyl]-5-[4-({bis[(2S,3R,4R,5R)-2,3,4,5,6-pentahydroxyhexyl]amino}methyl)piperidine-1-carbonyl]-1,3-diethyl-1H-1,3-benzodiazol-3-ium;

2-[({3-amino-5H-pyrrolo[2,3-b]pyrazin-2-yl}formamido)
methyl]-6-[(3R)-3-{bis[(2S,3R,4R,5R)-2,3,4,5,6-pentahydroxyhexyl]amino}pyrrolidine-1-carbonyl]-1,3-diethyl-1H-1,3-benzodiazol-3-ium;

2-[({3-amino-5H-pyrrolo[2,3-b]pyrazin-2-yl}formamido)
methyl]-6-[(3S)-3-{bis[(2S,3R,4R,5R)-2,3,4,5,6-pentahydroxyhexyl]amino}pyrrolidine-1-carbonyl]-1,3-diethyl-1H-1,3-benzodiazol-3-ium;

2-[({3-amino-5H-pyrrolo[2,3-b]pyrazin-2-yl}formamido)
methyl]-1,3-diethyl-6-{[(1r,4r)-4-{bis[(2S,3R,4R,5R)-2,3,4,5,6-pentahydroxyhexyl]amino}cyclohexyl]carbamoyl}-1H-1,3-benzodiazol-3-ium;

2-[({3-amino-5H-pyrrolo[2,3-b]pyrazin-2-yl}formamido)
methyl]-1,3-diethyl-6-{[(1s,4s)-4-{bis[(2S,3R,4R,5R)-2,3,4,5,6-pentahydroxyhexyl]amino}cyclohexyl]carbamoyl}-1H-1,3-benzodiazol-3-ium;

and a suitable anion, for example halide, sulfate, nitrate, phosphate, formate, acetate, trifluoroacetate, fumarate, citrate, tartrate, oxalate, succinate, mandelate, methane sulfonate or p-toluene sulfonate.

The invention is illustrated by the following non-limiting Examples and to the drawing in which:

FIG. 1 is an example trace from a whole-cell patch clamp (Qpatch) TMEM16A potentiator assay as used in Biological Example 95 and illustrates the methodology used in the assay.

EXAMPLES

The invention is illustrated by the following Examples.
General Conditions:

Mass spectra were run on LC-MS systems using electrospray ionization. These were run using either a Waters Acquity uPLC system with Waters PDA and ELS detectors or Shimadzu LCMS-2010EV systems. [M+H]+ refers to mono-isotopic molecular weights. NMR spectra were recorded on a Bruker Avance III HD 500 MHz with a 5 mm Broad Band Inverse probe, a Bruker Avance III HD 250 MHz or a 400 MHz Avance III HD Nanobay fitted with a 5 mm Broad Band Observed SmartProbe using the solvent as internal deuterium lock. Spectra were recorded at room temperature unless otherwise stated and were referenced using the solvent peak.

Referring to the examples that follow, compounds of the preferred embodiments were synthesized using the methods described herein, or other methods, which are known in the art.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

Compounds were purified by flash column chromatography on normal phase silica on Biotage® Isolera systems using the appropriate SNAP cartridge and gradient. Alternatively, compounds were purified on reverse phase silica using Biotage® Isolera systems with the appropriate SNAP C18 cartridges and reverse phase eluent or by preparative HPLC (if stated otherwise).

Preparative HPLC Using Acidic pH, Early Elution Method

Purifications by were performed on a Gilson LC system using Waters Sunfire C18 columns (30 mm×100 mm, 10 μM; temperature: RT) and a gradient of 10-95% B (A=0.1% formic acid in water; B=0.1% formic acid in acetonitrile) over 14.44 min then 95% B for 2.11 min, with an injection volume of 1500 μL and a flow rate of 40 mL/min. UV spectra were recorded at 215 nm using a Gilson detector.

Preparative HPLC Using Acidic pH, Standard Elution Method

Purifications by preparative HPLC (acidic pH, standard elution method) were performed on a Gilson LC system using Waters Sunfire C18 columns (30 mm×100 mm, 10 μM; temperature: RT) and a gradient of 30-95% B (A=0.1% formic acid in water; B=0.1% formic acid in acetonitrile) over 11 min then 95% B for 2.11 min, with an injection volume of 1500 μL and a flow rate of 40 mL/min. UV spectra were recorded at 215 nm using a Gilson detector.

Preparative HPLC Using Basic pH, Early Elution Method

Purifications by preparative HPLC (basic pH, early elution method) were performed on a Gilson LC system using Waters Xbridge C18 columns (30 mm×100 mm, 10 μM; temperature: RT) and a gradient of 10-95% (A=0.2% ammonium hydroxide in water; B=0.2% ammonium hydroxide in acetonitrile) over 14.44 min then 95% B for 2.11 min, with an injection volume of 1500 μL and a flow rate of 40 mL/min. UV spectra were recorded at 215 nm using a Gilson detector.

Preparative HPLC Using Basic pH, Standard Elution Method

Purifications by preparative HPLC (basic pH, standard elution method) were performed on a Gilson LC system using Waters Xbridge C18 columns (30 mm×100 mm, 10 μM; temperature: RT) and a gradient of 30-95% (A=0.2% ammonium hydroxide in water; B=0.2% ammonium hydroxide in acetonitrile) over 11 min then 95% B for 2.11 min, with an injection volume of 1500 μL and a flow rate of 40 mL/min. UV spectra were recorded at 215 nm using a Gilson detector.

If not indicated otherwise, the analytical HPLC conditions are as follows:

Method A
  Column: Phenomenex Kinetix-XB C18 2.1×100 mm, 1.7 μm
  Column Temp 40° C.
  Eluents: A: H20 0.1% formic acid, B: acetonitrile, 0.1% formic acid
  Flow Rate: 0.6 mL/min
  Gradient: 0-5.3 mins 5-100% B, 5.3-5.8 mins 100% B, 5.8-5.82 mins 100-5% B, 5.82-7.00 mins 5% B Method B
  Column: Waters UPLC® CSH™ 018 2.1×100 mm 1.7 μm
  Column Temp 40° C.
  Eluents: A: 2 mM amm. Bicarbonate, buffered to pH10, B: acetonitrile
  Flow Rate: 0.6 mL/min
  Gradient: 0-5.3 mins 5-100% B, 5.3-5.8 mins 100% B, 5.8-5.82 mins 100-5% B, 5.82-7.00 mins 5% B Method C
Column: Waters UPLC® BEH™ 018 2.1×100 mm 1.7 μm
Column Temp 40° C.
Eluents: A: 2 mM ammonium bicarbonate, buffered to pH10, B: acetonitrile
Flow Rate: 0.6 mL/min
Gradient: 0-5.3 mins 5-100% B, 5.3-5.8 mins 100% B, 5.8-5.82 mins 100-5% B, 5.82-7.00 mins 5% B Method D
Column: Waters Atlantis dC18 2.1×100 mm 3 μm
Column Temp 40° C.
Eluents: A: H20+0.1% formic acid, B: acetonitrile+0.1% formic acid
Flow Rate: 0.6 mL/min
Gradient: 0-5 mins 5-100% B, 5-5.4 mins 100% B, 5.4-5.42 mins 100-5% B, 5.42-7.00 mins 5% B Method E
Column: Kinetex Core-Shell C18 2.1×50 mm 5 μm
Column Temp 40° C.
Eluents: A: H20+0.1% formic acid, B: acetonitrile+0.1% formic acid
Flow Rate: 1.2 mL/min
Gradient: 0-1.20 mins 5-100% B, 1.20-1.30 mins 100% B, 1.30-1.31 mins 100-5% B Method F
Column: Phenomenex Gemini-NX C18 2×50 mm 3 μm
Column Temp 40° C.
Eluents: A: 2 mM ammonium bicarbonate, buffered to pH10, B: acetonitrile
Flow Rate: 1 mL/min
Gradient: 0-1.80 mins 1-100% B, 1.80-2.10 mins 100% B, 2.10-2.30 mins 100-1% B The following examples are intended to illustrate the invention and are not to be construed as being limitations thereon. Temperatures are given in degrees centigrade. If not mentioned otherwise, all evaporations are performed in vacuo, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, and NMR. Abbreviations used are those conventional in the art. If not defined, the terms have their generally accepted meanings.

Abbreviation aq. aqueous
br broad
d doublet
dd doublet of doublets
DCM dichloromethane
DIPEA diisopropylethylamine
DMF N,N-dimethylformamide
EDCI 1-ethyl-3-(3-dimethylaminopropyl)carbodiimide
EtOAc ethyl acetate
HOAt 1-hydroxy-7-azabenzotriazole
HATU 2-(7-aza-1H-benzotriazole-1-yl)-1,1,3,3-tetramethyluronium hexafluorophosphate
HPLC high pressure liquid chromatography
MeCN acetonitrile
MeOH methanol
MS mass spectrometry
m multiplet
min minute(s)
mL milliliter(s)
m/z mass to charge ratio
NCS N-chlorosuccinimide
NMR nuclear magnetic resonance
PTFE polytetrafluoroethylene
Rt retention time
s singlet
t triplet
TBME methyl tert-butyl ether
TBTU N,N,N',N'-tetramethyl-O-(benzotriazol-1-yl)uronium tetrafluoroborate
TEA triethylamine
TFA trifluoroacetic acid
THF tetrahydrofuran
T3P® 1,2. propylphosphonic anhydride

PREPARATION OF EXAMPLES

Example 1

N-tert-Butyl-4-[[2-(2-hydroxyphenyl)acetyl]amino]pyridine-2-carboxamide

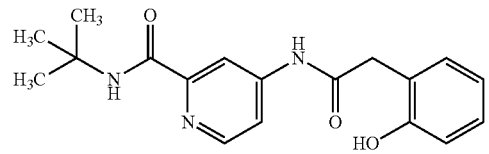

Step 1: Methyl 4-[[2-(2-methoxyphenyl)acetyl]amino]pyridine-2-carboxylate

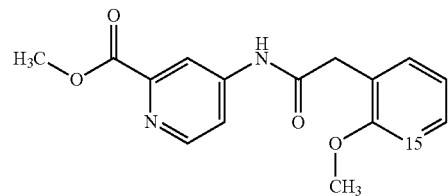

To a solution of 2-(2-methoxyphenyl)acetic acid (218 mg, 1.31 mmol) in DMF (4 mL) was added HOAt (179 mg, 1.31 mmol), EDCI (328 mg, 1.71 mmol), DIPEA (574 μL, 3.29 mmol) and methyl 4-aminopyridine-2-carboxylate (200 mg, 1.31 mmol) and the mixture was stirred at room temperature for 6 hours 15 minutes. The resulting mixture was partitioned between H₂O (30 mL) and DCM (30 mL) and the two phases separated. The aqueous was further extracted with DCM (30 mL) and the combined organic extracts were washed with brine, dried over Na₂SO₄, filtered and concentrated in vacuo. The crude product was purified by chromatography on silica eluting with EtOAc in heptane to afford the titled compound as a pale yellow gum.

1H NMR (500 MHz, Chloroform-d) δ 8.58 (d, J=5.5 Hz, 1H), 8.10 (s, 1H), 7.92 (dd, J=5.5, 2.2 Hz, 1H), 7.84 (d, J=2.1 Hz, 1H), 7.37-7.32 (m, 1H), 7.29 (dd, J=7.4, 1.5 Hz, 1H), 7.04-6.97 (m, 2H), 3.98 (s, 3H), 3.97 (s, 3H), 3.75 (s, 2H).

LC-MS (Method E): Rt 0.96 mins; MS m/z 301.1=[M+H]+ (99% @ 215 nm)

Step 2: 4-[[2-(2-Hydroxyphenyl)acetyl]amino]pyridine-2-carboxylic acid

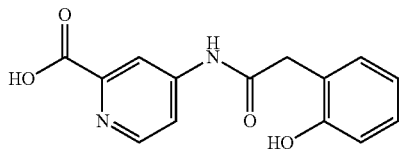

A solution of methyl 4-[[2-(2-methoxyphenyl)acetyl]amino]pyridine-2-carboxylate (step 1) (119 mg, 0.4 mmol) in DCM (1.2 mL) was cooled to 0° C. and treated with 1M BBr₃ in DCM (2.38 mL, 2.38 mmol) over 15 minutes and stirred at 0° C. for 1 hr. After warming to room temperature and the reaction was stirred was further 19 hours. A further portion of 1M BBr₃ in DCM (1.19 mL, 1.19 mmol) was added at room temperature and stirring continued for a further 72 hours. Water (25 mL) was slowly added to the reaction mixture and then the biphasic solution was concentrated in vacuo to yield the titled compound as a brown solid.

1H NMR (500 MHz, Methanol-d4) δ 8.68-8.60 (m, 2H), 8.39 (dd, J=6.7, 2.4 Hz, 1H), 7.18 (dd, J=7.7, 1.6 Hz, 1H), 7.15-7.10 (m, 1H), 6.85-6.79 (m, 2H), 3.84 (s, 2H). (Compound purity 85%).

LC-MS (Method E): Rt 0.74 mins; MS m/z 273.0=[M+H]+ (92% @ 215 nm)

Step 3: N-tert-Butyl-4-[[2-(2-hydroxyphenyl)acetyl]amino]pyridine-2-carboxamide

A solution of 4-[[2-(2-hydroxyphenyl)acetyl]amino]pyridine-2-carboxylic acid (step 2) (138 mg, 0.43 mmol) in DMF (1.5 mL) was treated with EDCI (107 mg, 0.56 mmol), HOAt (59 mg, 0.43 mmol), DIPEA (113 μL, 0.65 mmol) and 2-methylpropan-2-amine (45 μL, 0.43 mmol). The reaction mixture was stirred for 21 hours at room temperature and then concentrated in vacuo. The crude residue was purified by preparative HPLC (acidic pH, early elution method) and the product containing fractions freeze-dried to afford the titled compound as a white solid.

1H NMR (500 MHz, DMSO-d6) δ 10.65 (s, 1H), 9.49 (s, 1H), 8.43 (d, J=5.5 Hz, 1H), 8.18 (d, J=2.0 Hz, 1H), 8.03 (s, 1H), 7.82 (dd, J=5.5, 2.2 Hz, 1H), 7.13 (dd, J=7.5, 1.5 Hz, 1H), 7.07 (td, J=7.8, 1.7 Hz, 1H), 6.79 (dd, J=8.0, 0.9 Hz, 1H), 6.75 (td, J=7.4, 1.1 Hz, 1H), 3.65 (s, 2H), 1.39 (s, 9H).

LC-MS (Method A): Rt 2.86 mins; MS m/z 328.2=[M+H]+ (100% @ 215 nm)

Example 1.1

N-(1,1-Dimethylpropyl)-3-[[2-(2-hydroxyphenyl)acetyl]amino]benzamide

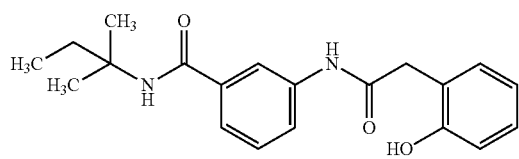 [SMILES: CCC(C)(C)NC(=O)c1cccc(NC(=O)Cc2ccccc2O)c1]

Step 1: Methyl 3-[[2-(2-methoxyphenyl)acetyl]amino]benzoate

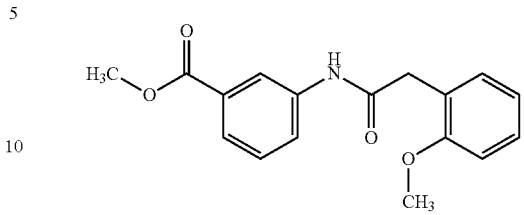

2-(2-Methoxyphenyl)acetic acid (1.09 g, 6.62 mmol) in DMF (1.5 mL) was treated with HOAt (900 mg, 6.62 mmol), EDCI (1.65 g, 8.6 mmol), DIPEA (2.89 mL, 16.54 mmol) and methyl 3-aminobenzoate (1.0 g, 6.62 mmol) and the mixture was stirred at room temperature for 3.5 hours. The resulting mixture was partitioned between H₂O (30 mL) and DCM (30 mL) and the two phases separated. The aqueous was further extracted with DCM (30 mL) and the combined organic extracts were washed with brine, dried over Na₂SO₄, filtered and concentrated in vacuo. The crude product was purified by chromatography on silica eluting with EtOAc in heptane to afford the titled compound as a beige crystalline solid.

1H NMR (500 MHz, DMSO-d6) δ 10.28 (s, 1H), 8.30 (t, J=1.8 Hz, 1H), 7.86-7.80 (m, 1H), 7.62 (dt, J=7.7, 1.2 Hz, 1H), 7.44 (t, J=7.9 Hz, 1H), 7.28-7.19 (m, 2H), 6.98 (d, J=7.9 Hz, 1H), 6.90 (td, J=7.4, 0.9 Hz, 1H), 3.84 (s, 3H), 3.76 (s, 3H), 3.64 (s, 2H).

LC-MS (Method E): Rt 1.10 mins; MS m/z 300.0=[M+H]+ (100% @ 215 nm)

Step 2: 3-[[2-(2-Hydroxyphenyl)acetyl]amino]benzoic acid

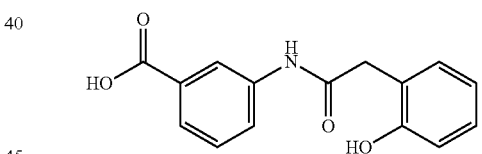

A solution of methyl 3-[[2-(2-methoxyphenyl)acetyl]amino]benzoate (step 1) (1.21 g, 4.04 mmol) in DCM (15 mL) was cooled to 0° C. and treated with 1M BBr₃ in DCM (16.17 mL, 16.17 mmol) over 15 minutes. After completion of addition, the mixture was stirred at 0° C. for 1 hour and then stirred at room temperature for 19 hours. Water (50 mL) was slowly added to the mixture and the DCM concentrated in vacuo. The aqueous residue was extracted with EtOAc (2×50 mL) and the combined organic extracts were washed with brine (15 mL), dried over Na₂SO₄, filtered and concentrated in vacuo. The recovered material was suspended in DCM (7.5 mL), cooled to 0° C. and treated with 1M BBr₃ in DCM (7.0 mL, 7.0 mmol) over 10 minutes. The reaction mixture was stirred at 0° C. for 1 hour and then at room temperature for 4 hours. Water (100 mL) was slowly added to the reaction mixture and the DCM was concentrated in vacuo. The resulting mixture was extracted with EtOAc (2×100 mL). The combined organic extracts were washed with brine (15 mL), dried over Na₂SO₄, filtered and concentrated in vacuo to afford the titled compound as a straw-coloured solid.

1H NMR (500 MHz, DMSO-d6) δ 12.89 (s, 1H), 10.22 (s, 1H), 9.47 (s, 1H), 8.24 (t, J=1.7 Hz, 1H), 7.86-7.80 (m, 1H), 7.60 (dt, J=7.7, 1.2 Hz, 1H), 7.41 (t, J=7.9 Hz, 1H), 7.14 (dd, J=7.5, 1.4 Hz, 1H), 7.07 (td, J=7.8, 1.7 Hz, 1H), 6.80 (dd, J=8.0, 0.9 Hz, 1H), 6.75 (td, J=7.4, 1.1 Hz, 1H), 3.61 (s, 2H).

LC-MS (Method E): Rt 0.93 mins; MS m/z 272.1=[M+H]+ (92% @ 215 nm)

Step 3: N-(1,1-Dimethylpropyl)-3-[[2-(2-hydroxyphenyl)acetyl]amino]benzamide

To a solution of 3-[[2-(2-hydroxyphenyl)acetyl]amino] benzoic acid (step 2) (70 mg, 0.24 mmol) in DMF (1 mL) was added EDCI (59 mg, 0.31 mmol), HOAt (32 mg, 0.24 mmol), DIPEA (62.2 µL, 0.36 mmol) and 2-methylbutan-2-amine (36.1 µL, 0.31 mmol) and the mixture stirred at room temperature for 17 hours. The resulting mixture was partitioned between water (5 mL) and DCM (5 mL). The organic layer was collected using a hydrophobic frit and concentrated in vacuo. The residue was purified by preparative HPLC (acidic pH, early elution method) and the product fractions lyophilised overnight to afford the titled compound as an off-white powder.

1H NMR (500 MHz, DMSO-d6) δ 10.15 (s, 1H), 9.49 (s, 1H), 7.89 (t, J=1.8 Hz, 1H), 7.80-7.74 (m, 1H), 7.54 (s, 1H), 7.40 (dt, J=7.7, 1.2 Hz, 1H), 7.33 (t, J=7.9 Hz, 1H), 7.14 (dd, J=7.5, 1.6 Hz, 1H), 7.06 (td, J=7.8, 1.7 Hz, 1H), 6.80 (dd, J=8.0, 1.0 Hz, 1H), 6.75 (td, J=7.4, 1.1 Hz, 1H), 3.60 (s, 2H), 1.77 (q, J=7.5 Hz, 2H), 1.30 (s, 6H), 0.80 (t, J=7.5 Hz, 3H).

LC-MS (Method A): Rt 2.96 mins; MS m/z 341.2=[M+H]+ (99% @ 215 nm).

The compounds of the following tabulated Examples (Table 1) were prepared analogously to Example 1 by replacing 2-(2-methoxyphenyl)acetic acid (step 1) and methyl 4-aminopyridine-2-carboxylate (step 1) with the appropriate commercially available acid and amine and by replacing 2-methylpropan-2-amine (step 3) with the appropriate amine.

TABLE 1

| Ex. | Structure and Name | 1H NMR, LCMS Retention Time, [M+H]+ |
|---|---|---|
| 1.2 | 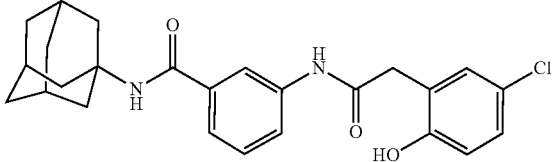<br>N-(1-Adamantyl)-3-[[2-(5-chloro-2-hydroxyphenyl)acetyl]amino]benzamide | 1H NMR (500 MHz, DMSO-d6) δ 10.20 (br. s, 1H), 9.81 (br. s, 1H), 7.87 (t, J = 1.8 Hz, 1H), 7.78-7.72 (m, 1H), 7.55 (s, 1H), 7.44-7.37 (m, 1H), 7.32 (t, J = 7.9 Hz, 1H), 7.20 (d, J = 2.7 Hz, 1H), 7.11 (dd, J = 8.6, 2.7 Hz, 1H), 6.80 (d, J = 8.6 Hz, 1H), 3.61 (s, 2H), 2.05 (s, 9H), 1.65 (s, 6H). LC-MS (Method A): Rt 3.86 mins; MS m/z 439.3/441.3 = [M + H]+ (100% @ 215 nm) |
| 1.3 | 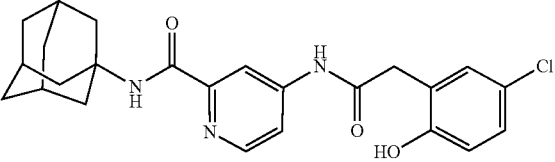<br>N-(1-Adamantyl)-4-[[2-(5-chloro-2-hydroxyphenyl)acetyl]amino]pyridine-2-carboxamide | 1H NMR (500 MHz, DMSO-d6) δ 10.70 (br. s, 1H), 9.83 (br. s, 1H), 8.44 (d, J = 5.5 Hz, 1H), 8.15 (d, J = 2.0 Hz, 1H), 7.91 (s, 1H), 7.82 (dd, J = 5.5, 2.2 Hz, 1H), 7.21 (d, J = 2.7 Hz, 1H), 7.12 (dd, J = 8.6, 2.7 Hz, 1H), 6.80 (d, J = 8.6 Hz, 1H), 3.67 (s, 2H), 2.06 (s, 9H), 1.67 (s, 6H). LC-MS (Method A): Rt 4.12 mins; MS m/z 440.3/442.3 = [M + H]+ (100% @ 215 nm) |
| 1.4 | 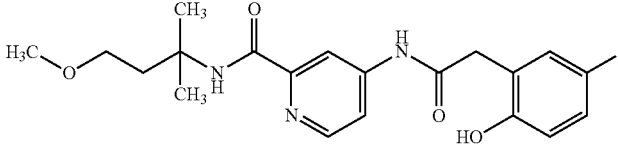<br>4-[[2-(5-Chloro-2-hydroxy-phenyl)acetyl]amino]-N-(3-methoxy-1,1-dimethyl-propyl)pyridine-2-carboxamide | 1H NMR (500 MHz, DMSO-d6) δ 10.63 (br. s, 1H), 9.82 (br. s, 1H), 8.47-8.41 (m, 2H), 8.18-8.13 (m, 1H), 7.80 (dd, J = 5.5, 2.0 Hz, 1H), 7.24-7.18 (m, 1H), 7.14-7.08 (m, 1H), 6.82-6.77 (m, 1H), 3.66 (s, 2H), 3.44 (t, J = 6.3 Hz, 2H), 3.23 (s, 3H), 1.95 (t, J = 6.3 Hz, 2H), 1.40 (s, 6H). LC-MS (Method A): Rt 3.15 mins; MS m/z 406.3/408.3 = [M + H]+ (100% @ 215 nm) |
| 1.5 | 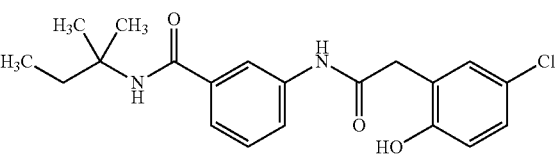<br>3-[[2-(5-Chloro-2-hydroxy-phenyl)acetyl]amino]-N-(1,1-dimethyl propyl)benzamide | 1H NMR (500 MHz, DMSO-d6) δ 10.19 (s, 1H), 9.78 (br. s, 1H), 7.88 (t, J = 1.8 Hz, 1H), 7.82-7.70 (m, 1H), 7.54 (s, 1H), 7.43-7.39 (m, 1H), 7.33 (t, J = 7.9 Hz, 1H), 7.20 (d, J = 2.7 Hz, 1H), 7.11 (dd, J = 8.6, 2.7 Hz, 1H), 6.80 (d, J = 8.6 Hz, 1H), 3.61 (s, 2H), 1.77 (q, J = 7.5 Hz, 2H), 1.30 (s, 6H), 0.80 (t, J = 7.5 Hz, 3H). LC-MS (Method A): Rt 3.31 mins; MS m/z 375.2/377.2 = [M + H]+ (100% @ 215 nm) |

TABLE 1-continued

| Ex. | Structure and Name | 1H NMR, LCMS Retention Time, [M+H]+, |
|---|---|---|
| 1.6 | Synthesis details given at the end of the table | |
| 1.7 | 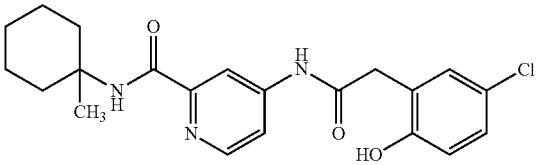  4-[[2-(5-Chloro-2-hydroxy-phenyl)acetyl]amino]-N-(1-methylcyclohexyl)pyridine-2-carboxamide | 1H NMR (500 MHz, DMSO-d6) δ 10.74 (s, 1H), 9.84 (s, 1H), 8.45 (d, J = 5.5 Hz, 1H), 8.17 (d, J = 2.1 Hz, 1H), 7.97 (s, 1H), 7.82 (dd, J = 5.5, 2.2 Hz, 1H), 7.21 (d, J = 2.6 Hz, 1H), 7.12 (dd, J = 8.6, 2.7 Hz, 1H), 6.80 (d, J = 8.6 Hz, 1H), 3.67 (s, 2H), 2.18-2.08 (m, 2H), 1.55-1.32 (m, 10H), 1.32-1.20 (m, 1H). LC-MS (Method A): Rt 3.78 mins; MS m/z 402.3/404.3 = [M + H]+ (100% @ 215 nm) |
| 1.8 | 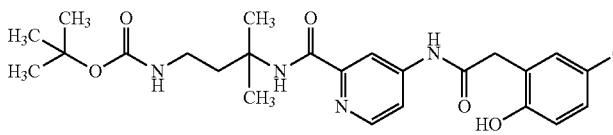  tert-Butyl N-[3-[[4-[[2-(5-chloro-2-hydroxy-phenyl)acetyl]amino]pyridine-2-carbonyl]amino]-3-methyl-butyl]carbamate | 1H NMR (500 MHz, Methanol-d4) δ 8.43 (d, J = 5.5 Hz, 1H), 8.13-8.11 (m, 1H), 7.90 (dd, J = 5.5, 2.2 Hz, 1H), 7.19 (d, J = 2.6 Hz, 1H), 7.09 (dd, J = 8.6, 2.6 Hz, 1H), 6.78 (d, J = 8.6 Hz, 1H), 3.71 (s, 2H), 3.15-3.09 (m, 2H), 2.06-2.01 (m, 2H), 1.46 (s, 6H), 1.37 (s, 9H). LC-MS (Method A): Rt 3.44 mins; MS m/z 491.3/493.3 = [M + H]+ (100% @ 215 nm) |
| 1.9 | 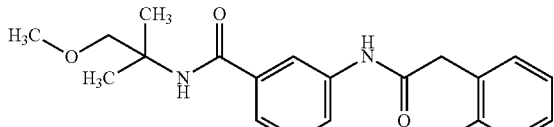  3-[[2-(2-Hydroxyphenyl)acetyl]amino]-N-(2-methoxy-1,1-dimethyl-ethyl)benzamide | 1H NMR (500 MHz, DMSO-d6) δ 10.15 (s, 1H), 9.48 (s, 1H), 7.90 (t, J = 1.8 Hz, 1H), 7.81-7.73 (m, 1H), 7.56 (s, 1H), 7.43-7.38 (m, 1H), 7.33 (t, J = 7.9 Hz, 1H), 7.14 (dd, J = 7.5, 1.5 Hz, 1H), 7.06 (td, J = 7.8, 1.7 Hz, 1H), 6.80 (dd, J = 8.0, 1.0 Hz, 1H), 6.75 (td, J = 7.4, 1.1 Hz, 1H), 3.60 (s, 2H), 3.51 (s, 2H), 3.27 (s, 3H), 1.32 (s, 6H). LC-MS (Method A): Rt 2.70 mins; MS m/z 357.2 = [M + H]+ (99% @ 215 nm) |

Example 1.6

4-[[2-(5-Chloro-2-hydroxy-phenyl)acetyl]amino]-N-(1-methylcyclobutyl)pyridine-2-carboxamide

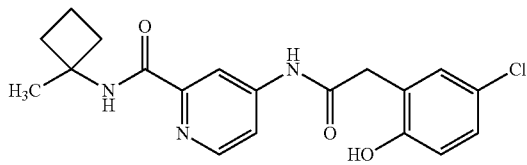 [SMILES: CC1(NC(=O)c2cc(NC(=O)Cc3cc(Cl)ccc3O)ccn2)CCC1]

To a solution of 4-[[2-(5-chloro-2-hydroxy-phenyl)acetyl]amino]pyridine-2-carboxylic acid (Example 31 step 1)(800 mg, 2.61 mmol), 1-methylcyclobutanamine hydrochloride (381 mg, 3.13 mmol) and TEA (800 µL, 5.74 mmol) in DMF (15 mL) was added HATU (1.19 g, 3.13 mmol) and the mixture was stirred at room temperature overnight. The resulting mixture was concentrated in vacuo and the residue was dissolved in EtOAc and washed sequentially with aqueous 1M HCl, sat. aqueous NaHCO₃, brine and 1M NaOH solution. The organic extracts were dried over Na₂SO₄ and concentrated in vacuo. Purification of the crude product by chromatography on silica eluting with 50-100% ethyl acetate in heptanes afforded a pale yellow foam. The isolated material was recrystallised by dissolving in methanol (15 mL) and heating to reflux until all solids had dissolved. The mixture was allowed to cool slowly to room temperature. The resulting crystals were filtered to afford the titled compound as a pale yellow solid.

1H NMR (500 MHz, DMSO-d6) δ 10.67 (s, 1H), 9.81 (s, 1H), 8.47 (s, 1H), 8.45 (d, J=5.5 Hz, 1H), 8.15 (d, J=1.9 Hz, 1H), 7.82 (dd, J=5.5, 2.2 Hz, 1H), 7.22 (d, J=2.7 Hz, 1H), 7.12 (dd, J=8.6, 2.7 Hz, 1H), 6.80 (d, J=8.6 Hz, 1H), 3.67 (s, 2H), 2.42-2.36 (m, 2H), 2.02-1.96 (m, 2H), 1.84-1.77 (m, 2H), 1.47 (s, 3H).

LC-MS (Method A): Rt 3.24 mins; MS m/z 374.3/376.3= [M+H]+ (100% @ 215 nm)

Example 1.10

4-[[2-(5-Chloro-2-hydroxy-phenyl)acetyl]amino]-N-cyclohexyl-pyridine-2-carboxamide

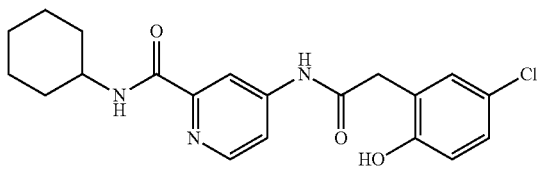 [SMILES: O=C(Cc1cc(Cl)ccc1O)Nc1ccnc(C(=O)NC2CCCCC2)c1]

Step 1: 4-[[2-(5-Chloro-2-methoxy-phenyl)acetyl]amino]-N-cyclohexyl-pyridine-2-carboxamide

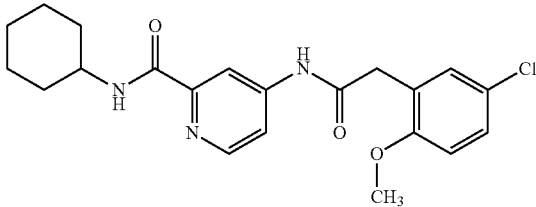 [SMILES: COc1ccc(Cl)cc1CC(=O)Nc1ccnc(C(=O)NC2CCCCC2)c1]

A solution of 4-[[2-(5-chloro-2-methoxy-phenyl)acetyl]amino]pyridine-2-carboxylic acid (Example 8.1 step 2) (3.0 g, 9.07 mmol), cyclohexanamine (1.25 mL, 10.89 mmol), EDCI (2.09 g, 10.89 mmol), HOAt (1.48 g, 10.89 mmol) and DIPEA (3.17 mL, 18.15 mmol) in DMF (30 mL) was stirred at room temperature for 19.5 hours. The resulting mixture was concentrated in vacuo and the residue partitioned between EtOAc (200 mL) and water (200 mL). The organic portion was separated and the aqueous layer re-extracted with EtOAc (2×100 mL). The combined organic extracts were washed with water (2×100 mL), brine (2×100 mL), dried over $Na_2SO_4$ and concentrated in vacuo to afford the titled compound as red/brown solid.

1H NMR (500 MHz, DMSO-d6) δ 10.69 (s, 1H), 8.47 (d, J=5.5 Hz, 1H), 8.38 (d, J=8.6 Hz, 1H), 8.18 (d, J=2.1 Hz, 1H), 7.81 (dd, J=5.5, 2.2 Hz, 1H), 7.35-7.27 (m, 2H), 7.05-6.98 (m, 1H), 3.76 (s, 3H), 3.71 (s, 2H), 1.85-1.67 (m, 4H), 1.64-1.53 (m, 1H), 1.45-1.27 (m, 4H), 1.25-1.03 (m, 2H).

LC-MS (Method E): Rt 1.26 mins; MS m/z 402.0/404.1= [M+H]+ (89% @ 215 nm)

Step 2: 4-[[2-(5-Chloro-2-hydroxy-phenyl)acetyl]amino]-N-cyclohexyl-pyridine-2-carboxamide 1M $BBr_3$ in DCM (21.26 mL, 21.26 mmol) was added to a stirred suspension of 4-[[2-(5-chloro-2-methoxy-phenyl)acetyl]amino]-N-cyclohexyl-pyridine-2-carboxamide (step 1) (3.2 g, 7.09 mmol) in DCM (50 mL) at 0° C. After addition the ice bath was removed and the reaction was stirred at room temperature for 2 hours. The reaction was quenched by slow addition of water (~70 mL) and the mixture was partially concentrated in vacuo to remove volatile solvent. EtOAc (200 mL) was added followed by water (100 mL). The organic portion was separated and the aqueous layer extracted with EtOAc (100 mL). The combined organics were washed with sat. $NaHCO_3$ (2×150 mL), brine (100 mL), dried over $Na_2SO_4$ and concentrated in vacuo. The crude material was purified by C18 reverse phase chromatography eluting with 10-100% MeCN in water with 0.1% formic acid to afford a dark brown/orange solid. The solid was dissolved in a minimum volume of boiling MeCN (~100 mL) and allowed to stand overnight. The resulting crystals were collected by vacuum filtration and dried in a vacuum oven at 40° C. for 5 hours to afford the titled compound as pale beige needles.

1H NMR (500 MHz, DMSO-d6) δ 10.68 (br s, 1H), 9.81 (br s, 1H), 8.46 (d, J=5.5 Hz, 1H), 8.38 (d, J=8.6 Hz, 1H), 8.18 (d, J=2.1 Hz, 1H), 7.82 (dd, J=5.5, 2.2 Hz, 1H), 7.21 (d, J=2.7 Hz, 1H), 7.12 (dd, J=8.6, 2.7 Hz, 1H), 6.80 (d, J=8.6 Hz, 1H), 3.83-3.70 (m, 1H), 3.66 (s, 2H), 1.85-1.75 (m, 2H), 1.75-1.65 (m, 2H), 1.63-1.54 (m, 1H), 1.45-1.25 (m, 4H), 1.21-1.07 (m, 1H).

LC-MS (Method A): Rt 3.46 mins; MS m/z 388.2/390.1= [M+H]+ (100% @ 215 nm)

Example 2

N-tert-Butyl-3-[[2-(5-chloro-2-hydroxy-phenyl)acetyl]amino]benzamide

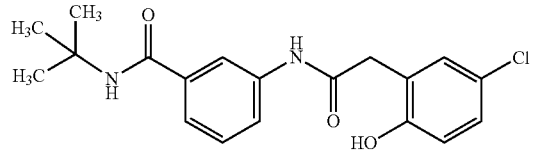 [SMILES: CC(C)(C)NC(=O)c1cccc(NC(=O)Cc2cc(Cl)ccc2O)c1]

Step 1a: tert-Butyl N-[3-(tert-butylcarbamoyl)phenyl]carbamate

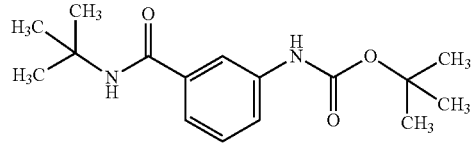

Commercially available 3-(tert-butoxycarbonylamino)benzoic acid (2.5 g, 10.54 mmol) in DMF (40 mL) was treated with HOAt (1.43 g, 10.54 mmol), EDCI (2.63 g, 13.7 mmol), TEA (1.9 mL, 13.7 mmol) and 2-methylpropan-2-amine (1.44 mL, 13.7 mmol) and stirred at room temperature for 2 hours. The resulting mixture was diluted with water (100 mL) with stirring and the resulting white suspension collected by filtration. The filter cake was washed with water (3×15 mL) and oven-dried to afford the titled compound as an off-white solid.

1H NMR (500 MHz, Methanol-d4) δ 7.78-7.70 (m, 1H), 7.52-7.46 (m, 1H), 7.38-7.28 (m, 2H), 1.53 (s, 9H), 1.45 (s, 9H).

LC-MS (Method E): Rt 1.17 mins; MS m/z 293.0=[M+H]+ (100% @ 215 nm)

Step 1b: 3-Amino-N-tert-butyl-benzamide hydrochloride

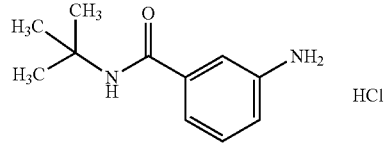

tert-butyl N-[3-(tert-butylcarbamoyl)phenyl]carbamate (step 1a) (5.3 g, 18.13 mmol) was suspended in 1,4-dioxane (20 mL) and then 4M HCl in dioxane (9.59 mL, 271.92 mmol) was added. After stirring at room temperature for 24 hours, the resulting mixture was concentrated in vacuo and azeotroped with methanol. The resulting foam was dried in the vacuum oven at 40° C. for a further 3 hours to afford the titled compound as a light orange foam.

1H NMR (500 MHz, DMSO-d6) δ 10.25 (br s, 2H), 7.91 (s, 1H), 7.76 (d, J=7.1 Hz, 1H), 7.71-7.68 (m, 1H), 7.50 (t, J=7.8 Hz, 1H), 7.47-7.43 (m, 1H), 1.37 (s, 9H).

LC-MS (Method E): Rt 0.73 mins; MS m/z 193.1=[M+H]+ (99% @ 215 nm)

Step 2: 2-(5-Chloro-2-methoxy-phenyl)acetic acid

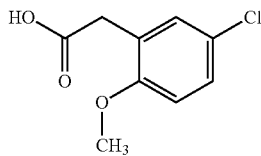

To a cooled (−10° C.), stirred solution of 2-(2-methoxy-phenyl)acetic acid (2.0 g, 12.04 mmol) in THF (34.8 mL) was added dropwise sulfuryl chloride (1.37 mL, 16.85 mmol) over 15 mins and stirring continued for 1 hour. The reaction was quenched with ice cold water (34.8 mL) and extracted into EtOAc (3×50 mL). The combined organic layers were dried over $Na_2SO_4$ and concentrated in vacuo to afford the titled compound as a pink solid.

1H NMR (250 MHz, DMSO-d6) δ 12.24 (s, 1H), 7.30 (d, J=2.7 Hz, 2H), 6.99 (d, J=8.8 Hz, 1H), 3.76 (s, 3H), 3.51 (s, 2H).

LC-MS (Method E): Rt 1.01 mins; MS m/z no characteristic mass ion observed

Step 3: N-tert-Butyl-3-[[2-(5-chloro-2-methoxy-phenyl)acetyl]amino]benzamide

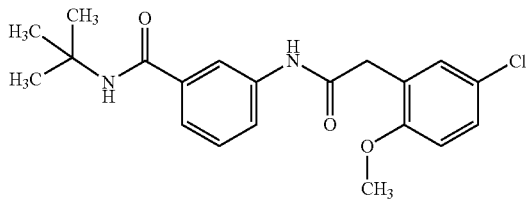 [SMILES: COc1ccc(Cl)cc1CC(=O)Nc1cccc(C(=O)NC(C)(C)C)c1]

To 2-(5-chloro-2-methoxy-phenyl)acetic acid (step 2) (114 mg, 0.57 mmol) in DMF (3 mL) was added HOAt (77 mg, 0.57 mmol), EDCI (142 mg, 0.74 mmol), DIPEA (248 μL, 1.42 mmol) and 3-amino-N-tert-butyl-benzamide hydrochloride (step 1b) (130 mg, 0.57 mmol). The reaction mixture was stirred at room temperature for 1 hour. The resulting mixture was partitioned between water (8 mL) and (DCM (8 mL) and the phases separated using a PTFE-fritted phase separator. The organic layer was concentrated in vacuo and the crude product purified by chromatography on silica eluting with EtOAc in heptane. The product fractions were in vacuo to afford the titled compound as a white solid.

1H NMR (500 MHz, Chloroform-d) δ 7.76-7.64 (m, 3H), 7.41-7.37 (m, 1H), 7.36-7.31 (m, 1H), 7.30-7.26 (m, 2H), 6.88 (d, J=8.6 Hz, 1H), 5.97 (br. s, 1H), 3.92 (s, 3H), 3.68 (s, 2H), 1.45 (s, 9H).

LC-MS (Method E): Rt 1.20 mins; MS m/z 375.0/377.0=[M+H]+ (94% @ 215 nm)

Step 4: N-tert-Butyl-3-[[2-(5-chloro-2-hydroxy-phenyl)acetyl]amino]benzamide

A solution of N-tert-butyl-3-[[2-(5-chloro-2-methoxy-phenyl)acetyl]amino]benzamide (step 3) (3.83 g, 10.2 mmol) in DCM (80 mL) was cooled to 0° C. and 1M $BBr_3$ in DCM (20.4 mL, 20.4 mmol) was added. The reaction mixture was allowed to warm to room temperature and stirred for 4 hours. The resulting mixture was diluted with water (10 mL) and the volatile solvent was removed in vacuo to afford a gummy residue. The residue was dissolved in EtOAc (60 mL) and saturated sodium bicarbonate (60 mL) and stirred for 1 hour to ensure full dissolution. The biphasic mixture was separated and the organic portion was washed with saturated sodium bicarbonate solution (80 mL), brine (80 mL), dried over $Na_2SO_4$ and concentrated in vacuo to afford a thick beige oil. Purification of the crude product by chromatography on silica eluting with 0-100% EtOAc in heptane yielded a white foam. The material was azeotroped with MeCN (2×80 mL) then dissolved in boiling MeCN (~30 mL) and allowed to cool to room temperature. After 3 hours, the resulting crystalline solid was collected by filtration and recrystallized again from boiling MeCN (40 mL) to afford the titled compound as a white crystalline solid.

1H NMR (500 MHz, DMSO-d6) δ 10.22 (s, 1H), 9.81 (s, 1H), 7.90 (t, J=1.7 Hz, 1H), 7.78-7.72 (m, 1H), 7.69 (s, 1H), 7.42 (dt, J=7.8, 1.1 Hz, 1H), 7.33 (t, J=7.9 Hz, 1H), 7.20 (d, J=2.7 Hz, 1H), 7.10 (dd, J=8.6, 2.7 Hz, 1H), 6.80 (d, J=8.6 Hz, 1H), 3.61 (s, 2H), 1.36 (s, 9H).

LC-MS (Method A): Rt 3.19 mins; MS m/z 361.1/363.2=[M+H]+ (100% @ 215 nm)

The compounds of the following tabulated Examples (Table 2) were prepared analogously to Example 2 by replacing 2-(5-chloro-2-methoxy-phenyl)acetic acid (step 2) with the appropriate commercially available acid.

TABLE 2

| Ex. | Structure and Name | 1H NMR, LCMS Retention Time, [M + H]+, |
|---|---|---|
| 2.1 | N-tert-Butyl-3-[[2-(5-fluoro-2-hydroxy-phenyl)acetyl]amino]benzamide | 1H NMR (500 MHz, DMSO-d6) δ 10.17 (br. s, 1H), 9.49 (br. s, 1H), 7.94-7.86 (m, 1H), 7.79-7.73 (m, 1H), 7.69 (s, 1H), 7.44-7.37 (m, 1H), 7.33 (t, J = 7.9 Hz, 1H), 7.00 (dd, J = 9.4, 3.2 Hz, 1H), 6.89 (td, J = 8.6, 3.2 Hz, 1H), 6.77 (dd, J = 8.8, 4.9 Hz, 1H), 3.61 (s, 2H), 1.36 (s, 9H). LC-MS (Method A): Rt 2.83 mins; MS m/z 345.2 = [M + H]+ (99% @ 215 nm) |

TABLE 2-continued

| Ex. | Structure and Name | 1H NMR, LCMS Retention Time, [M + H]+, |
|---|---|---|
| 2.2 | N-tert-Butyl-3-[[2-(3-fluoro-2-hydroxyphenyl)acetyl]amino]benzamide | 1H NMR (500 MHz, DMSO-d6) δ 10.25 (br. s, 1H), 9.65 (br. s, 1H), 7.90 (t, J = 1.7 Hz, 1H), 7.79-7.73 (m, 1H), 7.69 (s, 1H), 7.47-7.39 (m, 1H), 7.33 (t, J = 7.9 Hz, 1H), 7.09-7.01 (m, 1H), 7.01-6.94 (m, 1H), 6.81-6.69 (m, 1H), 3.68 (s, 2H), 1.36 (s, 9H). LC-MS (Method A): Rt 2.80 mins; MS m/z 345.2 = [M + H]+ (99% @ 215 nm) |
| 2.3 | N-tert-Butyl-3-[[2-(4-fluoro-2-hydroxyphenyl)acetyl]amino]benzamide | 1H NMR (500 MHz, DMSO-d6) δ 10.15 (s, 1H), 10.03 (br. s, 1H), 7.90 (t, J = 1.8 Hz, 1H), 7.4-3679-7.73 (m, 1H), 7.70 (s, 1H), 7.47-7.38 (m, 1H), 7.32 (t, J = 7.9 Hz, 1H), 7.20-7.11 (m, 1H), 6.62-6.52 (m, 2H), 3.57 (s, 2H), 1.36 (s, 9H). LC-MS (Method A): Rt 2.87 mins; MS m/z 345.2 = [M + H]+ (100% @ 215 nm) |
| 2.4 | N-tert-Butyl-3-[[2-(2,6-dihydroxyphenyl)acetyl]amino]benzamide | 1H NMR (500 MHz, DMSO-d6) δ 9.98 (s, 1H), 9.29 (br. s, 2H), 7.88 (t, J = 1.8 Hz, 1H), 7.77-7.71 (m, 1H), 7.69 (s, 1H), 7.42-7.36 (m, 1H), 7.31 (t, J = 7.9 Hz, 1H), 6.84 (t, J = 8.1 Hz, 1H), 6.30 (d, J = 8.1 Hz, 2H), 3.59 (s, 2H), 1.36 (s, 9H). LC-MS (Method A): Rt 2.36 mins; MS m/z 343.2 = [M + H]+ (99% @ 215 nm) |
| 2.5 | N-tert-Butyl-3-[3-(2-hydroxyphenyl)propanamido]benzamide | 1H NMR (500 MHz, DMSO-d6) δ 9.99 (br. s, 1H), 9.35 (br. s, 1H), 7.92-7.85 (m, 1H), 7.80-7.73 (m, 1H), 7.70 (s, 1H), 7.44-7.38 (m, 1H), 7.32 (t, J = 7.9 Hz, 1H), 7.09 (dd, J = 7.4, 1.3 Hz, 1H), 7.00 (td, J = 7.8, 1.6 Hz, 1H), 6.81-6.77 (m, 1H), 6.70 (td, J = 7.4, 0.9 Hz, 1H), 2.87-2.79 (m, 2H), 2.61-2.55 (m, 2H), 1.37 (s, 9H). LC-MS (Method A): Rt 2.83 mins; MS m/z 341.2 = [M + H]+ (100% @ 215 nm) |
| 2.6 | N-tert-Butyl-3-[[2-(2-hydroxy-6-methoxyphenyl)acetyl]amino]benzamide | 1H NMR (500 MHz, DMSO-d6) δ 10.00 (s, 1H), 9.44 (br. s, 1H), 7.89 (t, J = 1.8 Hz, 1H), 7.76-7.70 (m, 1H), 7.68 (s, 1H), 7.43-7.36 (m, 1H), 7.31 (t, J = 7.9 Hz, 1H), 7.02 (t, J = 8.2 Hz, 1H), 6.49-6.43 (m, 2H), 3.71 (s, 3H), 3.61 (s, 2H), 1.36 (s, 9H). LC-MS (Method A): Rt 2.76 mins; MS m/z 357.2 = [M + H]+ (100% @ 215 nm) |
| 2.7 | N-tert-Butyl-3-[2-(2-hydroxyphenyl)propanamido]benzamide | 1H NMR (500 MHz, DMSO-d6) δ 10.03 (s, 1H), 9.67 (br. s, 1H), 7.97-7.86 (m, 1H), 7.80-7.74 (m, 1H), 7.69 (s, 1H), 7.43-7.38 (m, 1H), 7.31 (t, J = 7.9 Hz, 1H), 7.21 (dd, J = 7.6, 1.3 Hz, 1H), 7.05 (td, J = 8.0, 1.4 Hz, 1H), 6.84-6.79 (m, 1H), 6.79-6.72 (m, 1H), 4.10 (q, J = 7.0 Hz, 1H), 1.49-1.21 (m, 12H). LC-MS (Method A): Rt 2.96 mins; MS m/z 341.2 = [M + H]+ (100% @ 215 nm) |

TABLE 2-continued

| Ex. | Structure and Name | 1H NMR, LCMS Retention Time, [M + H]+, |
|---|---|---|
| 2.8 | N-tert-Butyl-3-[[2-(2-hydroxy-3-methoxy-phenyl)acetyl]amino] benzamide | 1H NMR (500 MHz, DMSO-d6) δ 10.15 (s, 1H), 8.72 (br. s, 1H), 7.94-7.86 (m, 1H), 7.80-7.73 (m, 1H), 7.70 (s, 1H), 7.44-7.38 (m, 1H), 7.32 (t, J = 7.9 Hz, 1H), 6.86 (dd, J = 7.9, 1.5 Hz, 1H), 6.80-6.75 (m, 1H), 6.75-6.68 (m, 1H), 3.78 (s, 3H), 3.61 (s, 2H), 1.36 (s, 9H). LC-MS (Method A): Rt 2.79 mins; MS m/z 357.3 = [M + H]+ (98% @ 215 nm) |
| 2.9 | N-tert-Butyl-3-[[2-(3,5-difluoro-2-hydroxy-phenyl)acetyl]amino]benzamide | 1H NMR (500 MHz, DMSO-d6) δ 10.26 (s, 1H), 9.60 (br. s, 1H), 7.90 (t, J = 1.8 Hz, 1H), 7.78-7.73 (m, 1H), 7.71 (s, 1H), 7.45-7.40 (m, 1H), 7.33 (t, J = 7.9 Hz, 1H), 7.14-7.06 (m, 1H), 6.95-6.88 (m, 1H), 3.70 (s, 2H), 1.36 (s, 9H). LC-MS (Method A): Rt 2.91 mins; MS m/z 363.2 = [M + H]+ (98% @ 215 nm) |
| 2.10 | 3-[[2-(5-Bromo-2-hydroxy-phenyl)acetyl]amino]-N-tert-butyl-benzamide | 1H NMR (500 MHz, DMSO-d6) δ 10.18 (s, 1H), 9.83 (s, 1H), 7.90 (t, J = 1.8 Hz, 1H), 7.80-7.73 (m, 1H), 7.70 (s, 1H), 7.45-7.39 (m, 1H), 7.37-7.29 (m, 2H), 7.23 (dd, J = 8.6, 2.6 Hz, 1H), 6.76 (d, J = 8.6 Hz, 1H), 3.61 (s, 2H), 1.36 (s, 9H). LC-MS (Method A): Rt 3.14 mins; MS m/z 405.2/407.2 = [M + H]+ (100% @ 215 nm) |
| 2.11 | N-tert-Butyl-3-[[2-(2,3-difluoro-6-hydroxy-phenyl)acetyl]amino] benzamide | 1H NMR (500 MHz, DMSO-d6) δ 10.29 (s, 1H), 10.01 (s, 1H), 7.89 (t, J = 1.8 Hz, 1H), 7.76-7.68 (m, 2H), 7.42 (d, J = 7.8 Hz, 1H), 7.33 (t, J = 7.9 Hz, 1H), 7.12 (q, J = 9.4 Hz, 1H), 6.61 (ddd, J = 8.9, 3.9, 1.6 Hz, 1H), 3.69 (s, 2H), 1.36 (s, 9H). LC-MS (Method A): Rt 2.91 mins; MS m/z 363.2 = [M + H]+ (100% @ 215 nm) |
| 2.12 | N-tert-Butyl-3-[[2-(4,5-difluoro-2-hydroxy-phenyl)acetyl]amino]benzamide | 1H NMR (500 MHz, DMSO-d6) δ 10.20 (s, 1H), 7.89 (t, J = 1.7 Hz, 1H), 7.78-7.73 (m, 1H), 7.70 (s, 1H), 7.44-7.39 (m, 1H), 7.33 (t, J = 7.9 Hz, 1H), 7.22 (dd, J = 11.4, 9.5 Hz, 1H), 6.75 (dd, J = 12.3, 7.2 Hz, 1H), 3.59 (s, 2H), 1.36 (s, 9H). LC-MS (Method A): Rt 2.99 mins; MS m/z 363.2 = [M + H]+ (100% @ 215 nm) |
| 2.13 | N-(1,1-Dimethylpropyl)-3-[[2-(4-fluoro-2-hydroxy-phenyl)acetyl]amino]benzamide | 1H NMR (500 MHz, Methanol-d4) δ 7.88 (t, J = 1.8 Hz, 1H), 7.67 (ddd, J = 8.0, 2.1, 1.1 Hz, 1H), 7.53 (s, 1H), 7.47-7.41 (m, 1H), 7.36 (t, J = 7.9 Hz, 1H), 7.16 (dd, J = 8.1, 6.9 Hz, 1H), 6.59-6.50 (m, 2H), 3.66 (s, 2H), 1.86 (q, J = 7.5 Hz, 2H), 1.38 (s, 6H), 0.90 (t, J = 7.5 Hz, 3H). LC-MS (Method A): Rt 3.08 mins; MS m/z 359.2 = [M + H]+ (100% @ 215 nm) |

TABLE 2-continued

| Ex. | Structure and Name | 1H NMR, LCMS Retention Time, [M + H]+ |
|---|---|---|
| 2.14 | N-tert-Butyl-3-[[2-(2-hydroxy-4-methoxy-phenyl)acetyl]amino]benzamide | 1H NMR (500 MHz, DMSO-d6) δ 10.08 (s, 1H), 9.58 (br. s, 1H), 7.90 (t, J = 1.6 Hz, 1H), 7.80-7.73 (m, 1H), 7.70 (s, 1H), 7.46-7.38 (m, 1H), 7.32 (t, J = 7.9 Hz, 1H), 7.04 (d, J = 8.3 Hz, 1H), 6.39 (d, J = 2.5 Hz, 1H), 6.35 (dd, J = 8.3, 2.5 Hz, 1H), 3.68 (s, 3H), 3.52 (s, 2H), 1.36 (s, 9H). LC-MS (Method A): Rt 2.78 mins; MS m/z 357.3 = [M + H]+ (100% @ 215 nm) |
| 2.15 | N-tert-Butyl-3-[[2-(2-fluoro-6-hydroxy-phenyl)acetyl]amino]benzamide | 1H NMR (500 MHz, DMSO-d6) δ 10.25 (s, 1H), 10.15 (br. s, 1H), 7.94-7.86 (m, 1H), 7.76-7.72 (m, 1H), 7.71 (s, 1H), 7.44-7.38 (m, 1H), 7.33 (t, J = 7.9 Hz, 1H), 7.12-7.05 (m, 1H), 6.66 (d, J = 8.2 Hz, 1H), 6.60 (t, J = 8.8 Hz, 1H), 3.64 (s, 2H), 1.36 (s, 9H). LC-MS (Method A): Rt 2.82 mins; MS m/z 345.2 = [M + H]+ (97% @ 215 nm) |
| 2.16 | N-tert-Butyl-3-[[2-(2,3-dihydroxyphenyl)acetyl]amino]benzamide | 1H NMR (500 MHz, DMSO-d6) δ 10.14 (s, 1H), 9.21 (br. s, 1H), 8.50 (br. s, 1H), 7.89 (t, J = 1.8 Hz, 1H), 7.79-7.73 (m, 1H), 7.70 (s, 1H), 7.41 (dt, J = 7.6, 1.1 Hz, 1H), 7.33 (t, J = 7.9 Hz, 1H), 6.68 (dd, J = 7.6, 1.8 Hz, 1H), 6.61 (dd, J = 7.6, 1.8 Hz, 1H), 6.57 (t, J = 7.6 Hz, 1H), 3.59 (s, 2H), 1.36 (s, 9H). LC-MS (Method A): Rt 2.48 mins; MS m/z 343.2 = [M + H]+ (100% @ 215 nm) |
| 2.17 | N-tert-Butyl-3-[[2-[2-hydroxy-5-(trifluoromethyl)phenyl]acetyl]amino]benzamide | 1H NMR (500 MHz, DMSO-d6) δ 11.12-9.35 (m, 2H), 7.90 (t, J = 1.8 Hz, 1H), 7.77-7.72 (m, 1H), 7.70 (s, 1H), 7.52 (d, J = 2.1 Hz, 1H), 7.46-7.38 (m, 2H), 7.33 (t, J = 7.9 Hz, 1H), 6.95 (d, J = 8.4 Hz, 1H), 3.69 (s, 2H), 1.36 (s, 9H). LC-MS (Method A): Rt 3.27 mins; MS m/z 395.2 = [M + H]+ (100% @ 215 nm) |
| 2.18 | Methyl 3-[2-[3-(tert-butylcarbamoyl)anilino]-2-oxo-ethyl]-4-hydroxy-benzoate | 1H NMR (500 MHz, DMSO-d6) δ 10.48 (br s, 1H), 10.22 (s, 1H), 7.90 (t, J = 1.8 Hz, 1H), 7.82 (d, J = 2.2 Hz, 1H), 7.79-7.74 (m, 1H), 7.73 (dd, J = 8.5, 2.2 Hz, 1H), 7.71 (s, 1H), 7.46-7.39 (m, 1H), 7.33 (t, J = 7.9 Hz, 1H), 6.89 (d, J = 8.5 Hz, 1H), 3.78 (s, 3H), 3.66 (s, 2H), 1.36 (s, 9H). LC-MS (Method A): Rt 2.78 mins; MS m/z 385.2 = [M + H]+ (98% @ 215 nm) |
| 2.19 | N-tert-Butyl-3-[[2-[2-hydroxy-4-(trifluoromethyl)phenyl]acetyl]amino]benzamide | 1H NMR (500 MHz, DMSO-d6) δ 10.27 (s, 2H), 7.90 (t, J = 1.8 Hz, 1H), 7.80-7.73 (m, 1H), 7.70 (s, 1H), 7.47-7.40 (m, 1H), 7.37 (d, J = 7.8 Hz, 1H), 7.33 (t, J = 7.9 Hz, 1H), 7.12-7.08 (m, 1H), 7.08-7.05 (m, 1H), 3.69 (s, 2H), 1.36 (s, 9H). LC-MS (Method A): Rt 3.30 mins; MS m/z 395.2 = [M + H]+ (100% @ 215 nm) |

Example 3

N-tert-Butyl-4-[[2-(5-chloro-2-hydroxy-phenyl)acetyl]amino]pyridine-2-carboxamide

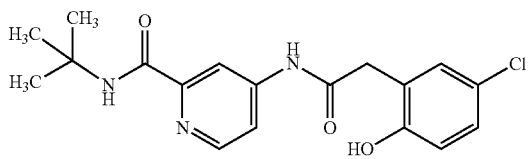

Step 1: 4-Amino-N-tert-butyl-pyridine-2-carboxamide

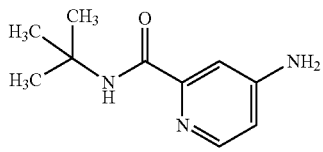

To a mixture of 4-aminopyridine-2-carboxylic acid (8.0 g, 57.92 mmol), TBTU (22.32 g, 69.5 mmol) and TEA (24.22 mL, 173.76 mmol) in DMF (100 mL) was added 2-methylpropan-2-amine (7.30 mL, 69.5 mmol). The resulting mixture was stirred at room temperature for 22 hours and then concentrated in vacuo. The crude material was purified by chromatography on silica eluting with 3.5M methanolic ammonia in DCM and product fractions combined and concentrated in vacuo to yield the titled compound as a light yellow solid.

1H NMR (500 MHz, Methanol-d4) δ 7.99 (d, J=5.6 Hz, 1H), 7.23 (d, J=2.2 Hz, 1H), 6.62 (dd, J=5.6, 2.4 Hz, 1H), 1.45 (s, 9H).

LC-MS (Method F): Rt 1.47 mins; MS m/z 194.3=[M+H]+ (100% @ 215 nm)

Step 2: N-tert-Butyl-4-[[2-(5-chloro-2-methoxyphenyl)acetyl]amino]pyridine-2-carboxamide

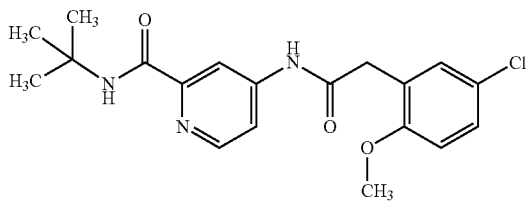

A solution of 2-(5-chloro-2-methoxy-phenyl)acetic acid (2.26 g, 11.27 mmol) in thionyl chloride (8.13 mL, 92.21 mmol) was heated at 70° C. for 30 minutes. After cooling to room temperature, excess thionyl chloride was removed in vacuo, azeotroping with toluene. The resulting residue was dissolved in DCM (5 mL) and added to a solution of 4-amino-N-tert-butyl-pyridine-2-carboxamide (step 1) (2.0 g, 10.25 mmol) and DIPEA (2.15 mL, 12.29 mmol) in DCM (25 mL). The mixture stirred at room temperature for 1 hour and then diluted with water (50 mL) and extracted with DCM. The combined organic extracts were washed with brine (50 mL), dried over Na₂SO₄ and concentrated in vacuo. The crude residue was purified by chromatography on silica eluting with 0-50% EtOAc in heptane to afford the titled compound as a pale orange powder.

1H NMR (500 MHz, Chloroform-d) δ 8.39 (d, J=5.6 Hz, 1H), 8.20 (dd, J=5.6, 2.2 Hz, 1H), 8.10 (br s, 1H), 7.98 (br s, 1H), 7.56 (d, J=2.1 Hz, 1H), 7.29-7.26 (m, 2H), 6.89 (d, J=9.5 Hz, 1H), 3.94 (s, 3H), 3.70 (s, 2H), 1.47 (s, 9H).

LC-MS (Method E): Rt 1.21 mins; MS m/z 376.1/378.1=[M+H]+ (92% @ 215 nm)

Step 3: N-tert-Butyl-4-[[2-(5-chloro-2-hydroxyphenyl)acetyl]amino]pyridine-2-carboxamide To a solution of N-tert-butyl-4-[[2-(5-chloro-2-methoxyphenyl)acetyl]amino]pyridine-2-carboxamide (step 2) (2.7 g, 6.82 mmol, 95%) in DCM (10 mL) at 0° C. was added dropwise 1M BBr₃ in DCM (27.3 mL, 27.3 mmol). Once addition was complete the mixture was allowed to warm to room temperature and stirred for 1 hour. The reaction was quenched by slow addition of water (10 mL) and the DCM removed in vacuo. The resulting residue was dissolved in EtOAc and washed with sat. NaHCO₃ solution (50 mL) and brine (50 mL). The organic portion was separated, dried Na₂SO₄ and concentrated in vacuo. The crude residue was purified by chromatography on silica eluting with 0-70% EtOAc in heptane to afford the product as an orange powder. This was further purified by reverse phase chromatography eluting with 0-100% MeCN in water with 0.1% formic acid to give the product as a colourless powder. The product was recrystallised from MeCN to afford the titled compound. A second crop was isolated by dropwise addition of water to the MeCN filtrate followed by heating and cooling of the mixture.

1H NMR (500 MHz, DMSO-d6) δ 10.69 (br s, 1H), 9.82 (br s, 1H), 8.44 (d, J=5.5 Hz, 1H), 8.17 (d, J=1.9 Hz, 1H), 8.03 (s, 1H), 7.82 (dd, J=5.5, 2.2 Hz, 1H), 7.22 (d, J=2.7 Hz, 1H), 7.12 (dd, J=8.6, 2.7 Hz, 1H), 6.80 (d, J=8.6 Hz, 1H), 3.67 (s, 2H), 1.40 (s, 9H).

LC-MS (Method A): Rt 3.28 mins; MS m/z 362.1/364.1=[M+H]+ (99% @ 215 nm)

Compounds of the following tabulated Examples (Table 3a) were prepared analogously to Example 3 by replacing 2-methylpropan-2-amine (step 1) with the appropriate amine and by replacing 2-(5-chloro-2-methoxy-phenyl)acetic acid (step 2) with the appropriate commercially available acid.

TABLE 3a

| Ex. | Structure and Name | 1H NMR, LCMS Retention Time, [M + H]+, |
|---|---|---|
| 3.1a | 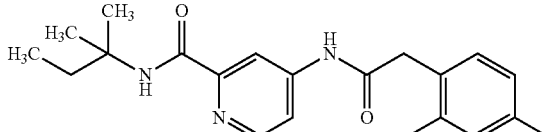<br>N-(1,1-Dimethylpropyl)-4-[[2-(4-fluoro-2-hydroxy-phenyl)acetyl]amino]pyridine-2-carboxamide | 1H NMR (500 MHz, DMSO-d6) δ 10.69 (s, 1H), 10.05 (br. s, 1H), 8.49-8.40 (m, 1H), 8.20-8.14 (m, 1H), 7.94 (s, 1H),7.81 (dd, J = 5.5, 2.2 Hz, 1H), 7.21-7.09 (m, 1H), 6.65-6.49 (m, 2H), 3.63 (s, 2H), 1.77 (q, J = 7.5 Hz, 2H), 1.34 (s, 6H), 0.81 (t, J = 7.5 Hz, 3H).<br>LC-MS (Method A): Rt 3.25 mins; MS m/z 360.3 = [M + H]+ (100% @ 215 nm) |
| 3.2a | 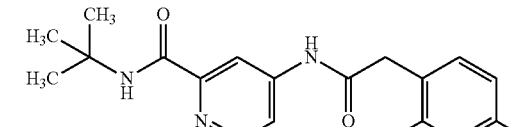<br>N-tert-Butyl-4-[[2-(4-fluoro-2-hydroxy-phenyl)acetyl]amino]pyridine-2-carboxamide | 1H NMR (500 MHz, DMSO-d6) δ 12.34-9.82 (m, 2H), 9.28-9.21 (m, 1H), 9.00-8.96 (m, 1H), 8.84 (s, 1H), 8.62 (dd, J = 5.5, 2.2 Hz, 1H), 8.01-7.92 (m, 1H), 7.43-7.35 (m, 2H), 4.44 (s, 2H), 2.20 (s, 9H). LC-MS (Method A): Rt 3.00 mins; MS m/z 346.2 = [M + H]+ (100% @ 215 nm) |
| 3.3a | 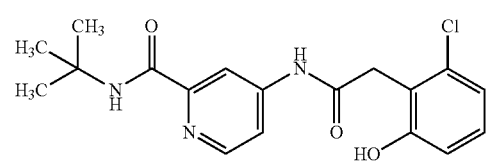<br>N-tert-Butyl-4-[[2-(2-chloro-6-hydroxy-phenyl)acetyl]amino]pyridine-2-carboxamide | 1H NMR (500 MHz, Methanol-d4) δ 8.44-8.39 (m, 1H), 8.11-8.07 (m, 1H), 7.91 (dd, J = 5.6, 2.2 Hz, 1H), 7.09 (t, J = 8.1 Hz, 1H), 6.91 (dd, J = 8.1, 1.0 Hz, 1H), 6.77 (dd, J = 8.2, 1.0 Hz, 1H), 3.96 (s, 2H), 1.47 (s, 9H). LC-MS (Method A): Rt 3.17 mins; MS m/z 362.2/364.2 = [M + H]+ (98% @ 215 nm) |
| 3.4a | <br>4-[[2-(4-Bromo-5-chloro-2-hydroxy-phenyl)acetyl]amino]-N-tert-butyl-pyridine-2-carboxamide | 1H NMR (500 MHz, DMSO-d6) δ 10.70 (s, 1H), 10.27 (s, 1H), 8.44 (d, J = 5.5 Hz, 1H), 8.16 (d, J = 2.0 Hz, 1H), 8.03 (s, 1H), 7.80 (dd, J = 5.5, 2.2 Hz, 1H), 7.43 (s, 1H), 7.12 (s, 1H), 3.67 (s, 2H), 1.40 (s, 9H).<br>LC-MS (Method A): Rt 3.59 mins; MS m/z 440.0/441.9/443.9 = [M + H]+ (95% @ 215 nm) |
| 3.5a | 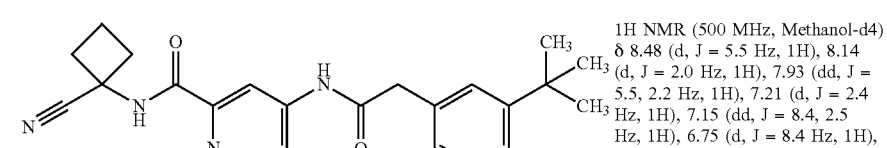<br>4-[[2-(5-tert-Butyl-2-hydroxy-phenyl)acetyl]amino]-N-(1-cyanocyclobutyl)pyridine-2-carboxamide | 1H NMR (500 MHz, Methanol-d4) δ 8.48 (d, J = 5.5 Hz, 1H), 8.14 (d, J = 2.0 Hz, 1H), 7.93 (dd, J = 5.5, 2.2 Hz, 1H), 7.21 (d, J = 2.4 Hz, 1H), 7.15 (dd, J = 8.4, 2.5 Hz, 1H), 6.75 (d, J = 8.4 Hz, 1H), 3.72 (s, 2H), 2.84-2.75 (m, 2H), 2.63-2.53 (m, 2H), 2.28-2.16 (m, 1H), 2.18-2.06 (m, 1H), 1.28 (s, 9H).<br>LC-MS (Method A): Rt 3.40 mins; MS m/z 407.4 = [M + H]+ (98% @ 215 nm) |
| 3.6a | 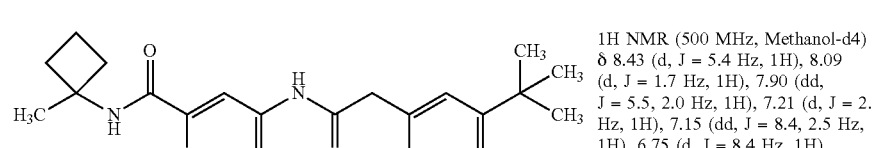<br>4-[[2-(5-tert-Butyl-2-hydroxy-phenyl)acetyl]amino]-N-(1-methyl cyclobutyl)pyridine-2-carboxamide | 1H NMR (500 MHz, Methanol-d4) δ 8.43 (d, J = 5.4 Hz, 1H), 8.09 (d, J = 1.7 Hz, 1H), 7.90 (dd, J = 5.5, 2.0 Hz, 1H), 7.21 (d, J = 2.4 Hz, 1H), 7.15 (dd, J = 8.4, 2.5 Hz, 1H), 6.75 (d, J = 8.4 Hz, 1H), 3.72 (s, 2H), 2.50-2.39 (m, 2H), 2.17-2.07 (m, 2H), 1.97-1.85 (m, 2H), 1.55 (s, 3H), 1.28 (s, 9H). LC-MS (Method A): Rt 3.77 mins; MS m/z 396.4 = [M + H]+ (100% @ 215 nm) |

TABLE 3a-continued

| Ex. | Structure and Name | 1H NMR, LCMS Retention Time, [M + H]+, |
|---|---|---|
| 3.7a | 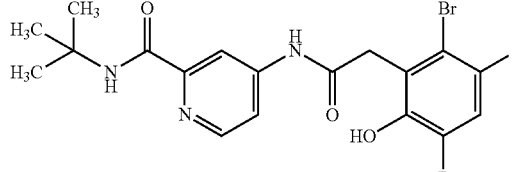<br>N-tert-butyl-4-[2-(2,5-dibromo-3-fluoro-6-hydroxyphenyl)acetamido]pyridine-2-carboxamide | 1H NMR (500 MHz, DMSO-d6) δ 10.87 (s, 1H), 9.74 (s, 1H), 8.45 (d, J = 5.5 Hz, 1H), 8.15 (d, J = 2.0 Hz, 1H), 8.03 (s, 1H), 7.80 (dd, J = 5.5, 2.2 Hz, 1H), 7.65 (d, J = 8.1 Hz, 1H), 4.03 (s, 2H), 1.40 (s, 9H).<br>LC-MS (Method A): Rt 3.61 mins; MS m/z 502.1/504.1/506.1 = [M + H]+ (99% @ 215 nm) |

Example 3.5b

N-tert-Butyl-4-[[2-[2-hydroxy-5-(trifluoromethyl) phenyl]acetyl]amino]pyridine-2-carboxamide

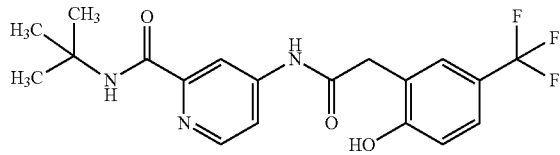

Step 1: N-tert-butyl-4-[[2-[2-methoxy-5-(trifluoromethyl)phenyl]acetyl]amino]pyridine-2-carboxamide

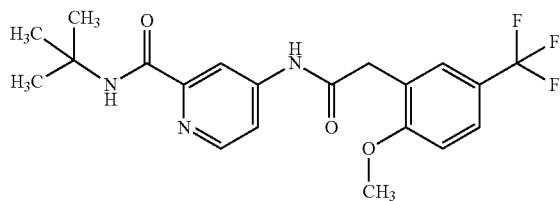 [SMILES: COc1ccc(C(F)(F)F)cc1CC(=O)Nc1ccnc(C(=O)NC(C)(C)C)c1]

To a solution of 4-amino-N-tert-butyl-pyridine-2-carboxamide (Example 3 step 1) (70 mg, 0.36 mmol), TEA (127 µL, 0.72 mmol) and 2-[2-methoxy-5-(trifluoromethyl)phenyl]acetic acid (102 mg, 0.43 mmol) in 1,4-dioxane (1 mL) was added T3P® 50% solution in EtOAc (948 µL, 0.8 mmol) and the reaction mixture was stirred at room temperature for 1 hour. The resulting mixture was partitioned between water (25 mL) and EtOAc (25 mL). The organic layer was separated, washed with water (20 mL), dried over Na₂SO₄ and concentrated in vacuo. The crude residue was purified by chromatography on silica eluting with EtOAc in heptane to afford the titled compound as a pale yellow solid.

1H NMR (500 MHz, DMSO-d6) δ 10.75 (s, 1H), 8.44 (d, J=5.5 Hz, 1H), 8.17 (d, J=2.1 Hz, 1H), 8.03 (s, 1H), 7.80 (dd, J=5.5, 2.2 Hz, 1H), 7.69-7.61 (m, 2H), 7.18 (d, J=8.5 Hz, 1H), 3.83 (s, 3H), 3.81 (s, 2H), 1.40 (s, 9H).

LC-MS (Method E): Rt 1.23 mins; MS m/z 410.0=[M+H]+ (93% @ 215 nm)

Step 2: N-tert-Butyl-4-[[2-[2-hydroxy-5-(trifluoromethyl)phenyl]acetyl]amino]pyridine-2-carboxamide The titled compound was prepared from N-tert-butyl-4-[[2-[2-methoxy-5-(trifluoromethyl)phenyl]acetyl]amino]pyridine-2-carboxamide (step 2) analogously to Example 3 step 3.

1H NMR (500 MHz, DMSO-d6) δ 11.32-9.82 (m, 2H), 8.44 (d, J=5.5 Hz, 1H), 8.17 (d, J=2.0 Hz, 1H), 8.03 (s, 1H), 7.82 (dd, J=5.5, 2.2 Hz, 1H), 7.54 (d, J=2.0 Hz, 1H), 7.45 (dd, J=8.5, 2.1 Hz, 1H), 6.95 (d, J=8.4 Hz, 1H), 3.76 (s, 2H), 1.40 (s, 9H).

LC-MS (Method A): Rt 3.41 mins; MS m/z 396.2=[M+H]+ (100% @ 215 nm)

Compounds of the following tabulated Examples (Table 3b) were prepared analogously Example 3.5b steps 1 and 2 by replacing 2-[2-methoxy-5-(trifluoromethyl)phenyl]acetic acid (step 1) with the appropriate commercially available acid.

TABLE 3b

| Ex. | Structure and Name | 1H NMR LCMS Retention Time, [M + H]+, |
|---|---|---|
| 3.6b | 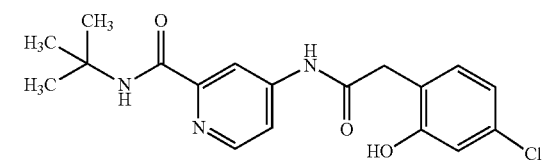 [SMILES: CC(C)(C)NC(=O)c1cc(NC(=O)Cc2ccc(Cl)cc2O)ccn1]<br>N-tert-Butyl-4-[[2-(4-chloro-2-hydroxyphenyl)acetyl]amino]pyridine-2-carboxamide | 1H NMR (500 MHz, Methanol-d4) δ 8.42 (d, J = 5.5 Hz, 1H), 8.12 (d, J = 2.0 Hz, 1H), 7.90 (dd, J = 5.5, 2.2 Hz, 1H), 7.14 (d, J = 8.0 Hz, 1H), 6.84 – 6.77 (m, 2H), 3.70 (s, 2H), 1.47 (s, 9H). LC-MS (Method A): Rt 3.33 mins; MS m/z 362.1/364.1 = [M + H]+ (98% @ 215 nm) |

TABLE 3b-continued

| Ex. | Structure and Name | 1H NMR LCMS Retention Time, [M + H]+, |
|---|---|---|
| 3.7b | 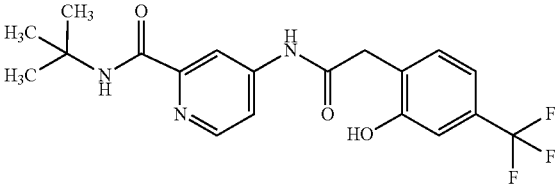 [SMILES: CC(C)(C)NC(=O)c1cc(NC(=O)Cc2ccc(C(F)(F)F)cc2O)ccn1]<br>N-tert-Butyl-4-[[2-[2-hydroxy-4-(trifluoro methyl)phenyl]acetyl]amino]pyridine-2-carboxamide | 1H NMR (500 MHz, DMSO-d6) δ 10.81 (brs, 1H), 10.30 (brs, 1H),8.44 (d, J = 5.5 Hz, 1H), 8.17 (d, J = 2.0 Hz, 1H), 8.03 (s, 1H), 7.81 (dd, J = 5.5, 2.2 Hz, 1H), 7.38 (d, J = 7.8 Hz, 1H), 7.16 – 7.00 (m, 2H), 3.75 (s, 2H), 1.40 (s, 9H) LC-MS (Method A): Rt 3.44 mins; MS m/z 396.2 = [M + H]+ (100% @ 215 nm) |
| 3.8b | 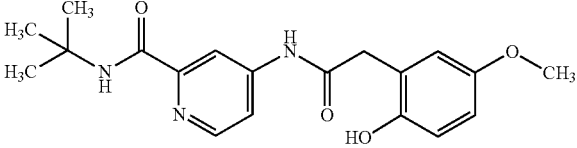 [SMILES: COc1ccc(O)c(CC(=O)Nc2ccnc(C(=O)NC(C)(C)C)c2)c1]<br>N-tert-Butyl-4-[[2-(2-hydroxy-5-methoxy-phenyl)acetyl]amino]pyridine-2-carboxamide | 1H NMR (500 MHz, DMSO-d6) δ 10.64 (s, 1H), 9.06 (s, 1H), 8.43 (d, J = 5.5 Hz, 1H), 8.18 (d, J = 1.9 Hz, 1H), 8.03 (s, 1H), 7.82 (dd, J = 5.5, 2.2 Hz, 1H), 6.76 (d, J = 3.0 Hz, 1H), 6.71 (d, J = 8.7 Hz, 1H), 6.67 (dd, J = 8.7, 3.0 Hz, 1H), 3.66 (s, 3H), 3.63 (s, 2H), 1.40 (s, 9H). LC-MS (Method A): Rt 2.87 mins; MS m/z 358.2 = [M + H]+ (99% @ 215 nm) |
| 3.9b | 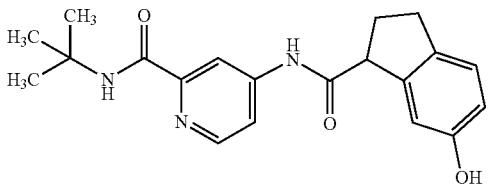 [SMILES: CC(C)(C)NC(=O)c1cc(NC(=O)C2CCc3ccc(O)cc32)ccn1]<br>N-tert-Butyl-4-[(6-hydroxyindane-1-carbonyl)amino]pyridine-2-carboxamide | 1H NMR (500 MHz, DMSO-d6) δ 10.83 (s, 1H), 9.16 (s, 1H), 8.47 (d, J = 5.5 Hz, 1H), 8.23 (d, J = 2.0 Hz, 1H), 8.05 (s, 1H), 7.90 (dd, J = 5.5, 2.2 Hz, 1H), 7.05 (d, J = 8.1 Hz, 1H), 6.73 (d, J = 1.9 Hz, 1H), 6.60 (dd, J = 8.1, 2.2 Hz, 1H), 4.07 (t, J = 7.4 Hz, 1H), 2.98 – 2.90 (m, 1H), 2.83 – 2.73 (m, 1H), 2.39 – 2.23 (m, 2H), 1.41 (s, 9H). LC-MS (Method A): Rt 3.00 mins; MS m/z 354.2 = [M + H]+ (100% @ 215 nm) |
| 3.10b | 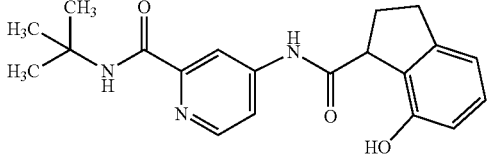 [SMILES: CC(C)(C)NC(=O)c1cc(NC(=O)C2CCc3cccc(O)c32)ccn1]<br>N-tert-Butyl-4-[(7-hydroxyindane-1-carbonyl)amino]pyridine-2-carboxamide | 1H NMR (500 MHz, DMSO-d6) δ 10.64 (s, 1H), 9.49 (s, 1H), 8.44 (d, J = 5.5 Hz, 1H), 8.20 (d, J = 2.1 Hz, 1H), 8.03 (s, 1H), 7.84 (dd, J = 5.5, 2.2 Hz, 1H), 7.02 (t, J = 7.7 Hz, 1H), 6.72 (d, J = 7.4 Hz, 1H), 6.58 (d, J = 7.9 Hz, 1H), 4.11 (dd, J = 8.6, 5.3 Hz, 1H), 3.06 – 2.98 (m, 1H), 2.89 – 2.81 (m, 1H), 2.36 – 2.29 (m, 1H), 2.25 – 2.17 (m, 1H), 1.41 (s, 9H). LC-MS (Method A): Rt 3.26 mins; MS m/z 354.2 = [M + H]+ (96% @ 215 nm) |
| 3.11b | 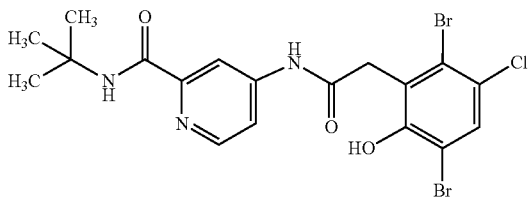 [SMILES: CC(C)(C)NC(=O)c1cc(NC(=O)Cc2c(O)c(Br)cc(Cl)c2Br)ccn1]<br>N-tert-Butyl-4-[[2-(2,5-dibromo-3-chloro-6-hydroxy-phenyl)acetyl]amino]pyridine-2-carboxamide | 1H NMR (500 MHz, DMSO-d6) δ 10.93 (s, 1H), 10.06 (s, 1H), 8.45 (d, J = 5.5 Hz, 1H), 8.14 (d, J = 2.1 Hz, 1H), 8.03 (s, 1H), 7.81 (s, 1H), 7.79 (dd, J = 5.5, 2.2 Hz, 1H), 4.07 (s, 2H), 1.40 (s, 9H). LC-MS (Method A): Rt 3.84 mins; MS m/z 518.0/520.0/522.1 = [M + H]+ (98% @ 215 nm) |
| 3.12b | 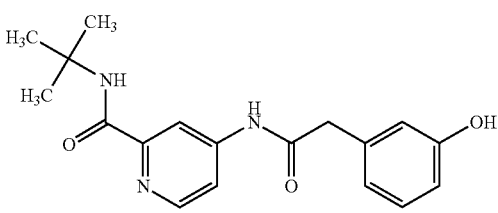 [SMILES: CC(C)(C)NC(=O)c1cc(NC(=O)Cc2cccc(O)c2)ccn1]<br>N-tert-Butyl-4-[[2-(3-hydroxyphenyl)acetyl]amino]pyridine-2-carboxamide | 1H NMR (500 MHz, DMSO-d6) δ 10.71 (s, 1H), 9.35 (s, 1H), 8.44 (d, J = 5.5 Hz, 1H), 8.19 (d, J = 2.0 Hz, 1H), 8.02 (s, 1H), 7.81 (dd, J = 5.5, 2.2 Hz, 1H), 7.11 (t, J = 7.9 Hz, 1H), 6.76 – 6.72 (m, 2H), 6.68 – 6.62 (m, 1H), 3.60 (s, 2H), 1.39 (s, 9H). LC-MS (Method A): Rt 2.68 mins; MS m/z 328.2 = [M + H]+ (99% @ 215 nm). |

TABLE 3b-continued

| Ex. | Structure and Name | 1H NMR LCMS Retention Time, [M + H]+, |
|---|---|---|
| 3.13b | 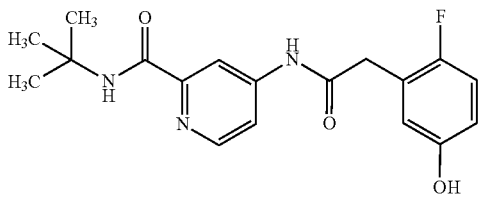 [SMILES: CC(C)(C)NC(=O)c1cc(NC(=O)Cc2cc(O)ccc2F)ccn1]<br>N-tert-Butyl-4-[[2-(2-fluoro-5-hydroxy-phenyl)acetyl]amino]pyridine-2-carboxamide | 1H NMR (500 MHz, DMSO-d6) δ 10.77 (s, 1H), 9.33 (s, 1H), 8.45 (d, J = 5.5 Hz, 1H), 8.18 (d, J = 2.0 Hz, 1H), 8.03 (s, 1H), 7.81 (dd, J = 5.5, 2.2 Hz, 1H), 6.97 (t, J = 9.2 Hz, 1H), 6.75 (dd, J = 6.2, 3.0 Hz, 1H), 6.65 (ddd, J = 8.8, 4.0, 3.2 Hz, 1H), 3.70 (s, 2H), 1.40 (s, 9H).<br>LC-MS (Method A): Rt 2.74 mins; MS m/z 346.2 = [M + H]+ (100% @ 215 nm) |
| 3.14b | 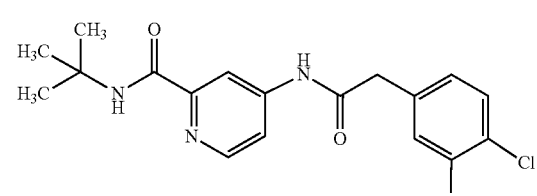<br>N-tert-Butyl-4-[[2-(4-chloro-3-hydroxy-phenyl)acetyl]amino]pyridine-2-carboxamide | 1H NMR (500 MHz, DMSO-d6) δ 10.74 (s, 1H), 10.14 (s, 1H), 8.45 (d, J = 5.5 Hz, 1H), 8.18 (d, J = 2.1 Hz, 1H), 8.02 (s, 1H), 7.80 (dd, J = 5.5, 2.2 Hz, 1H), 7.26 (d, J = 8.1 Hz, 1H), 6.95 (d, J = 2.0 Hz, 1H), 6.76 (dd, J = 8.1, 2.0 Hz, 1H), 3.62 (s, 2H), 1.40 (s, 9H).<br>LC-MS (Method A): Rt 3.01 mins; MS m/z 362.2/364.2 = [M + H]+ (100% @ 215 nm) |
| 3.15b | 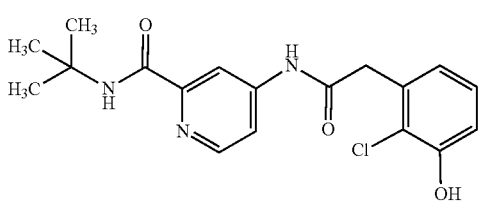 [SMILES: CC(C)(C)NC(=O)c1cc(NC(=O)Cc2cccc(O)c2Cl)ccn1]<br>N-tert-Butyl-4-[[2-(2-chloro-3-hydroxy-phenyl)acetyl]amino]pyridine-2-carboxamide | 1H NMR (500 MHz, DMSO-d6) δ 10.77 (s, 1H), 10.10 (br s, 1H), 8.44 (d, J = 5.5 Hz, 1H), 8.17 (d, J = 2.1 Hz, 1H), 8.03 (s, 1H), 7.80 (dd, J = 5.5, 2.2 Hz, 1H), 7.09 (t, J = 7.8 Hz, 1H), 6.90 (dd, J = 8.2, 1.4 Hz, 1H), 6.84 (dd, J = 7.6, 1.4 Hz, 1H), 3.85 (s, 2H), 1.39 (s, 9H).<br>LC-MS (Method A): Rt 2.97 mins; MS m/z 362.2/364.2 = [M + H]+ (100% @ 215 nm) |
| 3.16b | 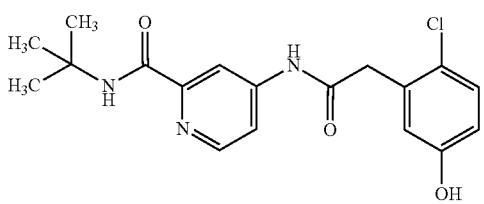 [SMILES: CC(C)(C)NC(=O)c1cc(NC(=O)Cc2cc(O)ccc2Cl)ccn1]<br>N-tert-Butyl-4-[[2-(2-chloro-5-hydroxy-phenyl)acetyl]amino]pyridine-2-carboxamide | 1H NMR (500 MHz, DMSO-d6) δ 10.78 (s, 1H), 9.64 (s, 1H), 8.45 (d, J = 5.5 Hz, 1H), 8.19 (d, J = 2.0 Hz, 1H), 8.03 (s, 1H), 7.80 (dd, J = 5.5, 2.2 Hz, 1H), 7.21 (d, J = 8.7 Hz, 1H), 6.83 (d, J = 2.9 Hz, 1H), 6.70 (dd, J = 8.7, 2.9 Hz, 1H), 3.79 (s, 2H), 1.40 (s, 9H).<br>LC-MS (Method A): Rt 2.98 mins; MS m/z 362.2/364.2 = [M + H]+ (100% @ 215 nm) |
| 3.17b | 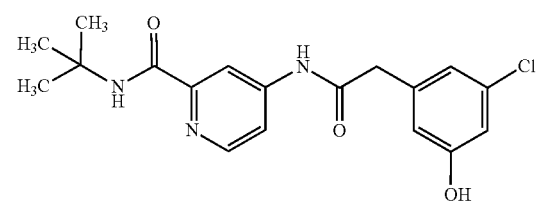 [SMILES: CC(C)(C)NC(=O)c1cc(NC(=O)Cc2cc(O)cc(Cl)c2)ccn1]<br>N-tert-Butyl-4-[[2-(3-chloro-5-hydroxy-phenyl)acetyl]amino]pyridine-2-carboxamide | 1H NMR (500 MHz, DMSO-d6) δ 10.75 (s, 1H), 9.96 (br. s, 1H), 8.46 (d, J = 5.5 Hz, 1H), 8.18 (d, J = 2.1 Hz, 1H), 8.03 (s, 1H), 7.81 (dd, J = 5.5, 2.2 Hz, 1H), 6.83 (t, J = 1.6 Hz, 1H), 6.73 – 6.68 (m, 2H), 3.64 (s, 2H), 1.40 (s, 9H).<br>LC-MS (Method A): Rt 3.12 mins; MS m/z 362.2/364.2 = [M + H]+ (100% @ 215 nm) |

Example 4

N-tert-Butyl-3-[[2-(3-hydroxyphenyl)acetyl]amino]benzamide

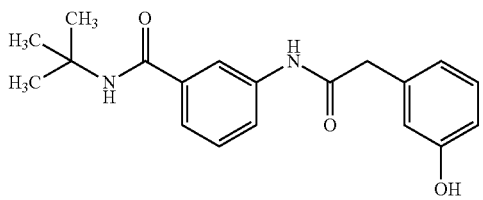 [SMILES: CC(C)(C)NC(=O)c1cccc(NC(=O)Cc2cccc(O)c2)c1]

A mixture comprising 3-amino-N-tert-butyl-benzamide hydrochloride (Example 2 step 1b) (50 mg, 0.22 mmol), EDCI (50 mg, 0.26 mmol), HOAt (36 mg, 0.26 mmol), DIPEA (0.09 mL, 0.52 mmol) in DCM (1.25 mL) was treated with 2-(3-hydroxyphenyl)acetic acid (33 mg, 0.22 mmol) and stirred at room temperature for 1 hour. The resulting mixture was diluted with water (5 mL) and extracted with DCM (3×5 mL). The combined organics were passed through a PTFE phase separator and concentrated in vacuo. The crude product was purified by preparative HPLC (acidic pH, early elution method) and the product fractions were concentrated and dried in vacuo to afford the titled compound as a white solid.

1H NMR (500 MHz, Methanol-d4) δ 7.90 (t, J=1.8 Hz, 1H), 7.72 (s, 1H), 7.69 (ddd, J=8.0, 2.1, 1.1 Hz, 1H), 7.49-7.45 (m, 1H), 7.39 (t, J=7.9 Hz, 1H), 7.19-7.13 (m, 1H), 6.87-6.81 (m, 2H), 6.73-6.68 (m, 1H), 3.63 (s, 2H), 1.46 (s, 9H).

LC-MS (Method B): Rt 2.56 mins; MS m/z 344.3=[M+NH$_3$]+ (99% @ 215 nm)

The compounds of the following tabulated Examples (Table 4) were prepared analogously to Example 4 by replacing 2-(3-hydroxyphenyl)acetic acid with the appropriate commercially available acid.

TABLE 4

| Ex. | Structure and Name | 1H NMR LCMS Retention Time, [M + H]+, |
|---|---|---|
| 4.1 | N-tert-Butyl-3-[[2-(1H-indazol-3-yl)acetyl]amino]benzamide | 1H NMR (500 MHz, Chloroform-d) δ 10.12 (s, 1H), 8.93 (s, 1H), 7.83 – 7.75 (m, 3H), 7.52 (d, J = 8.4 Hz, 1H), 7.47 – 7.43 (m, 1H), 7.40 (d, J = 7.7 Hz, 1H), 7.34 (t, J = 7.8 Hz, 1H), 7.23 (t, J = 7.5 Hz, 1H), 5.96 (s, 1H), 4.14 (s, 2H), 1.46 (s, 9H). LC-MS (Method A): Rt 2.64 mins; MS m/z 351.2 = [M + H]+ (100% @ 215 nm) |
| 4.2 | N-tert-Butyl-3-[[2-(5-fluoro-1H-indol-3-yl)acetyl]amino]benzamide | 1H NMR (500 MHz, Chloroform-d) δ 8.67 (s, 1H), 7.71 (d, J = 8.2 Hz, 1H), 7.61 – 7.57 (m, 2H), 7.35 (d, J = 7.8 Hz, 1H), 7.34 – 7.27 (m, 2H), 7.22 (dd, J = 9.5, 2.1 Hz, 2H), 6.98 (td, J = 9.0, 2.4 Hz, 1H), 5.97 (s, 1H), 3.82 (s, 2H), 1.44 (s, 9H). LC-MS (Method A): Rt 2.97 mins; MS m/z 368.2 = [M + H]+ (100% @ 215 nm) |
| 4.3 | N-tert-Butyl-3-[[2-(2-hydroxyphenyl)acetyl]amino]benzamide | 1H NMR (500 MHz, Methanol-d4) δ 7.86 (t, J = 1.7 Hz, 1H), 7.70-7.63 (m, 1H), 7.44 (d, J = 7.8 Hz, 1H), 7.36 (t, J = 7.9 Hz 6.75 (m, 2H), 3.70 (s, 2H), 1H), 7.19 (d, J = 7.5 Hz, 1H), 7.11 (td, J = 8.0, 1.6 Hz, 1H), 6.89 – 1.44 (s, 9H). LC-MS (Method A): Rt 2.72 mins; MS m/z 327.3 = [M + H]+ (100% @ 215 nm) |
| 4.4 | N-tert-Butyl-3-[[2-(7-fluoro-2-methyl-1H-indol-3-yl)acetyl]amino]benzamide | 1H NMR (500 MHz, Chloroform-d) δ 8.35 (s, 1H), 7.71 (ddd, J = 8.0, 2.0, 1.1 Hz, 1H), 7.54 (t, J = 1.9 Hz, 1H), 7.40 (s, 1H), 7.35 (dt, J = 7.7, 1.3 Hz, 1H), 7.30 (t, J = 7.8 Hz, 1H), 7.24 (d, J = 7.9 Hz, 1H), 7.04 (td, J = 7.9, 4.7 Hz, 1H), 6.90 (ddd, J = 11.0, 7.9, 0.6 Hz, 1H), 5.93 (s, 1H), 3.81 (s, 2H), 2.47 (s, 3H), 1.43 (s, 9H). LC-MS (Method A): Rt 3.15 mins; MS m/z 382.2 = [M + H]+ (100% @ 215 nm) |

TABLE 4-continued

| Ex. | Structure and Name | 1H NMR LCMS Retention Time, [M + H]+, |
|---|---|---|
| 4.5 | N-tert-Butyl-3-[[2-(1H-indol-3-yl)acetyl]amino]benzamide | 1H NMR (500 MHz, DMSO-d6) δ 10.91 (s, 1H), 10.19 (s, 1H), 7.89 (t, J = 1.8 Hz, 1H), 7.81 – 7.75 (m, 1H), 7.70 (s, 1H), 7.61 (d, J = 7.9 Hz, 1H), 7.41 (dt, J = 7.9, 1.3 Hz, 1H), 7.35 (d, J = 8.1 Hz, 1H), 7.32 (t, J = 7.9 Hz, 1H), 7.26 (d, J = 2.3 Hz, 1H), 7.07 (td, J = 8.0, 7.0, 1.1 Hz, 1H), 6.98 (td, J = 7.5, 7.1, 0.9 Hz, 1H), 3.73 (s, 2H), 1.36 (s, 9H). LC-MS (Method A): Rt 2.91 mins; MS m/z 350.2 = [M + H]+ (100% @ 215 nm) |
| 4.6 | N-tert-Butyl-3-[(2-phenylacetyl)amino]benzamide | 1H NMR (500 MHz, Chloroform-d) δ 7.72 (d, J = 7.9 Hz, 1H), 7.65 (d, J = 1.8 Hz, 1H), 7.44 – 7.38 (m, 3H), 7.38 – 7.31 (m, 4H), 7.13 (s, 1H), 5.95 (s, 1H), 3.76 (s, 2H), 1.45 (s, 9H). LC-MS (Method A): Rt 2.96 mins; MS m/z 311.2 = [M + H]+ (99% @ 215 nm) |
| 4.7 | N-tert-Butyl-3-[[2-(2-fluoro-6-methoxyphenyl)acetyl]amino]benzamide | 1H NMR (500 MHz, DMSO-d6) δ 10.24 (s, 1H), 7.92 – 7.87 (m, 1H), 7.75 – 7.67 (m, 2H), 7.41 (d, J = 7.8 Hz, 1H), 7.35 – 7.25 (m, 2H), 6.86 (d, J = 8.4 Hz, 1H), 6.80 (t, J = 8.7 Hz, 1H), 3.79 (s, 3H), 3.68 (s, 2H), 1.36 (s, 9H). LC-MS (Method A): Rt 3.01 mins; MS m/z 359.1 = [M + H]+ (100% @ 215 nm) |
| 4.8 | N-tert-Butyl-3-[[2-(2,3-difluoro-6-methoxyphenyl)acetyl]amino]benzamide | 1H NMR (500 MHz, Chloroform-d) δ 7.75 (t, J = 1.8 Hz, 1H), 7.71 (d, J = 8.0 Hz, 1H), 7.61 (s, 1H), 7.40 (d, J = 7.8 Hz, 1H), 7.34 (t, J = 7.9 Hz, 1H), 7.10 (q, J = 9.2 Hz, 1H), 6.65 (ddd, J = 9.2, 3.4, 2.0 Hz, 1H), 5.97 (s, 1H), 3.90 (s, 3H), 3.79 (d, J = 1.6 Hz, 2H), 1.45 (s, 9H). LC-MS (Method A): Rt 3.19 mins; MS m/z 377.3 = [M + H]+ (98% @ 215 nm) |
| 4.9 | N-tert-Butyl-3-[[2-[2-methoxy-4-(trifluoromethyl)phenyl]acetyl]amino]benzamide | 1H NMR (500 MHz, DMSO-d6) δ 10.24 (s, 1H), 7.90 (t, J = 1.8 Hz, 1H), 7.79 – 7.68 (m, 2H), 7.44 (dd, J = 14.6, 7.8 Hz, 2H), 7.33 (t, J = 7.9 Hz, 1H), 7.28 (d, J = 7.8 Hz, 1H), 7.25 (s, 1H), 3.85 (s, 3H), 3.73 (s, 2H), 1.36 (s, 9H). LC-MS (Method A): Rt 3.45 mins; MS m/z 409.2 = [M + H]+ (100% @ 215 nm) |

Example 5

N-tert-Butyl-4-[[2-(2-thienyl)acetyl]amino]pyridine-2-carboxamide

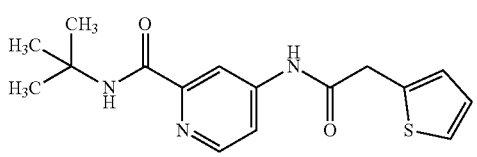

A solution of 4-amino-N-tert-butyl-pyridine-2-carboxamide (Example 3 step 1) (50 mg, 0.26 mmol), 2-(2-thienyl)acetic acid (37 mg, 0.26 mmol) and TEA (0.09 mL, 0.52 mmol) in 1,4-dioxane (2 mL) was treated with 50% T3P® solution in EtOAc (617 μL, 0.97 mmol) and stirred at room temperature under an inert atmosphere for 1 hour. The resulting mixture was diluted with EtOAc (10 mL) and washed with water (10 mL). The organic portion was separated and concentrated in vacuo. Purification by preparative HPLC (acidic pH, standard elution method) and freeze drying of the product fractions afforded the titled compound as a white solid.

1H NMR (500 MHz, DMSO-d6) δ 10.80 (s, 1H), 8.46 (d, J=5.5 Hz, 1H), 8.19 (d, J=2.0 Hz, 1H), 8.03 (s, 1H), 7.80 (dd,

J=5.5, 2.2 Hz, 1H), 7.41 (dd, J=5.0, 1.4 Hz, 1H), 7.03-6.94 (m, 2H), 3.95 (s, 2H), 1.40 (s, 9H)

LC-MS (Method A): Rt 3.19 mins; MS m/z 318.2=[M+H]+ (99% @ 215 nm).

Example 5.1

4-[[2-(2-Adamantyl)acetyl]amino]-N-tert-butyl-pyridine-2-carboxamide

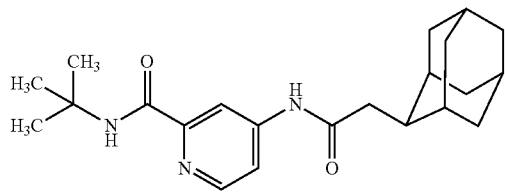 [SMILES: CC(C)(C)NC(=O)c1cc(NC(=O)CC2C3CC4CC(C3)CC2C4)ccn1]

A solution of 2-(2-adamantyl)acetic acid (40 mg, 0.21 mmol) in thionyl chloride (160 µL, 1.82 mmol) was heated at 70° C. for 30 minutes. Excess thionyl chloride was removed in vacuo (azeotropic drying with DCM) and the residue was treated with a mixture of 4-amino-N-tert-butyl-pyridine-2-carboxamide (Example 3 step 1) (40 mg, 0.21 mmol) and DIPEA (43 µL, 0.25 mmol) in DCM (1.5 mL) and stirred at room temperature for 1 hour. The resulting mixture was partitioned with water (5 mL) and DCM (5 mL). The phases were separated through a PTFE-fritted separator and the organic layer concentrated in vacuo. The crude product was purified by preparative HPLC (acidic pH, standard elution method) and the product fractions concentrated in vacuo to afford the titled compound as a white crystalline solid.

1H NMR (500 MHz, DMSO-d6) δ 10.50 (s, 1H), 8.42 (d, J=5.5 Hz, 1H), 8.19 (d, J=2.0 Hz, 1H), 8.02 (s, 1H), 7.79 (dd, J=5.5, 2.2 Hz, 1H), 2.54-2.51 (m, 2H), 2.27-2.19 (m, 1H), 1.94-1.87 (m, 2H), 1.87-1.83 (m, 1H), 1.83-1.77 (m, 3H), 1.77-1.71 (m, 2H), 1.71-1.65 (m, 4H), 1.54-1.49 (m, 2H), 1.39 (s, 9H).

LC-MS (Method A): Rt 4.29 mins; MS m/z 370.3=[M+H]+ (100% @ 215 nm)

The compounds of the following tabulated Examples (Table 5) were prepared analogously to either Example 5 (using T3P®) or Example 5.1 (using thionyl chloride) from 4-amino-N-tert-butyl-pyridine-2-carboxamide (Example 3 step 1) and the appropriate commercially available acid.

TABLE 5

| Ex. | Structure and Name | Activating Reagent | 1H NMR LCMS Retention Time, [M + H]+, |
|---|---|---|---|
| 5.2 | N-tert-Butyl-4-[[2-(4-fluoro-2-methoxyphenyl)acetyl]amino]pyridine-2-carboxamide | Thionyl Chloride | 1H NMR (500 MHz, Chloroform-d) δ 8.39 (d, J = 5.6 Hz, 1H), 8.21 (dd, J = 5.6, 2.2 Hz, 1H), 8.01-7.93 (m, 2H), 7.55 (d, J = 2.1 Hz, 1H), 7.23 (dd, J = 8.9, 6.5 Hz, 1H), 6.74 – 6.67 (m, 2H), 3.93 (s, 3H), 3.69 (s, 2H), 1.47 (s, 9H). LC-MS (Method A):Rt 3.31 mins; MS m/z 360.2 = [M + H]+ (97% @ 215 nm) |
| 5.3 | N-tert-Butyl-4-[[2-(5-chloro-2-fluorophenyl)acetyl]amino]pyridine-2-carboxamide | Thionyl Chloride | 1H NMR (500 MHz, DMSO-d6) δ 10.84 (s, 1H), 8.46 (d, J = 5.5 Hz, 1H), 8.16 (d, J = 1.9 Hz, 1H), 8.03 (s, 1H), 7.80 (dd, J = 5.5, 2.2 Hz, 1H), 7.51 (dd, J = 6.4, 2.7 Hz, 1H), 7.40 (ddd, J = 8.7, 4.4, 2.8 Hz, 1H), 7.26 (t, J = 9.1 Hz, 1H), 3.83 (s, 2H), 1.40 (s, 9H). LC-MS (Method A): Rt 3.61 mins; MS m/z 364.2/366.2 = [M + H]+ (97% @ 215 nm) |
| 5.4 | N-tert-Butyl-4-[[2-(2-furyl)acetyl]amino] pyridine-2-carboxamide | T3P ® | 1H NMR (500 MHz, DMSO-d6) δ 10.77 (s, 1H), 8.46 (d, J = 5.5 Hz, 1H), 8.18 (d, J = 2.0 Hz, 1H), 8.03 (s, 1H), 7.80 (dd, J = 5.5, 2.2 Hz, 1H), 7.58 (dd, J = 1.8, 0.7 Hz, 1H), 6.41 (dd, J = 3.1, 1.9 Hz, 1H), 6.36-6.24 (m, 1H), 3.81 (s, 2H), 1.40 (s, 9H). LC-MS (Method A): Rt 2.97 mins; MS m/z 302.2 = [M + H]+ (100% @ 215 nm) |
| 5.5 | | T3P ® | 1H NMR (500 MHz, DMSO-d6) δ 10.78 (s, 1H), 8.45 (d, J = 5.5 Hz, 1H), 8.18 (d, J = 2.0 Hz, 1H), 8.03 (s, 1H), 7.81 (dd, J = 5.5, 2.2 Hz, 1H), 7.43-7.41 (m, 1H), 7.39 – 7.31 (m, 2H), 7.31 – 7.27 (m, 1H), 3.75 (s, 2H), 1.39 (s, 9H) LC-MS (Method A): Rt 3.60 mins; MS m/z 346.2, 348.2 = [M + H]+ (100% @ 215 nm) |

TABLE 5-continued

| Ex. | Structure and Name | Activating Reagent | 1H NMR LCMS Retention Time, [M + H]+, |
|---|---|---|---|
| | N-tert-Butyl-4-[[2-(3-chlorophenyl) acetyl]amino]pyridine-2-carboxamide | | |
| 5.6 | N-tert-Butyl-4-[[2-(1H-indol-3-yl)acetyl] amino]pyridine-2-carboxamide | T3P ® | 1H NMR (500 MHz, DMSO-d6) δ 10.95 (s, 1H), 10.71 (s, 1H), 8.43 (d, J = 5.5 Hz, 1H), 8.20 (d, J = 2.1 Hz, 1H), 8.02 (s, 1H), 7.82 (dd, J = 5.5, 2.2 Hz, 1H), 7.58 (d, J = 7.9 Hz, 1H), 7.36 (d, J = 8.1 Hz, 1H), 7.28 (d, J = 2.1 Hz, 1H), 7.10 – 7.05 (m, 1H), 7.01 – 6.96 (m, 1H), 3.80 (s, 2H), 1.39 (s, 9H). LC-MS (Method A): Rt 3.19 mins; MS m/z 351.2 = [M + H]+ (97% @ 215 nm) |
| 5.7 | N-tert-Butyl-4-[[2-(o-tolyl)acetyl]amino]pyridine-2-carboxamide | T3P ® | 1H NMR (500 MHz, DMSO-d6) δ 10.76 (s, 1H), 8.45 (d, J = 5.5 Hz, 1H), 8.19 (d, J = 2.0 Hz, 1H), 8.03 (s, 1H), 7.81 (dd, J = 5.5, 2.2 Hz, 1H), 7.27 – 7.22 (m, 1H), 7.20 – 7.12 (m, 3H), 3.75 (s, 2H), 2.28 (s, 3H), 1.39 (s, 9H). LC-MS (Method A): Rt 3.46 mins; MS m/z 326.2 = [M + H]+ (98% @ 215 nm) |
| 5.8 | N-tert-Butyl-4-[[2-(3,4-dichlorophenyl) acetyl]amino]pyridine-2-carboxamide | T3P ® | 1H NMR (500 MHz, DMSO-d6) δ 11.62 (s, 1H), 9.26 (d, J = 5.5 Hz, 1H), 8.98 (d, J = 2.0 Hz, 1H), 8.84 (s, 1H), 8.61 (dd, J = 5.5, 2.2 Hz, 1H), 8.42 (d, J = 2.0 Hz, 1H), 8.41 (d, J = 8.3 Hz, 1H), 8.13 (dd, J = 8.3, 2.0 Hz, 1H), 4.59 (s, 2H), 2.20 (s, 9H). LC-MS (Method A): Rt 3.86 mins; MS m/z 380.1/ 382.1/384.1 = [M + H]+ (100% @ 215 nm) |
| 5.9 | N-tert-Butyl-4-[[2-(3-fluorophenyl)acetyl] amino]pyridine-2-carboxamide | T3P ® | 1H NMR (500 MHz, DMSO-d6) δ 10.79 (s, 1H), 8.45 (d, J = 5.5 Hz, 1H), 8.18 (d, J = 2.0 Hz, 1H), 8.02 (s, 1H), 7.81 (dd, J = 5.5, 2.1 Hz, 1H), 7.42 -7.33 (m, 1H), 7.21 – 7.14 (m, 2H), 7.12 – 7.05 (m, 1H), 3.76 (s, 2H), 1.39 (s, 9H). LC-MS (Method A): Rt 3.39 mins; MS m/z 330.2 = [M + H]+ (99% @ 215 nm) |
| 5.10 | N-tert-Butyl-4-[[2-(5-chloro-2-methoxy-phenyl)acetyl]amino]pyridine-2-carboxamide | Thionyl Chloride | 1H NMR (500 MHz, DMSO-d6) δ 10.70 (s, 1H), 8.44 (d, J = 5.5 Hz, 1H), 8.17 (d, J = 1.9 Hz, 1H), 8.03 (s, 1H), 7.80 (dd, J = 5.5, 2.2 Hz, 1H), 7.33 – 7.28 (m, 2H), 7.03 – 6.99 (m, 1H), 3.75 (s, 3H), 3.71 (s, 2H), 1.40 (s, 9H). LC-MS (Method A): Rt 3.61 mins; MS m/z 376.2/ 378.2 = [M + H]+ (98% @ 215 nm) |
| 5.11 | N-tert-Butyl-4-[[2-(p-tolyl)acetyl]amino]pyridine-2-carboxamide | T3P ® | 1H NMR (500 MHz, Methanol-d4) δ 8.42 (d, J = 5.5 Hz, 1H), 8.13 (d, J = 2.0 Hz, 1H), 7.89 (dd, J = 5.5, 2.2 Hz, 1H), 7.22 (d, J = 8.0 Hz, 2H), 7.14 (d, J = 7.9 Hz, 2H), 3.68 (s, 2H), 2.31 (s, 3H), 1.47 (s, 9H). LC-MS (Method A):Rt 3.52 mins; MS m/z 326.2 = [M + H]+ (98% @ 215 nm) |

TABLE 5-continued

| Ex. | Structure and Name | Activating Reagent | 1H NMR LCMS Retention Time, [M + H]+, |
|---|---|---|---|
| 5.12 | 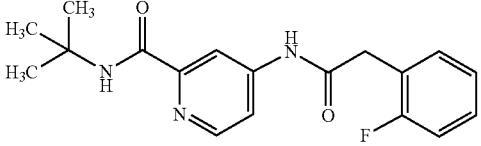 [SMILES: CC(C)(C)NC(=O)c1cc(NC(=O)Cc2ccccc2F)ccn1]<br>N-tert-Butyl-4-[[2-(2-fluorophenyl)acetyl]amino]pyridine-2-carboxamide | T3P ® | 1H NMR (500 MHz, Methanol-d4) δ 8.43 (d, J = 5.3 Hz, 1H), 8.13 (d, J = 1.8 Hz, 1H), 7.90 (dd, J = 5.5, 2.2 Hz, 1H), 7.36 (td, J = 7.6, 1.6 Hz, 1H), 7.31 (tdd, J = 7.4, 5.3, 1.8 Hz, 1H), 7.16 (td, J = 7.5, 1.1 Hz, 1H), 7.10 (ddd, J = 9.5, 8.3, 1.0 Hz, 1H), 3.82 (s, 2H), 1.47 (s, 9H).<br>LC-MS (Method A): Rt 3.30 mins; MS m/z 330.2 = [M + H]+ (98% @ 215 nm) |
| 5.13 | 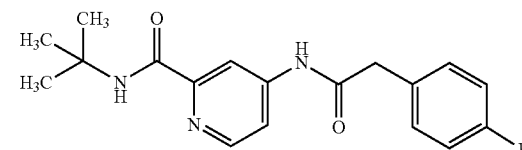<br>N-tert-Butyl-4-[[2-(4-fluorophenyl)acetyl]amino]pyridine-2-carboxamide | T3P ® | 1H NMR (500 MHz, Methanol-d4) δ 8.43 (d, J = 5.5 Hz, 1H), 8.13 (d, J = 1.9 Hz, 1H), 7.90 (dd, J = 5.5, 2.2 Hz, 1H), 7.36 (dd, J = 8.7, 5.4 Hz, 2H), 7.10 – 7.01 (m, 2H), 3.72 (s, 2H), 1.47 (s, 9H).<br>LC-MS (Method A): Rt 3.34 mins; MS m/z 330.2 = [M + H]+ (98% @ 215 nm) |
| 5.14 | 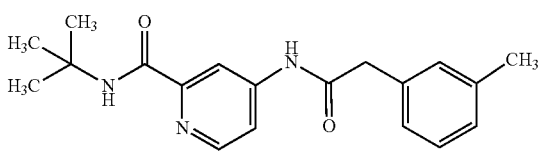 [SMILES: Cc1cccc(CC(=O)Nc2ccnc(C(=O)NC(C)(C)C)c2)c1]<br>N-tert-Butyl-4-[[2-(m-tolyl)acetyl]amino]pyridine-2-carboxamide | T3P ® | 1H NMR (500 MHz, DMSO-d6) δ 10.74 (s, 1H), 8.44 (d, J = 5.5 Hz, 1H), 8.18 (d, J = 2.1 Hz, 1H), 8.02 (s, 1H), 7.81 (dd, J = 5.5, 2.1 Hz, 1H), 7.21 (t, J = 7.5 Hz, 1H), 7.14 (s, 1H), 7.12 (d, J = 7.6 Hz, 1H), 7.07 (d, J = 7.6 Hz, 1H), 3.66 (s, 2H), 2.29 (s, 3H), 1.39 (s, 9H).<br>LC-MS (Method A): Rt 3.58 mins; MS m/z 326.2 = [M + H]+ (98% @ 215 nm) |
| 5.15 | 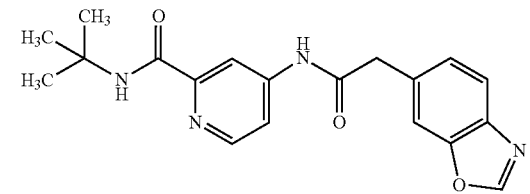 [SMILES: CC(C)(C)NC(=O)c1cc(NC(=O)Cc2ccc3ncoc3c2)ccn1]<br>4-[[2-(1,3-Benzoxazol-6-yl)acetyl]amino]-N-tert-butyl-pyridine-2-carboxamide | T3P ® | 1H NMR (500 MHz, Methanol-d4) δ 8.46 (s, 1H), 8.42 (d, J = 5.5 Hz, 1H), 8.14 (d, J = 1.9 Hz, 1H), 7.90 (dd, J = 5.6, 2.2 Hz, 1H), 7.79 – 7.73 (m, 1H), 7.64 (d, J = 8.4 Hz, 1H), 7.45 (dd, J = 8.5, 1.6 Hz, 1H), 3.88 (s, 2H), 1.47 (s, 9H).<br>LC-MS (Method A): Rt 2.82 mins; MS m/z 353.1 = [M + H]+ (98% @ 215 nm) |
| 5.16 | 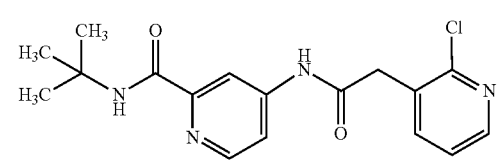 [SMILES: CC(C)(C)NC(=O)c1cc(NC(=O)Cc2cccnc2Cl)ccn1]<br>N-tert-Butyl-4-[[2-(2-chloro-3-pyridyl)acetyl]amino]pyridine-2-carboxamide | T3P ® | 1H NMR (500 MHz, DMSO-d6) δ 10.89 (s, 1H), 8.46 (d, J = 5.5 Hz, 1H), 8.35 (dd, J = 4.8, 1.8 Hz, 1H), 8.18 (d, J = 2.1 Hz, 1H), 8.03 (s, 1H), 7.90 (dd, J = 7.5, 1.8 Hz, 1H), 7.80 (dd, J = 5.5, 2.2 Hz, 1H), 7.44 (dd, J = 7.5, 4.8 Hz, 1H), 3.95 (s, 2H), 1.40 (s, 9H).<br>LC-MS (Method A): Rt 2.76 mins; MS m/z 347.1, 349.1 = [M + H]+ (97% @ 215 nm) |
| 5.17 | 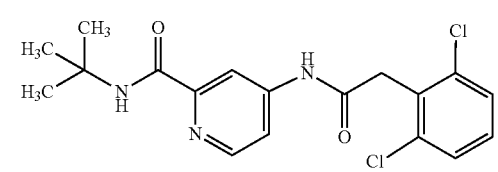 [SMILES: CC(C)(C)NC(=O)c1cc(NC(=O)Cc2c(Cl)cccc2Cl)ccn1]<br>N-tert-Butyl-4-[[2-(2,6-dichlorophenyl)acetyl]amino]pyridine-2-carboxamide | T3P ® | 1H NMR (500 MHz, DMS0-d6) δ 10.95 (s, 1H), 8.46 (d, J = 5.5 Hz, 1H), 8.16 (d, J = 2.1 Hz, 1H), 8.03 (s, 1H), 7.78 (dd, J = 5.5, 2.2 Hz, 1H), 7.51 (d, J = 8.1 Hz, 2H), 7.40 – 7.32 (m, 1H), 4.11 (s, 2H), 1.40 (s, 9H).<br>LC-MS (Method A): Rt 3.66 mins; MS m/z 380.1/382.1/384.1 = [M + H]+ (98% @ 215 nm) |
| 5.18 | 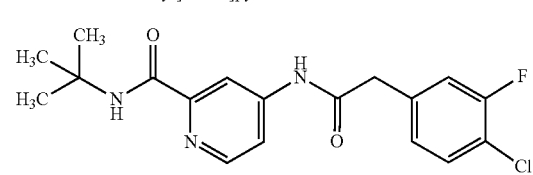<br>N-tert-Butyl-4-[[2-(4-chloro-3-fluoro-phenyl)acetyl]amino]pyridine-2-carboxamide | T3P ® | 1H NMR (500 MHz, DMSO-d6) δ 10.78 (s, 1H), 8.46 (d, J = 5.5 Hz, 1H), 8.17 (d, J = 2.1 Hz, 1H), 8.03 (s, 1H), 7.80 (dd, J = 5.5, 2.2 Hz, 1H), 7.55 (t, J = 8.1 Hz, 1H), 7.39 (dd, J = 10.5, 1.8 Hz, 1H), 7.20 (dd, J = 8.2, 1.6 Hz, 1H), 3.78 (s, 2H), 1.40 (s, 9H).<br>LC-MS (Method A): Rt 3.67 mins; MS m/z 364.1/366.1 = [M + H]+ (97% @ 215 nm) |

TABLE 5-continued

| Ex. | Structure and Name | Activating Reagent | 1H NMR LCMS Retention Time, [M + H]+, |
|---|---|---|---|
| 5.19 | 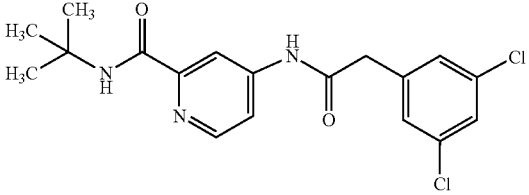 [SMILES: CC(C)(C)NC(=O)c1cc(NC(=O)Cc2cc(Cl)cc(Cl)c2)ccn1]<br>N-tert-Butyl-4-[[2-(3,5-dichloro phenyl)acetyl]amino]pyridine-2-carboxamide | T3P® | 1H NMR (250 MHz, DMSO-d6) δ 10.78 (s, 1H), 8.46 (d, J = 5.5 Hz, 1H), 8.16 (d, J = 1.9 Hz, 1H), 8.03 (s, 1H), 7.81 (dd, J = 5.5, 2.2 Hz, 1H), 7.52 (t, J = 1.9 Hz, 1H), 7.41 (d, J = 1.9 Hz, 2H), 3.80 (s, 2H), 1.40 (s, 9H).<br>LC-MS (Method A): Rt 3.99 mins; MS m/z 380.1/382.1/384.1 = [M + H]+ (94% @ 215 nm) |
| 5.20 | <br>N-tert-Butyl-4-[[2-(2-chlorophenyl) acetyl]amino]pyridine-2-carboxamide | T3P® | 1H NMR (500 MHz, DMSO-d6) δ 10.84 (s, 1H), 8.45 (d, J = 5.5 Hz, 1H), 8.19 (d, J = 2.0 Hz, 1H), 8.03 (s, 1H), 7.81 (dd, J = 5.5, 2.1 Hz, 1H), 7.50 – 7.40 (m, 2H), 7.36 – 7.28 (m, 2H), 3.92 (s, 2H), 1.40 (s, 9H).<br>LC-MS (Method A): Rt 3.44 mins; MS m/z 346.1/348.1 = [M + H]+ (100% @ 215 nm) |
| 5.21 | 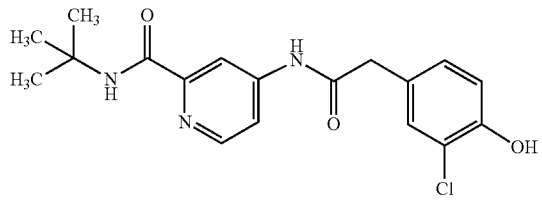 [SMILES: CC(C)(C)NC(=O)c1cc(NC(=O)Cc2ccc(O)c(Cl)c2)ccn1]<br>N-tert-Butyl-4-[[2-(3-chloro-4-hydroxy-phenyl)acetyl]amino]pyridine-2-carboxamide | T3P® | 1H NMR (500 MHz, Methanol-d4) δ 8.42 (d, J = 5.5 Hz, 1H), 8.12 (d, J = 2.0 Hz, 1H), 7.90 (dd, J = 5.5, 2.2 Hz, 1H), 7.29 (d, J = 2.1 Hz, 1H), 7.09 (dd, J = 8.3, 2.2 Hz, 1H), 6.87 (d, J = 8.3 Hz, 1H), 3.62 (s, 2H), 1.47 (s, 9H).<br>LC-MS (Method A): Rt 3.03 mins; MS m/z 362.1/364.1 = [M + H]+ (99% @ 215 nm) |
| 5.22 | 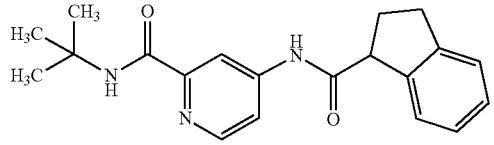 [SMILES: CC(C)(C)NC(=O)c1cc(NC(=O)C2CCc3ccccc32)ccn1]<br>N-tert-Butyl-4-(indane-1-carbonyl amino)pyridine-2-carboxamide | Thionyl Chloride | 1H NMR (500 MHz, DMSO-d6) δ 10.86 (s, 1H), 8.46 (d, J = 5.5 Hz, 1H), 8.23 (d, J = 2.1 Hz, 1H), 8.03 (s, 1H), 7.87 (dd, J = 5.5, 2.2 Hz, 1H), 7.30 (dd, J = 19.3, 7.3 Hz, 2H), 7.20 (t, J = 7.0 Hz, 1H), 7.16 (t, J = 7.0 Hz, 1H), 4.16 (t, J = 7.3 Hz, 1H), 3.10-3.03 (m, 1H), 2.94-2.86 (m, 1H), 2.39 – 2.27 (m, 2H), 1.40 (s, 9H).<br>LC-MS (Method A): Rt 3.58 mins; MS m/z 338.2 = [M + H]+ (100% @ 215 nm) |
| 5.23 | 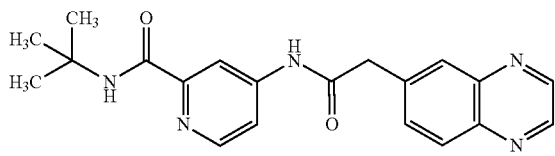 [SMILES: CC(C)(C)NC(=O)c1cc(NC(=O)Cc2ccc3nccnc3c2)ccn1]<br>N-tert-Butyl-4-[(2-quinoxalin-6-ylacetyl) amino]pyridine-2-carboxamide | T3P® | 1H NMR (500 MHz, DMSO-d6) δ 10.89 (s, 1H), 8.96-8.91 (m, 2H), 8.45 (d, J = 5.5 Hz, 1H), 8.20 (d, J = 2.1 Hz, 1H), 8.09-8.06 (m, 2H), 8.02 (s, 1H), 7.87 – 7.81 (m, 2H), 4.04 (s, 2H), 1.39 (s, 9H).<br>LC-MS (Method A): Rt 2.66 mins; MS m/z 364.2 = [M + H]+ (100% @ 215 nm) |
| 5.24 | 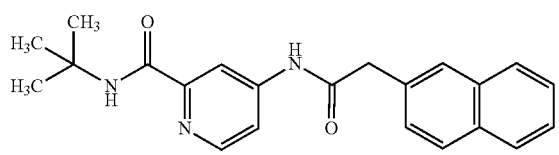 [SMILES: CC(C)(C)NC(=O)c1cc(NC(=O)Cc2ccc3ccccc3c2)ccn1]<br>N-tert-Butyl-4-[[2-(2-naphthyl) acetyl]amino]pyridine-2-carboxamide | T3P® | 1H NMR (500 MHz, DMSO-d6) δ 10.86 (s, 1H), 8.45 (d, J = 5.5 Hz, 1H), 8.21 (d, J = 2.1 Hz, 1H), 8.02 (s, 1H), 7.92 – 7.86 (m, 3H), 7.86 – 7.84 (m, 1H), 7.84 – 7.81 (m, 1H), 7.54 – 7.45 (m, 3H), 3.90 (s, 2H), 1.39 (s, 9H).<br>LC-MS (Method A): Rt 3.74 mins; MS m/z 362.2 = [M + H]+ (99% @ 215 nm) |

TABLE 5-continued

| Ex. | Structure and Name | Activating Reagent | 1H NMR LCMS Retention Time, [M + H]+, |
|---|---|---|---|
| 5.25 | N-tert-Butyl-4-(2,3-dihydrobenzofuran-3-carbonylamino)pyridine-2-carboxamide | T3P ® | 1H NMR (500 MHz, DMSO-d6) δ 10.99 (s, 1H), 8.48 (d, J = 5.5 Hz, 1H), 8.21 (d, J = 2.1 Hz, 1H), 8.03 (s, 1H), 7.87 (dd, J = 5.5, 2.1 Hz, 1H), 7.38 (d, J = 7.4 Hz, 1H), 7.17 (t, J = 7.7 Hz, 1H), 6.85 (t, J = 7.5 Hz, 1H), 6.82 (d, J = 8.0 Hz, 1H), 4.85 (dd, J = 9.0, 6.0 Hz, 1H), 4.70 (t, J = 9.2 Hz, 1H), 4.51 (dd, J = 9.3, 6.0 Hz, 1H), 1.40 (s, 9H). LC-MS (Method A): Rt 3.32 mins; MS m/z 340.2 = [M + H]+ (98% @ 215 nm) |
| 5.26 | N-tert-Butyl-4-(6,7,8,9-tetrahydro-5H-benzo[7]annulene-5-carbonylamino)pyridine-2-carboxamide | T3P ® | 1H NMR (500 MHz, DMSO-d6) δ 10.62 (s, 1H), 8.46 (d, J = 5.5 Hz, 1H), 8.26 (d, J = 2.0 Hz, 1H), 8.03 (s, 1H), 7.82 (dd, J = 5.5, 2.2 Hz, 1H), 7.19 (dd, J = 7.2, 1.6 Hz, 1H), 7.12 (dtd, J = 14.9, 7.3, 1.6 Hz, 2H), 7.00 – 6.97 (m, 1H), 4.06 – 4.01 (m, 1H), 2.93 – 2.80 (m, 2H), 2.06 – 2.00 (m, 1H), 1.91 – 1.63 (m, 4H), 1.43 – 1.32 (m, 10H). LC-MS (Method A): Rt 4.09 mins; MS m/z 366.2 = [M + H]+ (96% @ 215 nm) |
| 5.27 | N-tert-Butyl-4-(tetralin-1-carbonylamino)pyridine-2-carboxamide | T3P ® | 1H NMR (500 MHz, DMSO-d6) δ 10.79 (s, 1H), 8.46 (d, J = 5.5 Hz, 1H), 8.23 (d, J = 2.0 Hz, 1H), 8.03 (s, 1H), 7.85 (dd, J = 5.5, 2.1 Hz, 1H), 7.17 – 7.06 (m, 4H), 3.92 (t, J = 6.6 Hz, 1H), 2.84 – 2.69 (m, 2H), 2.11 – 1.95 (m, 3H), 1.73 – 1.63 (m, 1H), 1.40 (s, 9H). LC-MS (Method A): Rt 3.73 mins; MS m/z 352.2 = [M + H]+ (99% @ 215 nm) |
| 5.29 | N-tert-Butyl-4-[[2-(6-quinolyl)acetyl]amino]pyridine-2-carboxamide | T3P ® | 1H NMR (500 MHz, DMSO-d6) δ 10.87 (s, 1H), 8.87 (dd, J = 4.2, 1.7 Hz, 1H), 8.45 (d, J = 5.5 Hz, 1H), 8.37 – 8.32 (m, 1H), 8.21 (d, J = 2.0 Hz, 1H), 8.02 (s, 1H), 7.99 (d, J = 8.7 Hz, 1H), 7.90 (d, J = 1.5 Hz, 1H), 7.83 (dd, J = 5.5, 2.2 Hz, 1H), 7.74 (dd, J = 8.7, 2.0 Hz, 1H), 7.52 (dd, J = 8.3, 4.2 Hz, 1H), 3.95 (s, 2H), 1.39 (s, 9H). LC-MS (Method A): Rt 1.98 mins; MS m/z 363.2 = [M + H]+ (97% @ 215 nm) |
| 5.31 | N-tert-butyl-4-[[1-(3-chlorophenyl)cyclopropanecarbonyl]amino]pyridine-2-carboxamide | T3P ® | 1H NMR (500 MHz, Methanol-d4) δ 8.41 (d, J = 5.5 Hz, 1H), 8.12 (d, J = 2.1 Hz, 1H), 7.81 (dd, J = 5.6, 2.2 Hz, 1H), 7.52 – 7.47 (m, 1H), 7.40 (dd, J = 5.2, 2.7 Hz, 2H), 7.37 (ddt, J = 6.7, 4.4, 2.5 Hz, 1H), 1.66 -1.60 (m, 2H), 1.47 (s, 9H), 1.28 – 1.22 (m, 2H). LC-MS (Method A): Rt 4.01 mins; MS m/z 372.2/374.2 = [M + H]+ (100% @ 215 nm) |
| 5.32 | N-tert-Butyl-4-[[2-(2,3-dihydro-1,4-benzodioxin-6-yl)acetyl]amino]pyridine-2-carboxamide | Thionyl Chloride | 1H NMR (500 MHz, DMSO-d6) δ 10.67 (s, 1H), 8.44 (d, J = 5.5 Hz, 1H), 8.17 (d, J = 2.0 Hz, 1H), 8.02 (s, 1H), 7.80 (dd, J = 5.5, 2.2 Hz, 1H), 6.83 (d, J = 1.8 Hz, 1H), 6.79 (d, J = 8.2 Hz, 1H), 6.77 (dd, J = 8.3, 1.9 Hz, 1H), 4.21 (s, 4H), 3.57 (s, 2H), 1.39 (s, 9H). LC-MS (Method A): Rt 3.23 mins; MS m/z 370.3/371.3 = [M + H]+ (98% @ 215 nm) |

Example 5.33

N-(1,1-Dimethylprop-2-ynyl)-4-[(2-isochroman-1-ylacetyl)amino]pyridine-2-carboxamide

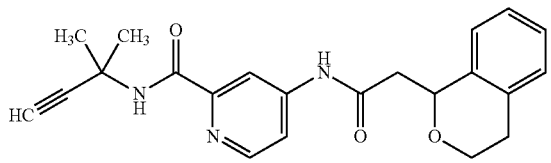 [SMILES: C#CC(C)(C)NC(=O)c1cc(NC(=O)CC2OCCc3ccccc32)ccn1]

The titled compound was prepared from 4-amino-N-(1,1-dimethylprop-2-ynyl)pyridine-2-carboxamide (Example 78 step 1) and 2-isochroman-1-ylacetic acid analogously to Example 5.1

1H NMR (500 MHz, DMSO-d6) δ 10.60 (s, 1H), 8.49 (d, J=5.5 Hz, 1H), 8.33 (s, 1H), 8.22 (d, J=2.0 Hz, 1H), 7.87 (dd, J=5.5, 2.2 Hz, 1H), 7.19 (tdd, J=12.4, 9.2, 5.5 Hz, 4H), 5.19 (dd, J=10.0, 3.1 Hz, 1H), 4.08-4.01 (m, 1H), 3.72 (ddd, J=11.4, 9.0, 4.1 Hz, 1H), 3.21 (s, 1H), 3.09 (dd, J=14.6, 3.4 Hz, 1H), 2.92-2.84 (m, 1H), 2.75-2.67 (m, 2H), 1.65 (s, 6H).

LC-MS (Method A): Rt 3.22 mins; MS m/z 378.3=[M+H]+ (100% @ 215 nm)

Example 5.34

4-[[2-(4,4-Difluorocyclohexyl)acetyl]amino]-N-(1,1-dimethylprop-2-ynyl)pyridine-2-carboxamide

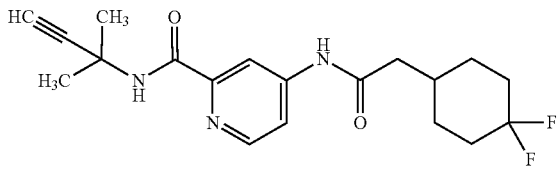 [SMILES: C#CC(C)(C)NC(=O)c1cc(NC(=O)CC2CCC(F)(F)CC2)ccn1]

The titled compound was prepared from 4-amino-N-(1,1-dimethylprop-2-ynyl)pyridine-2-carboxamide (Example 78 step 1) and 2-(4,4-difluorocyclohexyl)acetic acid analogously to Example 5.1

1H NMR (500 MHz, DMSO-d6) δ 10.52 (s, 1H), 8.46 (d, J=5.5 Hz, 1H), 8.30 (s, 1H), 8.20 (d, J=2.0 Hz, 1H), 7.80 (dd, J=5.5, 2.2 Hz, 1H), 3.21 (s, 1H), 2.34 (d, J=7.1 Hz, 2H), 2.05-1.90 (m, 3H), 1.90-1.82 (m, 1H), 1.82-1.75 (m, 3H), 1.64 (s, 6H), 1.32-1.18 (m, 2H).

LC-MS (Method A): Rt 3.26 mins; MS m/z 364.3=[M+H]+ (97% @ 215 nm)

Example 5.35

N-(1,1-Dimethylprop-2-ynyl)-4-[[2-[4-(trifluoromethyl)phenyl]acetyl]amino]pyridine-2-carboxamide

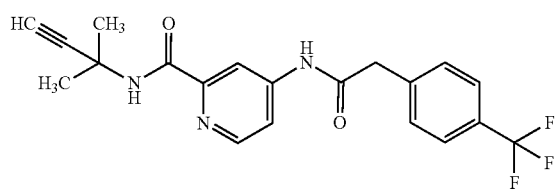 [SMILES: C#CC(C)(C)NC(=O)c1cc(NC(=O)Cc2ccc(C(F)(F)F)cc2)ccn1]

The titled compound was prepared from 4-amino-N-(1,1-dimethylprop-2-ynyl)pyridine-2-carboxamide (Example 78 step 1) and 2-[4-(trifluoromethyl)phenyl]acetic acid analogously to Example 5

1H NMR (500 MHz, DMSO-d6) δ 10.84 (s, 1H), 8.47 (d, J=5.5 Hz, 1H), 8.31 (s, 1H), 8.19 (d, J=2.0 Hz, 1H), 7.82 (dd, J=5.5, 2.2 Hz, 1H), 7.70 (d, J=8.1 Hz, 2H), 7.56 (d, J=8.1 Hz, 2H), 3.86 (s, 2H), 3.20 (s, 1H), 1.64 (s, 6H).

LC-MS (Method A): Rt 3.53 mins; MS m/z 390.2=[M+H]+ (100% @ 215 nm)

Example 5.36

N-(1,1-Dimethylprop-2-ynyl)-4-[[2-[3-(trifluoromethyl)-1H-pyrazol-4-yl]acetyl]amino]pyridine-2-carboxamide

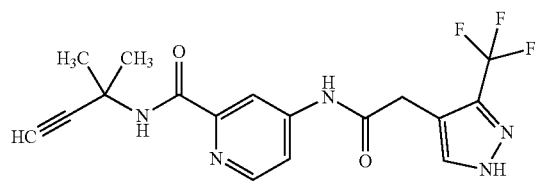 [SMILES: C#CC(C)(C)NC(=O)c1cc(NC(=O)Cc2c[nH]nc2C(F)(F)F)ccn1]

Step 1: 2-[3-(Trifluoromethyl)-1H-pyrazol-4-yl]acetic acid

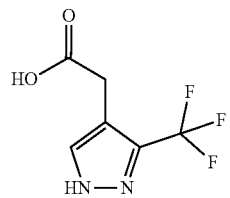 [SMILES: O=C(O)Cc1c[nH]nc1C(F)(F)F]

Periodic acid (278 mg, 1.22 mmol) was added to MeCN (4.5 mL) and stirred at room temperature for 20 mins. To this solution was added 2-[3-(trifluoromethyl)-1H-pyrazol-4-yl]ethanol (100 mg, 0.56 mmol) in MeCN (0.93 mL) and the mixture was cooled to 0° C. Pyridinium chlorochromate (8 mg, 0.04 mmol) was added and the mixture was warmed gradually to room temperature and stirred for 90 hours. The resulting mixture was diluted with excess water, acidified with 3M sulfuric acid and quenched with saturated aqueous sodium thiosulfate. After 3 days, the mixture was filtered and washed with water to afford the titled compound as a pale yellow solid.

1H NMR (400 MHz, DMSO-d6) δ 13.44 (s, 1H), 12.38 (s, 1H), 7.85 (s, 1H), 3.53 (s, 2H).

LC-MS (Method E): Rt 0.77 mins; MS m/z 195.0=[M+H]+ (95% @ 215 nm)

Step 2: N-(1,1-Dimethylprop-2-ynyl)-4-[[2-[3-(trifluoromethyl)-1H-pyrazol-4-yl]acetyl]amino]pyridine-2-carboxamide The titled compound was prepared from 4-amino-N-(1,1-dimethylprop-2-ynyl)pyridine-2-carboxamide (Example 78 step 1) and 2-[3-(trifluoromethyl)-1H-pyrazol-4-yl]acetic acid (step 1) analogously to Example 5.

1H NMR (400 MHz, DMSO-d6) δ 13.50 (s, 1H), 10.74 (s, 1H), 8.48 (d, J=5.5 Hz, 1H), 8.32 (s, 1H), 8.20 (d, J=2.1 Hz, 1H), 7.91 (s, 1H), 7.80 (dd, J=5.5, 2.1 Hz, 1H), 3.73 (s, 2H), 3.21 (s, 1H), 1.64 (s, 6H).

LC-MS (Method A): Rt 2.69 mins; MS m/z 380.2=[M+H]+ (100% @ 215 nm)

Example 5.37

N-(1,1-Dimethylprop-2-ynyl)-4-[[2-[3-(trifluoromethyl)phenyl]acetyl]amino]pyridine-2-carboxamide

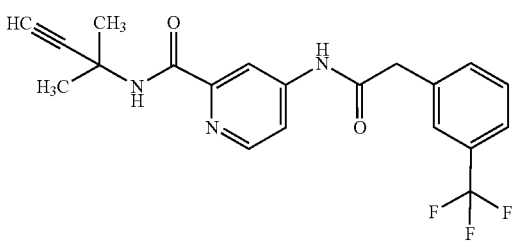 [SMILES: C#CC(C)(C)NC(=O)c1cc(NC(=O)Cc2cccc(C(F)(F)F)c2)ccn1]

The titled compound was prepared from 4-amino-N-(1,1-dimethylprop-2-ynyl)pyridine-2-carboxamide (Example 78 step 1) and 2-[3-(trifluoromethyl)phenyl]acetic acid analogously to Example 5.

1H NMR (500 MHz, DMSO-d6) δ 10.84 (s, 1H), 8.48 (d, J=5.5 Hz, 1H), 8.31 (s, 1H), 8.19 (d, J=2.0 Hz, 1H), 7.83 (dd, J=5.5, 2.2 Hz, 1H), 7.72-7.69 (m, 1H), 7.66-7.61 (m, 2H), 7.61-7.55 (m, 1H), 3.88 (s, 2H), 3.21 (s, 1H), 1.64 (s, 6H).

LC-MS (Method A): Rt 3.51 mins; MS m/z 390.2=[M+H]+ (100% @ 215 nm)

Example 5.38

N-(1,1-Dimethylprop-2-ynyl)-4-[[2-[2-(trifluoromethyl)phenyl]acetyl]amino]pyridine-2-carboxamide

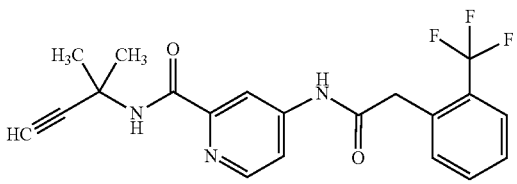 [SMILES: C#CC(C)(C)NC(=O)c1cc(NC(=O)Cc2ccccc2C(F)(F)F)ccn1]

The titled compound was prepared from 4-amino-N-(1,1-dimethylprop-2-ynyl)pyridine-2-carboxamide (Example 78 step 1) and 2-[2-(trifluoromethyl)phenyl]acetic acid analogously to Example 5.

1H NMR (500 MHz, DMSO-d6) δ 10.84 (s, 1H), 8.48 (d, J=5.5 Hz, 1H), 8.32 (s, 1H), 8.18 (d, J=2.0 Hz, 1H), 7.80 (dd, J=5.5, 2.2 Hz, 1H), 7.73 (d, J=7.8 Hz, 1H), 7.67 (t, J=7.6 Hz, 1H), 7.52 (dd, J=18.5, 7.7 Hz, 2H), 4.01 (s, 2H), 3.21 (s, 1H), 1.64 (s, 6H).

LC-MS (Method A): Rt 3.53 mins; MS m/z 390.2=[M+H]+ (100% @ 215 nm)

Example 5.39

4-[[2-(2,3-Dihydro-1,4-benzoxazin-4-yl)acetyl]amino]-N-(1,1-dimethylprop-2-ynyl)pyridine-2-carboxamide The titled compound was prepared from 4-amino-N-(1,1-dimethylprop-2-ynyl)pyridine-2-carboxamide (Example 78 step 1) and 2-(2,3-dihydro-1,4-benzoxazin-4-yl)acetic acid analogously to Example 5.

1H NMR (500 MHz, DMSO-d6) δ 10.65 (s, 1H), 8.48 (d, J=5.5 Hz, 1H), 8.31 (s, 1H), 8.20 (d, J=2.1 Hz, 1H), 7.86 (dd, J=5.5, 2.2 Hz, 1H), 6.74-6.67 (m, 2H), 6.59-6.52 (m, 2H), 4.26-4.21 (m, 2H), 4.17 (s, 2H), 3.52-3.47 (m, 2H), 3.21 (s, 1H), 1.64 (s, 6H).

LC-MS (Method A): Rt 3.32 mins; MS m/z 379.2=[M+H]+ (90% @ 215 nm)

Example 6

N-tert-Butyl-4-[[2-(5-cyano-2-hydroxy-phenyl)acetyl]amino]pyridine-2-carboxamide Step 1: 4-[[2-(5-Bromo-2-methoxy-phenyl)acetyl]amino]-N-tert-butyl-pyridine-2-carboxamide 2-(5-Bromo-2-methoxy-phenyl)acetic acid (348 mg, 1.42 mmol) in thionyl chloride (1.25 mL, 14.2 mmol) was stirred at 70° C. under an inert atmosphere for 1 hour. The resulting solution was cooled to room temperature and concentrated in vacuo (azeotroping with toluene and DCM). The dry acid chloride was dissolved in anhydrous DCM (10 mL) and added drop wise to a solution of 4-amino-N-tert-butyl-pyridine-2-carboxamide (Example 3 step 1) (274 mg, 1.42 mmol) and DIPEA (0.5 mL, 2.84 mmol) in anhydrous DCM (10 mL). The reaction mixture was stirred under an inert atmosphere at room temperature. After 1 hour, the mixture was diluted with DCM (25 mL) and washed with water (2×25 mL). The organic extracts were dried over Na$_2$SO$_4$ and concentrated in vacuo. The resulting crude oil was purified by chromatography on silica eluting with EtOAc in heptane. The column was flushed with methanol and the eluent collected and concentrated in vacuo to afford a beige solid. The solid was re-purified by chromatography on silica eluting with 0-10% MeOH in DCM and the product fractions concentrated in vacuo and dried in a vacuum oven at 40° C. for 2 hours to afford the titled compound.

1H NMR (500 MHz, DMSO-d6) δ 10.70 (s, 1H), 8.44 (d, J=5.5 Hz, 1H), 8.17 (d, J=2.0 Hz, 1H), 8.03 (s, 1H), 7.80 (dd, J=5.5, 2.2 Hz, 1H), 7.47-7.38 (m, 2H), 7.01-6.92 (m, 1H), 3.74 (s, 3H), 3.71 (s, 2H), 1.40 (s, 9H).

LC-MS (Method A): Rt 3.62 mins; MS m/z 420.2, 422.2= [M+H]+ (100% @ 215 nm)

Step 2: N-tert-Butyl-4-[[2-(5-cyano-2-methoxy-phenyl)acetyl]amino]pyridine-2-carboxamide

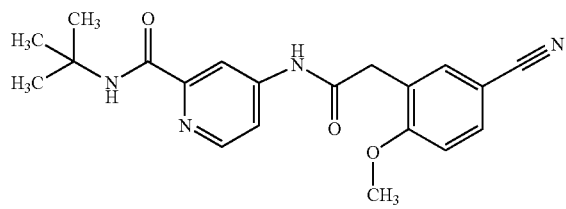 [SMILES: COc1ccc(C#N)cc1CC(=O)Nc1ccnc(C(=O)NC(C)(C)C)c1]

A solution of 4-[[2-(5-bromo-2-methoxy-phenyl)acetyl] amino]-N-tert-butyl-pyridine-2-carboxamide (step 1) (75 mg, 0.18 mmol) in DMF (2 mL) was de-gassed with nitrogen for 5 minutes before addition of tetrakis(triphenylphosphine)palladium(0) (21 mg, 0.02 mmol). The mixture was purged with nitrogen for a further 5 minutes then treated with zinc cyanide (27 mg, 0.23 mmol). The resulting mixture was stirred at 100° C. for 16 hours. A further portion of zinc cyanide (27 mg, 0.23 mmol) and tetrakis(triphenylphosphine)palladium(0) (21 mg, 0.02 mmol) was added, the mixture purged with nitrogen and stirring continued at 100° C. for a further 24 hours. The mixture was diluted with EtOAc (20 mL) and washed with water (20 mL), aqueous NaHCO$_3$ (sat.) (20 mL) and brine (20 mL). The organics were dried over Na$_2$SO$_4$ and concentrated in vacuo. The crude material was purified by chromatography on silica eluting with EtOAc in heptane. The product fractions were concentrated in vacuo and dried in a vacuum oven to afford the titled compound as a yellow solid.

1H NMR (500 MHz, Chloroform-d) δ 8.40 (d, J=5.6 Hz, 1H), 8.39 (br.s, 1H), 8.20 (dd, J=5.6, 2.2 Hz, 1H), 8.04 (s, 1H), 7.75-7.69 (m, 1H), 7.63 (dd, J=8.6, 2.1 Hz, 1H), 7.58 (d, J=2.0 Hz, 1H), 6.99 (d, J=8.6 Hz, 1H), 3.95 (s, 3H), 3.77 (s, 2H), 1.47 (s, 9H).

LC-MS (Method E): Rt 1.13 mins; MS m/z 367.1=[M+H]+ (95% @ 215 nm)

Step 3: N-tert-Butyl-4-[[2-(5-cyano-2-hydroxy-phenyl)acetyl]amino]pyridine-2-carboxamide

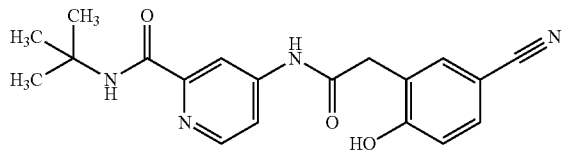 [SMILES: CC(C)(C)NC(=O)c1cc(NC(=O)Cc2cc(C#N)ccc2O)ccn1]

To a solution of N-tert-butyl-4-[[2-(5-cyano-2-methoxy-phenyl)acetyl]amino]pyridine-2-carboxamide (step 2) (20 mg, 0.05 mmol) in DCM (2 mL) was added 1M BBr$_3$ in DCM (164 μL, 0.16 mmol). The resulting mixture was stirred under an inert atmosphere for 2 hours. Additional 1M BBr$_3$ in DCM (164 μL, 0.16 mmol) was added and the mixture stirred at room temperature for a further 16 hours. Further 1M BBr$_3$ in DCM (164 μL, 0.16 mmol) was added and the mixture stirred for 24 hours at room temperature under nitrogen. The mixture was diluted with DCM (20 mL) and washed with water (2×20 mL). The organic portion was dried over Na$_2$SO$_4$ and concentrated in vacuo. The crude product was purified by C18 reverse phase chromatography eluting with 0-100% MeCN in water with 0.1% formic acid. The product fractions were freeze-dried to afford the titled compound as a white solid.

1H NMR (500 MHz, DMSO-d6) δ 10.78 (br s, 1H), 10.75 (s, 1H), 10.90-10.60 (m, 2H), 8.44 (d, J=5.5 Hz, 1H), 8.16 (d, J=1.9 Hz, 1H), 8.03 (s, 1H), 7.81 (dd, J=5.5, 2.2 Hz, 1H), 7.63 (d, J=2.1 Hz, 1H), 7.57 (dd, J=8.4, 2.2 Hz, 1H), 6.93 (d, J=8.4 Hz, 1H), 3.72 (s, 2H), 1.40 (s, 9H).

LC-MS (Method A): Rt 2.84 mins; MS m/z 353.3=[M+H]+ (94% @ 215 nm)

Example 7

3-[[2-(5-Chloro-2-hydroxy-phenyl)acetyl]amino]-N-(1,1,2,2-tetramethylpropyl)benzamide

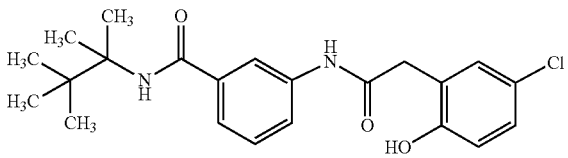 [SMILES: CC(C)(C)C(C)(C)NC(=O)c1cccc(NC(=O)Cc2cc(Cl)ccc2O)c1]

Step 1: Methyl 3-[[2-(5-chloro-2-methoxy-phenyl)acetyl]amino]benzoate

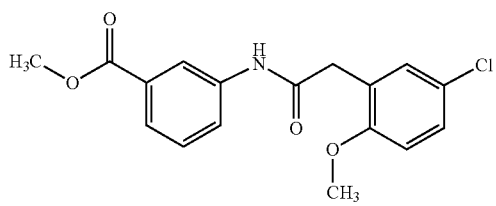 [SMILES: COC(=O)c1cccc(NC(=O)Cc2cc(Cl)ccc2OC)c1]

A solution of 2-(5-chloro-2-methoxy-phenyl)acetic acid (1200 mg, 5.98 mmol), EDCI (1376 mg, 7.18 mmol), HOAt (814 mg, 5.98 mmol), DIPEA (2.61 mL, 14.95 mmol) and methyl 3-aminobenzoate (904 mg, 5.98 mmol) in DMF (5 mL) was stirred at room temperature for 17 hours. The reaction mixture was diluted with water (35 mL) and extracted with EtOAc (2×40 mL). The combined organic portions were washed with water (2×40 mL), dried over $Na_2SO_4$ and concentrated in vacuo. The crude material was purified by chromatography on silica eluting with 10-70% EtOAc in heptane. The product fractions were concentrated in vacuo to afford the titled compound as an off-white solid.

1H NMR (500 MHz, DMSO-d6) δ 10.32 (s, 1H), 8.29 (t, J=1.8 Hz, 1H), 7.82 (ddd, J=8.1, 2.1, 1.0 Hz, 1H), 7.63 (dt, J=7.7, 1.2 Hz, 1H), 7.45 (t, J=7.9 Hz, 1H), 7.32-7.28 (m, 2H), 7.05-6.95 (m, 1H), 3.84 (s, 3H), 3.76 (s, 3H), 3.66 (s, 2H).

LC-MS (Method E): Rt 1.21 mins; MS m/z 334.1/336.1= [M+H]+ (96% @ 215 nm)

Step 2: 3-[[2-(5-Chloro-2-methoxy-phenyl)acetyl]amino]benzoic acid

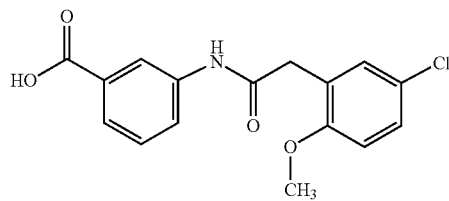 [SMILES: COc1ccc(Cl)cc1CC(=O)Nc1cccc(C(=O)O)c1]

2 M LiOH (7.71 mL, 15.42 mmol) was added to a solution of methyl 3-[[2-(5-chloro-2-methoxy-phenyl)acetyl]amino]benzoate (step 1) (1751 mg, 5.14 mmol) in THF (8 mL). The reaction mixture was stirred at room temperature for 7 hours. The resulting mixture was concentrated in vacuo, diluted with water (8 mL) and acidified to pH 2 with aqueous 2M HCl. A precipitate formed which was collected by vacuum filtration and washed with $Et_2O$ (2×20 mL). The solid was dried in a vacuum oven at 40° C. for 3 hours to afford the titled compound as a pale beige solid.

1H NMR (500 MHz, DMSO-d6) δ 10.32 (s, 1H), 8.23 (s, 1H), 7.87-7.74 (m, 1H), 7.61 (d, J=7.7 Hz, 1H), 7.41 (t, J=7.9 Hz, 1H), 7.31-7.27 (m, 2H), 7.03-6.95 (m, 1H), 3.76 (s, 3H), 3.66 (s, 2H).

LC-MS (Method E): Rt 1.07 mins; MS m/z 320.1/322.1= [M+H]+ (100% @ 215 nm)

Step 3: 3-[[2-(5-Chloro-2-methoxy-phenyl)acetyl]amino]-N-(1,1,2,2-tetramethylpropyl)benzamide

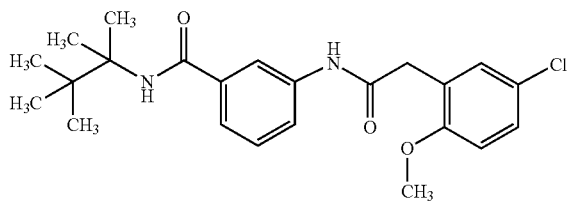 [SMILES: COc1ccc(Cl)cc1CC(=O)Nc1cccc(C(=O)NC(C)(C)C(C)(C)C)c1]

A solution of 3-[[2-(5-chloro-2-methoxy-phenyl)acetyl]amino]benzoic acid (step 2) (70 mg, 0.22 mmol), EDCI (50 mg, 0.26 mmol), HOAt (36 mg, 0.26 mmol), DIPEA (0.11 mL, 0.66 mmol) and 2,3,3-trimethylbutan-2-amine hydrochloride (33 mg, 0.22 mmol) in DMF (0.5 mL) was stirred at room temperature for 3 hours. The resulting mixture was diluted with EtOAc (5 mL) and water (5 mL). The aqueous layer was extracted with EtOAc (5 mL) and the combined organic extracts were washed with water (5 mL), brine (5 mL), dried over $Na_2SO_4$ and concentrated in vacuo. The crude residue was purified by preparative HPLC (acidic pH, early elution method) and the product fractions concentrated in vacuo to afford the titled compound as an off-white powder.

1H NMR (500 MHz, DMSO-d6) δ 10.19 (s, 1H), 7.85 (s, 1H), 7.74 (dt, J=6.8, 2.1 Hz, 1H), 7.37-7.32 (m, 2H), 7.32-7.26 (m, 2H), 7.09 (s, 1H), 7.02-6.98 (m, 1H), 3.76 (s, 3H), 3.65 (s, 2H), 1.39 (s, 6H), 0.97 (s, 9H).

LC-MS (Method E): Rt 1.32 mins; MS m/z 417.2/419.2= [M+H]+ (97% @ 215 nm)

Step 4: 3-[[2-(5-Chloro-2-hydroxy-phenyl)acetyl]amino]-N-(1,1,2,2-tetramethylpropyl)benzamide To a cooled (0° C.) solution of 3-[[2-(5-chloro-2-methoxy-phenyl)acetyl]amino]-N-(1,1,2,2-tetramethylpropyl)benzamide (step 3) (53 mg, 0.13 mmol) in DCM (0.5 mL) was added 1M $BBr_3$ in DCM (0.38 mL, 0.38 mmol) and the mixture was stirred at room temperature for 1 hour. The resulting mixture was diluted with water (5 mL) and extracted with EtOAc (2×8 mL). The combined organic extracts were dried over $Na_2SO_4$ and concentrated in vacuo. The crude residue was purified by preparative HPLC (acidic pH, early elution method) and the product fractions concentrated in vacuo to afford the titled compound as an off-white powder.

1H NMR (500 MHz, DMSO-d6) δ 10.19 (s, 1H), 9.81 (br s, 1H), 7.86 (s, 1H), 7.75 (dt, J=6.6, 2.2 Hz, 1H), 7.38-7.31 (m, 2H), 7.20 (d, J=2.7 Hz, 1H), 7.13-7.05 (m, 2H), 6.80 (d, J=8.6 Hz, 1H), 3.61 (s, 2H), 1.39 (s, 6H), 0.97 (s, 9H).

LC-MS (Method D): Rt 4.52 mins; MS m/z 403.2/405.2= [M+H]+ (100% @ 215 nm).

The compounds of the following tabulated Examples (Table 6) were prepared analogously to Example 7 from the appropriate amino ester and acid (step 1) and by replacing 2,3,3-trimethylbutan-2-amine hydrochloride (step 3) with the appropriate commercially available amine. The amide coupling step was carried out using either (i) EDCI/HOAt/DIPEA or (ii) TBTU/TEA or (iii) T3P®/TEA

TABLE 6

| Ex. | Structure and Name | Coupling Reagents | 1H NMR LCMS Retention Time, [M + H]+, |
|---|---|---|---|
| 7.1 | 3-[[2-(5-Chloro-2-hydroxy-phenyl)acetyl]amino]-N-(1,1-dimethylbutyl)benzamide | EDCI/ HOAt/ DIPEA | 1H NMR (500 MHz, DMSO-d6) δ 10.19 (s, 1H), 9.74 (br s, 1H), 7.87 (t, J = 1.8 Hz, 1H), 7.84 – 7.71 (m, 1H), 7.56 (s, 1H), 7.40 (d, J = 7.8 Hz, 1H), 7.33 (t, J = 7.9 Hz, 1H), 7.20 (d, J = 2.7 Hz, 1H), 7.11 (dd, J = 8.6, 2.7 Hz, 1H), 6.80 (d, J = 8.6 Hz, 1H), 3.61 (s, 2H), 1.78 – 1.64 (m, 2H), 1.37 – 1.20 (m, 8H), 0.86 (t, J = 7.3 Hz, 3H). LC-MS (Method D): Rt 4.40 mins; MS m/z 389.2/391.2 = [M + H]+ (98% @ 215 nm) |
| 7.2 | 4-[[2-(5-Chloro-2-hydroxy-phenyl)acetyl]amino]-N-(1,1-dimethylbutyl)pyridine-2-carboxamide | EDCI/ HOAt/ DIPEA | 1H NMR (250 MHz, DMSO-d6) δ 10.69 (br s, 1H), 9.86 (br s, 1H), 8.44 (d, J = 5.8 Hz, 1H), 8.17 (d, J = 1.8 Hz, 1H), 7.95 (s, 1H), 7.80 (dd, J = 5.5, 2.2 Hz, 1H), 7.21 (d, J = 2.7 Hz, 1H), 7.12 (dd, J = 8.6, 2.7 Hz 1H), 6.80 (d, J = 8.6 Hz, 1H), 3.67 (s, 2H), 1.80 – 1.63 (m, 2H), 1.35 (s, 6H), 1.32 – 1.16 (m, 2H), 0.87 (t, J = 7.3 Hz, 3H). LC-MS (Method A): Rt 3.79 mins; MS m/z 390.2/392 = [M + H]+ (100% @ 215 nm) |
| 7.3 | 3-[[2-(5-Chloro-2-hydroxy-phenyl)acetyl]amino]-N-cyclohexyl-benzamide | EDCI/ HOAt/ DIPEA | 1H NMR (500 MHz, DMSO-d6) δ 10.23 (s, 1H), 9.79 (s, 1H), 8.16 (d, J = 8.0 Hz, 1H), 7.96 (t, J = 1.8 Hz, 1H), 7.80 – 7.75 (m, 1H), 7.48 (d, J = 7.8 Hz, 1H), 7.35 (t, J = 7.9 Hz, 1H), 7.20 (d, J = 2.7 Hz, 1H), 7.11 (dd, J = 8.6, 2.7 Hz, 1H), 6.80 (d, J = 8.6 Hz, 1H), 3.79 – 3.69 (m, 1H), 3.61 (s, 2H), 1.84- 1.68 (m, 4H), 1.64 – 1.57 (m, 1H), 1.36 – 1.23 (m, 4H), 1.17 – 1.06 (m, 1H). LC-MS (Method A): Rt 3.31 mins; MS m/z 387.2/389.2 = [M + H]+ (100% @ 215 nm) |
| 7.4 | 3-[[2-(5-Chloro-2-hydroxy-phenyl)acetyl]amino]-N-tetrahydropyran-4-yl-benzamide | EDCI/ HOAt/ DIPEA | 1H NMR (500 MHz, DMSO-d6) δ 10.22 (s, 1H), 9.80 (br s, 1H), 8.29 (d, J = 7.8 Hz, 1H), 7.99 (t, J = 1.8 Hz, 1H), 7.87 – 7.69 (m, 1H), 7.49 (d, J = 7.9 Hz, 1H), 7.37 (t, J = 7.9 Hz, 1H), 7.21 (d, J = 2.7 Hz, 1H), 7.11 (dd, J = 8.6, 2.7 Hz, 1H), 6.80 (d, J = 8.6 Hz, 1H), 3.98 (m, 1H), 3.92 – 3.80 (m, 2H), 3.61 (s, 2H), 3.41 – 3.36 (m, 2H), 1.80 – 1.65 (m, 2H), 1.63 – 1.51 (m, 2H). LC-MS (Method A): Rt 2.57 mins; MS m/z 389.2/391.2 = [M + H]+ (100% @ 215 nm) |
| 7.5 | 3-[[2-(5-Chloro-2-hydroxy-phenyl)acetyl]amino]-N-(1,1,2-trimethylpropyl)benzamide | EDCI/ HOAt/ DIPEA | 1H NMR (500 MHz, DMSO-d6) δ 10.19 (s, 1H), 9.80 (br s, 1H), 7.87 (t, J = 1.8 Hz, 1H), 7.81 – 7.71 (m, 1H), 7.52 (s, 1H), 7.39 (dd, J = 6.5, 1.3 Hz, 1H), 7.33 (t, J = 7.8 Hz, 1H), 7.20 (d, J = 2.7 Hz, 1H), 7.11 (dd, J = 8.6, 2.7 Hz, 1H), 6.80 (d, J = 8.6 Hz, 1H), 3.61 (s, 2H), 1.27 (s, 6H), 0.85 (d, J = 6.9 Hz, 6H). LC-MS (Method A): Rt 3.52 mins; MS m/z 389.3/391.3 = [M + H]+ (100% @ 215 nm) |
| 7.6 | 4-[[2-(5-Chloro-2-hydroxy-phenyl)acetyl]amino]-N-(1,1,2-trimethylpropyl)pyridine-2-carboxamide | EDCI/ HOAt/ DIPEA | 1H NMR (500 MHz, DMSO-d6) δ 10.71 (br s, 1H), 9.86 (br s, 1H), 8.44 (d, J = 5.6 Hz, 1H), 8.17 (d, J = 2.0 Hz, 1H), 7.99 (s, 1H), 7.81 (dd, J = 5.5, 2.2 Hz, 1H), 7.21 (d, J = 2.7 Hz, 1H), 7.12 (dd, J = 8.6, 2.7 Hz, 1H), 6.80 (d, J = 8.6 Hz, 1H), 3.66 (s, 2H), 2.36 – 2.28 (m, 1H), 1.32 (s, 6H), 0.88 (d, J = 6.9 Hz, 6H). LC-MS (Method A): Rt 3.74 mins; MS m/z 390.2/392.2 = [M + H]+ (99% @ 215 nm) |
| 7.7 | 4-[[2-(5-Chloro-2-hydroxy-phenyl)acetyl]amino]-N-isopropyl-pyridine-2-carboxamide | TBTU/ TEA | 1H NMR (500 MHz, DMSO-d6) δ 10.69 (br s, 1H), 9.77 (br s, 1H), 8.46 (d, J = 5.5 Hz, 1H), 8.39 (d, J = 8.4 Hz, 1H), 8.18 (d, J = 2.1 Hz, 1H), 7.81 (dd, J = 5.5, 2.2 Hz, 1H), 7.21 (d, J = 2.7 Hz, 1H), 7.12 (dd, J = 8.6, 2.7 Hz, 1H), 6.80 (d, J = 8.6 Hz, 1H), 4.16 – 4.03 (m, 1H), 3.66 (s, 2H), 1.18 (d, J = 6.6 Hz, 6H). LC-MS (Method A): Rt 2.89 mins; MS m/z 348.1/350.1 = [M + H]+ (99% @ 215 nm) |
| 7.8 | 3-[[2-(5-Chloro-2-hydroxy-phenyl)acetyl]amino]-N-(4-methyltetrahydropyran-4-yl)benzamide | EDCI/ HOAt/ DIPEA | 1H NMR (500 MHz, DMSO-d6) δ 10.21 (s, 1H), 9.80 (s, 1H), 7.99 – 7.84 (m, 1H), 7.80 – 7.60 (m, 1H), 7.72 (s, 1H), 7.44 (d, J = 7.7 Hz, 1H), 7.35 (t, J = 7.9 Hz, 1H), 7.20 (d, J = 2.7 Hz, 1H), 7.11 (dd, J = 8.6, 2.7 Hz, 1H), 6.80 (d, J = 8.6 Hz, 1H), 3.67 – 3.52 (m, 6H), 2.26 – 2.19 (m, 2H), 1.58 – 1.49 (m, 2H), 1.38 (s, 3H). LC-MS (Method A): Rt 2.79 mins; MS m/z 403.2/405.2 = [M + H]+ (100% @ 215 nm) |

TABLE 6-continued

| Ex. | Structure and Name | Coupling Reagents | 1H NMR LCMS Retention Time, [M + H]+, |
|---|---|---|---|
| 7.9 | 4-[[2-(5-Chloro-2-hydroxy-phenyl)acetyl]amino]-N-(4-methyltetrahydropyran-4-yl)pyridine-2-carboxamide | T3P ®/ TEA | 1H NMR (500 MHz, DMSO-d6) δ 10.72 (br s, 1H), 9.74 (br s, 1H), 8.47 (d, J = 5.5 Hz, 1H), 8.18 (d, J = 2.1 Hz, 1H), 8.11 (s, 1H), 7.82 (dd, J = 5.5, 2.2 Hz, 1H), 7.21 (d, J = 2.7 Hz, 1H), 7.12 (dd, J = 8.6, 2.7 Hz, 1H), 6.80 (d, J = 8.6 Hz, 1H), 3.70 – 3.60 (m, 4H), 3.55 – 3.46 (m, 2H), 2.23 – 2.14 (m, 2H), 1.67-1.58 (m, 2H), 1.42 (s, 3H). LC-MS (Method A): Rt 2.90 mins; MS m/z 404.2/406.2 = [M + H]+ (96% @ 215 nm) |
| 7.10 | 3-[[2-(5-Chloro-2-hydroxy-phenyl)acetyl]amino]-N-(1-methylcyclobutyl)benzamide | EDCI/ HOAt/ DIPEA | 1H NMR (500 MHz, DMSO-d6) δ 10.20 (s, 1H), 9.80 (s, 1H), 8.32 (s, 1H), 7.95 (t, J = 1.8 Hz, 1H), 7.77-7.42 (m, 1H), 7.49-7.44 (m, 1H), 7.34 (t, J = 7.9 Hz, 1H), 7.20 (d, J = 2.7 Hz, 1H), 7.11 (dd, J = 8.6, 2.7 Hz, 1H), 6.80 (d, J = 8.6 Hz, 1H), 3.61 (s, 2H), 2.34 – 2.28 (m, 2H), 2.00 – 1.92 (m, 2H), 1.84 – 1.75 (m, 2H), 1.45 (s, 3H). LC-MS (Method A): Rt 3.15 mins; MS m/z 373.2/375.1 = [M + H]+ (99% @ 215 nm) |
| 7.11 | 4-[[2-(5-Chloro-2-hydroxy-phenyl)acetyl]amino]-N-tetrahydropyran-4-yl-pyridine-2-carboxamide | TBTU/ TEA | 1H NMR (500 MHz, DMSO-d6) δ 10.69 (br s, 1H), 9.86 (br s, 1H), 8.58 (d, J = 8.5 Hz, 1H), 8.48 (d, J = 5.5 Hz, 1H), 8.20 (d, J = 2.0 Hz, 1H), 7.82 (dd, J = 5.5, 2.2 Hz, 1H), 7.21 (d, J = 2.7 Hz, 1H), 7.12 (dd, J = 8.6, 2.7 Hz, 1H), 6.80 (d, J = 8.6 Hz, 1H), 4.06 – 3.95 (m, 1H), 3.89 – 3.83 (m, 2H), 3.66 (s, 2H), 1.75 – 1.61 (m, 4H). LC-MS (Method A): Rt 2.57 mins; MS m/z 390.2/392.2 = [M + H]+ (98% @ 215 nm) |
| 7.12 | 4-[2-(5-Chloro-2-hydroxyphenyl)acetamido]-N-[(1s,4s)-4-hydroxycyclohexyl]pyridine-2-carboxamide | EDCI/ HOAt/ DIPEA | 1H NMR (500 MHz, DMSO-d6) δ 10.68 (s, 1H), 9.82 (br s, 1H), 8.47 (d, J = 5.5 Hz, 1H), 8.30 (d, J = 8.2 Hz, 1H), 8.19 (d, J = 2.0 Hz, 1H), 7.81 (dd, J = 5.5, 2.2 Hz, 1H), 7.22 (d, J = 2.7 Hz, 1H), 7.12 (dd, J = 8.6, 2.7 Hz, 1H), 6.80 (d, J = 8.6 Hz, 1H), 4.41 (d, J = 3.4 Hz, 1H), 3.87 – 3.76 (m, 1H), 3.74 – 3.68 (m, 1H), 3.66 (s, 2H), 1.83 – 1.66 (m, 2H), 1.65 – 1.47 (m, 6H). LC-MS (Method A): Rt 2.45 mins; MS m/z 404.2/ 406.2 = [M + H]+ (100% @ 215 nm) |
| 7.13 | 4-[[2-(5-Chloro-2-hydroxy-phenyl)acetyl]amino]-N-sec-butyl-pyridine-2-carboxamide | T3P ®/ TEA | 1H NMR (500 MHz, DMSO-d6) δ 10.69 (br s, 1H), 9.82 (br s, 1H), 8.47 (d, J = 5.5 Hz, 1H), 8.34 (d, J = 8.9 Hz, 1H), 8.18 (d, J = 2.0 Hz, 1H), 7.82 (dd, J = 5.5, 2.2 Hz, 1H), 7.22 (d, J = 2.7 Hz, 1H), 7.12 (dd, J = 8.6, 2.7 Hz, 1H), 6.80 (d, J = 8.6 Hz, 1H), 3.96-3.85 (m, 1H), 3.66 (s, 2H), 1.64 – 1.44 (m, 2H), 1.15 (d, J = 6.6 Hz, 3H), 0.84 (t, J = 7.4 Hz, 3H). LC-MS (Method A): Rt 3.16 mins; MS m/z 362.1/364.1 = [M + H]+ (98% @ 215 nm) |
| 7.14 | 4-[[2-(5-Chloro-2-hydroxy-phenyl)acetyl]amino]-N-(2-hydroxy-1,1,2-trimethyl-propyl)pyridine-2-carboxamide | T3P ®/ TEA | 1H NMR (500 MHz, DMSO-d6) δ 10.67 (s, 1H), 9.81 (br s, 1H), 8.71 (s, 1H), 8.44 (d, J = 5.5 Hz, 1H), 8.18 (d, J = 2.0 Hz, 1H), 7.80 (dd, J = 5.5, 2.2 Hz, 1H), 7.22 (d, J = 2.7 Hz, 1H), 7.12 (dd, J = 8.6, 2.7 Hz, 1H), 6.80 (d, J = 8.6 Hz, 1H), 4.99 (s, 1H), 3.67 (s, 2H), 1.39 (s, 6H), 1.16 (s, 6H). LC-MS (Method A): Rt 3.01 mins; MS m/z 406.2/408.2 = [M + H]+ (99% @ 215 nm) |
| 7.15 | N-(3-Bicyclo[1.1.1]pentanyl)-4-[[2-(5-chloro-2-hydroxy-phenyl)acetyl]amino]pyridine-2-carboxamide | T3P ®/ TEA | 1H NMR (500 MHz, DMSO-d6) δ 10.71 (br s, 1H), 9.82 (br s, 1H), 9.09 (s, 1H), 8.46 (d, J = 5.5 Hz, 1H), 8.14 (d, J = 2.0 Hz, 1H), 7.84 (dd, J = 5.5, 2.2 Hz, 1H), 7.22 (d, J = 2.7 Hz, 1H), 7.13 (dd, J = 8.6, 2.7 Hz, 1H), 6.81 (d, J = 8.6 Hz, 1H), 3.67 (s, 2H), 2.45 (s, 1H), 2.10 (s, 6H). LC-MS (Method A): Rt 3.21 mins; MS m/z 372.1/374.1 = [M + H]+ (98% @ 215 nm) |

TABLE 6-continued

| Ex. | Structure and Name | Coupling Reagents | 1H NMR LCMS Retention Time, [M + H]+, |
|---|---|---|---|
| 7.16 | 4-[[2-(5-Chloro-2-hydroxy-phenyl)acetyl]amino]-N-(1-cyanocyclobutyl)pyridine-2-carboxamide | *T3P ®/ TEA | 1H NMR (500 MHz, DMSO-d6) δ 10.73 (s, 1H), 9.82 (br s, 1H), 9.59 (s, 1H), 8.52 (d, J = 5.5 Hz, 1H), 8.19 (d, J = 2.0 Hz, 1H), 7.88 (dd, J = 5.5, 2.2 Hz, 1H), 7.22 (d, J = 2.7 Hz, 1H), 7.12 (dd, J = 8.6, 2.7 Hz, 1H), 6.81 (d, J = 8.6 Hz, 1H), 3.68 (s, 2H), 2.69 – 2.62 (m, 2H), 2.59 – 2.53 (m, 2H), 2.11 – 1.93 (m, 2H).<br>LC-MS (Method A): Rt 2.89 mins; MS m/z 385.1/387.1 = [M + H]+ (95% @ 215 nm) |

Example 8 tert-Butyl-3-[[3-[[2-(5-chloro-2-hydroxy-phenyl)acetyl]amino]benzoyl]amino]piperidine-1-carboxylate

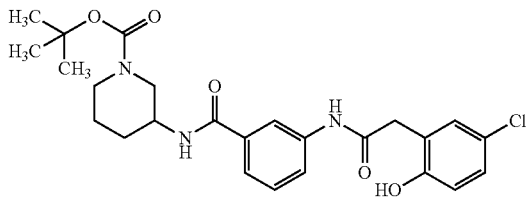 [SMILES: CC(C)(C)OC(=O)N1CCCC(NC(=O)c2cccc(NC(=O)Cc3cc(Cl)ccc3O)c2)C1]

Step 1: 3-[[2-(5-Chloro-2-hydroxy-phenyl)acetyl]amino]-N-(3-piperidyl)benzamide

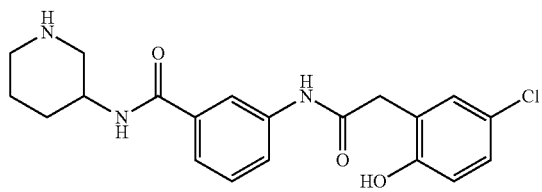 [SMILES: O=C(Cc1cc(Cl)ccc1O)Nc1cccc(C(=O)NC2CCCNC2)c1]

The titled compound was prepared analogously to Example 7 by replacing 2,3,3-trimethylbutan-2-amine hydrochloride (step 3) with tert-butyl 3-aminopiperidine-1-carboxylate.

1H NMR (500 MHz, DMSO-d6) δ 10.22 (s, 1H), 8.15 (d, J=7.9 Hz, 1H), 7.98 (s, 1H), 7.82-7.70 (m, 1H), 7.50-7.46 (m, 1H), 7.36 (t, J=7.9 Hz, 1H), 7.20 (d, J=2.7 Hz, 1H), 7.11 (dd, J=8.6, 2.7 Hz, 1H), 6.80 (d, J=8.6 Hz, 1H), 3.88-3.80 (m, 1H), 3.61 (s, 2H), 3.02-2.95 (m, 1H), 2.88-2.80 (m, 1H), 2.48-2.42 (m, 2H), 1.90-1.77 (m, 1H), 1.74-1.59 (m, 1H), 1.54-1.37 (m, 2H).

LC-MS (Method A): Rt 1.66 mins; MS m/z 388.2/390.2= [M+H]+ (96% @ 215 nm)

Step 2: tert-Butyl-3-[[3-[[2-(5-chloro-2-hydroxy-phenyl)acetyl]amino]benzoyl]amino]piperidine-1-carboxylate To a solution of 3-[[2-(5-chloro-2-hydroxy-phenyl)acetyl]amino]-N-(3-piperidyl)benzamide (step 1)(19 mg, 0.05 mmol) in THF (0.5 mL) was added BOC anhydride (12 mg, 0.06 mmol). The resulting mixture was stirred at room temperature for 3 hr. Additional BOC anhydride (12 mg, 0.06 mmol) was added and stirring continued for a further hour. The reaction mixture was concentrated in vacuo and purification of the crude product by chromatography on silica eluting with EtOAc in heptane afforded the titled compound as an off-white powder.

1H NMR (500 MHz, DMSO-d6) δ 10.26 (br s, 1H), 9.81 (br s, 1H), 8.24 (d, J=7.0 Hz, 1H), 7.99 (s, 1H), 7.83-7.74 (m, 1H), 7.49 (d, J=7.8 Hz, 1H), 7.37 (m, 1H), 7.20 (d, J=2.7 Hz, 1H), 7.11 (dd, J=8.6, 2.7 Hz, 1H), 6.80 (d, J=8.6 Hz, 1H), 4.05-3.67 (m, 3H), 3.61 (s, 2H), 3.03-2.70 (m, 2H), 1.91-1.81 (m, 1H), 1.76-1.67 (m, 1H), 1.60-1.46 (m, 1H), 1.45-1.31 (m, 10H).

LC-MS (Method A): Rt 3.41 mins; MS m/z 488.3/490.4= [M+H]+ (99% @ 215 nm)

Example 8.1 tert-Butyl-3-[[4-[[2-(5-chloro-2-hydroxy-phenyl)acetyl]amino]pyridine-2-carbonyl]amino]piperidine-1-carboxylate

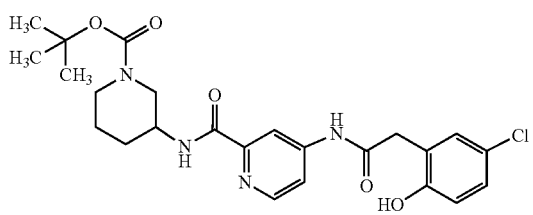 [SMILES: CC(C)(C)OC(=O)N1CCCC(NC(=O)c2cc(NC(=O)Cc3cc(Cl)ccc3O)ccn2)C1]

Step 1: Methyl 4-[[2-(5-chloro-2-methoxy-phenyl)acetyl]amino]pyridine-2-carboxylate

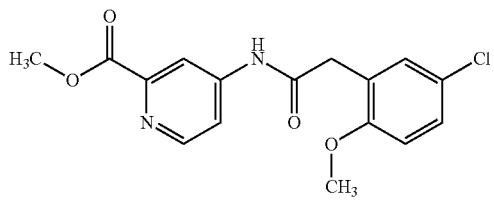 [SMILES: COC(=O)c1cc(NC(=O)Cc2cc(Cl)ccc2OC)ccn1]

2-(5-Chloro-2-methoxy-phenyl)acetic acid (24.19 g, 120.59 mmol) was suspended in thionyl chloride (103.68 mL, 1427.48 mmol) and heated at 70° C. for 1.5 hours. After cooling to room temperature the mixture was concentrated in vacuo. The residue was then dissolved in DCM (135 mL) and re-concentrated. The resulting brown viscous oil was dissolved in DCM (135 mL) and added dropwise to a cooled (ice bath) suspension of methyl 4-aminopyridine-2-carboxylate (17.9 g, 117.65 mmol) and DIPEA (30.82 mL, 176.47 mmol) in DCM (225 mL). The reaction mixture was allowed to warm to room temperature and stirred overnight. The resulting mixture was diluted with water (180 mL) and stirred for 10 mins. The organic portion was separated, dried over anhydrous Na₂SO₄, filtered and concentrated in vacuo. The residue was purified by chromatography on silica eluting with EtOAc to afford the titled compound as an orange glassy solid.

1H NMR (500 MHz, DMSO-d6) δ 10.72 (s, 1H), 8.54 (d, J=5.5 Hz, 1H), 8.30 (d, J=1.9 Hz, 1H), 7.77 (dd, J=5.5, 2.2 Hz, 1H), 7.32-7.29 (m, 2H), 7.02-6.99 (m, 1H), 3.86 (s, 3H), 3.75 (s, 3H), 3.71 (s, 2H).

LC-MS (Method E): Rt 1.04 mins; MS m/z 335.0/337.0= [M+H]+ (98% @ 215 nm)

Step 2: 4-[[2-(5-Chloro-2-methoxy-phenyl)acetyl] amino]pyridine-2-carboxylic acid

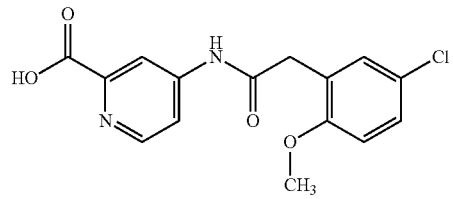 [SMILES: COc1ccc(Cl)cc1CC(=O)Nc1ccnc(C(=O)O)c1]

To a solution of methyl 4-[[2-(5-chloro-2-methoxy-phenyl)acetyl]amino]pyridine-2-carboxylate (step 1) (95%, 38.09 g, 108.1 mmol) in THF (200 mL) was added a 2M aqueous solution of lithium hydroxide hydrate (162.15 mL, 324.29 mmol) and the resulting mixture was stirred at room temperature for 1 hour. The volatile organics were removed in vacuo and the aqueous residue cooled (ice-bath) and treated with the gradual addition of 3M aqueous HCl (150 mL). The resulting suspension was filtered, washed with water (3×200 mL), diethyl ether (2×250 mL), dried under suction and then further dried in a high vacuum oven at 40° C. to afford the titled compound as a beige solid.

1H NMR (500 MHz, DMSO-d6) δ 10.78 (s, 1H), 8.53 (d, J=5.6 Hz, 1H), 8.27 (d, J=2.0 Hz, 1H), 7.81 (dd, J=5.6, 2.2 Hz, 1H), 7.34-7.28 (m, 2H), 7.04-6.98 (m, 1H), 3.75 (s, 3H), 3.72 (s, 2H).

LC-MS (Method E): Rt 0.88 mins; MS m/z 320.9/323.0= [M+H]+ (97% @ 215 nm)

Step 3: tert-Butyl 3-[[4-[[2-(5-chloro-2-methoxy-phenyl)acetyl]amino]pyridine-2-carbonyl]amino] piperidine-1-carboxylate

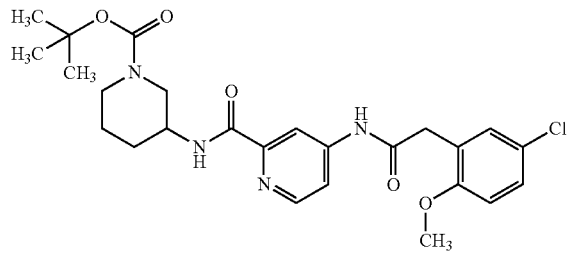 [SMILES: COc1ccc(Cl)cc1CC(=O)Nc1ccnc(C(=O)NC2CCCN(C(=O)OC(C)(C)C)C2)c1]

A solution of 4-[[2-(5-chloro-2-methoxy-phenyl)acetyl] amino]pyridine-2-carboxylic acid (step 2) (70 mg, 0.22 mmol), EDCI (50 mg, 0.26 mmol), HOAt (36 mg, 0.26 mmol), DIPEA (0.08 mL, 0.44 mmol) and tert-butyl 3-aminopiperidine-1-carboxylate (27.2 µL, 0.26 mmol) in DMF (0.5 mL) was stirred at room temperature for 20 hours. The resulting mixture was diluted with EtOAc (5 mL) and water (5 mL). The aqueous layer was extracted with EtOAc (5 mL) and the combined organic extracts washed with water (5 mL), brine (5 mL), dried over Na₂SO₄ and concentrated in vacuo. The residue was purified by preparative HPLC (acidic pH, early elution method) to afford the titled compound as an off-white solid.

1H NMR (500 MHz, DMSO-d6) δ 10.71 (br s, 1H), 8.52 (br s, 1H), 8.46 (m, 1H), 8.19 (br s, 1H), 7.87-7.79 (m, 1H), 7.35-7.26 (m, 2H), 7.08-6.93 (m, 1H), 3.87-3.78 (m, 1H), 3.75 (s, 3H), 3.71 (s, 2H), 3.17-2.83 (m, 2H), 1.87-1.77 (m, 1H), 1.77-1.58 (m, 2H), 1.57-1.20 (m, 10H).

LC-MS (Method E): Rt 1.28 mins; MS m/z 503.3/505.2= [M+H]+ (93% @ 215 nm)

Step 4 and 5: tert-Butyl-3-[[4-[[2-(5-chloro-2-hydroxy-phenyl)acetyl]amino]pyridine-2-carbonyl] amino]piperidine-1-carboxylate The titled compound was prepared analogously to Example 8 from tert-butyl 3-[[4-[[2-(5-chloro-2-methoxy-phenyl)acetyl]amino]pyridine-2-carbonyl]amino]piperidine-1-carboxylate (step 3).

1H NMR (500 MHz, DMSO-d6) δ 10.71 (br s, 1H), 9.83 (br s, 1H), 8.61-8.40 (m, 2H), 8.20 (s, 1H), 7.83 (dd, J=5.5, 2.0 Hz, 1H), 7.21 (d, J=2.7 Hz, 1H), 7.12 (dd, J=8.6, 2.7 Hz, 1H), 6.80 (d, J=8.6 Hz, 1H), 3.90-3.76 (m, 2H), 3.66 (s, 2H), 3.57-3.49 (m, 1H), 3.11-2.80 (m, 1H), 1.87-1.76 (m, 1H), 1.75-1.57 (m, 2H), 1.45-1.27 (m, 10H).

LC-MS (Method A): Rt 3.51 mins; MS m/z 489.3/491.3= [M+H]+ (99% @ 215 nm)

The compounds of the following tabulated Examples (Table 7) were prepared analogously to Example 8 from the appropriate aryl acid and by replacing tert-butyl 3-aminopiperidine-1-carboxylate (Example 8, step 1) with the appropriate commercially available amine.

TABLE 7

| Ex. | Structure and Name | 1H NMR; LCMS Retention Time, [M + H]+, |
|---|---|---|
| 8.2 | tert-Butyl 4-[[3-[[2-(5-chloro-2-hydroxy-phenyl)acetyl]amino]benzoyl]amino]-4-methyl-piperidine-1-carboxylate | 1H NMR (500 MHz, DMSO-d6) δ 10.20 (s, 1H), 9.81 (br s, 1H), 7.92 – 7.85 (m. 1H), 7.81-7.77 (m. 1H), 7.70 (s, 1H), 7.42 (d, J = 7.8 Hz, 1H), 7.34 (t, J = 7.9 Hz, 1H), 7.20 (d, J = 2.7 Hz, 1H), 7.10 (dd, J = 8.6, 2.7 Hz, 1H), 6.80 (d, J = 8.6 Hz, 1H), 3.66 – 3.54 (m, 4H), 3.08 (m, 2H), 2.29-2.21 (m, 2H), 1.45 – 1.36 (m, 11H), 1.35 (s, 3H). LC-MS (Method A): Rt 3.61 mins; MS m/z 524.2/526.2 = [M + Na]+ (99% @ 215 nm) |
| 8.3 | tert-Butyl (1r,5s,6s)-6-{4-[2-(5-chloro-2-hydroxyphenyl)acetamido]pyridine-2-amido}-3-azabicyclo[3.1.0]hexane-3-carboxylate | 1H), 8.85 (d, J = 4.9 Hz, 1H), 8.46 (d, J = 5.5 Hz, 1H), 8.16 (d, J = 2.1 Hz, 1H), 7.84 (dd, J = 5.5, 2.2 Hz, 1H), 7.21 (d, J = 2.7 Hz, 1H), 7.12 (dd, J = 8.6, 2.7 Hz, 1H), 6.80 (d, J = 8.6 Hz, 1H), 3.66 (s, 2H), 3.52 (m, 2H), 2.54 – 2.52 (m, 1H), 1.95 – 1.82 (m, 2H), 1.40 (s, 9H). LC-MS (Method A): Rt 3.44 mins; MS m/z 487.2/489.2 = [M + H]+ (99% @ 215 nm) |

Example 9

N-tert-Butyl-3-[[2-(5-chloro-2-hydroxy-phenyl)acetyl]amino]-4-fluoro-benzamide

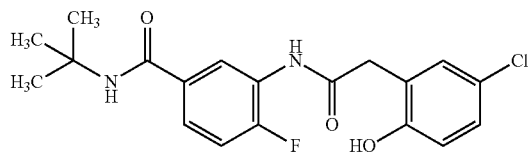 [SMILES: CC(C)(C)NC(=O)c1ccc(F)c(NC(=O)Cc2cc(Cl)ccc2O)c1]

Step 1: 3-Amino-N-tert-butyl-4-fluoro-benzamide

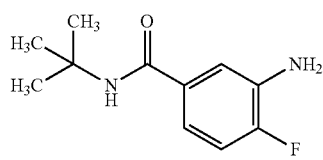

To a solution of 3-amino-4-fluoro-benzoic acid (205 mg, 1.32 mmol) in DCM (5 mL) was added sequentially 2-methylpropan-2-amine (306 μL, 2.91 mmol), DIPEA (0.92 mL, 5.29 mmol) and HATU (553 mg, 1.46 mmol) and the mixture was shaken at room temperature overnight. The resulting mixture washed with 2M HCl (5 mL) and sat. NaHCO₃ solution (5 mL). The organic phase was separated by passing through a hydrophobic frit and concentrated in vacuo. Purification by flash chromatography on silica eluting with 0-100% EtOAc in heptane afforded the titled compound as an off-white solid.

1H NMR (500 MHz, Chloroform-d) δ 7.25-7.19 (m, 1H), 6.99-6.95 (m, 2H), 5.82 (s, 1H), 3.82 (s, 2H), 1.45 (s, 9H).

LC-MS (Method E): Rt 0.95 mins; MS m/z 211.1=[M+H]+ (97% @ 215 nm)

Step 2: N-tert-Butyl-3-[[2-(5-chloro-2-hydroxy-phenyl)acetyl]amino]-4-fluoro-benzamide A suspension of 3-amino-N-tert-butyl-4-fluoro-benzamide (step 1) (105 mg, 0.5 mmol) and 5-chloro-3H-benzofuran-2-one (84 mg, 0.5 mmol) in toluene (3 mL) was heated to 110° C. in a sealed tube for 4 days. After cooling to room temperature, the mixture was concentrated in vacuo and crude residue was purified by preparative HPLC (acidic pH, early elution method) to afford the titled compound as an off-white powder.

1H NMR (500 MHz, MeOD) δ 8.28 (dd, J=7.4, 2.1 Hz, 1H), 7.56-7.49 (m, 1H), 7.24-7.18 (m, 2H), 7.10 (dd, J=8.6, 2.6 Hz, 1H), 6.81 (d, J=8.6 Hz, 1H), 3.74 (s, 2H), 1.43 (s, 9H).

LC-MS (Method A): Rt 3.18 mins; MS m/z 379.1/381.1= [M+H]+ (97% @ 215 nm)

Example 9.1

N-tert-Butyl-3-[[2-(5-chloro-2-hydroxy-phenyl)acetyl]amino]-5-methyl-benzamide

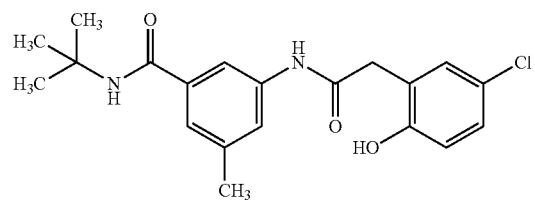 [SMILES: Cc1cc(NC(=O)Cc2cc(Cl)ccc2O)cc(C(=O)NC(C)(C)C)c1]

The titled compound was prepared analogously to Example 9 by replacing 3-amino-4-fluoro-benzoic acid (step 1) with 3-amino-5-methyl-benzoic acid.

1H NMR (500 MHz, Methanol-d4) δ 7.67 (s, 1H), 7.50 (s, 1H), 7.28 (s, 1H), 7.19 (d, J=2.6 Hz, 1H), 7.08 (dd, J=8.6, 2.6 Hz, 1H), 6.78 (d, J=8.6 Hz, 1H), 3.67 (s, 2H), 2.36 (s, 3H), 1.44 (s, 9H).

LC-MS (Method A): Rt 3.32 mins; MS m/z 375.2/377.2=[M+H]+ (99% @ 215 nm).

Example 9.2

4-[[2-(5-Chloro-2-hydroxy-phenyl)acetyl]amino]-N-(1,1-dimethylpropyl)pyridine-2-carboxamide

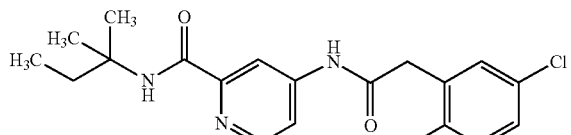

Step 1: 4-Amino-N-(1,1-dimethylpropyl)pyridine-2-carboxamide

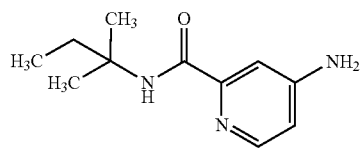

To a mixture of 2-methylbutan-2-amine (1.69 mL, 14.48 mmol), TBTU (1023 mg, 3.19 mmol) and TEA (0.81 mL, 5.79 mmol) was added 4-aminopyridine-2-carboxylic acid (400 mg, 2.9 mmol) and the mixture was stirred at room temperature for 5 hours.

The resulting mixture was partitioned between water (40 mL) and DCM (40 mL). The phases were separated and the organic portion concentrated in vacuo. The crude product was purified by C18 reverse phase chromatography eluting with MeCN in H₂O with 0.1% ammonium hydroxide to afford the titled compound as a white solid.

1H NMR (500 MHz, DMSO-d6) δ 7.97 (d, J=5.6 Hz, 1H), 7.92 (s, 1H), 7.17 (d, J=2.3 Hz, 1H), 6.56 (dd, J=5.6, 2.4 Hz, 1H), 6.32 (s, 2H), 1.74 (q, J=7.5 Hz, 2H), 1.31 (s, 6H), 0.80 (t, J=7.5 Hz, 3H).

LC-MS (Method F): Rt 1.55 mins; MS m/z 208.3=[M+H]+ (100% @ 215 nm)

Step 2: 4-[[2-(5-Chloro-2-hydroxy-phenyl)acetyl]amino]-N-(1,1-dimethylpropyl)pyridine-2-carboxamide The titled compound was prepared analogously to Example 9 (step 2) from 4-amino-N-(1,1-dimethylpropyl)pyridine-2-carboxamide and 5-chloro-3H-benzofuran-2-one.

¹H NMR (500 MHz, Methanol-d₄) δ 8.42 (d, J=5.6 Hz, 1H), 8.13-8.08 (m, 1H), 7.91 (dd, J=5.5, 2.2 Hz, 1H), 7.19 (d, J=2.6 Hz, 1H), 7.09 (dd, J=8.6, 2.6 Hz, 1H), 6.77 (d, J=8.6 Hz, 1H), 3.71 (s, 2H), 1.86 (q, J=7.5 Hz, 2H), 1.42 (s, 6H), 0.91 (t, J=7.5 Hz, 3H).

LC-MS (Method A): Rt 3.50 mins; MS m/z 376.0/378.0=[M+H]+ (98% @ 215 nm).

Example 10

N-tert-Butyl-4-[[2-(5-tert-butyl-2-hydroxy-phenyl)acetyl]amino]pyridine-2-carboxamide

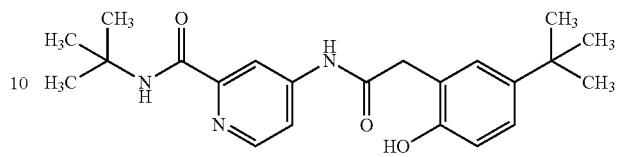

Step 1: N-tert-Butyl-4-[[2-(5-tert-butyl-2-methoxy-phenyl)acetyl]amino]pyridine-2-carboxamide

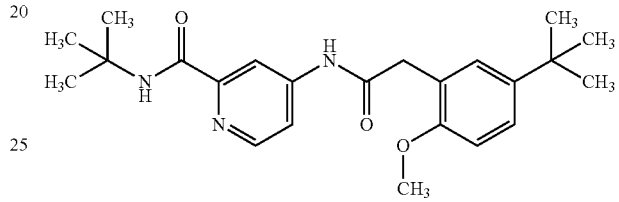

The titled compound was prepared from 4-amino-N-tert-butyl-pyridine-2-carboxamide (Example 3 step 1) and commercially available 2-(5-tert-butyl-2-methoxy-phenyl)acetic acid analogously to Example 4.

1H NMR (500 MHz, Chloroform-d) δ 8.45 (br s, 1H), 8.38 (d, J=5.7 Hz, 1H), 8.29 (d, J=5.3 Hz, 1H), 8.16 (br s, 1H), 7.57 (s, 1H), 7.34 (dd, J=8.6, 2.5 Hz, 1H), 7.28 (d, J=2.5 Hz, 1H), 6.92 (d, J=8.6 Hz, 1H), 3.98 (s, 3H), 3.75 (s, 2H), 1.48 (s, 9H), 1.30 (s, 9H).

LC-MS (Method E): Rt 1.31 mins; MS m/z 398.2=[M+H]+ (85% @ 215 nm)

Step 2: N-tert-Butyl-4-[[2-(5-tert-butyl-2-hydroxy-phenyl)acetyl]amino]pyridine-2-carboxamide The titled compound was prepared analogously to Example 3 (step 3) from N-tert-Butyl-4-[[2-(5-tert-butyl-2-methoxy-phenyl)acetyl]amino]pyridine-2-carboxamide.

1H NMR (500 MHz, Methanol-d4) δ 8.42 (d, J=5.5 Hz, 1H), 8.09 (d, J=1.8 Hz, 1H), 7.91 (dd, J=5.5, 2.2 Hz, 1H), 7.21 (d, J=2.5 Hz, 1H), 7.15 (dd, J=8.4, 2.5 Hz, 1H), 6.75 (d, J=8.4 Hz, 1H), 3.72 (s, 2H), 1.47 (s, 9H), 1.28 (s, 9H).

LC-MS (Method A): Rt 3.81 mins; MS m/z 384.3=[M+H]+ (97% @ 215 nm)

Example 11

N-tert-Butyl-5-[[2-(5-chloro-2-hydroxy-phenyl)acetyl]amino]-2-hydroxy-benzamide

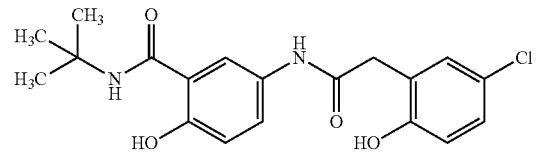 [SMILES: CC(C)(C)NC(=O)c1cc(NC(=O)Cc2cc(Cl)ccc2O)ccc1O]

Step 1: Methyl 5-[[2-(5-chloro-2-hydroxy-phenyl)acetyl]amino]-2-methoxy-benzoate

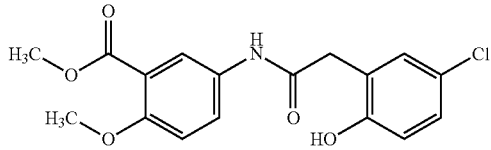 [SMILES: COC(=O)c1cc(NC(=O)Cc2cc(Cl)ccc2O)ccc1OC]

A mixture of 5-chloro-3H-benzofuran-2-one (75 mg, 0.44 mmol) and methyl 5-amino-2-methoxy-benzoate (81 mg, 0.44 mmol) in toluene (2 mL) was stirred at 100° C. in a sealed tube for 2 hours. The resulting mixture was allowed to cool to room temperature, toluene was added and the suspension was filtered, washing with toluene. The solid was dried in vacuo to afford the titled compound as an off-white solid.

1H NMR (500 MHz, Chloroform-d) δ 7.79 (s, 1H), 7.77 (d, J=2.8 Hz, 1H), 7.72 (dd, J=9.0, 2.8 Hz, 1H), 7.14 (dd, J=8.6, 2.6 Hz, 1H), 7.08 (d, J=2.6 Hz, 1H), 6.93 (d, J=9.0 Hz, 1H), 6.90 (d, J=8.6 Hz, 1H), 3.88 (s, 3H), 3.87 (s, 3H), 3.67 (s, 2H).

LC-MS (Method E): Rt 1.05 mins; MS m/z 350.0/351.9= [M+H]+ (98% @ 215 nm)

Step 2: 5-[[2-(5-Chloro-2-hydroxy-phenyl)acetyl]amino]-2-methoxy-benzoic acid

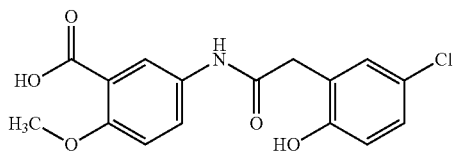 [SMILES: COc1ccc(NC(=O)Cc2cc(Cl)ccc2O)cc1C(=O)O]

To a solution of methyl 5-[[2-(5-chloro-2-hydroxy-phenyl)acetyl]amino]-2-methoxy-benzoate (step 1) (105 mg, 0.29 mmol) in 1,4-dioxane (2 mL) was added aqueous 2M LiOH (0.29 mL, 0.59 mmol) and the mixture was shaken at room temperature for 5 hours. A further equivalence of aqueous 2M LiOH (0.15 mL, 0.29 mmol) was added and shaking continued for an hour. Dioxane was removed in vacuo and the resulting mixture acidified to pH 1 with 1M HCl (1 mL). The mixture was extracted with EtOAc (2×5 mL) and the combined extracts were dried over Na2SO4 and concentrated in vacuo to afford the titled compound as an off-white solid.

1H NMR (500 MHz, DMSO-d6) δ 12.60 (br s, 1H), 10.05 (s, 1H), 9.79 (s, 1H), 7.89 (d, J=2.7 Hz, 1H), 7.70 (dd, J=9.0, 2.8 Hz, 1H), 7.19 (d, J=2.7 Hz, 1H), 7.10 (dd, J=8.6, 2.7 Hz, 1H), 7.07 (d, J=9.1 Hz, 1H), 6.80 (d, J=8.6 Hz, 1H), 3.77 (s, 3H), 3.57 (s, 2H).

LC-MS (Method E): Rt 0.99 mins; MS m/z 336.0/338.0= [M+H]+ (99% @ 215 nm)

Step 3: N-tert-Butyl-5-[[2-(5-Chloro-2-hydroxy-phenyl)acetyl]amino]-2-methoxy-benzamide

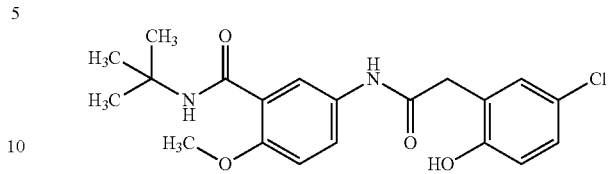

The titled compound was prepared from 5-[[2-(5-chloro-2-hydroxy-phenyl)acetyl]amino]-2-methoxy-benzoic acid (step 2) analogously to Example 1 step 3.

1H NMR (500 MHz, DMSO-d6) δ 10.13 (s, 1H), 9.80 (s, 1H), 7.90 (d, J=2.8 Hz, 1H), 7.85 (s, 1H), 7.74 (dd, J=8.9, 2.8 Hz, 1H), 7.18 (d, J=2.7 Hz, 1H), 7.09 (dd, J=8.6, 2.7 Hz, 1H), 7.07 (d, J=9.0 Hz, 1H), 6.79 (d, J=8.6 Hz, 1H), 3.86 (s, 3H), 3.56 (s, 2H), 1.36 (s, 9H).

LC-MS (Method A): Rt 3.34 mins; MS m/z 391.2/393.2= [M+H]+ (99% @ 215 nm)

Step 4: N-tert-Butyl-5-[[2-(5-chloro-2-hydroxy-phenyl)acetyl]amino]-2-hydroxy-benzamide The titled compound was prepared from N-tert-butyl-5-[[2-(5-chloro-2-hydroxy-phenyl)acetyl]amino]-2-methoxy-benzamide (step 3) analogously to Example 3 step 3.

1H NMR (500 MHz, DMSO-d6) δ 11.50 (br.s, 1H), 9.94 (s, 1H), 9.82 (s, 1H), 8.24 (s, 1H), 7.98-7.88 (m, 1H), 7.60-7.53 (m, 1H), 7.19 (d, J=2.6 Hz, 1H), 7.10 (dd, J=8.6, 2.7 Hz, 1H), 6.83 (d, J=8.7 Hz, 1H), 6.80 (d, J=8.6 Hz, 1H), 3.56 (s, 2H), 1.38 (s, 9H).

LC-MS (Method A): Rt 3.29 mins; MS m/z 377.2/379.2= [M+H]+ (95% @ 215 nm)

Example 12

N-tert-Butyl-3-[[2-(5-cyano-2-hydroxy-phenyl)acetyl]amino]benzamide

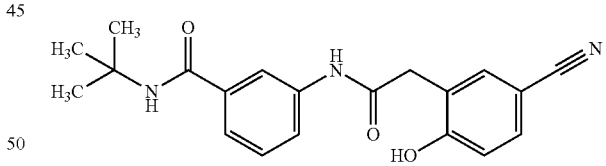

Step 1: 3-[[2-(5-Bromo-2-methoxy-phenyl)acetyl]amino]-N-tert-butyl-benzamide

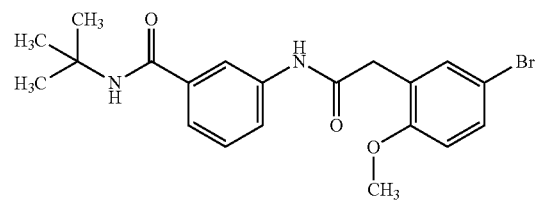 [SMILES: COc1ccc(Br)cc1CC(=O)Nc1cccc(C(=O)NC(C)(C)C)c1]

The titled compound was prepared analogously to Example 4 from 3-amino-N-tert-butyl-benzamide hydrochloride (Example 2 step 1b) and 2-(5-bromo-2-methoxyphenyl)acetic acid.

1H NMR (500 MHz, DMSO-d6) δ 10.19 (s, 1H), 7.89 (s, 1H), 7.74 (d, 1H), 7.70 (s, 1H), 7.44-7.40 (m, 3H), 7.33 (t, J=7.9 Hz, 1H), 6.99-6.92 (m, 1H), 3.76 (s, 3H), 3.65 (s, 2H), 1.36 (s, 9H).

LC-MS (Method A): Rt 3.41 mins; MS m/z 419.2, 421.2= [M+H]+ (100% @ 215 nm)

Steps 2-3: N-tert-Butyl-3-[[2-(5-cyano-2-hydroxyphenyl)acetyl]amino]benzamide

The titled compound was prepared analogously to Example 6 steps 2 and 3 from 3-[[2-(5-bromo-2-methoxyphenyl)acetyl]amino]-N-tert-butyl-benzamide (step 1).

1H NMR (500 MHz, DMSO-d6) δ 10.76 (br. S, 1H), 10.23 (s, 1H), 7.89 (t, J=1.8 Hz, 1H), 7.80-7.72 (m, 1H), 7.70 (s, 1H), 7.61 (d, J=2.1 Hz, 1H), 7.56 (dd, J=8.4, 2.2 Hz, 1H), 7.42 (d, J=7.8 Hz, 1H), 7.33 (m, 1H), 6.93 (d, J=8.4 Hz, 1H), 3.66 (s, 2H), 1.36 (s, 9H).

LC-MS (Method A): Rt 2.66 mins; MS m/z 352.2=[M+H]+ (98% @ 215 nm)

Example 13

Methyl 3-[2-[[2-(tert-butylcarbamoyl)-4-pyridyl]amino]-2-oxo-ethyl]-4-hydroxy-benzoate

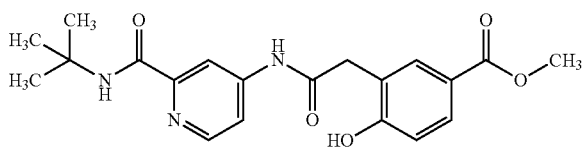 [SMILES: COC(=O)c1ccc(O)c(CC(=O)Nc2ccnc(C(=O)NC(C)(C)C)c2)c1]

Step 1: 4-[[2-(5-Bromo-2-hydroxy-phenyl)acetyl]amino]-N-tert-butyl-pyridine-2-carboxamide

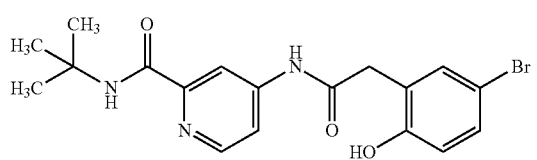 [SMILES: CC(C)(C)NC(=O)c1cc(NC(=O)Cc2cc(Br)ccc2O)ccn1]

A solution of 4-[[2-(5-bromo-2-methoxy-phenyl)acetyl]amino]-N-tert-butyl-pyridine-2-carboxamide (Example 6, step 1) (500 mg, 1.19 mmol) in DCM (25 mL) was treated with 1M BBr3 in DCM (3.57 mL, 3.57 mmol) and stirred at room temperature under nitrogen overnight. The resulting mixture was diluted with DCM (50 mL) and washed with water (25 mL×2). The organic extracts were dried over Na2SO4 and concentrated in vacuo. Purification of the crude solid by C18 reverse phase chromatography eluting with 0-100% MeCN in water with 0.1% formic acid afforded the titled compound as a light yellow solid.

1H NMR (500 MHz, DMSO-d6) δ 10.69 (s, 1H), 9.86 (s, 1H), 8.44 (d, J=5.5 Hz, 1H), 8.17 (d, J=2.0 Hz, 1H), 8.03 (s, 1H), 7.81 (dd, J=5.5, 2.2 Hz, 1H), 7.34 (d, J=2.5 Hz, 1H), 7.24 (dd, J=8.6, 2.6 Hz, 1H), 6.76 (d, J=8.6 Hz, 1H), 3.67 (s, 2H), 1.40 (s, 9H).

LC-MS (Method A): Rt 3.34 mins; MS m/z 406.1/408.1= [M+H]+ (90% @ 215 nm)

Step 2: Methyl 3-[2-[[2-(tert-butylcarbamoyl)-4-pyridyl]amino]-2-oxo-ethyl]-4-hydroxy-benzoate All reagents charged to Coware equipment (carbon monoxide generating system) according to the following procedure; To chamber A was added sodium carbonate (53 mg, 0.50 mmol), 4-[[2-(5-bromo-2-hydroxy-phenyl)acetyl]amino]-N-tert-butyl-pyridine-2-carboxamide (step 1) (75 mg, 0.16 mmol), XantPhos Pd-G3 (third generation (G3) Buchwald precatalyst) (8 mg, 0.01 mmol) and toluene (2 mL). The reaction mixture was de-gassed for 5 minutes and MeOH (0.25 mL) was added. To chamber B was added formic acid (19 µL, 0.50 mmol) in toluene (2 mL) followed by mesyl chloride (39 µL, 0.50 mmol). Both chambers were sealed and TEA (139 µL, 0.99 mmol) added to chamber B to generate carbon monoxide. The Coware equipment was heated at 75° C. for 7 hours. The resulting mixture was concentrated in vacuo, dissolved in EtOAc (20 mL) and washed with water (2×20 mL). The organic portion was concentrated in vacuo and purified by preparative HPLC (acidic pH, early elution method). The product fractions were isolated and freeze-dried to afford the titled compound as an off-white solid.

1H NMR (500 MHz, DMSO-d6) δ 10.78 (br s, 1H), 10.55 (br s, 1H), 8.44 (d, J=5.5 Hz, 1H), 8.17 (d, J=2.0 Hz, 1H), 8.03 (s, 1H), 7.83-7.80 (m, 2H), 7.74 (dd, J=8.5, 2.2 Hz, 1H), 6.88 (d, J=8.5 Hz, 1H), 3.79 (s, 3H), 3.72 (s, 2H), 1.40 (s, 9H).

LC-MS (Method A): Rt 2.94 mins; MS m/z 386.3=[M+H]+ (95% @ 215 nm)

Example 14

N-tert-Butyl-3-[[2-(5-chloro-2-hydroxy-phenyl)acetyl]amino]-4-hydroxy-benzamide

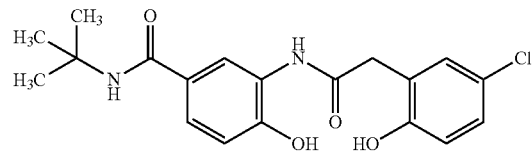 [SMILES: CC(C)(C)NC(=O)c1ccc(O)c(NC(=O)Cc2cc(Cl)ccc2O)c1]

Step 1: Methyl 3-[[2-(5-chloro-2-methoxy-phenyl)acetyl]amino]-4-methoxy-benzoate

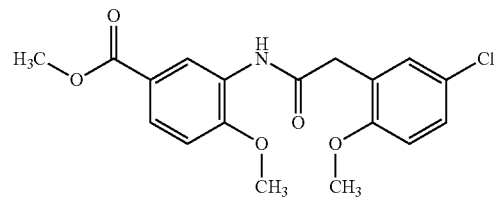 [SMILES: COC(=O)c1ccc(OC)c(NC(=O)Cc2cc(Cl)ccc2OC)c1]

The titled compound was prepared analogously to Example 6 (step 1) from methyl 3-amino-4-methoxy-benzoate and 2-(5-chloro-2-methoxy-phenyl)acetic acid.

1H NMR (500 MHz, Chloroform-d) δ 8.98 (m, 1H), 8.28 (s, 1H), 7.77 (dd, J=8.6, 2.1 Hz, 1H), 7.31 (d, J=2.6 Hz, 1H), 7.24 (dd, J=8.7, 2.6 Hz, 1H), 6.86 (dd, J=8.7, 6.1 Hz, 2H), 3.90 (s, 3H), 3.90 (s, 3H), 3.86 (s, 3H), 3.71 (s, 2H).

LC-MS (Method E): Rt 1.20 mins; MS m/z 364.1/366.1= [M+H]+ (72% @ 215 nm)

Step 2: 3-[[2-(5-Chloro-2-methoxy-phenyl)acetyl] amino]-4-methoxy-benzoic acid

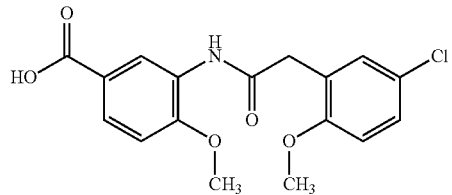 [SMILES: COc1ccc(Cl)cc1CC(=O)Nc1cc(C(=O)O)ccc1OC]

To a solution of methyl 3-[[2-(5-chloro-2-methoxy-phenyl)acetyl]amino]-4-methoxy-benzoate (step 1)(301 mg, 0.83 mmol) in 1,4-dioxane (4 mL) was added aqueous 2M LiOH (1.24 mL, 2.48 mmol) and the mixture was shaken at room temperature overnight. The dioxane was removed in vacuo and the resulting mixture acidified to pH 1 with 1M HCl. The mixture was washed with EtOAc (2×5 mL). The aqueous phase was concentrated in vacuo and the resultant solid sonicated with MeOH (20 mL). The suspension was filtered, washed with further MeOH (5 mL) and the combined filtrate concentrated in vacuo to give an off-white solid.

1H NMR (500 MHz, DMSO-d6) δ 9.26 (s, 1H), 8.56 (s, 1H), 7.68 (dd, J=8.5, 2.1 Hz, 1H), 7.35-7.20 (m, 3H), 7.13 (d, J=8.6 Hz, 1H), 7.03 (d, J=8.5 Hz, 1H), 3.92 (s, 3H), 3.82 (s, 2H), 3.80 (s, 3H).

LC-MS (Method E): Rt 1.08 mins; MS m/z 350.1/352.1= [M+H]+ (85% @ 215 nm)

Step 3: N-tert-Butyl-3-[[2-(5-chloro-2-methoxy-phenyl)acetyl]amino]-4-methoxy-benzamide

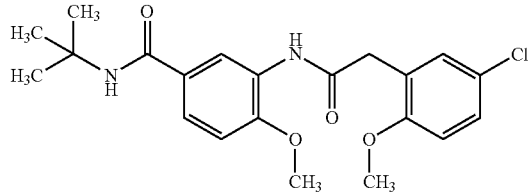 [SMILES: COc1ccc(Cl)cc1CC(=O)Nc1cc(C(=O)NC(C)(C)C)ccc1OC]

To a solution of 3-[[2-(5-chloro-2-methoxy-phenyl) acetyl]amino]-4-methoxy-benzoic acid (step 2)(201 mg, 0.57 mmol) in DMF (2 mL) was added EDCI (110 mg, 0.57 mmol), HOAt (78 mg, 0.57 mmol), DIPEA (251 μL, 1.44 mmol) and 2-methylpropan-2-amine (79 μL, 0.75 mmol). The reaction mixture was shaken at room temperature overnight and then partitioned between DCM (6 mL) and water (6 mL). The organic layer collected using a hydrophobic frit and concentrated in vacuo. Chromatography on silica eluting with EtOAc in heptane afforded the titled compound as a colourless glass.

1H NMR (500 MHz, Chloroform-d) δ 8.63 (d, J=2.2 Hz, 1H), 8.36 (s, 1H), 7.64 (dd, J=8.6, 2.3 Hz, 1H), 7.30 (d, J=2.6 Hz, 1H), 7.25 (dd, J=8.8, 2.6 Hz, 1H), 6.87 (dd, J=10.9, 8.7 Hz, 2H), 5.99 (s, 1H), 3.90 (s, 3H), 3.88 (s, 3H), 3.70 (s, 2H), 1.43 (s, 9H).

LC-MS (Method E): Rt 1.20 mins; MS m/z 405.1/407.1= [M+H]+ (62% @ 215 nm)

Step 4: N-tert-Butyl-3-[[2-(5-chloro-2-hydroxy-phenyl)acetyl]amino]-4-hydroxy-benzamide The titled compound was prepared from N-tert-butyl-3-[[2-(5-chloro-2-methoxy-phenyl)acetyl]amino]-4-methoxy-benzamide (step 3) analogously to Example 3 step 3.

1H NMR (500 MHz, Methanol-d4) δ 8.23 (d, J=2.2 Hz, 1H), 7.48 (s, 1H), 7.39 (dd, J=8.4, 2.2 Hz, 1H), 7.24 (d, J=2.6 Hz, 1H), 7.11 (dd, J=8.6, 2.6 Hz, 1H), 6.86 (d, J=8.4 Hz, 1H), 6.82 (d, J=8.6 Hz, 1H), 3.72 (s, 2H), 1.43 (s, 9H).

LC-MS (Method A): Rt 2.93 mins; MS m/z 377.3/379.2= [M+H]+ (99% @ 215 nm).

Example 15

N-tert-Butyl-4-[[2-(2-hydroxy-5-methyl-phenyl) acetyl]amino]pyridine-2-carboxamide

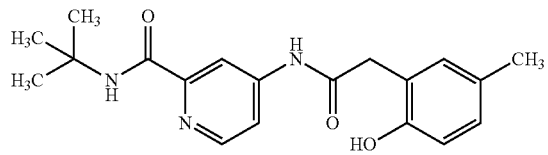 [SMILES: Cc1ccc(O)c(CC(=O)Nc2ccnc(C(=O)NC(C)(C)C)c2)c1]

Step 1: N-tert-Butyl-4-[[2-(2-methoxy-5-methyl-phenyl)acetyl]amino]pyridine-2-carboxamide

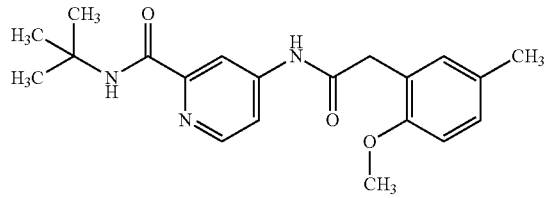 [SMILES: COc1ccc(C)cc1CC(=O)Nc1ccnc(C(=O)NC(C)(C)C)c1]

To a solution of 4-[[2-(5-bromo-2-methoxy-phenyl) acetyl]amino]-N-tert-butyl-pyridine-2-carboxamide (Example 6 step 1) (200 mg, 0.48 mmol) and potassium carbonate (132 mg, 0.95 mmol) in diglyme (5 mL) was added Pd(dppf)2Cl2 (17 mg, 0.02 mmol) followed by 2,4,6-trimethyl-1,3,5,2,4,6-trioxatriborinane in THF (50%, 0.16 mL, 0.57 mmol). The resulting mixture was degassed with nitrogen for 5 minutes and then stirred in a pressure tube at 100° C. for 16 hours. The resulting mixture was diluted with EtOAc (25 mL) and washed with water (2×25 mL) and brine (2×25 mL). The organic portion was dried over Na2SO4, concentrated in vacuo and purified by chromatography on silica eluting with EtOAc in heptane. The product fractions were concentrated in vacuo to afford the titled compound as a beige solid.

1H NMR (500 MHz, DMSO-d6) δ 10.65 (s, 1H), 8.43 (d, J=5.5 Hz, 1H), 8.18 (d, J=2.0 Hz, 1H), 8.03 (s, 1H), 7.81 (dd, J=5.5, 2.2 Hz, 1H), 7.06-7.01 (m, 2H), 6.86 (d, J=8.2 Hz, 1H), 3.71 (s, 3H), 3.65 (s, 2H), 2.23 (s, 3H), 1.40 (s, 9H).

LC-MS (Method E): Rt 1.22 mins; MS m/z 356.2=[M+H]+ (97% @ 215 nm)

Step 2: N-tert-Butyl-4-[[2-(2-hydroxy-5-methyl-phenyl)acetyl]amino]pyridine-2-carboxamide The titled compound was prepared from N-tert-Butyl-4-[[2-(2-methoxy-5-methyl-phenyl)acetyl]amino]pyridine-2-carboxamide (step 1) analogously to Example 3 (step 3).

1H NMR (500 MHz, DMSO-d6) δ 10.63 (s, 1H), 9.25 (s, 1H), 8.43 (d, J=5.5 Hz, 1H), 8.18 (d, J=2.0 Hz, 1H), 8.03 (s, 1H), 7.82 (dd, J=5.5, 2.2 Hz, 1H), 6.94 (d, J=1.9 Hz, 1H), 6.87 (dd, J=8.1, 1.9 Hz, 1H), 6.68 (d, J=8.1 Hz, 1H), 3.61 (s, 2H), 2.18 (s, 3H), 1.40 (s, 9H).

LC-MS (Method A): Rt 3.19 mins; MS m/z 342.3=[M+H]+ (100% @ 215 nm)

Example 16

N-tert-Butyl-3-[[2-(5-chloro-2-hydroxy-phenyl)acetyl]amino]-4-methoxy-benzamide

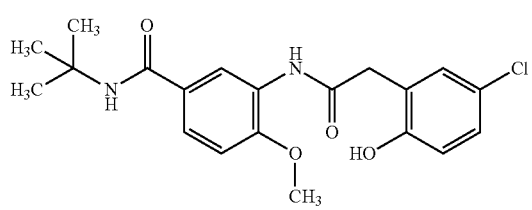 [SMILES: COc1ccc(C(=O)NC(C)(C)C)cc1NC(=O)Cc1cc(Cl)ccc1O]

The titled compound was prepared from methyl 3-amino-4-methoxy-benzoate and 5-chloro-3H-benzofuran-2-one analogously to Example 11 steps 1-3.

1H NMR (500 MHz, Methanol-d4) δ 8.36 (d, J=2.1 Hz, 1H), 7.51 (dd, J=8.6, 2.2 Hz, 1H), 7.24 (d, J=2.6 Hz, 1H), 7.12 (dd, J=8.6, 2.6 Hz, 1H), 7.03 (d, J=8.6 Hz, 1H), 6.83 (d, J=8.6 Hz, 1H), 3.91 (s, 3H), 3.72 (s, 2H), 1.43 (s, 9H).

LC-MS (Method A): Rt 3.18 mins; MS m/z 391.2/393.2=[M+H]+ (95% @ 215 nm)

Example 17

N-tert-Butyl-5-[[2-(5-chloro-2-hydroxy-phenyl)acetyl]amino]-2-fluoro-benzamide

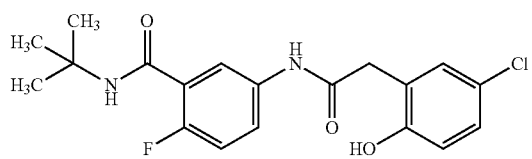 [SMILES: CC(C)(C)NC(=O)c1cc(NC(=O)Cc2cc(Cl)ccc2O)ccc1F]

Steps 1-2: 5-[[2-(5-Chloro-2-methoxy-phenyl)acetyl]amino]-2-fluoro-benzoic acid

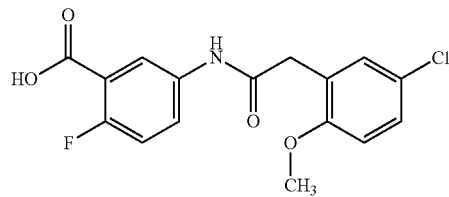 [SMILES: COc1ccc(Cl)cc1CC(=O)Nc1ccc(F)c(C(=O)O)c1]

The titled compound was prepared from methyl 5-amino-2-fluoro-benzoate and 2-(5-chloro-2-methoxy-phenyl)acetic acid analogously to Example 7 steps 1 and 2.

1H NMR (500 MHz, DMSO-d6) δ 13.25 (br s, 1H), 10.29 (s, 1H), 8.14 (dd, J=6.6, 2.8 Hz, 1H), 7.83-7.76 (m, 1H), 7.32-7.28 (m, 2H), 7.25 (dd, J=10.5, 9.0 Hz, 1H), 7.03-6.98 (m, 1H), 3.77 (s, 3H), 3.65 (s, 2H).

LC-MS (Method E): Rt 1.04 mins; MS m/z 338.0, 340.1=[M+H]+ (95% @ 215 nm)

Step 3: N-tert-Butyl-5-[[2-(5-chloro-2-methoxy-phenyl)acetyl]amino]-2-fluoro-benzamide

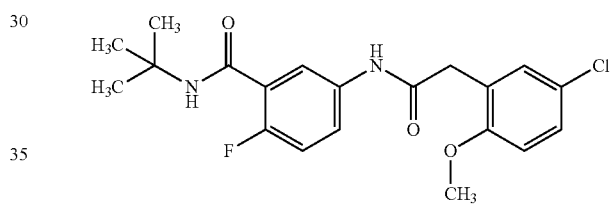

To a mixture of 5-[[2-(5-chloro-2-methoxy-phenyl)acetyl]amino]-2-fluoro-benzoic acid (step 2) (100 mg, 0.28 mmol), TBTU (108 mg, 0.34 mmol) and TEA (0.08 mL, 0.56 mmol) in DMF (1.5 mL) was added 2-methylpropan-2-amine (35 μL, 0.34 mmol) and the mixture was stirred at room temperature for 3 hours. The resulting mixture was concentrated in vacuo and the residue was partitioned between water (10 mL) and DCM (10 mL). The organic phase was separated and concentrated in vacuo. Purification of the crude product by chromatography on silica eluting with EtOAc in heptane afforded the titled compound as a white solid.

1H NMR (500 MHz, DMSO-d6) δ 10.21 (s, 1H), 7.83 (s, 1H), 7.73 (dd, J=6.3, 2.7 Hz, 1H), 7.65 (ddd, J=8.8, 4.4, 2.8 Hz, 1H), 7.32-7.29 (m, 1H), 7.29-7.27 (m, 1H), 7.17 (t, J=9.4 Hz, 1H), 7.02-6.98 (m, 1H), 3.76 (s, 3H), 3.63 (s, 2H), 1.34 (s, 9H).

LC-MS (Method E): Rt 1.22 mins; MS m/z 393.2, 395.1=[M+H]+ (99% @ 215 nm)

Step 4: N-tert-Butyl-5-[[2-(5-chloro-2-hydroxy-phenyl)acetyl]amino]-2-fluoro-benzamide The titled compound was prepared from N-tert-butyl-5-[[2-(5-chloro-2-methoxy-phenyl)acetyl]amino]-2-fluoro-benzamide (step 3) analogously to Example 7, step 4.

1H NMR (500 MHz, DMSO-d6) δ 10.21 (s, 1H), 9.84 (s, 1H), 7.83 (s, 1H), 7.73 (dd, J=6.3, 2.7 Hz, 1H), 7.66 (ddd, J=8.9, 4.4, 2.8 Hz, 1H), 7.24-7.13 (m, 2H), 7.11 (dd, J=8.6, 2.7 Hz, 1H), 6.80 (d, J=8.6 Hz, 1H), 3.59 (s, 2H), 1.34 (s, 9H).

LC-MS (Method A): Rt 3.30 mins; MS m/z 379.2/381.1= [M+H]+ (99% @ 215 nm)

Example 18

N-tert-Butyl-3-[[2-(5-chloro-2-hydroxy-phenyl)acetyl]amino]-5-fluoro-benzamide

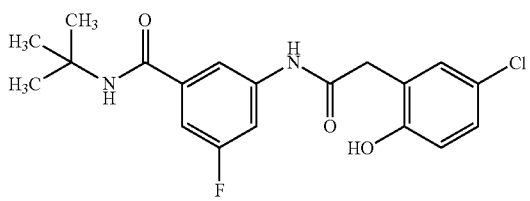 [SMILES: CC(C)(C)NC(=O)c1cc(F)cc(NC(=O)Cc2cc(Cl)ccc2O)c1]

Step 1: 3-Amino-N-tert-butyl-5-fluoro-benzamide

The titled compound was prepared from 3-amino-5-fluoro-benzoic acid analogously to Example 9 step 1.

1H NMR (500 MHz, Chloroform-d) δ 6.85-6.80 (m, 1H), 6.69 (dt, J=9.1, 1.8 Hz, 1H), 6.45 (dt, J=10.2, 2.2 Hz, 1H), 5.81 (s, 1H), 3.89 (s, 2H), 1.45 (s, 9H).

LC-MS (Method E): Rt 0.96 mins; MS m/z 211.1=[M+H]+ (100% @ 215 nm)

Steps 2-3: N-tert-Butyl-3-[[2-(5-chloro-2-hydroxy-phenyl)acetyl]amino]-5-fluoro-benzamide The titled compound was prepared from 3-amino-N-tert-butyl-5-fluoro-benzamide (step 1) analogously to Example 3 steps 2 and 3.

1H NMR (500 MHz, DMSO-d6) δ 10.41 (s, 1H), 9.81 (s, 1H), 7.81 (s, 1H), 7.75 (dt, J=11.2, 2.0 Hz, 1H), 7.66 (s, 1H), 7.32-7.24 (m, 1H), 7.20 (d, J=2.7 Hz, 1H), 7.11 (dd, J=8.6, 2.7 Hz, 1H), 6.80 (d, J=8.6 Hz, 1H), 3.62 (s, 2H), 1.36 (s, 9H).

LC-MS (Method A): Rt 3.34 mins; MS m/z 379.1/381.1= [M+H]+ (97% @ 215 nm)

Example 19

N-tert-Butyl-4-[[2-(3-hydroxy-2-pyridyl)acetyl]amino]pyridine-2-carboxamide

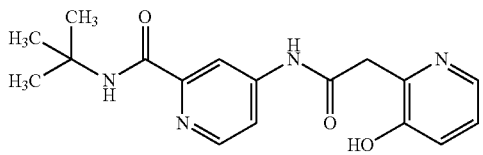 [SMILES: CC(C)(C)NC(=O)c1cc(NC(=O)Cc2ncccc2O)ccn1]

Step 1: N-tert-Butyl-4-[[2-(3-methoxy-2-pyridyl)acetyl]amino]pyridine-2-carboxamide

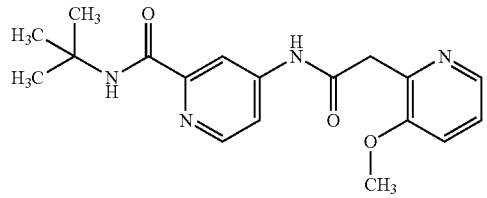

The titled compound was prepared from 4-amino-N-tert-butyl-pyridine-2-carboxamide (Example 3 step 1) and 2-(3-methoxy-2-pyridyl)acetic acid analogously to Example 5.

1H NMR (500 MHz, DMSO-d6) δ 10.75 (s, 1H), 8.44 (d, J=5.5 Hz, 1H), 8.18 (d, J=2.1 Hz, 1H), 8.07 (dd, J=4.7, 1.3 Hz, 1H), 8.03 (s, 1H), 7.80 (dd, J=5.5, 2.2 Hz, 1H), 7.42 (dd, J=8.3, 1.2 Hz, 1H), 7.30 (dd, J=8.3, 4.7 Hz, 1H), 3.88 (s, 2H), 3.81 (s, 3H), 1.40 (s, 9H).

LC-MS (Method A): Rt 2.11 mins; MS m/z 343.2=[M+H]+ (100% @ 215 nm)

Step 2: N-tert-Butyl-4-[[2-(3-hydroxy-2-pyridyl)acetyl]amino]pyridine-2-carboxamide The titled compound was prepared from N-tert-Butyl-4-[[2-(3-methoxy-2-pyridyl)acetyl]amino]pyridine-2-carboxamide (step 1) analogously to Example 7, step 4.

1H NMR (500 MHz, DMSO-d6) δ 10.73 (s, 1H), 10.01 (br s, 1H), 8.44 (d, J=5.5 Hz, 1H), 8.18 (d, J=2.1 Hz, 1H), 8.03 (s, 1H), 7.95 (dd, J=4.4, 1.6 Hz, 1H), 7.81 (dd, J=5.5, 2.2 Hz, 1H), 7.20-7.09 (m, 2H), 3.84 (s, 2H), 1.40 (s, 9H).

LC-MS (Method A): Rt 1.60 mins; MS m/z 329.1=[M+H]+ (98% @ 215 nm)

Example 20

N-tert-Butyl-4-[[2-(5-fluoro-2-hydroxy-phenyl)acetyl]amino]pyridine-2-carboxamide

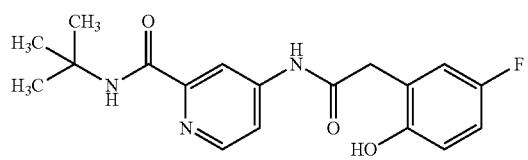

Step 1: N-tert-Butyl-4-[[2-(5-fluoro-2-methoxy-phenyl)acetyl]amino]pyridine-2-carboxamide

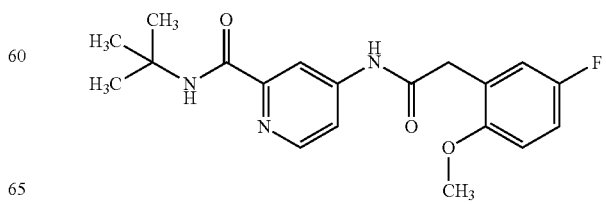

A solution of 2-(5-fluoro-2-methoxy-phenyl)acetic acid (57 mg, 0.31 mmol) in thionyl chloride (246 μL, 2.79 mmol) was heated at 70° C. for 1 hr. Excess thionyl chloride was removed in vacuo, azeotroping with DCM. The residue was added to a mixture of 4-amino-N-tert-butyl-pyridine-2-carboxamide (Example 3 step 1) (60 mg, 0.31 mmol) and DIPEA (65 μL, 0.37 mmol) in DCM (30 mL) and the mixture was stirred at room temperature. After 1 hour, the mixture was partitioned between water (25 mL) and DCM (25 mL). The organic layer was separated, dried over Na$_2$SO$_4$, filtered and concentrated in vacuo. Purification of the crude residue by chromatography on silica eluting with EtOAc in heptane followed by freeze drying of the product fractions afforded the titled compound as a white solid.

1H NMR (500 MHz, DMSO-d6) δ 10.68 (s, 1H), 8.44 (d, J=5.5 Hz, 1H), 8.17 (d, J=2.0 Hz, 1H), 8.03 (s, 1H), 7.81 (dd, J=5.5, 2.2 Hz, 1H), 7.12 (dd, J=9.2, 3.2 Hz, 1H), 7.08 (td, J=8.6, 3.2 Hz, 1H), 6.98 (dd, J=9.0, 4.6 Hz, 1H), 3.74 (s, 3H), 3.71 (s, 2H), 1.40 (s, 9H).

LC-MS (Method E): Rt 1.16 mins; MS m/z 360.1=[M+H]+ (98% @ 215 nm)

Step 2: N-tert-Butyl-4-[[2-(5-fluoro-2-hydroxy-phenyl)acetyl]amino]pyridine-2-carboxamide To a solution of N-tert-butyl-4-[[2-(5-fluoro-2-methoxy-phenyl)acetyl]amino]pyridine-2-carboxamide (step 1) (54.1 mg, 0.15 mmol) in DCM (1.3 mL) was added 1M BBr$_3$ in DCM (452 μL, 0.45 mmol) slowly at room temperature. The reaction was stirred at room temperature for 2.5 hours and then concentrated in vacuo. The residue was partitioned between H$_2$O (10 mL) and EtOAc (10 mL) and the organic portion separated and concentrated in vacuo. The crude product was purified by preparative HPLC (acidic pH, early elution method) to afford the titled compound as a white solid.

1H NMR (500 MHz, DMSO-d6) δ 10.67 (s, 1H), 9.52 (s, 1H), 8.44 (d, J=5.5 Hz, 1H), 8.18 (d, J=2.1 Hz, 1H), 8.03 (s, 1H), 7.82 (dd, J=5.5, 2.2 Hz, 1H), 7.01 (dd, J=9.4, 3.2 Hz, 1H), 6.91 (td, J=8.6, 3.2 Hz, 1H), 6.77 (dd, J=8.8, 4.9 Hz, 1H), 3.67 (s, 2H), 1.40 (s, 9H).

LC-MS (Method A): Rt 3.01 mins; MS m/z 346.1=[M+H]+ (98% @ 215 nm)

Example 21

Racemic N-tert-butyl-4-[[-indane-1-carbonyl]amino]pyridine-2-carboxamide

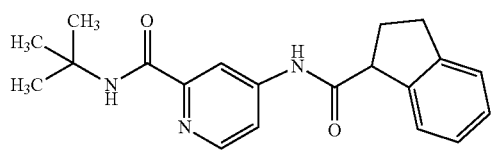 [SMILES: CC(C)(C)NC(=O)c1cc(NC(=O)C2CCc3ccccc32)ccn1]

A mixture of 4-amino-N-tert-butyl-pyridine-2-carboxamide (Example 3 step 1) (100 mg, 0.52 mmol) and indane-1-carboxylic acid (84 mg, 0.52 mmol) in 1,4-dioxane (1 mL) was treated with 50% T3P® solution in EtOAc (616 μL, 1.03 mmol) and TEA (181 μL, 1.03 mmol) and stirred at room temperature for 1.5 hours. The resulting mixture was diluted with EtOAc (20 mL) and water (20 mL). The organic portion was separated, dried over Na$_2$SO$_4$, filtered and concentrated in vacuo. The crude product was purified by chromatography on silica eluting with EtOAc in heptane to afford racemic N-tert-butyl-4-[[-indane-1-carbonyl]amino]pyridine-2-carboxamide.

Example 21a: N-tert-Butyl-4-[[(1R) or (1S)-indane-1-carbonyl]amino]pyridine-2-carboxamide and
Example 21b: N-tert-Butyl-4-[[(1R) or (1S)-indane-1-carbonyl]amino]pyridine-2-carboxamide

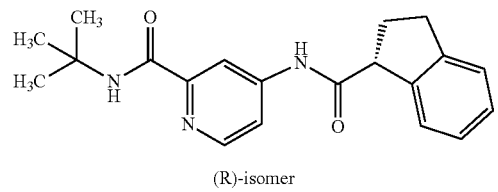

(R)-isomer

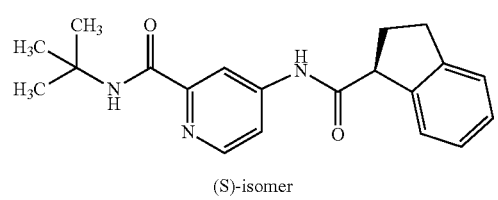

(S)-isomer

Chiral separation of racemic N-tert-butyl-4-[[-indane-1-carbonyl]amino]pyridine-2-carboxamide using Supercritical Fluid Chromatography [chiral phase column (25% IPA: 75% CO2 with Chiralcel OD-H 25 cm column at 15 ml/min)] afforded the individual enantiomers:

Example 21a: First eluted peak: N-tert-Butyl-4-[[(1R)-indane-1-carbonyl]amino]pyridine-2-carboxamide or N-tert-Butyl-4-[[(1S)-indane-1-carbonyl]amino]pyridine-2-carboxamide SFC Retention time: 5.46 min, MS m/z 338.3=[M+H]+ (100% @ 215 nm)

1H NMR (500 MHz, DMSO-d6) δ 10.85 (s, 1H), 8.46 (d, J=5.5 Hz, 1H), 8.23 (d, J=2.0 Hz, 1H), 8.03 (s, 1H), 7.87 (dd, J=5.5, 2.2 Hz, 1H), 7.32 (d, J=7.4 Hz, 1H), 7.28 (d, J=7.3 Hz, 1H), 7.20 (m, 1H), 7.16 (m, 1H), 4.16 (m, 1H), 3.11-3.03 (m, 1H), 2.95-2.87 (m, 1H), 2.40-2.27 (m, 2H), 1.40 (s, 9H). e.e 100%

Example 21b: Second eluted peak: N-tert-Butyl-4-[[(1R)-indane-1-carbonyl]amino]pyridine-2-carboxamide or N-tert-Butyl-4-[[(1S)-indane-1-carbonyl]amino]pyridine-2-carboxamide SFC Retention time: 8.00 min, MS m/z 338.3=[M+H]+ (91% @ 215 nm)

1H NMR (500 MHz, DMSO-d6) δ 10.85 (s, 1H), 8.46 (d, J=5.5 Hz, 1H), 8.23 (d, J=2.0 Hz, 1H), 8.03 (s, 1H), 7.87 (dd, J=5.5, 2.2 Hz, 1H), 7.32 (d, J=7.3 Hz, 1H), 7.28 (d, J=7.3

Hz, 1H), 7.20 (m, 1H), 7.16 (m, 1H), 4.16 (m, 1H), 3.11-3.03 (m, 1H), 2.95-2.87 (m, 1H), 2.39-2.27 (m, 2H), 1.40 (s, 9H). e.e 88%

Example 22

N-tert-Butyl-4-[(2-phenylacetyl)amino]pyridine-2-carboxamide

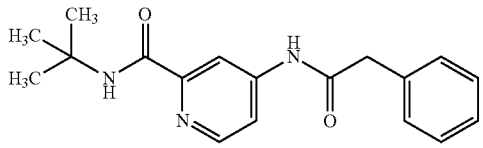 [SMILES: CC(C)(C)NC(=O)c1cc(NC(=O)Cc2ccccc2)ccn1]

To a mixture of 4-amino-N-tert-butyl-pyridine-2-carboxamide (Example 3 step 1) (50 mg, 0.26 mmol) in DCM (2.59 mL) was added TEA (113 µL, 0.65 mmol) and 2-phenylacetyl chloride (41 µL, 0.31 mmol) and the mixture was stirred for 16 hours. The resulting mixture was diluted with DCM (10 mL) and washed with water (2×10 mL) followed by saturated aqueous NaHCO₃ (10 mL). The organic layer was separated and dried over Na₂SO₄, filtered and concentrated in vacuo. The crude residue was dissolved in a mixture of DMSO:MeCN (800 µl, 1:1), filtered and purified by preparative HPLC (acidic pH, early elution method). The product fractions were combined, the pH of the mixture adjusted to pH 7 using saturated aqueous NaHCO₃ (20 mL) and extracted with DCM (3×20 mL). The combined organic extracts were dried over Na₂SO₄, filtered and concentrated in vacuo to afford the titled compound as an off-white solid.

1H NMR (500 MHz, DMSO-d6) δ 10.75 (s, 1H), 8.44 (d, J=5.5 Hz, 1H), 8.18 (d, J=1.9 Hz, 1H), 8.02 (s, 1H), 7.81 (dd, J=5.5, 2.2 Hz, 1H), 7.33 (d, J=4.4 Hz, 4H), 7.29-7.23 (m, 1H), 3.71 (s, 2H), 1.39 (s, 9H).

LC-MS (Method A): Rt 3.23 mins; MS m/z 312.2=[M+H]+ (100% @ 215 nm)

Example 22.1

4-(3,3-Dimethylbutanoylamino)-N-(1,1-dimethylprop-2-ynyl)pyridine-2-carboxamide

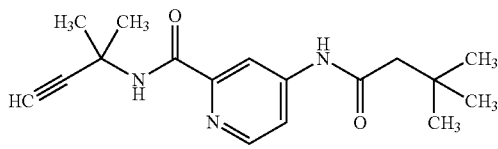 [SMILES: C#CC(C)(C)NC(=O)c1cc(NC(=O)CC(C)(C)C)ccn1]

The titled compound was prepared from 4-amino-N-(1,1-dimethylprop-2-ynyl)pyridine-2-carboxamide (Example 78 step 1) and 3,3-dimethylbutanoyl chloride analogously to Example 22.

1H NMR (500 MHz, DMSO-d6) δ 10.41 (s, 1H), 8.45 (d, J=5.5 Hz, 1H), 8.31 (s, 1H), 8.22 (d, J=2.1 Hz, 1H), 7.81 (dd, J=5.5, 2.2 Hz, 1H), 3.21 (s, 1H), 2.25 (s, 2H), 1.64 (s, 6H), 1.02 (s, 9H).

LC-MS (Method A): Rt 3.22 mins; MS m/z 302.2=[M+H]+ (100% @ 215 nm)

Example 22.2

4-[(2-Cyclopentylacetyl)amino]-N-(1,1-dimethylprop-2-ynyl)pyridine-2-carboxamide

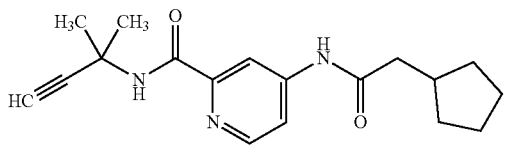 [SMILES: C#CC(C)(C)NC(=O)c1cc(NC(=O)CC2CCCC2)ccn1]

The titled compound was prepared from 4-amino-N-(1,1-dimethylprop-2-ynyl)pyridine-2-carboxamide (Example 78 step 1) and 2-cyclopentylacetyl chloride analogously to Example 22.

1H NMR (500 MHz, DMSO-d6) δ 10.47 (s, 1H), 8.45 (d, J=5.5 Hz, 1H), 8.31 (s, 1H), 8.21 (d, J=2.1 Hz, 1H), 7.81 (dd, J=5.5, 2.2 Hz, 1H), 3.21 (s, 1H), 2.39-2.35 (m, 2H), 2.28-2.19 (m, 1H), 1.80-1.72 (m, 2H), 1.64 (s, 6H), 1.63-1.56 (m, 2H), 1.56-1.47 (m, 2H), 1.23-1.13 (m, 2H).

LC-MS (Method A): Rt 3.33 mins; MS m/z 314.2=[M+H]+ (97% @ 215 nm)

Example 22.3

4-[[2-(3-Chloro-4-pyridyl)acetyl]amino]-N-(1,1-dimethylprop-2-ynyl)pyridine-2-carboxamide

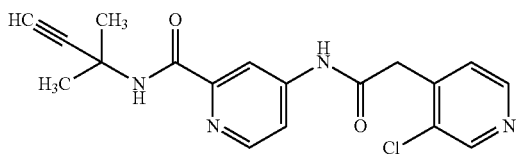 [SMILES: C#CC(C)(C)NC(=O)c1cc(NC(=O)Cc2ccncc2Cl)ccn1]

The titled compound was prepared from 4-amino-N-(1,1-dimethylprop-2-ynyl)pyridine-2-carboxamide (Example 78 step 1) and 2-(3-chloro-4-pyridyl)acetic acid hydrochloride analogously to Example 22.

1H NMR (500 MHz, DMSO-d6) δ 10.95 (s, 1H), 8.63 (s, 1H), 8.49 (t, J=5.3 Hz, 2H), 8.32 (s, 1H), 8.19 (d, J=2.0 Hz, 1H), 7.81 (dd, J=5.5, 2.2 Hz, 1H), 7.51 (d, J=4.9 Hz, 1H), 3.99 (s, 2H), 3.21 (s, 1H), 1.64 (s, 6H).

LC-MS (Method A): Rt 2.53 mins; MS m/z 357.1/359.1=[M+H]+ (100% @ 215 nm)

Example 23

4-[[2-(4-Chlorophenyl)acetyl]amino]-N-(1-cyanocyclopropyl)pyridine-2-carboxamide

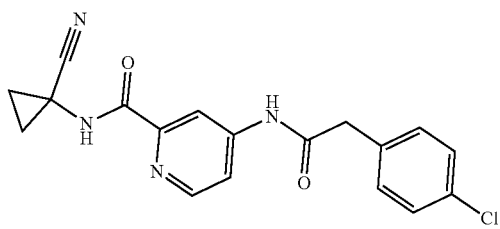 [SMILES: N#CC1(NC(=O)c2cc(NC(=O)Cc3ccc(Cl)cc3)ccn2)CC1]

Step 1: 4-Amino-N-(1-cyanocyclopropyl)pyridine-2-carboxamide

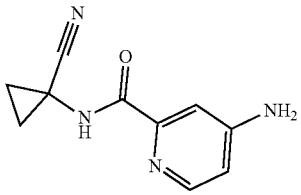 [SMILES: N#CC1(NC(=O)c2cc(N)ccn2)CC1]

To a mixture of 4-aminopyridine-2-carboxylic acid (1 g, 7.24 mmol), TBTU (2.79 g, 8.69 mmol) and TEA (1.21 mL, 8.69 mmol) in DMF (8 mL) was added 1-aminocyclopropanecarbonitrile (22.82 mL, 8.69 mmol) and the mixture was stirred at 40° C. for 2 days. The resulting mixture was concentrated in vacuo and the crude residue dissolved in EtOAc (15 mL). The mixture was washed with water (20 mL), NaHCO$_3$ (15 mL) dried over Na$_2$SO$_4$ and concentrated in vacuo to afford the titled compound as an orange solid.

1H NMR (500 MHz, DMSO-d6) δ 9.41 (s, 1H), 8.01 (d, J=5.6 Hz, 1H), 7.22 (d, J=2.3 Hz, 1H), 6.62 (dd, J=5.6, 2.4 Hz, 1H), 6.37 (s, 2H), 1.51-1.47 (m, 2H), 1.31-1.27 (m, 2H).

LC-MS (Method E): Rt 0.25 mins; MS m/z 203.1=[M+H]+

Step 2: 4-[[2-(4-Chlorophenyl)acetyl]amino]-N-(1-cyanocyclopropyl)pyridine-2-carboxamide To a solution of 4-amino-N-(1-cyanocyclopropyl)pyridine-2-carboxamide (step 1) (100 mg, 0.45 mmol), 2-(4-chlorophenyl)acetic acid (83.52 mg, 0.49 mmol) and TEA (155 μL, 0.89 mmol) in 1,4-dioxane (2 mL) was slowly added 50% T3P® solution in EtOAc (529.41 μL, 0.89 mmol). The reaction mixture was stirred at room temperature for 1 hour and concentrated in vacuo. The crude residue was dissolved in EtOAc (10 mL) washed with NaHCO$_3$ (15 mL), brine (15 mL) dried over Na$_2$SO$_4$ and concentrated in vacuo. Purification by preparative HPLC (acidic pH, early elution method) afforded the titled compound as an off-white solid.

1H NMR (500 MHz, DMSO-d6) δ=10.80 (s, 1H), 9.65 (s, 1H), 8.49 (d, J=5.5, 1H), 8.21 (d, J=1.9, 1H), 7.86 (dd, J=5.5, 2.2, 1H), 7.41-7.34 (m, 4H), 3.74 (s, 2H), 1.55-1.51 (m, 2H), 1.34-1.30 (m, 2H).

LC-MS (Method A): Rt 2.92 mins; MS m/z 355.3=[M+H]+ (98% @ 215 nm)

The compounds of the following tabulated Examples (Table 8) were prepared analogously to Example 23 by replacing 1-aminocyclopropanecarbonitrile (step 1) with the appropriate amine and by replacing 2-(4-chlorophenyl)acetic acid (step 2) with the appropriate commercially available acid.

TABLE 8

| Ex. | Structure and Name | 1H NMR; LCMS Retention Time, [M + H]+, |
|---|---|---|
| 23.1 | 4-[[2-(3-Chlorophenyl)acetyl]amino]-N-(1-cyanocyclo propyl)pyridine-2-carboxamide | 1H NMR (500 MHz, DMSO-d6) δ =10.81 (s, 1H), 9.66 (s, 1H), 8.50 (d, J = 5.5, 1H), 8.21 (d, J = 2.0, 1H), 7.86 (dd, J = 5.5, 2.2, 1H), 7.42 - 7.41 (m, 1H), 7.39 - 7.28 (m, 3H), 3.76 (s, 2H), 1.55 - 1.51 (m, 2H), 1.34 - 1.31 (m, 2H). LC-MS (Method A): Rt 2.92 mins; MS m/z 355.3/357.3 = [M + H]+ (96% @ 215 nm) |
| 23.2 | 4-[[2-(2-Chloro-5-fluoro-phenyl)acetyl]amino]-N-(1-cyanocyclo propyl)pyridine-2-carboxamide | 1H NMR (500 MHz, DMSO-d6) δ = 10.89 (s, 1H), 9.66 (s, 1H), 8.50 (d, J = 5.5, 1H), 8.21 (d, J = 2.0, 1H), 7.85 (dd, J = 5.5, 2.2, 1H), 7.51 (dd, J = 8.8, 5.3, 1H), 7.37 (dd, J = 9.4, 3.1, 1H), 7.21 (td, J = 8.5, 3.1, 1H), 3.94 LC-MS (Method A): Rt 2.86 mins; MS m/z 373.3/375.3 = [M + H]+ (99% @ 215 nm) |
| 23.3 | N-tert-Butyl-4-(indane-2-carbonyl amino)pyridine-2-carboxamide | 1H NMR (500 MHz, DMSO-d6) δ 10.64 (s, 1H), 8.45 (d, J = 5.5 Hz, 1H), 8.22 (d, J = 2.0 Hz, 1H), 8.03 (s, 1H), 7.86 (dd, J = 5.5, 2.2 Hz, 1H), 7.25 - 7.20 (m, 2H), 7.17 - 7.13 (m, 2H), 3.45 (p, J = 8.4 Hz, 1H), 3.25 - 3.13 (m, 4H), 1.40 (s, 9H). LC-MS (MethodA): Rt 3.62 mins; MS m/z 338.2 = [M + H]+ (3.62% @ 215 nm) |

TABLE 8-continued

| Ex. | Structure and Name | 1H NMR; LCMS Retention Time, [M + H]+, |
|---|---|---|
| 23.4 | 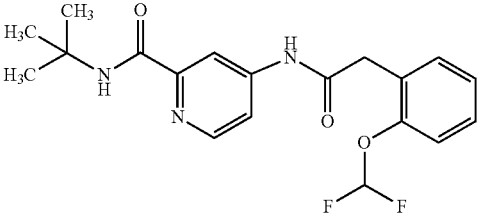 [SMILES: CC(C)(C)NC(=O)c1cc(NC(=O)Cc2ccccc2OC(F)F)ccn1]<br>N-tert-Butyl-4-[[2-[2-(difluoromethoxy)phenyl]acetyl]amino]pyridine-2-carboxamide | 1H NMR (500 MHz, Methanol-d4) δ 8.44 (d, J = 5.5 Hz, 1H), 8.17 – 8.14 (m, 1H), 7.90 (dd, J = 5.5, 2.2 Hz, 1H), 7.39 (dd, J = 7.5, 1.5 Hz, 1H), 7.36 (td, J = 7.9, 1.7 Hz, 1H), 7.24 (td, J = 7.5, 1.1 Hz, 1H), 7.20 – 7.18 (m, 1H), 6.78 (t, J = 74.2 Hz, 1H), 3.85 (s, 2H).<br>LC-MS (Method A): Rt 3.42 mins; MS m/z 378.3 = [M + H]+ (99% @ 215 nm) |
| 23.5 | 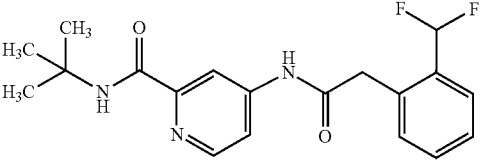 [SMILES: CC(C)(C)NC(=O)c1cc(NC(=O)Cc2ccccc2C(F)F)ccn1]<br>N-tert-Butyl-4-[[2-[2-(difluoromethyl)phenyl]acetyl]amino]pyridine-2-carboxamide | 1H NMR (500 MHz, DMSO-d6) δ 10.80 (s, 1H), 8.46 (d, J = 5.5 Hz, 1H), 8.18 (d, J = 2.0 Hz, 1H), 8.03 (s, 1H), 7.80 (dd, J = 5.5, 2.2 Hz, 1H), 7.60 (d, J = 7.8 Hz, 1H), 7.54 – 7.50 (m, 1H), 7.46 – 7.42 (m, 2H), 7.20 (t, J = 54.8 Hz, 1H), 3.96 (s, 2H), 1.40 (s, 9H).<br>LC-MS (Method A): Rt 3.41 mins; MS m/z 362.2 = [M + H]+ |
| 23.6 | 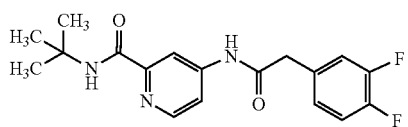 [SMILES: CC(C)(C)NC(=O)c1cc(NC(=O)Cc2ccc(F)c(F)c2)ccn1]<br>N-tert-Butyl-4-[[2-(3,4-difluorophenyl)acetyl]amino]pyridine-2-carboxamide | 1H NMR (500 MHz, Methanol-d4) δ 8.45 (dd, J = 5.5, 0.5 Hz, 1H), 8.15 (dd, J = 2.2, 0.5 Hz, 1H), 7.91 (dd, J = 5.5, 2.2 Hz, 1H), 7.32 – 7.20 (m, 2H), 7.18 – 7.13 (m, 1H), 3.75 (s, 2H), 1.49 (s, 9H).<br>LC-MS (Method A): Rt 3.43 mins; MS m/z 348.3 = [M + H]+ (99% @ 215 nm) |
| 23.7 | 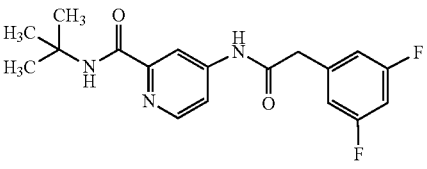 [SMILES: CC(C)(C)NC(=O)c1cc(NC(=O)Cc2cc(F)cc(F)c2)ccn1]<br>N-tert-Butyl-4-[[2-(3,5-difluorophenyl)acetyl]amino]pyridine-2-carboxamide | 1H NMR (500 MHz, Methanol-d4) δ 8.45 (dd, J = 5.7, 0.5 Hz, 1H), 8.15 (dd, J = 2.2, 0.5 Hz, 1H), 7.91 (dd, J = 5.5, 2.2 Hz, 1H), 7.03 – 6.95 (m, 2H), 6.88 (tt, J = 9.2, 2.3 Hz, 1H), 3.78 (s, 2H), 1.49 (s, 9H).<br>LC-MS (Method A): Rt 3.46 mins; MS m/z 348.3 = [M + H]+ (97% @ 215 nm) |
| 23.8 | 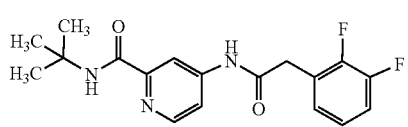 [SMILES: CC(C)(C)NC(=O)c1cc(NC(=O)Cc2cccc(F)c2F)ccn1]<br>N-tert-Butyl-4-[[2-(2,3-difluorophenyl)acetyl]amino]pyridine-2-carboxamide | 1H NMR (500 MHz, Methanol-d4) δ 8.45 (dd, J = 5.5, 0.4 Hz, 1H), 8.15 (dd, J = 2.2, 0.5 Hz, 1H), 7.92 (dd, J = 5.5, 2.2 Hz, 1H), 7.25 – 7.12 (m, 3H), 3.89 (d, J = 1.4 Hz, 2H), 1.49 (s, 9H).<br>LC-MS (Method A): Rt 3.36 mins; MS m/z 348.2 = [M + H]+ (98% @ 215 nm) |
| 23.9 | 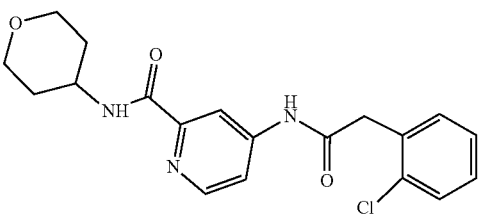 [SMILES: O=C(Cc1ccccc1Cl)Nc1ccnc(C(=O)NC2CCOCC2)c1]<br>4-[[2-(2-Chlorophenyl)acetyl]amino]-N-tetrahydropyran-4-yl-pyridine-2-carboxamide | 1H NMR (500 MHz, Methanol-d6) δ 10.83 (s, 1H), 8.59 (d, J = 8.5 Hz, 1H), 8.50 (d, J = 5.5 Hz, 1H), 8.21 (d, J = 1.9 Hz, 1H), 7.82 (dd, J = 5.5, 2.2 Hz, 1H), 7.48 – 7.42 (m, 2H), 7.35 – 7.31 (m, 2H), 4.06 – 3.97 (m, 1H), 3.92 (s, 2H), 3.89 – 3.84 (m, 2H), 3.43 – 3.36 (m, 2H), 1.72-1.63 (m, 4H).<br>LC-MS (Method A): Rt 2.64 mins; MS m/z 374.2/376.2 = [M + H]+ (100% @ 215 nm) |

TABLE 8-continued

| Ex. | Structure and Name | 1H NMR; LCMS Retention Time, [M + H]+, |
|---|---|---|
| 23.11 | 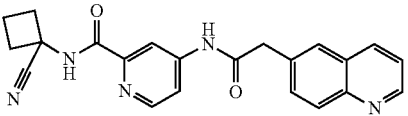 [SMILES: N#CC1(NC(=O)c2cc(NC(=O)Cc3ccc4ncccc4c3)ccn2)CCC1]<br>N-(1-Cyanocyclobutyl)-4-[[2-(6-quinolyl)acetyl]amino]pyridine-2-carboxamide | 1H NMR (500 MHz, DMSO-d6) δ 10.90 (s, 1H), 9.59 (s, 1H), 8.88 (dd, J = 4.2, 1.7 Hz, 1H), 8.53 (d, J = 5.7 Hz, 1H), 8.39 – 8.32 (m, 1H), 8.22 (d, J = 1.9 Hz, 1H), 7.99 (d, J = 8.6 Hz, 1H), 7.93 – 7.84 (m, 2H), 7.75 (dd, J = 8.7, 2.0 Hz, 1H), 7.52 (dd, J = 8.3, 4.2 Hz, 1H), 3.96 (s, 2H), 2.73 – 2.61 (m, 2H), 2.59 – 2.51 (m, 2H), 2.09 – 1.94 (m, 2H).<br>LC-MS (Method A): Rt 1.65 mins; MS m/z 386.3 = [M + H]+ (98% @ 215 nm) |
| 23.12 | 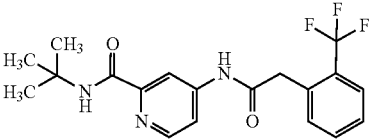 [SMILES: CC(C)(C)NC(=O)c1cc(NC(=O)Cc2ccccc2C(F)(F)F)ccn1]<br>N-tert-Butyl-4-[[2-[2-(trifluoromethyl)phenyl]acetyl]amino]pyridine-2-carboxamide | 1H NMR (500 MHz, DMSO-d6) δ 10.81 (s, 1H), 8.45 (d, J = 5.5 Hz, 1H), 8.17 (d, J = 2.1 Hz, 1H), 8.03 (s, 1H), 7.78 (dd, J = 5.5, 2.2 Hz, 1H), 7.72 (d, J = 7.8 Hz, 1H), 7.69 – 7.63 (m, 1H), 7.57 – 7.47 (m, 2H), 4.00 (s, 2H), 1.40 (s, 9H).<br>LC-MS (Method A): Rt 3.58 mins; MS m/z 380.2 = [M + H]+ (100% @ 215 nm) |
| 23.13 | 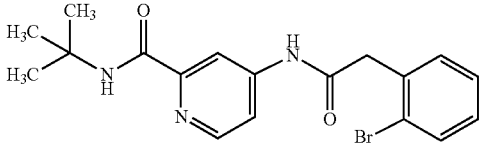 [SMILES: CC(C)(C)NC(=O)c1cc(NC(=O)Cc2ccccc2Br)ccn1]<br>4-[[2-(2-Bromophenyl)acetyl]amino]-N-tert-butyl-pyridine-2-carboxamide | 1H NMR (500 MHz, DMSO-d6) δ 10.83 (s, 1H), 8.45 (d, J = 5.5 Hz, 1H), 8.18 (d, J = 2.0 Hz, 1H), 8.03 (s, 1H), 7.81 (dd, J = 5.5, 2.2 Hz, 1H), 7.62 (dd, J = 8.0, 1.1 Hz, 1H), 7.43 (dd, J = 7.6, 1.7 Hz, 1H), 7.41 – 7.30 (m, 1H), 7.27 – 7.20 (m, 1H), 3.92 (s, 2H), 1.40 (s, 9H).<br>LC-MS (Method A): Rt 3.49 mins; MS m/z 390.2/392.2 = [M + H]+ (99% @ 215 nm) |
| 23.14 | 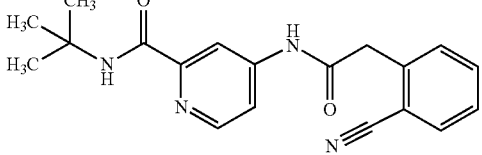<br>N-tert-Butyl-4-[[2-(2-cyanophenyl)acetyl]amino]pyridine-2-carboxamide | 1H NMR (500 MHz, DMSO-d6) δ 10.92 (s, 1H), 8.47 (d, J = 5.5 Hz, 1H), 8.18 (d, J = 2.0 Hz, 1H), 8.03 (s, 1H), 7.85 (dd, J = 7.7, 1.1 Hz, 1H), 7.80 (dd, J = 5.5, 2.2 Hz, 1H), 7.72 – 7.66 (m, 1H), 7.57 (d, J = 7.3 Hz, 1H), 7.53 – 7.44 (m, 1H), 4.03 (s, 2H), 1.40 (s, 9H).<br>LC-MS (Method A): Rt 3.06 mins; MS m/z 337.3 = [M + H]+ (100% @ 215 nm) |
| 23.15 | 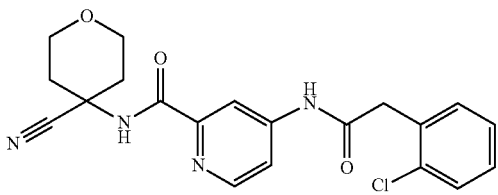 [SMILES: N#CC1(NC(=O)c2cc(NC(=O)Cc3ccccc3Cl)ccn2)CCOCC1]<br>4-[[2-(2-Chlorophenyl)acetyl]amino]-N-(4-cyanotetrahydropyran-4-yl)pyridine-2-carboxamide | 1H NMR (500 MHz, DMSO-d6) δ 10.89 (s, 1H), 9.01 (s, 1H), 8.54 (d, J = 5.5 Hz, 1H), 8.24 (d, J = 2.1 Hz, 1H), 7.86 (dd, J = 5.5, 2.2 Hz, 1H), 7.49 – 7.42 (m, 2H), 7.36 – 7.28 (m, 2H), 3.93 (s, 2H), 3.87 (dt, J = 12.2, 3.8 Hz, 2H), 3.62 – 3.54 (m, 2H), 2.39-2.34 (m, 2H), 2.12-2.03 (m, 2H).<br>LC-MS (Method A): Rt 2.83 mins; MS m/z 399.2/401.3 = [M + H]+ (100% @ 215 nm) |
| 23.16 | 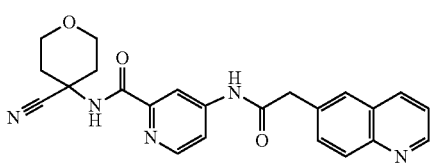 [SMILES: N#CC1(NC(=O)c2cc(NC(=O)Cc3ccc4ncccc4c3)ccn2)CCOCC1]<br>N-(4-Cyanotetrahydropyran-4-yl)-4-[[2-(6-quinolyl)acetyl]amino]pyridine-2-carboxamide | 1H NMR (500 MHz, DMSO-d6) δ 10.91 (s, 1H), 9.01 (s, 1H), 8.88 (dd, J = 4.2, 1.7 Hz, 1H), 8.54 (d, J = 5.5 Hz, 1H), 8.36 – 8.33 (m, 1H), 8.26 (d, J = 2.1 Hz, 1H), 8.00 (d, J = 8.7 Hz, 1H), 7.91 (d, J = 1.6 Hz, 1H), 7.89 (dd, J = 5.5, 2.2 Hz, 1H), 7.75 (dd, J = 8.7, 2.0 Hz, 1H), 7.52 (dd, J = 8.3, 4.2 Hz, 1H), 3.97 (s, 2H), 3.86 (dt, J = 12.2, 3.8 Hz, 2H), 3.61 – 3.56 (m, 2H), 2.37 (d, J = 13.5 Hz, 2H), 2.07 (td, J = 10.1, 5.2 Hz, 2H)<br>LC-MS (Method A): Rt 1.52 mins; MS m/z 416.3 = [M + H]+ (100% @ 215 nm) |

Example 24

4-[[2-(2-Chloro-5-methoxy-phenyl)acetyl]amino]-N-(1-cyanocyclopropyl)pyridine-2-carboxamide

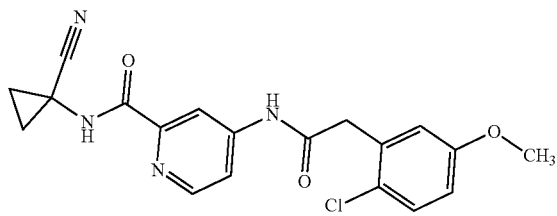 [SMILES: COc1ccc(Cl)c(CC(=O)Nc2ccnc(C(=O)NC3(C#N)CC3)c2)c1]

Steps 1 and 2: N-(1-Cyanocyclopropyl)-4-[[2-(3-methoxyphenyl)acetyl]amino]pyridine-2-carboxamide The titled compound was prepared analogously to Example 23 by replacing 2-(4-chlorophenyl)acetic acid (step 2) with 2-(3-methoxyphenyl)acetic acid.

1H NMR (500 MHz, DMSO-d6) δ=10.77 (s, 1H), 9.65 (s, 1H), 8.49 (d, J=5.5, 1H), 8.21 (d, J=2.1, 1H), 7.86 (dd, J=5.5, 2.2, 1H), 7.24 (t, J=7.8, 1H), 6.92-6.88 (m, 2H), 6.83 (dd, J=8.0, 2.1, 1H), 3.74 (s, 3H), 3.68, (s, 2H), 1.55-1.51 (m, 2H), 1.34-1.30 (m, 2H).

LC-MS (Method E): Rt 1.03 mins; MS m/z 351.0=[M+H]+ (97% @ 215 nm)

Step 2: 4-[[2-(2-Chloro-5-methoxy-phenyl)acetyl]amino]-N-(1-cyanocyclopropyl)pyridine-2-carboxamide To a solution of N-(1-cyanocyclopropyl)-4-[[2-(3-methoxyphenyl)acetyl]amino]pyridine-2-carboxamide (step 1) (81 mg, 0.23 mmol) in MeCN (33.7 mL) was added NCS (77 mg, 0.58 mmol) and the mixture was stirred at 60° C. for 16 hours. The resulting mixture was concentrated in vacuo to yield a crude dry residue. The dry residue was dissolved in EtOAc (10 mL), washed with water (10 mL), NaHCO3 (10 ml) and concentrated in vacuo. Purification by preparative HPLC (acidic pH, standard elution method) afforded the titled compound as an off-white solid.

1H NMR (500 MHz, DMSO-d6) δ 10.84 (s, 1H), 9.66 (s, 1H), 8.50 (d, J=5.5 Hz, 1H), 8.21 (d, J=2.0 Hz, 1H), 7.86 (dd, J=5.5, 2.2 Hz, 1H), 7.35 (d, J=8.8 Hz, 1H), 7.04 (d, J=3.1 Hz, 1H), 6.90 (dd, J=8.8, 3.1) Hz, 1H), 3.87 (s, 2H), 3.76 (s, 3H), 1.55-1.51 (m, 2H), 1.35-1.30 (m, 2H).

LC-MS (Method A): Rt 2.84 mins; MS m/z 385.2/387.2=[M+H]+ (100% @ 215 nm)

Example 25

N-(3-Bicyclo[1.1.1]pentanyl)-4-[[2-(5-tert-butyl-2-hydroxy-phenyl)acetyl]amino]pyridine-2-carboxamide

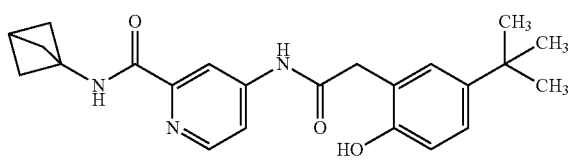 [SMILES: CC(C)(C)c1ccc(O)c(CC(=O)Nc2ccnc(C(=O)NC34CC(C3)C4)c2)c1]

Step 1: Methyl 4-[[2-(5-tert-butyl-2-methoxy-phenyl)acetyl]amino]pyridine-2-carboxylate

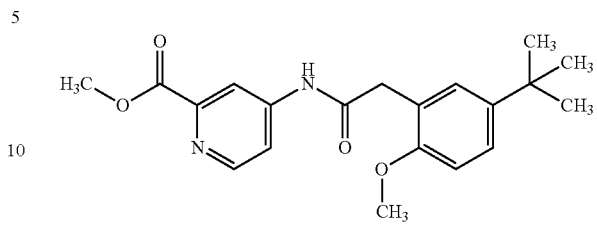

2-(5-tert-Butyl-2-methoxy-phenyl)acetic acid (700 mg, 3.15 mmol) was dissolved in thionyl chloride (2.5 mL, 28.37 mmol) and stirred at 70° C. for 30 mins. The resulting mixture was concentrated in vacuo and azeotroped with toluene (3×5 mL). The residue was dissolved in DCM (15 mL) to form a solution of acid chloride and added to a stirred solution of methyl 4-aminopyridine-2-carboxylate (527 mg, 3.46 mmol) in DCM (15 mL). After stirring for 10 mins, the mixture was concentrated in vacuo to yield a brown gum. The gum was purified by chromatography on silica eluting with 25-100% EtOAc in heptane to afford the titled compound as a dark yellow glass.

1H NMR (250 MHz, DMSO-d6) δ 10.68 (s, 1H), 8.54 (d, J=5.5 Hz, 1H), 8.31 (d, J=2.0 Hz, 1H), 7.77 (dd, J=5.5, 2.1 Hz, 1H), 7.29-7.20 (m, 2H), 6.89 (d, J=9.3 Hz, 1H), 3.86 (s, 3H), 3.72 (s, 3H), 3.68 (s, 2H), 1.26 (s, 9H).

LC-MS (Method E): Rt 1.17 mins; MS m/z 357=[M+H]+

Step 2: 4-[[2-(5-tert-Butyl-2-methoxy-phenyl)acetyl]amino]pyridine-2-carboxylic acid

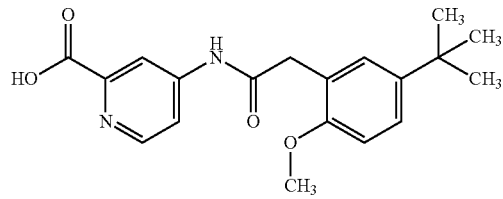 [SMILES: COc1ccc(C(C)(C)C)cc1CC(=O)Nc1ccnc(C(=O)O)c1]

To a solution of methyl 4-[[2-(5-tert-butyl-2-methoxy-phenyl)acetyl]amino]pyridine-2-carboxylate (step 1) (594 mg, 1.55 mmol) in THF (12 mL) was added 1M sodium hydroxide solution (1.86 mL, 1.86 mmol) and the mixture stirred for 30 mins. The pH of resulting mixture was adjusted to pH 4 by addition of hydrochloric acid. The mixture was partitioned between EtOAc (20 mL) and water (20 mL) at which point a precipitate formed in the organic layer. The organic suspension was washed with water (20 mL), brine (20 mL), filtered through a phase separator and dried to afford the titled compound as a fine powder.

1H NMR (250 MHz, DMSO-d6) δ 10.70 (s, 1H), 8.52 (d, J=5.6 Hz, 1H), 8.28 (d, J=1.9 Hz, 1H), 7.80 (dd, J=5.6, 2.2 Hz, 1H), 7.29-7.20 (m, 2H), 6.89 (d, J=9.4 Hz, 1H), 3.72 (s, 3H), 3.69 (s, 2H), 1.26 (s, 9H).

LC-MS (Method E): Rt 0.98 mins; MS m/z 343=[M+H]+

Step 3: 4-[[2-(5-tert-Butyl-2-hydroxy-phenyl)acetyl]amino]pyridine-2-carboxylic acid

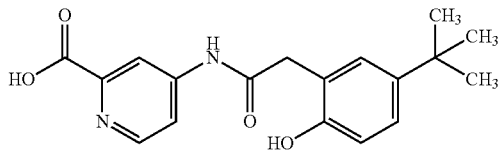 [SMILES: CC(C)(C)c1ccc(O)c(CC(=O)Nc2ccnc(C(=O)O)c2)c1]

An ice-cooled suspension of 4-[[2-(5-tert-butyl-2-methoxy-phenyl)acetyl]amino]pyridine-2-carboxylic acid (step 2) (330 mg, 0.93 mmol) in DCM (9 mL) was treated with 1M BBr₃ in DCM (1.85 mL, 1.85 mmol) and stirred for 70 mins. The reaction was quenched with methanol (1 mL) and the mixture was partitioned between EtOAc (20 mL) and water (20 mL) resulting in the formation of a fine white precipitate. The precipitate was filtered and dried to afford the titled compound as a solid.

1H NMR (250 MHz, DMSO-d6) δ 11.51 (s, 1H), 8.65 (d, J=6.4 Hz, 1H), 8.51 (d, J=2.2 Hz, 1H), 8.14 (dd, J=6.4, 2.3 Hz, 1H), 7.18 (d, J=2.4 Hz, 1H), 7.10 (dd, J=8.4, 2.5 Hz, 1H), 6.74 (d, J=8.4 Hz, 1H), 3.75 (s, 2H), 1.23 (s, 9H).

LC-MS (Method E): Rt 0.97 mins; MS m/z 329=[M+H]+ (91% @ 215 nm)

Step 4: N-(3-Bicyclo[1.1.1]pentanyl)-4-[[2-(5-tert-butyl-2-hydroxy-phenyl)acetyl]amino]pyridine-2-carboxamide To a suspension of 4-[[2-(5-tert-butyl-2-hydroxy-phenyl)acetyl]amino]pyridine-2-carboxylic acid (step 3) (25 mg, 0.08 mmol) in DMF (0.5 mL) was added bicyclo[1.1.1]pentan-3-amine hydrochloride (11 mg, 0.09 mmol), DIPEA (0.05 mL, 0.3 mmol) and HATU (43 mg, 0.11 mmol). After stirring at room temperature for 18 hours, the mixture was partitioned between EtOAc (10 mL) and water (10 mL) and the aqueous portion extracted with EtOAc (2×20 mL). The combined organic extracts were washed with water (20 mL), brine (20 mL), dried over Na₂SO₄ and concentrated in vacuo. The crude residue was purified by C18 reverse phase chromatography eluting with 45-65% MeCN in water with 0.1% formic acid to afford the titled compound as a white powder.

1H NMR (500 MHz, DMSO-d6) δ 10.70 (s, 1H), 9.28 (s, 1H), 9.07 (s, 1H), 8.44 (d, J=5.5 Hz, 1H), 8.16 (d, J=2.1 Hz, 1H), 7.84 (dd, J=5.5, 2.2 Hz, 1H), 7.16 (d, J=2.5 Hz, 1H), 7.08 (dd, J=8.4, 2.5 Hz, 1H), 6.72 (d, J=8.4 Hz, 1H), 3.65 (s, 2H), 2.44 (s, 1H), 2.09 (s, 6H), 1.23 (s, 9H).

LC-MS (Method A): Rt 3.71 mins; MS m/z 394=[M+H]+

Example 25.1

4-[[2-(5-tert-Butyl-2-hydroxy-phenyl)acetyl]amino]-N-(4-cyanotetrahydropyran-4-yl)pyridine-2-carboxamide

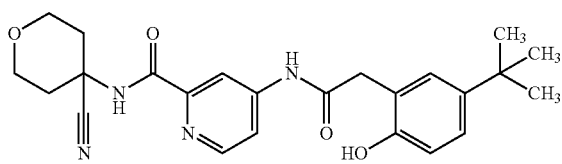 [SMILES: CC(C)(C)c1ccc(O)c(CC(=O)Nc2ccnc(C(=O)NC3(C#N)CCOCC3)c2)c1]

The titled compound was prepared from 4-[[2-(5-tert-butyl-2-hydroxy-phenyl)acetyl]amino]pyridine-2-carboxylic acid (Example 25, step 3) and 4-aminotetrahydropyran-4-carbonitrile analogously to Example 25 step 4.

1H NMR (500 MHz, Methanol-d4) δ 8.47 (d, J=5.5 Hz, 1H), 8.17 (d, J=1.8 Hz, 1H), 7.94 (dd, J=5.5, 2.2 Hz, 1H), 7.22 (d, J=2.4 Hz, 1H), 7.15 (dd, J=8.4, 2.5 Hz, 1H), 6.75 (d, J=8.4 Hz, 1H), 3.96 (dt, J=12.5, 4.0 Hz, 2H), 3.80-3.74 (m, 2H), 3.72 (s, 2H), 2.49-2.43 (m, 2H), 2.14-2.07 (m, 2H), 1.28 (s, 9H).

LC-MS (Method A): Rt 3.22 mins; MS m/z 437=[M+H]+ (100% @ 215 nm)

Example 26

N-tert-Butyl-4-[[2-(2-hydroxy-5-phenyl-phenyl)acetyl]amino]pyridine-2-carboxamide

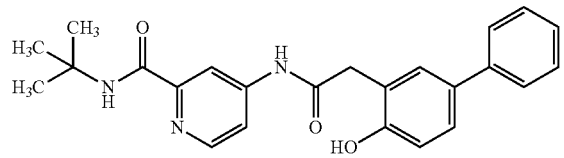 [SMILES: CC(C)(C)NC(=O)c1cc(NC(=O)Cc2cc(-c3ccccc3)ccc2O)ccn1]

Step 1: N-tert-butyl-4-[[2-(2-methoxy-5-phenyl-phenyl)acetyl]amino]pyridine-2-carboxamide

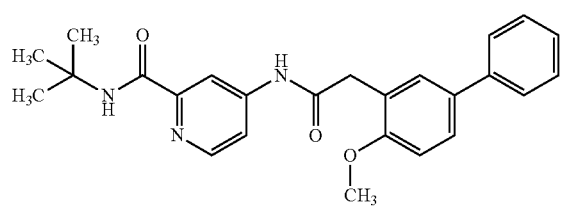 [SMILES: COc1ccc(-c2ccccc2)cc1CC(=O)Nc1ccnc(C(=O)NC(C)(C)C)c1]

A pressure tube was charged with 4-[[2-(5-bromo-2-methoxy-phenyl)acetyl]amino]-N-tert-butyl-pyridine-2-carboxamide (Example 6, step 1) (250 mg, 0.59 mmol), tripotassium phosphate (379 mg, 1.78 mmol), phenylboronic acid (80 mg, 0.65 mmol) in 1,4-dioxane (4 mL) and the suspension was degassed with nitrogen. Bis[3-(diphenylphosphanyl)cyclopenta-2,4-dien-1-yl]iron; dichloromethane; dichloropalladium (24 mg, 0.03 mmol) was added under an atmosphere of nitrogen and the sealed tube was heated to 80° C. for 23 hours. The reaction mixture was concentrated in vacuo and the crude residue re-dissolved in EtOAc. The mixture was filtered through Celite® (filter material) and the filtrate concentrated in vacuo to afford a brown oil. The oil was purified by chromatography on silica eluting 25-100% EtOAc in heptane to afford the titled compound as a white solid.

1H NMR (250 MHz, Chloroform-d) δ 8.38 (d, J=5.6 Hz, 1H), 8.26-8.14 (m, 2H), 7.97 (s, 1H), 7.59-7.50 (m, 5H), 7.46-7.37 (m, 2H), 7.37-7.28 (m, 1H), 7.05 (d, J=8.3 Hz, 1H), 4.01 (s, 3H), 3.80 (s, 2H), 1.47 (s, 9H).

LC-MS (Method E): Rt 1.29 mins; MS m/z 418=[M+H]+

Step 2: N-tert-Butyl-4-[[2-(2-hydroxy-5-phenyl-phenyl)acetyl]amino]pyridine-2-carboxamide To an ice-cooled solution of N-tert-butyl-4-[[2-(2-methoxy-5-phenyl-phenyl)acetyl]amino]pyridine-2-carboxamide (step 1) (160 mg, 0.38 mmol) in DCM (2.5 mL) was added dropwise 1M BBr$_3$ in DCM (1.92 mL, 1.92 mmol). After stirring for 10 mins, the reaction was quenched by addition of methanol (1 mL). The resulting mixture was concentrated in vacuo and the residue partitioned between EtOAc (20 mL) and water (20 mL). The organic layer was separated and the aqueous portion re-extracted with EtOAc (2×20 mL). The combined organic extracts were washed with water (20 mL), brine (20 mL), dried over Na$_2$SO$_4$ and concentrated in vacuo to afford the titled compound as an amber-coloured glass.

$^1$H NMR (500 MHz, Chloroform-d) δ 10.14-9.39 (m, 2H), 8.32 (d, J=5.6 Hz, 1H), 8.16 (s, 1H), 8.04 (dd, J=5.6, 1.9 Hz, 1H), 7.94 (s, 1H), 7.42 (d, J=7.3 Hz, 2H), 7.39 (d, J=2.1 Hz, 1H), 7.36-7.29 (m, 3H), 7.25 (t, J=7.3 Hz, 1H), 7.00 (d, J=8.3 Hz, 1H), 3.83 (s, 2H), 1.49 (s, 9H).

LC-MS (Method A): Rt 3.64 mins; MS m/z 404=[M+H]+

Example 27

N-tert-Butyl-4-[[2-[5-chloro-2-hydroxy-4-(pyrrolidin-1-ylmethyl)phenyl]acetyl]amino]pyridine-2-carboxamide

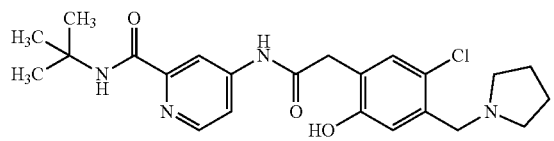 [SMILES: CC(C)(C)NC(=O)c1cc(NC(=O)Cc2cc(Cl)c(CN3CCCC3)cc2O)ccn1]

Step 1:
2-(4-Bromo-5-chloro-2-methoxy-phenyl)acetic acid

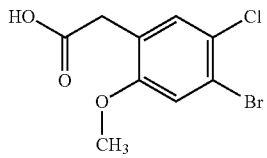

2-(4-Bromo-2-methoxy-phenyl)acetic acid (2 g, 8.16 mmol) and NCS (1.14 g, 8.57 mmol) were dissolved in MeCN (40.8 mL) and stirred at 50° C. for 22 hours. The resulting mixture was concentrated in vacuo and the residue purified by chromatography on silica eluting with 20-100% EtOAc in heptane. The product was further purified by dissolving in EtOAc (100 mL) and extracting into saturated aqueous NaHCO$_3$ (3×100 mL). The combined aqueous extracts were acidified with 1M HCl and extracted with EtOAc (3×150 mL). The combined organic extracts were dried over Na$_2$SO$_4$, filtered and concentrated in vacuo to afford the titled compound as a colourless solid.

1H NMR (250 MHz, DMSO-d6) δ 11.97 (s, 1H), 7.46 (s, 1H), 7.34 (s, 1H), 3.79 (s, 3H), 3.50 (s, 2H).

LC-MS (Method E): Rt 1.07 mins; MS m/z not observed=[M+H]+

Step 2: 4-[[2-(4-Bromo-5-chloro-2-methoxy-phenyl)acetyl]amino]-N-tert-butyl-pyridine-2-carboxamide

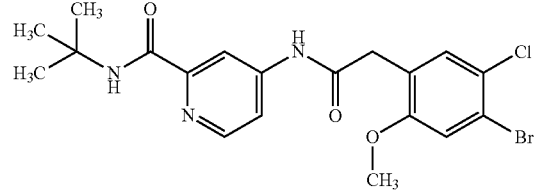 [SMILES: COc1cc(Br)c(Cl)cc1CC(=O)Nc1ccnc(C(=O)NC(C)(C)C)c1]

The titled compound was prepared from 4-amino-N-tert-butyl-pyridine-2-carboxamide and 2-(4-bromo-5-chloro-2-methoxy-phenyl)acetic acid (step 1) analogously to Example 3.5b step 1

1H NMR (250 MHz, DMSO-d6) δ 10.70 (s, 1H), 8.44 (d, J=5.6 Hz, 1H), 8.16 (d, J=1.9 Hz, 1H), 8.03 (s, 1H), 7.79 (dd, J=5.5, 2.2 Hz, 1H), 7.51 (s, 1H), 7.36 (s, 1H), 3.78 (s, 3H), 3.71 (s, 2H), 1.40 (s, 9H).

LC-MS (Method E): Rt 1.28 mins; MS m/z 454=[M+H]+ 97% @ 215 nm)

Step 3: N-tert-Butyl-4-[[2-[5-chloro-2-methoxy-4-(pyrrolidin-1-ylmethyl)phenyl]acetyl]amino]pyridine-2-carboxamide

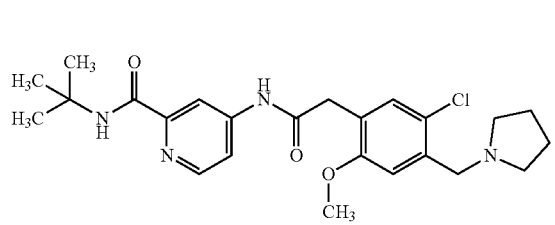 [SMILES: COc1cc(CN2CCCC2)c(Cl)cc1CC(=O)Nc1ccnc(C(=O)NC(C)(C)C)c1]

A vessel was charged with 4-[[2-(4-bromo-5-chloro-2-methoxy-phenyl)acetyl]amino]-N-tert-butyl-pyridine-2-carboxamide (step 2)(100 mg, 0.21 mmol), potassium trifluoropyrrolin-1-ylmethyl)boranuide (45 mg, 0.23 mmol), Xphos (6 mg, 0.01 mmol), Pd(Oac)$_2$ (1.4 mg, 0.01 mmol) and Cs$_2$CO$_3$ (209 mg, 0.64 mmol) and placed under an atmosphere of nitrogen. THF:water (1 mL of a 10:1 mixture) was added and the mixture was heated at 80° C. for 20 hours. The resulting mixture was diluted with water (2 mL) and extracted with DCM (3×10 mL). The combined organic extracts were dried over Na$_2$SO$_4$, filtered and concentrated in vacuo. The residue was purified by chromatography on silica eluting with 0-100% EtOAc in heptane to afford the titled compound as a colourless solid.

1H NMR (500 MHz, DMSO-d6) δ 10.68 (s, 1H), 8.44 (d, J=5.5 Hz, 1H), 8.16 (dd, J=6.4, 2.0 Hz, 1H), 8.03 (s, 1H), 7.80 (dd, J=5.5, 2.2 Hz, 1H), 7.29 (s, 1H), 7.07 (s, 1H), 3.75 (s, 3H), 3.69 (s, 2H), 3.65 (s, 2H), 2.51-2.49 (obscured m, 4H), 1.73-1.71 (m, 4H), 1.40 (s, 9H).

LC-MS (Method E): Rt 1.04 mins; MS m/z 459/461=[M+H]+ (78% @ 215 nm)

Step 4: N-tert-Butyl-4-[[2-[5-chloro-2-hydroxy-4-(pyrrolidin-1-ylmethyl)phenyl]acetyl]amino]pyridine-2-carboxamide The titled compound was prepared from N-tert-Butyl-4-[[2-[5-chloro-2-methoxy-4-(pyrrolidin-1-ylmethyl)phenyl]

acetyl]amino]pyridine-2-carboxamide N-tert-butyl-4-[[2-[5-(step 3) analogously to Example 26 step 2.

1H NMR (500 MHz, DMSO-d6) δ 10.72 (s, 1H), 9.70 (s, 1H), 8.44 (d, J=5.5 Hz, 1H), 8.17 (d, J=2.0 Hz, 1H), 8.03 (s, 1H), 7.81 (dd, J=5.5, 2.2 Hz, 1H), 7.18 (s, 1H), 6.97 (s, 1H), 3.64 (s, 2H), 3.57 (s, 2H), 2.51-2.49 (obscured m, 4H), 1.72-1.70 (m, 4H), 1.40 (s, 9H).

LC-MS (Method A): Rt 2.08 mins; MS m/z 445.3/447.3= [M+H]+ (99% @ 215 nm)

The compounds of the following tabulated Examples (Table 9) were prepared analogously to Example 27 by replacing potassium trifluoropyrrolin-1-ylmethyl)boranuide (step 3) with the appropriate boranuide Step 1: N-(2-Chloro-5-fluoro-4-pyridyl)-2-(5-chloro-2-methoxy-phenyl)acetamide

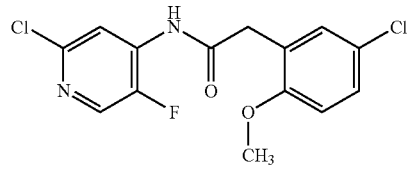

TABLE 9

| Ex. | Structure and Name | 1H NMR<br>LCMS Retention Time, [M + H]+, |
|---|---|---|
| 27.1 | N-tert-Butyl-4-[[2-[4-[(tert-butylamino)methyl]-5-chloro-2-hydroxy-phenyl]acetyl]amino]pyridine-2-carboxamide | 1H NMR (500 MHz, DMSO-d6) δ 10.67 (s, 1H), 9.66 (s, 1H), 8.43 (d, J = 5.5 Hz, 1H), 8.17 (d, J = 2.1 Hz, 1H), 8.03 (s, 1H), 7.81 (dd, J = 5.5, 2.2 Hz, 1H), 7.16 (s, 1H), 7.06 (s, 1H), 3.63-3.61 (m, 4H), 1.40 (s, 9H), 1.09 (s, 9H).<br>LC-MS (Method A): Rt 2.08 mins; MS m/z 445.4/447.4 = [M + H]+ (99% @ 215 nm) |
| 27.2 | N-tert-Butyl-4-[[2-[5-chloro-2-hydroxy-4-(morpholinomethyl)phenyl]acetyl]amino]pyridine-2-carboxamide | 1H NMR (500 MHz, DMSO-d6) δ 10.68 (s, 1H), 9.74 (s, 1H), 8.44 (d, J = 5.5 Hz, 1H), 8.17 (d, J = 2.0 Hz, 1H), 8.03 (s, 1H), 7.81 (dd, J = 5.5, 2.2 Hz, 1H), 7.21 (s, 1H), 6.98 (s, 1H), 3.65 (s, 2H), 3.62 – 3.56 (m, 4H), 3.46 (s, 2H), 2.42-2.40 (m, 4H), 1.40 (s, 9H).<br>LC-MS (Method A): Rt 1.91 mins; MS m/z 459.3/460.3 = [M + H]+ (100% @ 215 nm) |
| 27.3 | N-tert-Butyl-4-[[2-[5-chloro-4-[(3,3-difluoropyrrolidin-1-yl)methyl]-2-hydroxy-phenyl]acetyl]amino]pyridine-2-carboxamide | 1H NMR (500 MHz, DMSO-d6) δ 10.70 (s, 1H), 9.78 (s, 1H), 8.44 (d, J = 5.5 Hz, 1H), 8.17 (d, J = 2.1 Hz, 1H), 8.03 (s, 1H), 7.81 (dd, J = 5.5, 2.2 Hz, 1H), 7.22 (s, 1H), 6.95 (s, 1H), 3.64 (s, 2H), 2.93 (t, J = 13.3 Hz, 2H), 2.76 (t, J = 7.0 Hz, 2H), 2.31-2.22 (m, 2H), 1.40 (s, 9H).<br>LC-MS (Method A): Rt 2.6 mins; MS m/z 481.3/483.3 = [M + H]+ (98% @ 215 nm) |

Example 28

N-tert-butyl-4-[[2-(5-chloro-2-hydroxy-phenyl)acetyl]amino]-5-fluoro-pyridine-2-carboxamide

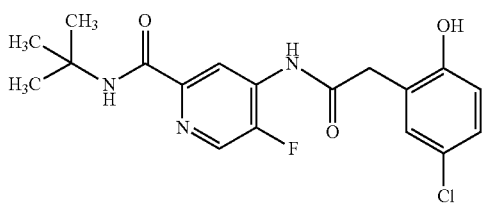 [SMILES: CC(C)(C)NC(=O)c1cc(NC(=O)Cc2cc(Cl)ccc2O)c(F)cn1]

A solution of 2-(5-chloro-2-methoxy-phenyl)acetic acid (753 mg, 3.75 mmol) in thionyl chloride (6.01 mL, 68.24 mmol) was stirred at 70° C. for 1 hour. The resulting mixture was concentrated to dryness and azeotroped with toluene (2×10 mL). The crude residue was dissolved in DMF (10 mL) and treated dropwise with a solution of 2-chloro-5-fluoro-pyridin-4-amine (500 mg, 3.41 mmol) in DMF (3 mL) followed by DIPEA (1.49 mL, 8.53 mmol). After stirring at room temperature under an inert atmosphere for 16 hours, the mixture was diluted with EtOAc (100 mL) and washed with water (2×50 mL) and brine (2×50 mL). The organic portion was dried over $Na_2SO_4$ and concentrated in vacuo. The crude material was purified by C18 reverse phase chromatography eluting with 0-100% MeCN in water with 0.1% formic acid modifier to afford the titled compound as a light yellow solid.

1H NMR (250 MHz, DMSO-d6) δ 10.58 (s, 1H), 8.41 (d, J=2.7 Hz, 1H), 8.24 (d, J=5.6 Hz, 1H), 7.33-7.28 (m, 2H), 7.01 (d, J=9.5 Hz, 1H), 3.83 (s, 2H), 3.75 (s, 3H).

LC-MS (Method E): Rt 1.25 mins; MS m/z 328.9, 330.9=[M+H]+

Step 2: N-tert-Butyl-4-[[2-(5-chloro-2-methoxy-phenyl)acetyl]amino]-5-fluoro-pyridine-2-carboxamide

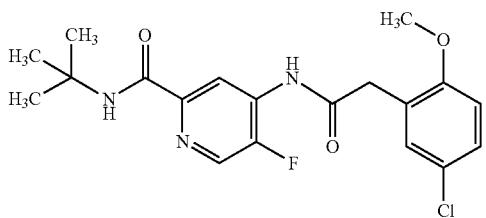 [SMILES: COc1ccc(Cl)cc1CC(=O)Nc1cc(C(=O)NC(C)(C)C)ncc1F]

All reagents charged to Coware equipment (carbon monoxide generating system) according to the following procedure; To chamber A was added N-(2-chloro-5-fluoro-4-pyridyl)-2-(5-chloro-2-methoxy-phenyl)acetamide (step 1) (170 mg, 0.52 mmol), sodium carbonate (164 mg, 1.55 mmol), XantPhos Pd-G3 (third generation (G3) Buchwald precatalyst) (49 mg, 0.05 mmol) and toluene (5 mL) followed by 2-methylpropan-2-amine (64 mg, 0.88 mmol). The resulting solution was de-gassed with nitrogen for 5 minutes. To chamber B was added formic acid (49 µL, 1.29 mmol) in toluene (5 mL) followed by mesyl chloride (100 µL, 1.29 mmol). The vessel was sealed and TEA (288 µL, 2.07 mmol) added to chamber B to generate carbon monoxide. The Coware equipment was heated at 100° C. overnight and allowed to cool to room temperature. The resulting mixture was concentrated in vacuo, dissolved in EtOAc (30 mL) and washed with water (2×25 mL). The organic portion was dried over Na₂SO₄ and concentrated in vacuo. Purification of the crude residue by preparative HPLC (acidic pH, early elution method) afforded the titled compound as a beige solid.

1H NMR (250 MHz, Methanol-d4) δ 8.91 (d, J=6.5 Hz, 1H), 8.41 (d, J=2.6 Hz, 1H), 7.29-7.23 (m, 2H), 7.00-6.94 (m, 1H), 3.84 (s, 3H), 3.79 (s, 2H), 1.45 (s, 9H).

LC-MS (Method E): Rt 1.25 mins; MS m/z 394.1, 396.1=[M+H]+ (97% @ 215 nm)

Step 3: N-tert-Butyl-4-[[2-(5-chloro-2-hydroxy-phenyl)acetyl]amino]-5-fluoro-pyridine-2-carboxamide To a cooled (0° C.) solution of N-tert-butyl-4-[[2-(5-chloro-2-methoxy-phenyl)acetyl]amino]-5-fluoro-pyridine-2-carboxamide (step 2) (30 mg, 0.08 mmol) in DCM (2 mL) was added 1M BBr₃ in DCM (190 µL, 0.19 mmol). The reaction mixture was allowed to warm to room temperature and stirring continued for a further 1 hour. The reaction was quenched by addition of water (0.5 mL) and concentrated in vacuo. The crude material was re-dissolved in EtOAc (2 mL) and washed with sat. NaHCO₃ (2 mL). The organic portion was concentrated in vacuo and purification of the crude residue was carried out by C18 reverse phase chromatography (0-100% MeCN in water with 0.1% formic acid modifier). The product fractions were concentrated in vacuo and freeze-dried to afford the titled compound as a white solid.

1H NMR (500 MHz, DMSO-d6) δ 10.02 (br. S, 1H), 8.82 (d, J=6.6 Hz, 1H), 8.54 (d, J=2.5 Hz, 1H), 7.91 (s, 1H), 7.22 (d, J=2.7 Hz, 1H), 7.12 (dd, J=8.6, 2.7 Hz, 1H), 6.81 (d, J=8.6 Hz, 1H), 3.79-3.74 (m, 2H), 1.38 (s, 9H).

LC-MS (Method A): Rt 3.37 mins; MS m/z 380.3/381.3/382.3=[M+H]+ (99% @ 215 nm)

Example 28.1

N-tert-Butyl-4-[[2-(5-chloro-2-hydroxy-phenyl)acetyl]amino]-3-fluoro-pyridine-2-carboxamide

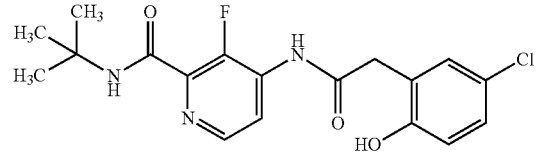 [SMILES: CC(C)(C)NC(=O)c1nccc(NC(=O)Cc2cc(Cl)ccc2O)c1F]

The titled compound was prepared from 2-chloro-3-fluoro-pyridin-4-amine and 2-(5-chloro-2-methoxy-phenyl)acetic acid analogously to Example 28 steps 1-3.

1H NMR (500 MHz, DMSO-d6) δ 8.29-8.25 (m, 2H), 8.02 (s, 1H), 7.21 (d, J=2.7 Hz, 1H), 7.12 (dd, J=8.6, 2.7 Hz, 1H), 6.81 (d, J=8.6 Hz, 1H), 3.78 (s, 2H), 1.38 (s, 9H).

LC-MS (Method A): Rt 3.30 mins; MS m/z 380.2/382.2=[M+H]+

Example 30

4-[[2-(2-Chlorophenyl)acetyl]amino]-N-(1-cyanocyclobutyl)pyridine-2-carboxamide

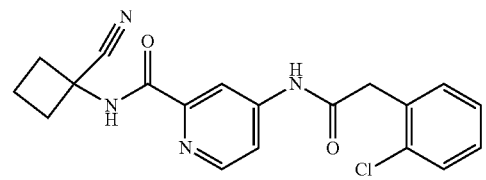 [SMILES: N#CC1(NC(=O)c2cc(NC(=O)Cc3ccccc3Cl)ccn2)CCC1]

Step 1: Methyl 4-[[2-(2-chlorophenyl)acetyl]amino]pyridine-2-carboxylate

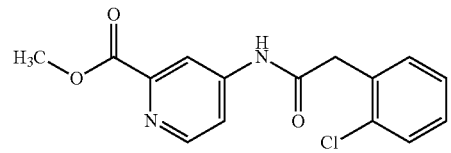 [SMILES: COC(=O)c1cc(NC(=O)Cc2ccccc2Cl)ccn1]

To a stirred solution of 2-(2-chlorophenyl)acetic acid (3.08 g, 18.07 mmol), methyl 4-aminopyridine-2-carboxylate (2.5 g, 16.43 mmol) and TEA (4.3 mL, 24.65 mmol) in 1,4-dioxane (40 mL) was added 50% T3P® solution in EtOAc (14.68 mL, 24.65 mmol). The resulting mixture was stirred at room temperature for 2 hour and then diluted with EtOAc (100 mL) and water (100 mL). The organic layer was separated, dried over Na₂SO₄ and concentrated in vacuo. The crude residue was purified by chromatography on silica eluting with 10-100% EtOAc in heptane to afford the titled compound as a pale orange solid.

1H NMR (500 MHz, DMSO-d6) δ 10.85 (s, 1H), 8.55 (d, J=5.5 Hz, 1H), 8.31 (d, J=1.9 Hz, 1H), 7.77 (dd, J=5.5, 2.2 Hz, 1H), 7.48-7.40 (m, 2H), 7.36-7.28 (m, 2H), 3.91 (s, 2H), 3.86 (s, 3H).

LC-MS (Method E): Rt 1.00 mins; MS m/z 305.0/307.0=[M+H]+ (96% @ 215 nm)

Step 2: 4-[[2-(2-Chlorophenyl)acetyl]amino]pyridine-2-carboxylic acid

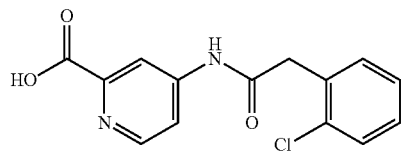 [SMILES: O=C(Cc1ccccc1Cl)Nc1ccnc(C(=O)O)c1]

2M LiOH (16.07 mL, 32.13 mmol) was added to a stirred solution of methyl 4-[[2-(2-chlorophenyl)acetyl]amino]pyridine-2-carboxylate (step 2) (3.4 g, 10.71 mmol) in THF (40 mL) and stirred at room temperature for 20 minutes. The resulting mixture was partially concentrated in vacuo to remove the volatile solvent and acidified to pH 2 with 2M aq HCl. The resulting suspension was filtered and dried in a vacuum oven at 40° C. to afford the titled compound as an off-white solid.

1H NMR (500 MHz, DMSO-d6) δ 10.89 (s, 1H), 8.53 (d, J=5.5 Hz, 1H), 8.27 (d, J=2.1 Hz, 1H), 7.79 (dd, J=5.5, 2.2 Hz, 1H), 7.49-7.41 (m, 2H), 7.35-7.29 (m, 2H), 3.92 (s, 2H).

LC-MS (Method E): Rt 0.89 mins; MS m/z 290.9/292.9=[M+H]+ (100% @ 215 nm)

Step 3: 4-[[2-(2-Chlorophenyl)acetyl]amino]-N-(1-cyanocyclobutyl)pyridine-2-carboxamide A solution of 1-aminocyclobutanecarbonitrile (33 mg, 0.34 mmol), DIPEA (0.07 mL, 0.41 mmol), HATU (131 mg, 0.34 mmol) and 4-[[2-(2-chlorophenyl)acetyl]amino]pyridine-2-carboxylic acid (step 2) (100 mg, 0.34 mmol) in DMF (2 mL) was stirred at room temperature for 2 hours. The resulting mixture was concentrated in vacuo and the residue partitioned between EtOAc (10 mL) and water (10 mL). The organic layer was separated, dried over Na2SO4 and concentrated in vacuo. The residue was purified by preparative HPLC (acidic pH, early elution method) and the product fractions lyophilised overnight to afford the titled compound as an off-white powder.

1H NMR (500 MHz, DMSO-d6) δ 10.87 (s, 1H), 9.60 (s, 1H), 8.53 (d, J=5.5 Hz, 1H), 8.20 (d, J=1.9 Hz, 1H), 7.87 (dd, J=5.5, 2.2 Hz, 1H), 7.52-7.38 (m, 2H), 7.38-7.24 (m, 2H), 3.92 (s, 2H), 2.70-2.62 (m, 2H), 2.59-2.52 (m, 2H), 2.09-1.93 (m, 2H).

LC-MS (Method A): Rt 3.02 mins; MS m/z 369.2=[M+H]+ (100% @ 215 nm)

Example 30.1

4-[[2-(2-Chlorophenyl)acetyl]amino]-N-(1,1-dimethylprop-2-ynyl)pyridine-2-carboxamide

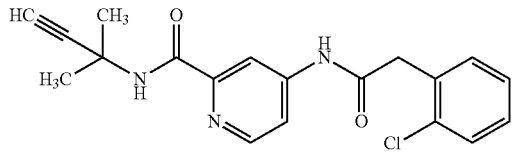 [SMILES: C#CC(C)(C)NC(=O)c1cc(NC(=O)Cc2ccccc2Cl)ccn1]

A solution of 2-methylbut-3-yn-2-amine (14 mg, 0.17 mmol), DIPEA (0.08 mL, 0.43 mmol), HATU (65 mg, 0.17 mmol) and 4-[[2-(2-chlorophenyl)acetyl]amino]pyridine-2-carboxylic acid (Example 30, step 2)(50 mg, 0.17 mmol) in DMF (1 mL) was stirred at room temperature for 2 hours. The resulting mixture was concentrated in vacuo then the residue partitioned between EtOAc (10 mL) and water (10 mL). The organic layer was separated, dried over Na2SO4 and concentrated in vacuo. The residue was purified by preparative HPLC (acidic pH, early elution method) and the product fractions were combined and lyophilised overnight to afford the titled compound as an off-white powder.

1H NMR (500 MHz, DMSO-d6) δ 10.85 (s, 1H), 8.48 (d, J=5.5 Hz, 1H), 8.32 (s, 1H), 8.19 (d, J=2.0 Hz, 1H), 7.83 (dd, J=5.5, 2.2 Hz, 1H), 7.49-7.39 (m, 2H), 7.37-7.29 (m, 2H), 3.92 (s, 2H), 3.21 (s, 1H), 1.64 (s, 6H).

LC-MS (Method A): Rt 3.25 mins; MS m/z 356.3/358.2=[M+H]+ (100% @ 215 nm)

Example 30.2

4-[[2-(2-Chlorophenyl)acetyl]amino]-N-(4-fluoro-1-bicyclo[2.1.1]hexanyl)pyridine-2-carboxamide

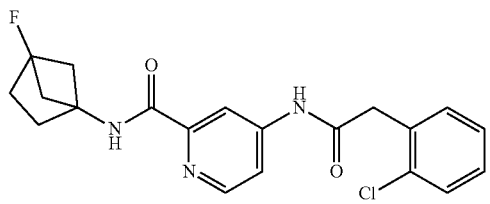 [SMILES: O=C(Cc1ccccc1Cl)Nc1ccnc(C(=O)NC23CCC(F)(C2)C3)c1]

A solution of 4-fluorobicyclo[2.1.1]hexan-1-amine hydrochloride (26 mg, 0.17 mmol), DIPEA (0.08 mL, 0.43 mmol), HATU (65 mg, 0.17 mmol) and 4-[[2-(2-chlorophenyl) acetyl]amino]pyridine-2-carboxylic acid (Example 30, step 2) (50 mg, 0.17 mmol) in DMF (1 mL) was stirred at room temperature for 2 hours. The resulting mixture was concentrated in vacuo and the residue partitioned between EtOAc (10 mL) and water (10 mL). The organic layer was separated, dried over Na2SO4 and concentrated in vacuo. The residue was purified by preparative HPLC (acidic pH, early elution method) and the product fractions were combined and lyophilised overnight to afford the titled compound as an off-white powder.

1H NMR (500 MHz, DMSO-d6) δ 10.83 (s, 1H), 9.05 (s, 1H), 8.48 (d, J=5.5 Hz, 1H), 8.16 (d, J=2.0 Hz, 1H), 7.83 (dd, J=5.5, 2.2 Hz, 1H), 7.54-7.40 (m, 2H), 7.40-7.25 (m, 2H), 3.91 (s, 2H), 2.14-2.08 (m, 2H), 2.08-2.04 (m, 2H), 2.00-1.94 (m, 2H), 1.87-1.81 (m, 2H).

LC-MS (Method A): Rt 3.39 mins; MS m/z 388.3/390.3= [M+H]+ (99% @ 215 nm)

Example 30.3

4-[[2-(2-Chlorophenyl)acetyl]amino]-N-(1-cyclopropyl-1-methyl-ethyl)pyridine-2-carboxamide

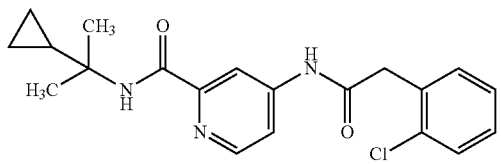 [SMILES: CC(C)(NC(=O)c1cc(NC(=O)Cc2ccccc2Cl)ccn1)C1CC1]

The titled compound was prepared from 4-[[2-(2-chlorophenyl)acetyl]amino]pyridine-2-carboxylic acid (Example 30 step 2) and 2-cyclopropylpropan-2-amine analogously to Example 30 step 3.

1H NMR (500 MHz, DMSO-d6) δ 10.84 (s, 1H), 8.47 (d, J=5.5 Hz, 1H), 8.20 (d, J=2.1 Hz, 1H), 8.03 (s, 1H), 7.81 (dd, J=5.5, 2.2 Hz, 1H), 7.49-7.42 (m, 2H), 7.35-7.31 (m, 2H), 3.92 (s, 2H), 1.41-1.34 (m, 1H), 1.31 (s, 6H), 0.43-0.36 (m, 4H).

LC-MS (Method A): Rt 3.73 mins; MS m/z 372.2/374.2= [M+H]+ (100% @ 215 nm)

The compounds of the following tabulated Examples (Table 9a) were prepared analogously to Example 30 by replacing 1-aminocyclobutanecarbonitrile (step 3) with the appropriate commercially available amine.

TABLE 9a

| Ex. | Structure and Name | 1H NMR LCMS Retention Time, [M + H]+, |
|---|---|---|
| 30.3a | 4-[[2-(2-Chlorophenyl)acetyl]amino]-N-(1-cyano-1-methyl-ethyl)pyridine-2-carboxamide | 1H NMR (500 MHz, DMSO-d6) δ 10.89 (s, 1H), 8.84 (s, 1H), 8.53 (d, J = 5.5 Hz, 1H), 8.23 (d, J = 2.0 Hz, 1H), 7.87 (dd, J = 5.5, 2.2 Hz, 1H), 7.50 – 7.42 (m, 2H), 7.38 – 7.29 (m, 2H), 3.93 (s, 2H), 1.73 (s, 6H). LC-MS (Method A): Rt 2.96 mins; MS m/z 357.2/359.3 = [M + H]+ (99% @ 215 nm) |
| 30.4 | 4-[[2-(2-Chlorophenyl)acetyl]amino]-N-(1-methyl-3-bicyclo[1.1.1]pentanyl)pyridine-2-carboxamide | 1H NMR (500 MHz, DMSO-d6) δ 10.82 (s, 1H), 8.99 (s, 1H), 8.45 (d, J = 5.5 Hz, 1H), 8.13 (d, J = 2.0 Hz, 1H), 7.82 (dd, J = 5.5, 2.2 Hz, 1H), 7.49 – 7.40 (m, 2H), 7.36 – 7.29 (m, 2H), 3.91 (s, 2H), 1.96 (s, 6H), 1.22 (s, 3H). LC-MS (Method A): Rt 3.65 mins; MS m/z 370.3/372.3 = [M + H]+ (97% @ 215 nm) |
| 30.5 | 4-[[2-(2-Chlorophenyl)acetyl]amino]-N-(1-cyano-3-bicyclo[1.1.1]pentanyl)pyridine-2-carboxamide | 1H NMR (500 MHz, DMSO-d6) δ 10.84 (s, 1H), 9.49 (s, 1H), 8.47 (d, J = 5.5 Hz, 1H), 8.14 (d, J = 2.0 Hz, 1H), 7.84 (dd, J = 5.5, 2.2 Hz, 1H), 7.49 – 7.38 (m, 2H), 7.36 – 7.28 (m, 2H), 3.91 (s, 2H), 2.57 (s, 6H). LC-MS (Method A): Rt 3.08 mins; MS m/z 381.2/383.2 = [M + H]+ (100% @ 215 nm) |
| 30.6 | 4-[[2-(2-Chlorophenyl)acetyl]amino]-N-(2,2-difluorocyclopropyl)pyridine-2-carboxamide | 1H NMR (500 MHz, DMSO-d6) δ 10.85 (s, 1H), 9.07 (t, J = 3.3 Hz, 1H), 8.50 (d, J = 5.5 Hz, 1H), 8.21 (d, J = 2.0 Hz, 1H), 7.84 (dd, J = 5.5, 2.2 Hz, 1H), 7.56 – 7.40 (m, 2H), 7.40 – 7.25 (m, 2H), 3.92 (s, 2H), 3.57 – 3.42 (m, 1H), 2.03 – 1.80 (m, 2H). LC-MS (Method A): Rt 3.04 mins; MS m/z 366.1/368.2 = [M + H]+ (99% @ 215 nm) |

TABLE 9a-continued

| Ex. | Structure and Name | 1H NMR LCMS Retention Time, [M + H]+, |
|---|---|---|
| 30.7 | 4-[[2-(2-Chlorophenyl)acetyl]amino]-N-(1-cyanocyclopropyl)pyridine-2-carboxamide | 1H NMR (500 MHz, DMSO-d6) δ 10.87 (s, 1H), 9.66 (s, 1H), 8.50 (d, J = 5.5 Hz, 1H), 8.22 (d, J = 2.1 Hz, 1H), 7.86 (dd, J = 5.5, 2.2 Hz, 1H), 7.50 – 7.40 (m, 2H), 7.36 – 7.27 (m, 2H), 3.92 (s, 2H), 1.59 – 1.46 (m 2H), 1.37 – 1.28 (m, 2H). LC-MS (Method A): Rt 2.77 mins; MS m/z 355.2/357.2 = [M + H]+ (98% @ 215 nm) |
| 30.8 | 4-[[2-(2-Clorophenyl)acetyl]amino]-N-(1-methylcyclopropyl)pyridine-2-carboxamide | 1H NMR (500 MHz, DMSO-d6) δ 10.81 (s, 1H), 8.76 (s, 1H), 8.44 (d, J = 5.5 Hz, 1H), 8.16 (d, J = 2.1 Hz, 1H), 7.80 (dd, J = 5.5, 2.2 Hz, 1H), 7.44 (m, 2H), 7.36 – 7.17 (m, 2H), 3.91 (s, 2H), 1.36 (s, 3H), 0.91 – 0.72 (m, 2H), 0.72 – 0.57 (m, 2H). LC-MS (Method A): Rt 3.02 mins; MS m/z 344.2/346.2 = [M + H]+ (100% @ 215 nm) |
| 30.9 | 4-[[2-(2-Chlorophenyl)acetyl]amino]-N-(3-fluoro-1-bicyclo[1.1.1]pentanyl)pyridine-2-carboxamide | 1H NMR (500 MHz, DMSO-d6) δ 10.84 (s, 1H), 9.37 (s, 1H), 8.48 (d, J = 5.5 Hz, 1H), 8.15 (d, J = 2.0 Hz, 1H),7.84 (dd, J = 5.5, 2.2 Hz, 1H), 7.48 – 7.40 (m, 2H), 7.35 – 7.30 (m, 2H), 3.91 (s, 2H), 2.41 (d, J = 2.2 Hz, 6H). LC-MS (Method A): Rt 3.30 mins; MS m/z 374.3/376.2 = [M + H]+ (100% @ 215 nm) |
| 30.10 | 4-[[2-(2-Chlorophenyl)acetyl]amino]-N-(2-fluoro-1,1-dimethyl-ethyl)pyridine-2-carboxamide | 1H NMR (500 MHz, DMSO-d6) δ 10.85 (s, 1H), 8.47 (d, J = 5.5 Hz, 1H), 8.20 (d, J = 2.0 Hz, 1H), 8.12 (s, 1H), 7.81 (dd, J = 5.5, 2.2 Hz, 1H), 7.44 (d, J = 11.9 Hz, 2H), 7.35 – 7.31 (m, 2H), 4.58 (d, J = 47.5 Hz, 2H), 3.92 (s, 2H), 1.39 (d, J = 1.9 Hz, 6H). LC-MS (Method A): Rt 3.32 mins; MS m/z 364.2/366.2 = [M + H]+ (100% @ 215 nm) |
| 30.11* | 4-[[2-(2-Chlorophenyl)acetyl]amino]-N-(4-ethynyltetrahydropyran-4-yl)pyridine-2-carboxamide. | 1H NMR (500 MHz, DMSO-d6) δ 10.86 (s, 1H), 8.50 (d, J = 5.5 Hz, 1H), 8.45 (s, 1H), 8.20 (d, J = 2.1 Hz, 1H), 7.83 (dd, J = 5.5, 2.2 Hz, 1H), 7.48 – 7.41 (m, 2H), 7.35 – 7.30 (m, 2H), 3.92 (s, 2H), 3.76 (dt, J = 11.7, 3.9 Hz, 2H), 3.67 – 3.59 (m, 2H), 3.38 (s, 1H), 2.19-2.13 (m, 2H), 2.09-2.01 (m, 2H). LC-MS (Method A): Rt 2.95 mins; MS m/z 398.2/400.2 = [M + H]+ (100% @ 215 nm) |
| 30.12 | 4-[[2-(2-Chlorophenyl)acetyl]amino]-N-(1-cyanocyclopentyl)pyridine-2-carboxamide | 1H NMR (500 MHz, DMSO-d6) δ 10.88 (s, 1H), 9.05 (s, 1H), 8.52 (d, J = 5.5 Hz, 1H), 8.22 (d, J = 1.9 Hz, 1H), 7.85 (dd, J = 5.5, 2.2 Hz, 1H), 7.48 – 7.42 (m, 2H), 7.35 – 7.30 (m, 2H), 3.92 (s, 2H), 2.33 – 2.27 (m, 4H), 1.79 – 1.72 (m, 4H). LC-MS (Method A): Rt 3.24 mins; MS m/z 383.2/385.2 = [M + H]+ (99% @ 215 nm) |

TABLE 9a-continued

| Ex. | Structure and Name | 1H NMR<br>LCMS Retention Time, [M + H]+, |
|---|---|---|
| 30.13 | 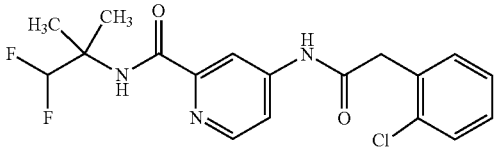 [SMILES: CC(C)(NC(=O)c1cc(NC(=O)Cc2ccccc2Cl)ccn1)C(F)F]<br>4-[[2-(2-Chlorophenyl)acetyl]amino]-N-(2,2-difluoro-1,1-dimethyl-ethyl)pyridine-2-carboxamide | 1H NMR (500 MHz, DMSO-d6) δ 10.86 (s, 1H), 8.49 (d, J = 5.5 Hz, 1H), 8.29 (s, 1H), 8.22 (d, J = 2.0 Hz, 1H), 7.82 (dd, J = 5.5, 2.2 Hz, 1H), 7.47 – 7.41 (m, 2H), 7.34 – 7.30 (m, 2H), 6.46 (t, J = 57.0 Hz, 1H), 3.92 (s, 2H), 1.44 (s, 6H)<br>LC-MS (Method A): Rt 3.53 mins; MS m/z 382.2/384.2 = [M + H]+ |

*Example 30.11: the amine, 4-ethynyltetrahydropyran-4-amine hydrochloride was prepared according to the procedure described in *Journal of Organic Chemistry*, 71(18), 7110-7112; 2006

Example 31

4-[[2-(5-Chloro-2-hydroxy-phenyl)acetyl]amino]-N-(4-cyanotetrahydropyran-4-yl)pyridine-2-carboxamide

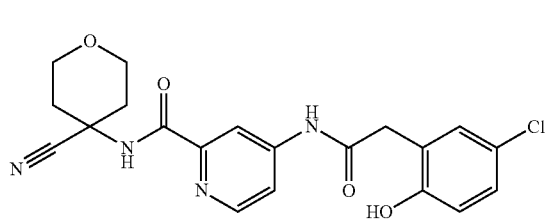 [SMILES: N#CC1(NC(=O)c2cc(NC(=O)Cc3cc(Cl)ccc3O)ccn2)CCOCC1]

Step 1: 4-[[2-(5-Chloro-2-hydroxy-phenyl)acetyl]amino]pyridine-2-carboxylic acid

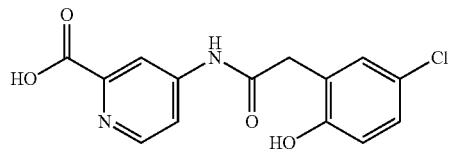 [SMILES: O=C(Cc1cc(Cl)ccc1O)Nc1ccnc(C(=O)O)c1]

1M BBr₃ in DCM (308.67 mL, 308.67 mmol) was added slowly over 1 hour to a suspension of 4-[[2-(5-chloro-2-methoxy-phenyl)acetyl]amino]pyridine-2-carboxylic acid (Example 8.1, step 2) (25.0 g, 77.17 mmol, 99%) in DCM (500 mL) at 0-5° C. under an inert atmosphere of N₂. The mixture was allowed to warm to room temperature and stirred for a further hour. The reaction mixture was concentrated in vacuo and the residue was suspended in EtOAc (500 mL) and water (500 mL) at 0° C. The resulting mixture was allowed to warm to room temperature and the aqueous layer adjusted to pH 4 by portion-wise addition of sat. aq. NaHCO₃ (350 mL). The precipitate was collected by filtration, washed with water (2×100 mL), EtOAc (2×100 mL), diethyl ether (2×150 mL) and dried in a high vacuum oven at 40° C. to afford the titled compound as a beige solid.

1H NMR (500 MHz, DMSO-d6) δ 10.72 (s, 1H), 9.82 (br. s, 1H), 8.53 (d, J=5.5 Hz, 1H), 8.27 (d, J=2.0 Hz, 1H), 7.80 (dd, J=5.6, 2.2 Hz, 1H), 7.22 (d, J=2.7 Hz, 1H), 7.13 (dd, J=8.6, 2.7 Hz, 1H), 6.80 (d, J=8.6 Hz, 1H), 3.67 (s, 2H).

LC-MS (Method E): Rt 0.86 mins; MS m/z 306.9/308.9= [M+H]+ (97% @ 215 nm)

Step 2: 4-[[2-(5-Chloro-2-hydroxy-phenyl)acetyl]amino]-N-(4-cyanotetrahydropyran-4-yl)pyridine-2-carboxamide

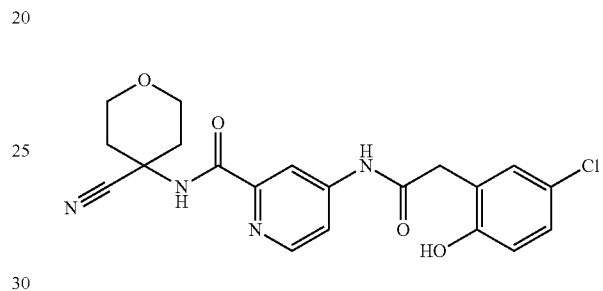

HATU (19.34 g, 50.86 mmol) was added to a stirred solution of 4-[[2-(5-chloro-2-hydroxy-phenyl)acetyl]amino]pyridine-2-carboxylic acid (Example 31 step 1) (13 g, 42.39 mmol), 4-aminotetrahydropyran-4-carbonitrile (8.02 g, 63.58 mmol) and DIPEA (18.51 mL, 105.97 mmol) in DMF (150 mL) and the reaction mixture was stirred at room temperature for 2 hours. The resulting mixture was diluted with 0.5 M aq. NaOH (100 mL) and stirred at room temperature for 30 mins. Water (500 mL) and EtOAc (500 mL) were added and the resulting precipitate was removed by filtration. The aqueous portion was extracted with EtOAc (250 mL) and the combined organics were washed with water (2×750 mL), sat. NaHCO₃ (500 mL), brine (700 mL), dried over Na₂SO₄ and concentrated in vacuo to afford a yellow oil. The material was purified on chromatography on silica eluting with 0-100% EtOAc in heptane then 0-15% MeOH in EtOAc. The product fractions were combined and concentrated in vacuo. The residue was subsequently purified on KP-NH silica eluting with 50-100% EtOAc in heptane then 0-15% MeOH in EtOAc. The clean product fractions were combined and concentrated in vacuo and azeotroped with MeCN (3×500 mL) to afford the titled compound.

1H NMR (500 MHz, DMSO-d6) δ 10.74 (br s, 1H), 9.83 (s, 1H), 9.00 (s, 1H), 8.52 (d, J=5.5 Hz, 1H), 8.23 (d, J=2.1 Hz, 1H), 7.87 (dd, J=5.5, 2.2 Hz, 1H), 7.22 (d, J=2.7 Hz, 1H), 7.13 (dd, J=8.6, 2.7 Hz, 1H), 6.81 (d, J=8.6 Hz, 1H), 3.86 (td, J=12.5 Hz, 3.9 Hz, 2H), 3.68 (s, 2H), 3.64-3.53 (m, 2H), 2.41-2.32 (m, 2H), 2.12-2.00 (m, 2H).

LC-MS (Method A): Rt 2.67 mins; MS m/z 415.2/417.2= [M+H]+

Step 3: Recrystallisation 4-[[2-(5-Chloro-2-hydroxy-phenyl)acetyl]amino]-N-(4-cyanotetrahydropyran-4-yl)pyridine-2-carboxamide 4-[[2-(5-Chloro-2-hydroxy-phenyl)acetyl]amino]-N-(4-cyanotetrahydropyran-4-yl)pyridine-2-carboxamide (step 2)

(1881 mg, 4.44 mmol) was suspended in MeCN (16 mL) and heated at reflux for 10 min. Additional MeCN (2 mL) was added and the mixture was heated at reflux for 30 mins at which point it was observed that all the material had gone into solution. The heat was reduced to 55° C. and the mixture was seeded with a crystal of 4-[[2-(5-chloro-2-hydroxy-phenyl)acetyl]amino]-N-(4-cyanotetrahydropyran-4-yl)pyridine-2-carboxamide. The temperature of the mixture was maintained at 55° C. for 1 hour and then allowed to cool slowly to room temperature overnight. The resulting crystals were collected by filtration, washed with minimum volume of ice cold MeCN (~5 mL) and dried in a vacuum oven at 40° C. for 2 hours to afford the titled compound as an off-white crystalline solid.

1H NMR (500 MHz, DMSO-d6) δ 10.74 (br s, 1H), 9.82 (br s, 1H), 9.00 (s, 1H), 8.53 (d, J=5.5 Hz, 1H), 8.23 (d, J=2.0 Hz, 1H), 7.87 (dd, J=5.5, 2.2 Hz, 1H), 7.22 (d, J=2.7 Hz, 1H), 7.13 (dd, J=8.6, 2.7 Hz, 1H), 6.81 (d, J=8.6 Hz, 1H), 3.86 (td, J=12.5 Hz, 3.9 Hz, 2H), 3.68 (s, 2H), 3.63-3.54 (m, 2H), 2.40-2.34 (m, 2H), 2.12-2.03 (m, 2H).

LC-MS (Method A): Rt 2.68 mins; MS m/z 415.3/417.2= [M+H]+ (99% @ 215 nm)

Example 31.2

4-[[2-(5-Chloro-2-hydroxy-phenyl)acetyl]amino]-N-(1-ethynylcyclopentyl)pyridine-2-carboxamide

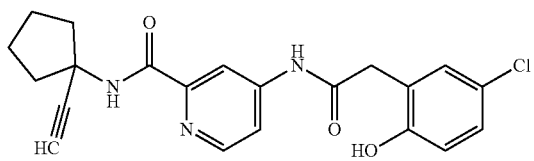 [SMILES: C#CC1(NC(=O)c2cc(NC(=O)Cc3cc(Cl)ccc3O)ccn2)CCCC1]

The titled compound was prepared from 4-[[2-(5-chloro-2-hydroxy-phenyl)acetyl]amino]pyridine-2-carboxylic acid (Example 31 step 1) and 1-ethynylcyclopentanamine hydrochloride analogously to Example 31 step 2.

1H NMR (500 MHz, DMSO-d6) δ 10.70 (s, 1H), 9.82 (br. s, 1H), 8.48-8.45 (m, 2H), 8.17 (d, J=1.9 Hz, 1H), 7.84 (dd, J=5.5, 2.2 Hz, 1H), 7.22 (d, J=2.7 Hz, 1H), 7.12 (dd, J=8.6, 2.7 Hz, 1H), 6.81 (d, J=8.6 Hz, 1H), 3.67 (s, 2H), 3.16 (s, 1H), 2.30-2.22 (m, 2H), 2.14-2.05 (m, 2H), 1.77-1.66 (m, 4H).

LC-MS (Method A): Rt 3.34 mins; MS m/z 398.2/400.2= [M+H]+ (100% @ 215 nm)

Example 31.3

4-[2-(5-Chloro-2-hydroxyphenyl)acetamido]-N-[(1s,2s)-2-hydroxycyclohexyl]pyridine-2-carboxamide

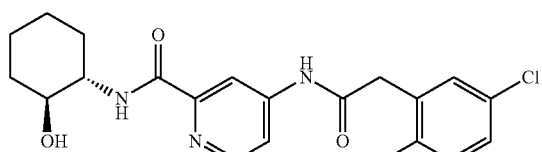

4-[[2-(5-Chloro-2-hydroxy-phenyl)acetyl]amino]-N-(2-hydroxycyclohexyl)pyridine-2-carboxamide was prepared from 4-[[2-(5-chloro-2-hydroxy-phenyl)acetyl]amino]pyridine-2-carboxylic acid (Example 31 step 1) and trans-2-aminocyclohexanol analogously to Example 31 step 2.

1H NMR (500 MHz, DMSO-d6) δ 10.74 (s (br), 1H), 9.82 (s (br), 1H), 8.47 (d, J=5.5 Hz, 1H), 8.34 (d, J=8.1 Hz, 1H), 8.19 (d, J=2.1 Hz, 1H), 7.82 (dd, J=5.5, 2.2 Hz, 1H), 7.21 (d, J=2.6 Hz, 1H), 7.11 (dd, J=8.6, 2.7 Hz, 1H), 6.79 (d, J=8.6 Hz, 1H), 4.68 (d, J=5.5 Hz, 1H), 3.66 (s, 2H), 3.60-3.53 (m, 1H), 3.45-3.41 (m, 1H), 1.94-1.85 (m, 2H), 1.67-1.57 (m, 2H), 1.30-1.18 (m, 4H).

LC-MS (Method A): Rt 2.64 mins; MS m/z 404.3/406.3= [M+H]+ (97% @ 215 nm)

Example 31.3a

4-[[2-(5-Chloro-2-hydroxy-phenyl)acetyl]amino]-N-[(1S,2S)-2-hydroxycyclo hexyl]pyridine-2-carboxamide or 4-[[2-(5-Chloro-2-hydroxy-phenyl)acetyl]amino]-N-[(1R,2R)-2-hydroxycyclohexyl]pyridine-2-carboxamide

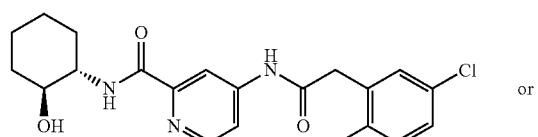

(1S,2S)-isomer or

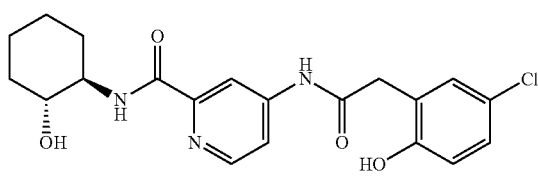 [SMILES: O=C(Cc1cc(Cl)ccc1O)Nc1ccnc(C(=O)N[C@H]2CCCC[C@@H]2O)c1]

(1R,2R)-isomer

Chiral separation of 4-[2-(5-chloro-2-hydroxyphenyl)acetamido]-N-[(1s,2s)-2-hydroxycyclohexyl]pyridine-2-carboxamide (Example 31.3) using Supercritical Fluid Chromatography SFC (15% Methanol+0.2% DEA: 85% CO2 with Chiralcel OJ-H 25 cm column at 4 ml/min) afforded the titled compound.

SFC Retention Time (second eluted peak)=23.32 mins MS (ESIPos): m/z=404.1 (M+H)+.

1H NMR (500 MHz, DMSO-d6) δ 8.47 (d, J=5.5 Hz, 1H), 8.34 (d, J=8.1 Hz, 1H), 8.18 (d, J=2.1 Hz, 1H), 7.82 (dd, J=5.5, 2.2 Hz, 1H), 7.20 (d, J=2.5 Hz, 1H), 7.10 (dd, J=8.6, 2.6 Hz, 1H), 6.78 (d, J=8.6 Hz, 1H), 4.69 (d, J=5.5 Hz, 1H), 3.66 (s, 2H), 3.61-3.53 (m, 1H), 3.47-3.41 (m, 1H), 1.95-1.86 (m, 2H), 1.68-1.58 (m, 2H), 1.28-1.23 (m, 4H).

LC-MS (Method A): Rt 2.64 mins; MS m/z 404.2/406.2= [M+H]+ (100% @ 215 nm)

Example 31.4

4-[[2-(5-Chloro-2-hydroxy-phenyl)acetyl]amino]-N-(4-ethynyltetrahydropyran-4-yl)pyridine-2-carboxamide

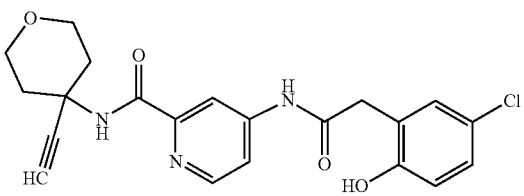 [SMILES: C#CC1(NC(=O)c2cc(NC(=O)Cc3cc(Cl)ccc3O)ccn2)CCOCC1]

Step 1: 2-Methyl-N-tetrahydropyran-4-ylidene-propane-2-sulfinamide

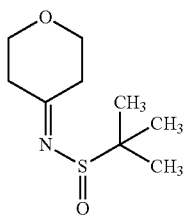

A solution of tetrahydropyran-4-one (2.4 g, 23.97 mmol) in THF (50 mL) under an inert atmosphere was treated with tetraethoxytitanium (9.57 g, 41.95 mmol) followed by 2-methylpropane-2-sulfinamide (2.91 g, 23.97 mmol) and the reaction mixture was stirred at room temperature overnight. The mixture was poured into sat. aq. NaHCO$_3$ (100 mL) and stirred for 5 minutes. A resulting suspension was filtered and the solid washed further with water (50 mL) and EtOAc (100 mL). The filtrate was separated and the aqueous layer washed once more with EtOAc (50 mL). The combined organic portions were washed with brine (50 mL), dried over Na$_2$SO$_4$ and concentrated in vacuo to afford a crude oil. The oil was purified by chromatography on silica eluting with 0-100% EtOAc in heptane to afford the titled compound as a colourless oil.

LC-MS (Method E): Rt 0.74 mins; MS m/z 204.0=[M+H]+ (100% @ 215 nm)

Step 2: 4-Ethynyltetrahydropyran-4-amine hydrochloride

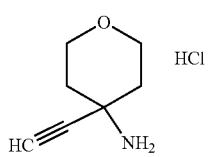

A cooled (−78° C.) solution of ethynyl(trimethyl)silane (725 mg, 7.38 mmol) in toluene (10 mL) under nitrogen was treated dropwise with n-BuLi (1.6M in hexanes) (3.38 mL, 5.41 mmol). After stirring at −78° C. for 15 mins, the mixture was treated with a cooled (−78° C.) solution of 2-methyl-N-tetrahydropyran-4-ylidene-propane-2-sulfinamide (500 mg, 2.46 mmol) in toluene (5 mL) and trimethylalumane (1.48 mL, 2.95 mmol) via cannula. Stirring was continued at −78° C. for 2 hours and then the solution was allowed to warm to room temperature and stirred overnight. The resulting mixture was cooled to 0° C. and quenched with sat. aq. Na$_2$SO$_4$ (~20 mL). The mixture was filtered and washed with EtOAc (~50 mL). The biphasic filtrate was separated and organic portion washed further with water (25 mL). The aqueous layer was back-extracted with EtOAc (50 mL) and the combined organic extracts were washed with brine (25 mL), dried over Na$_2$SO$_4$ and concentrated in vacuo to afford an off-white solid. The solid was dissolved in anhydrous dioxane (2 mL) and treated with 4M HCl (2 mL). After stirring at room temperature for 4 hours, the resulting precipitate was filtered and washed with cold dioxane to afford the titled compound as a beige solid.

1H NMR (500 MHz, DMSO-d6) δ 8.98 (s, 3H), 3.91 (s, 1H), 3.91-3.86 (m, 2H), 3.48 (td, J=11.9, 2.0 Hz, 2H), 1.95 (td, J=12.4, 4.5 Hz, 2H), 1.89-1.84 (m, 2H).

LC-MS (Method E): Rt 0.2 mins; MS m/z 126.0=[M+H]+

Step 3: 4-[[2-(5-Chloro-2-hydroxy-phenyl) acetyl]amino]-N-(4-ethynyltetrahydro pyran-4-yl)pyridine-2-carboxamide The titled compound was prepared from 4-[[2-(5-chloro-2-hydroxy-phenyl)acetyl]amino]pyridine-2-carboxylic acid (Ex 31 step 1) and 4-ethynyltetrahydropyran-4-amine hydrochloride (step 2) analogously to Example 31 step 2.

1H NMR (500 MHz, DMSO-d6) δ 10.70 (s, 1H), 9.81 (s, 1H), 8.48 (d, J=5.5 Hz, 1H), 8.45 (s, 1H), 8.19 (d, J=2.1 Hz, 1H), 7.85 (dd, J=5.5, 2.2 Hz, 1H), 7.22 (d, J=2.7 Hz, 1H), 7.12 (dd, J=8.6, 2.7 Hz, 1H), 6.80 (d, J=8.6 Hz, 1H), 3.76 (dt, J=7.7, 4.0 Hz, 2H), 3.68 (s, 2H), 3.66-3.60 (m, 2H), 3.38 (s, 1H), 2.18-2.13 (m, 2H), 2.09-2.01 (m, 2H).

LC-MS (Method A): Rt 2.80 mins; MS m/z 414.2/416.2=[M+H]+ (99% @ 215 nm)

Example 32

N-[(6-Amino-2-pyridyl)methyl]-4-[[2-(5-chloro-2-hydroxy-phenyl)acetyl]amino]pyridine-2-carboxamide

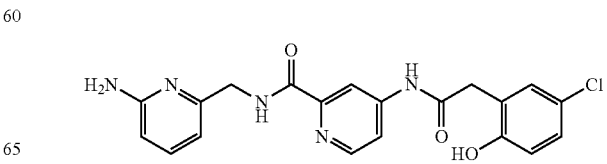

Step 1: tert-butyl N-[6-[[[4-[[2-(5-chloro-2-methoxy-phenyl)acetyl]amino]pyridine-2-carbonyl]amino]methyl]-2-pyridyl]carbamate

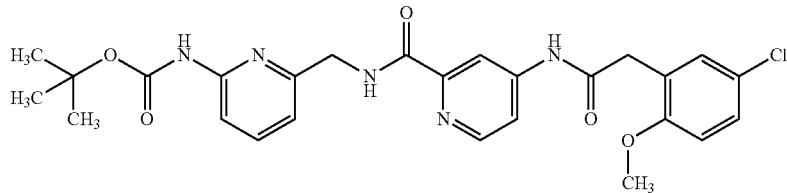 [SMILES: COc1ccc(Cl)cc1CC(=O)Nc1ccnc(C(=O)NCc2cccc(NC(=O)OC(C)(C)C)n2)c1]

To a solution of 4-[[2-(5-chloro-2-methoxy-phenyl)acetyl]amino]pyridine-2-carboxylic acid (Example 8.1 step 2)(100 mg, 0.3 mmol) in DMF (1 mL) was added tert-butyl N-[6-(aminomethyl)-2-pyridyl]carbamate (68 mg, 0.3 mmol) followed by DIPEA (63 μL, 0.36 mmol) and the mixture stirred at room temperature for 15 mins. HATU (126 mg, 0.33 mmol) was added and the stirring continued at room temperature for 1 hour. The resulting mixture was diluted with H₂O (2 mL) and the pH adjusted to pH 6 by addition of sat. aq. NH₄Cl. The mixture was extracted with EtOAc (2×5 mL) and the combined organic extracts were washed with brine, dried over Na₂SO₄ and concentrated in vacuo. The crude residue was triturated with MeCN and water to afford the titled compound as white solid.

1H NMR (500 MHz, DMSO-d6) δ 10.71 (s, 1H), 9.70 (s, 1H), 9.23 (t, J=6.1 Hz, 1H), 8.52 (d, J=5.5 Hz, 1H), 8.22 (d, J=2.1 Hz, 1H), 7.84 (dd, J=5.5, 2.2 Hz, 1H), 7.69-7.63 (m, 2H), 7.32-7.29 (m, 2H), 7.03-7.00 (m, 1H), 6.91 (dd, J=6.9, 1.2 Hz, 1H), 4.49 (d, J=6.1 Hz, 2H), 3.75 (s, 3H), 3.72 (s, 2H), 1.46 (s, 9H).

LC-MS (Method A): Rt 3.78 mins; MS m/z 526.3/528.2= [M+H]+ (100% @ 215 nm)

Step 2: N-[(6-Amino-2-pyridyl)methyl]-4-[[2-(5-chloro-2-hydroxy-phenyl)acetyl]amino]pyridine-2-carboxamide tert-Butyl N-[6-[[[4-[[2-(5-chloro-2-methoxy-phenyl)acetyl]amino]pyridine-2-carbonyl]amino]methyl]-2-pyridyl]carbamate (step 1)(107 mg, 0.2 mmol) was added to a cooled (0-5° C.) suspension of 1M BBr₃ in DCM (895 μL, 0.9 mmol) in DCM (1.1 mL). The ice bath was removed and the mixture was stirred at room temperature for 2 hours. The resulting mixture was concentrated in vacuo and the residue partitioned between EtOAc (5 mL) and water (4 mL). The pH of the aqueous layer to pH7 by addition of sat. aq. NaHCO₃ and the organic layer was separated, dried over Na₂SO₄ and concentrated in vacuo. The crude residue was triturated in MeCN:H₂O (4:1), filtered, washed with MeCN and dried in a high vacuum oven to afford the titled compound as a light tan solid.

1H NMR (500 MHz, DMSO-d6) δ 10.68 (s, 1H), 9.81 (s, 1H), 9.05 (t, J=5.9 Hz, 1H), 8.50 (d, J=5.5 Hz, 1H), 8.22 (d, J=2.0 Hz, 1H), 7.84 (dd, J=5.5, 2.1 Hz, 1H), 7.31 (t, J=7.7 Hz, 1H), 7.22 (d, J=2.6 Hz, 1H), 7.12 (dd, J=8.6, 2.7 Hz, 1H), 6.80 (d, J=8.6 Hz, 1H), 6.40 (d, J=7.2 Hz, 1H), 6.32 (d, J=8.2 Hz, 1H), 5.93 (br. S, 2H), 4.36 (d, J=5.9 Hz, 2H), 3.67 (s, 2H).

LC-MS (Method A): Rt 1.70 mins; MS m/z 412.2/414.4= [M+H]+ (97% @ 215 nm)

The compounds of the following tabulated Examples (Table 10) were prepared analogously to Example 32 by replacing tert-butyl N-[6-(aminomethyl)-2-pyridyl]carbamate (step 1) with the appropriate commercially available amine.

TABLE 10

| Ex. | Structure and Name | 1H NMR LCMS Retention Time, [M + H]+, |
|---|---|---|
| 32.1 | 12-[[4-[[2-(5-Chloro-2-hydroxy-phenyl)acetyl]amino]pyridine-2-carbonyl]amino]dodecanoic acid | 1H NMR (500 MHz, Methanol-d4) δ 8.47 (d, J = 5.6 Hz, 1H), 8.24 – 8.17 (m, 1H), 7.93 – 7.89 (m, 1H), 7.19 (d, J = 2.4 Hz, 1H), 7.09 (d, J = 8.6, 2.2 Hz, 1H), 6.78 (d, J = 8.6 Hz, 1H), 3.72 (s, 2H), 3.40 (t, J = 7.1 Hz, 2H), 2.27 (t, J = 7.4 Hz, 2H), 1.67-1.55 (m, 4H), 1.42-1.26 (m, 14H). <br> LC-MS (Method A): Rt 3.71 mins; MS m/z 504.4/506.4 = [M + H]+ |
| 32.2 | 4-[[2-(5-Chloro-2-hydroxy-phenyl)acetyl]amino]-N-(3-pyridylmethyl)pyridine-2-carboxamide | 1H NMR (500 MHz, DMSO-d6) δ 10.84 (s, 1H), 9.89 (s, 1H), 9.40 (t, J = 6.4 Hz, 1H), 8.55 (d, J = 1.8 Hz, 1H), 8.49 (d, J = 5.5 Hz, 1H), 8.45 (dd, J = 4.8, 1.6 Hz, 1H), 8.21 (d, J = 2.0 Hz, 1H), 7.84 (dd, J = 5.5, 2.2 Hz, 1H), 7.73 (dt, J = 7.8, 1.9 Hz, 1H), 7.34 (dd, J = 7.8, 4.8 Hz, 1H), 7.21 (d, J = 2.9 Hz, 1H),7.11 (dd, J = 8.6, 2.7 Hz, 1H), 6.79 (d, J = 8.6 Hz, 1H), 4.51 (d, J = 6.4 Hz, 2H), 3.67 (s, 2H). <br> LC-MS (Method A): Rt 1.80 mins; MS m/z 397.2/399.2 = [M + H]+ (96% @ 215 nm) |

TABLE 10-continued

| Ex. | Structure and Name | 1H NMR<br>LCMS Retention Time, [M + H]+, |
|---|---|---|
| 32.3 | 4-[[2-(5-Chloro-2-hydroxy-phenyl)acetyl]amino]-N-(2-pyridylmethyl)pyridine-2-carboxamide | 1H NMR (500 MHz, DMSO-d6) δ 10.70 (s, 1H), 9.82 (s, 1H), 9.33 (t, J = 5.7 Hz, 1H), 8.56-8.50 (m, 2H), 8.24 (s, 1H), 7.86 (d, J = 3.7 Hz, 1H), 7.76 (t, J = 7.2 Hz, 1H), 7.32 (d, J = 7.9 Hz, 1H), 7.31 – 7.25 (m, 1H), 7.25 – 7.20 (m, 1H), 7.13 (dd, J = 8.5, 2.2 Hz, 1H), 6.81 (d, J = 8.6 Hz, 1H), 4.62 (d, J = 5.8 Hz, 2H), 3.68 (s, 2H).<br>LC-MS (Method A): Rt 1.98 mins; MS m/z 397.2/399.2 = [M + H]+ (97% @ 215 nm) |
| 32.4 | 4-[[2-(5-Chloro-2-hydroxy-phenyl)acetyl]amino]-N-(4-pyridylmethyl)pyridine-2-carboxamide | 1H NMR (500 MHz, DMSO-d6) δ 10.74 (s, 1H), 9.82 (s, 1H), 9.43 (t, J = 6.4 Hz, 1H), 8.52 (d, J = 5.5 Hz, 1H), 8.52 – 8.46 (m, 2H), 8.22 (d, J = 2.1 Hz, 1H), 7.86 (dd, J = 5.5, 2.2 Hz, 1H), 7.29 (d, J = 6.0 Hz, 2H), 7.22 (d, J = 2.7 Hz, 1H), 7.13 (dd, J = 8.6, 2.7 Hz, 1H), 6.81 (d, J = 8.6 Hz, 1H), 4.51 (d, J = 6.4 Hz, 2H), 3.68 (s, 2H).<br>LC-MS (Method A): Rt 1.63 mins; MS m/z 397.2/399.2 = [M + H]+ (96% @ 215 nm) |
| 32.5 | 4-[[2-(5-Chloro-2-hydroxy-phenyl)acetyl]amino]-N-[(2-hydroxyphenyl) methyl]pyridine-2-carboxamide | 1H NMR (500 MHz, Methanol-d4) δ 8.35 dd, J = 5.01, 0.52 Hz, 1H), 8.06 (dd, J = 1.71, 0.49, 1H), 7.80 (dd, J = 5.5, 2.2 Hz, 1H), 7.11 (dd, J = 7.5, 1.5 Hz, 1H), 7.08 (d, J = 2.6 Hz, 1H), 7.04 – 6.96 (m, 2H), 6.74 – 6.70 (m, 1H), 6.69 – 6.65 (m, 2H), 4.47 (s, 2H), 3.60 (s, 2H).<br>LC-MS (Method A): Rt 3.01 mins; MS m/z 412.2/414.2 = [M + H]+ (97% @ 215 nm) |
| 32.6 | 4-[[2-(5-Chloro-2-hydroxy-phenyl)acetyl]amino]-N-(1,1-dimethyl-2-morpholino-ethyl)pyridine-2-carboxamide | 1H NMR (500 MHz, DMSO-d6) δ 10.66 (s, 1H), 9.80 (s, 1H), 8.44 (d, J = 5.5 Hz, 1H), 8.33 (s, 1H), 8.17 (d, J = 2.1 Hz, 1H), 7.80 (dd, J = 5.5, 2.2 Hz, 1H), 7.22 (d, J = 2.7 Hz, 1H), 7.12 (dd, J = 8.6, 2.7 Hz, 1H), 6.80 (d, J = 8.6 Hz, 1H), 3.67 (s, 2H), 3.58 – 3.54 (m, 4H), 2.57 (s, 2H), 1.37 (s, 6H), 1.24 (s, 2H).<br>LC-MS (Method A): Rt 1.80 mins; MS m/z 447.3/449.3 = [M + H]+ (100% @ 215 nm) |
| 32.7 | 4-[[2-(5-Chloro-2-hydroxy-phenyl)acetyl]amino]-N-(2-hydroxy-1,1-dimethyl-ethyl)pyridine-2-carboxamide | 1H NMR (500 MHz, DMSO-d6) δ 10.67 (s, 1H), 9.81 (s, 1H), 8.44 (d, J = 5.5 Hz, 1H), 8.24 (s, 1H), 8.17 (d, J = 2.0 Hz, 1H), 7.81 (dd, J = 5.5, 2.2 Hz, 1H), 7.22 (d, J = 2.7 Hz, 1H), 7.12 (dd, J = 8.6, 2.7 Hz, 1H), 6.80 (d, J = 8.6 Hz, 1H), 5.12 (t, J = 5.5 Hz, 1H), 3.67 (s, 2H), 3.44 (d, J = 5.5 Hz, 2H), 1.33 (s, 6H).<br>LC-MS (Method A): Rt 2.56 mins; MS m/z 378.2/380.2 = [M + H]+ (100% @ 215 nm) |
| 32.8 | 4-[[2-(5-Chloro-2-hydroxy-phenyl)acetyl]amino]-N-(3,3-difluoro-4-piperidyl)pyridine-2-carboxamide | 1H NMR (500 MHz, DMSO-d6) δ 10.71 (s, 1H), 9.82 (s, 1H), 8.51 (d, J = 5.5 Hz, 1H), 8.42 (d, J = 9.6 Hz, 1H), 8.27 (d, J = 1.9 Hz, 1H), 7.84 (dd, J = 5.5, 2.2 Hz, 1H), 7.23 (d, J = 2.7 Hz, 1H), 7.13 (dd, J = 8.6, 2.7 Hz, 1H), 6.81 (d, J = 8.6 Hz, 1H), 4.60 – 4.32 (m, 1H), 3.68 (s, 2H), 3.18 – 3.07 (m, 1H), 2.97 – 2.79 (m, 2H), 2.69 – 2.62 (m, 1H), 1.90 – 1.79 (m, 1H), 1.78 – 1.63 (m, 1H).<br>LC-MS (Method A): Rt 1.95 mins; MS m/z 425.2/427.2 = [M + H]+ (99% @ 215 nm) |
| 32.9 | 4-[[2-(5-Chloro-2-hydroxy-phenyl)acetyl]amino]-N-(1H-imidazol-2-yl)pyridine-2-carboxamide | 1H NMR (500 MHz, DMSO-d6) δ 11.88 (s, 1H), 10.89 – 10.63 (m, 2H), 9.86 (s, 1H), 8.56 (d, J = 5.5 Hz, 1H), 8.38 (d, J = 2.0 Hz, 1H), 7.85 (dd, J = 5.5, 2.2 Hz, 1H), 7.23 (d, J = 2.7 Hz, 1H), 7.13 (dd, J = 8.6, 2.7 Hz, 1H), 6.91 (m, 3H), 3.69 (s, 2H).<br>LC-MS (Method A): Rt 1.65 mins; MS m/z 372.2/374.2 = [M + H]+ (97% @ 215 nm) |

Example 33

4-[[2-(5-Chloro-2-hydroxy-phenyl)acetyl]amino]-N-[(1R,2R)-2-hydroxycyclopentyl]pyridine-2-carboxamide

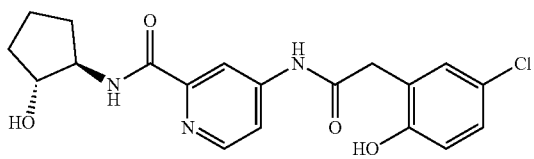 [SMILES: O=C(Cc1cc(Cl)ccc1O)Nc1ccnc(C(=O)N[C@@H]2CCC[C@H]2O)c1]

To a solution of 4-[[2-(5-chloro-2-hydroxy-phenyl)acetyl]amino]pyridine-2-carboxylic acid (Example 31 step 1)(100 mg, 0.33 mmol), (1R,2R)-2-aminocyclopentanol hydrochloride (45 mg, 0.33 mmol) and DIPEA (228 µL, 1.3 mmol) in DMF (2 mL) was added HATU (149 mg, 0.39 mmol) and the mixture was stirred at room temperature for 1 hour. The resulting mixture was partitioned between EtOAc (10 mL) and water (15 mL) then washed with sat. aq NaHCO$_3$ (10 mL). The combined aqueous washes were extracted with EtOAc (2×10 mL). The combined organic extracts were dried over Na$_2$SO$_4$ and concentrated in vacuo. Purification of the crude residue by chromatography on silica using a Biotage Isolera 11 g KP-NH system eluting with 0-15% MeOH in EtOAc afforded the titled compound as an off-white solid.

1H NMR (500 MHz, DMSO-d6) δ 10.75 (s, 1H), 9.83 (s, 1H), 8.47 (d, J=5.5 Hz, 1H), 8.43 (d, J=7.6 Hz, 1H), 8.19 (d, J=2.1 Hz, 1H), 7.82 (dd, J=5.5, 2.2 Hz, 1H), 7.21 (d, J=2.7 Hz, 1H), 7.12 (dd, J=8.6, 2.7 Hz, 1H), 6.79 (d, J=8.6 Hz, 1H), 4.80 (s, 1H), 4.03-3.94 (m, 2H), 3.66 (s, 2H), 2.03-1.96 (m, 1H), 1.89-1.81 (m, 1H), 1.71-1.58 (m, 2H), 1.54-1.42 (m, 2H).

LC-MS (Method A): Rt 2.50 mins; MS m/z 390.3/392.3=[M+H]+ (99% @ 215 nm)

Example 34

4-[[2-(5-Chloro-2-hydroxy-phenyl)acetyl]amino]-N-(1-cyano-1-methyl-ethyl)pyridine-2-carboxamide

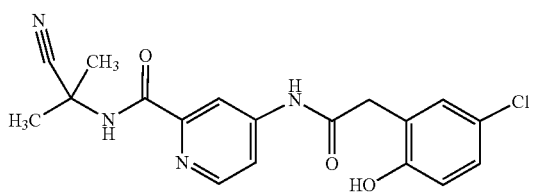 [SMILES: CC(C)(C#N)NC(=O)c1cc(NC(=O)Cc2cc(Cl)ccc2O)ccn1]

4-[[2-(5-Chloro-2-hydroxy-phenyl)acetyl]amino]pyridine-2-carboxylic acid (Example 31 step 1)(4.0 g, 13.04 mmol) and 2-amino-2-methyl-propanenitrile hydrochloride (3.15 g, 26.08 mmol) were suspended in DMF (40 mL) and treated with DIPEA (9.11 mL, 52.17 mmol) and stirred to form a solution. HATU (5.95 g, 15.65 mmol) was added the reaction mixture was stirred at room temperature for 3 hours. The resulting mixture was diluted with water (60 mL) and 4:1 EtOAc/heptane (100 ml). The biphasic suspension was filtered using minimal EtOAc and the organic portion was separated, washed with water, dried over Na$_2$SO$_4$ and concentrated in vacuo. Purification of the residue by chromatography on silica eluting with 0-100% EtOAc in heptane followed by 0-100% MeOH in EtOAc afforded a yellow glassy solid. TBME (10 mL) was added to the solid and the mixture was heated to reflux (90° C.) and further TBME (90 mL) was added gradually. MeCN was added in 0.5 mL aliquots until full dissolution occurred (9 mL). The mixture was cooled to 60° C. then to 0° C. for 3 hours. The resulting mixture was allowed to stand at room temperature for 4 days and then filtered and dried in a vacuum oven to afford the titled compound as a white crystalline solid.

1H NMR (500 MHz, DMSO-d6) δ 10.88 (s, 1H), 9.87 (s, 1H), 8.82 (s, 1H), 8.50 (d, J=5.5 Hz, 1H), 8.21 (d, J=1.9 Hz, 1H), 7.86 (dd, J=5.5, 2.2 Hz, 1H), 7.21 (d, J=2.7 Hz, 1H), 7.11 (dd, J=8.6, 2.7 Hz, 1H), 6.79 (d, J=8.6 Hz, 1H), 3.67 (s, 2H), 1.72 (s, 6H).

LC-MS (Method A): Rt 2.81 mins; MS m/z 373.2/375.2=[M+H]+ (98% @ 215 nm)

Example 35

4-[[2-(5-Chloro-2-hydroxy-phenyl)acetyl]amino]-N-[3-(hydroxymethyl)tetrahydrofuran-3-yl]pyridine-2-carboxamide

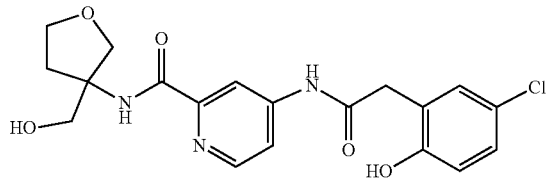 [SMILES: O=C(Cc1cc(Cl)ccc1O)Nc1ccnc(C(=O)NC2(CO)CCOC2)c1]

4-[[2-(5-Chloro-2-hydroxy-phenyl)acetyl]amino]pyridine-2-carboxylic acid (Example 31 step 1) (150 mg, 0.49 mmol) and DIPEA (256.27 µL, 1.47 mmol) were suspended in DMF (2 mL) and treated with (3-aminotetrahydrofuran-3-yl)methanol (69 mg, 0.59 mmol) and HATU (223 mg, 0.59 mmol). The reaction mixture was stirred at room temperature for 30 min and then partitioned between EtOAc (15 mL) and water (15 mL). The organic portion was washed with sat. aq. NaHCO$_3$ (10 mL). The combined aqueous washes were extracted with EtOAc (2×10 mL) and the combined organic extracts dried over Na$_2$SO$_4$ and concentrated in vacuo. Purification by chromatography on silica using a Biotage Isolera 11 g KP-NH system, eluting with 0-15% DCM/MeOH afforded the titled compound as an off-white solid.

1H NMR (500 MHz, DMSO-d6) δ=10.73 (s, 1H), 9.82 (s, 1H), 8.46 (d, J=5.5 Hz, 1H), 8.41 (s, 1H), 8.19 (d, J=2.0 Hz, 1H), 7.82 (dd, J=5.5, 2.2 Hz, 1H), 7.21 (d, J=2.7 Hz, 1H), 7.12 (dd, J=8.6, 2.7 Hz, 1H), 6.80 (d, J=8.6 Hz, 1H), 5.17 (s, 1H), 3.88-3.77 (m, 4H), 3.67 (s, 2H), 3.62-3.59 (m, 2H), 2.34-2.28 (m, 1H), 2.00-1.94 (m, 1H).

LC-MS (Method A): Rt 2.36 mins; MS m/z 406.3/408.3=[M+H]+ (97% @ 215 nm)

Example 35a and 35b

Enantiomers of 4-[[2-(5-chloro-2-hydroxy-phenyl)acetyl]amino]-N-3-(hydroxymethyl)tetrahydrofuran-3-ylpyridine-2-carboxamide Chiral separation of racemic 4-[[2-(5-chloro-2-hydroxy-phenyl)acetyl]amino]-N-3-(hydroxymethyl)tetrahydrofuran-3-ylpyridine-2-carboxamide (Example 35) using Supercritical Fluid Chromatography [chiral phase column (5 µL at 1 mg/mL MeOH+95/5% CO2/(IPOH)+0.5% IPAm with Chiralpak IG (300 mm×4.6) 20 µm column at 2.4 mL/min)] afforded the individual enantiomers:

Example 35a: 4-[[2-(5-Chloro-2-hydroxy-phenyl)acetyl]amino]-N-[(3R)-3-(hydroxymethyl)tetrahydrofuran-3-yl]pyridine-2-carboxamide or 4-[[2-(5-chloro-2-hydroxy-phenyl)acetyl]amino]-N-[(3S)-3-(hydroxymethyl)tetrahydrofuran-3-yl]pyridine-2-carboxamide

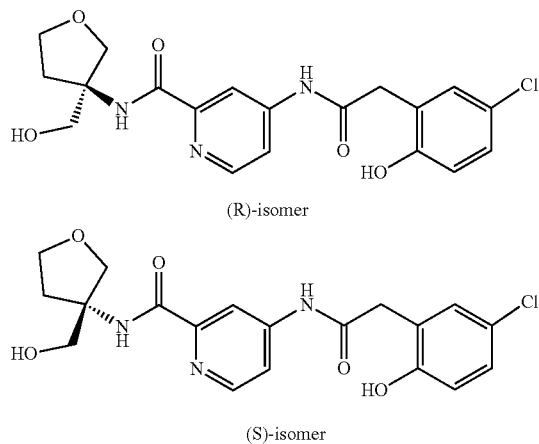

First eluted peak: SFC Retention Time=6.10 mins

1H NMR (500 MHz, DMSO-d6) δ 10.71 (s, 1H), 9.76 (s, 1H), 8.46 (d, J=5.5 Hz, 1H), 8.41 (s, 1H), 8.19 (d, J=2.0 Hz, 1H), 7.82 (dd, J=5.5, 2.2 Hz, 1H), 7.21 (d, J=2.7 Hz, 1H), 7.12 (dd, J=8.6, 2.7 Hz, 1H), 6.80 (d, J=8.6 Hz, 1H), 5.16 (t, J=5.3 Hz, 1H), 3.88-3.77 (m, 4H), 3.67 (s, 2H), 3.61 (m, 2H), 2.34-2.29 (m, 1H), 2.00-1.94 (m, 1H).

LC-MS (Method A): Rt 2.23 mins; MS m/z 406.2/408.2= [M+H]+ (97% @ 215 nm)

Example 35b: 4-[[2-(5-Chloro-2-hydroxy-phenyl)acetyl]amino]-N-[(3R)-3-(hydroxymethyl)tetrahydrofuran-3-yl]pyridine-2-carboxamide or 4-[[2-(5-chloro-2-hydroxy-phenyl)acetyl]amino]-N-[(3S)-3-(hydroxymethyl)tetrahydrofuran-3-yl]pyridine-2-carboxamide

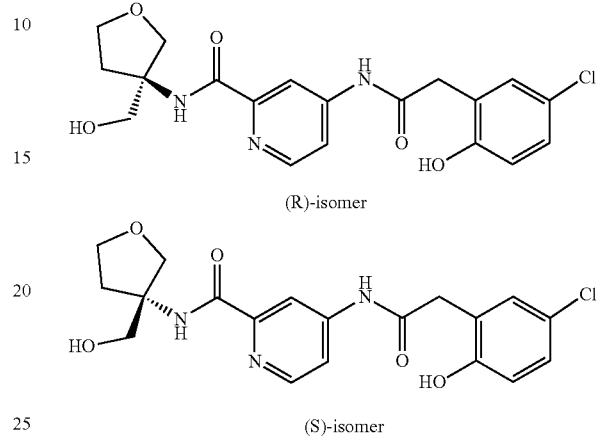

Second eluted peak: SFC Retention Time=7.70 mins

1H NMR (500 MHz, DMSO-d6) δ 10.72 (s, 1H), 9.77 (s, 1H), 8.46 (d, J=5.5 Hz, 1H), 8.41 (s, 1H), 8.19 (d, J=2.1 Hz, 1H), 7.82 (dd, J=5.5, 2.2 Hz, 1H), 7.21 (d, J=2.7 Hz, 1H), 7.12 (dd, J=8.6, 2.7 Hz, 1H), 6.80 (d, J=8.6 Hz, 1H), 5.17 (s, 1H), 3.89-3.76 (m, 4H), 3.67 (s, 2H), 3.61 (d, J=3.0 Hz, 2H), 2.35-2.28 (m, 1H), 2.01-1.93 (m, 1H).

LC-MS (Method A): Rt 2.23 mins; MS m/z 406.2/408.2= [M+H]+ (97% @ 215 nm)

The compounds of the following tabulated Examples (Table 11) were prepared analogously to Example 35 from either 4-[[2-(5-chloro-2-hydroxy-phenyl)acetyl]amino]pyridine-2-carboxylic acid (Example 31 step 1) or 3-[[2-(5-fluoro-2-hydroxy-phenyl)acetyl]amino]benzoic acid (Example 41 step 3) and the appropriate commercially available amine.

TABLE 11

| Ex. | Structure and Name | 1H NMR LCMS Retention Time, [M + H]+, |
|---|---|---|
| 35.1 | 4-[[2-(5-Chloro-2-hydroxy-phenyl)acetyl]amino]-N-(4-hydroxy-4-methyl-cyclohexyl)pyridine-2-carboxamide as a 6:4 mixture of stereoisomers | 1H NMR (500 MHz, DMSO-d6) δ = 8.46 (dd, J = 5.6, 2.1 Hz, 1H), 8.43 – 8.23 (m, 1H), 8.18 (t, J = 2.5 Hz, 1H), 7.83 – 7.80 (m, 1H), 7.21 (d, J = 2.7 Hz, 1H), 7.12 (dd, J = 8.6, 2.7Hz, 1H), 6.80 (d, J = 8.6 Hz, 1H), 4.35 – 4.00 (m, 1H), 3.84 – 3.67 (m, 1H), 3.66 (s, 2H), 1.77 – 1.67 (m, 2H), 1.61 – 1.50 (m, 4H), 1.49 – 1.34 (m, 2H), 1.17 – 1.10 (m, 3H). LC-MS (Method A): Rt 2.52 mins; MS m/z 418.3/420.3 = [M + H]+ (96% @ 215 nm) |
| 35.2 | 4-[[2-(5-Chloro-2-hydroxy-phenyl)acetyl]amino]-N-[(1s,2r)-2-(hydroxy methyl)cyclohexyl]pyridine-2-carboxamide | 1H NMR (500 MHz, DMSO-d6) δ = 10.78 (s, 1H), 9.31 (s, 1H), 8.67 (d, J = 8.3 Hz, 1H), 8.47 (d, J = 5.6 Hz, 1H), 8.20 (d, J = 2.1 Hz, 1H), 7.81 (dd, J = 5.5 Hz, 2.2, 1H), 7.21 (d, J = 2.6 Hz, 1H), 7.12 (dd, J = 8.6, 2.7 Hz, 1H), 6.79 (d, J = 8.6 Hz, 1H), 4.63 (t, J = 4.3 Hz, 1H), 4.19 – 4.13 (m, 1H), 3.66 (s, 2H), 3.51 – 3.45 (m, 2H), 1.84 (s, 1H), 1.76 – 1.69 (m, 1H), 1.61 – 1.53 (m, 3H), 1.51 – 1.44 (m, 2H), 1.36-1.28 (m, 2H). LC-MS (Method A): Rt 3.03 mins; MS m/z 418.3/420.3 = [M + H]+ (99% @ 215 nm) |

TABLE 11-continued

| Ex. | Structure and Name | 1H NMR<br>LCMS Retention Time, [M + H]+, |
|---|---|---|
| 35.3 | 4-[[2-(5-Chloro-2-hydroxy-phenyl)acetyl]amino]-N-[(1s,3r)-3-hydroxycyclopentyl]pyridine-2-carboxamide | 1H NMR (500 MHz, DMSO-d6) δ = 10.70 (s, 1H), 9.80 (s, 1H), 8.68 (d, J = 8.8 Hz, 1H), 8.46 (d, J = 5.5 Hz, 1H), 8.20 (d, J = 2.1 Hz, 1H), 7.81 (dd, J = 5.5, 2.2 Hz, 1H), 7.22 (d, J = 2.7 Hz, 1H), 7.12 (dd, J = 8.6 Hz, 2.7, 1H), 6.80 (d, J = 8.6 Hz, 1H), 4.81 (d, J = 2.6 Hz, 1H), 4.40 – 4.33 (m, 1H), 4.23 – 4.17 (m, 1H), 3.67 (s, 2H), 2.01 – 1.93 (m, 2H), 1.75-1.65 (m, 3H), 1.61 – 1.55 (m, 1H).<br>LC-MS (Method A): Rt 2.36 mins; MS m/z 390.3/ 392.3 = [M + H]+ (98% @ 215 nm) |
| 35.4 | 4-[[2-(5-Chloro-2-hydroxy-phenyl)acetyl]amino]-N-[2-hydroxy-1-(hydroxymethyl)-1-methyl-ethyl]pyridine-2-carboxamide | 1H NMR (500 MHz, DMSO-d6) δ = 8.43 (d, J = 5.6, 1H), 8.36 (s, 1H), 8.17 (d , J = 2.1 Hz, 1H), 7.78 (dd, J = 5.4, 2.1 Hz, 1H), 7.17 (s, 1H), 7.08 (d, J = 8.2 Hz, 1H), 6.75 (d, J = 8.4 Hz, 1H), 4.96 (t, J = 5.6 Hz, 2H), 3.64 (s, 2H), 3.59 – 3.62 (m, 2H), 3.48 – 3.51 (m, 2H), 1.29 (s, 3H).<br>LC-MS (Method A): Rt 2.21 mins; MS m/z 394.3/337.3 = [M + H]+ (95% @ 215 nm) |
| 35.6 | 4-[[2-(5-Chloro-2-hydroxy-phenyl)acetyl]amino]-N-(3-hydroxycyclohexyl)pyridine-2-carboxamide as a mixture of stereoisomers | 1H NMR (500 MHz, DMSO-d6) δ 8.52 (d, J = 5.5 Hz, 1H), 8.37 (d, J = 8.8 Hz, 1H), 8.24 (d, J = 2.1 Hz, 1H), 7.88 (dd, J = 5.5, 2.2 Hz, 1H), 7.27 (d, J = 2.6 Hz, 1H), 7.18 (dd, J = 8.6, 2.7 Hz, 1H), 6.86 (d, J = 8.6 Hz, 1H), 4.54 (d, J = 3.2 Hz, 1H), 4.31 – 4.21 (m, 1H), 3.99 (s, 1H), 3.72 (s, 2H), 1.82 – 1.74 (m, 3H), 1.75 – 1.64 (m, 1H), 1.62 – 1.55 (m, 1H), 1.55 – 1.49 (m, 1H), 1.49 – 1.39 (m, 2H).<br>LC-MS (Method A): Rt 2.56 mins; MS m/z 404.2/406.2 = [M + H]+ (100% @ 215 nm) |
| 35.7 | 4-[[2-(5-Chloro-2-hydroxy-phenyl)acetyl]amino]-N-(3-phenoxypropyl)pyridine-2-carboxamide | 1H NMR (500 MHz, DMSO-d6) δ 10.40 (s, 1H), 9.82 (s, 1H), 8.87 (t, J = 6.0 Hz, 1H), 8.48 (d, J = 5.5 Hz, 1H), 8.18 (d, J = 2.1 Hz, 1H), 7.82 (dd, 1H), 7.30 – 7.25 (m, 2H), 7.21 (d, J = 2.6 Hz, 1H), 7.11 (dd, J = 8.6, 2.7 Hz, 1H), 6.96 – 6.89 (m, 3H), 6.79 (d, J = 8.6 Hz, 1H), 4.02 (t, J = 6.2 Hz, 2H), 3.66 (s, 2H), 3.46 (q, J = 6.7 Hz, 2H), 2.02 – 1.94 (m, 2H).<br>LC-MS (Method A): Rt 3.45 mins; MS m/z 440.3/442.3 = [M + H]+ (98% @ 215 nm) |
| 35.8 | 4-[[2-(5-Chloro-2-hydroxy-phenyl)acetyl]amino]-N-(1-methylcyclo propyl)pyridine-2-carboxamide | 1H NMR (500 MHz, DMSO-d6) δ 10.66 (s, 1H), 9.80 (s, 1H), 8.76 (s, 1H), 8.43 (d, J = 5.5 Hz, 1H), 8.16 (d, J = 1.9 Hz, 1H), 7.82 (dd, J = 5.5, 2.2 Hz, 1H), 7.22 (d, J = 2.7 Hz, 1H), 7.12 (dd, J = 8.6, 2.7 Hz, 1H), 6.80 (d, J = 8.6 Hz, 1H), 3.67 (s, 2H), 1.36 (s, 3H), 0.80 – 0.75 (m, 2H), 0.64 – 0.57 (m, 2H).<br>LC-MS (Method A): Rt 2.85 mins; MS m/z 360.1/362.1 = [M + H]+ |
| 35.9 | 4-[[2-(5-Chloro-2-hydroxy-phenyl)acetyl]amino]-N-[1-methyl-1-(2-pyridyl)ethyl]pyridine-2-carboxamide | 1H NMR (500 MHz, DMSO-d6) δ 10.68 (s, 1H), 9.81 (s, 1H), 9.63 (s, 1H), 8.60 (m, 1H), 8.53 (d, J = 5.5 Hz, 1H), 8.18 (d, J = 2.0 Hz, 1H), 7.90 – 7.80 (m, 2H), 7.60 (d, J = 8.1 Hz, 1H), 7.39 – 7.27 (m, 1H), 7.22 (d, J = 2.7 Hz, 1H), 7.12 (dd, J = 8.6, 2.7 Hz, 1H), 6.80 (d, J = 8.6 Hz, 1H), 3.67 (s, 2H), 1.76 (s, 6H).<br>LC-MS (Method A): Rt 2.34 mins; MS m/z 425.3/ 427.2 = [M + H]+ (98% @ 215 nm) |

TABLE 11-continued

| Ex. | Structure and Name | 1H NMR<br>LCMS Retention Time, [M + H]+, |
|---|---|---|
| 35.10 | 4-[[2-(5-Chloro-2-hydroxy-phenyl)acetyl]amino]-N-(3-phenylpropyl)pyridine-2-carboxamide | 1H NMR (500 MHz, DMSO-d6) δ 10.81 (s, 1H), 9.83 (s, 1H), 8.78 (t, J = 6.1 Hz, 1H), 8.47 (d, J = 5.5 Hz, 1H), 8.18 (d, J = 2.0 Hz, 1H), 7.82 (dd, J = 5.5, 2.2 Hz, 1H), 7.31 – 7.25 (m, 2H), 7.25 – 7.20 (m, 3H), 7.20 – 7.15 (m, 1H), 7.14-7.09 (m, 1H), 6.80 (d, 1H), 3.66 (s, 2H), 2.61 (t, J = 7.8 Hz, 2H), 1.85 (p, J = 7.6 Hz, 2H).<br>LC-MS (Method A): Rt 3.53 mins; MS m/z 424.3/426.3 = [M + H]+ (98% @ 215 nm) |
| 35.11 | 4-[[2-(5-Chloro-2-hydroxy-phenyl)acetyl]amino]-N-[2-hydroxy-1-(2-pyridyl)ethyl]pyridine-2-carboxamide | 1H NMR (500 MHz, DMSO-d6) δ 10.72 (br. S, 1H), 9.80 (br. s, 1H), 9.08(d, J = 8.2 Hz, 1H), 8.60 – 8.55 (m, 1H), 8.53 (d, J = 5.6 Hz, 1H), 8.23 (d, J = 2.0 Hz, 1H), 7.84 (dd, J = 5.5, 2.2 Hz, 1H), 7.76 (td, J = 7.7, 1.8 Hz, 1H), 7.41 – 7.38 (m, 1H), 7.31 – 7.28 (m, 1H), 7.21 (d, J = 2.7 Hz, 1H), 7.12 (dd, J = 8.6, 2.7 Hz, 1H), 6.80 (d, J = 8.6 Hz, 1H), 5.10 (dt, J = 8.2, 5.5 Hz, 1H), 5.03 (t, J = 5.6 Hz, 1H), 3.87 – 3.80 (m, 1H), 3.76 – 3.70 (m, 1H), 3.67 (s, 2H).<br>LC-MS (Method A): Rt 2.09 mins; MS m/z 427.2/429.2 = [M + H]+ (98% @ 215 nm) |
| 35.12 | 4-[[2-(5-Chloro-2-hydroxy-phenyl)acetyl]amino]-N-[(5-methoxy-2-pyridyl)methyl]pyridine-2-carboxamide | 1H NMR (500 MHz, DMSO-d6) δ 10.74 (br. S, 1H), 9.82 (br. S, 1H), 9.23 (t, J = 6.0 Hz, 1H), 8.50 (d, J = 5.5 Hz, 1H), 8.23 (dd, J = 9.5, 2.5 Hz, 2H), 7.84 (dd, J = 5.5, 2.2 Hz, 1H), 7.36 (dd, J = 8.6, 3.0 Hz, 1H), 7.28 (d, J = 8.6 Hz, 1H), 7.21 (d, J = 2.7 Hz, 1H), 7.12 (dd, J = 8.6, 2.7 Hz, 1H), 6.79 (d, J = 8.6 Hz, 1H), 4.54 (d, J = 6.0 Hz, 2H), 3.81 (s, 3H), 3.67 (s, 2H).<br>LC-MS (Method A): Rt 2.39 mins; MS m/z 427.2/429.2 = [M + H]+ (100% @ 215 nm) |
| 35.13 | Ethyl 3-[[4-[[2-(5-chloro-2-hydroxy-phenyl)acetyl]amino]pyridine-2-carbonyl]amino]-3-methyl-butanoate | 1H NMR (500 MHz, DMSO-d6) δ 10.74 (s, 1H), 9.80 (s, 1H), 8.45 (d, J = 5.5 Hz, 1H), 8.35 (s, 1H), 8.18 (d, J = 2.1 Hz, 1H), 7.82 (dd, J = 5.5, 2.2 Hz, 1H), 7.22 (d, J = 2.7 Hz, 1H), 7.12 (dd, J = 8.6, 2.7 Hz, 1H), 6.80 (d, J = 8.6 Hz, 1H), 4.03 (q, J = 7.1 Hz, 2H), 3.67 (s, 2H), 2.81 (s, 2H), 1.47 (s, 6H), 1.11 (t, J = 7.1 Hz, 3H).<br>LC-MS (Method A): Rt 3.39 mins; MS m/z 434.3/436.3 = [M + H]+ (92% @ 215 nm) |
| 35.14 | 4-[[2-(5-Chloro-2-hydroxy-phenyl)acetyl]amino]-N-(3-hydroxy-1,1-dimethyl-propyl)pyridine-2-carboxamide | 1H NMR (500 MHz, DMSO-d6) δ 10.71 (s, 1H), 9.82 (s, 1H), 8.53 (s, 1H), 8.42 (d, J = 5.5 Hz, 1H), 8.16 (d, J = 2.0 Hz, 1H), 7.80 (dd, J = 5.5, 2.2 Hz, 1H), 7.22 (d, J = 2.7 Hz, 1H), 7.12 (dd, J = 8.6, 2.7 Hz, 1H), 6.80 (d, J = 8.6 Hz, 1H), 4.63 (t, J = 4.7 Hz, 1H), 3.67 (s, 2H), 3.56 (q, J = 6.4 Hz, 2H), 1.86 (t, J = 6.5 Hz, 2H), 1.41 (s, 6H). LC-MS (Method A): Rt 2.56 mins;<br>MS m/z 392.2/394.2 = [M + H]+ (100% @ 215 nm) |
| 35.15 | N-Benzyl-4-[[2-(5-chloro-2-hydroxy-phenyl)acetyl]amino]pyridine-2-carboxamide | 1H NMR (500 MHz, DMSO-d6) δ 10.70 (s, 1H), 9.81 (s, 1H), 9.25 (t, J = 6.4 Hz, 1H), 8.48 (d, J = 5.5 Hz, 1H), 8.20 (d, J = 2.1 Hz, 1H), 7.83 (dd, J = 5.5, 2.2 Hz, 1H), 7.32 (s, 2H), 7.31 (d, J = 1.2 Hz, 2H), 7.26 – 7.21 (m, 1H), 7.20 (d, J = 2.6 Hz, 1H), 7.11 (dd, J = 8.6, 2.6 Hz, 1H), 6.78 (d, J = 8.6 Hz, 1H), 4.48 (d, J = 6.4 Hz, 2H), 3.66 (s, 2H).<br>LC-MS (Method A): Rt 3.23 mins; MS m/z 396.4/398.4 = [M + H]+ (100% @ 215 nm) |
| 35.16 | 4-[[2-(5-Chloro-2-hydroxy-phenyl)acetyl]amino]-N-phenyl-pyridine-2-carboxamide | 1H NMR (500 MHz, DMSO-d6) δ 10.78 (s, 1H), 10.56 (s, 1H), 9.83 (s, 1H), 8.58 (d, J = 5.5 Hz, 1H), 8.33 (d, J = 2.0 Hz, 1H), 7.92 – 7.86 (m, 3H), 7.39 – 7.33 (m, 2H), 7.23 (d, J = 2.7 Hz, 1H), 7.16 – 7.08 (m, 2H), 6.81 (d, J = 8.6 Hz, 1H), 3.69 (s, 2H). LC-MS (Method A): Rt 3.41 mins;<br>MS m/z 382.3/384.3 = [M + H]+ (100% @ 215 nm) |

TABLE 11-continued

| Ex. | Structure and Name | 1H NMR LCMS Retention Time, [M + H]+, |
|---|---|---|
| 35.17 | 4-[[2-(5-Chloro-2-hydroxy-phenyl)acetyl]amino]-N-[(1S,2S)-2-hydroxycyclopentyl]pyridine-2-carboxamide | 1H NMR (500 MHz, DMSO-d6) δ 10.70 (s, 1H), 9.82 (s, 1H), 8.47 (d, J = 5.5 Hz, 1H), 8.43 (d, J = 7.6 Hz, 1H), 8.19 (d, J = 1.9 Hz, 1H), 7.82 (dd, J = 5.5, 2.2 Hz, 1H), 7.22 (d, J = 2.7 Hz, 1H), 7.12 (dd, J = 8.6, 2.7 Hz, 1H), 6.80 (d, J = 8.6 Hz, 1H), 4.80 (d, J = 4.4 Hz, 1H), 4.02 – 3.94 (m, 2H), 3.67 (s, 2H), 2.03 – 1.95 (m, 1H), 1.90 – 1.81 (m, 1H), 1.71 – 1.59 (m,2H), 1.54 – 1.42 (m, 2H). LC-MS (Method A): Rt 2.50 mins; MS m/z 390.2/ 392.2 = [M + H]+ (99% @ 215 nm) |
| 35.18 | 4-[[2-(5-Chloro-2-hydroxy-phenyl)acetyl]amino]-N-[(1R,2S)-2-hydroxy cyclopentyl]pyridine-2-carboxamide | 1H NMR (500 MHz, DMSO-d6) δ 10.75 (s, 1H), 9.81 (s, 1H), 8.46 (d. 1H), 8.43 (d, J = 7.8 Hz, 1H), 8.22 (d, J = 1.9 Hz, 1H), 7.81 (dd, J = 5.5, 2.2 Hz, 1H), 7.21 (d, J = 2.7 Hz, 1H), 7.12 (dd, J = 8.6, 2.7 Hz, 1H), 6.79 (d, J = 8.6 Hz, 1H), 5.09 (s, 1H), 4.05 – 3.98 (m, 2H), 3.66 (s, 2H), 1.99 – 1.88 (m, 1H), 1.88 – 1.79 (m, 1H), 1.79 – 1.71 (m, 1H), 1.64 – 1.57 (m, 1H), 1.56 – 1.46 (m, 2H). LC-MS (Method A): Rt 2.58 mins; MS m/z 390.3/ 392.3 = [M + H]+ (100% @ 215 nm) |
| 35.19 | 4-[[2-(5-Chloro-2-hydroxy-phenyl)acetyl]amino]-N-[(1S,2R)-2-hydroxy cyclopentyl]pyridine-2-carboxamide | 1H NMR (500 MHz, DMSO-d6) δ 10.73 (s, 1H), 9.83 (s, 1H), 8.47 (d, J = 5.5 Hz, 1H), 8.44 (d, J = 7.8 Hz, 1H), 8.22 (d, J = 2.0 Hz, 1H), 7.81 (dd, J = 5.5, 2.2 Hz, 1H), 7.22 (d, J = 2.7 Hz, 1H), 7.12 (dd, J = 8.6, 2.7 Hz, 1H), 6.80 (d, J = 8.6 Hz, 1H), 5.09 (s, 1H), 4.06 – 3.97 (m, 2H), 3.67 (s, 2H), 2.01 – 1.90 (m, 1H), 1.89 – 1.79 (m, 1H), 1.80 – 1.71 (m, 1H), 1.65 – 1.58 (m, 1H), 1.57 – 1.46 (m, 2H). LC-MS (Method A): Rt 2.63 mins; MS m/z 390.3/ 392.3 = [M + H]+ (99% @ 215 nm) |
| 35.20 | 3-[[2-(5-Fluoro-2-hydroxy-phenyl)acetyl]amino]-N-(1-methylcyclohexyl)benzamide | 1H NMR (500 MHz, DMSO-d6) δ 10.17 (s, 1H), 9.49 (s, 1H), 7.90 (t, J = 1.7 Hz, 1H), 7.77 (d, J = 8.1 Hz, 1H), 7.43 – 7.40 (m, 2H), 7.34 (t, J = 7.9 Hz, 1H), 7.00 (dd, J = 9.4, 3.2 Hz, 1H), 6.89 (td, J = 8.6, 3.2 Hz, 1H), 6.77 (dd, J = 8.8, 4.9 Hz, 1H), 3.61 (s, 2H), 2.21 (d, J = 13.3 Hz, 2H), 1.54 – 1.41 (m, 5H), 1.38 – 1.29 (m, 2H), 1.32 (s, 3H), 1.28 – 1.22 (m, 1H). LC-MS (Method A): Rt 3.36 mins; MS m/z 385.3 = [M + H]+ (98% @ 215 nm) |
| 35.21 | N-(1,1-Dimethylprop-2-ynyl)-3-[[2-(5-fluoro-2-hydroxy-phenyl)acetyl]amino]benzamide | 1H NMR (500 MHz, DMSO-d6) δ 10.19 (s, 1H), 9.48 (s, 1H), 8.20 (S. 1H), 7.94 (t, J = 1.8 Hz, 1H), 7.79 – 7.75 (m, 1H), 7.44 (dt, J = 7.8, 1.29 Hz, 1H), 7.35 (t, J = 7.9 Hz, 1H), 7.00 (dd, J = 9.4, 3.2 Hz, 1H), 6.89 (td, J = 8.6, 3.2 Hz, 1H), 6.77 (dd, J = 8.8, 4.9 Hz, 1H), 3.62 (s, 2H), 3.08 (s, 1H), 1.59 (s, 6H). LC-MS (Method A): Rt 2.67 mins; MS m/z 355.3 = [M + H]+ (97% @ 215 nm) |
| 35.22 | N-Cyclohexyl-3-[[2-(5-fluoro-2-hydroxy-phenyl)acetyl]amino]benzamide | 1H NMR (500 MHz, DMSO-d6) δ 10.18 (s, 1H), 9.46 (s, 1H), 8.15 (d, J = 7.9 Hz, 1H), 7.96 (t, J = 1.8 Hz, 1H), 7.79-7.75 (m, 1H), 7.47 (d, J = 7.8 Hz, 1H), 7.35 (t, J = 7.9 Hz, 1H), 7.00 (dd, J = 9.4, 3.2 Hz, 1H), 6.89 (td, J = 8.6, 3.2 Hz, 1H), 6.79 – 6.75 (m, 1H), 3.78 – 3.68 (m, 1H), 3.61 (s, 2H), 1.85 – 1.68 (m, 4H), 1.60 (d, J = 12.6 Hz, 1H), 1.31 (q, J = 10.7, 8.8 Hz, 4H), 1.18 – 1.06 (m, 1H). LC-MS (Method A): Rt 3.03 mins; MS m/z 371.3 = [M + H]+ (98% @ 215 nm) |

TABLE 11-continued

| Ex. | Structure and Name | 1H NMR LCMS Retention Time, [M + H]+, |
|---|---|---|
| 35.23 | 3-[[2-(5-Fluoro-2-hydroxy-phenyl)acetyl]amino]-N-[3-(hydroxymethyl)tetrahydro furan-3-yl]benzamide | 1H NMR (500 MHz, DMSO-d6) δ 10.18 (s, 1H), 9.48 (s, 1H), 8.12 (s, 1H), 7.95 (t, J = 1.8 Hz, 1H), 7.81 – 7.75 (m, 1H), 7.50 (d, J = 7.9 Hz, 1H), 7.36 (t, J = 7.9 Hz, 1H), 7.00 (dd, J = 9.4, 3.2 Hz, 1H), 6.89 (td, J = 8.6, 3.2 Hz, 1H), 6.77 (dd, J = 8.8, 4.9 Hz, 1H), 4.97 (s, 1H), 3.89 (d, J = 9.2 Hz, 1H), 3.81 – 3.73 (m, 3H), 3.69 – 3.61 (m, 4H), 2.22 (dt, J = 12.8, 6.4 Hz, 1H), 2.05 (dt, J = 12.9, 7.7 Hz, 1H). LC-MS (Method A): Rt 1.98 mins; MS m/z 389.2 = [M + H]+ (98% @ 215 nm) |
| 35.24 | 4-[[2-(5-Chloro-2-hydroxy-phenyl)acetyl]amino]-N-(1-ethynylcyclohexyl)pyridine-2-carboxamide | 1H NMR (500 MHz, DMSO-d6) δ 10.72 (s, 1H), 9.82 (s, 1H), 8.47 (d, J = 5.5 Hz, 1H), 8.24 (s, 1H), 8.19 (d, J = 1.9 Hz, 1H), 7.84 (dd, J = 5.5, 2.2 Hz, 1H), 7.22 (d, J = 2.7 Hz, 1H), 7.13 (dd, J = 8.6, 2.7 Hz, 1H), 6.81 (d, J = 8.6 Hz, 1H), 3.68 (s, 2H), 3.27 (s, 1H), 2.15 – 2.08 (m, 2H), 1.95 – 1.86 (m, 2H), 1.62 – 1.50 (m, 5H), 1.34 – 1.23 (m, 1H). LC-MS (Method A): Rt 3.62 mins; MS m/z 412.1/414.1 = [M + H]+ (98% @ 215 nm) |
| 35.25 | 4-[[2-(5-Chloro-2-hydroxy-phenyl)acetyl]amino]-N-[1-(hydroxymethyl)cyclobutyl]pyridine-2-carboxamide | 1H NMR (500 MHz, DMSO-d6) δ 10.68 (s, 1H), 9.82 (brs, 1H), 8.45 (d, J = 5.5 Hz, 1H), 8.40 (s, 1H), 8.21 – 8.14 (m, 1H), 7.82 (dd, J = 5.5, 2.2 Hz, 1H), 7.22 (d, J = 2.7 Hz, 1H), 7.12 (dd, J = 8.6, 2.7 Hz, 1H), 6.80 (d, J = 8.6 Hz, 1H), 5.00 (t, J = 5.3 Hz, 1H), 3.67 (s, 2H), 3.61 (d, J = 4.7 Hz, 2H), 2.07 – 2.01 (m, 2H), 1.89 – 1.78 (m, 1H), 1.78 – 1.66 (m, 1H). LC-MS (Method A): Rt 2.53 mins; MS m/z 390.2/392.2 = [M + H]+ (98% @ 215 nm) |
| 35.26 | 4-[[2-(5-Chloro-2-hydroxy-phenyl)acetyl]amino]-N-[3-(hydroxymethyl)oxetan-3-yl]pyridine-2-carboxamide | 1H NMR (500 MHz, DMSO-d6) δ 10.69 (s, 1H), 9.82 (s, 1H), 9.00 (s, 1H), 8.49 (d, J = 5.5 Hz, 1H), 8.17 (d, J = 2.0 Hz, 1H), 7.84 (dd, J = 5.5, 2.2 Hz, 1H), 7.22 (d, J = 2.7 Hz, 1H), 7.12 (dd, J = 8.6, 2.7 Hz, 1H), 6.80 (d, J = 8.6 Hz, 1H), 5.18 (t, J = 5.9 Hz, 1H), 4.73 (d, J = 6.5 Hz, 2H), 4.53 (d, J = 6.6 Hz, 2H), 3.70 (d, J = 5.9 Hz, 2H), 3.67 (s, 2H). LC-MS (Method A): Rt 2.11 mins; MS m/z 392.2/394.2 = [M + H]+ (98% @ 215 nm) |
| 35.27 | 4-[[2-(5-Chloro-2-hydroxy-phenyl)acetyl]amino]-N-(1-cyano-2-methoxy-1-methyl-ethyl)pyridine-2-carboxamide | 1H NMR (500 MHz, DMSO-d6) δ 10.78 (s, 1H), 9.77 (s, 1H), 8.77 (s, 1H), 8.52 (d, J = 5.5 Hz, 1H), 8.24 (d, J = 2.0 Hz, 1H), 7.87 (dd, J = 5.5, 2.2 Hz, 1H), 7.23 (d, J = 2.7 Hz, 1H), 7.13 (dd, J = 8.6, 2.7 Hz, 1H), 6.81 (d, J = 8.6 Hz, 1H), 3.86 (d, J = 9.5 Hz, 1H), 3.69 (s, 2H), 3.67 (d, J = 9.5 Hz, 1H), 3.42 (s, 3H), 1.71 (s, 3H). LC-MS (Method A): Rt 3.02 mins; MS m/z 403.2/405.2 = [M + H]+ (98% @ 215 nm) |
| 35.28 | 4-[[2-(5-Chloro-2-hydroxy-phenyl)acetyl]amino]-N-[(1-hydroxycyclobutyl)methyl]pyridine-2-carboxamide | 1H NMR (500 MHz, DMSO-d6) δ 10.68 (s, 1H), 9.81 (s, 1H), 8.48 (d, J = 5.5 Hz, 1H), 8.42 (t, J = 5.9 Hz, 1H), 8.23 (d, J = 2.1 Hz, 1H), 7.82 (dd, J = 5.5, 2.2 Hz, 1H), 7.22 (d, J = 2.7 Hz, 1H), 7.12 (dd, J = 8.6, 2.7 Hz, 1H), 6.80 (d, J = 8.6 Hz, 1H), 5.38 (s, 1H), 3.67 (s, 2H), 3.43 (d, J = 5.9 Hz, 2H), 2.00 – 1.86 (m, 4H), 1.70 – 1.57 (m, 1H), 1.57 – 1.41 (m, 1H). LC-MS (Method A): Rt 2.59 mins; MS m/z 390.1/392.1 = [M + H]+ (95% @ 215 nm) |

Example 36

4-[[2-(5-Chloro-2-hydroxy-phenyl)acetyl]amino]-N-(1,1-dimethylprop-2-ynyl)pyridine-2-carboxamide

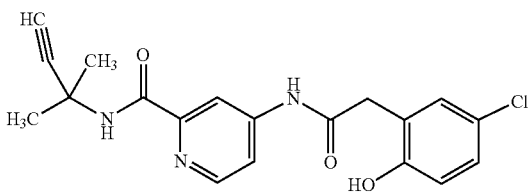 [SMILES: C#CC(C)(C)NC(=O)c1cc(NC(=O)Cc2cc(Cl)ccc2O)ccn1]

To a solution of 4-[[2-(5-chloro-2-hydroxy-phenyl)acetyl]amino]pyridine-2-carboxylic acid (Example 31 step 1) (20 g, 63.25 mmol, 97%), 2-methylbut-3-yn-2-amine (7.99 mL, 75.9 mmol) and DIPEA (16.57 mL, 94.88 mmol) in DMF (315 mL) was added HATU (28.86 g, 75.9 mmol) and the mixture stirred at room temperature for 1 hour. The resulting mixture was concentrated in vacuo and the residue was dissolved in EtOAc and washed sequentially with 1M HCl, 1M NaOH and brine. The acid washing was re-extracted with EtOAc and the combined organic extracts were washed with 1M NaOH, brine, dried over $Na_2SO_4$ and concentrated in vacuo to afford a yellow foam. The foam was absorbed onto silica and purified by chromatography eluting with 0-100% EtOAc in heptanes. The isolated material was suspended in MeCN (50 mL) and heated to reflux until all solids had dissolved. The resulting solution was allowed to cool to room temperature and stand for 8 hours to yield crystals. The crystals were filtered, washed with ice cooled MeCN and dried in a vacuum oven overnight to afford crop 1 of the titled compound. The filtrate from was combined with the impure fractions from chromatography and repurified by chromatography on silica eluting with 0-100% EtOAc in heptanes. The isolated material was combined with crop 1 and recrystallised again by heating at reflux in MeCN. The solution was allowed to cool and stand at room temperature to afford crystals which were filtered, washed with ice-cooled MeCN and dried in a vacuum oven to afford the titled compound as a crystalline solid. 1H NMR (500 MHz, DMSO-d6) δ 10.71 (br s, 1H), 9.82 (br s, 1H), 8.46 (d, J=5.5 Hz, 1H), 8.31 (s, 1H), 8.19 (d, J=1.9 Hz, 1H), 7.84 (dd, J=5.5, 2.2 Hz, 1H), 7.22 (d, J=2.7 Hz, 1H), 7.12 (dd, J=8.6, 2.7 Hz, 1H), 6.81 (d, J=8.6 Hz, 1H), 3.68 (s, 2H), 3.20 (s, 1H), 1.64 (s, 6H).

LC-MS (Method A): Rt 3.07 mins; MS m/z 372.1/374.1=[M+H]+ (99% @ 215 nm)

Example 37

4-[[2-(5-Chloro-2-hydroxy-phenyl)acetyl]amino]-N-(1-cyano-1,2-dimethyl-propyl)pyridine-2-carboxamide

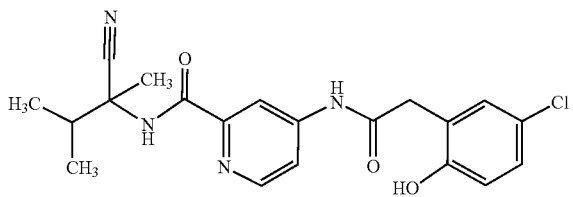 [SMILES: CC(C)C(C)(C#N)NC(=O)c1cc(NC(=O)Cc2cc(Cl)ccc2O)ccn1]

Step 1: 4-[[2-(5-Chloro-2-methoxy-phenyl)acetyl]amino]-N-(1-cyano-1,2-dimethyl-propyl)pyridine-2-carboxamide

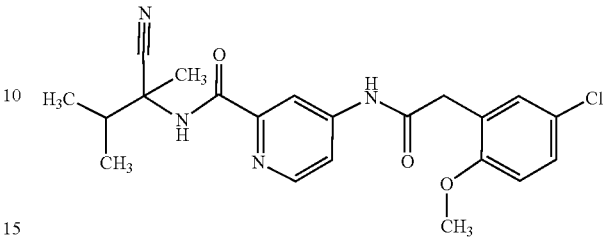

To a solution of 4-[[2-(5-chloro-2-methoxy-phenyl)acetyl]amino]pyridine-2-carboxylic acid (Example 8.1 step 2)(100 mg, 0.31 mmol) in DMF (2 mL) was added DIPEA (0.06 mL, 0.33 mmol) and HATU (124 mg, 0.33 mmol) and the mixture stirred for 15 mins. The resulting mixture was treated with 2-amino-2,3-dimethyl-butanenitrile (37 mg, 0.33 mmol) and stirring continued for 55 minutes. The mixture was diluted with water (10 mL) and extracted with EtOAc (3×10 mL). The combined organic extracts were washed with water (10 mL), brine (10 mL), dried over $Na_2SO_4$ and concentrated in vacuo to afford a crude oil. The crude oil was adsorbed onto silica and purified by chromatography on silica eluting with 10-100% EtOAc in heptane to yield an oil. The oil was triturated with ether to afford the titled compound as a white solid.

1H NMR (250 MHz, DMSO-d6) δ 10.75 (s, 1H), 8.69 (s, 1H), 8.51 (d, J=5.5 Hz, 1H), 8.21 (d, J=1.9 Hz, 1H), 7.86 (dd, J=5.5, 2.2 Hz, 1H), 7.37-7.25 (m, 2H), 7.07-6.95 (m, 1H), 3.75 (s, 3H), 3.73 (s, 2H), 2.63-2.53 (m, 1H), 1.61 (s, 3H), 1.08 (d, J=6.8 Hz, 3H), 0.97 (d, J=6.8 Hz, 3H).

LC-MS (Method E): Rt 1.21 mins; MS m/z 415.1/417.1=[M+H]+ (95%®215 nm)

Step 2: 4-[[2-(5-Chloro-2-hydroxy-phenyl)acetyl]amino]-N-(1-cyano-1,2-dimethyl-propyl)pyridine-2-carboxamide A cooled (0° C.) solution 4-[[2-(5-chloro-2-methoxy-phenyl)acetyl]amino]-N-(1-cyano-1,2-dimethyl-propyl)pyridine-2-carboxamide (step 1) (84 mg, 0.19 mmol) in DCM (2 mL) was treated with 1M $BBr_3$ in DCM (962 μL, 0.96 mmol) and stirred at room temperature for 15 mins. The reaction was quenched with methanol (1 mL) the resulting mixture was reduced in vacuo. The residue was redissolved in EtOAc and washed with saturated $NaHCO_3$ and brine. The organic layer was separated, dried over $Na_2SO_4$ and concentrated in vacuo. The residue was dissolved in DMSO:MeOH (800 μl, 1:1), filtered and purified via preparative HPLC (acidic pH, standard elution method). The product fractions were combined, concentrated in vacuo and the residue re-dissolved in MeCN:H2O (5 mL, 1:2) and freeze dried to afford the titled compound as a white powder.

1H NMR (500 MHz, DMSO-d6) δ 10.76 (s, 1H), 9.83 (s, 1H), 8.68 (s, 1H), 8.51 (d, J=5.6 Hz, 1H), 8.21 (d, J=2.0 Hz, 1H), 7.87 (dd, J=5.5, 2.2 Hz, 1H), 7.22 (d, J=2.7 Hz, 1H), 7.12 (dd, J=8.6, 2.7 Hz, 1H), 6.81 (d, J=8.6 Hz, 1H), 3.68 (s, 2H), 2.56 (hept, J=6.8 Hz, 1H), 1.61 (s, 3H), 1.08 (d, J=6.8 Hz, 3H), 0.97 (d, J=6.8 Hz, 3H).

LC-MS (Method A): Rt 3.25 mins; MS m/z 401.2/403.2=[M+H]+ (100%®215 nm)

Example 38

4-[[2-(5-Chloro-2-hydroxy-phenyl)acetyl]amino]-N-(1-methylcyclopentyl)pyridine-2-carboxamide

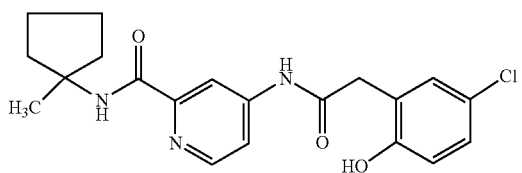 [SMILES: CC1(NC(=O)c2cc(NC(=O)Cc3cc(Cl)ccc3O)ccn2)CCCC1]

4-[[2-(5-Chloro-2-hydroxy-phenyl)acetyl]amino]pyridine-2-carboxylic acid (Example 31 step 1) (100 mg, 0.33 mmol) and DIPEA (0.23 mL, 1.3 mmol) were suspended in DMF (2.1 mL) and treated with 1-methylcyclopentanamine hydrochloride (66 mg, 0.49 mmol) followed by HATU (149 mg, 0.39 mmol) and the mixture stirred at room temperature for 24 hours. The resulting mixture was diluted with EtOAc (10 mL) and washed with sat. aq NaHCO$_3$ (10 mL), water (10 ml), brine (10 mL), dried over Na$_2$SO$_4$ and concentrated in vacuo. The residue was dissolved in MeOH (800 µl), filtered and purified by preparative HPLC (acidic pH, early elution method) to afford the titled compound as a white solid.

1H NMR (500 MHz, DMSO-d6) δ 10.69 (s, 1H), 9.82 (s, 1H), 8.44 (d, J=5.5 Hz, 1H), 8.17 (d, J=2.1 Hz, 1H), 8.10 (s, 1H), 7.81 (dd, J=5.5, 2.2 Hz, 1H), 7.21 (d, J=2.7 Hz, 1H), 7.12 (dd, J=8.6, 2.7 Hz, 1H), 6.80 (d, J=8.6 Hz, 2H), 2.14-2.05 (m, 2H), 1.70-1.60 (m, 6H), 1.43 (s, 3H).

LC-MS (Method A): Rt 3.54 mins; MS m/z 388.2/390.2= [M+H]+ (100% @ 215 nm)

Example 39

N-(4-tert-Butylcyclohexyl)-4-[[2-(5-chloro-2-hydroxy-phenyl)acetyl]amino]pyridine-2-carboxamide (1:1 mixture cis/trans)

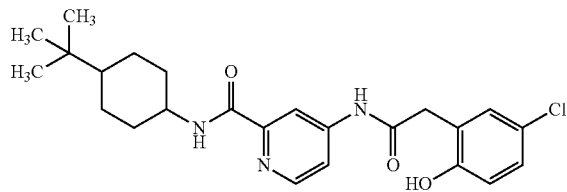 [SMILES: CC(C)(C)C1CCC(NC(=O)c2cc(NC(=O)Cc3cc(Cl)ccc3O)ccn2)CC1]

4-[[2-(5-Chloro-2-hydroxy-phenyl)acetyl]amino]pyridine-2-carboxylic acid (Example 31 step 1) (150 mg, 0.49 mmol) and DIPEA (0.26 mL, 1.47 mmol) were suspended in DMF (1.95 mL) and treated with 4-tert-butylcyclohexanamine (1:1 mixture cis/trans) (91 mg, 0.59 mmol) and HATU (223 mg, 0.59 mmol) and the mixture was stirred for 3 hours. The mixture was diluted with EtOAc (10 mL) and the organics were washed with saturated aqueous NaHCO$_3$ (2×10 mL). The organic layer was dried over Na$_2$SO$_4$, filtered and concentrated in vacuo. The residue was dissolved in DMSO:MeCN (800 µl, 1:1), filtered and purified by preparative HPLC (acidic pH, early elution method). The product fractions were combined, neutralised with saturated sodium bicarbonate and extracted with EtOAc (3×20 mL). The combined organic extracts where concentrated in vacuo to afford the titled compound as a pale yellow solid.

1H NMR (500 MHz, DMSO-d6) δ 10.95-10.61 (m, 2H), 9.93-9.68 (m, 2H), 8.49 (d, J=5.6 Hz, 1H), 8.46 (d, J=5.5 Hz, 1H), 8.36 (d, J=8.7 Hz, 1H), 8.28 (d, J=7.6 Hz, 1H), 8.21 (d, J=2.0 Hz, 1H), 8.19 (d, J=2.1 Hz, 1H), 7.83 (d, J=2.1 Hz, 1H), 7.81 (d, J=2.2 Hz, 1H), 7.24-7.19 (m, 2H), 7.13 (d, J=2.6 Hz, 1H), 7.12 (d, J=2.7 Hz, 1H), 6.80 (d, J=8.6 Hz, 2H), 4.13-4.07 (m, 1H), 3.68-3.65 (m, 4H), 1.93-1.83 (m, 4H), 1.81-1.73 (m, 2H), 1.69-1.60 (m, 2H), 1.60-1.51 (m, 2H), 1.42-1.33 (m, 2H), 1.24 (s, 1H), 1.17-1.03 (m, 5H), 1.03-0.97 (m, 1H), 0.89-0.83 (m, 18H). Contains a 1:1 mixture of the cis and trans products.

LC-MS (Method A): Rt 4.34 mins; MS m/z 444.4/446.4= [M+H]+ (42% @ 215 nm)

LC-MS (Method A): Rt 4.36 mins; MS m/z 444.4/446.4= [M+H]+ (52% @ 215 nm)

Example 40

N-tert-Butyl-4-[[2-(2-chloro-3-fluoro-phenyl)acetyl]amino]pyridine-2-carboxamide

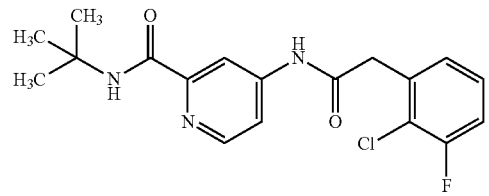 [SMILES: CC(C)(C)NC(=O)c1cc(NC(=O)Cc2cccc(F)c2Cl)ccn1]

To a solution of 2-(2-chloro-3-fluoro-phenyl)acetic acid (146 mg, 0.78 mmol) in THF (3 mL) was added DIPEA (271 µL, 1.55 mmol), 4-amino-N-tert-butyl-pyridine-2-carboxamide (Example 3 step 1) (100 mg, 0.52 mmol) and HATU (236 mg, 0.62 mmol) and the mixture was stirred at room temperature for 90 mins. The resulting mixture was partitioned between EtOAc (20 mL) and water (20 mL) and the aqueous portion extracted with EtOAc (2×20 mL). The combined organic extracts were washed with water (20 mL), brine (20 mL), dried over Na$_2$SO$_4$ and concentrated in vacuo. The residue was purified by chromatography on silica eluting with EtOAc in heptane to afford the titled compound as white amorphous solid.

1H NMR (500 MHz, Chloroform-d) δ 8.40 (d, J=5.5 Hz, 1H), 8.18 (dd, J=5.5, 2.1 Hz, 1H), 8.11 (s, 1H), 8.01 (s, 1H), 7.75 (d, J=2.1 Hz, 1H), 7.30-7.23 (m, 1H), 7.21-7.10 (m, 2H), 3.94 (s, 2H), 1.47 (s, 9H).

LC-MS (Method A): Rt 3.49 mins; MS m/z 364.2/366.2= [M+H]+ (100%®215)

Example 40.1

N-tert-Butyl-4-[[2-(2-chloro-5-fluoro-phenyl)acetyl]amino]pyridine-2-carboxamide

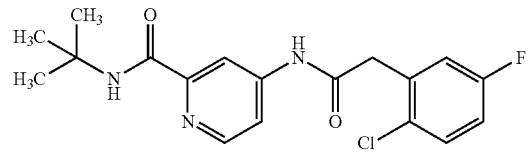

The titled compound was prepared from 4-amino-N-tert-butyl-pyridine-2-carboxamide (Example 3 step 1) and 2-(2-chloro-5-fluoro-phenyl)acetic acid analogously to Example 40.

1H NMR (500 MHz, DMSO-d6) δ 10.90 (s, 1H), 8.46 (d, J=5.5 Hz, 1H), 8.18 (d, J=2.1 Hz, 1H), 8.03 (s, 1H), 7.80 (dd, J=5.5, 2.2 Hz, 1H), 7.51 (dd, J=8.8, 5.3 Hz, 1H), 7.36 (dd, J=9.4, 3.1 Hz, 1H), 7.20 (td, J=8.5, 3.1 Hz, 1H), 3.93 (s, 2H), 1.40 (s, 9H).

LC-MS (Method A): Rt 3.51 mins; MS m/z 364=[M+H]+

Example 41

N-(4-Cyanotetrahydropyran-4-yl)-3-[[2-(5-fluoro-2-hydroxy-phenyl)acetyl]amino]benzamide

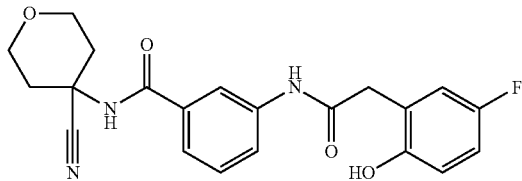 [SMILES: N#CC1(NC(=O)c2cccc(NC(=O)Cc3cc(F)ccc3O)c2)CCOCC1]

Step 1: Ethyl 3-[[2-(5-fluoro-2-methoxy-phenyl)acetyl]amino]benzoate

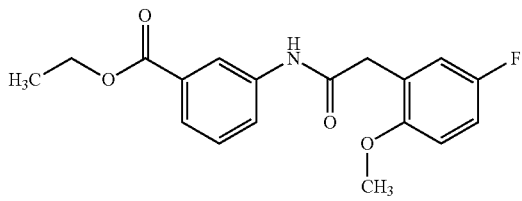 [SMILES: CCOC(=O)c1cccc(NC(=O)Cc2cc(F)ccc2OC)c1]

A mixture of ethyl 3-aminobenzoate (300 mg, 1.82 mmol) and 2-(5-fluoro-2-methoxy-phenyl)acetic acid (334 mg, 1.82 mmol) in 1,4-dioxane (5 mL) was treated with 50% T3P® solution in EtOAc (2.31 mL, 1.82 mmol) and TEA (634 µL, 3.63 mmol). After stirring at room temperature for 2 hours, the mixture was partitioned between water (20 mL) and EtOAc (20 mL). The organic layer was separated, dried over Na2SO4 and concentrated in vacuo. Purification of the crude residue by chromatography on silica eluting with EtOAc in heptane afforded the titled compound as a white solid.

1H NMR (500 MHz, DMSO-d6) δ 10.31 (s, 1H), 8.26 (t, J=1.8 Hz, 1H), 7.86-7.82 (m, 1H), 7.63 (dt, J=7.79, 1.2 Hz, 1H), 7.45 (t, J=7.9 Hz, 1H), 7.11 (dd, J=9.2, 3.1 Hz, 1H), 7.07 (td, J=8.6, 3.2 Hz, 1H), 6.98 (dd, J=9.0, 4.6 Hz, 1H), 4.31 (q, J=7.1 Hz, 2H), 3.75 (s, 3H), 3.66 (s, 2H), 1.31 (t, J=7.1 Hz, 3H).

LC-MS (Method E): Rt 1.20 mins; MS m/z 332.1=[M+H]+ (100% @ 215 nm)

Step 2: 3-[[2-(5-Fluoro-2-methoxy-phenyl)acetyl]amino]benzoic acid

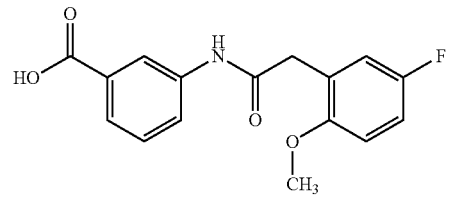 [SMILES: COc1ccc(F)cc1CC(=O)Nc1cccc(C(=O)O)c1]

Ethyl 3-[[2-(5-fluoro-2-methoxy-phenyl)acetyl]amino]benzoate (step 1) (470 mg, 1.42 mmol) in THF (3 mL) and MeOH (1 mL) was treated with 2M aqueous LiOH solution (2.84 mL, 5.67 mmol) and the reaction mixture was stirred at room temperature for 2 hours. The volatile solvents were removed in vacuo and the aqueous portion was diluted with water (100 mL) and acidified with 2M HCl solution to pH 2. The resulting precipitate was collected by filtration, washed with water (30 mL) and under vacuum to afford the titled compound as a white solid.

1H NMR (500 MHz, DMSO-d6) δ 12.92 (s, 1H), 10.26 (s, 1H), 8.23 (t, J=1.7 Hz, 1H), 7.84-7.78 (m, 1H), 7.63-7.58 (m, 1H), 7.42 (t, J=7.9 Hz, 1H), 7.11 (dd, J=9.2, 3.1 Hz, 1H), 7.07 (td, J=8.6, 3.2 Hz, 1H), 6.98 (dd, J=9.0, 4.7 Hz, 1H), 3.75 (s, 3H), 3.66 (s, 2H).

LC-MS (Method E): Rt 1.02 mins; MS m/z 304.0=[M+H]+ (98% @ 215 nm)

Step 3: 3-[[2-(5-Fluoro-2-hydroxy-phenyl)acetyl]amino]benzoic acid

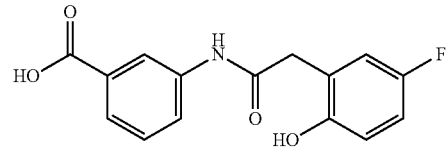

To a solution of 3-[[2-(5-fluoro-2-methoxy-phenyl)acetyl]amino]benzoic acid (step 2)(400 mg, 1.29 mmol) in DCM (5 mL) was added 1M BBr3 in DCM (5.17 mL, 5.17 mmol) the reaction mixture was stirred at room temperature for 3 hours. The resulting mixture was concentrated in vacuo and the crude residue was partitioned between water (60 mL) and EtOAc (60 mL). The organic layer was separated, dried over Na2SO4 and concentrated in vacuo to afford the titled compound as a grey-purple solid.

1H NMR (500 MHz, DMSO-d6) δ 12.91 (s, 1H), 10.25 (s, 1H), 9.47 (s, 1H), 8.24 (t, 1.7 Hz, 1H), 7.87-7.79 (m, 1H), 7.62-7.59 (m, 1H), 7.42 (t, J=7.9 Hz, 1H), 7.00 (dd, J=9.4, 3.1 Hz, 1H), 6.89 (td, J=8.6, 3.2 Hz, 1H), 6.77 (dd, J=8.8, 4.9 Hz, 1H), 3.62 (s, 2H).

LC-MS (Method E): Rt 0.98 mins; MS m/z 290.0=[M+H]+ (89% @ 215 nm)

Step 4: N-(4-Cyanotetrahydropyran-4-yl)-3-[[2-(5-fluoro-2-hydroxy-phenyl)acetyl]amino]benzamide The titled compound was prepared from 3-[[2-(5-Fluoro-2-hydroxy-phenyl)acetyl]amino]benzoic acid (step 3) and 4-aminotetrahydropyran-4-carbonitrile analogously to Example 1.1 step 3.

1H NMR (500 MHz, DMSO-d6) δ 10.27 (s, 1H), 9.58 (s, 1H), 8.83 (s, 1H), 8.05 (t, J=1.8 Hz, 1H), 7.86-7.79 (m, 1H), 7.52 (d, J=7.8, 1.3 Hz, 1H), 7.42 (t, J=7.9 Hz, 1H), 7.00 (dd, J=9.4, 3.2 Hz, 1H), 6.89 (td, J=8.6, 3.2 Hz, 1H), 6.78 (dd, J=8.8, 4.9 Hz, 1H), 3.87 (dt, J=12.2, 4.0 Hz, 2H), 3.63 (s, 2H), 3.62-3.56 (m, 2H), 2.35-2.28 (m, 2H), 2.04-1.97 (m, 2H).

LC-MS (Method A): Rt 2.41 mins; MS m/z 398.2=[M+H]+ (97% @ 215 nm)

Example 42

4-[[2-(5-Chloro-2-hydroxy-phenyl)acetyl]amino]-N-[4-(2-hydroxyethyl)tetrahydropyran-4-yl]pyridine-2-carboxamide

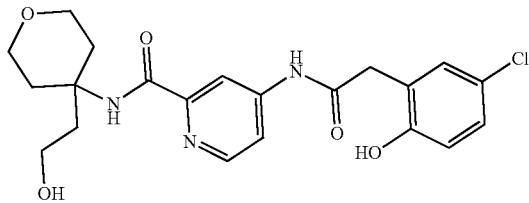 [SMILES: O=C(Cc1cc(Cl)ccc1O)Nc1ccnc(C(=O)NC2(CCO)CCOCC2)c1]

Step 1: Methyl 2-[4-[[4-[[2-(5-chloro-2-hydroxy-phenyl)acetyl]amino]pyridine-2-carbonyl]amino]tetrahydropyran-4-yl]acetate

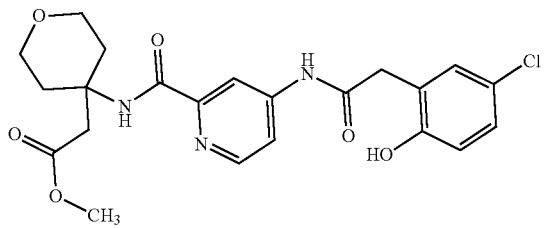 [SMILES: COC(=O)CC1(NC(=O)c2cc(NC(=O)Cc3cc(Cl)ccc3O)ccn2)CCOCC1]

The titled compound was prepared from methyl 2-(4-aminotetrahydropyran-4-yl)acetate and 4-[[2-(5-chloro-2-hydroxy-phenyl)acetyl]amino]pyridine-2-carboxylic acid (Example 31 step 1) analogously to Example 33.

1H NMR (500 MHz, DMSO-d6) δ 8.47 (d, J=5.6 Hz, 1H), 8.19-8.17 (m, 2H), 7.81 (dd, J=5.5, 2.2 Hz, 1H), 7.20 (d, J=2.6 Hz, 1H), 7.10 (dd, J=8.6, 2.7 Hz, 1H), 6.78 (d, J=8.6 Hz, 1H), 3.71-3.66 (m, 2H), 3.66 (s, 2H), 3.53-3.45 (m, 5H), 2.91 (s, 2H), 2.33-2.27 (m, 2H), 1.79-1.72 (m, 2H).

LC-MS (Method E): Rt 1.06 mins; MS m/z 462.1=[M+H]+ (87% @ 215 nm)

Step 2: 4-[[2-(5-Chloro-2-hydroxy-phenyl)acetyl]amino]-N-[4-(2-hydroxyethyl)tetrahydropyran-4-yl]pyridine-2-carboxamide A cooled (−78° C.) solution of methyl 2-[4-[[4-[[2-(5-chloro-2-hydroxy-phenyl) acetyl]amino]pyridine-2-carbonyl]amino]tetrahydropyran-4-yl]acetate (step 1) (50 mg, 0.11 mmol) in anhydrous THF (2 mL) was treated with 2.4M lithium aluminium hydride in THF (90 µL, 0.22 mmol) and stirred at −78° C. for 10 mins. A further portion of 2.4 M lithium aluminium hydride in THF (45 µL, 0.11 mmol) was added and stirring continued at −78° C. for 5 minutes. The resulting mixture was allowed to warm to room temperature and stirred for 16 hours. 2M NaOH (3 mL) was added and the mixture was extracted with EtOAc (10 mL). The organic phase was washed with Rochelle Salt solution (2×10 mL), dried over Na2SO4 and concentrated in vacuo. Purification by preparative HPLC (acidic pH, standard elution method) afforded the titled compound as an off-white solid.

1H NMR (500 MHz, DMSO-d6) δ 10.70 (s, 1H), 9.87 (s, 1H), 8.47 (d, J=5.5 Hz, 1H), 8.18 (d, J=1.9 Hz, 1H), 8.15 (s, 1H), 7.83 (dd, J=5.5, 2.2 Hz, 1H), 7.22 (d, J=2.7 Hz, 1H), 7.12 (dd, J=8.6, 2.7 Hz, 1H), 6.81 (d, J=8.6 Hz, 1H), 4.38 (s, 1H), 3.68-3.62 (m, 4H), 3.51-3.45 (m, 4H), 2.31-2.24 (m, 2H), 1.99 (t, J=7.0 Hz, 2H), 1.68-1.61 (m, 2H).

LC-MS (Method A): Rt 2.32 mins; MS m/z 434.2/434.6=[M+H]+ (100% @ 215 nm)

Example 43

4-[[2-(5-Chloro-2-hydroxy-phenyl)acetyl]amino]-N-[1,1-dimethyl-3-(2,2,2-trifluoro ethylamino)propyl]pyridine-2-carboxamide

Step 1: tert-Butyl N-[3-[[4-[[2-(5-chloro-2-hydroxy-phenyl)acetyl]amino]pyridine-2-carbonyl]amino]-3-methyl-butyl]carbamate

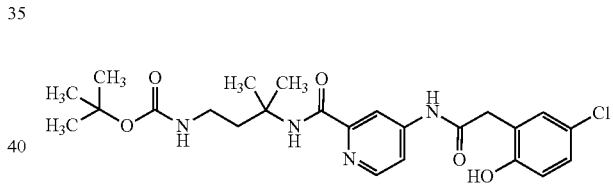

The titled compound was prepared from tert-butyl N-(3-amino-3-methyl-butyl)carbamate and 4-[[2-(5-chloro-2-hydroxy-phenyl)acetyl]amino]pyridine-2-carboxylic acid (Example 31 step 1) analogously to Example 33.

1H NMR (500 MHz, DMSO-d6) δ=1.33 (s, 9H), 1.37 (s, 6H), 1.85-1.93 (m, 2H), 2.91-2.98 (m, 2H), 3.66 (s, 2H), 6.73 (s, 1H), 6.79 (d, J=8.6, 1H), 7.11 (dd, J=8.6, 2.7, 1H), 7.20 (d, J=2.7, 1H), 7.81 (dd, J=5.5, 2.2, 1H), 8.00 (s, 1H), 8.17 (d, J=2.0, 1H), 8.44 (d, J=5.5, 1H), 10.84 (s, 1H).

LC-MS (Method E): Rt 1.18 mins; MS m/z 491/493=[M+H]+ (92% @ 215 nm)

Step 2: N-(3-Amino-1,1-dimethyl-propyl)-4-[[2-(5-chloro-2-hydroxy-phenyl)acetyl]amino]pyridine-2-carboxamide

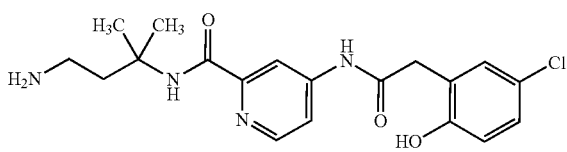 [SMILES: CC(C)(CCN)NC(=O)c1cc(NC(=O)Cc2cc(Cl)ccc2O)ccn1]

tert-Butyl N-[3-[[4-[[2-(5-chloro-2-hydroxy-phenyl)acetyl]amino]pyridine-2-carbonyl]amino]-3-methyl-butyl] carbamate (step 1) (302 mg, 0.62 mmol) was dissolved in 20% TFA in DCM (2.0 mL) and the mixture was agitated at room temperature for 18 hours. The resulting mixture was loaded under gravity onto a 2 g Isolute® SCX-2 cartridge washing the column with 1:1 DCM/MeOH (100 mL). The product was eluted with 1:1 DCM/1M NH₃ in MeOH (100 mL) to afford the titled compound as a white crystalline solid 1H NMR (500 MHz, DMSO-d6) δ 11.13 (s, 1H), 8.59 (s, 1H), 8.42 (d, J=5.5 Hz, 1H), 8.15 (d, J=2.1 Hz, 1H), 7.79 (dd, J=5.5, 2.2 Hz, 1H), 7.18 (d, J=2.6 Hz, 1H), 7.09 (dd, J=8.6, 2.7 Hz, 1H), 6.76 (d, J=8.6 Hz, 1H), 3.65 (s, 2H), 2.65-2.63 (m, 2H), 1.83-1.77 (m, 2H), 1.39 (s, 6H).

LC-MS (Method E): Rt 0.86 mins; MS m/z 391.1/393.1= [M+H]+ (99% @ 215 nm)

Step 3: 4-[[2-(5-Chloro-2-hydroxy-phenyl)acetyl]amino]-N-[1,1-dimethyl-3-(2,2,2-trifluoro ethylamino)propyl]pyridine-2-carboxamide

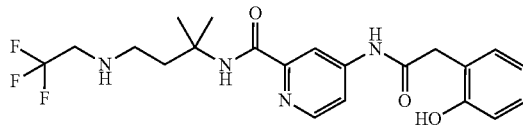

A solution of N-(3-amino-1,1-dimethyl-propyl)-4-[[2-(5-chloro-2-hydroxy-phenyl)acetyl]amino]pyridine-2-carboxamide (step 2) (39 mg, 0.1 mmol) in THF (1 mL) was treated with 2,2,2-trifluoroethyl trifluoromethanesulfonate (0.015 mL, 0.10 mmol) and stirred at room temperature for 16 hours. A further portion of 2,2,2-trifluoroethyl trifluoromethanesulfonate (0.015 mL, 0.10 mmol) was added and the mixture was stirred for a further 2 hours. The reaction mixture was concentrated in vacuo and purification of the crude product by chromatography on silica eluting with 75% EtOAc in heptane (isocratic gradient) afforded the titled compound as a white solid.

1H NMR (500 MHz, DMSO-d6) δ 10.74 (s, 1H), 9.83 (s, 1H), 8.42 (d, J=5.5 Hz, 1H), 8.36 (s, 1H), 8.15 (d, J=2.1 Hz, 1H), 7.80 (dd, J=5.5, 2.2 Hz, 1H), 7.21 (d, J=2.7 Hz, 1H), 7.11 (dd, J=8.6, 2.7 Hz, 1H), 6.79 (d, J=8.6 Hz, 1H), 3.66 (s, 2H), 3.22-3.15 (m, 2H), 2.67-2.64 (m, 2H), 2.35-2.31 (m, 1H), 1.90-1.85 (m, 2H), 1.38 (s, 6H).

LC-MS (Method A): Rt 2.10 mins; MS m/z 473.2/475.2= [M+H]+ (100% @ 215 nm)

Example 44

4-[[2-(5-Chloro-2-hydroxy-phenyl)acetyl]amino]-N-(4-fluoro-1-bicyclo[2.1.1]hexanyl)pyridine-2-carboxamide

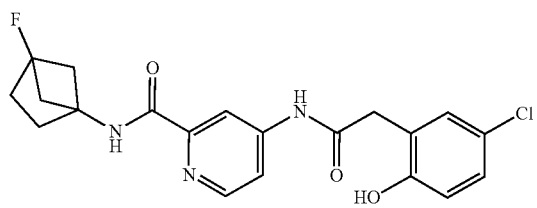 [SMILES: O=C(Cc1cc(Cl)ccc1O)Nc1ccnc(C(=O)NC23CCC(F)(C2)C3)c1]

To a solution of 4-fluorobicyclo[2.1.1]hexan-1-amine hydrochloride (21 mg, 0.14 mmol), DIPEA (0.09 mL, 0.52 mmol) and 4-[[2-(5-chloro-2-hydroxy-phenyl)acetyl]amino]pyridine-2-carboxylic acid (Example 31 step 1) (40 mg, 0.13 mmol) in DMF (1 mL) was added HATU (55 mg, 0.14 mmol) and the reaction mixture stirred at room temperature for 2 hours. The resulting mixture was diluted with EtOAc (10 mL) and water (10 mL). The organic layer was separated, dried over Na₂SO₄ and concentrated in vacuo. The residue was dissolved in DMSO:MeCN:H2O (1.4 mL, 3:3:1), filtered and purified by preparative HPLC (basic pH, early elution method) to afford the titled compound as an off-white solid.

1H NMR (500 MHz, Methanol-d4) δ 8.47 (dd, J=5.5, 0.5 Hz, 1H), 8.14 (dd, J=1.7, 0.5 Hz, 1H), 7.91 (dd, J=5.5, 2.2 Hz, 1H), 7.20 (d, J=2.6 Hz, 1H), 7.11 (dd, J=8.6, 2.6 Hz, 1H), 6.79 (d, J=8.6 Hz, 1H), 3.73 (s, 2H), 2.22-2.11 (m, 4H), 2.09-2.05 (dd, 2H), 1.96-1.89 (m, 2H).

LC-MS (Method A): Rt 3.21 mins; MS m/z 404.3/406.3= [M+H]+ (100% @ 215 nm)

Example 45

4-[[2-(5-Chloro-2-hydroxy-phenyl)acetyl]amino]-N-[3-(2,2-dimethylpropanoyl amino)-1,1-dimethyl-propyl]pyridine-2-carboxamide

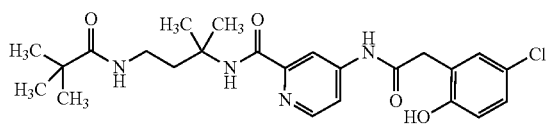 [SMILES: CC(C)(CCNC(=O)C(C)(C)C)NC(=O)c1cc(NC(=O)Cc2cc(Cl)ccc2O)ccn1]

The titled compound was prepared from N-(3-amino-1,1-dimethyl-propyl)-4-[[2-(5-chloro-2-hydroxy-phenyl)acetyl]amino]pyridine-2-carboxamide (Example 43 step 2) and 2,2-dimethylpropanoic acid analogously to Example 33.

1H NMR (500 MHz, DMSO-d6) δ 10.68 (s, 1H), 9.80 (s, 1H), 8.45 (d, J=5.5 Hz, 1H), 8.19 (d, J=2.0 Hz, 1H), 8.02 (s, 1H), 7.81 (dd, J=5.5, 2.2 Hz, 1H), 7.40 (t, J=5.5 Hz, 1H), 7.22 (d, J=2.7 Hz, 1H), 7.12 (dd, J=8.6, 2.7 Hz, 1H), 6.80 (d, J=8.6 Hz, 1H), 3.67 (s, 2H), 3.12-3.02 (m, 2H), 1.95-1.87 (m, 2H), 1.39 (s, 6H), 1.04 (s, 9H).

LC-MS (Method A): Rt 3.0 mins; MS m/z 475.4/477.4= [M+H]+ (100% @ 215 nm)

Example 46

4-[[2-(5-Chloro-2-hydroxy-phenyl)acetyl]amino]-N-(1-cyano-2-hydroxy-1-methyl-ethyl)pyridine-2-carboxamide

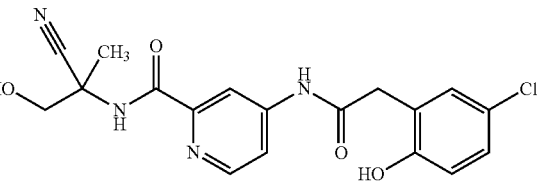

4-[[2-(5-Chloro-2-hydroxy-phenyl)acetyl]amino]pyridine-2-carboxylic acid (Example 31 step 1) (120 mg, 0.39 mmol) and DIPEA (273 μL, 1.57 mmol) were suspended in THF (2 mL) and treated with 2-amino-3-hydroxy-2-methyl-propanenitrile hydrochloride (64 mg, 0.47 mmol) followed by HATU (179 mg, 0.47 mmol). After stirring at room temperature for 18 hours, the resulting mixture was partitioned between DCM (10 ml) and water (10 ml). The organic portion was separated, dried over Na₂SO₄, filtered and concentrated in vacuo. The residue was purified by chromatography on silica eluting with 0-100% TBME in heptane 0-100% TBME in MeOH. The resulting residue was dissolved in DMSO:MeOH (1200 µl, 1:1) and purified by preparative HPLC (acidic pH, early elution method) and the product fractions were concentrated in vacuo to remove the volatile organics. The resulting aqueous mixture was treated with sat. aq. NaHCO₃ (3 mL) and DCM (5 ml) and agitated until clear. The organic portion was separated by filtration through a hydrophobic PTFE fritted tube and concentrated in vacuo to afford the titled compound as a white crystalline solid.

1H NMR (500 MHz, DMSO-d6) δ 10.80 (s, 1H), 9.80 (s, 1H), 8.72 (s, 1H), 8.50 (d, J=5.6 Hz, 1H), 8.23 (d, J=2.0 Hz, 1H), 7.87 (dd, J=5.5, 2.2 Hz, 1H), 7.22 (d, J=2.7 Hz, 1H), 7.12 (dd, J=8.6, 2.7 Hz, 1H), 6.80 (d, J=8.6 Hz, 1H), 5.90 (t, J=5.8 Hz, 1H), 3.81 (dd, J=10.9, 5.4 Hz, 1H), 3.73 (dd, J=10.9, 5.2 Hz, 1H), 3.68 (s, 2H), 1.66 (s, 3H).

LC-MS (Method A): Rt 2.47 mins; MS m/z 389.3/391.2= [M+H]+ (99% @ 215 nm)

Chiral separation of racemic 4-[[2-(5-chloro-2-hydroxy-phenyl)acetyl]amino]-N-(1-cyano-2-hydroxy-1-methyl-ethyl)pyridine-2-carboxamide using Supercritical Fluid Chromatography [chiral phase column: 25% Ethanol: 75% CO₂ with Chiralpak IC 25 cm column at 4 ml/min] afforded the individual enantiomers:

Example 46a: 4-[[2-(5-Chloro-2-hydroxy-phenyl)acetyl]amino]-N-[(1S)-1-cyano-2-hydroxy-1-methyl-ethyl]pyridine-2-carboxamide or 4-[[2-(5-chloro-2-hydroxy-phenyl)acetyl]amino]-N-[(1R)-1-cyano-2-hydroxy-1-methyl-ethyl]pyridine-2-carboxamide

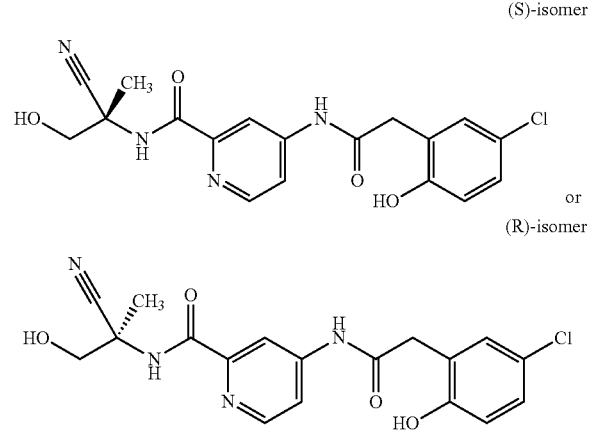

First eluted peak: SFC Retention Time=8.89 mins; MS m/z 389.0/391.0

1H NMR (500 MHz, DMSO-d6) δ 10.86 (s, 1H), 9.78 (s, 1H), 8.72 (s, 1H), 8.50 (d, J=5.5 Hz, 1H), 8.22 (d, J=2.0 Hz, 1H), 7.86 (dd, J=5.5, 2.2 Hz, 1H), 7.21 (d, J=2.7 Hz, 1H), 7.11 (dd, J=8.6, 2.7 Hz, 1H), 6.79 (d, J=8.6 Hz, 1H), 5.90 (t, J=5.1 Hz, 1H), 3.81 (dd, J=11.0, 4.6 Hz, 1H), 3.73 (dd, J=11.3, 4.7 Hz, 1H), 3.67 (s, 2H), 1.66 (s, 3H).

100% e.e

Example 46b: 4-[[2-(5-Chloro-2-hydroxy-phenyl)acetyl]amino]-N-[(1S)-1-cyano-2-hydroxy-1-methyl-ethyl]pyridine-2-carboxamide or 4-[[2-(5-chloro-2-hydroxy-phenyl)acetyl]amino]-N-[(1R)-1-cyano-2-hydroxy-1-methyl-ethyl]pyridine-2-carboxamide

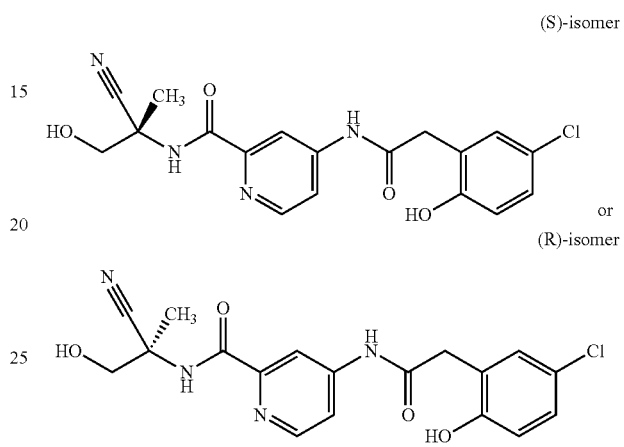

Second eluted peak: SFC Retention Time=10.84 mins; MS m/z 389.0/391.0

1H NMR (500 MHz, DMSO-d6) δ 10.98 (s, 1H), 9.82 (s, 1H), 8.72 (s, 1H), 8.50 (d, J=5.5 Hz, 1H), 8.22 (d, J=2.0 Hz, 1H), 7.86 (dd, J=5.5, 2.1 Hz, 1H), 7.20 (d, J=2.5 Hz, 1H), 7.10 (dd, J=8.5, 2.7 Hz, 1H), 6.78 (d, J=8.7 Hz, 1H), 5.90 (s, 1H), 3.82 (dd, J=10.7, 3.3 Hz, 1H), 3.73 (dd, J=10.4, 2.9 Hz, 1H), 3.67 (s, 2H), 1.66 (s, 3H).

88% e.e.

Example 47

4-[[2-(5-Chloro-2-hydroxy-phenyl)acetyl]amino]-N-(3-cyanotetrahydrofuran-3-yl)pyridine-2-carboxamide

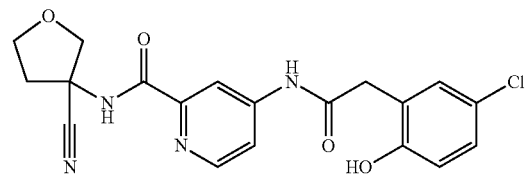 [SMILES: N#CC1(NC(=O)c2cc(NC(=O)Cc3cc(Cl)ccc3O)ccn2)CCOC1]

To a mixture comprising 3-aminotetrahydrofuran-3-carbonitrile hydrochloride (31 mg, 0.21 mmol) and 4-[[2-(5-chloro-2-hydroxy-phenyl)acetyl]amino]pyridine-2-carboxylic acid (Example 31 step 1) (60 mg, 0.18 mmol, 90%) in DMF (2 mL) was added EDCI (74 mg, 0.39 mmol), HOAt (53 mg, 0.39 mmol) and DIPEA (123 µL, 0.7 mmol). The reaction mixture was stirred at room temperature for 30 minutes. The resulting mixture was diluted with water (10 mL) then acidified with 10% citric acid aqueous solution to pH 4 and extracted with DCM (10 mL). The organic layer was separated using a PTFE fritted tube and concentrated in vacuo. The crude residue was purified by preparative HPLC (acidic pH, early elution method) and the product fractions were freeze-dried to afford the titled compound as a white solid.

1H NMR (500 MHz, DMSO-d6) δ 10.75 (s, 1H), 9.85 (s, 1H), 9.51 (s, 1H), 8.53 (d, J=5.5 Hz, 1H), 8.22 (d, J=1.9 Hz, 1H), 7.88 (dd, J=5.5, 2.2 Hz, 1H), 7.22 (d, J=2.7 Hz, 1H), 7.13 (dd, J=8.6, 2.7 Hz, 1H), 6.81 (d, J=8.6 Hz, 1H), 4.27 (d, J=9.5 Hz, 1H), 4.04 (d, J=9.5 Hz, 1H), 3.97-3.91 (m, 1H), 3.90-3.84 (m, 1H), 3.68 (s, 2H), 2.74-2.67 (m, 1H), 2.65-2.58 (m, 1H).

LC-MS (Method A): Rt 2.68 mins; MS m/z 401.1/403.1= [M+H]+ (98% @ 215 nm)

The compounds of the following tabulated Examples (Table 12) were prepared analogously to Example 47 by replacing 3-aminotetrahydrofuran-3-carbonitrile hydrochloride with the appropriate commercially available amine.

Steps 1-3: 4-[[2-(5-Fluoro-2-hydroxy-phenyl)acetyl]amino]pyridine-2-carboxylic acid

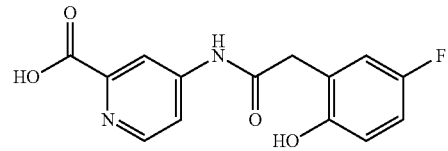

The titled compound was prepared from methyl 4-aminopyridine-2-carboxylate and 2-(5-fluoro-2-methoxy-phenyl)acetic acid analogously to Example 41 steps 1-3.

TABLE 12

| Ex. | Structure and Name | 1H NMR<br>LCMS Retention Time, [M + H]+, |
|---|---|---|
| 47.1 | Methyl 2-[4-[[4-[[2-(5-chloro-2-hydroxy-phenyl)acetyl]amino]pyridine-2-carbonyl]amino]tetrahydropyran-4-yl]acetate | 1H NMR (500 MHz, DMSO-d6) δ 10.71 (s, 1H), 9.84 (s, 1H), 8.49 (d, J = 5.5 Hz, 1H), 8.19 (m, 2H), 7.83 (dd, J = 5.5, 2.2 Hz, 1H), 7.23 (d, J = 2.6 Hz, 1H), 7.13 (dd, J = 8.6, 2.7 Hz, 1H), 6.81 (d, J = 8.6 Hz, 1H), 3.72-3.67 (m, 4H), 3.54-3.48 (m, 5H), 2.92 (s, 2H), 2.35-2.28 (m, 2H), 1.80-1.72 (m, 2H).<br>LC-MS (Method A): Rt 2.80 mins; MS m/z 462.2/464.1 = [M + H]+ (98% @ 215 nm) |
| 47.2 | Methyl 4-[[4-[[2-(5-chloro-2-hydroxy-phenyl)acetyl]amino]pyridine-2-carbonyl]amino]tetrahydropyran-4-carboxylate | 1H NMR (500 MHz, DMSO-d6) δ 10.69 (s, 1H), 9.81 (s, 1H), 8.77 (s, 1H), 8.52 (d, J = 5.5 Hz, 1H), 8.16 (d, J = 2.0 Hz, 1H), 7.84 (dd, J = 5.5, 2.1 Hz, 1H), 7.22 (d, J = 2.7 Hz, 1H), 7.12 (dd, J = 8.6, 2.7 Hz, 1H), 6.80 (d, J = 8.6 Hz, 1H), 3.71 (dt, J = 11.7, 4.1 Hz, 2H), 3.67 (s, 2H), 3.61 (s, 3H), 3.60-3.55 (m, 2H), 2.13-2.08 (m, 2H), 2.06-1.99 (m, 2H).<br>LC-MS (Method A): Rt 2.72 mins; MS m/z 448.2/450.2 = [M + H]+ (100% @ 215 nm) |
| 47.3 | 4-[[2-(5-Chloro-2-hydroxy-phenyl)acetyl]amino]-N-(3-cyanooxetan-3-yl)pyridine-2-carboxamide | 1H NMR (500 MHz, DMSO-d6) δ 10.77 (br. s, 1H), 10.07 (s, 1H), 9.84 (br. s, 1H), 8.54 (d, J = 5.6 Hz, 1H), 8.22 (d, J = 1.9 Hz, 1H), 7.89 (dd, J = 5.5, 2.2 Hz, 1H), 7.22 (d, J = 2.7 Hz, 1H), 7.12 (dd, J = 8.6, 2.7 Hz, 1H), 6.80 (d, J = 8.6 Hz, 1H), 4.94 (d, J = 7.6 Hz, 2H), 4.84 (d, J = 7.6 Hz, 2H), 3.68 (s, 2H).<br>LC-MS (Method A): Rt 2.59 mins; MS m/z 387.1/389.1 = [M + H]+ (98% @ 215 nm) |

Example 48

4-[[2-(5-Fluoro-2-hydroxy-phenyl)acetyl]amino]-N-(1-methylcyclobutyl)pyridine-2-carboxamide

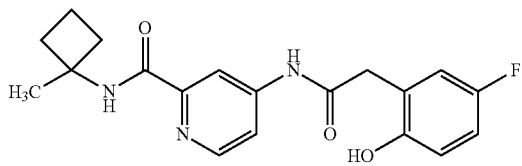 [SMILES: CC1(NC(=O)c2cc(NC(=O)Cc3cc(F)ccc3O)ccn2)CCC1]

1H NMR (500 MHz, DMSO-d6) δ 10.72 (s, 1H), 9.51 (s, 1H), 8.52 (d, J=5.5 Hz, 1H), 8.28 (d, J=1.7 Hz, 1H), 7.81 (dd, J=5.5, 1.7 Hz, 1H), 7.02 (dd, J=9.2, 3.0 Hz, 1H), 6.91 (td, J=8.6, 3.1 Hz, 1H), 6.77 (dd, J=8.8, 4.9 Hz, 1H), 3.67 (s, 2H).

LC-MS (Method E): Rt 0.76 mins; MS m/z 291.0=[M+H]+ (84% @ 215 nm)

Step 4: 4-[[2-(5-Fluoro-2-hydroxy-phenyl)acetyl]amino]-N-(1-methylcyclobutyl)pyridine-2-carboxamide The titled compound was prepared from 4-[[2-(5-fluoro-2-hydroxy-phenyl)acetyl]amino]pyridine-2-carboxylic acid (steps 1-3) and 1-methylcyclobutanamine hydrochloride analogously to Example 47.

1H NMR (500 MHz, DMSO-d6) δ 10.67 (s, 1H), 9.50 (s, 1H), 8.48 (s, 1H), 8.45 (d, J=5.5 Hz, 1H), 8.16 (d, J=2.1 Hz, 1H), 7.83 (dd, J=5.5, 2.2 Hz, 1H), 7.01 (dd, J=9.4, 3.2 Hz, 1H), 6.91 (td, J=8.6, 3.2 Hz, 1H), 6.77 (dd, J=8.8, 4.9 Hz, 1H), 3.67 (s, 2H), 2.43-2.35 (m, 2H), 2.03-1.96 (m, 2H), 1.84-1.77 (m, 2H), 1.47 (s, 3H).

LC-MS (Method A): Rt 3.00 mins; MS m/z 358.2/359.2= [M+H]+ (95% @ 215 nm)

Example 48.1

N-(4-Cyanotetrahydropyran-4-yl)-4-[[2-(5-fluoro-2-hydroxy-phenyl)acetyl]amino]pyridine-2-carboxamide

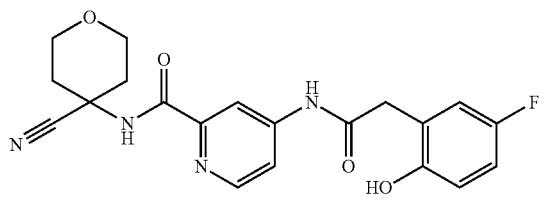 [SMILES: N#CC1(NC(=O)c2cc(NC(=O)Cc3cc(F)ccc3O)ccn2)CCOCC1]

The titled compound was prepared from 4-[[2-(5-fluoro-2-hydroxy-phenyl)acetyl]amino]pyridine-2-carboxylic acid (Example 48, steps 1-3) and 4-aminotetrahydropyran-4-carbonitrile analogously to Example 47.

1H NMR (500 MHz, DMSO-d6) δ 10.75 (s, 1H), 9.50 (s, 1H), 9.01 (s, 1H), 8.53 (d, J=5.8 Hz, 1H), 8.24 (d, J=1.8 Hz, 1H), 7.88 (dd, J=5.5, 2.2 Hz, 1H), 7.03 (dd, J=9.4, 3.2 Hz, 1H), 6.92 (td, J=8.6, 3.2 Hz, 1H), 6.78 (dd, J=8.8, 4.9 Hz, 1H), 3.87 (dt, J=12.2, 3.8 Hz, 2H), 3.69 (s, 2H), 3.63-3.56 (m, 2H), 2.41-2.35 (m, 2H), 2.12-2.04 (m, 2H).

LC-MS (Method A): Rt 2.45 mins; MS m/z 399.2/400.2= [M+H]+ (99% @ 215 nm)

Example 49

N-[3-(tert-Butylamino)-1,1-dimethyl-3-oxo-propyl]-4-[[2-(5-chloro-2-hydroxy-phenyl) acetyl]amino]pyridine-2-carboxamide

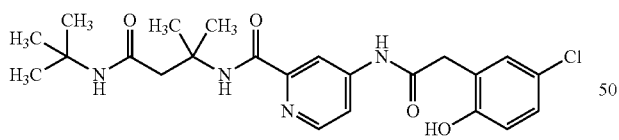

Step 1: 3-[[4-[[2-(5-Chloro-2-hydroxy-phenyl) acetyl]amino]pyridine-2-carbonyl]amino]-3-methyl-butanoic acid

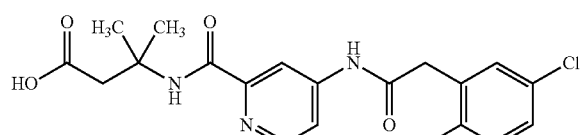

A solution of ethyl 3-[[4-[[2-(5-chloro-2-hydroxy-phenyl)acetyl]amino]pyridine-2-carbonyl]amino]-3-methyl-butanoate (Example 35.13)(688 mg, 1.57 mmol) in THF (7.5 mL) was treated with 2M aqueous sodium hydroxide (1.57 mL, 3.14 mmol) and the reaction mixture was stirred at room temperature for 2 hours. The resulting mixture was partitioned between DCM (25 ml) and water (10 mL) and 2M aqueous KHSO$_4$ (10 mL) was added. The biphasic solution agitated until clarification of the solution. The organic layer was separated, dried over Na$_2$SO$_4$ and concentrated in vacuo to afford titled compound as a yellow viscous gel.

1H NMR (500 MHz, DMSO-d6) δ=12.21 (s, 1H), 10.67 (s, 1H), 9.80 (s, 1H), 8.44 (d, J=5.5, 1H), 8.39 (s, 1H), 8.17 (d, J=2.0, 1H), 7.81 (dd, J=5.5, 2.2, 1H), 7.22 (d, J=2.7, 1H), 7.12 (dd, J=8.6, 2.7, 1H), 6.79 (t, J=8.6, 1H), 3.67 (s, 2H), 2.73 (s, 2H), 1.48 (s, 6H).

LC-MS (Method E): Rt 1.04 mins; MS m/z 406.2/408.1= [M+H]+ (83% @ 215 nm)

Step 2: N-[3-(tert-Butylamino)-1,1-dimethyl-3-oxo-propyl]-4-[[2-(5-chloro-2-hydroxy-phenyl) acetyl]amino]pyridine-2-carboxamide 3-[[4-[[2-(5-Chloro-2-hydroxy-phenyl)acetyl]amino]pyridine-2-carbonyl]amino]-3-methyl-butanoic acid (step 1)(120 mg, 0.39 mmol) and DIPEA (205 μL, 1.17 mmol) were suspended in THF (2 mL) and treated with 2-methyl-propan-2-amine (62 μL, 0.59 mmol) followed by HATU (179 mg, 0.47 mmol). The resulting mixture was stirred at room temperature for 42 hours and then partitioned between DCM (10 ml) and water (10 ml). The organic portion was separated by filtration through a hydrophobic PTFE fritted tube and concentrated in vacuo. Purification of the residue by preparative HPLC (acidic pH, early elution method) afforded the titled compound as a white crystalline solid.

1H NMR (500 MHz, DMSO-d6) δ 10.68 (s, 1H), 9.05 (s, 1H), 8.46 (d, J=5.5 Hz, 1H), 8.28 (s, 1H), 8.19 (d, J=2.0 Hz, 1H), 7.80 (dd, J=5.5, 2.2 Hz, 1H), 7.59 (s, 1H), 7.22 (d, J=2.7 Hz, 1H), 7.13 (dd, J=8.6, 2.7 Hz, 1H), 6.81 (d, J=8.6 Hz, 1H), 3.68 (s, 2H), 2.38 (s, 2H), 1.45 (s, 6H).

LC-MS (Method A): Rt 3.16 mins; MS m/z 461.3/463.3= [M+H]+ (99% @ 215 nm)

Example 50

4-[[2-(5-Chloro-2-hydroxy-phenyl)acetyl]amino]-N-[3-(methanesulfonamido)-1,1-dimethyl-propyl]pyridine-2-carboxamide

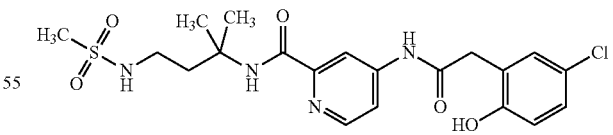

A solution of N-(3-amino-1,1-dimethyl-propyl)-4-[[2-(5-chloro-2-hydroxy-phenyl)acetyl]amino]pyridine-2-carboxamide (Example 43, step 2)(76 mg, 0.19 mmol) in THF (0.5 mL) was treated with K$_2$CO$_3$ (54 mg, 0.39 mmol) and the reaction mixture was stirred at room temperature. A solution of methane sulfonyl chloride (63.2 μL in 1000 μL in THF) was prepared and a 250 μL aliquot was added dropwise to the reaction mixture and stirred for 1 hour at room temperature. The resulting mixture was partitioned between DCM and water (8 mL 1:1) and the organic portion was separated by filtration through a hydrophobic PTFE fritted tube and concentrated in vacuo. The residue was dissolved in DMSO:MeOH (1200 μl, 1:1) and purified by (acidic pH, early elution method) and the first major product peak fractions were concentrated in vacuo. The resulting turbid aqueous mixture was treated with saturated aqueous NaHCO₃ (3 mL) and DCM (5 mL) and the biphasic solution was agitated until a clear biphasic solution was obtained. The organic portion was separated by filtration through a hydrophobic PTFE fritted tube and concentrated in vacuo to afford the titled compound as a white crystalline solid 1H NMR (500 MHz, DMSO-d6) δ=10.79 (s, 1H), 9.82 (s, 1H), 8.45 (d, J=5.5, 1H), 8.18 (d, J=1.9, 1H), 8.04 (s, 1H), 7.81 (dd, J=5.5, 2.2, 1H), 7.21 (d, J=2.7, 1H), 7.12 (dd, J=8.6, 2.7, 1H), 6.92 (t, J=5.8, 1H), 6.79 (d, J=8.6, 1H), 3.66 (s, 2H), 2.95 (dt, J=10.9, 5.9, 2H), 2.86 (s, 3H), 1.97-2.06 (m, 2H), 1.38 (s, 6H).

LC-MS (Method A): Rt 2.73 mins; MS m/z 469.2/471.2=[M+H]+ (99% @ 215 nm)

Example 51

N-(3-Acetamido-1,1-dimethyl-propyl)-4-[[2-(5-chloro-2-hydroxy-phenyl)acetyl]amino]pyridine-2-carboxamide

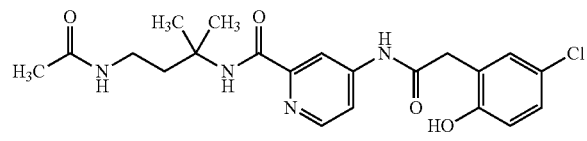 [SMILES: CC(=O)NCCC(C)(C)NC(=O)c1cc(NC(=O)Cc2cc(Cl)ccc2O)ccn1]

A solution of N-(3-amino-1,1-dimethyl-propyl)-4-[[2-(5-chloro-2-hydroxy-phenyl) acetyl]amino]pyridine-2-carboxamide; 2,2,2-trifluoroacetic acid (TFA salt of Example 43, step 2) (100 mg, 0.16 mmol) in THF (2.5 mL) was treated with DIPEA (113 μL, 0.65 mmol) followed by acetic anhydride (17 μL, 0.18 mmol) and the mixture was stirred at room temperature for 6 hours. 1M aqueous NaOH (0.5 mL) was added and stirring continued at room temperature for 1 hour. Further 1M aqueous NaOH (0.5 mL) was added followed by MeOH (~0.25 mL) and the mixture was stirred overnight. The resulting mixture was partitioned between DCM (5 mL) and water (3 mL) and the organic portion was separated. The aqueous layer was concentrated in vacuo and the crude residue was dissolved in 1:1 DCM/MeOH and purified by chromatography on silica eluting with 0-100% TBME in heptane followed by MeOH in TBME to afford the titled compound as a clear white crystalline solid.

1H NMR (500 MHz, DMSO-d6) δ=8.40 (d, J=5.5, 1H), 8.11 (d, J=1.8, 1H), 8.02 (s, 1H), 7.81-7.79 (m, 1H), 7.75 (dd, J=5.5, 2.1, 1H), 7.08 (s, 1H), 7.00 (d, J=8.2, 1H), 6.64 (d, J=8.1, 1H), 4.09 (s, 1H), 3.58 (s, 2H), 3.00-3.09 (m, 2H), 1.88-1.95 (m, 2H), 1.73 (s, 3H), 1.38 (s, 6H).

LC-MS (Method A): Rt 2.51 mins; MS m/z 433.3/435.3=[M+H]+ (97% @ 215 nm)

Example 53

4-[[2-(5-Chloro-2-hydroxy-phenyl)acetyl]amino]-N-[4-(hydroxymethyl)tetrahydro pyran-4-yl]pyridine-2-carboxamide

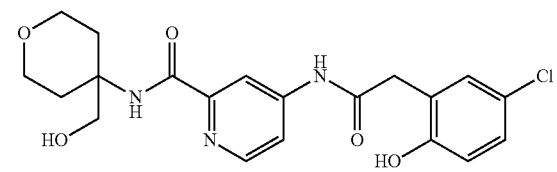 [SMILES: O=C(Cc1cc(Cl)ccc1O)Nc1ccnc(C(=O)NC2(CO)CCOCC2)c1]

To a cooled (−78° C.) solution of methyl 4-[[4-[[2-(5-chloro-2-hydroxy-phenyl)acetyl]amino]pyridine-2-carbonyl]amino]tetrahydropyran-4-carboxylate (Example 47.2) (52 mg, 0.1161 mmol) in THF (1.5 mL) under a nitrogen atmosphere was added dropwise a solution of 2.4M lithium aluminium hydride in THF (97 μL, 0.23 mmol). After stirring at −78° C. for 45 minutes, the mixture was allowed to warm to room temperature and stirred for 1 hour. The solvent was removed in vacuo and purification by preparative HPLC (acidic pH, early elution method) afforded the titled compound as a white solid.

1H NMR (500 MHz, DMSO-d6) δ 10.70 (s, 1H), 9.87 (s, 1H), 8.47 (d, J=5.5 Hz, 1H), 8.19 (d, J=2.0 Hz, 1H), 8.06 (s, 1H), 7.82 (dd, J=5.5, 2.2 Hz, 1H), 7.22 (d, J=2.7 Hz, 1H), 7.12 (dd, J=8.6, 2.7 Hz, 1H), 6.81 (d, J=8.6 Hz, 1H), 4.89 (s, 1H), 3.71-3.65 (m, 4H), 3.62 (s, 2H), 3.54-3.47 (m, 2H), 2.23-2.16 (m, 2H), 1.66 (ddd, J=14.0, 10.2, 4.2 Hz, 2H).

LC-MS (Method A): Rt 2.33 mins; MS m/z 420.1/422.1=[M+H]+ (98% @ 215 nm)

Example 54

N-tert-Butyl-4-[[2-[3-(1-hydroxyethyl)phenyl]acetyl]amino]pyridine-2-carboxamide

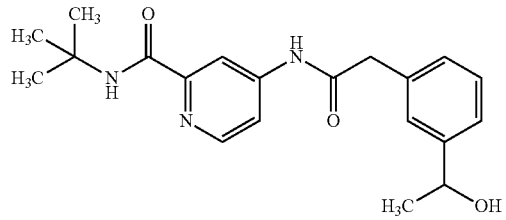 [SMILES: CC(O)c1cccc(CC(=O)Nc2ccnc(C(=O)NC(C)(C)C)c2)c1]

Step 1: 4-[[2-(3-Bromophenyl)acetyl]amino]-N-tert-butyl-pyridine-2-carboxamide

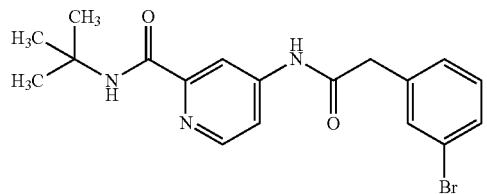 [SMILES: CC(C)(C)NC(=O)c1cc(NC(=O)Cc2cccc(Br)c2)ccn1]

The titled compound was prepared from 2-(3-bromophenyl)acetic acid and 4-amino-N-tert-butyl-pyridine-2-carboxamide (Example 3 step 1) analogously to Example 21.

1H NMR (250 MHz, DMSO-d6) δ 10.77 (s, 1H), 8.45 (d, J=5.5 Hz, 1H), 8.17 (d, J=1.9 Hz, 1H), 8.02 (s, 1H), 7.80 (dd, J=5.5, 2.2 Hz, 1H), 7.57-7.54 (m, 1H), 7.47 (dt, J=6.9, 2.1 Hz, 1H), 7.36-7.27 (m, 2H), 3.75 (s, 2H), 1.39 (s, 9H).

LC-MS (Method E): Rt 1.23 mins; MS m/z 390.1/392.1= [M+H]+ (98% @ 215 nm)

Step 2: 4-[[2-(3-Acetylphenyl)acetyl]amino]-N-tert-butyl-pyridine-2-carboxamide

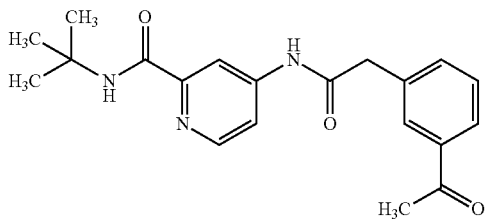 [SMILES: CC(=O)c1cccc(CC(=O)Nc2ccnc(C(=O)NC(C)(C)C)c2)c1]

A solution of 4-[[2-(3-bromophenyl)acetyl]amino]-N-tert-butyl-pyridine-2-carboxamide (step 1)(200 mg, 0.51 mmol), 1-vinyloxybutane (332 μL, 2.56 mmol), triphenylphosphine (27 mg, 0.1 mmol) and TEA (107 μL, 0.61 mmol) in MeCN (1 mL) was degassed with nitrogen and treated with Pd(OAc)₂ (12 mg, 0.05 mmol). The mixture was sealed and heated at 100° C. overnight. Further portions of 1-vinyloxybutane (332 μL, 2.56 mmol), TEA (107 μL, 0.61 mmol), triphenylphosphine (27 mg, 0.1 mmol) and Pd(OAc)₂ (12 mg, 0.05 mmol) were added and heating continued at 100° C. for a further 8 hours. The resulting mixture was filtered through Celite® and washed with EtOAc. The filtrate was absorbed onto silica and purification by chromatography eluting with 0-100% EtOAc in heptane afforded the titled compound as an orange glassy solid.

1H NMR (250 MHz, Chloroform-d) δ 8.34 (d, J=5.6 Hz, 1H), 8.11 (dd, J=5.5, 2.3 Hz, 1H), 7.90-7.84 (m, 2H), 7.59 (s, 1H), 7.50-7.43 (m, 2H), 3.77 (s, 2H), 2.56 (s, 3H), 1.39 (s, 9H).

LC-MS (Method E): Rt 1.13 mins; MS m/z 354.1=[M+H]+ (93% @ 215 nm)

Step 3: N-tert-Butyl-4-[[2-[3-(1-hydroxyethyl)phenyl]acetyl]amino]pyridine-2-carboxamide To a solution of 4-[[2-(3-acetylphenyl)acetyl]amino]-N-tert-butyl-pyridine-2-carboxamide (step 2) (45 mg, 0.12 mmol) in methanol (1 mL) at 0° C. was added NaBH₄ (4.5 mg, 0.12 mmol) and the mixture was allowed to warm to room temperature. After stirring for 1 hour, the reaction was quenched by addition of 3 drops of sat. NaHCO₃ solution and purification by preparative HPLC (acidic pH, standard elution method) afforded the titled compound as a colourless powder.

1H NMR (500 MHz, Methanol-d4) δ 8.42 (d, J=5.5 Hz, 1H), 8.14 (d, J=2.1 Hz, 1H), 7.89 (dd, J=5.5, 2.2 Hz, 1H), 7.37 (s, 1H), 7.33-7.22 (m, 3H), 4.85-4.79 (m, 1H), 3.74 (s, 2H), 1.47 (s, 9H), 1.43 (d, J=6.5 Hz, 3H).

LC-MS (Method A): Rt 2.77 mins; MS m/z 356.3=[M+H]+

Example 55

N-tert-Butyl-5-chloro-4-[[2-(5-chloro-2-hydroxyphenyl)acetyl]amino]pyridine-2-carboxamide

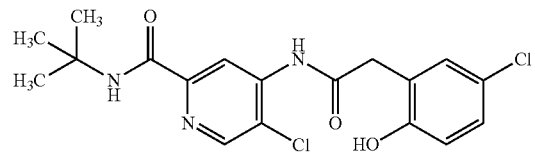 [SMILES: CC(C)(C)NC(=O)c1cc(NC(=O)Cc2cc(Cl)ccc2O)c(Cl)cn1]

Step 1: Methyl 4-amino-5-chloro-pyridine-2-carboxylate

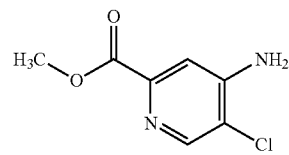

NCS (483 mg, 3.61 mmol) was added to a solution of methyl 4-aminopyridine-2-carboxylate (500 mg, 3.29 mmol) in DMF (10 mL) and the reaction mixture was stirred at 60° C. overnight. The resulting mixture was diluted with EtOAc (50 mL) and washed with water (2×50 mL), brine (2×50 mL), dried over sodium sulfate and concentrated in vacuo. The resulting crude residue was purified by chromatography on KP-NH silica eluting 0-10% MeOH in DCM. The mixed fractions were combined and concentrated in vacuo. The resulting crude residue was further purified by chromatography on KP-NH silica eluting 0-100% EtOAc in heptane to afford the titled compound as a light pink solid.

1H NMR (250 MHz, DMSO-d6) δ 8.22 (s, 1H), 7.42 (s, 1H), 6.68 (s, 2H), 3.82 (s, 3H).

LC-MS (Method C): Rt 1.61 mins; MS m/z 186.8/188.8= [M+H]+ (90% @ 215 nm)

Step 2: Methyl 5-chloro-4-[[2-(5-chloro-2-methoxyphenyl)acetyl]amino]pyridine-2-carboxylate

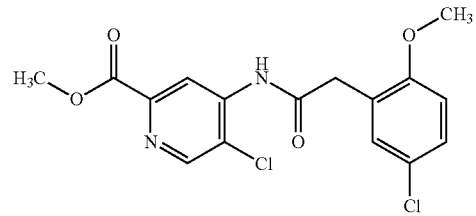 [SMILES: COC(=O)c1cc(NC(=O)Cc2cc(Cl)ccc2OC)c(Cl)cn1]

To a solution of 2-(5-chloro-2-methoxy-phenyl)acetic acid (106 mg, 0.53 mmol) and methyl 4-amino-5-chloro-pyridine-2-carboxylate (step 1) (100. mg, 0.48 mmol) in 1,4-dioxane (5 mL) was added TEA (0.17 mL, 0.96 mmol) followed by 50% T3P® solution in EtOAc (0.57 mL, 0.96 mmol). The resulting mixture was stirred at room temperature under an inert atmosphere overnight. The reaction mixture was diluted with EtOAc (20 mL) and washed with water (2×10 mL) and brine (10 mL). The organic portion was dried over Na₂SO₄ and concentrated in vacuo. The crude residue was purified by chromatography on silica eluting with 0-100% EtOAc in heptane to afford the titled compound as a white solid.

1H NMR (250 MHz, DMSO-d6) δ 9.94 (s, 1H), 8.77 (s, 1H), 8.72 (s, 1H), 7.36-7.29 (m, 2H), 7.06-6.99 (m, 1H), 3.88 (s, 2H), 3.86 (s, 3H), 3.78 (s, 3H).

LC-MS (Method E): Rt 1.15 mins; MS m/z 369.0/371.0= [M+H]+ (91% @ 215 nm)

Step 3: 5-Chloro-4-[[2-(5-chloro-2-methoxy-phenyl) acetyl]amino]pyridine-2-carboxylic acid

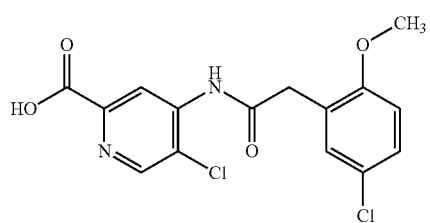 [SMILES: COc1ccc(Cl)cc1CC(=O)Nc1cc(C(=O)O)ncc1Cl]

A solution of methyl 5-chloro-4-[[2-(5-chloro-2-methoxy-phenyl)acetyl]amino]pyridine-2-carboxylate (step 2)(106 mg, 0.26 mmol) in THF (3 mL) was treated with 1M NaOH (392 μL, 0.39 mmol) and stirred at room temperature for 2 hours. The resulting mixture was concentrated in vacuo and the residue dissolved in water (15 mL). The pH of was adjusted to pH 5 by addition of 1M HCl and the resulting precipitate filtered and dried in a vacuum oven at 40° C. to afford the titled compound as a white solid.

1H NMR (250 MHz, DMSO-d6) δ 13.33 (br. s, 1H), 9.90 (s, 1H), 8.75 (s, 1H), 8.71 (s, 1H), 7.36-7.30 (m, 2H), 7.07-7.01 (m, 1H), 3.88 (s, 2H), 3.79 (s, 3H).

LC-MS (Method E): Rt 1.05 mins; MS m/z 355.0/357.0= [M+H]+ (79% @ 215 nm)

Step 4-5: N-tert-Butyl-5-chloro-4-[[2-(5-chloro-2-hydroxy-phenyl)acetyl]amino]pyridine-2-carboxamide The titled compound was prepared from 5-chloro-4-[[2-(5-chloro-2-methoxy-phenyl)acetyl]amino]pyridine-2-carboxylic acid (step 3) and 2-methylpropan-2-amine analogously to Example 32, steps 1 and 2.

1H NMR (500 MHz, DMSO-d6) δ 10.30-9.70 (m, 2H), 8.74 (s, 1H), 8.61 (s, 1H), 7.94 (s, 1H), 7.26 (d, J=2.7 Hz, 1H), 7.15 (dd, J=8.6, 2.7 Hz, 1H), 6.84 (d, J=8.6 Hz, 1H), 3.81 (s, 2H), 1.39 (s, 9H).

LC-MS (Method A): Rt 3.64 mins; MS m/z 396.2/398.2= [M+H]+ (97% @ 215 nm)

Example 56

N-tert-Butyl-4-[[2-[5-chloro-2-[(4-methoxyphenyl)methoxy]phenyl]acetyl]amino]pyridine-2-carboxamide

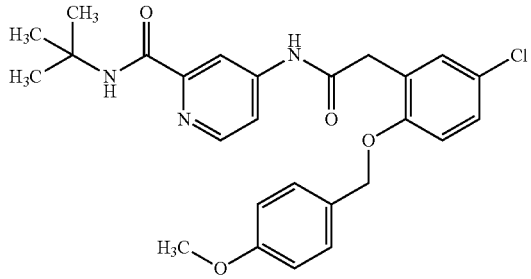 [SMILES: COc1ccc(COc2ccc(Cl)cc2CC(=O)Nc2ccnc(C(=O)NC(C)(C)C)c2)cc1]

N-tert-Butyl-4-[[2-(5-chloro-2-hydroxy-phenyl)acetyl]amino]pyridine-2-carboxamide (Example 3)(164 mg, 0.45 mmol) was suspended in anhydrous acetone (10 mL) and treated with K₂CO₃ (94 mg, 0.68 mmol) followed by 1-(bromomethyl)-4-methoxy-benzene (100 mg, 0.5 mmol). The reaction mixture was heated in a pressure tube at 50° C. overnight. The resulting mixture was concentrated in vacuo and then re-dissolved in EtOAc (25 mL). The mixture was washed with water (25 mL) and brine (25 mL), dried over Na₂SO₄ and concentrated in vacuo. The solid was dissolved in EtOAc/MeOH (2:1 ~15 mL) and the suspension was filtered and washed with EtOAc (20 mL) to afford the titled compound as a white solid.

1H NMR (500 MHz, DMSO-d6) δ 10.65 (s, 1H), 8.45 (d, J=5.5 Hz, 1H), 8.11 (d, J=2.0 Hz, 1H), 8.05 (s, 1H), 7.82 (dd, J=5.5, 2.2 Hz, 1H), 7.34 (d, J=2.7 Hz, 1H), 7.30 (dd, J=8.7, 2.7 Hz, 1H), 7.22 (d, J=8.7 Hz, 2H), 7.09 (d, J=8.8 Hz, 1H), 6.67-6.63 (m, 2H), 4.97 (s, 2H), 3.71 (s, 2H), 3.65 (s, 3H), 1.41 (s, 9H).

LC-MS (Method A): Rt 4.13 mins; MS m/z 482.3/484.3= [M+H]+ (91% @ 215 nm)

Example 57a: N-tert-butyl-4-[[(1S) or (1R)-4-chloro-7-hydroxy-indane-1-carbonyl]amino]pyridine-2-carboxamide and Example 57b: N-tert-butyl-4-[[(1S) or (1R)-4-chloro-7-hydroxy-indane-1-carbonyl]amino]pyridine-2-carboxamide

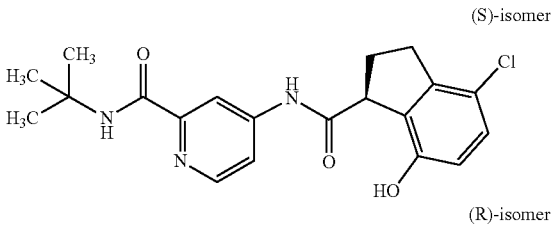

or

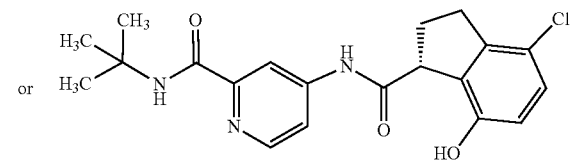

Step 1: N-tert-Butyl-4-[(7-methoxyindane-1-carbonyl)amino]pyridine-2-carboxamide

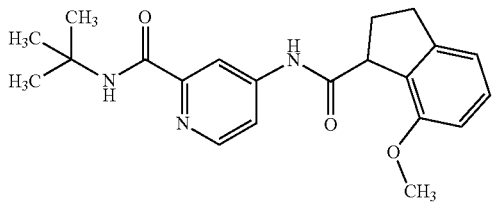 [SMILES: COc1cccc2c1C(C(=O)Nc1ccnc(C(=O)NC(C)(C)C)c1)CC2]

To a mixture of 4-amino-N-tert-butyl-pyridine-2-carboxamide (Example 3 step 1) (200 mg, 1.03 mmol) and 7-methoxyindane-1-carboxylic acid (199 mg, 1.03 mmol) in 1,4-dioxane (5 mL) was added 50% T3P® solution in EtOAc (1231 µL, 2.07 mmol) and TEA (362 µL, 2.07 mmol). The reaction mixture was stirred at room temperature under an inert atmosphere for 16 hours. The resulting mixture was diluted with EtOAc (20 mL) and the organic mixture was washed with water (20 mL), sat. NaHCO$_3$ (20 mL) and brine (20 mL). The organic portion was dried over Na$_2$SO$_4$ and concentrated in vacuo. The crude residue was purified by chromatography on KP-NH silica eluting with 0-80% heptane in EtOAc to afford the titled compound as a light pink foam.

1H NMR (500 MHz, DMSO-d6) δ 10.67 (s, 1H), 8.44 (d, J=5.5 Hz, 1H), 8.22 (d, J=2.1 Hz, 1H), 8.03 (s, 1H), 7.83 (dd, J=5.5, 2.2 Hz, 1H), 7.20 (t, J=7.8 Hz, 1H), 6.87 (d, J=7.4 Hz, 1H), 6.77 (d, J=8.1 Hz, 1H), 4.12 (dd, J=8.8, 5.4 Hz, 1H), 3.68 (s, 3H), 3.09-2.99 (m, 1H), 2.92-2.85 (m, 1H), 2.41-2.34 (m, 1H), 2.24-2.15 (m, 1H), 1.40 (s, 9H).

LC-MS (Method E): Rt 1.21 mins; MS m/z 368.1=[M+H]+ (100% @ 215 nm)

Step 2: N-tert-Butyl-4-[(4-chloro-7-methoxy-indane-1-carbonyl)amino]pyridine-2-carboxamide

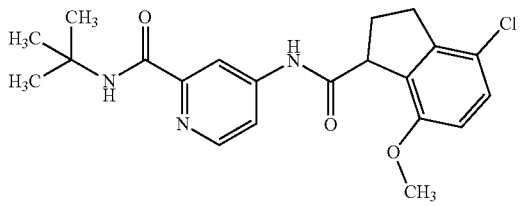 [SMILES: COc1ccc(Cl)c2c1C(C(=O)Nc1ccnc(C(=O)NC(C)(C)C)c1)CC2]

The titled compound was prepared from N-tert-butyl-4-[(7-methoxyindane-1-carbonyl)amino]pyridine-2-carboxamide (step 1) analogously to Example 24, step 2.

1H NMR (250 MHz, Chloroform-d) δ 8.83 (s, 1H), 8.37 (d, J=5.6 Hz, 1H), 8.20 (dd, J=5.6, 2.2 Hz, 1H), 8.01 (s, 1H), 7.58 (d, J=2.0 Hz, 1H), 7.19 (d, J=8.7 Hz, 1H), 6.74 (d, J=8.7 Hz, 1H), 4.22 (d, J=7.5 Hz, 1H), 4.02 (s, 3H), 3.23-2.77 (m, 3H), 2.32-2.15 (m, 1H), 1.47 (s, 9H).

LC-MS (Method E): Rt 1.27 mins; MS m/z 402.1/404.1=[M+H]+

Step 3: Example 57a: N-tert-butyl-4-[[(1S) or (1R)-4-chloro-7-hydroxy-indane-1-carbonyl]amino]pyridine-2-carboxamide and Example 57b: N-tert-butyl-4-[[(1S) or (1R)-4-chloro-7-hydroxy-indane-1-carbonyl]amino]pyridine-2-carboxamide To a solution of N-tert-butyl-4-[(4-chloro-7-methoxy-indane-1-carbonyl)amino]pyridine-2-carboxamide (step 2) (50 mg, 0.12 mmol) in DCM (2 mL) was added 1M BBr$_3$ in DCM (249 µL, 0.25 mmol). The resulting mixture was stirred at room temperature under an inert atmosphere for 1 hour. Further 1M BBr$_3$ in DCM (249 µL, 0.25 mmol) was added and the mixture stirred for a further 24 hours. The reaction was quenched with water (1 mL) and concentrated in vacuo. The crude material was dissolved in EtOAc (20 mL) and the organic mixture was washed with sat. NaHCO$_3$ (20 mL), water (20 mL) and brine (20 mL). The organic portion was concentrated in vacuo to afford a racemic mixture Chiral separation of racemic N-tert-butyl-4-[[4-chloro-7-hydroxy-indane-1-carbonyl]amino]pyridine-2-carboxamide using Supercritical Fluid Chromatography [chiral phase column (15% Ethanol: 95% CO2 with Chiralpak IC 25 cm column at 15 ml/min)] afforded the individual enantiomers:

Example 57a: N-tert-butyl-4-[[(1S) or (1R)-4-chloro-7-hydroxy-indane-1-carbonyl]amino]pyridine-2-carboxamide SFC retention Time: 6.00 mins 1H NMR (500 MHz, DMSO-d6) δ 10.77 (br. s, 1H), 9.76 (br. s, 1H), 8.44 (d, J=5.5 Hz, 1H), 8.19 (d, J=2.0 Hz, 1H), 8.02 (s, 1H), 7.83 (dd, J=5.5, 2.2 Hz, 1H), 7.07 (d, J=8.5 Hz, 1H), 6.61 (d, J=8.5 Hz, 1H), 4.18 (dd, J=8.9, 5.2 Hz, 1H), 3.05-2.96 (m, 1H), 2.93-2.84 (m, 1H), 2.43-2.36 (m, 1H), 2.27-2.19 (m, 1H), 1.40 (s, 9H).

LC-MS (Method A): Rt 3.58 mins; MS m/z 388.2/390.2=[M+H]+ (96% @ 215 nm)

Example 57b: N-tert-butyl-4-[[(1S) or (1R)-4-chloro-7-hydroxy-indane-1-carbonyl]amino]pyridine-2-carboxamide SFC retention Time: 7.84 mins 1H NMR (500 MHz, DMSO-d6) δ 10.89 (br. s, 1H), 9.76 (br. s, 1H), 8.43 (d, J=5.5 Hz, 1H), 8.19 (d, J=2.1 Hz, 1H), 8.02 (s, 1H), 7.82 (dd, J=5.5, 2.1 Hz, 1H), 7.06 (d, J=8.5 Hz, 1H), 6.60 (d, J=8.5 Hz, 1H), 4.18 (dd, J=8.9, 5.1 Hz, 1H), 3.04-2.95 (m, 1H), 2.94-2.84 (m, 1H), 2.42-2.36 (m, 1H), 2.29-2.21 (m, 1H), 1.40 (s, 9H).

LC-MS (Method A): Rt 3.58 mins; MS m/z 388.2/390.2=[M+H]+ (95% @ 215 nm)

Example 58

N-tert-Butyl-4-[[2-(2-cyclopropylphenyl)acetyl]amino]pyridine-2-carboxamide

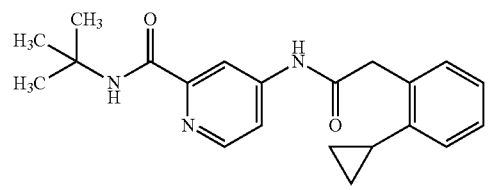 [SMILES: CC(C)(C)NC(=O)c1cc(NC(=O)Cc2ccccc2C2CC2)ccn1]

A mixture comprising 4-[[2-(2-bromophenyl)acetyl]amino]-N-tert-butyl-pyridine-2-carboxamide ((Example 23.13)(100 mg, 0.25 mmol), cyclopropylboronic acid (44 mg, 0.51 mmol), tripotassium phosphate (215 mg, 1.01 mmol) in toluene (5 mL) and water (0.5 mL) was degassed with nitrogen for 10 mins and treated with Pd(OAc)$_2$ (11 mg, 0.05 mmol) and P(Cy)$_3$ (28 mg, 0.1 mmol). The reaction mixture was sealed and heated at 100° C. for 5 hours. After cooling to room temperature, the mixture was filtered through Celite® and the filtrate diluted with EtOAc (10 mL) and water (10 mL). The organic layer was separated, dried over Na₂SO₄ and concentrated in vacuo. The crude material was purified by preparative HPLC (basic pH, early elution method) followed by preparative HPLC (acidic pH, early elution method). Further purification using chromatography on silica eluting with 0-100% EtOAc in heptane afforded the titled compound as an off-white solid.

1H NMR (500 MHz, Methanol-d4) δ 8.43 (dd, J=5.6, 0.4 Hz, 1H), 8.13 (dd, J=2.2, 0.4 Hz, 1H), 7.92 (dd, J=5.5, 2.2 Hz, 1H), 7.23 (dd, J=7.3, 1.5 Hz, 1H), 7.21-7.13 (m, 2H), 7.07 (dd, J=7.3, 1.2 Hz, 1H), 3.98 (s, 2H), 2.01-1.91 (m, 1H), 1.47 (s, 9H), 0.95-0.82 (m, 2H), 0.67-0.58 (m, 2H).

LC-MS (Method A): Rt 3.69 mins; MS m/z 352.3=[M+H]+ (99% @ 215 nm)

Example 59

4-[[2-(3-Bromo-5-chloro-2-hydroxy-phenyl)acetyl]amino]-N-tert-butyl-pyridine-2-carboxamide

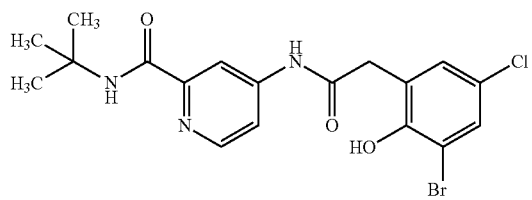 [SMILES: CC(C)(C)NC(=O)c1cc(NC(=O)Cc2cc(Cl)cc(Br)c2O)ccn1]

Step 1:
2-(3-Bromo-5-chloro-2-methoxy-phenyl)acetic acid

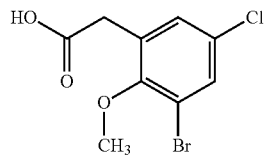

Bromine (8 mL, 139.34 mmol) was added to a stirred solution of 2-(5-chloro-2-methoxy-phenyl)acetic acid (1 g, 4.98 mmol) in acetic acid (8 mL) and the mixture was stirred at room temperature for 1 hour. The reaction mixture was cooled to 0° C. and treated with EtOAc (50 mL) followed by saturated aqueous Na₂S₂O₃ (ca. 30 mL). The organic layer was separated and concentrated in vacuo to obtain a yellow gummy solid. The solid was purified by C18 reverse phase chromatography eluting with 10-100% (0.1% formic acid in water: 0.1% formic acid in MeCN) to afford the titled compound as an off-white solid.

1H NMR (500 MHz, DMSO-d6) δ 12.53 (s, 1H), 7.67 (d, J=2.6 Hz, 1H), 7.41 (d, J=2.6 Hz, 1H), 3.73 (s, 3H), 3.65 (s, 2H).

LC-MS (Method E): Rt 1.08 mins; MS m/z not observed=[M+H]+ (100% @ 215 nm)

Step 2: 4-[[2-(3-Bromo-5-chloro-2-methoxy-phenyl)acetyl]amino]-N-tert-butyl-pyridine-2-carboxamide

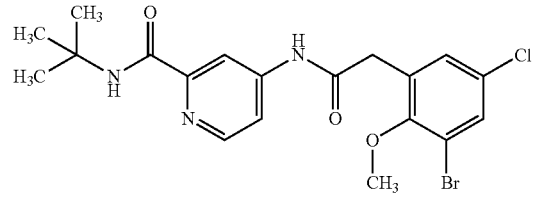 [SMILES: COc1c(Br)cc(Cl)cc1CC(=O)Nc1ccnc(C(=O)NC(C)(C)C)c1]

To a stirred solution of 2-(3-bromo-5-chloro-2-methoxy-phenyl)acetic acid (step 1)(755 mg, 2.7 mmol), 4-amino-N-tert-butyl-pyridine-2-carboxamide (Example 3 step 1) (475. mg, 2.46 mmol) and TEA (644 μL, 3.69 mmol) in 1,4-dioxane (10 mL) was added 50% T3P® solution in EtOAc (2.19 mL, 3.69 mmol). The resulting mixture was stirred at room temperature for 2 hours and then diluted with water (40 mL) and EtOAc (50 mL). The organic layer was separated, washed with water (50 mL), dried over Na₂SO₄ and concentrated in vacuo. The crude material was purified by chromatography on silica eluting with 0-100% EtOAc in heptane to afford the titled compound as an off-white solid.

1H NMR (500 MHz, DMSO-d6) δ 10.83 (s, 1H), 8.47 (d, J=5.5 Hz, 1H), 8.18 (d, J=2.0 Hz, 1H), 8.04 (s, 1H), 7.82 (dd, J=5.5, 2.2 Hz, 1H), 7.71 (d, J=2.6 Hz, 1H), 7.48 (d, J=2.6 Hz, 1H), 3.84 (s, 2H), 3.75 (s, 3H), 1.41 (s, 9H).

LC-MS (Method E): Rt 1.29 mins; MS m/z 454.0/456.0/458.0=[M+H]+ (99% @ 215 nm)

Step 3: 4-[[2-(3-Bromo-5-chloro-2-hydroxy-phenyl)acetyl]amino]-N-tert-butyl-pyridine-2-carboxamide 1M BBr₃ in DCM (0.2 mL, 0.2 mmol) was added to a stirred suspension of 4-[[2-(3-bromo-5-chloro-2-methoxy-phenyl)acetyl]amino]-N-tert-butyl-pyridine-2-carboxamide (step 2) (30 mg, 0.07 mmol) in DCM (1 mL) at 0° C. The mixture was allowed to warm to room temperature and stirred for 1 hour. The reaction was quenched by dropwise addition of sat. NaHCO₃ (20 mL) then diluted with EtOAc (20 mL). The organic layer was separated, dried over Na₂SO₄ and concentrated in vacuo. The crude product was purified by preparative HPLC (acidic pH, early elution method) and the product containing fractions were combined and lyophilised overnight to afford the titled compound as an off-white powder.

1H NMR (500 MHz, DMSO-d6) δ 10.93 (s, 1H), 9.62 (s, 1H), 8.45 (d, J=5.5 Hz, 1H), 8.15 (d, J=2.0 Hz, 1H), 8.03 (s, 1H), 7.81 (dd, J=5.5, 2.2 Hz, 1H), 7.52 (d, J=2.6 Hz, 1H), 7.28 (d, J=2.5 Hz, 1H), 3.78 (s, 2H), 1.40 (s, 9H).

LC-MS (Method A): Rt 3.81 mins; MS m/z 440.1/442.1=[M+H]+ (99% @ 215 nm)

Example 60

N-(4-Fluoro-1-bicyclo[2.1.1]hexanyl)-4-[[2-(2-fluorophenyl)acetyl]amino]pyridine-2-carboxamide

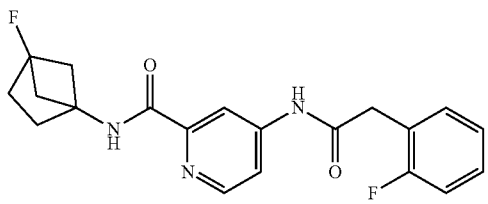 [SMILES: O=C(Cc1ccccc1F)Nc1ccnc(C(=O)NC23CCC(F)(C2)C3)c1]

Step 1-2: 4-[[2-(2-Fluorophenyl)acetyl]amino]pyridine-2-carboxylic acid

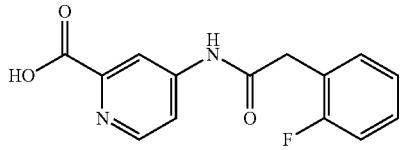 [SMILES: O=C(Cc1ccccc1F)Nc1ccnc(C(=O)O)c1]

The titled compound was prepared from 2-(2-fluorophenyl)acetic acid and methyl 4-aminopyridine-2-carboxylate analogously to Example 30 steps 1-2.

1H NMR (500 MHz, DMSO-d6) δ 10.82 (s, 1H), 8.51 (d, J=5.5 Hz, 1H), 8.23 (d, J=1.8 Hz, 1H), 7.78 (dd, J=5.5, 2.1 Hz, 1H), 7.39 (t, J=7.6 Hz, 1H), 7.36-7.31 (m, 1H), 7.21-7.15 (m, 2H), 3.81 (s, 2H).

LC-MS (Method E): Rt 0.81 mins; MS m/z 275.0=[M+H]+ (100% @ 215 nm)

Step 3: N-(4-Fluoro-1-bicyclo[2.1.1]hexanyl)-4-[[2-(2-fluorophenyl)acetyl]amino]pyridine-2-carboxamide The titled compound was prepared from 4-[[2-(2-fluorophenyl)acetyl]amino]pyridine-2-carboxylic acid (step 1-2) and 4-fluorobicyclo[2.1.1]hexan-1-amine hydrochloride analogously to Example 30 step 3.

1H NMR (500 MHz, DMSO-d6) δ 10.82 (s, 1H), 9.05 (s, 1H), 8.47 (d, J=5.5 Hz, 1H), 8.16 (d, J=2.0 Hz, 1H), 7.83 (dd, J=5.5, 2.2 Hz, 1H), 7.40 (td, J=7.6, 1.6 Hz, 1H), 7.36-7.31 (m, 1H), 7.21-7.15 (m, 2H), 3.81 (s, 2H), 2.13-2.05 (m, 4H), 1.99-1.95 (m, 2H), 1.87-1.82 (m, 2H).

LC-MS (Method A): Rt 3.22 mins; MS m/z 372.3=[M+H]+ (98% @ 215 nm)

Example 60.1

N-(1-Cyano-2-hydroxy-1-methyl-ethyl)-4-[[2-(2-fluorophenyl)acetyl]amino]pyridine-2-carboxamide

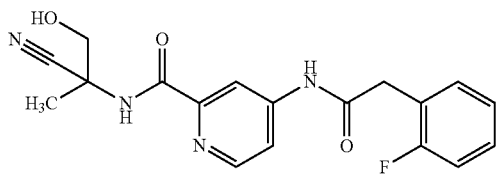 [SMILES: CC(C#N)(CO)NC(=O)c1cc(NC(=O)Cc2ccccc2F)ccn1]

The titled compound was prepared from 4-[[2-(2-fluorophenyl)acetyl]amino]pyridine-2-carboxylic acid (step 1-2) and 2-amino-3-hydroxy-2-methyl-propanenitrile hydrochloride analogously to Example 30 step 3.

1H NMR (500 MHz, DMSO-d6) δ 10.86 (s, 1H), 8.72 (s, 1H), 8.51 (d, J=5.5 Hz, 1H), 8.23 (d, J=2.1 Hz, 1H), 7.86 (dd, J=5.5, 2.2 Hz, 1H), 7.43-7.37 (m, 1H), 7.37-7.28 (m, 1H), 7.22-7.14 (m, 2H), 5.99-5.79 (m, 1H), 3.86-3.78 (m, 3H), 3.72 (dd, J=10.9, 4.7 Hz, 1H), 1.65 (s, 3H).

LC-MS (Method A): Rt 2.41 mins; MS m/z 357.2=[M+H]+ (99% @ 215 nm)

Example 60.2

N-(1,1-Dimethylprop-2-ynyl)-4-[[2-(2-fluorophenyl)acetyl]amino]pyridine-2-carboxamide

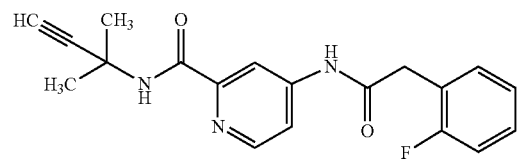 [SMILES: C#CC(C)(C)NC(=O)c1cc(NC(=O)Cc2ccccc2F)ccn1]

The titled compound was prepared from 4-[[2-(2-fluorophenyl)acetyl]amino]pyridine-2-carboxylic acid (step 1-2) and 2-methylbut-3-yn-2-amine analogously to Example 30 step 3.

1H NMR (500 MHz, DMSO-d6) δ 10.83 (s, 1H), 8.48 (d, J=5.5 Hz, 1H), 8.32 (s, 1H), 8.19 (d, J=2.1 Hz, 1H), 7.83 (dd, J=5.5, 2.2 Hz, 1H), 7.43-7.37 (m, 1H), 7.37-7.30 (m, 1H), 7.22-7.15 (m, 2H), 3.82 (s, 2H), 3.21 (s, 1H), 1.64 (s, 6H).

LC-MS (Method A): Rt 3.08 mins; MS m/z 340.2=[M+H]+ (99% @ 215 nm)

Example 61

N-tert-Butyl-4-[[2-(5-chloro-2-hydroxy-3-isopropylphenyl)acetyl]amino]pyridine-2-carboxamide

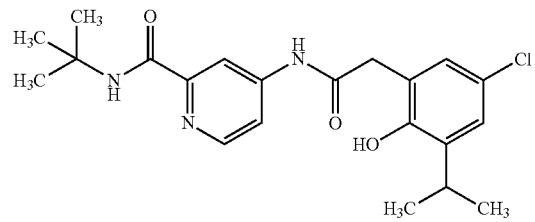 [SMILES: CC(C)c1cc(Cl)cc(CC(=O)Nc2ccnc(C(=O)NC(C)(C)C)c2)c1O]

Step 1: N-tert-Butyl-4-[[2-(5-chloro-3-isopropenyl-2-methoxy-phenyl)acetyl]amino]pyridine-2-carboxamide

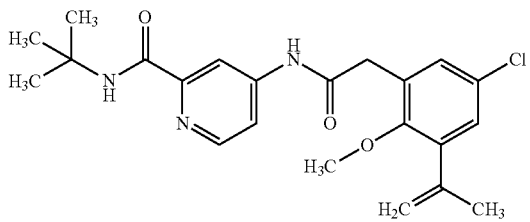 [SMILES: C=C(C)c1cc(Cl)cc(CC(=O)Nc2ccnc(C(=O)NC(C)(C)C)c2)c1OC]

The titled compound was prepared from 4-[[2-(3-bromo-5-chloro-2-methoxy-phenyl)acetyl]amino]-N-tert-butyl-pyridine-2-carboxamide (Example 59 step 2) and 2-isopropenyl-4,4,5,5-tetramethyl-1,3,2-dioxaborolane analogously to Example 58.

1H NMR (500 MHz, DMSO-d6) δ 10.84-10.75 (m, 1H), 8.48-8.42 (m, 1H), 8.23-8.17 (m, 1H), 8.03 (s, 1H), 7.84-7.79 (m, 1H), 7.33 (d, J=2.7 Hz, 1H), 7.17 (d, J=2.7 Hz, 1H), 5.25-5.22 (m, 1H), 5.17-5.15 (m, 1H), 3.77 (d, J=2.8 Hz, 2H), 3.58 (s, 3H), 2.14-2.04 (m, 3H), 1.40 (s, 9H).

LC-MS (Method E): Rt 1.33 mins; MS m/z 416.1=[M+H]+ (86% @ 215 nm)

Step 2: N-tert-Butyl-4-[[2-(5-chloro-3-isopropyl-2-methoxy-phenyl)acetyl]amino]pyridine-2-carboxamide

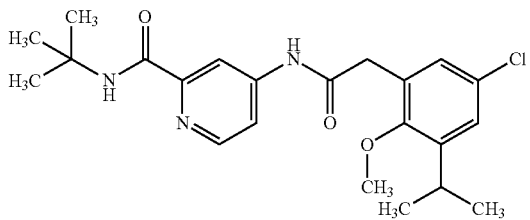 [SMILES: COc1c(CC(=O)Nc2ccnc(C(=O)NC(C)(C)C)c2)cc(Cl)cc1C(C)C]

10% Pd/C (9 mg, 0.01 mmol) was added to a stirred solution of N-tert-butyl-4-[[2-(5-chloro-3-isopropenyl-2-methoxy-phenyl)acetyl]amino]pyridine-2-carboxamide (step 1) (120 mg, 0.17 mmol) in EtOH (10 mL). The resulting mixture was placed under an atmosphere of hydrogen and after stirring for 16 hours the mixture was filtered through Celite® and washed through with EtOH (15 mL). The filtrate was concentrated in vacuo and purification by preparative HPLC (acidic pH, early elution method) afforded the titled compound as a pale yellow solid.

1H NMR (500 MHz, DMSO-d6) δ 10.80 (s, 1H), 8.46 (d, J=5.5 Hz, 1H), 8.19 (d, J=2.0 Hz, 1H), 8.03 (s, 1H), 7.82 (dd, J=5.5, 2.2 Hz, 1H), 7.26 (d, J=2.7 Hz, 1H), 7.22 (d, J=2.7 Hz, 1H), 3.77 (s, 2H), 3.66 (s, 3H), 3.21 (hept, J=6.9 Hz, 1H), 1.40 (s, 9H), 1.18 (d, J=6.9 Hz, 6H).

LC-MS (Method E): Rt 1.34 mins; MS m/z 418.2=[M+H]+ (99% @ 215 nm)

Step 3: N-tert-Butyl-4-[[2-(5-chloro-2-hydroxy-3-isopropyl-phenyl)acetyl]amino]pyridine-2-carboxamide 1M BBr3 in DCM (0.34 mL, 0.34 mmol) was added to a stirred suspension of N-tert-butyl-4-[[2-(5-chloro-3-isopropyl-2-methoxy-phenyl)acetyl]amino]pyridine-2-carboxamide (step 2)(48 mg, 0.11 mmol) in DCM (2 mL). The resulting mixture was stirred at room temperature for 1 hour. The reaction was quenched with MeOH (5 mL) and the mixture was concentrated in vacuo. The resulting residue was diluted with EtOAc (5 mL), washed with sat. NaHCO3 (5 mL) and the organic portion was dried over Na2SO4 and concentrated in vacuo. The crude material was purified by preparative HPLC (acidic pH, early elution method) and the product fractions were combined, lyophilised overnight to afford the titled compound as an off-white powder.

1H NMR (500 MHz, DMSO-d6) δ 10.73 (s, 1H), 8.75 (s, 1H), 8.45 (d, J=5.5 Hz, 1H), 8.18 (d, J=1.9 Hz, 1H), 8.03 (s, 1H), 7.82 (dd, J=5.5, 2.2 Hz, 1H), 7.10-7.01 (m, 2H), 3.74 (s, 2H), 3.29-3.22 (m, 1H), 1.40 (s, 9H), 1.14 (d, J=6.8 Hz, 6H).

LC-MS (Method A): Rt 3.25 mins; MS m/z 356.3=[M+H]+ (100% @ 215 nm)

Example 62

N-tert-Butyl-4-[[2-[5-chloro-2-hydroxy-3-(1-methoxyethyl)phenyl]acetyl]amino]pyridine-2-carboxamide

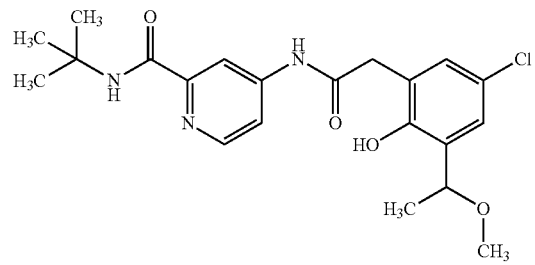 [SMILES: COC(C)c1cc(Cl)cc(CC(=O)Nc2ccnc(C(=O)NC(C)(C)C)c2)c1O]

Step 1: N-tert-Butyl-4-[[2-[5-chloro-3-(1-hydroxyethyl)-2-methoxy-phenyl]acetyl]amino]pyridine-2-carboxamide

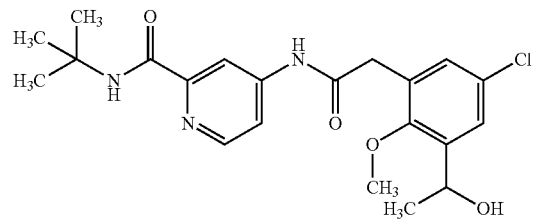 [SMILES: COc1c(CC(=O)Nc2ccnc(C(=O)NC(C)(C)C)c2)cc(Cl)cc1C(C)O]

The titled compound was prepared from 4-[[2-(3-bromo-5-chloro-2-methoxy-phenyl)acetyl]amino]-N-tert-butyl-pyridine-2-carboxamide (Example 59, step 2) and 1-vinyloxybutane analogously to Example 54 steps 2-3.

1H NMR (500 MHz, DMSO-d6) δ 10.80 (s, 1H), 8.45 (d, J=5.5 Hz, 1H), 8.19 (d, J=2.1 Hz, 1H), 8.03 (s, 1H), 7.81 (dd, J=5.5, 2.2 Hz, 1H), 7.39 (d, J=2.7 Hz, 1H), 7.27 (d, J=2.7 Hz, 1H), 5.23 (d, J=4.5 Hz, 1H), 5.06-4.87 (m, 1H), 3.77 (d, J=2.6 Hz, 2H), 3.68 (s, 3H), 1.40 (s, 9H), 1.31 (d, J=6.4 Hz, 3H).

LC-MS (Method E): Rt 1.18 mins; MS m/z 420.2/422.2=[M+H]+ (100% @ 215 nm)

Step 2: N-tert-Butyl-4-[[2-[5-chloro-2-hydroxy-3-(1-methoxyethyl)phenyl]acetyl]amino]pyridine-2-carboxamide 1M BBr₃ in DCM (0.5 mL, 0.5 mmol) was added to a cooled (0° C.) suspension of N-tert-butyl-4-[[2-[5-chloro-3-(1-hydroxyethyl)-2-methoxy-phenyl]acetyl]amino]pyridine-2-carboxamide (70 mg, 0.17 mmol) in DCM (2 mL) and stirred at room temperature for 1 hour. The reaction was quenched by addition of sat NaHCO₃ (1 mL) then diluted with DCM (7 mL). The organic layer was separated, concentrated in vacuo and purification of the crude residue by preparative HPLC (acidic pH, early elution method) afforded the titled compound as an off-white powder.

1H NMR (500 MHz, DMSO-d6) δ 10.76 (s, 1H), 8.87 (s, 1H), 8.45 (d, J=5.5 Hz, 1H), 8.18 (d, J=1.9 Hz, 1H), 8.03 (s, 1H), 7.81 (dd, J=5.5, 2.2 Hz, 1H), 7.15 (d, J=2.7 Hz, 1H), 7.11 (d, J=2.7 Hz, 1H), 4.68 (q, J=6.3 Hz, 1H), 3.76 (s, 2H), 3.17 (s, 3H), 1.40 (s, 9H), 1.29 (d, J=6.4 Hz, 3H).

LC-MS (Method A): Rt 3.80 mins; MS m/z 420.3=[M+H]+ (100% @ 215 nm)

Example 63

4-[[2-(6-Quinolyl)acetyl]amino]-N-tetrahydropyran-4-yl-pyridine-2-carboxamide

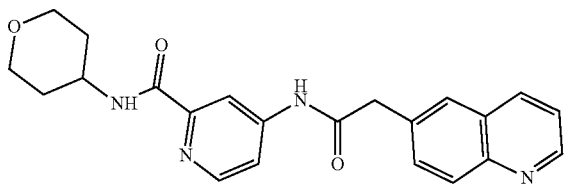 [SMILES: O=C(Cc1ccc2ncccc2c1)Nc1ccnc(C(=O)NC2CCOCC2)c1]

Step 1: 4-Nitro-N-tetrahydropyran-4-yl-pyridine-2-carboxamide

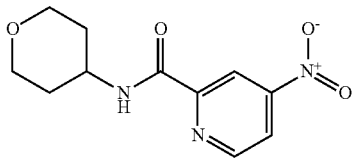 [SMILES: O=C(NC1CCOCC1)c1cc([N+](=O)[O-])ccn1]

To a stirred solution of HATU (724 mg, 1.9 mmol) in DMF (1 mL) was added DIPEA (363 μL, 2.08 mmol) and 4-nitropyridine-2-carboxylic acid (320 mg, 1.9 mmol) and the mixture was stirred for 15 mins. Tetrahydropyran-4-amine (0.18 mL, 1.73 mmol) was added in one portion and the mixture was stirred at room temperature for 1 hour. The resulting mixture was washed with water (10 mL), NaHCO₃ (10 mL) and extracted with EtOAc (2×10 mL). The combined organic extracts were dried over Na₂SO₄ and concentrated in vacuo to afford the titled compound as a pale orange solid.

1H NMR (500 MHz, DMSO-d6) δ=1.70-1.75 (m, 4H), 3.37-3.44 (m, 2H), 3.88 (dt, J=11.2, 3.2, 2H), 4.05 (s, 1H), 8.33 (dd, J=5.3, 2.3, 1H), 8.53 (dd, J=2.3, 0.5, 1H), 8.92 (d, J=8.2, 1H), 9.02 (dd, J=5.3, 0.5, 1H).

Step 2: 4-Amino-N-tetrahydropyran-4-yl-pyridine-2-carboxamide

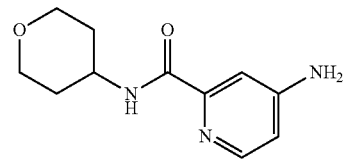 [SMILES: Nc1ccnc(C(=O)NC2CCOCC2)c1]

A mixture comprising 4-nitro-N-tetrahydropyran-4-yl-pyridine-2-carboxamide (step 1) (338 mg, 1.35 mmol) and 10% Pd—C (29 mg, 0.13 mmol) in EtOH (4 mL) was stirred under an atmosphere of hydrogen for 16 hours. The resulting mixture was filtered and the filtrate washed with EtOAc (2×10 mL). The combined organic extracts were concentrated in vacuo and purification of the crude residue by chromatography on silica eluting with 0-100% EtOAc in heptane afforded the titled compound as a pale orange solid.

1H NMR (500 MHz, DMSO-d6) δ=1.57-1.67 (m, 2H), 1.67-1.73 (m, 2H), 3.38 (td, J=11.6, 2.3, 2H), 3.81-3.88 (m, 2H), 3.90-3.99 (m, 1H), 6.30 (s, 2H), 6.58 (dd, J=5.6, 2.4, 1H), 7.21 (d, J=2.3, 1H), 8.01 (d, J=5.5, 1H), 8.37 (d, J=8.4, 1H).

LC-MS (Method C): Rt 0.32 mins; MS m/z 222.0=[M+H]+ (98% @ 215 nm)

Step 3: 4-[[2-(6-Quinolyl)acetyl]amino]-N-tetrahydropyran-4-yl-pyridine-2-carboxamide A mixture of 4-amino-N-tetrahydropyran-4-yl-pyridine-2-carboxamide (step 2) (104 mg, 0.47 mmol) and 2-(6-quinolyl)acetic acid (87.99 mg, 0.47 mmol) in 1,4-dioxane (2 mL) was treated with 50% T3P® solution in EtOAc (1118 μL, 0.94 mmol) and TEA (164 μL, 0.94 mmol). After stirring at room temperature for 1.5 hours, the mixture was concentrated in vacuo. The crude residue was washed with water (15 mL), NaHCO₃ (10 mL) and extracted with EtOAc (2×10 mL). The combined organic extracts were dried over Na₂SO₄ and concentrated in vacuo. Purification by chromatography on silica eluting with 0-20% EtOAc/MeOH afforded the titled compound an off-white solid.

1H NMR (500 MHz, DMSO-d6) δ=1.64-1.73 (m, 4H), 3.38 (td, J=11.4, 3.2, 2H), 3.83-3.89 (m, 2H), 3.95 (s, 2H), 3.97-4.05 (m, 1H), 7.50-7.55 (m, 1H), 7.74 (dd, J=8.7, 2.0, 1H), 7.84 (dd, J=5.5, 2.2, 1H), 7.90 (d, J=1.7, 1H), 7.99 (d, J=8.6, 1H), 8.22 (d, J=2.0, 1H), 8.35 (d, J=7.4, 1H), 8.49 (d, J=5.5, 1H), 8.58 (d, J=8.4, 1H), 8.88 (dd, J=4.2, 1.7, 1H), 10.86 (s, 1H).

LC-MS (Method A): Rt 1.51 mins; MS m/z 391.0=[M+H]+ (99% @ 215 nm)

Example 64

4-(Benzylcarbamoylamino)-N-tert-butyl-pyridine-2-carboxamide

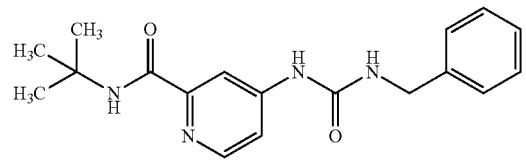 [SMILES: CC(C)(C)NC(=O)c1cc(NC(=O)NCc2ccccc2)ccn1]

A mixture of isocyanatomethylbenzene (72 μL, 0.52 mmol) and 4-amino-N-tert-butyl-pyridine-2-carboxamide (Example 3 step 1)(100 mg, 0.52 mmol) in anhydrous DMF (1 mL) was stirred at 80° C. overnight. The resulting mixture was concentrated in vacuo and the residue partitioned between EtOAc (2 mL) and brine (2 mL). The organic portion was separated and the aqueous layer was re-extracted with EtOAc (2 mL). The combined organic extracts were dried over Na$_2$SO$_4$, filtered and concentrated in vacuo. The residue was dissolved in DMSO:MeCN:H$_2$O (1.1 mL, 5:4:1), filtered and purified by preparative HPLC (acidic pH, early elution method) to afford the titled compound as an off-white solid.

1H NMR (250 MHz, DMSO-d6) δ 9.34 (s, 1H), 8.31 (d, J=5.6 Hz, 1H), 8.05-7.97 (m, 2H), 7.62 (dd, J=5.6, 2.3 Hz, 1H), 7.38-7.20 (m, 5H), 6.97 (t, J=5.9 Hz, 1H), 4.32 (d, J=5.9 Hz, 2H), 1.39 (s, 9H).

LC-MS (Method A): Rt 2.74 mins; MS m/z 327.3=[M+H]+ (98% @ 215 nm)

The compounds of the following tabulated Examples (Table 13) were prepared from 4-amino-N-tert-butyl-pyridine-2-carboxamide (Example 3 step 1) and the appropriate isocyanate analogously to Example 64

TABLE 13

| Ex. | Structure and Name | 1H NMR LCMS Retention Time, [M + H]+, |
|---|---|---|
| 64.1 | 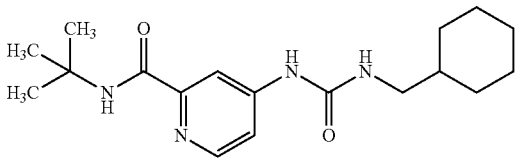<br>N-tert-Butyl-4-(cyclohexylmethylcarbamoyl amino)pyridine-2-carboxamide | 1H NMR (250 MHz, DMSO-d6) δ 9.10 (s, 1H), 8.30 (d, J = 5.5 Hz, 1H), 8.01 (s, 1H), 7.96 (d, J = 2.0 Hz, 1H), 7.58 (dd, J = 5.6, 2.3 Hz, 1H), 6.43 (t, J = 5.8 Hz, 1H), 2.96 (t, J = 6.3 Hz, 2H), 1.75-1.55 (m, 5H), 1.48-1.31 (m, 10H), 1.29-1.08 (m, 3H), 0.99-0.80 (m, 2H).<br>LC-MS (Method A): Rt 3.21 mins; MS m/z 333.3 = [M + H]+ (98% @ 215 nm) |
| 64.2 | 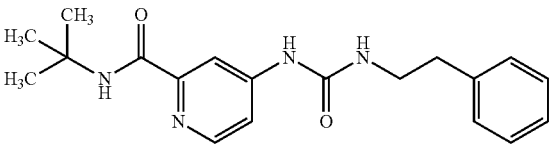<br>N-tert-Butyl-4-(2-phenylethylcarbamoyl amino)pyridine-2-carboxamide | 1H NMR (500 MHz, DMSO-d6) δ 9.23 (s, 1H), 8.30 (d, J = 5.6 Hz, 1H), 8.01 (s, 1H), 7.97 (d, J = 2.1 Hz, 1H), 7.60 (dd, J = 5.6, 2.2 Hz, 1H), 7.33-7.29 (m, 2H), 7.26-7.17 (m, 3H), 6.42 (t, J = 5.6 Hz, 1H), 3.39-3.34 (m, 2H), 2.77 (t, J = 7.2 Hz, 2H), 1.39 (s, 9H).<br>LC-MS (Method A): Rt 2.91 mins; MS m/z 341.3 = [M + H]+ (95% @ 215 nm) |
| 64.3 | 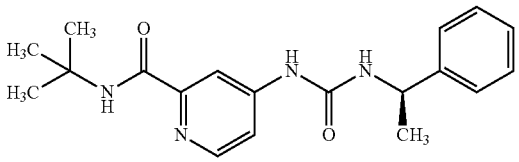<br>N-tert-Butyl-4-[[(1R)-1-phenylethyl]carbamoyl amino]pyridine-2-carboxamide | 1H NMR (500 MHz, DMSO-d6) δ 9.10 (s, 1H), 8.30 (d, J = 5.6 Hz, 1H), 8.00 (s, 1H), 7.95 (d, J = 2.2 Hz, 1H), 7.57 (dd, J = 5.6, 2.3 Hz, 1H), 7.37-7.33 (m, 4H), 7.26-7.22 (m, 1H), 6.93 (d, J = 7.8 Hz, 1H), 4.84 (p, J = 7.0 Hz, 1H), 1.41 (d, J = 7.0 Hz, 3H), 1.38 (s, 9H).<br>LC-MS (Method A): Rt 2.92 mins; MS m/z 341.4 = [M + H]+ (98% @ 215 nm) |
| 64.4 | 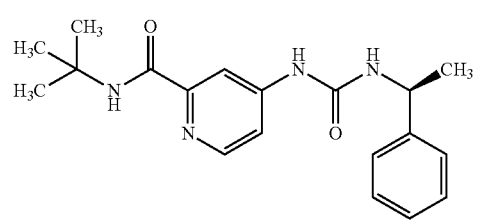<br>N-tert-Butyl-4-[[(1S)-1-phenylethyl] carbamoylamino]pyridine-2-carboxamide | 1H NMR (500 MHz, Methanol-d4) δ 8.34 (d, J = 5.7 Hz, 1H), 7.94-7.89 (m, 1H), 7.75 (dd, J = 5.7, 2.1 Hz, 1H), 7.41-7.31 (m, 4H), 7.30-7.22 (m, 1H), 4.95 (q, J = 7.0 Hz, 1H), 1.51 (d, J = 7.0 Hz, 3H), 1.48 (s, 9H).<br>LC-MS (Method A): Rt 2.91 mins; MS m/z 341.3 = [M + H]+ (99% @ 215 nm) |
| 64.5 | 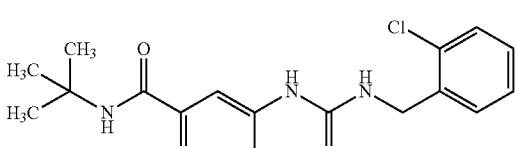<br>N-tert-Butyl-4-[(2-chlorophenyl) methylcarbamoylamino]pyridine-2-carboxamide | 1H NMR (500 MHz, Methanol-d4) δ 8.34 (d, J = 5.3 Hz, 1H), 7.92 (s, 1H), 7.79-7.73 (m, 1H), 7.45 (dd, J = 7.4, 1.8 Hz, 1H), 7.42 (dd, J = 7.6, 1.6 Hz, 1H), 7.35-7.24 (m, 2H), 4.52 (s, 2H), 1.48 (s, 9H).<br>LC-MS (Method A): Rt 3.07 mins; MS m/z 361.2/363.2 = [M + H]+ (100% @ 215 nm) |

TABLE 13-continued

| Ex. | Structure and Name | 1H NMR<br>LCMS Retention Time, [M + H]+, |
|---|---|---|
| 64.6 | 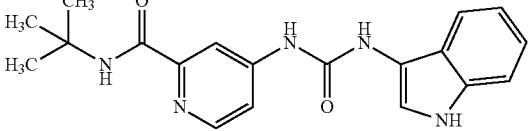<br>N-tert-butyl-4-(1H-indol-3-ylcarbamoyl amino)pyridine-2-carboxamide | 1H NMR (500 MHz, Methanol-d4) δ 8.38 (d, J = 5.6 Hz, 1H), 8.29 (s, 1H), 7.99 (d, J = 2.0 Hz, 1H), 7.85 (dd, J = 5.6, 2.2 Hz, 1H), 7.55 (dt, J = 8.1, 0.9 Hz, 1H), 7.50 (s, 1H), 7.40-7.35 (m, 1H), 7.19-7.12 (m, 1H), 7.11-7.03 (m, 1H), 1.50 (s, 9H).<br>LC-MS (Method A): Rt 2.68 mins; MS m/z 352.3 = [M + H]+ (99% @ 215 nm) |
| 64.7 | 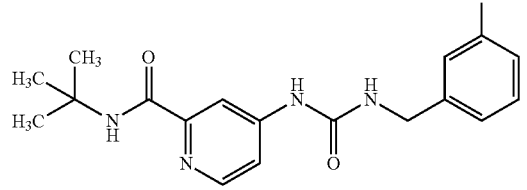<br>N-tert-Butyl-4-[(3-chlorophenyl)methyl carbamoylamino]pyridine-2-carboxamide | 1H NMR (500 MHz, Methanol-d4) δ 8.38-8.33 (m, 1H), 7.96-7.91 (m, 1H), 7.77 (dd, J = 5.6, 2.3 Hz, 1H), 7.38 (s, 1H), 7.38 (t, J = 1.5 Hz, 1H), 7.31-7.25 (m, 2H), 4.42 (s, 2H), 1.49 (s, 9H).<br>LC-MS (Method A): Rt 3.12 mins; MS m/z 361.3/363.3 = [M + H]+ (100% @ 215 nm) |
| 64.8 | 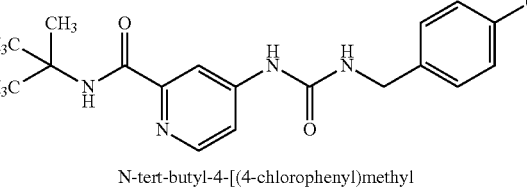<br>N-tert-butyl-4-[(4-chlorophenyl)methyl carbamoylamino]pyridine-2-carboxamide | 1H NMR (500 MHz, Methanol-d4) δ 8.37-8.32 (m, 1H), 7.95-7.91 (m, 1H), 7.77 (dd, J = 5.6, 2.3 Hz, 1H), 7.35 (s, 4H), 4.41 (s, 2H), 1.49 (s, 9H).<br>LC-MS (Method A): Rt 3.12 mins; MS m/z 361.3/363.2 = [M + H]+ (100% @ 215 nm) |

Example 65

N-tert-Butyl-4-[(2-hydroxyphenyl)carbamoylamino]pyridine-2-carboxamide

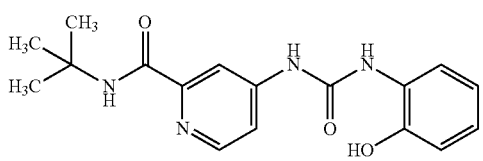 [SMILES: CC(C)(C)NC(=O)c1cc(NC(=O)Nc2ccccc2O)ccn1]

Step 1: N-tert-Butyl-4-[(2-methoxyphenyl)carbamoylamino]pyridine-2-carboxamide

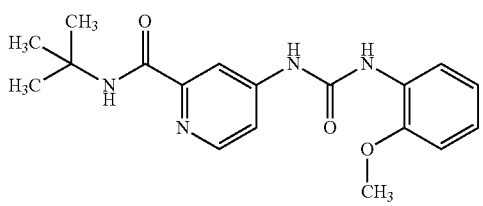 [SMILES: COc1ccccc1NC(=O)Nc1ccnc(C(=O)NC(C)(C)C)c1]

The titled compound was prepared from 1-isocyanato-2-methoxy-benzene and 4-amino-N-tert-butyl-pyridine-2-carboxamide (Example 3 step 1) analogously to Example 64.

1H NMR (500 MHz, DMSO-d6) δ 9.95 (s, 1H), 8.43-8.37 (m, 2H), 8.11 (dd, J=8.0, 1.6 Hz, 1H), 8.06-8.03 (m, 2H), 7.63 (dd, J=5.5, 2.3 Hz, 1H), 7.06-6.98 (m, 2H), 6.92 (td, J=7.8, 1.5 Hz, 1H), 3.89 (s, 3H), 1.41 (s, 9H).

LC-MS (Method A): Rt 3.21 mins; MS m/z 343.2=[M+H]+ (100% @ 215 nm)

Step 2: N-tert-Butyl-4-[(2-hydroxyphenyl)carbamoylamino]pyridine-2-carboxamide N-tert-Butyl-4-[(2-methoxyphenyl)carbamoylamino]pyridine-2-carboxamide (step 1) (41 mg, 0.12 mmol) was added to a suspension of 1M BBr₃ in DCM (532 μL, 0.53 mmol) in DCM (1 mL) at 0° C.-5° C. After stirring at room temperature for 2.5 hours, the mixture was concentrated in vacuo and the residue partitioned between EtOAc (4 mL) and water (4 mL). The pH of the aqueous layer was adjusted to pH 5-6 with sat. aq. NaHCO₃ and the organic layer separated, washed with brine (2 mL), dried over Na₂SO₄ and concentrated in vacuo. The residue was dissolved in MeCN:H₂O (1.1 mL, 4:1), filtered and purified by preparative HPLC (acidic pH, early elution method) to afford the titled compound as a beige solid.

1H NMR (250 MHz, DMSO-d6) δ 10.38-9.64 (m, 2H), 8.50-8.26 (m, 2H), 8.07-7.99 (m, 3H), 7.63 (dd, J=5.6, 2.3 Hz, 1H), 6.89-6.72 (m, 3H), 1.40 (s, 9H).

LC-MS (Method A): Rt 2.72 mins; MS m/z 329.3=[M+H]+ (100% @ 215 nm)

Example 65.1

N-tert-Butyl-4-[(2-methoxyphenyl)methylcarbamoylamino]pyridine-2-carboxamide

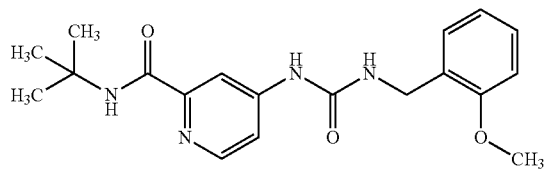 [SMILES: COc1ccccc1CNC(=O)Nc1ccnc(C(=O)NC(C)(C)C)c1]

The titled compound was prepared from 4-amino-N-tert-butyl-pyridine-2-carboxamide (Example 3 step 1) and 1-(isocyanatomethyl)-2-methoxy-benzene analogously to Example 65 step 1.

1H NMR (500 MHz, DMSO-d6) δ 9.33 (s, 1H), 8.31 (d, J=5.6 Hz, 1H), 8.02 (s, 1H), 7.98 (d, J=2.1 Hz, 1H), 7.60 (dd, J=5.6, 2.3 Hz, 1H), 7.29-7.21 (m, 2H), 7.03-6.99 (m, 1H), 6.94-6.88 (m, 1H), 6.75 (t, J=5.9 Hz, 1H), 4.28 (d, J=5.9 Hz, 2H), 3.84 (s, 3H), 1.40 (s, 9H).

LC-MS (Method A): Rt 2.86 mins; MS m/z 357.3=[M+H]+ (99% @ 215 nm)

Example 65.2

N-tert-Butyl-4-[(2-hydroxyphenyl)methylcarbamoylamino]pyridine-2-carboxamide

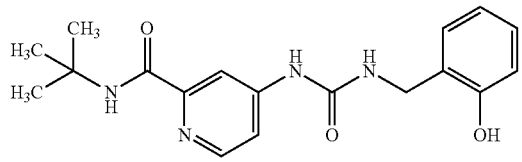 [SMILES: CC(C)(C)NC(=O)c1cc(NC(=O)NCc2ccccc2O)ccn1]

The titled compound was prepared from N-tert-butyl-4-[(2-methoxyphenyl)methylcarbamoylamino]pyridine-2-carboxamide (Example 65.1) analogously to Example 65 step 2

1H NMR (500 MHz, DMSO-d6) δ 9.60 (s, 1H), 9.31 (s, 1H), 8.31 (d, J=5.6 Hz, 1H), 8.01 (s, 1H), 7.96 (d, J=2.1 Hz, 1H), 7.60 (dd, J=5.6, 2.3 Hz, 1H), 7.16 (dd, J=7.5, 1.5 Hz, 1H), 7.08 (td, J=7.8, 1.7 Hz, 1H), 6.82 (dd, J=8.0, 1.0 Hz, 1H), 6.76 (td, J=7.4, 1.1 Hz, 1H), 6.72 (t, J=5.9 Hz, 1H), 4.24 (d, J=5.8 Hz, 2H), 1.39 (s, 9H).

LC-MS (Method A): Rt 2.56 mins; MS m/z 343.2=[M+H]+ (97% @ 215 nm)

Example 65.3

N-tert-Butyl-4-[(3-hydroxyphenyl)methylcarbamoylamino]pyridine-2-carboxamide

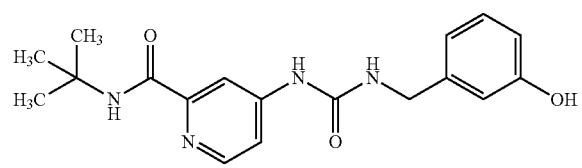 [SMILES: CC(C)(C)NC(=O)c1cc(NC(=O)NCc2cccc(O)c2)ccn1]

The titled compound was prepared from 4-amino-N-tert-butyl-pyridine-2-carboxamide (Example 3 step 1) and 1-(isocyanatomethyl)-3-methoxy-benzene analogously to Example 65 steps 1 and 2.

1H NMR (500 MHz, Methanol-d4) δ 8.34 (d, J=5.6 Hz, 1H), 7.92 (d, J=2.1 Hz, 1H), 7.77 (dd, J=5.6, 2.2 Hz, 1H), 7.16 (t, J=7.8 Hz, 1H), 6.83-6.77 (m, 2H), 6.72-6.65 (m, 1H), 4.35 (s, 2H), 1.48 (s, 9H).

LC-MS (Method A): Rt 2.24 mins; MS m/z 343.3=[M+H]+ (96% @ 215 nm)

Example 65.4

N-tert-Butyl-4-[(4-hydroxyphenyl)methylcarbamoylamino]pyridine-2-carboxamide

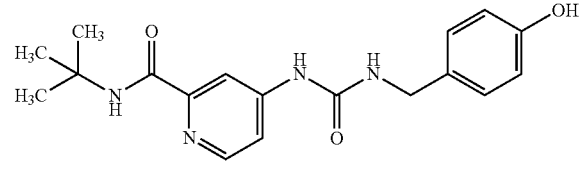 [SMILES: CC(C)(C)NC(=O)c1cc(NC(=O)NCc2ccc(O)cc2)ccn1]

The titled compound was prepared from 4-amino-N-tert-butyl-pyridine-2-carboxamide (Example 3 step 1) and 1-(isocyanatomethyl)-4-methoxy-benzene analogously to Example 65 steps 1 and 2.

1H NMR (500 MHz, Methanol-d4) δ 8.34 (d, J=5.6 Hz, 1H), 7.91 (d, J=1.9 Hz, 1H), 7.77 (dd, J=5.6, 2.3 Hz, 1H), 7.21-7.14 (m, 2H), 6.80-6.73 (m, 2H), 4.31 (s, 2H), 1.48 (s, 9H).

LC-MS (Method A): Rt 2.16 mins; MS m/z 343.3=[M+H]+ (98% @ 215 nm)

Example 66

N-tert-Butyl-4-[[2-[2-hydroxy-5-(1-hydroxyethyl)phenyl]acetyl]amino]pyridine-2-carboxamide

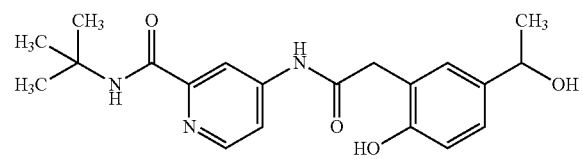 [SMILES: CC(O)c1ccc(O)c(CC(=O)Nc2ccnc(C(=O)NC(C)(C)C)c2)c1]

Step 1: 4-[[2-(5-Acetyl-2-methoxy-phenyl)acetyl]amino]-N-tert-butyl-pyridine-2-carboxamide

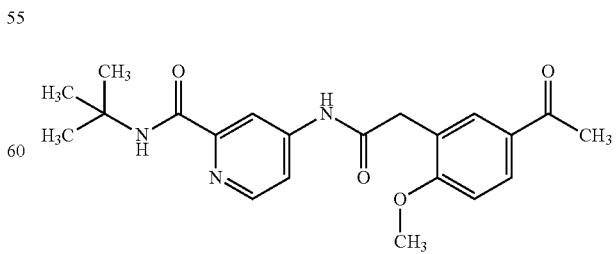

4-[[2-(5-Bromo-2-methoxy-phenyl)acetyl]amino]-N-tert-butyl-pyridine-2-carboxamide (Example 6, step 1) (985 mg, 2.34 mmol), ZnF₂ (218 mg, 1.87 mmol) and Pd(dba)₂ (135 mg, 0.23 mmol) were dissolved in anhydrous DMF (10 mL) at room temperature and degassed with N₂ in a sealed pressure vial. To the mixture was added tri-tert-butylphosphine (1M in toluene, 0.47 mL, 0.47 mmol) followed by trimethyl(vinyloxy)silane (0.42 mL, 2.81 mmol) and the vial heated at 70° C. overnight. Additional trimethyl(vinyloxy)silane (105 µL, 0.70 mmol) was added and the mixture heated at 70° C. for a further 4 hours. After cooling to room temperature, the mixture was diluted with TBME (40 mL) and filtered through a pad of kieselguhr. The filtrate was concentrated in vacuo and purification of the residue by chromatography on silica eluting with 0-100% TBME in heptane afforded the titled compound as a yellow solid.

1H NMR (500 MHz, Chloroform-d) δ 8.40-8.37 (m, 1H), 8.21 (dd, J=5.6, 2.2 Hz, 1H), 7.99-7.92 (m, 3H), 7.83 (s, 1H), 7.53 (d, J=2.2 Hz, 1H), 7.02 (d, J=8.6 Hz, 1H), 4.02 (s, 3H), 3.78 (s, 2H), 2.58 (s, 3H), 1.47 (s, 9H).

LC-MS (Method E): Rt 1.11 mins, MS m/z 384.1=[M+H]+ (78% @ 215 nm)

Step 2: N-tert-Butyl-4-[[2-[5-(1-hydroxyethyl)-2-methoxyphenyl]acetyl]amino]pyridine-2-carboxamide

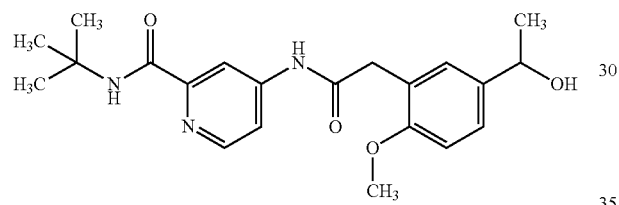

A solution of 4-[[2-(5-acetyl-2-methoxy-phenyl)acetyl]amino]-N-tert-butyl-pyridine-2-carboxamide (step 1) (45 mg, 0.09 mmol) in MeOH (1 mL) was treated with NaBH₄ (4 mg, 0.1 mmol) and stirred at room temperature for 2 hours. The reaction was quenched by addition to 10% aq. H₃PO₄ (1 mL) and the mixture extracted with EtOAc (2×2 mL). The combined organic extracts were washed with water (2 mL) and brine (2 mL), dried over Na₂SO₄ and concentrated in vacuo to afford the titled compound as an off-white solid.

1H NMR (500 MHz, DMSO-d6) δ 10.66 (s, 1H), 8.44 (d, J=5.5 Hz, 1H), 8.19 (d, J=2.0 Hz, 1H), 8.04 (s, 1H), 7.81 (dd, J=5.5, 2.2 Hz, 1H), 7.23-7.17 (m, 2H), 6.94-6.89 (m, 1H), 4.65 (q, J=6.4 Hz, 1H), 3.73 (s, 3H), 3.68 (s, 2H), 1.40 (s, 9H), 1.29 (d, J=6.4 Hz, 3H)

LC-MS (Method E): Rt 1.06 mins; MS m/z 386.1=[M+H]+ (97% @ 215 nm)

Step 3: N-tert-Butyl-4-[[2-[2-hydroxy-5-(1-hydroxyethyl)phenyl]acetyl]amino]pyridine-2-carboxamide N-tert-butyl-4-[[2-[5-(1-hydroxyethyl)-2-methoxy-phenyl]acetyl]amino]pyridine-2-carboxamide (step 2) (39 mg, 0.09 mmol) was added to a suspension of 1M BBr₃ in DCM (303 µL, 0.3 mmol) in DCM (1 mL) in DCM (1 mL) at 0-5° C. After stirring at room temperature for 2 hours, the mixture was concentrated in vacuo and the residue partitioned between EtOAc (4 mL) and water (4 mL). The pH of the aqueous layer was adjusted to pH 5-6 with sat. aq. NaHCO₃ and the organic layer separated, washed with brine (2 mL), dried over Na₂SO₄ and concentrated in vacuo. The residue was dissolved in MeCN:H₂O (1.1 mL, 4:1), filtered and purified by preparative HPLC (acidic pH, early elution method) to afford the titled compound as a beige powder.

1H NMR (500 MHz, DMSO-d6) δ 10.64 (br. s, 1H), 9.34 (br. s, 1H), 8.43 (d, J=5.5 Hz, 1H), 8.18 (d, J=1.9 Hz, 1H), 8.03 (s, 1H), 7.82 (dd, J=5.5, 2.2 Hz, 1H), 7.12 (d, J=2.1 Hz, 1H), 7.03 (dd, J=8.2, 2.2 Hz, 1H), 6.73 (d, J=8.2 Hz, 1H), 4.93 (d, J=4.1 Hz, 1H), 4.63-4.57 (m, 1H), 3.64 (s, 2H), 1.40 (s, 9H), 1.27 (d, J=6.4 Hz, 3H).

LC-MS (Method A): Rt 2.45 mins; MS m/z 372.3=[M+H]+ (99% @ 215 nm)

Example 67

N-tert-Butyl-4-[[2-[2-hydroxy-5-[1-(2,2,2-trifluoroethylamino)ethyl]phenyl]acetyl]amino]pyridine-2-carboxamide

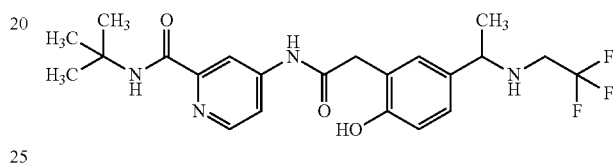

Step 1: N-tert-Butyl-4-[[2-[2-methoxy-5-[1-(2,2,2-trifluoroethylamino)ethyl]phenyl]acetyl]amino]pyridine-2-carboxamide

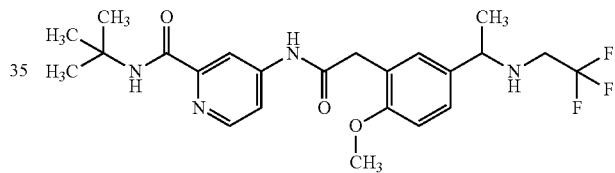

To a solution of 4-[[2-(5-acetyl-2-methoxy-phenyl)acetyl]amino]-N-tert-butyl-pyridine-2-carboxamide (Example 66 step 1)(73 mg, 0.15 mmol) in dichloroethane (1.5 mL) was added the 2,2,2-trifluoroethanamine (14 µL, 0.18 mmol) and acetic acid (17 µL, 0.3 mmol) and the mixture was stirred at room temperature for 30 mins. Sodium triacetoxyborohydride (40 mg, 0.19 mmol) was added and the reaction mixture stirred at room temperature overnight. The resulting mixture was concentrated in vacuo and the residue dissolved in EtOAc (4 mL). The mixture was washed with sat. aq. NaHCO₃ (4 mL), brine (4 mL), dried over Na₂SO₄ and concentrated in vacuo. The residue was purified by preparative HPLC (acidic pH, early elution method) and the product fractions were combined and the pH was adjusted to pH8 using sat. aq. NaHCO₃. The mixture was extracted with DCM using a hydrophobic phase separator and the filtrate was concentrated in vacuo to afford the titled compound as an off-white solid.

LC-MS (Method E): Rt 1.07 mins; MS m/z 467.2=[M+H]+ (99% @ 215 nm)

Step 2: N-tert-Butyl-4-[[2-[2-hydroxy-5-[1-(2,2,2-trifluoroethylamino)ethyl]phenyl]acetyl]amino]pyridine-2-carboxamide The titled compound was prepared from N-tert-Butyl-4-[[2-[2-methoxy-5-[1-(2,2,2-trifluoroethylamino)ethyl]phenyl]acetyl]amino]pyridine-2-carboxamide (step 1) analogously to Example 66 step 3.

1H NMR (500 MHz, DMSO-d6) δ 10.63 (s, 1H), 9.39 (s, 1H), 8.43 (d, J=5.5 Hz, 1H), 8.18 (d, J=2.1 Hz, 1H), 8.03 (s, 1H), 7.82 (dd, J=5.5, 2.2 Hz, 1H), 7.08 (d, J=2.0 Hz, 1H), 7.04 (dd, J=8.2, 2.2 Hz, 1H), 6.75 (d, J=8.2 Hz, 1H), 3.71-3.62 (m, 3H), 3.03-2.91 (m, 2H), 2.67 (q, J=8.7, 8.1 Hz, 1H), 1.40 (s, 9H), 1.23 (d, J=6.6 Hz, 3H).

LC-MS (Method A): Rt 2.22 mins; MS m/z 453.3=[M+H]+ (97% @ 215 nm)

Example 68

N-tert-Butyl-4-[[2-[3-(cyanomethyl)phenyl]acetyl]amino]pyridine-2-carboxamide

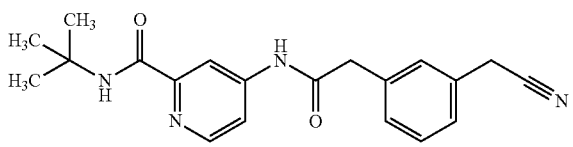 [SMILES: CC(C)(C)NC(=O)c1cc(NC(=O)Cc2cccc(CC#N)c2)ccn1]

Step 1: 4-[[2-[3-(Bromomethyl)phenyl]acetyl]amino]-N-tert-butyl-pyridine-2-carboxamide

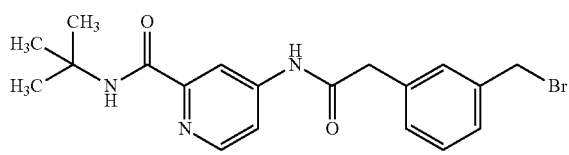 [SMILES: CC(C)(C)NC(=O)c1cc(NC(=O)Cc2cccc(CBr)c2)ccn1]

The titled compound was prepared from 2-[3-(bromomethyl)phenyl]acetic acid and 4-amino-N-tert-butyl-pyridine-2-carboxamide (Example 3 step 1) analogously to Example 3.5b step 1.

LC-MS (Method E): Rt 1.20 mins; MS m/z 404.0/406.0=[M+H]+ (44% @ 215 nm)

Step 2: N-tert-Butyl-4-[[2-[3-(cyanomethyl)phenyl]acetyl]amino]pyridine-2-carboxamide 4-[[2-[3-(Bromomethyl)phenyl]acetyl]amino]-N-tert-butyl-pyridine-2-carboxamide (Step 1) (50 mg, 0.05 mmol) was treated with sodium cyanide (5 mg, 0.11 mmol) and tetrabutylammonium bromide (2 mg, 0.01 mmol) in a 1:1 mixture of DCM:water (2 mL) and stirred at room temperature for 18 hours. The resulting mixture was diluted with sat. aq. NaHCO3 (5 mL) and extracted into DCM (3×5 mL). The combined organic extracts were concentrated in vacuo and the residue was dissolved in DMSO:MeCN (800 μl, 1:1), filtered and purified by preparative HPLC (acidic pH, early elution method) to afford the titled compound as a colourless glassy solid.

1H NMR (500 MHz, DMSO-d6) δ 10.78 (s, 1H), 8.45 (d, J=5.5 Hz, 1H), 8.18 (d, J=2.0 Hz, 1H), 8.02 (s, 1H), 7.81 (dd, J=5.5, 2.2 Hz, 1H), 7.36 (t, J=7.6 Hz, 1H), 7.33-7.28 (m, 2H), 7.24 (d, J=7.7 Hz, 1H), 4.04 (s, 2H), 3.74 (s, 2H), 1.39 (s, 9H).

LC-MS (Method A): Rt 3.04 mins; MS m/z 351.2=[M+H]+ (96% @ 215 nm)

Example 69

N-tert-Butyl-4-[[2-[3-(methoxymethyl)phenyl]acetyl]amino]pyridine-2-carboxamide

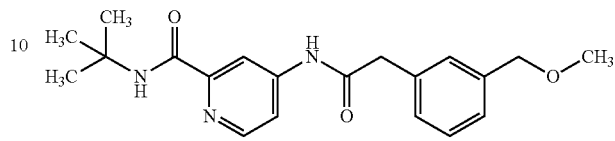

A vessel was charged with 4-[[2-(3-bromophenyl)acetyl]amino]-N-tert-butyl-pyridine-2-carboxamide (Example 54 step 1)(50 mg, 0.13 mmol) PdCl2dppf (3 mg), potassium trifluoro(methoxymethyl)boranuide (0.45 mL, 0.26 mmol) 2M aq. sodium carbonate (0.26 mL, 0.51 mmol) and heated at 80° C. for 16 hours. The mixture was allowed to cool to room temperature, poured onto water (20 mL) and extracted into EtOAc (3×20 mL). The combined organic extracts were washed with brine (50 mL), dried over Na2SO4 and concentrated in vacuo. The residue was dissolved in DMSO:MeCN (800 μl, 1:1), filtered and purified by preparative HPLC (acidic pH, early elution method) to afford the titled compound as an off-white solid.

1H NMR (500 MHz, DMSO-d6) δ 10.76 (s, 1H), 8.44 (d, J=5.5 Hz, 1H), 8.18 (d, J=2.1 Hz, 1H), 8.02 (s, 1H), 7.81 (dd, J=5.5, 2.2 Hz, 1H), 7.34-7.27 (m, 2H), 7.25 (d, J=7.7 Hz, 1H), 7.20 (d, J=7.5 Hz, 1H), 4.40 (s, 2H), 3.71 (s, 2H), 3.29 (s, 3H), 1.39 (s, 9H).

LC-MS (Method C): Rt 3.18 mins; MS m/z 356.3=[M+H]+ (94% @ 215 nm)

Example 70

N-tert-Butyl-4-[[2-[2-hydroxy-5-(morpholinomethyl)phenyl]acetyl]amino]pyridine-2-carboxamide

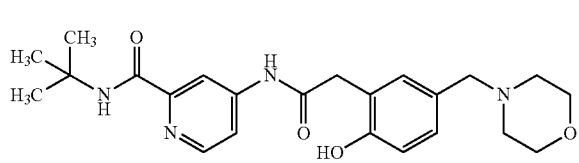 [SMILES: CC(C)(C)NC(=O)c1cc(NC(=O)Cc2cc(CN3CCOCC3)ccc2O)ccn1]

The titled compound was prepared from 4-[[2-(5-bromo-2-methoxy-phenyl)acetyl]amino]-N-tert-butyl-pyridine-2-carboxamide (Example 6 step 1) and potassium trifluoro(morpholinomethyl)boranuide analogously to Example 27 steps 3 and 4.

1H NMR (500 MHz, DMSO-d6) δ 10.64 (br s, 1H), 9.43 (br s, 1H), 8.43 (d, J=5.5 Hz, 1H), 8.18 (d, J=2.1 Hz, 1H), 8.03 (s, 1H), 7.81 (dd, J=5.5, 2.2 Hz, 1H), 7.06 (d, J=2.0 Hz, 1H), 6.99 (dd, J=8.1, 2.1 Hz, 1H), 6.74 (d, J=8.1 Hz, 1H), 3.64 (s, 2H), 3.55-3.51 (m, 4H), 2.34-2.25 (m, 4H), 1.40 (s, 9H).

LC-MS (Method A): Rt 1.66 mins; MS m/z 427.4=[M+H]+ (98% @ 215 nm)

Example 71

3-[[2-(5-Chloro-2-hydroxy-phenyl)acetyl]amino]-N-(3-cyanotetrahydrofuran-3-yl)benzamide

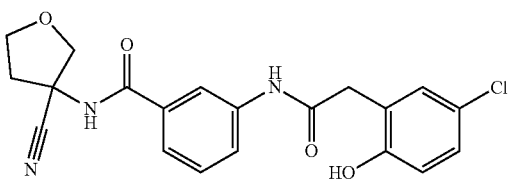 [SMILES: N#CC1(NC(=O)c2cccc(NC(=O)Cc3cc(Cl)ccc3O)c2)CCOC1]

Step 1: Methyl 3-[[2-(5-chloro-2-methoxy-phenyl)acetyl]amino]benzoate

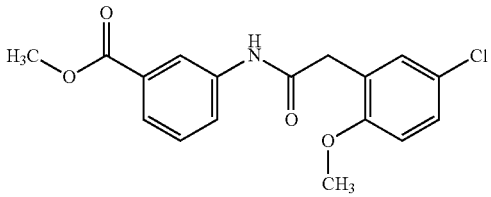

A solution comprising methyl 3-aminobenzoate (1 g, 6.62 mmol) and 2-(5-chloro-2-methoxy-phenyl)acetic acid (1.39 g, 6.95 mmol) in DMF (10 mL) was treated with DIPEA (1.73 mL, 9.92 mmol) followed by HATU (3019 mg, 7.94 mmol) and stirred at room temperature for 1 hour. The resulting mixture was diluted with water (50 mL) and EtOAc (60 mL) to form a biphasic solution. Heptane (15 ml) was added and the organic portion was separated, washed with water, dried over $Na_2SO_4$ and concentrated in vacuo. The residue was treated with TBME (50 ml) and the resultant suspension filtered, washing with through with TBME and dried in vacuo to afford the titled compound as an off-white powdery solid.

1H NMR (500 MHz, DMSO-d6) δ 10.31 (s, 1H), 8.28 (t, J=1.8 Hz, 1H), 7.84-7.80 (m, 1H), 7.63 (dt, J=7.7, 1.2 Hz, 1H), 7.45 (t, J=7.9 Hz, 1H), 7.29 (dd, J=6.5, 2.9 Hz, 2H), 7.03-6.98 (m, 1H), 3.84 (s, 3H), 3.76 (s, 3H), 3.66 (s, 2H).

LC-MS (Method E): Rt 1.17 mins; MS m/z 334.0/336.0= [M+H]+ (98% @ 215 nm)

Step 2: 3-[[2-(5-Chloro-2-methoxy-phenyl)acetyl]amino]benzoic acid

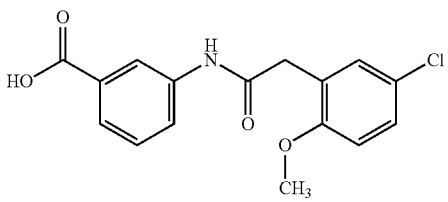

The titled compound was prepared from methyl 3-[[2-(5-chloro-2-methoxy-phenyl)acetyl]amino]benzoate (step 1) analogously to Example 41 step 2.

1H NMR (500 MHz, DMSO-d6) δ 12.82 (s, 1H), 10.26 (s, 1H), 8.22 (s, 1H), 7.81 (dd, J=8.1, 1.1 Hz, 1H), 7.61 (dt, J=7.7, 1.2 Hz, 1H), 7.41 (t, J=7.9 Hz, 1H), 7.29 (dd, J=6.9, 2.7 Hz, 2H), 7.03-6.98 (m, 1H), 3.76 (s, 3H), 3.66 (s, 2H).

LC-MS (Method E): Rt 1.06 mins; MS m/z 319.9/321.7= [M+H]+ (99% @ 215 nm)

Step 3: 3-[[2-(5-Chloro-2-hydroxy-phenyl)acetyl]amino]benzoic acid

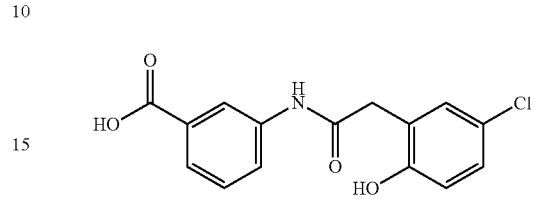

The titled compound was prepared from 3-[[2-(5-chloro-2-methoxy-phenyl)acetyl]amino]benzoic acid (step 2) analogously to Example 41 step 3.

1H NMR (500 MHz, DMSO-d6) δ 12.91 (br s, 1H), 10.25 (s, 1H), 9.78 (s, 1H), 8.23 (t, J=1.8 Hz, 1H), 7.82 (dd, J=8.1, 1.1 Hz, 1H), 7.61 (dt, J=7.7, 1.2 Hz, 1H), 7.42 (t, J=7.9 Hz, 1H), 7.21 (d, J=2.7 Hz, 1H), 7.11 (dd, J=8.6, 2.7 Hz, 1H), 6.80 (d, J=8.6 Hz, 1H), 3.62 (s, 2H).

LC-MS (Method E): Rt 1.01 mins; MS m/z 305.9/308.0= [M+H]+ (99% @ 215 nm)

Step 4: 3-[[2-(5-Chloro-2-hydroxy-phenyl)acetyl]amino]-N-(3-cyanotetrahydrofuran-3-yl)benzamide To a solution of 3-[[2-(5-Chloro-2-hydroxy-phenyl)acetyl]amino]benzoic acid (step 3) (150 mg, 0.49 mmol), 3-aminotetrahydrofuran-3-carbonitrile hydrochloride (73 mg, 0.49 mmol) and DIPEA (343 µL, 1.96 mmol) in DMF (1.5 mL) was added HATU (224 mg, 0.59 mmol) and the reaction mixture was stirred at room temperature for 16 hours. The resulting mixture was diluted with EtOAc and washed with 1M NaOH (3×20 mL). The aqueous layer was extracted into EtOAc (2×10 mL), then acidified with 1M HCl and the remaining product extracted into EtOAc (3×30 mL). The combined organic extracts were dried over $Na_2SO_4$ and concentrated in vacuo. Purification by preparative HPLC (acidic pH, early elution method) afforded the titled compound as an off-white solid.

1H NMR (500 MHz, DMSO-d6) δ 10.29 (s, 1H), 9.82 (br s, 1H), 9.21 (s, 1H), 8.08 (t, J=1.8 Hz, 1H), 7.81 (dd, J=8.1, 1.1 Hz, 1H), 7.53 (d, J=8.0 Hz, 1H), 7.43 (t, J=7.9 Hz, 1H), 7.21 (d, J=2.7 Hz, 1H), 7.11 (dd, J=8.6, 2.7 Hz, 1H), 6.81 (d, J=8.6 Hz, 1H), 4.26 (d, J=9.5 Hz, 1H), 3.96 (d, J=9.5 Hz, 1H), 3.94-3.86 (m, 2H), 3.62 (s, 2H), 2.62-2.55 (m, 2H).

LC-MS (Method A): Rt 2.64 mins; MS m/z 400.3/402.2= [M+H]+ (99% @ 215 nm)

Example 71.1

3-[[2-(5-Chloro-2-hydroxy-phenyl)acetyl]amino]-N-(1-methylcyclohexyl)benzamide

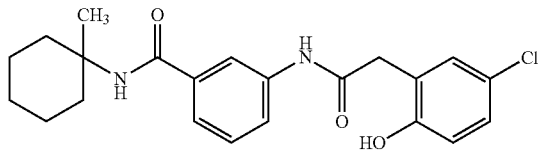 [SMILES: CC1(NC(=O)c2cccc(NC(=O)Cc3cc(Cl)ccc3O)c2)CCCCC1]

The titled compound was prepared from 3-[[2-(5-chloro-2-hydroxy-phenyl)acetyl]amino]benzoic acid (Example 71 step 3) and 1-methylcyclohexanamine analogously to Example 71.

1H NMR (500 MHz, Methanol-d4) δ 7.94 (t, J=1.8 Hz, 1H), 7.75-7.72 (m, 1H), 7.51-7.47 (m, 1H), 7.42 (t, J=7.9 Hz, 1H), 7.24 (d, J=2.6 Hz, 1H), 7.12 (dd, J=8.6, 2.6 Hz, 1H), 6.83 (s, 1H), 3.72 (s, 2H), 2.27 (d, J=13.1 Hz, 2H), 1.68-1.56 (m, 5H), 1.54-1.47 (m, 2H), 1.46 (s, 3H), 1.45-1.36 (m, 1H).

LC-MS (Method A): Rt 3.58 mins; MS m/z 401.2/403.2=[M+H]+ (96% @ 215 nm)

Example 72

4-[[2-(5-Fluoro-2-hydroxy-phenyl)acetyl]amino]-N-[3-(hydroxymethyl)tetrahydro furan-3-yl]pyridine-2-carboxamide

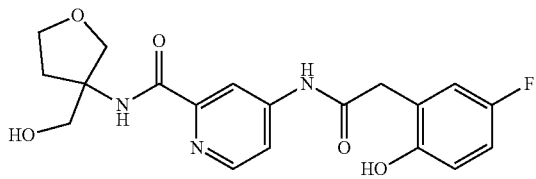 [SMILES: O=C(Cc1cc(F)ccc1O)Nc1ccnc(C(=O)NC2(CO)CCOC2)c1]

The titled compound was prepared from 4-[[2-(5-fluoro-2-hydroxy-phenyl)acetyl]amino]pyridine-2-carboxylic acid (Example 49 steps 1-3) and (3-aminotetrahydrofuran-3-yl)methanol analogously to Example 35.

1H NMR (500 MHz, DMSO-d6) δ 9.52 (br s, 1H), 8.47 (d, J=5.5 Hz, 1H), 8.42 (s, 1H), 8.20 (d, J=2.1 Hz, 1H), 7.83 (dd, J=5.5, 2.2 Hz, 1H), 7.02 (dd, J=9.4, 3.2 Hz, 1H), 6.91 (td, J=8.6, 3.2 Hz, 1H), 6.79-6.75 (m, 1H), 5.17 (s, 1H), 3.90-3.77 (m, 4H), 3.67 (s, 2H), 3.62 (s, 2H), 2.35-2.29 (m, 1H), 2.01-1.95 (m, 1H).

LC-MS (Method A): Rt 1.99 mins; MS m/z 390.2/392.3=[M+H]+ (100% @ 215 nm)

Example 73

4-[[2-(5-Chloro-2-hydroxy-phenyl)acetyl]amino]-N-[1-(hydroxymethyl)-2-methoxy-1-methyl-ethyl]pyridine-2-carboxamide

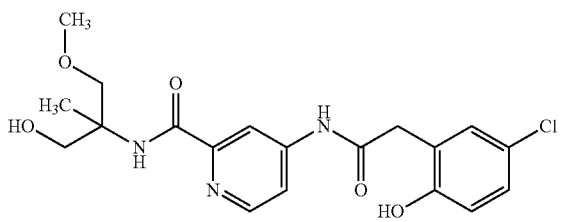 [SMILES: COCC(C)(CO)NC(=O)c1cc(NC(=O)Cc2cc(Cl)ccc2O)ccn1]

The titled compound was prepared from 4-[[2-(5-chloro-2-hydroxy-phenyl)acetyl]amino]pyridine-2-carboxylic acid (Example 31, step 1) and 2-amino-3-methoxy-2-methyl-propan-1-ol hydrochloride (prepared according to Tetrahedron, Volume 56, Issue 23, 2 Jun. 2000, Pages 3799-3816) analogously to Example 35.

1H NMR (500 MHz, Methanol-d4) δ 8.45 (dd, J=5.5, 0.5 Hz, 1H), 8.19-8.14 (m, 1H), 7.91 (dd, J=5.5, 2.2 Hz, 1H), 7.20 (d, J=2.6 Hz, 1H), 7.10 (dd, J=8.6, 2.6 Hz, 1H), 6.79 (d, J=8.6 Hz, 1H), 3.83 (d, J=11.1 Hz, 1H), 3.76-3.69 (m, 3H), 3.65 (d, J=9.1 Hz, 1H), 3.59 (d, J=9.1 Hz, 1H), 3.42 (s, 3H), 1.44 (s, 3H).

LC-MS (Method A): Rt 2.63 mins; MS m/z 408.2=[M+H]+ (99% @ 215 nm)

Example 73.1

4-[[2-(5-Chloro-2-hydroxy-phenyl)acetyl]amino]-N-(1,1-dimethylbut-2-ynyl)pyridine-2-carboxamide

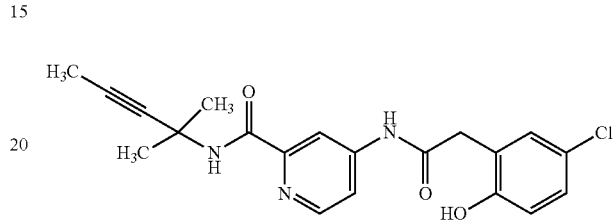

The titled compound was prepared from 4-[[2-(5-chloro-2-hydroxy-phenyl)acetyl]amino]pyridine-2-carboxylic acid (Example 31, step 1) and 2-methylpent-3-yn-2-amine hydrochloride (prepared according to WO 03048128 A1 page 55) analogously to Example 73.

1H NMR (500 MHz, DMSO-d6) δ 10.70 (br s, 1H), 9.81 (br s, 1H), 8.46 (d, J=5.5 Hz, 1H), 8.25 (s, 1H), 8.18 (d, J=2.0 Hz, 1H), 7.82 (dd, J=5.5, 2.2 Hz, 1H), 7.22 (d, J=2.7 Hz, 1H), 7.12 (dd, J=8.6, 2.7 Hz, 1H), 6.80 (d, J=8.6 Hz, 1H), 3.67 (s, 2H), 1.78 (s, 3H), 1.63 (s, 6H).

LC-MS (Method A): Rt 3.31 mins; MS m/z 386.3/388.2=[M+H]+ (97% @ 215 nm)

Example 74

3-[[2-(5-Chloro-2-hydroxy-phenyl)acetyl]amino]-N-(1,1-dimethylprop-2-ynyl)benzamide

2-Methylbut-3-yn-2-amine (49 mg, 0.59 mmol) and 3-[[2-(5-chloro-2-hydroxy-phenyl)acetyl]amino]benzoic acid (Example 71, step 3)(150 mg, 0.49 mmol) were dissolved in DMF (1 mL) and treated with TEA (0.26 mL, 1.47 mmol) followed by HATU (224 mg, 0.59 mmol) and stirred for 2 hours. The resulting mixture was diluted with EtOAc and washed with sat. aq. Na$_2$CO$_3$ (10 mL). The aqueous layer was extracted with EtOAc (2×10 mL) and the combined organic extracts were washed with 1M NaOH (3×20 mL). The aqueous layer was acidified with 1M HCl and the remaining product extracted into EtOAc (3×30 mL). The combined organic extracts were neutralised with a saturated aqueous sodium bicarbonate wash, dried over Na$_2$SO$_4$ and concentrated in vacuo. The crude residue was purified by preparative HPLC (acidic pH, early elution method) to afford the titled compound as an off-white foamy solid.

1H NMR (500 MHz, DMSO-d6) δ 10.21 (s, 1H), 9.79 (s, 1H), 8.20 (s, 1H), 7.94 (t, J=1.8 Hz, 1H), 7.80-7.74 (m, 1H), 7.47-7.42 (m, 1H), 7.36 (t, J=7.9 Hz, 1H), 7.20 (d, J=2.7 Hz, 1H), 7.11 (dd, J=8.6, 2.7 Hz, 1H), 6.80 (d, J=8.6 Hz, 1H), 3.61 (s, 2H), 3.08 (s, 1H), 1.59 (s, 6H).

LC-MS (Method A): Rt 2.92 mins; MS m/z 371.2/373.2= [M+H]+ (97% @ 215 nm)

Example 74.1

3-[[2-(5-Chloro-2-hydroxy-phenyl)acetyl]amino]-N-[3-(hydroxymethyl)tetra hydrofuran-3-yl]benzamide

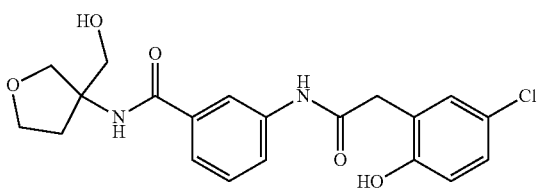 [SMILES: O=C(Cc1cc(Cl)ccc1O)Nc1cccc(C(=O)NC2(CO)CCOC2)c1]

The titled compound was prepared from 3-[[2-(5-chloro-2-hydroxy-phenyl)acetyl]amino]benzoic acid (Example 71, step 3) and (3-aminotetrahydrofuran-3-yl)methanol analogously to Example 74.

1H NMR (500 MHz, DMSO-d6) δ 10.20 (s, 1H), 9.80 (s, 1H), 8.12 (s, 1H), 7.95 (t, J=1.8 Hz, 1H), 7.81-7.74 (m, 1H), 7.53-7.47 (m, 1H), 7.36 (t, J=7.9 Hz, 1H), 7.20 (d, J=2.7 Hz, 1H), 7.11 (dd, J=8.6, 2.7 Hz, 1H), 6.80 (d, J=8.6 Hz, 1H), 4.97 (t, J=5.8 Hz, 1H), 3.89 (d, J=9.2 Hz, 1H), 3.81-3.73 (m, 3H), 3.67 (dd, J=10.8, 5.7 Hz, 1H), 3.64-3.59 (m, 3H), 2.23 (dt, J=12.8, 6.4 Hz, 1H), 2.05 (dt, J=12.9, 7.7 Hz, 1H).

LC-MS (Method A): Rt 2.24 mins; MS m/z 405.2/407.2= [M+H]+ (100% @ 215 nm)

Example 75

N-tert-Butyl-4-[[2-[2-hydroxy-5-(3-hydroxypropyl)phenyl]acetyl]amino]pyridine-2-carboxamide

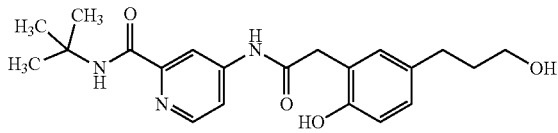 [SMILES: CC(C)(C)NC(=O)c1cc(NC(=O)Cc2cc(CCCO)ccc2O)ccn1]

Step 1: Ethyl (E)-3-[3-[2-[[2-(tert-butylcarbamoyl)-4-pyridyl]amino]-2-oxo-ethyl]-4-methoxy-phenyl]prop-2-enoate

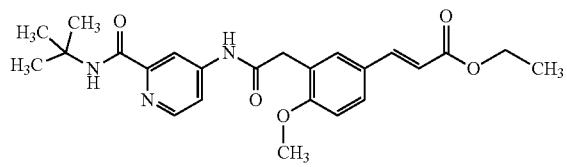 [SMILES: CCOC(=O)/C=C/c1ccc(OC)c(CC(=O)Nc2ccnc(C(=O)NC(C)(C)C)c2)c1]

A mixture comprising 4-[[2-(5-bromo-2-methoxy-phenyl)acetyl]amino]-N-tert-butyl-pyridine-2-carboxamide (Example 6 step 1)(500 mg, 1.19 mmol), ethyl prop-2-enoate (0.52 mL, 4.76 mmol), Pd₂(dba)₃ (109 mg, 0.12 mmol), tri-o-tolyl phosphine (109 mg, 0.36 mmol), TEA (1.04 mL, 5.95 mmol) in DMF (10 mL) under a nitrogen atmosphere was stirred at 90° C. for 18 hours. The resulting mixture was filtered, diluted with EtOAc (10 mL) and washed with brine (1×10 mL). The brine was re-extracted with EtOAc (2×10 mL) and the combined organic extracts were dried over Na₂SO₄ and concentrated in vacuo. The residue was purified by chromatography on silica eluting with 0-100% EtOAc in heptane to afford the titled compound as an orange/brown solid.

1H NMR (250 MHz, DMSO-d6) δ 10.69 (s, 1H), 8.44 (d, J=5.6 Hz, 1H), 8.19-8.16 (m, 1H), 8.03 (s, 1H), 7.81 (dd, J=5.5, 2.2 Hz, 1H), 7.67-7.60 (m, 2H), 7.56 (s, 1H), 7.04 (d, J=9.2 Hz, 1H), 6.46 (d, J=16.0 Hz, 1H), 4.17 (q, J=7.1 Hz, 2H), 3.80 (s, 3H), 3.72 (s, 2H), 1.40 (s, 9H), 1.25 (t, J=7.1 Hz, 3H).

LC-MS (Method E): Rt 1.23 mins; MS m/z 440.0=[M+ H]+ (65% @ 215 nm)

Step 2: Ethyl 3-[3-[2-[[2-(tert-butylcarbamoyl)-4-pyridyl]amino]-2-oxo-ethyl]-4-methoxy-phenyl]propanoate

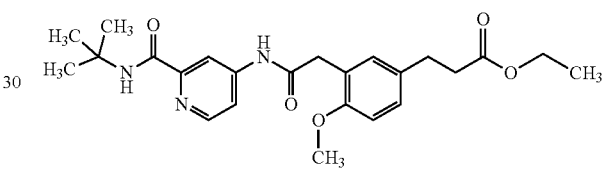

Ethyl (E)-3-[3-[2-[[2-(tert-butylcarbamoyl)-4-pyridyl]amino]-2-oxo-ethyl]-4-methoxy-phenyl]prop-2-enoate (step 1)(625 mg, 0.92 mmol) in EtOH (9.24 mL) under nitrogen, was treated with 10% Pd—C (50% w/w, 20 mg, 0.09 mmol) and placed under hydrogen. After stirring at room temperature for 19 hours, the mixture was filtered through kieselguhr (diatomaceous earth) and washed with through with EtOAc. The filtrate was concentrated in vacuo to afford the titled compound as an off-white solid.

1H NMR (250 MHz, DMSO-d6) δ 10.64 (s, 1H), 8.43 (d, J=5.5 Hz, 1H), 8.18 (d, J=1.8 Hz, 1H), 8.03 (s, 1H), 7.81 (dd, J=5.5, 2.2 Hz, 1H), 7.13-7.04 (m, 2H), 6.89 (d, J=8.3 Hz, 1H), 4.02 (qd, J=7.1, 1.1 Hz, 2H), 3.72 (s, 3H), 3.65 (s, 2H), 2.78 (t, J=7.4 Hz, 2H), 2.60-2.52 (m, 2H), 1.40 (s, 9H), 1.14 (t, J=7.2 Hz, 3H).

LC-MS (Method E): Rt 1.23 mins; MS m/z 442.3=[M+ H]+ (61% @ 215 nm)

Step 3: 3-[3-[2-[[2-(tert-Butylcarbamoyl)-4-pyridyl]amino]-2-oxo-ethyl]-4-methoxy-phenyl]propanoic acid

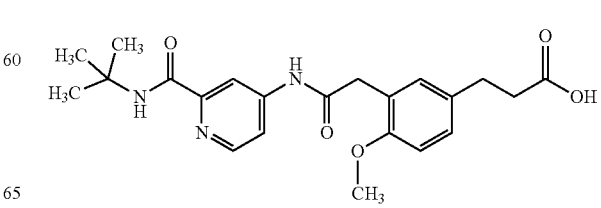

To a solution of ethyl 3-[3-[2-[[2-(tert-butylcarbamoyl)-4-pyridyl]amino]-2-oxo-ethyl]-4-methoxy-phenyl]propanoate (step 2) (332 mg, 0.75 mmol) in THF (4.3 mL)/water (1 mL), 1M LiOH (631 mg, 15.04 mmol) was added and the reaction mixture was stirred at room temperature for 5.5 hours. The resulting mixture was extracted with EtOAc and the aqueous layer was diluted with water and acidified to pH 3-4 with 6M HCl. The resulting mixture was extracted with EtOAc (3×25 ml) and the combined organic extracts were filtered, dried over $Na_2SO_4$ and concentrated in vacuo to afford the titled compound as a yellow oil.

1H NMR (500 MHz, DMSO-d6) δ 10.64 (s, 1H), 8.43 (d, J=5.5 Hz, 1H), 8.18 (d, J=2.0 Hz, 1H), 8.03 (s, 1H), 7.81 (dd, J=5.5, 2.2 Hz, 1H), 7.11-7.06 (m, 2H), 6.89 (d, J=8.3 Hz, 1H), 3.72 (s, 3H), 3.66 (s, 2H), 2.75 (t, J=7.7 Hz, 2H), 1.40 (s, 9H).

LC-MS (Method E): Rt 1.08 mins; MS m/z 414.2=[M+H]+ (79% @ 215 nm)

Step 4: N-tert-Butyl-4-[[2-[5-(3-hydroxypropyl)-2-methoxy-phenyl]acetyl]amino]pyridine-2-carboxamide

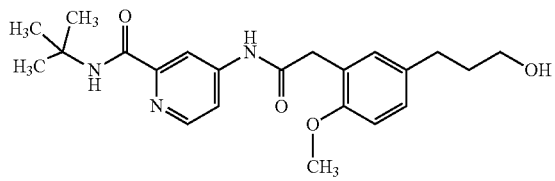 [SMILES: COc1ccc(CCCO)cc1CC(=O)Nc1ccnc(C(=O)NC(C)(C)C)c1]

To a cooled (0° C.) solution of 3-[3-[2-[[2-(tert-butylcarbamoyl)-4-pyridyl]amino]-2-oxo-ethyl]-4-methoxy-phenyl]propanoic acid (step 3)(196 mg, 0.47 mmol) in THF (3.96 mL) was added TEA (0.17 mL, 1.19 mmol) followed by the dropwise addition of methyl carbonochloridate (0.09 mL, 1.19 mmol). The reaction mixture was stirred for 30 minutes at 0° C. then treated with $NaBH_4$ (90 mg, 2.37 mmol) followed by dropwise addition of MeOH (0.5 mL). After stirring at 0° C. for a further 90 minutes, the mixture was diluted with water and extracted with EtOAc (3×20 mL). The combined organic extracts were washed with saturated $NaHCO_3$ (10 mL), brine (20 mL) then dried over $Na_2SO_4$ and concentrated in vacuo. The residue was purified by chromatography on silica eluting with 0-100% EtOAc in heptane to afford the titled compound as an off-white solid.

1H NMR (500 MHz, DMSO-d6) δ 10.64 (s, 1H), 8.43 (d, J=5.5 Hz, 1H), 8.18 (d, J=2.1 Hz, 1H), 8.03 (s, 1H), 7.81 (dd, J=5.5, 2.2 Hz, 1H), 7.08-7.03 (m, 2H), 6.88 (d, J=8.3 Hz, 1H), 4.42 (t, J=5.1 Hz, 1H), 3.72 (s, 3H), 3.66 (s, 2H), 3.40 (q, J=6.4 Hz, 2H), 1.71-1.64 (m, 2H), 1.40 (s, 9H).

LC-MS (Method E): Rt 1.09 mins; MS m/z 400.1=[M+H]+ (100% @ 215 nm)

Step 5: N-tert-Butyl-4-[[2-[2-hydroxy-5-(3-hydroxypropyl)phenyl]acetyl]amino]pyridine-2-carboxamide The titled compound was prepared from N-tert-butyl-4-[[2-[5-(3-hydroxypropyl)-2-methoxy-phenyl]acetyl]amino]pyridine-2-carboxamide (step 4) analogously to Example 41 step 3.

1H NMR (500 MHz, Methanol-d4) δ 8.41 (d, J=5.5 Hz, 1H), 8.10 (d, J=2.0 Hz, 1H), 7.90 (dd, J=5.5, 2.2 Hz, 1H), 7.02 (d, J=2.0 Hz, 1H), 6.96 (dd, J=8.2, 2.2 Hz, 1H), 6.74 (d, J=8.2 Hz, 1H), 3.70 (s, 2H), 3.55 (t, J=6.5 Hz, 2H), 2.63-2.54 (m, 2H), 1.84-1.75 (m, 2H), 1.47 (s, 9H).

LC-MS (Method A): Rt 2.57 mins; MS m/z 386.3=[M+H]+ (97% @ 215 nm)

Example 76

4-[[2-(5-Chloro-4-fluoro-2-hydroxy-phenyl)acetyl]amino]-N-(1-methylcyclo butyl)pyridine-2-carboxamide

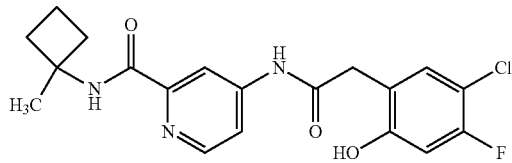 [SMILES: CC1(NC(=O)c2cc(NC(=O)Cc3cc(Cl)c(F)cc3O)ccn2)CCC1]

Step 1: 4-Amino-N-(1-methylcyclobutyl)pyridine-2-carboxamide

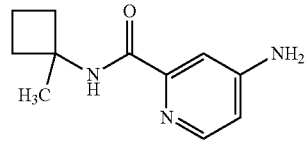

4-Aminopyridine-2-carboxylic acid (700 mg, 5.07 mmol) and DIPEA (3.54 mL, 20.27 mmol) were suspended in DMF (39 mL) and treated with 1-methylcyclobutanamine hydrochloride (924 mg, 7.6 mmol) and HATU (2312 mg, 6.08 mmol). After stirring at room temperature for 4 days the reaction mixture was filtered and the solid washed with DMF (2×2 mL). The filtrate was concentrated in vacuo and the crude residue dissolved in EtOAc (20 mL) and washed with sat. $NaHCO_3$ solution (20 mL). The aqueous layer was re-extracted with EtOAc (20 mL) and the combined organic layers were washed with brine (2×20 mL), dried over $Na_2SO_4$ and concentrated in vacuo. Purification of the crude residue by C18 reverse phase chromatography eluting with 5-100% MeCN in water afforded the titled compound as a white solid 1H NMR (500 MHz, DMSO-d6) δ 8.42 (s, 1H), 7.99 (d, J=5.7 Hz, 1H), 7.17 (d, J=2.3 Hz, 1H), 6.60 (dd, J=5.7, 2.3 Hz, 1H), 6.53 (br s, 2H), 2.40-2.32 (m, 2H), 2.00-1.94 (m, 2H), 1.83-1.76 (m, 2H), 1.45 (s, 3H).

LC-MS (Method E): Rt 0.62 mins; MS m/z 206.0=[M+H]+ (99% @ 215 nm)

Step 2: 4-[[2-(5-Chloro-4-fluoro-2-methoxy-phenyl)acetyl]amino]-N-(1-methylcyclobutyl)pyridine-2-carboxamide

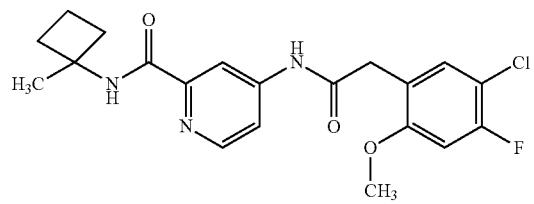 [SMILES: COc1cc(F)c(Cl)cc1CC(=O)Nc1ccnc(C(=O)NC2(C)CCC2)c1]

A solution of 4-amino-N-(1-methylcyclobutyl)pyridine-2-carboxamide (step 1)(81 mg, 0.4 mmol) and 2-(5-chloro-4-fluoro-2-methoxy-phenyl)acetic acid (100 mg, 0.36 mmol) in DMF (1.9 mL) was treated with TEA (0.16 mL, 0.9 mmol) and T3P® (50% solution in EtOAc) (0.21 mL, 0.72 mmol) and stirred at room temperature for 17 hours. The reaction was quenched with sat NaHCO$_3$ (2 mL) and extracted with EtOAc (3×5 mL). The combined organic extracts were washed with brine (5 mL), dried over Na$_2$SO$_4$ and concentrated in vacuo. The residue was purified by chromatography on silica eluting with 0-100% EtOAc in heptane to afford the titled compound as an off-white solid.

1H NMR (500 MHz, Methanol-d4) δ 8.49-8.47 (m, 1H), 8.15 (dd, J=2.2, 0.4 Hz, 1H), 7.92 (dd, J=5.5, 2.2 Hz, 1H), 7.37 (d, J=8.4 Hz, 1H), 6.97 (d, J=11.2 Hz, 1H), 3.86 (s, 3H), 3.74 (s, 2H), 2.49 (dd, J=9.7, 2.4 Hz, 2H), 2.19-2.13 (m, 2H), 1.99-1.93 (m, 2H), 1.59 (s, 3H).

LC-MS (Method E): Rt 1.22 mins; MS m/z 406.1/408.2=[M+H]+ (79% @ 215 nm)

Step 3: 4-[[2-(5-Chloro-4-fluoro-2-hydroxy-phenyl)acetyl]amino]-N-(1-methylcyclo butyl)pyridine-2-carboxamide The titled compound was prepared from 4-[[2-(5-chloro-4-fluoro-2-methoxy-phenyl)acetyl]amino]-N-(1-methylcyclobutyl)pyridine-2-carboxamide (step 2) analogously to Example 41 step 3.

1H NMR (500 MHz, DMSO-d6) δ 10.76 (br s, 1H), 10.32 (br s, 1H), 8.48-8.43 (m, 2H), 8.13 (d, J=2.1 Hz, 1H), 7.81 (dd, J=5.5, 2.2 Hz, 1H), 7.35 (d, J=8.7 Hz, 1H), 6.75 (d, J=11.0 Hz, 1H), 3.65 (s, 2H), 2.43-2.38 (m, 2H), 2.03-1.96 (m, 2H), 1.85-1.77 (m, 2H), 1.47 (s, 3H).

LC-MS (Method A): Rt 3.34 mins; MS m/z 392.2/394.2=[M+H]+ (100% @ 215 nm)

Example 77

4-[[2-(2,5-Difluorophenyl)acetyl]amino]-N-(1,1-dimethylprop-2-ynyl)pyridine-2-carboxamide

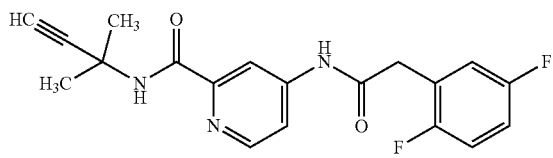 [SMILES: C#CC(C)(C)NC(=O)c1cc(NC(=O)Cc2cc(F)ccc2F)ccn1]

Step 1: Methyl 4-[[2-(2,5-difluorophenyl)acetyl]amino]pyridine-2-carboxylate

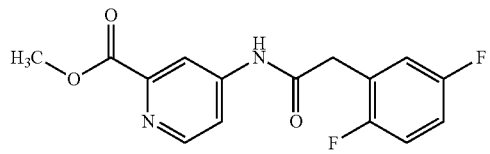 [SMILES: COC(=O)c1cc(NC(=O)Cc2cc(F)ccc2F)ccn1]

2-(2,5-Difluorophenyl)acetic acid (407 mg, 2.37 mmol) was dissolved in thionyl chloride (1.8 mL, 20.43 mmol) and the mixture heated at 70° C. for 1 h. The resulting mixture was concentrated in vacuo and the residue azeotropically dried with toluene. The crude acid chloride was dissolved in DCM (4 mL) and added dropwise to a cooled (0° C.) solution of methyl 4-aminopyridine-2-carboxylate (300 mg, 1.97 mmol) and DIPEA (0.69 mL, 3.94 mmol) in DCM (6 mL). The mixture was allowed to warm to room temperature and stirred overnight. The resulting mixture was transferred to a separating funnel and washed sequentially with water (10 mL) and sat. NaHCO$_3$ solution (10 mL). The organic portion was separated, dried over Na$_2$SO$_4$ and concentrated in vacuo. Purification of the crude material by chromatography on silica eluting with 50-100% EtOAc in heptane afforded the titled compound as a colourless glass.

1H NMR (500 MHz, Chloroform-d) δ 8.56 (d, J=5.2 Hz, 1H), 8.04 (s, 1H), 7.89-7.81 (m, 2H), 7.12-7.06 (m, 2H), 7.04-6.99 (m, 1H), 3.98 (s, 3H), 3.76-3.74 (m, 2H)

LC-MS (Method E): Rt 0.99 mins; MS m/z 307.0=[M+H]+

Step 2: 4-[[2-(2,5-Difluorophenyl)acetyl]amino]pyridine-2-carboxylic acid

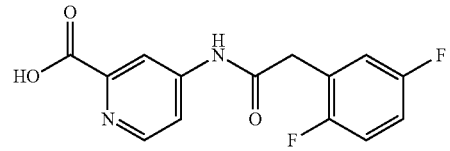 [SMILES: O=C(Cc1cc(F)ccc1F)Nc1ccnc(C(=O)O)c1]

To a solution of methyl 4-[[2-(2,5-difluorophenyl)acetyl]amino]pyridine-2-carboxylate (step 1)(364 mg, 1.07 mmol) in THF (2 mL)/MeOH (2 mL)/water (2 mL) was added 1M LiOH (31 mg, 1.28 mmol) and the mixture stirred at room temperature overnight. A further 0.5 equivalent of 1M LiOH was added and stirring continued for 2 hours. The resulting mixture was acidified to pH 2 using 1M HCl solution (2 mL) resulting in the formation of a precipitate. Water (5 mL) was added to the mixture, stirred for 5 mins and the solid was filtered and dried in a vacuum oven to afford the titled compound as a colourless powder.

1H NMR (500 MHz, DMSO-d6) δ 10.87 (s, 1H), 8.55 (d, J=5.5 Hz, 1H), 8.27 (d, J=2.0 Hz, 1H), 7.79 (dd, J=5.6, 2.2 Hz, 1H), 7.31-7.27 (m, 1H), 7.26-7.22 (m, 1H), 7.20-7.15 (m, 1H), 3.83 (s, 2H).

LC-MS (Method E): Rt 0.83 mins; MS m/z 293.0=[M+H]+

Step 3: 4-[[2-(2,5-Difluorophenyl)acetyl]amino]-N-(1,1-dimethylprop-2-ynyl)pyridine-2-carboxamide To a solution of 4-[[2-(2,5-difluorophenyl)acetyl]amino]pyridine-2-carboxylic acid (step 2) (50 mg, 0.16 mmol) and DIPEA (60 μL, 0.34 mmol) in DMF (1 mL) was added HATU (68 mg, 0.18 mmol) and the mixture stirred for 5 mins then treated with 2-methylbut-3-yn-2-amine (19 μL, 0.18 mmol). The resulting mixture was stirred at room temperature for 1 hour and then diluted with EtOAc. The mixture was washed with 1M HCl solution, brine, dried over Na$_2$SO$_4$ and concentrated in vacuo. The crude residue was purified by preparative HPLC to afford the titled compound as a colourless powder.

1H NMR (500 MHz, DMSO-d6) δ 10.85 (s, 1H), 8.48 (d, J=5.5 Hz, 1H), 8.32 (s, 1H), 8.18 (d, J=1.9 Hz, 1H), 7.82 (dd, J=5.5, 2.2 Hz, 1H), 7.31-7.27 (m, 1H), 7.24 (dt, J=9.1, 4.6 Hz, 1H), 7.21-7.14 (m, 1H), 3.83 (s, 2H), 3.21 (s, 1H), 1.64 (s, 6H).

LC-MS (Method A): Rt 3.16 mins; MS m/z 358.2=[M+H]+

Example 77.1

4-[[2-(2,5-Difluorophenyl)acetyl]amino]-N-(4-fluoro-1-bicyclo[2.1.1]hexanyl)pyridine-2-carboxamide

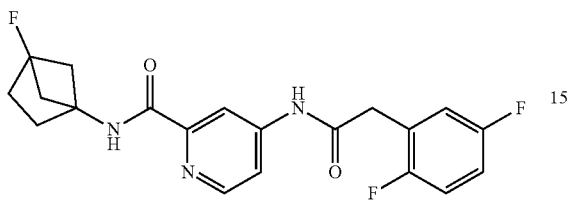

The titled compound was prepared from 4-[[2-(2,5-difluorophenyl)acetyl]amino]pyridine-2-carboxylic acid (Example 77 step 2) and 4-fluorobicyclo[2.1.1]hexan-1-amine hydrochloride analogously to Example 77 step 3.

1H NMR (500 MHz, DMSO-d6) δ 10.83 (s, 1H), 9.05 (s, 1H), 8.48 (d, J=5.5 Hz, 1H), 8.14 (d, J=2.1 Hz, 1H), 7.82 (dd, J=5.5, 2.2 Hz, 1H), 7.31-7.27 (m, 1H), 7.27-7.22 (m, 1H), 7.20-7.15 (m, 1H), 3.83 (s, 2H), 2.13-2.09 (m, 2H), 2.08-2.04 (m, 2H), 1.99-1.95 (m, 2H), 1.86-1.82 (m, 2H).

LC-MS (Method A): Rt 3.28 mins; MS m/z 390.2=[M+H]+

Example 78

4-[[2-(4-Chloro-2-hydroxy-phenyl)acetyl]amino]-N-(1,1-dimethylprop-2-ynyl)pyridine-2-carboxamide

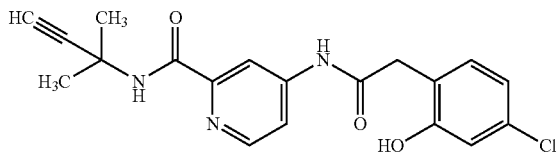 [SMILES: C#CC(C)(C)NC(=O)c1cc(NC(=O)Cc2ccc(Cl)cc2O)ccn1]

Step 1: 4-Amino-N-(1,1-dimethylprop-2-ynyl)pyridine-2-carboxamide

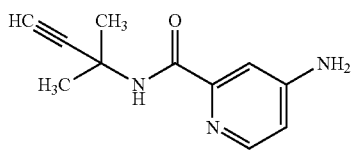

To a mixture of 4-aminopyridine-2-carboxylic acid (2 g, 14.48 mmol), TBTU (5.58 g, 17.38 mmol) and TEA (2.42 mL, 17.38 mmol) in DMF (36 mL) was added 2-methylbut-3-yn-2-amine (22.82 mL, 17.38 mmol) and the mixture was stirred at room temperature for 3 days. The reaction mixture was filtered and the filtrate concentrated in vacuo. The crude residue was dissolved in EtOAc (40 mL) and washed with sat. NaHCO3 solution (40 mL). The aqueous was further extracted with EtOAc (40 mL) and the combined organic portions were washed with brine (2×40 mL), dried over anhydrous Na2SO4 and concentrated in vacuo. The crude material was triturated with the minimum amount of ether at 0° C. to afford the titled compound as an off-white crystalline solid.

1H NMR (500 MHz, DMSO-d6) δ 8.23 (s, 1H), 7.99 (d, J=5.6 Hz, 1H), 7.19 (d, J=2.3 Hz, 1H), 6.59 (dd, J=5.6, 2.4 Hz, 1H), 6.36 (s, 2H), 3.19 (s, 1H), 1.62 (s, 6H).

LC-MS (Method F): Rt 1.28 mins; MS m/z 204.3=[M+H]+

Step 2: 4-[[2-(4-Chloro-2-methoxy-phenyl)acetyl]amino]-N-(1,1-dimethylprop-2-ynyl)pyridine-2-carboxamide

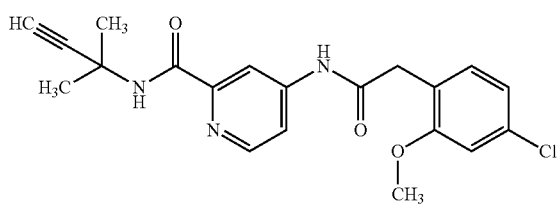 [SMILES: C#CC(C)(C)NC(=O)c1cc(NC(=O)Cc2ccc(Cl)cc2OC)ccn1]

The titled compound was prepared from 4-amino-N-(1,1-dimethylprop-2-ynyl)pyridine-2-carboxamide (step 1) and 2-(4-chloro-2-methoxy-phenyl)acetic acid analogously to Example 3.5b.

1H NMR (500 MHz, DMSO-d6) δ 10.71 (s, 1H), 8.47 (d, J=5.5 Hz, 1H), 8.32 (s, 1H), 8.19 (d, J=2.1 Hz, 1H), 7.83 (dd, J=5.5, 2.2 Hz, 1H), 7.25 (d, J=8.1 Hz, 1H), 7.07 (d, J=2.0 Hz, 1H), 6.99 (dd, J=8.0, 2.0 Hz, 1H), 3.79 (s, 3H), 3.70 (s, 2H), 3.21 (s, 1H), 1.65 (s, 6H).

LC-MS (Method A): Rt 3.44 mins; MS m/z 386.2/388.2=[M+H]+ (96% @ 215 nm)

Step 3: 4-[[2-(4-Chloro-2-hydroxy-phenyl)acetyl]amino]-N-(1,1-dimethylprop-2-ynyl)pyridine-2-carboxamide The titled compound was prepared from 4-[[2-(4-chloro-2-methoxy-phenyl)acetyl]amino]-N-(1,1-dimethylprop-2-ynyl)pyridine-2-carboxamide (step 2) analogously to Example 3 step 3.

1H NMR (500 MHz, DMSO-d6) δ 10.71 (br s, 1H), 10.04 (br s, 1H), 8.46 (d, J=5.5 Hz, 1H), 8.31 (s, 1H), 8.18 (d, J=1.9 Hz, 1H), 7.83 (dd, J=5.5, 2.2 Hz, 1H), 7.17 (d, J=7.8 Hz, 1H), 6.83-6.79 (m, 2H), 3.65 (s, 2H), 3.20 (s, 1H), 1.64 (s, 6H).

LC-MS (Method A): Rt 3.09 mins; MS m/z 372.2/374.2=[M+H]+ (99% @ 215 nm)

Example 78.1

N-(1,1-Dimethylprop-2-ynyl)-4-[[2-[2-hydroxy-4-(trifluoromethyl)phenyl]acetyl]amino]pyridine-2-carboxamide

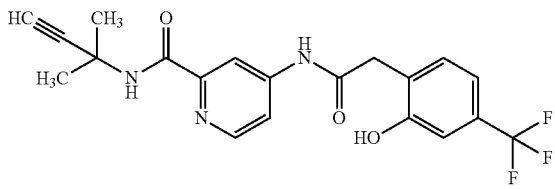 [SMILES: C#CC(C)(C)NC(=O)c1cc(NC(=O)Cc2ccc(C(F)(F)F)cc2O)ccn1]

The titled compound was prepared from 4-amino-N-(1,1-dimethylprop-2-ynyl)pyridine-2-carboxamide (Example 78, step 1) and 2-[2-methoxy-4-(trifluoromethyl)phenyl]acetic acid analogously to Example 78 steps 2 and 3.

1H NMR (500 MHz, DMSO-d6) δ 10.79 (s, 1H), 10.30 (s, 1H), 8.47 (d, J=5.5 Hz, 1H), 8.31 (s, 1H), 8.19 (d, J=2.0 Hz, 1H), 7.83 (dd, J=5.5, 2.2 Hz, 1H), 7.38 (d, J=7.8 Hz, 1H), 7.10 (d, J=7.9 Hz, 1H), 7.07 (s, 1H), 3.76 (s, 2H), 3.21 (s, 1H), 1.64 (s, 6H).

LC-MS (Method A): Rt 3.27 mins; MS m/z 406.2=[M+H]+ (98% @ 215 nm)

Example 78.2

N-(1,1-Dimethylprop-2-ynyl)-4-[[2-[2-hydroxy-5-(trifluoromethyl)phenyl]acetyl]amino]pyridine-2-carboxamide

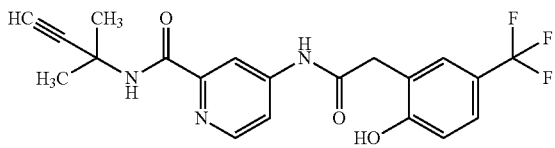 [SMILES: C#CC(C)(C)NC(=O)c1cc(NC(=O)Cc2cc(C(F)(F)F)ccc2O)ccn1]

The titled compound was prepared from 4-amino-N-(1,1-dimethylprop-2-ynyl)pyridine-2-carboxamide (Example 78, step 1) and 2-[2-methoxy-5-(trifluoromethyl)phenyl]acetic acid analogously to Example 78 steps 2 and 3.

1H NMR (500 MHz, DMSO-d6) δ 10.79 (s, 1H), 10.48 (s, 1H), 8.47 (d, J=5.5 Hz, 1H), 8.32 (s, 1H), 8.19 (d, J=2.0 Hz, 1H), 7.84 (dd, J=5.5, 2.2 Hz, 1H), 7.54 (d, J=2.2 Hz, 1H), 7.45 (dd, J=8.5, 2.1 Hz, 1H), 6.96 (d, J=8.4 Hz, 1H), 3.77 (s, 2H), 3.21 (s, 1H), 1.65 (s, 6H).

LC-MS (Method A): Rt 3.25 mins; MS m/z 406.2=[M+H]+ (98% @ 215 nm)

Example 79

4-[(2-Chroman-4-ylacetyl)amino]-N-(1,1-dimethyl-prop-2-ynyl)pyridine-2-carboxamide

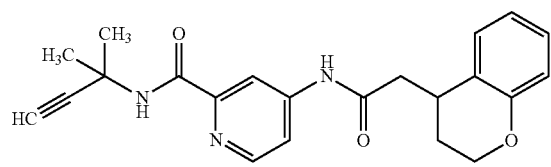 [SMILES: C#CC(C)(C)NC(=O)c1cc(NC(=O)CC2CCOc3ccccc32)ccn1]

The titled compound was prepared from 4-amino-N-(1,1-dimethylprop-2-ynyl)pyridine-2-carboxamide (Example 78, step 1) and 2-chroman-4-ylacetic acid analogously to Example 3.5b 1H NMR (500 MHz, Methanol-d4) δ 8.46 (d, J=5.5 Hz, 1H), 8.19 (d, J=1.7 Hz, 1H), 7.92 (dd, J=5.5, 2.2 Hz, 1H), 7.16 (d, J=7.7 Hz, 1H), 7.09-7.04 (m, 1H), 6.81 (td, J=7.5, 1.2 Hz, 1H), 6.75 (dd, J=8.2, 1.1 Hz, 1H), 4.22-4.18 (m, 2H), 3.44 (dq, J=10.4, 5.1 Hz, 1H), 2.92 (dd, J=14.7, 5.7 Hz, 1H), 2.73 (s, 1H), 2.62 (dd, J=14.7, 9.3 Hz, 1H), 2.20-2.11 (m, 1H), 1.94-1.84 (m, 1H), 1.73 (s, 6H).

LC-MS (Method A): Rt 3.38 mins; MS m/z 378.3=[M+H]+ (98% @ 215 nm)

Example 79.1

N-(1,1-Dimethylprop-2-ynyl)-4-[[2-(1-isopropyl-3,5-dimethyl-pyrazol-4-yl)acetyl]amino]pyridine-2-carboxamide

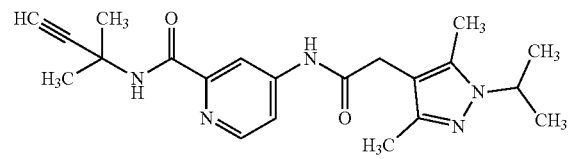 [SMILES: C#CC(C)(C)NC(=O)c1cc(NC(=O)Cc2c(C)nn(C(C)C)c2C)ccn1]

The titled compound was prepared from 4-amino-N-(1,1-dimethylprop-2-ynyl)pyridine-2-carboxamide (Example 78, step 1) and 2-(1-isopropyl-3,5-dimethyl-pyrazol-4-yl)acetic acid analogously to Example 3.5b.

1H NMR (500 MHz, DMSO-d6) δ 10.62 (s, 1H), 8.46 (d, 1H), 8.31 (s, 1H), 8.19 (d, J=1.9 Hz, 1H), 7.84 (dd, J=5.5, 2.2 Hz, 1H), 4.43-4.34 (m, 1H), 3.43 (s, 2H), 3.21 (s, 1H), 2.18 (s, 3H), 2.08 (s, 3H), 1.64 (s, 6H), 1.31 (d, J=6.6 Hz, 6H).

LC-MS (Method A): Rt 2.54 mins; MS m/z 382.3=[M+H]+ (100% @ 215 nm)

Example 79.2

N-(1,1-Dimethylprop-2-ynyl)-4-[[2-(1H-indazol-4-yl)acetyl]amino]pyridine-2-carboxamide

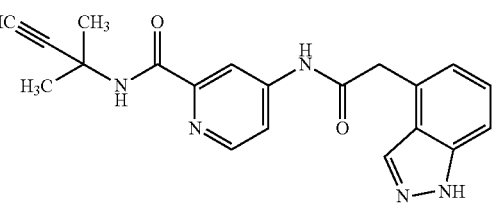

The titled compound was prepared from 4-amino-N-(1,1-dimethylprop-2-ynyl)pyridine-2-carboxamide (Example 78, step 1) and 2-(1H-indazol-4-yl)acetic acid analogously to Example 3.5b.

1H NMR (500 MHz, Methanol-d4) δ 8.44 (dd, J=5.4, 0.5 Hz, 1H), 8.19 (d, J=1.0 Hz, 1H), 8.17 (dd, J=2.3, 0.5 Hz, 2H), 7.93 (dd, J=5.6, 2.2 Hz, 1H), 7.47 (d, J=8.5 Hz, 1H), 7.36 (dd, J=8.4, 7.0 Hz, 1H), 7.13-7.10 (m, 1H), 4.56 (br s, 1H), 4.08 (s, 2H), 2.72 (s, 1H), 1.72 (s, 6H).

LC-MS (Method A): Rt 2.51 mins; MS m/z 362.2=[M+H]+

Example 79.3

N-(1,1-Dimethylprop-2-ynyl)-4-[[2-(1H-indol-7-yl)acetyl]amino]pyridine-2-carboxamide

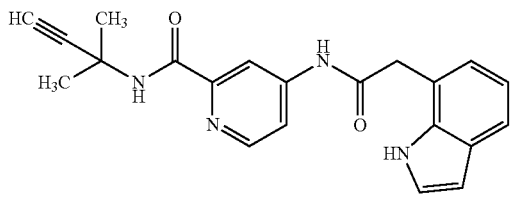 [SMILES: C#CC(C)(C)NC(=O)c1cc(NC(=O)Cc2cccc3cc[nH]c23)ccn1]

The titled compound was prepared from 4-amino-N-(1,1-dimethylprop-2-ynyl)pyridine-2-carboxamide (Example 78, step 1) and 2-(1H-indol-7-yl)acetic acid analogously to Example 3.5b.

1H NMR (500 MHz, DMSO-d6) δ 11.05 (br s, 1H), 10.82 (s, 1H), 8.48 (d, J=5.5 Hz, 1H), 8.32 (s, 1H), 8.21 (d, J=2.0 Hz, 1H), 7.86 (dd, J=5.5, 2.1 Hz, 1H), 7.46 (d, J=7.5 Hz, 1H), 7.36 (t, J=2.7 Hz, 1H), 7.02-6.94 (m, 2H), 6.48-6.42 (m, 1H), 4.01 (s, 2H), 3.21 (s, 1H), 1.65 (s, 6H).

LC-MS (Method A): Rt 3.19 mins; MS m/z 361.2=[M+H]+

Example 80

3-[[2-(5-Chloro-2-hydroxy-phenyl)acetyl]amino]-N-(4-cyanotetrahydropyran-4-yl)benzamide

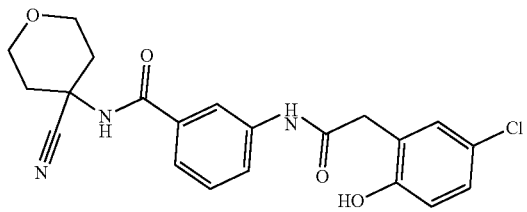 [SMILES: N#CC1(NC(=O)c2cccc(NC(=O)Cc3cc(Cl)ccc3O)c2)CCOCC1]

Step 1: 3-[[2-[5-Chloro-2-[(4-methoxyphenyl)methoxy]phenyl]acetyl]amino]benzoic acid

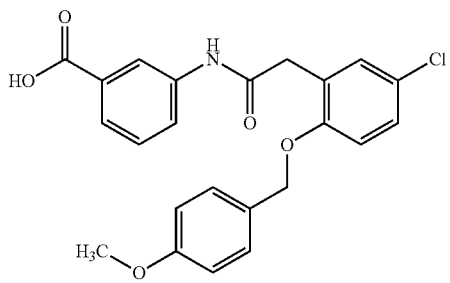 [SMILES: COc1ccc(COc2ccc(Cl)cc2CC(=O)Nc2cccc(C(=O)O)c2)cc1]

To a solution of 3-[[2-(5-chloro-2-hydroxy-phenyl)acetyl]amino]benzoic acid (Example 71 step 3)(464 mg, 1.046 mmol) in DMF (5 mL) was added K₂CO₃ (619 mg, 4.48 mmol) and 1-(bromomethyl)-4-methoxy-benzene (751 mg, 3.73 mmol) and the reaction mixture was stirred at room temperature for 1 hour. The resulting mixture was diluted with water (10 mL) to form a precipitate which was filtered and washed with water. The solid was dissolved in THF (7 mL) and treated with aq. 1M LiOH (8.96 mL, 8.96 mmol) and stirred at room temperature for 20 hours. The volatile solvents were removed in vacuo causing the formation of a precipitate. The mixture was diluted with water (50 mL) and neutralised with aq. 3M HCl solution. The precipitate was filtered and washed with water to afford the titled compound as an off-white solid.

1H NMR (500 MHz, DMSO-d6) δ 10.24 (s, 1H), 8.20 (s, 1H), 7.82 (d, J=8.9 Hz, 1H), 7.62 (dt, J=7.7, 1.1 Hz, 1H), 7.42 (t, J=7.9 Hz, 1H), 7.32 (d, J=2.7 Hz, 1H), 7.30-7.24 (m, 3H), 7.08 (d, J=8.8 Hz, 1H), 6.70-6.66 (m, 2H), 5.00 (s, 2H), 3.67 (s, 2H), 3.66 (s, 3H).

LC-MS (Method E): Rt 1.18 mins; MS m/z 448.0/450.1=[M+Na]+ (96% @ 215 nm)

Step 2: 3-[[2-[5-Chloro-2-[(4-methoxyphenyl)methoxy]phenyl]acetyl]amino]-N-(4-cyanotetrahydropyran-4-yl)benzamide

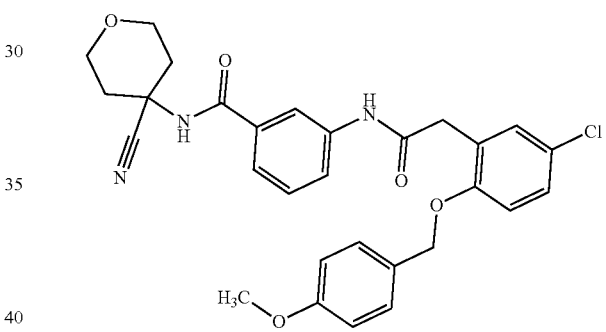

The titled compound was prepared from 3-[[2-[5-chloro-2-[(4-methoxyphenyl)methoxy]phenyl]acetyl]amino]benzoic acid (step 1) and 4-aminotetrahydropyran-4-carbonitrile analogously to Example 31 step 2.

1H NMR (500 MHz, DMSO-d6) δ 10.26 (s, 1H), 8.82 (s, 1H), 8.04 (t, J=1.7 Hz, 1H), 7.83 (d, J=9.4 Hz, 1H), 7.56 (dt, J=7.6, 1.1 Hz, 1H), 7.44 (t, J=7.9 Hz, 1H), 7.32 (d, J=2.7 Hz, 1H), 7.30-7.26 (m, 3H), 7.08 (d, J=8.8 Hz, 1H), 6.73-6.70 (m, 2H), 5.00 (s, 2H), 3.90-3.84 (m, 2H), 3.68 (s, 2H), 3.67 (s, 3H), 3.63-3.57 (m, 2H), 2.33 (d, J=13.5 Hz, 2H), 2.04-1.97 (m, 2H).

LC-MS (Method E): Rt 1.20 mins; MS m/z 556.1/558.0=[M+H]+ (95% @ 215 nm)

Step 3: 3-[[2-(5-Chloro-2-hydroxy-phenyl)acetyl]amino]-N-(4-cyanotetrahydropyran-4-yl)benzamide 3-[[2-[5-Chloro-2-[(4-methoxyphenyl)methoxy]phenyl]acetyl]amino]-N-(4-cyanotetra hydropyran-4-yl)benzamide (step 2)(70 mg, 0.13 mmol) was dissolved in 1M HCl in dioxane (1.97 mL, 1.97 mmol) and stirred at room temperature for 4 hours. The reaction mixture was diluted with EtOAc (5 mL) and water (5 mL). The organic portion was separated, dried over Na₂SO₄ and concentrated in vacuo. Purification of the crude material by preparative HPLC (acidic pH, standard elution method) afforded the titled compound as an off-white solid.

1H NMR (500 MHz, DMSO-d6) δ 10.27 (s, 1H), 9.66 (br s, 1H), 8.82 (s, 1H), 8.04 (t, J=1.8 Hz, 1H), 7.84-7.79 (m, 1H), 7.52 (dt, J=7.6, 1.0 Hz, 1H), 7.42 (t, J=7.9 Hz, 1H), 7.21 (d, J=2.7 Hz, 1H), 7.11 (dd, J=8.6, 2.7 Hz, 1H), 6.80 (d, J=8.6 Hz, 1H), 3.91-3.83 (m, 2H), 3.62 (s, 2H), 3.62-3.57 (m, 2H), 2.35-2.29 (m, 2H), 2.04-1.97 (m, 2H).

LC-MS (Method A): Rt 2.66 mins; MS m/z 414.2/416.2=[M+H]+ (100% @ 215 nm)

Example 81

N-(1-Cyano-1-methyl-ethyl)-4-[[2-(5-fluoro-2-hydroxy-phenyl)acetyl]amino]pyridine-2-carboxamide

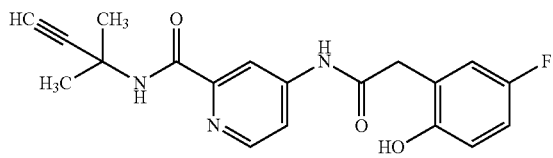 [SMILES: C#CC(C)(C)NC(=O)c1cc(NC(=O)Cc2cc(F)ccc2O)ccn1]

Step 1: Methyl 4-[[2-(5-fluoro-2-methoxy-phenyl)acetyl]amino]pyridine-2-carboxylate

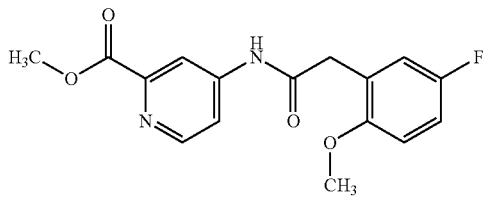 [SMILES: COC(=O)c1cc(NC(=O)Cc2cc(F)ccc2OC)ccn1]

The titled compound was prepared from methyl 4-aminopyridine-2-carboxylate and 2-(5-fluoro-2-methoxy-phenyl)acetic acid analogously to Example 8 step 1.

1H NMR (250 MHz, DMSO-d6) δ 10.71 (s, 1H), 8.54 (d, J=5.5 Hz, 1H), 8.30 (d, J=1.9 Hz, 1H), 7.77 (dd, J=5.5, 2.2 Hz, 1H), 7.15-7.03 (m, 2H), 7.02-6.93 (m, 1H), 3.86 (s, 3H), 3.74 (s, 3H), 3.71 (s, 2H).

LC-MS (Method E): Rt 0.99 mins; MS m/z 319.0 (83% @ 215 nm)

Step 2: 4-[[2-(5-Fluoro-2-methoxy-phenyl)acetyl]amino]pyridine-2-carboxylic acid

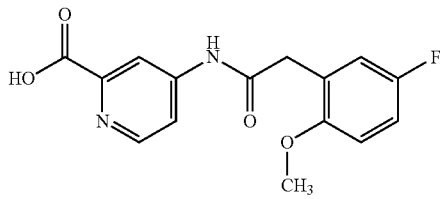 [SMILES: COc1ccc(F)cc1CC(=O)Nc1ccnc(C(=O)O)c1]

The titled compound was prepared from methyl 4-[[2-(5-fluoro-2-methoxy-phenyl)acetyl]amino]pyridine-2-carboxylate (step 1) analogously to Example 7 step 2.

1H NMR (500 MHz, DMSO-d6) δ 10.77 (s, 1H), 8.53 (d, J=5.6 Hz, 1H), 8.27 (d, J=2.0 Hz, 1H), 7.80 (dd, J=5.6, 2.2 Hz, 1H), 7.14-7.05 (m, 2H), 6.98 (dd, J=9.0, 4.6 Hz, 1H), 3.74 (s, 3H), 3.72 (s, 2H).

LC-MS (Method A): Rt 0.87 mins; MS m/z 305.0=[M+H]+

Step 3: N-(1-Cyano-1-methyl-ethyl)-4-[[2-(5-fluoro-2-methoxy-phenyl)acetyl]amino]pyridine-2-carboxamide

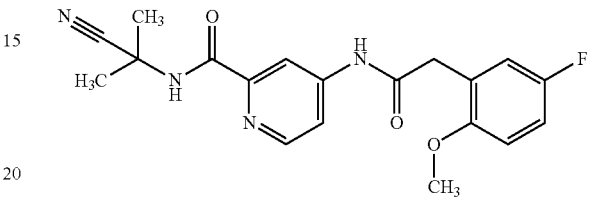

The titled compound was prepared from 4-[[2-(5-fluoro-2-methoxy-phenyl)acetyl]amino]pyridine-2-carboxylic acid (step 2) and 2-amino-2-methyl-propanenitrile hydrochloride acid analogously to Example 77 step 3.

1H NMR (500 MHz, DMSO-d6) δ 10.74 (s, 1H), 8.82 (s, 1H), 8.51 (d, J=5.5 Hz, 1H), 8.22 (d, J=1.9 Hz, 1H), 7.86 (dd, J=5.5, 2.2 Hz, 1H), 7.17-7.05 (m, 2H), 6.99 (dd, J=9.0, 4.6 Hz, 1H), 3.74 (s, 3H), 3.73 (s, 2H), 1.72 (s, 6H).

LC-MS (Method E): Rt 1.09 mins; MS m/z 371.1=[M+H]+ (87% @ 215 nm)

Step 4: N-(1-Cyano-1-methyl-ethyl)-4-[[2-(5-fluoro-2-hydroxy-phenyl)acetyl]amino]pyridine-2-carboxamide The titled compound was prepared from N-(1-cyano-1-methyl-ethyl)-4-[[2-(5-fluoro-2-methoxy-phenyl)acetyl]amino]pyridine-2-carboxamide (step 3) analogously to Example 3 step 3.

1H NMR (500 MHz, DMSO-d6) δ 10.72 (br s, 1H), 9.52 (br s, 1H), 8.82 (s, 1H), 8.50 (d, J=5.5 Hz, 1H), 8.22 (d, J=2.0 Hz, 1H), 7.87 (dd, J=5.5, 2.1 Hz, 1H), 7.02 (dd, J=9.4, 3.1 Hz, 1H), 6.91 (td, J=8.6, 3.2 Hz, 1H), 6.77 (dd, J=8.8, 4.9 Hz, 1H), 3.68 (s, 2H), 1.72 (s, 6H).

LC-MS (Method A): Rt 2.53 mins; MS m/z 357.2=[M+H]+ (99% @ 215 nm)

Example 81.1

N-(1-Cyano-2-hydroxy-1-methyl-ethyl)-4-[[2-(5-fluoro-2-hydroxy-phenyl)acetyl]amino]pyridine-2-carboxamide

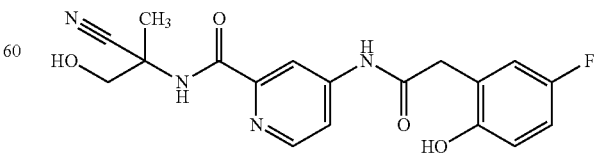

The titled compound was prepared from 4-[[2-(5-fluoro-2-methoxy-phenyl)acetyl]amino]pyridine-2-carboxylic acid (Example 81 step 2) and 2-amino-3-hydroxy-2-methyl-propanenitrile analogously to Example 81 step 3 and 4.

1H NMR (500 MHz, DMSO-d6) δ 10.76 (br s, 1H), 9.53 (br s, 1H), 8.73 (s, 1H), 8.50 (d, J=5.5 Hz, 1H), 8.24 (d, J=2.1 Hz, 1H), 7.87 (dd, J=5.5, 2.2 Hz, 1H), 7.02 (dd, J=9.3, 3.2 Hz, 1H), 6.95-6.87 (m, 1H), 6.78 (dd, J=8.8, 4.9 Hz, 1H), 5.91 (t, J=5.8 Hz, 1H), 3.82 (dd, J=11.1, 5.2 Hz, 1H), 3.73 (dd, J=10.9, 4.9 Hz, 1H), 3.68 (s, 2H), 1.66 (s, 3H).

LC-MS (Method A): Rt 2.20 mins; MS m/z 373.3=[M+H]+ (100% @ 215 nm)

Example 81.2

4-[[2-(5-Fluoro-2-hydroxy-phenyl)acetyl]amino]-N-isopropyl-pyridine-2-carboxamide

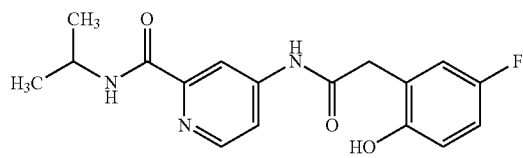 [SMILES: CC(C)NC(=O)c1cc(NC(=O)Cc2cc(F)ccc2O)ccn1]

The titled compound was prepared from 4-[[2-(5-fluoro-2-methoxy-phenyl)acetyl]amino]pyridine-2-carboxylic acid (Example 81 step 2) and analogously to Example 81 steps 3 and 4.

1H NMR (500 MHz, DMSO-d6) δ 10.65 (br s, 1H), 9.50 (br s, 1H), 8.45 (d, J=5.5 Hz, 1H), 8.37 (d, J=8.4 Hz, 1H), 8.18 (d, J=1.9 Hz, 1H), 7.81 (dd, J=5.5, 2.2 Hz, 1H), 7.00 (dd, J=9.4, 3.2 Hz, 1H), 6.95-6.86 (m, 1H), 6.76 (dd, J=8.8, 4.9 Hz, 1H), 4.16-4.02 (m, 1H), 3.66 (s, 2H), 1.17 (d, J=6.6 Hz, 6H).

LC-MS (Method A): Rt 2.56 mins; MS m/z 322.2=[M+H]+ (100% @ 215 nm)

Example 81.3

N-(1,1-Dimethylprop-2-ynyl)-4-[[2-(5-fluoro-2-hydroxy-phenyl)acetyl]amino]pyridine-2-carboxamide

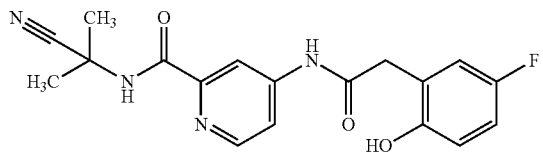 [SMILES: CC(C)(C#N)NC(=O)c1cc(NC(=O)Cc2cc(F)ccc2O)ccn1]

The titled compound was prepared from 4-[[2-(5-fluoro-2-methoxy-phenyl)acetyl]amino]pyridine-2-carboxylic acid (Example 81 step 2) and 2-methylbut-3-yn-2-amine analogously to Example 81 steps 3 and 4.

1H NMR (500 MHz, DMSO-d6) δ 10.70 (br s, 1H), 9.52 (br s, 1H), 8.46 (d, J=5.5 Hz, 1H), 8.31 (s, 1H), 8.18 (d, J=2.0 Hz, 1H), 7.83 (dd, J=5.5, 2.2 Hz, 1H), 7.01 (dd, J=9.4, 3.2 Hz, 1H), 6.90 (td, J=8.6, 3.2 Hz, 1H), 6.77 (dd, J=8.8, 4.9 Hz, 1H), 3.67 (s, 2H), 3.20 (s, 1H), 1.64 (s, 6H).

LC-MS (Method A): Rt 2.84 mins; MS m/z 356.2=[M+H]+ (97% @ 215 nm)

Example 81.4

N-(4-Fluoro-1-bicyclo[2.1.1]hexanyl)-4-[[2-(5-fluoro-2-hydroxy-phenyl)acetyl]amino]pyridine-2-carboxamide

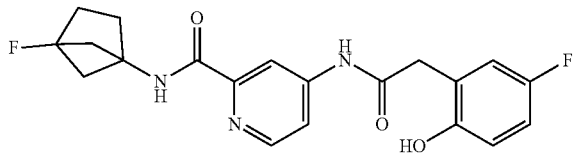 [SMILES: O=C(Cc1cc(F)ccc1O)Nc1ccnc(C(=O)NC23CCC(F)(C2)C3)c1]

The titled compound was prepared from 4-[[2-(5-fluoro-2-methoxy-phenyl)acetyl]amino]pyridine-2-carboxylic acid (Example 81 step 2) and 4-fluorobicyclo[2.1.1]hexan-1-amine hydrochloride analogously to Example 81 steps 3 and 4.

1H NMR (500 MHz, DMSO-d6) δ 10.68 (s, 1H), 9.51 (br s, 1H), 9.04 (s, 1H), 8.46 (d, J=5.5 Hz, 1H), 8.15 (d, J=2.1 Hz, 1H), 7.84 (dd, J=5.5, 2.1 Hz, 1H), 7.01 (dd, J=9.3, 3.1 Hz, 1H), 6.91 (td, J=8.6, 3.1 Hz, 1H), 6.77 (dd, J=8.8, 4.9 Hz, 1H), 3.67 (s, 2H), 2.16-2.02 (m, 4H), 2.00-1.91 (m, 2H), 1.89-1.79 (m, 2H).

LC-MS (Method A): Rt 2.97 mins; MS m/z 388.2=[M+H]+ (98% @ 215 nm)

Example 81.5

4-[[2-(5-Fluoro-2-hydroxy-phenyl)acetyl]amino]-N-[1-(hydroxymethyl)cyclobutyl]pyridine-2-carboxamide

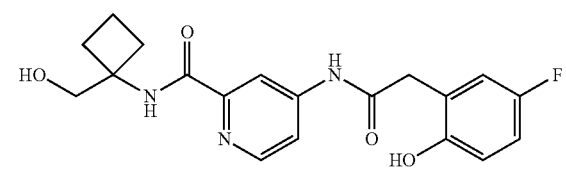 [SMILES: O=C(Cc1cc(F)ccc1O)Nc1ccnc(C(=O)NC2(CO)CCC2)c1]

The titled compound was prepared from 4-[[2-(5-fluoro-2-methoxy-phenyl)acetyl]amino]pyridine-2-carboxylic acid (Example 81 step 2) and (1-aminocyclobutyl)methanol hydrochloride analogously to Example 81 steps 3 and 4.

1H NMR (500 MHz, DMSO-d6) δ 10.68 (s, 1H), 9.52 (s, 1H), 8.45 (d, J=5.5 Hz, 1H), 8.40 (s, 1H), 8.18 (d, J=2.1 Hz, 1H), 7.82 (dd, J=5.5, 2.2 Hz, 1H), 7.01 (dd, J=9.4, 3.2 Hz, 1H), 6.91 (td, J=8.6, 3.2 Hz, 1H), 6.77 (dd, J=8.8, 4.9 Hz, 1H), 5.00 (s, 1H), 3.67 (s, 2H), 3.61 (s, 2H), 2.09-2.01 (m, 2H), 1.88-1.79 (m, 1H), 1.78-1.67 (m, 1H).

LC-MS (Method A): Rt 2.33 mins; MS m/z 374.2=[M+H]+ (96% @ 215 nm)

Example 82

N-tert-Butyl-6-[[2-(5-chloro-2-methoxy-phenyl)acetyl]amino]pyrimidine-4-carboxamide

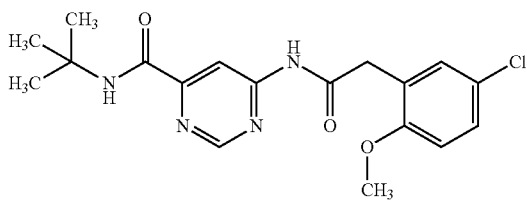 [SMILES: COc1ccc(Cl)cc1CC(=O)Nc1cc(C(=O)NC(C)(C)C)ncn1]

Step 1: 2-(5-Chloro-2-methoxy-phenyl)-N-(6-chloropyrimidin-4-yl)acetamide

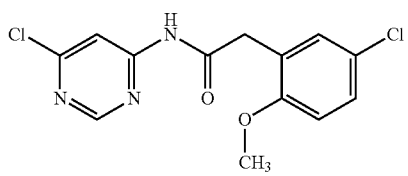 [SMILES: COc1ccc(Cl)cc1CC(=O)Nc1cc(Cl)ncn1]

A suspension of 6-chloropyrimidin-4-amine (250 mg, 1.93 mmol) and 2-(5-chloro-2-methoxy-phenyl)acetic acid (0.14 mL, 2.03 mmol) in 1,4-dioxane (2.5 mL) was treated with DIPEA (1.01 mL, 5.79 mmol) followed by T3P® (50% in EtOAc) (2754 μL, 2.32 mmol) and the mixture was stirred at room temperature for 2 hours. The resulting mixture was partitioned between EtOAc (10 mL) and saturated aqueous NaHCO$_3$ (10 mL) and the organic portion was separated, washed with water, dried over Na$_2$SO$_4$ and concentrated in vacuo. The residue was purified by chromatography on silica eluting with a gradient of 0 to 100% EtOAc in heptane followed by 0 to 100% MeOH in EtOAc to afford the titled compound as an orange powdery solid.

1H NMR (500 MHz, DMSO-d6) δ 11.40 (s, 1H), 8.77 (d, J=1.0 Hz, 1H), 8.07 (d, J=1.0 Hz, 1H), 7.33-7.29 (m, 2H), 7.03-6.98 (m, 1H), 3.79 (s, 2H), 3.74 (s, 3H).

LC-MS (Method E): Rt 1.14 mins; MS m/z 311.9/313.9= [M+H]+ (100% @ 215 nm)

Step 2: N-tert-Butyl-6-[[2-(5-chloro-2-methoxyphenyl)acetyl]amino]pyrimidine-4-carboxamide The following procedure was based on the literature reference: CA 2915356 Page 131.

All reagents charged to COware equipment (carbon monoxide generating system):
Chamber A: Aryl chloride, 2-methylpropan-2-amine, BINAP, Pd(OAc)$_2$, TEA 1,4-dioxane
Chamber B: formic acid, MsCl, TEA, 1,4-dioxane To chamber A was added 2-(5-chloro-2-methoxy-phenyl)-N-(6-chloropyrimidin-4-yl)acetamide (step 1) (202 mg, 0.65 mmol), Pd(OAc)$_2$ (15 mg, 0.06 mmol), 2-methylpropan-2-amine (95 mg, 1.29 mmol) and BINAP (81 mg, 0.13 mmol). The reaction vessel was flushed with nitrogen then 1,4-dioxane (2.5 mL) was added. To chamber B was added 1,4-dioxane (2.5 mL) followed by mesyl chloride (125 μL, 1.62 mmol) and formic acid (61 μL, 1.62 mmol) and the mixtures were stirred. To chamber A was added triethylamine (283 μL, 1.94 mmol) and to chamber B was added triethylamine (361 μL, 2.59 mmol) which quickly evolved CO gas. The COware equipment was heated at 80° C. for 22 hours and allowed to cool to room temperature. The mixture from chamber A was partitioned between DCM (5 mL) and water (5 mL) and the organic portion separated via filtration through a hydrophobic PTFE fritted tube. The filtrate was and concentrated in vacuo and the residue purified by preparative HPLC (acidic pH, standard elution method). The product fractions were combined and concentrated in vacuo to remove the volatile solvents. The aqueous residue was treated with DCM (10 mL) and saturated aqueous NaHCO$_3$ (10 mL) and the organic portion was separated by filtration through a hydrophobic PTFE fritted tube. The filtrate was concentrated in vacuo to afford the titled compound as a peach crystalline solid.

1H NMR (500 MHz, DMSO-d6) δ 11.29 (s, 1H), 8.95 (d, J=1.2 Hz, 1H), 8.53 (d, J=1.2 Hz, 1H), 8.04 (s, 1H),), 7.33-7.29 (m, 2H), 7.03-6.99 (m, 1H), 3.80 (s, 2H), 3.74 (s, 3H), 1.39 (s, 9H).

LC-MS (Method A): Rt 3.56 mins; MS m/z 377.2/379.2= [M+H]+ (97% @ 215 nm)

Example 83

N-(1-Cyano-1-methyl-ethyl)-4-(thiophene-3-carbonylamino)pyridine-2-carboxamide

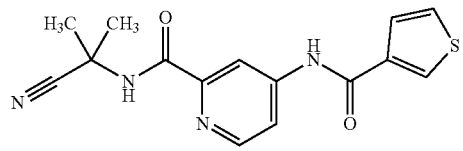 [SMILES: CC(C)(C#N)NC(=O)c1cc(NC(=O)c2ccsc2)ccn1]

Step 1: 4-Amino-N-(1-cyano-1-methyl-ethyl)pyridine-2-carboxamide

To a mixture of 4-aminopyridine-2-carboxylic acid (15 g, 108.6 mmol), TBTU (41.84 g, 130.32 mmol) and triethylamine (37.84 mL, 271.5 mmol) in DMF (271.52 mL) was added 2-amino-2-methyl-propanenitrile hydrochloride (14.4 g, 119.46 mmol) and the mixture was stirred at room temperature for 3 days. The reaction mixture was filtered and the solid washed with DMF (2×30 mL). The combined filtrate was concentrated in vacuo and the crude residue dissolved in EtOAc (300 mL) and washed with sat. NaHCO$_3$ solution (2×300 mL). The aqueous portion was re-extracted with EtOAc (30 mL) and the organic layers were combined, washed with brine (160 mL×2), dried over anhydrous Na$_2$SO$_4$ and concentrated in vacuo. Purification of the resulting solid by chromatography on silica eluting with 0-100% EtOAc in heptane yielded a solid which was triturated with ice cold TBME:heptane (3:1 mixture) to afford the titled compound as a colourless crystalline solid.

1H NMR (400 MHz, DMSO-d6) δ 8.60 (s, 1H), 8.03 (d, J=5.6 Hz, 1H), 7.21 (d, J=2.3 Hz, 1H), 6.62 (dd, J=5.6, 2.4 Hz, 1H), 6.40 (s, 2H), 1.70 (s, 6H).

LCMS (Method E) Rt 0.35 mins; MS m/z 205.0=[M+H]+

Step 2: N-(1-Cyano-1-methyl-ethyl)-4-(thiophene-3-carbonylamino)pyridine-2-carboxamide Oxalyl chloride (29 µL, 0.331 mmol) was added to a stirred solution of thiophene-3-carboxylic acid (47 mg, 0.368 mmol) dissolved in DMF (1 drop, ~5 µL) in 1,4-dioxane (1 mL). The mixture was sealed and stirred at room temperature for 1 hour. The resulting acid chloride mixture was treated with a stock solution (1.6 mL) of 4-amino-N-(1-cyano-1-methyl-ethyl)pyridine-2-carboxamide (step 1) (45 mg, 0.22 mmol) and TEA (100 µL, 0.72 mmol) in 1,4-dioxane (1.5 mL). The mixture was re-sealed and stirred at room temperature overnight. The resulting mixture was concentrated in vacuo and purification of the crude residue by preparative HPLC (acidic pH, standard elution method) afforded the titled compound as an off-white powder.

1H NMR (500 MHz, DMSO-d6) δ 10.63 (s, 1H), 8.85 (s, 1H), 8.56 (d, J=5.5 Hz, 1H), 8.49-8.46 (m, 1H), 8.44 (d, J=2.1 Hz, 1H), 8.09 (dd, J=5.5, 2.2 Hz, 1H), 7.71-7.69 (m, 1H), 7.68-7.66 (m, 1H), 1.74 (s, 6H).

LCMS (Method A) Rt 2.60 mins; MS m/z 315.2=[M+H]+ (99% @ 215 nm)

The compounds of the following tabulated Examples (Table 14) were prepared from 4-amino-N-(1-cyano-1-methyl-ethyl)pyridine-2-carboxamide (Example 83 step 1) analogously to Example 83 step 2 by replacing thiophene-3-carboxylic acid with the appropriate commercially available acid.

TABLE 14

| Ex. | Structure and Name | 1H NMR, LCMS Retention Time, [M + H]+, |
|---|---|---|
| 83.1 | 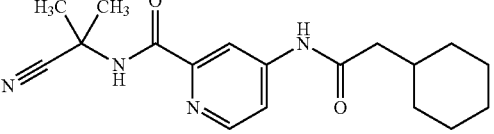<br>N-(1-Cyano-1-methyl-ethyl)-4-[(2-cyclohexylacetyl)amino]pyridine-2-carboxamide | 1H NMR (500 MHz, DMSO-d6) δ 10.50 (s, 1H), 8.81 (s, 1H), 8.49 (d, J = 5.5 Hz, 1H), 8.24 (d, J = 2.0 Hz, 1H), 7.84 (dd, J = 5.5, 2.2 Hz, 1H), 2.26 (d, J = 7.1 Hz, 2H), 1.83-1.75 (m, 1H), 1.72 (s, 6H), 1.71-1.64 (m, 4H), 1.63-1.58 (m, 1H), 1.28-1.09 (m, 3H), 1.03-0.93 (m, 2H). |
| 83.2 | 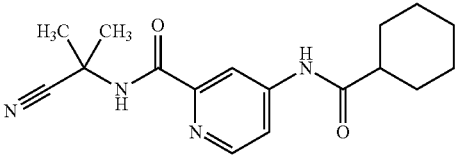<br>N-(1-Cyano-1-methyl-ethyl)-4-(cyclohexane carbonylamino)pyridine-2-carboxamide | 1H NMR (500 MHz, DMSO-d6) δ 10.46 (s, 1H), 8.81 (s, 1H), 8.49 (d, J = 5.5 Hz, 1H), 8.24 (d, J = 2.0 Hz, 1H), 7.87 (dd, J = 5.5, 2.2 Hz, 1H), 2.41-2.34 (m, 1H), 1.87-1.80 (m, 2H), 1.79-1.74 (m, 2H), 1.72 (s, 6H), 1.68-1.62 (m, 1H), 1.41 (qd, J = 12.4, 2.8 Hz, 2H), 1.33-1.14 (m, 3H). |
| 83.3 | 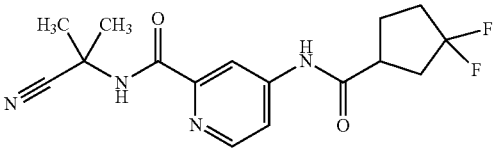<br>N-(1-Cyano-1-methyl-ethyl)-4-[(3,3-difluorocyclo pentanecarbonyl)amino]pyridine-2-carboxamide | 1H NMR (500 MHz, DMSO-d6) δ 10.65 (s, 1H), 8.83 (s, 1H), 8.52 (d, J = 5.5 Hz, 1H), 8.26-8.21 (m, 1H), 7.87 (dd, J = 5.5, 2.2 Hz, 1H), 3.16 (p, J = 8.6 Hz, 1H), 2.43-2.31 (m, 2H), 2.27-2.05 (m, 3H), 1.98-1.90 (m, 1H), 1.73 (s, 6H).<br>LCMS (Method A) Rt 2.74 mins; MS m/z 337.3 = [M + H]+ (97% @ 215 nm) |
| 83.4 | 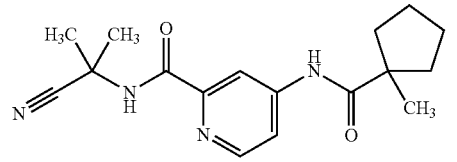<br>N-(1-Cyano-1-methyl-ethyl)-4-[(1-methylcyclo pentanecarbonyl)amino]pyridine-2-carboxamide | 1H NMR (500 MHz, DMSO-d6) δ 9.92 (s, 1H), 8.81 (s, 1H), 8.49 (d, J = 5.5 Hz, 1H), 8.36 (d, J = 2.1 Hz, 1H), 7.99 (dd, J = 5.5, 2.2 Hz, 1H), 2.18-2.07 (m, 2H), 1.73 (s, 6H), 1.70-1.56 (m, 4H), 1.55-1.49 (m, 2H), 1.32 (s, 3H).<br>LCMS (Method A) Rt 3.08 mins; MS m/z 315.3 = [M + H]+ (100% @ 215 nm) |
| 83.5 | 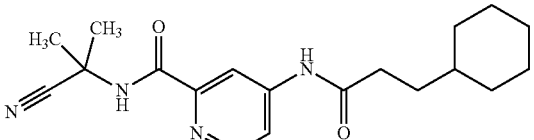<br>N-(1-Cyano-1-methyl-ethyl)-4-(3-cyclohexyl propanoylamino)pyridine-2-carboxamide | 1H NMR (500 MHz, DMSO-d6) δ 10.51 (s, 1H), 8.81 (s, 1H), 8.49 (d, J = 5.5 Hz, 1H), 8.23 (d, J = 2.0 Hz, 1H), 7.84 (dd, J = 5.5, 2.2 Hz, 1H), 2.41-2.36 (m, 2H), 1.75-1.64 (m, 10H), 1.63-1.57 (m, 1H), 1.54-1.47 (m, 2H), 1.28-1.07 (m, 4H), 0.94-0.85 (m, 2H).<br>LCMS (Method A) Rt 3.64 mins; MS m/z 343.3 = [M + H]+ (100% @ 215 nm) |

TABLE 14-continued

| Ex. | Structure and Name | 1H NMR, LCMS Retention Time, [M + H]+, |
|---|---|---|
| 83.6 | 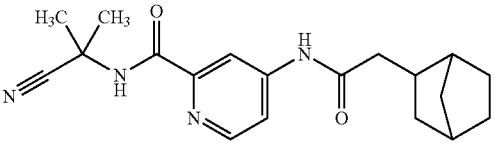<br>4-(2-{Bicyclo[2.2.1]heptan-2-yl}acetamido)-N-(1-cyano-1-methylethyl)pyridine-2-carboxamide | 1H NMR (500 MHz, DMSO-d6) δ 10.50 (s, 1H), 8.81 (s, 1H), 8.49 (d, J = 5.5 Hz, 1H), 8.23 (d, J = 1.9 Hz, 1H), 7.84 (dd, J = 5.5, 2.2 Hz, 1H), 2.38-2.32 (m, 1H), 2.24-2.18 (m, 2H), 2.00-1.97 (m, 1H), 1.94-1.87 (m, 1H), 1.72 (s, 6H), 1.52-1.40 (m, 3H), 1.38-1.33 (m, 1H), 1.21-1.06 (m, 4H).<br>LCMS (Method A) Rt 3.39 mins; MS m/z 341.3 = [M + H]+ (99% @ 215 nm) |
| 83.7 | 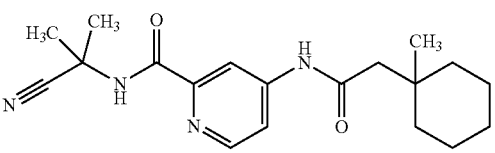<br>N-(1-Cyano-1-methyl-ethyl)-4-[[2-(1-methylcyclohexyl)acetyl]amino]pyridine-2-carboxamide | 1H NMR (500 MHz, DMSO-d6) δ 10.45 (s, 1H), 8.82 (s, 1H), 8.49 (d, J = 5.5 Hz, 1H), 8.24 (d, J = 2.0 Hz, 1H), 7.85 (dd, J = 5.5, 2.2 Hz, 1H), 2.29 (s, 2H), 1.72 (s, 6H), 1.52-1.36 (m, 7H), 1.36-1.27 (m, 3H), 1.02 (s, 3H).<br>LCMS (Method A) Rt 3.56 mins; MS m/z 343.3 = [M + H]+ (100% @ 215 nm) |
| 83.8 | 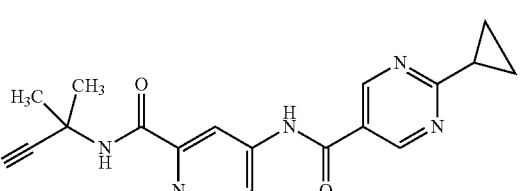<br>N-[2-[(1-Cyano-1-methyl-ethyl)carbamoyl]-4-pyridyl]-2-cyclopropyl-pyrimidine-5-carboxamide | 1H NMR (500 MHz, DMSO-d6) δ 11.02 (s, 1H), 9.13 (s, 2H), 8.88 (s, 1H), 8.60 (d, J = 5.5 Hz, 1H), 8.42 (d, J = 2.0 Hz, 1H), 8.05 (dd, J = 5.5, 2.2 Hz, 1H), 2.35-2.29 (m, 1H), 1.74 (s, 6H), 1.20-1.15 (m, 2H), 1.13-1.09 (m, 2H).<br>LCMS (Method A) Rt 2.56 mins; MS m/z 351.3 = [M + H]+ (99% @ 215 nm) |
| 83.9 | 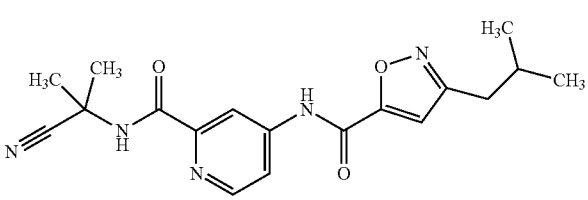<br>N-[2-[(1-Cyano-1-methyl-ethyl)carbamoyl]-4-pyridyl]-3-isobutyl-isoxazole-5-carboxamide | 1H NMR (500 MHz, DMSO-d6) δ 11.28 (br. s, 1H), 8.88 (s, 1H), 8.60 (d, J = 5.5 Hz, 1H), 8.47 (d, J = 2.1 Hz, 1H), 8.03 (dd, J = 5.5, 2.2 Hz, 1H), 7.25 (s, 1H), 2.61 (d, J = 7.1 Hz, 2H), 2.05-1.96 (m, 1H), 1.74 (s, 6H), 0.94 (d, J = 6.7 Hz, 6H).<br>LCMS (Method A) Rt 3.23 mins; MS m/z 356.3 = [M + H]+ (100% @ 215 nm) |
| 83.10 | 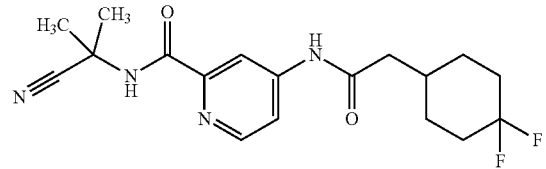<br>N-(1-Cyano-1-methyl-ethyl)-4-[[2-(4,4-difluorocyclohexyl)acetyl]amino]pyridine-2-carboxamide | 1H NMR (500 MHz, DMSO-d6) δ 10.57 (s, 1H), 8.82 (s, 1H), 8.50 (d, J = 5.5 Hz, 1H), 8.24 (d, J = 2.0 Hz, 1H), 7.83 (dd, J = 5.5, 2.2 Hz, 1H), 2.35 (d, J = 7.1 Hz, 2H), 2.03-1.92 (m, 3H), 1.90-1.83 (m, 1H), 1.82-1.75 (m, 3H), 1.72 (s, 6H), 1.31-1.21 (m, 2H).<br>LCMS (Method A) Rt 2.99 mins; MS m/z 365.3 = [M + H]+ (100% @ 215 nm) |
| 83.11 | 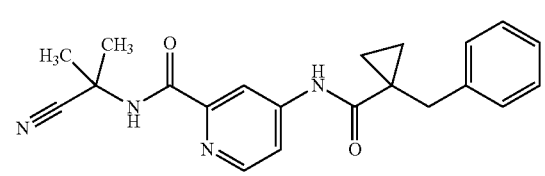<br>4-[(1-Benzylcyclopropanecarbonyl)amino]-N-(1-cyano-1-methyl-ethyl)pyridine-2-carboxamide | 1H NMR (500 MHz, DMSO-d6) δ 9.94 (s, 1H), 8.80 (s, 1H), 8.46 (d, J = 5.5 Hz, 1H), 8.28 (d, J = 2.0 Hz, 1H), 7.90 (dd, J = 5.6, 2.2 Hz, 1H), 7.28-7.23 (m, 4H), 7.20-7.14 (m, 1H), 3.12 (s, 2H), 1.72 (s, 6H), 1.24 (q, J = 4.2 Hz, 2H), 0.87 (q, J = 4.4 Hz, 2H).<br>LCMS (Method A) Rt 3.26 mins; MS m/z 363.3 = [M + H]+ (100% @ 215 nm) |

TABLE 14-continued

| Ex. | Structure and Name | 1H NMR, LCMS Retention Time, [M + H]+, |
|---|---|---|
| 83.13 | 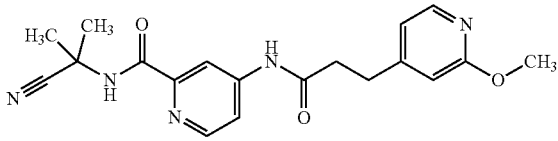<br>N-(1-Cyano-1-methyl-ethyl)-4-[3-(2-methoxy-4-pyridyl)propanoylamino]pyridine-2-carboxamide | 1H NMR (500 MHz, DMSO-d6) δ 10.61 (s, 1H), 8.83 (s, 1H), 8.51 (d, J = 5.5 Hz, 1H), 8.22 (d, J = 2.0 Hz, 1H), 8.06 (d, J = 5.3 Hz, 1H), 7.83 (dd, J = 5.5, 2.2 Hz, 1H), 6.90 (dd, J = 5.3, 1.3 Hz, 1H), 6.70 (s, 1H), 3.82 (s, 3H), 2.91 (t, J = 7.5 Hz, 2H), 2.75 (t, J = 7.5 Hz, 2H), 1.73 (s, 6H).<br>LCMS (Method A) Rt 2.29 mins; MS m/z 368.3 = [M + H]+ (97% @ 215 nm) |
| 83.14 | 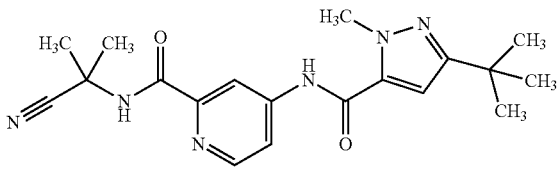<br>4-[(5-tert-Butyl-2-methyl-pyrazole-3-carbonyl)amino]-N-(1-cyano-1-methyl-ethyl)pyridine-2-carboxamide | 1H NMR (500 MHz, DMSO-d6) δ 10.66 (s, 1H), 8.86 (s, 1H), 8.58-8.55 (m, 1H), 8.45-8.41 (m, 1H), 8.05 (dd, J = 5.5, 2.2 Hz, 1H), 7.06 (s, 1H), 4.05 (s, 3H), 1.74 (s, 6H), 1.29 (s, 9H).<br>LCMS (Method A) Rt 3.32 mins; MS m/z 369.3 = [M + H]+ (100% @ 215 nm) |
| 83.15 | 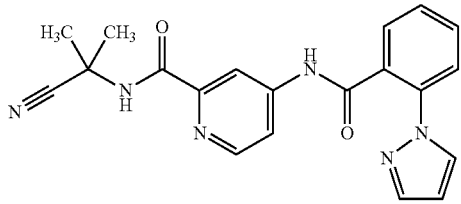<br>N-(1-Cyano-1-methyl-ethyl)-4-[(2-pyrazol-1-ylbenzoyl)amino]pyridine-2-carboxamide | 1H NMR (500 MHz, DMSO-d6) δ 10.86 (s, 1H), 8.83 (s, 1H), 8.51 (d, J = 5.5 Hz, 1H), 8.23 (d, J = 1.6 Hz, 1H), 8.19 (d, J = 2.4 Hz, 1H), 7.82-7.79 (m, 1H), 7.71-7.65 (m, 3H), 7.59 (d, J = 1.6 Hz, 1H), 7.55-7.51 (m, 1H), 6.47-6.45 (m, 1H), 1.73 (s, 6H).<br>LCMS (Method A) Rt 2.50 mins; MS m/z 375.30 = [M + H]+ (98% @ 215 nm) |
| 83.16 | 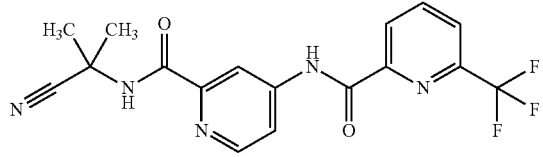<br>N-[2-[(1-Cyano-1-methyl-ethyl)carbamoyl]-4-pyridyl]-6-(trifluoromethyl)pyridine-2-carboxamide | 1H NMR (500 MHz, DMSO-d6) δ 11.05 (s, 1H), 8.88 (s, 1H), 8.64 (d, J = 2.1 Hz, 1H), 8.62 (d, J = 5.5 Hz, 1H), 8.43 (d, J = 7.5 Hz, 1H), 8.38 (t, J = 7.8 Hz, 1H), 8.22 (d, 1H), 8.18 (dd, J = 5.5, 2.2 Hz, 1H), 1.75 (s, 6H).<br>LCMS (Method A) Rt 3.23 mins; MS m/z 378.20 = [M + H]+ (100% @ 215 nm) |
| 83.17 | 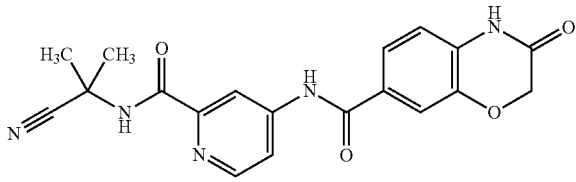<br>N-[2-[(1-Cyano-1-methyl-ethyl)carbamoyl]-4-pyridyl]-3-oxo-4H-1,4-benzoxazine-7-carboxamide | 1H NMR (500 MHz, DMSO-d6) δ 11.04 (s, 1H), 10.68 (s, 1H), 8.85 (s, 1H), 8.56 (d, J = 5.5 Hz, 1H), 8.46 (d, J = 2.1 Hz, 1H), 8.09 (dd, J = 5.5, 2.2 Hz, 1H), 7.67-7.64 (m, 2H), 7.03 (d, J = 8.0 Hz, 1H), 4.68 (s, 2H), 1.74 (s, 6H).<br>LCMS (Method A) Rt 2.32 mins; MS m/z 380.20 = [M + H]+ (94% @ 215 nm) |
| 83.18 | 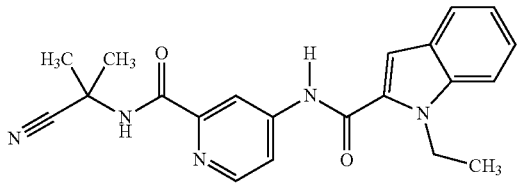<br>N-[2-[(1-Cyano-1-methyl-ethyl)carbamoyl]-4-pyridyl]-1-ethyl-indole-2-carboxamide | 1H NMR (500 MHz, DMSO-d6) δ 10.86 (s, 1H), 8.86 (s, 1H), 8.57 (d, J = 5.5 Hz, 1H), 8.52 (d, J = 2.0 Hz, 1H), 8.07 (dd, J = 5.5, 2.2 Hz, 1H), 7.74 (d, J = 7.9 Hz, 1H), 7.62 (d, J = 8.4 Hz, 1H), 7.49 (s, 1H), 7.37-7.33 (m, 1H), 7.18-7.14 (m, 1H), 4.61 (q, J = 7.0 Hz, 2H), 1.75 (s, 6H), 1.34 (t, J = 7.0 Hz, 3H).<br>LCMS (Method A) Rt 3.64 mins; MS m/z 376.3 = [M + H]+ (94% @ 215 nm) |

TABLE 14-continued

| Ex. | Structure and Name | 1H NMR, LCMS Retention Time, [M + H]+, |
|---|---|---|
| 83.19 | 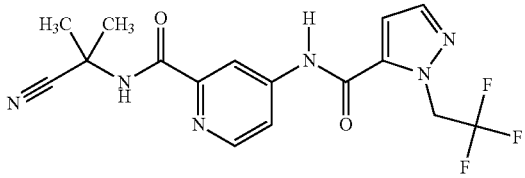<br>N-(1-Cyano-1-methyl-ethyl)-4-[[2-(2,2,2-trifluoroethyl)pyrazole-3-carbonyl]amino]pyridine-2-carboxamide | 1H NMR (500 MHz, DMSO-d6) δ 10.92 (s, 1H), 8.88 (s, 1H), 8.60 (d, J = 5.5 Hz, 1H), 8.44 (d, J = 2.1 Hz, 1H), 8.01 (dd, J = 5.5, 2.2 Hz, 1H), 7.81 (d, J = 2.0 Hz, 1H), 7.33 (d, J = 2.0 Hz, 1H), 5.53 (q, J = 8.9 Hz, 2H), 1.74 (s, 6H).<br>LCMS (Method A) Rt 2.85 mins; MS m/z 381.3 = [M + H]+ (100% @ 215 nm) |
| 83.20 | 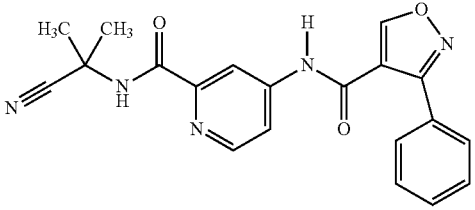<br>N-[2-[(1-Cyano-1-methyl-ethyl)carbamoyl]-4-pyridyl]-3-phenyl-isoxazole-4-carboxamide | 1H NMR (500 MHz, DMSO-d6) δ 11.07 (s, 1H), 9.64 (s, 1H), 8.87 (s, 1H), 8.57 (d, J = 5.5 Hz, 1H), 8.32 (d, J = 2.1 Hz, 1H), 7.91 (dd, J = 5.5, 2.2 Hz, 1H), 7.75-7.71 (m, 2H), 7.54-7.49 (m, 3H), 1.73 (s, 6H).<br>LCMS (Method A) Rt 3.02 mins; MS m/z 376.3 = [M + H]+ (99% @ 215 nm) |
| 83.21 | 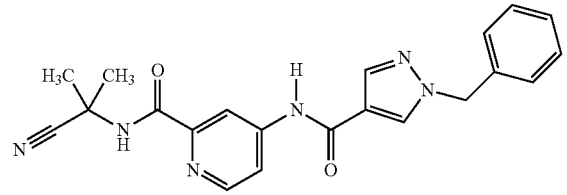<br>4-[(1-Benzylpyrazole-4-carbonyl)amino]-N-(1-cyano-1-methyl-ethyl)pyridine-2-carboxamide | 1H NMR (500 MHz, DMSO-d6) δ 10.42 (s, 1H), 8.84 (s, 1H), 8.53 (d, J = 5.6 Hz, 2H), 8.36 (d, J = 2.1 Hz, 1H), 8.12 (s, 1H), 8.03 (dd, J = 5.6, 2.2 Hz, 1H), 7.40-7.36 (m, 2H), 7.34-7.28 (m, 3H), 5.41 (s, 2H), 1.73 (s, 6H).<br>LCMS (Method A) Rt 2.89 mins; MS m/z 389.3 = [M + H]+ (100% @ 215 nm) |
| 83.22 | 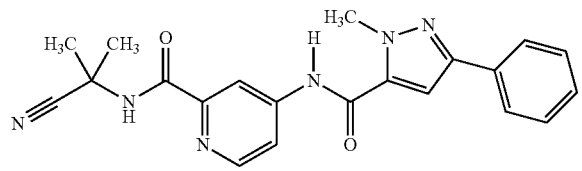<br>N-(1-Cyano-1-methyl-ethyl)-4-[(2-methyl-5-phenyl-pyrazole-3-carbonyl)amino]pyridine-2-carboxamide | 1H NMR (500 MHz, DMSO-d6) δ 10.86 (s, 1H), 8.88 (s, 1H), 8.60 (d, J = 5.5 Hz, 1H), 8.46 (d, J = 2.1 Hz, 1H), 8.06 (dd, J = 5.5, 2.2 Hz, 1H), 7.85-7.80 (m, 2H), 7.58 (s, 1H), 7.47 (t, J = 7.7 Hz, 2H), 7.36 (t, J = 7.4 Hz, 1H), 4.16 (s, 3H), 1.75 (s, 6H).<br>LCMS (Method A) Rt 3.44 mins; MS m/z 389.3 = [M + H]+ (100% @ 215 nm) |
| 83.23 | 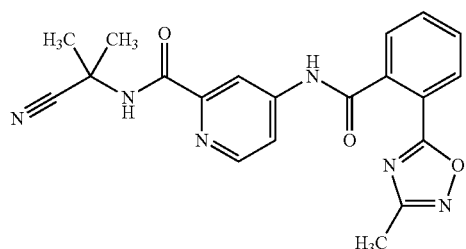<br>N-(1-Cyano-1-methyl-ethyl)-4-[[2-(3-methyl-1,2,4-oxadiazol-5-yl)benzoyl]amino]pyridine-2-carboxamide | 1H NMR (500 MHz, DMSO-d6) δ 11.16 (s, 1H), 8.87 (s, 1H), 8.58 (d, J = 5.5 Hz, 1H), 8.31 (d, J = 1.9 Hz, 1H), 8.11-8.07 (m, 1H), 7.89 (dd, J = 5.5, 2.0 Hz, 1H), 7.85-7.76 (m, 3H), 2.32 (s, 3H), 1.74 (s, 6H).<br>LCMS (Method A) Rt 2.61 mins; MS m/z 391.3 = [M + H]+ (96% @ 215 nm) |
| 83.24 | 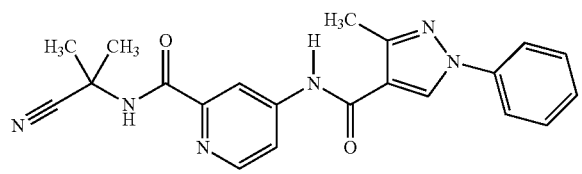<br>N-(1-Cyano-1-methyl-ethyl)-4-[(3-methyl-1-phenyl-pyrazole-4-carbonyl)amino]pyridine-2-carboxamide | 1H NMR (500 MHz, DMSO-d6) δ 10.43 (s, 1H), 9.15 (s, 1H), 8.86 (s, 1H), 8.56 (d, J = 5.5 Hz, 1H), 8.35 (d, J = 2.1 Hz, 1H), 8.06 (dd, J = 5.5, 2.2 Hz, 1H), 7.83-7.79 (m, 2H), 7.59-7.54 (m, 2H), 7.39 (t, J = 7.4 Hz, 1H), 1.74 (s, 6H). Pyrazole CH3 behind DMSO peak at 2.50.<br>LCMS (Method A) Rt 3.32 mins; MS m/z 389.3 = [M + H]+ (99% @ 215 nm) |

TABLE 14-continued

| Ex. | Structure and Name | 1H NMR, LCMS Retention Time, [M + H]+, |
|---|---|---|
| 83.25 | 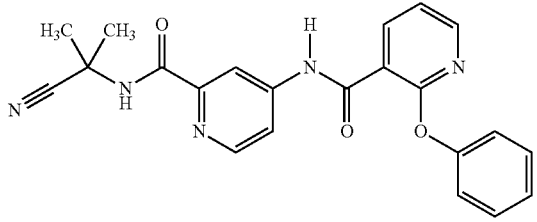<br>N-[2-[(1-Cyano-1-methyl-ethyl)carbamoyl]-4-pyridyl]-2-phenoxy-pyridine-3-carboxamide | 1H NMR (500 MHz, DMSO-d6) δ 11.11 (s, 1H), 8.87 (s, 1H), 8.58 (d, J = 5.5 Hz, 1H), 8.35 (d, J = 2.0 Hz, 1H), 8.27 (dd, J = 4.9, 1.9 Hz, 1H), 8.15 (dd, J = 7.4, 1.9 Hz, 1H), 7.99 (dd, J = 5.5, 2.1 Hz, 1H), 7.45-7.40 (m, 2H), 7.29 (dd, J = 7.4, 4.9 Hz, 1H), 7.25-7.20 (m, 3H), 1.73 (s, 6H).<br>LCMS (Method A) Rt 3.24 mins; MS m/z 402.3 = [M + H]+ (100% @ 215 nm) |
| 83.26 | 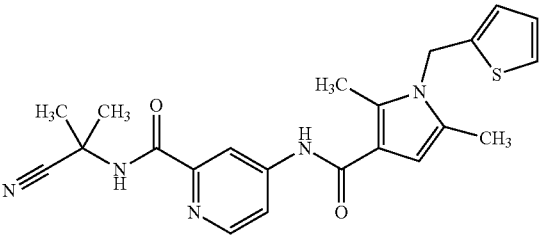<br>N-(1-Cyano-1-methyl-ethyl)-4-[[2,5-dimethyl-1-(2-thienylmethyl)pyrrole-3-carbonyl]amino]pyridine-2-carboxamide | 1H NMR (500 MHz, DMSO-d6) δ 9.90 (s, 1H), 8.80 (s, 1H), 8.47 (d, J = 5.6 Hz, 1H), 8.44 (d, J = 2.1 Hz, 1H), 8.05 (dd, J = 5.6, 2.2 Hz, 1H), 7.45 (dd, J = 5.1, 1.2 Hz, 1H), 6.99 (dd, J = 5.1, 3.5 Hz, 1H), 6.92 (dd, J = 3.4, 1.0 Hz, 1H), 6.56 (s, 1H), 5.30 (s, 2H), 2.53 (s, 3H), 2.24 (s, 3H), 1.73 (s, 6H).<br>LCMS (Method A) Rt 3.47 mins; MS m/z 422.3 = [M + H]+ (100% @ 215 nm) |
| 83.27 | 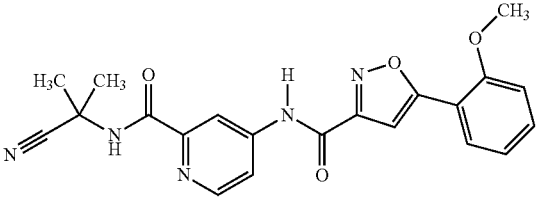<br>N-[2-[(1-Cyano-1-methyl-ethyl)carbamoyl]-4-pyridyl]-5-(2-methoxyphenyl)isoxazole-3-carboxamide | 1H NMR (500 MHz, DMSO-d6) δ 11.39 (s, 1H), 8.88 (s, 1H), 8.62 (d, J = 5.5 Hz, 1H), 8.56 (d, J = 2.1 Hz, 1H), 8.08 (dd, J = 5.5, 2.2 Hz, 1H), 7.95 (dd, J = 7.8, 1.7 Hz, 1H), 7.59-7.55 (m, 1H), 7.30-7.28 (m, 2H), 7.19-7.14 (m, 1H), 4.00 (s, 3H), 1.75 (s, 6H).<br>LCMS (Method A) Rt 3.58 mins; MS m/z 406.2 = [M + H]+ (77% @ 215 nm) |
| 83.28 | 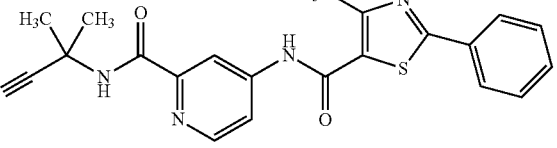<br>N-[2-[(1-Cyano-1-methyl-ethyl)carbamoyl]-4-pyridyl]-4-methyl-2-phenyl-thiazole-5-carboxamide | 1H NMR (500 MHz, DMSO-d6) δ 10.85 (s, 1H), 8.87 (s, 1H), 8.58 (d, J = 5.5 Hz, 1H), 8.40 (d, J = 2.1 Hz, 1H), 8.02-7.97 (m, 3H), 7.58-7.54 (m, 3H), 2.69 (s, 3H), 1.74 (s, 6H).<br>LCMS (Method A) Rt 3.52 mins; MS m/z 406.2 = [M + H]+ (100% @ 215 nm) |
| 83.29 | 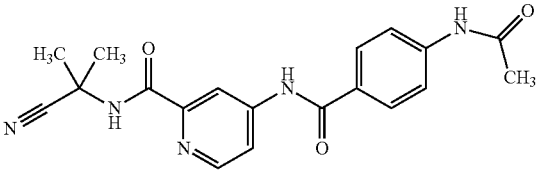<br>4-[(4-Acetamidobenzoyl)amino]-N-(1-cyano-1-methyl-ethyl)pyridine-2-carboxamide | LCMS (Method A) Rt 2.29 mins; MS m/z 366.2 = [M + H]+ (94% @ 215 nm) |

TABLE 14-continued

| Ex. | Structure and Name | 1H NMR, LCMS Retention Time, [M + H]+, |
|---|---|---|
| 83.30 | 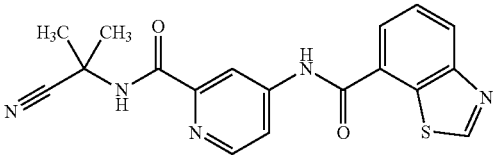<br>N-[2-[(1-Cyano-1-methyl-ethyl)carbamoyl]-4-pyridyl]-1,3-benzothiazole-7-carboxamide | 1H NMR (500 MHz, DMSO-d6) δ 11.13 (s, 1H), 9.54 (s, 1H), 8.90 (s, 1H), 8.62 (d, J = 5.5 Hz, 1H), 8.57 (d, J = 2.1 Hz, 1H), 8.45 (d, J = 7.5 Hz, 1H), 8.41-8.38 (m, 1H), 8.15 (dd, J = 5.5, 2.2 Hz, 1H), 7.81 (t, J = 7.8 Hz, 1H), 1.75 (s, 6H).<br>LCMS (Method A) Rt 2.71 mins; MS m/z 366.2 = [M + H]+ (94% @ 215 nm) |
| 83.31 | 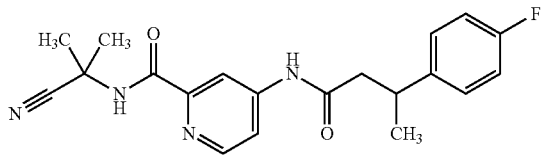<br>N-(1-Cyano-1-methyl-ethyl)-4-[3-(4-fluorophenyl)butanoylamino]pyridine-2-carboxamide | 1H NMR (500 MHz, DMSO-d6) δ 10.52 (s, 1H), 8.81 (s, 1H), 8.48 (d, J = 5.5 Hz, 1H), 8.20 (d, J = 2.0 Hz, 1H), 7.79 (dd, J = 5.5, 2.2 Hz, 1H), 7.34-7.28 (m, 2H), 7.15-7.07 (m, 2H), 3.30-3.26 (m, 1H), 2.68-2.62 (m, 2H), 1.72 (s, 6H), 1.25 (d, J = 7.0 Hz, 3H).<br>LCMS (Method A) Rt 3.21 mins; MS m/z 369.3 = [M + H]+ (97% @ 215 nm) |
| 83.32 | 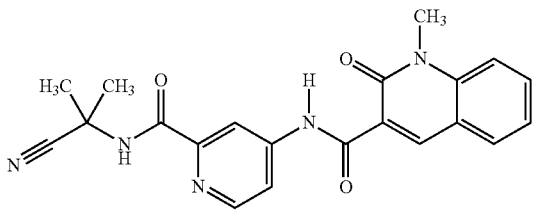<br>N-[2-[(1-Cyano-1-methyl-ethyl)carbamoyl]-4-pyridyl]-1-methyl-2-oxo-quinoline-3-carboxamide | 1H NMR (500 MHz, DMSO-d6) δ 12.52 (s, 1H), 9.02 (s, 1H), 8.89 (s, 1H), 8.60 (d, J = 5.4 Hz, 1H), 8.47 (s, 1H), 8.11 (d, J = 7.6 Hz, 1H), 7.90 (d, J = 3.7 Hz, 1H), 7.85 (t, J = 7.7 Hz, 1H), 7.74 (d, J = 8.5 Hz, 1H), 7.45 (t, J = 7.4 Hz, 1H), 3.82 (s, 3H), 1.75 (s, 6H).<br>LCMS (Method A) Rt 3.33 mins; MS m/z 390.2 = [M + H]+ (99% @ 215 nm) |

Example 84

N-tert-Butyl-3-[[2-(2-hydroxycyclohexyl)acetyl]amino]benzamide

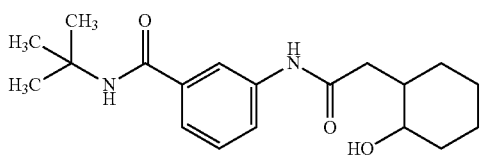 [SMILES: CC(C)(C)NC(=O)c1cccc(NC(=O)CC2CCCCC2O)c1]

HATU (268 mg, 0.7 mmol) was added to a stirred solution of 2-(2-oxocyclohexyl)acetic acid (100 mg, 0.64 mmol), 3-amino-N-tert-butyl-benzamide hydrochloride (146 mg, 0.64 mmol) and DIPEA (0.28 mL, 1.6 mmol) in DMF (2 mL) the resulting mixture was stirred at room temperature for 1 hour. The reaction mixture was diluted with EtOAc (10 mL) and water (10 mL). The aqueous layer was extracted with EtOAc (10 mL) and the combined organic extracts were washed with water (2×20 mL), brine (15 mL), dried over Na₂SO₄ and concentrated in vacuo. The crude material was then dissolved in MeOH (2 mL) and treated with NaBH₄ (36 mg, 0.96 mmol). The resulting mixture was stirred at room temperature for 10 minutes and then concentrated in vacuo. The crude residue was partitioned between water (20 mL) and EtOAc (20 mL). The organic layer was separated, dried over Na₂SO₄ and concentrated in vacuo. Purification by preparative HPLC (acidic pH, early elution method) afforded the titled compound as an off white powder as a 7:3 mixture of diastereoisomers.

1H NMR (400 MHz, DMSO-d6) δ 9.93 (s, 1H), 7.93-7.81 (m, 1H), 7.82-7.73 (m, 1H), 7.71-7.63 (m, 1H), 7.43-7.36 (m, 1H), 7.31 (t, J=7.8 Hz, 1H), 4.70-4.18 (m, 1H), 3.74-2.93 (m, 1H), 2.87-2.35 (m, 1H), 2.27-1.97 (m, 1H), 1.96-1.77 (m, 1H), 1.76-0.88 (m, 17H).

LCMS (Method A) Rt 2.63 mins; MS m/z 333.3=[M+H]+ (61% @ 215 nm); Rt 2.65 mins; MS m/z 333.3=[M+H]+ (38%®215 nm)

Example 85

N-tert-Butyl-6-[[2-(5-chloro-2-hydroxy-phenyl)acetyl]amino]pyrimidine-4-carboxamide

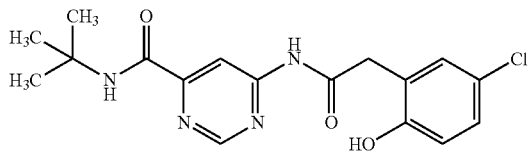 [SMILES: CC(C)(C)NC(=O)c1cc(NC(=O)Cc2cc(Cl)ccc2O)ncn1]

The titled compound was prepared from N-tert-butyl-6-[[2-(5-chloro-2-methoxy-phenyl)acetyl]amino]pyrimidine-4-carboxamide (Example 82) and analogously to Example 1 step 2.

1H NMR (500 MHz, DMSO-d6) δ 11.30 (s, 1H), 9.84 (s, 1H), 8.94 (d, J=1.2 Hz, 1H), 8.54 (d, J=1.2 Hz, 1H), 8.04 (s, 1H), 7.21 (d, J=2.7 Hz, 1H), 7.11 (dd, J=8.6, 2.7 Hz, 1H), 6.79 (d, J=8.6 Hz, 1H), 3.75 (s, 2H), 1.39 (s, 9H).

LCMS (Method A) Rt 3.16 mins; MS m/z 363.2=[M+H]+ (98% @ 215 nm)

Example 86

4-[[2-(5-Chloro-2-hydroxy-phenyl)acetyl]amino]-N-[1-cyano-2-methoxy-1-(methoxy methyl)ethyl]pyridine-2-carboxamide

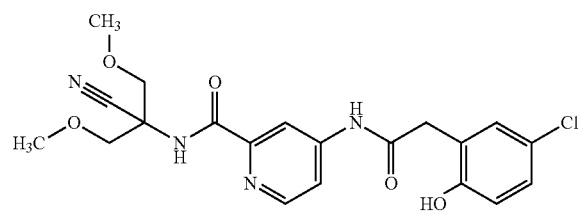 [SMILES: COCC(C#N)(COC)NC(=O)c1cc(NC(=O)Cc2cc(Cl)ccc2O)ccn1]

Step 1: Methyl 2-(5-chloro-2-hydroxy-phenyl)acetate

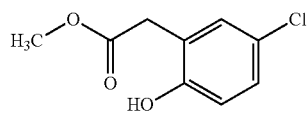

Methyl 2-(2-hydroxyphenyl)acetate (1.68 g, 10.11 mmol), NCS (1.35 g, 10.11 mmol) and triphenylphosphine sulfide (298 mg, 1.01 mmol) were dissolved in chloroform (40 mL) and stirred at room temperature for 1 hour. The resulting mixture was concentrated in vacuo and the residue dissolved in EtOAc (50 mL). The mixture was washed with water (2×50 mL), dried over anhydrous Na₂SO₄ and concentrated in vacuo. The residue was purified by chromatography on silica eluting with 0-50% EtOAc in heptane to afford the titled compound as a colourless viscous oil that solidified upon standing at room temperature.

1H NMR (500 MHz, DMSO-d6) δ 9.81 (br. s, 1H), 7.18 (d, J=2.7 Hz, 1H), 7.11 (dd, J=8.6, 2.7 Hz, 1H), 6.79 (d, J=8.6 Hz, 1H), 3.59 (s, 3H), 3.56 (s, 2H).

LC-MS (Method E): Rt 1.02 mins; MS m/z no ionisaton observed

Step 2: Methyl 2-[5-chloro-2-[(4-methoxyphenyl)methoxy]phenyl]acetate

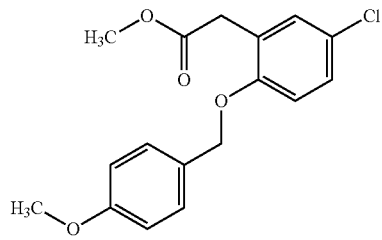 [SMILES: COC(=O)Cc1cc(Cl)ccc1OCc1ccc(OC)cc1]

Methyl 2-(5-chloro-2-hydroxy-phenyl)acetate (step 1)(1.83 mL, 7.76 mmol) was suspended in anhydrous acetone (50 mL) and treated with K₂CO₃ (1.61 g, 11.64 mmol) followed by 1-(bromomethyl)-4-methoxy-benzene (1.2 mL, 8.55 mmol). After heating at reflux (60° C.) for 2 hours, the mixture was concentrated in vacuo. The residue was dissolved in EtOAc (50 mL) and washed with water (50 mL), brine (50 mL), dried over anhydrous Na₂SO₄ and concentrated in vacuo. The resulting crude residue was purified by chromatography on silica eluting with 0-25% EtOAc in heptane to afford the titled compound as a viscous yellow oil.

1H NMR (500 MHz, DMSO-d6) δ 7.32-7.27 (m, 4H), 7.07 (d, J=8.6 Hz, 1H), 6.96-6.92 (m, 2H), 5.01 (s, 2H), 3.75 (s, 3H), 3.62 (s, 2H), 3.55 (s, 3H).

LC-MS (Method E): Rt 1.23 mins; MS m/z no ionization observed=[M+H]+

Step 3: Lithium 2-[5-chloro-2-[(4-methoxyphenyl)methoxy]phenyl]acetate

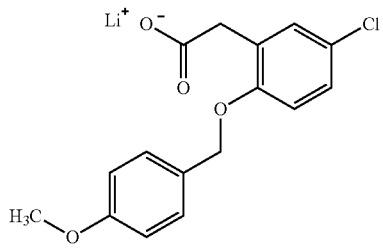 [SMILES: [Li+] ; COc1ccc(COc2ccc(Cl)cc2CC(=O)[O-])cc1]

Methyl 2-[5-chloro-2-[(4-methoxyphenyl)methoxy]phenyl]acetate (step 2) (2.4 g, 6.57 mmol) was dissolved in THF (5 mL) and treated with 2M aqueous lithium hydroxide hydrate solution (3.45 mL, 6.9 mmol). After stirring at room temperature for 1 hour, MeOH (5 mL) was added to the bi-phasic mixture and stirring continued at room temperature for 1 hour. Additional lithium hydroxide hydrate (13.8 mg, 0.33 mmol, 0.05 eq.) was added and the solution was stirred for another hour. A further portion of lithium hydroxide hydrate (13.8 mg, 0.33 mmol, 0.05 eq.) was added and stirring continued for 1 hour. The resulting mixture was concentrated in vacuo and azeotroped with MeCN (3×50 mL). The solid was suspended in diethyl ether (50 mL), filtered, washed with diethyl ether (2×25 mL) and dried under suction to afford the titled compound as a white powdery solid.

1H NMR (500 MHz, DMSO-d6) δ 7.40-7.36 (m, 2H), 7.22 (d, J=2.7 Hz, 1H), 7.07 (dd, J=8.7, 2.8 Hz, 1H), 6.94-6.89 (m, 3H), 4.97 (s, 2H), 3.75 (s, 3H), 3.17 (s, 2H).

LC-MS (Method E): Rt 1.17 mins; MS m/z 260.9=[M−H]− (95% @ 215 nm) [major mass ion observed for the decarboxylated ion fragment]

Step 4: Methyl 4-[[2-[5-chloro-2-[(4-methoxyphenyl)methoxy]phenyl]acetyl]amino]pyridine-2-carboxylate

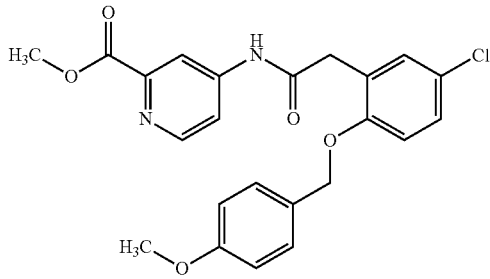 [SMILES: COC(=O)c1cc(NC(=O)Cc2cc(Cl)ccc2OCc2ccc(OC)cc2)ccn1]

To a mixture of lithium 2-[5-chloro-2-[(4-methoxyphenyl)methoxy]phenyl]acetate (step 3) (1.5 g, 4.8 mmol) and methyl 4-aminopyridine-2-carboxylate (0.8 g, 5.28 mmol) in anhydrous 1,4-dioxane (50 mL) was added simultaneously 50% T3P® solution in EtOAc (5.71 mL, 9.59 mmol) and TEA (3.35 mL, 19.19 mmol). The reaction mixture was stirred at room temperature, for 1 hour and then quenched by careful addition of NaHCO₃ (50 mL). H₂O (10 mL) was added to dissolve excess salts and the mixture was extracted with EtOAc (2×50 mL). The combined organic extracts were washed with brine (50 mL), dried over Na₂SO₄ and concentrated in vacuo. Purification by chromatography on NH-silica eluting with a gradient of 0-100% EtOAc in heptane afforded the titled compound as an off-white solid.

1H NMR (500 MHz, DMSO-d6) δ 10.65 (s, 1H), 8.54 (d, J=5.4 Hz, 1H), 8.21 (d, J=2.0 Hz, 1H), 7.75 (dd, J=5.5, 2.1 Hz, 1H), 7.33 (d, J=2.7 Hz, 1H), 7.30 (dd, J=8.7, 2.7 Hz, 1H), 7.22 (d, J=8.7 Hz, 2H), 7.09 (d, J=8.7 Hz, 1H), 6.65-6.61 (m, 2H), 4.97 (s, 2H), 3.87 (s, 3H), 3.70 (s, 2H), 3.64 (s, 3H).

LC-MS (Method F): Rt 1.63 mins; MS m/z 441.2/443.2= [M+H]+ (100% @ 215 nm)

Step 5: 4-[[2-[5-Chloro-2-[(4-methoxyphenyl)methoxy]phenyl]acetyl]amino]pyridine-2-carboxylic acid

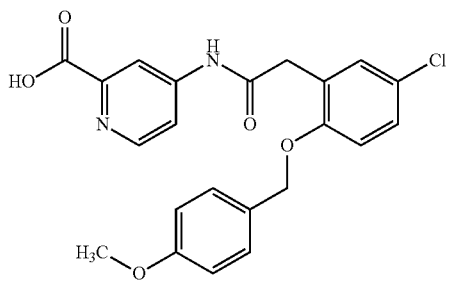 [SMILES: COc1ccc(COc2ccc(Cl)cc2CC(=O)Nc2ccnc(C(=O)O)c2)cc1]

Methyl 4-[[2-[5-chloro-2-[(4-methoxyphenyl)methoxy]phenyl]acetyl]amino]pyridine-2-carboxylate (step 4) (1.98 g, 4.49 mmol) was dissolved in THF (2.5 mL) and MeOH (2.5 mL) and treated with a 2M aqueous lithium hydroxide hydrate solution (2.47 mL, 4.94 mmol) and stirred at room temperature for 1 hour. Additional THF (2.5 mL), MeOH (2.5 mL) and water (2.5 mL) were added and stirring continued at room temperature overnight. The resulting mixture was diluted with EtOAc (50 mL) and water (50 mL). The pH was adjusted to pH 5 using 2M KHSO₄ (2 mL) and the precipitate was filtered. The filter cake was washed with water (20 mL), EtOAc (20 mL), diethyl ether (20 mL) and dried under vacuum to afford the titled compound as a white solid.

1H NMR (500 MHz, DMSO-d6) δ 10.61 (s, 1H), 8.43 (d, J=5.5 Hz, 1H), 8.11 (d, J=1.7 Hz, 1H), 7.75 (dd, J=5.6, 2.1 Hz, 1H), 7.33 (d, J=2.6 Hz, 1H), 7.30 (dd, J=8.7, 2.6 Hz, 1H), 7.23 (d, J=8.6 Hz, 2H), 7.08 (d, J=8.8 Hz, 1H), 6.68-6.64 (m, 2H), 4.98 (s, 2H), 3.71 (s, 2H), 3.65 (s, 3H) [OH not observed].

LC-MS (Method E): Rt 1.04 mins; MS m/z 427.0/429.0= [M+H]+ (98% @ 215 nm)

Step 6: 2-Amino-3-methoxy-2-(methoxymethyl)propanenitrile

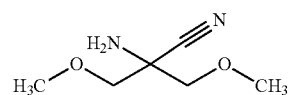

To a suspension of 1,3-dimethoxypropan-2-one (400 mg, 3.39 mmol) in 7M ammonia in MeOH (4.84 mL, 33.86 mmol) was added ammonium chloride (226 mg, 4.23 mmol) followed by sodium cyanide (207 mg, 4.23 mmol). After stirring at room temperature for 15 minutes, water (2.4 mL) was added and stirring continued for 3 hours. The mixture was diluted with EtOAc (30 mL) and washed with sat. sodium carbonate solution (3×20 mL) and brine (2×20 mL). The organic portion was separated, dried over Na₂SO₄ and concentrated in vacuo to afford the titled compound as a colorless oil.

1H NMR (500 MHz, Methanol-d4) δ 3.55 (d, J=9.5 Hz, 2H), 3.45 (d, J=9.5 Hz, 2H), 3.45 (s, 6H)

LC-MS (Method E): Rt 0.66 mins; MS m/z 145.1=[M+ H]+ (67% @ 215 nm)

Step 7: 4-[[2-(5-Chloro-2-hydroxy-phenyl)acetyl]amino]-N-[1-cyano-2-methoxy-1-(methoxymethyl)ethyl]pyridine-2-carboxamide To a solution of DIPEA (0.25 mL, 1.41 mmol), 4-[[2-[5-chloro-2-[(4-methoxyphenyl)methoxy]phenyl]acetyl]amino]pyridine-2-carboxylic acid (step 5) (200 mg, 0.47 mmol) and 50% T3P® solution in EtOAc (0.6 mL, 0.94 mmol) in DMF (2 mL) was added 2-amino-3-methoxy-2-(methoxymethyl)propanenitrile (step 6)(101 mg, 0.7 mmol) and the reaction mixture was stirred at room temperature for 6 hours. The resulting mixture was diluted with EtOAc (10 mL) and washed with brine (10 mL). The aqueous layer was re-extracted with EtOAc (10 mL) and the combined organic extracts were dried over Na₂SO₄ and concentrated in vacuo. The crude residue was dissolved in dioxane (2 mL) and treated with 4N HCl in dioxane (2 mL, 8.0 mmol). After stirring at room temperature for 2 hours, the mixture was concentrated in vacuo and purification of the crude product by preparative HPLC (acidic pH, early elution method) afforded the titled compound as an off white solid.

1H NMR (500 MHz, Methanol-d4) δ 8.48 (d, J=5.5 Hz, 1H), 8.21 (d, J=1.8 Hz, 1H), 7.96 (dd, J=5.5, 2.2 Hz, 1H), 7.21 (d, J=2.6 Hz, 1H), 7.11 (dd, J=8.6, 2.6 Hz, 1H), 6.80 (d, J=8.6 Hz, 1H), 4.00 (d, J=9.5 Hz, 2H), 3.83 (d, J=9.5 Hz, 2H), 3.73 (s, 2H), 3.50 (s, 6H).

Example 87

4-[[2-(3-Amino-4-tert-butyl-phenyl)acetyl]amino]-N-tert-butyl-pyridine-2-carboxamide and Example 88 4-[[2-(2-amino-4-tert-butyl-phenyl)acetyl]amino]-N-tert-butyl-pyridine-2-carboxamide

Step 1: A mixture of 2-(4-tert-butyl-2-nitro-phenyl)acetic acid and 2-(4-tert-butyl-3-nitro-phenyl)acetic acid

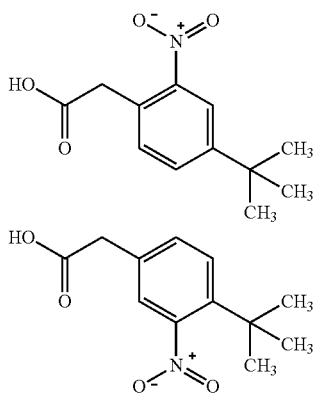

A stirred solution of 2-(4-tert-butylphenyl)acetic acid (1.0 g, 5.2 mmol) in water (5 mL) was treated dropwise with nitric acid (0.65 mL, 15.6 mmol) and sulfuric acid (0.55 mL, 10.4 mmol) and the mixture was stirred at room temperature for 10 hours. The resulting mixture was diluted with EtOAc (10 mL) and washed with brine (10 mL). The organic portion was separated, washed with brine (2 mL), dried over $Na_2SO_4$ and concentrated in vacuo. Purification by chromatography on silica eluting with 0-100% EtOAc in heptane afforded the titled mixture as a yellow oil.

1H NMR (500 MHz, DMSO-d6) δ 8.01 (d, J=2.1 Hz, 1H), 7.76 (dd, J=8.0, 2.1 Hz, 1H), 7.61 (d, J=8.1 Hz, 1H), 7.48 (d, J=8.1 Hz, 1H), 7.48-7.42 (m, 2H), 3.95 (s, 2H), 3.66 (s, 2H), 1.34 (s, 9H), 1.33 (s, 9H).

LC-MS (Method E): Rt 1.13 mins; MS m/z=no ionisation observed

Step 2: A mixture of N-tert-butyl-4-[[2-(4-tert-butyl-2-nitro-phenyl)acetyl]amino]pyridine-2-carboxamide and N-tert-butyl-4-[[2-(4-tert-butyl-3-nitro-phenyl)acetyl]amino]pyridine-2-carboxamide

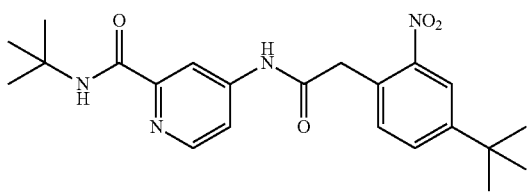

-continued

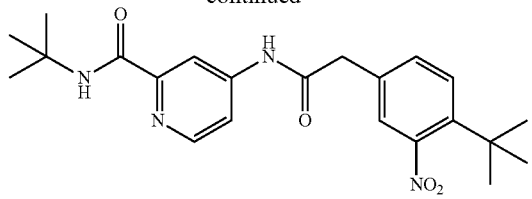

To a solution of DIPEA (1.36 mL, 7.76 mmol), 50% T3P® solution in EtOAc (0.6 mL, 5.17 mmol) and a mixture of 2-(4-tert-butyl-2-nitro-phenyl)acetic acid and 2-(4-tert-butyl-3-nitro-phenyl)acetic acid (step 1) (720 mg, 3.03 mmol) in DMF (5 mL) was added 4-amino-N-tert-butyl-pyridine-2-carboxamide (645 mg, 3.34 mmol) and the reaction mixture was stirred at room temperature for 6 hours. The resulting mixture was diluted with EtOAc (10 mL) and washed with brine (10 mL). The aqueous layer was re-extracted with EtOAc (10 mL) and the combined extracts were dried over $Na_2SO_4$ and concentrated in vacuo to afford the titled compounds as a yellow oil.

1H NMR (500 MHz, DMSO-d6) δ 10.81 (m, 2H), 8.46 (m, 2H), 8.16 (m, 2H), 8.03 (m, 3H), 7.84-7.74 (m, 3H), 7.64 (d, J=8.1 Hz, 1H), 7.55-7.47 (m, 3H), 4.15 (s, 2H), 3.81 (s, 2H), 1.40 (s, 18H), 1.34 (s, 18H).

LC-MS (Method E): Rt 1.29 mins; MS m/z 413.5=[M+H]+ (100% @ 215 nm)

Step 3: 4-[[2-(3-Amino-4-tert-butyl-phenyl)acetyl]amino]-N-tert-butyl-pyridine-2-carboxamide and 4-[[2-(2-amino-4-tert-butyl-phenyl)acetyl]amino]-N-tert-butyl-pyridine-2-carboxamide To a mixture of N-tert-butyl-4-[[2-(4-tert-butyl-2-nitro-phenyl)acetyl]amino]pyridine-2-carboxamide and N-tert-butyl-4-[[2-(4-tert-butyl-3-nitro-phenyl)acetyl]amino]pyridine-2-carboxamide (step 2)(950 mg, 2.3 mmol) in EtOH (5 mL) was added 10% Pd—C (123 mg, 1.15 mmol) and the mixture was stirred under an atmosphere of hydrogen for 18 hours. The resulting mixture was filtered through Celite® and washed through with methanol. The filtrate was concentrated in vacuo and purification of the crude by preparative HPLC (basic pH, early elution method) afforded the following compounds as white solids:

Example 87: 4-[[2-(3-Amino-4-tert-butyl-phenyl)acetyl]amino]-N-tert-butyl-pyridine-2-carboxamide

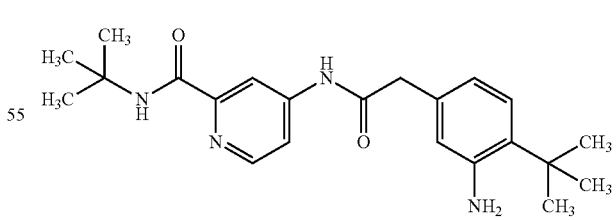

1H NMR (500 MHz, DMSO-d6) δ 10.67 (s, 1H), 8.44 (d, J=5.5 Hz, 1H), 8.19 (d, J=2.0 Hz, 1H), 8.03 (s, 1H), 7.82 (dd, J=5.5, 2.2 Hz, 1H), 7.00 (d, J=8.0 Hz, 1H), 6.59 (d, J=1.9 Hz, 1H), 6.48 (dd, J=8.0, 1.9 Hz, 1H), 4.76 (s, 2H), 3.50 (s, 2H), 1.40 (s, 9H), 1.31 (s, 9H).

LC-MS (Method A): Rt 3.56 mins; MS m/z 383.3=[M+H]+ (100% @ 215 nm)

Example 88: 4-[[2-(2-Amino-4-tert-butyl-phenyl)acetyl]amino]-N-tert-butyl-pyridine-2-carboxamide

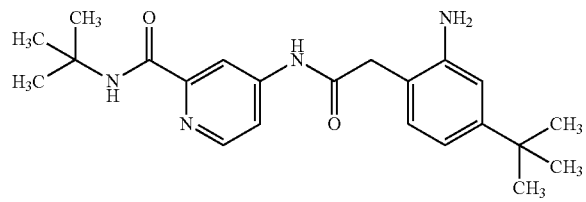 [SMILES: CC(C)(C)NC(=O)c1cc(NC(=O)Cc2ccc(C(C)(C)C)cc2N)ccn1]

1H NMR (500 MHz, DMSO-d6) δ 10.69 (s, 1H), 8.45 (d, J=5.5 Hz, 1H), 8.18 (d, J=2.1 Hz, 1H), 8.03 (s, 1H), 7.81 (dd, J=5.5, 2.2 Hz, 1H), 6.97 (d, J=8.0 Hz, 1H), 6.73 (d, J=2.0 Hz, 1H), 6.59 (dd, J=7.9, 2.0 Hz, 1H), 4.96 (s, 2H), 3.52 (s, 2H), 1.40 (s, 9H), 1.22 (s, 9H).

LC-MS (Method A): Rt 3.58 mins; MS m/z 383.3=[M+H]+ (99% @ 215 nm)

Example 89

N-tert-Butyl-4-[[2-(4-tert-butyl-3-hydroxy-phenyl)acetyl]amino]pyridine-2-carboxamide

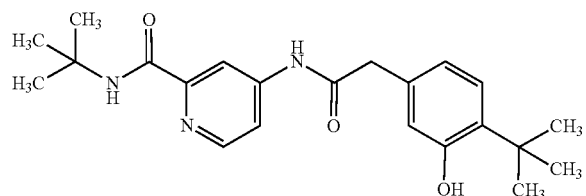

To a cooled (0° C.) solution of 4-[[2-(3-amino-4-tert-butyl-phenyl)acetyl]amino]-N-tert-butyl-pyridine-2-carboxamide (Example 87) (100 mg, 0.26 mmol) in water (0.2 mL) was added sulfuric acid (0.02 mL, 0.29 mmol) in water (0.3 mL) followed by sodium nitrite (20 mg, 0.29 mmol) in water (0.5 mL). After stirring at 5° C. for 3 hours, copper sulfate pentahydrate (326 mg, 1.31 mmol) and copper (I) oxide (112.23 mg, 0.78 mmol) in water (0.5 mL) were added and the mixture stirred at room temperature for 12 hours. The resulting mixture was diluted with EtOAc (10 mL) and water (10 mL). The organic layer was separated, dried over Na2SO4 and concentrated in vacuo. Purification of the crude material by preparative HPLC (acidic pH early elution method) afforded the titled compound as a white solid.

1H NMR (400 MHz, DMSO-d6) δ 10.71 (s, 1H), 9.30 (s, 1H), 8.45 (d, J=5.5 Hz, 1H), 8.20 (d, J=2.1 Hz, 1H), 8.03 (s, 1H), 7.81 (dd, J=5.5, 2.2 Hz, 1H), 7.08 (d, J=8.0 Hz, 1H), 6.76 (d, J=1.7 Hz, 1H), 6.68 (dd, J=7.9, 1.7 Hz, 1H), 3.56 (s, 2H), 1.40 (s, 9H), 1.32 (s, 9H).

LC-MS (Method A): Rt 3.76 mins; MS m/z 384.2=[M+H]+ (99% @ 215 nm)

Example 90

N-tert-Butyl-4-[[2-(4-tert-butyl-2-hydroxy-phenyl)acetyl]amino]pyridine-2-carboxamide

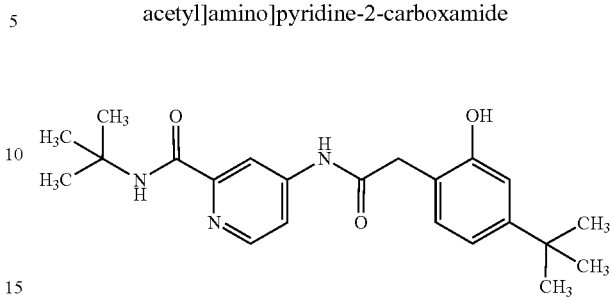

The titled compound was prepared from 4-[[2-(2-amino-4-tert-butyl-phenyl)acetyl]amino]-N-tert-butyl-pyridine-2-carboxamide (Example 88) analogously to Example 89.

1H NMR (500 MHz, DMSO-d6) δ 10.64 (s, 1H), 9.36 (s, 1H), 8.44 (d, J=5.5 Hz, 1H), 8.18 (d, J=2.0 Hz, 1H), 8.03 (s, 1H), 7.83 (dd, J=5.5, 2.2 Hz, 1H), 7.06 (d, J=7.9 Hz, 1H), 6.84 (d, J=1.9 Hz, 1H), 6.79 (dd, J=7.9, 1.9 Hz, 1H), 3.61 (s, 2H), 1.40 (s, 9H), 1.25 (s, 9H).

LC-MS (Method A): Rt 3.76 mins; MS m/z 384.2=[M+H]+ (100% @ 215 nm)

Example 91

N-tert-Butyl-4-[[2-(4-tert-butyl-2-fluoro-5-hydroxy-phenyl)acetyl]amino]pyridine-2-carboxamide

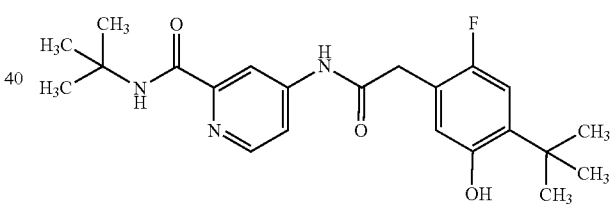

To a solution of N-tert-butyl-4-[[2-(2-fluoro-5-hydroxy-phenyl)acetyl]amino]pyridine-2-carboxamide (Example 3.13b) (300 mg, 0.87 mmol) in DCM (12 mL) was added tert-butanol (332 μL, 3.47 mmol) and H2SO4 (250 μL, 0.87 mmol) and the mixture stirred at room temperature for 1 hour. The resulting mixture was concentrated in vacuo and partitioned between EtOAc (20 mL) and water (20 mL). The organic portion was separated, washed with brine (20 mL) and concentrated in vacuo. Purification of the residue by preparative HPLC (acidic pH, standard elution method) afforded the titled compound as a white solid.

1H NMR (500 MHz, DMSO-d6) δ 10.78 (s, 1H), 9.31 (s, 1H), 8.46 (d, J=5.5 Hz, 1H), 8.19 (d, J=2.0 Hz, 1H), 8.03 (s, 1H), 7.80 (dd, J=5.5, 2.2 Hz, 1H), 6.87 (d, J=11.9 Hz, 1H), 6.74 (d, J=7.0 Hz, 1H), 3.65 (s, 2H), 1.40 (s, 9H), 1.32 (s, 9H).

LC-MS (Method A): Rt 3.89 mins; MS m/z 402.3=[M+H]+ (96% @ 215 nm)

Example 92

4-[[2-(4-Chloro-3-hydroxy-phenyl)acetyl]amino]-N-(4-cyanotetrahydropyran-4-yl)pyridine-2-carboxamide

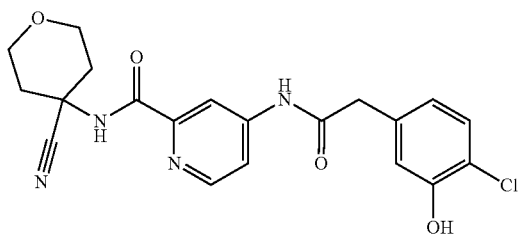 [SMILES: N#CC1(NC(=O)c2cc(NC(=O)Cc3ccc(Cl)c(O)c3)ccn2)CCOCC1]

Step 1: Methyl 4-[[2-(4-chloro-3-methoxy-phenyl)acetyl]amino]pyridine-2-carboxylate

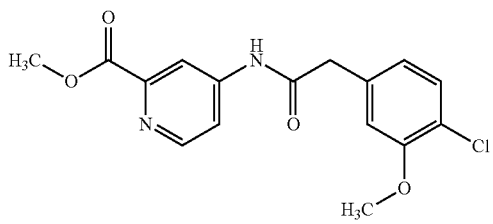 [SMILES: COC(=O)c1cc(NC(=O)Cc2ccc(Cl)c(OC)c2)ccn1]

The titled compound was prepared from 2-(4-chloro-3-methoxy-phenyl)acetic acid and methyl 4-aminopyridine-2-carboxylate analogously to Example 41 step 1.

1H NMR (400 MHz, DMSO-d6) δ 10.77 (s, 1H), 8.55 (d, J=5.5 Hz, 1H), 8.29 (d, J=2.0 Hz, 1H), 7.78 (dd, J=5.5, 2.1 Hz, 1H), 7.36 (d, J=8.1 Hz, 1H), 7.12 (d, J=1.7 Hz, 1H), 6.91 (dd, J=8.1, 1.7 Hz, 1H), 3.86 (s, 3H), 3.85 (s, 3H), 3.73 (s, 2H).

LC-MS (Method E): Rt 1.03 mins; MS m/z 335.0/337.0= [M+H]+ (95% @ 215 nm)

Step 2: 4-[[2-(4-Chloro-3-methoxy-phenyl)acetyl]amino]pyridine-2-carboxylic acid

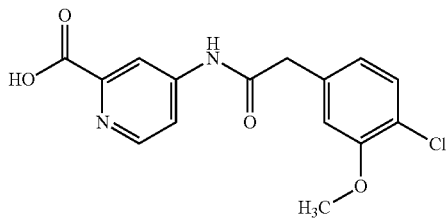 [SMILES: COc1cc(CC(=O)Nc2ccnc(C(=O)O)c2)ccc1Cl]

The titled compound was prepared from methyl 4-[[2-(4-chloro-3-methoxy-phenyl)acetyl]amino]pyridine-2-carboxylate (step 1) analogously to Example 41 step 2.

1H NMR (500 MHz, DMSO-d6) δ 10.77 (s, 1H), 8.53 (d, J=5.5 Hz, 1H), 8.26 (d, J=2.0 Hz, 1H), 7.79 (dd, J=5.5, 2.2 Hz, 1H), 7.36 (d, J=8.1 Hz, 1H), 7.13 (d, J=1.8 Hz, 1H), 6.91 (dd, J=8.1, 1.9 Hz, 1H), 3.85 (s, 3H), 3.73 (s, 2H).

LC-MS (Method E): Rt 0.88 mins; MS m/z 321.0/322.9= [M+H]+ (100% @ 215 nm)

Step 3: 4-[[2-(4-Chloro-3-hydroxy-phenyl)acetyl]amino]pyridine-2-carboxylic acid

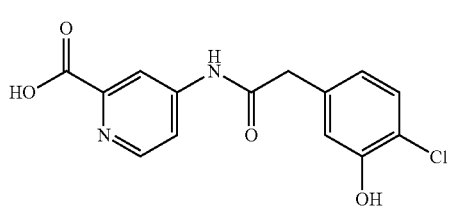 [SMILES: O=C(Cc1ccc(Cl)c(O)c1)Nc1ccnc(C(=O)O)c1]

The titled compound was prepared from 4-[[2-(4-Chloro-3-methoxy-phenyl)acetyl]amino]pyridine-2-carboxylic acid (step 2) and BBr3 analogously Example 31 step 1.

LC-MS (Method E): Rt 0.80 mins; MS m/z 306.9/308.9= [M+H]+ (62% @ 215 nm)

Step 4: 4-[[2-(4-Chloro-3-hydroxy-phenyl)acetyl]amino]-N-(4-cyanotetrahydropyran-4-yl)pyridine-2-carboxamide To a solution of 4-[[2-(4-chloro-3-hydroxy-phenyl)acetyl]amino]pyridine-2-carboxylic acid (step 3)(65%, 50 mg, 0.11 mmol), 4-aminotetrahydropyran-4-carbonitrile (16 mg, 0.13 mmol) and DIPEA (0.04 mL, 0.21 mmol) in DMF (0.5 mL) was added HATU (48 mg, 0.13 mmol). The resulting mixture was stirred at room temperature for 1 hour. The reaction mixture was diluted with 0.5 M NaOH (aq., 0.4 mL), stirred for 5 min then acidified to pH 5 with 2M aqueous HCl. The aqueous layer was extracted with EtOAc (2×5 mL) and the combined organic extracts were washed with water (5 mL), dried over Na2SO4 and concentrated in vacuo. Purification by preparative HPLC (acidic pH, early elution method) followed by lyophilisation of the clean fractions afforded the titled compound as an off white powder.

1H NMR (500 MHz, DMSO-d6) δ 10.79 (s, 1H), 10.11 (br s, 1H), 9.00 (s, 1H), 8.53 (d, J=5.5 Hz, 1H), 8.23 (d, J=2.1 Hz, 1H), 7.85 (dd, J=5.5, 2.2 Hz, 1H), 7.26 (d, J=8.1 Hz, 1H), 6.94 (d, J=1.9 Hz, 1H), 6.76 (dd, J=8.2, 1.9 Hz, 1H), 3.90-3.82 (m, 2H), 3.63 (s, 2H), 3.62-3.53 (m, 2H), 2.39-2.33 (m, 2H), 2.13-2.00 (m, 2H).

LC-MS (Method A): Rt 2.50 mins; MS m/z 415.1/417.1= [M+H]+ (100% @ 215 nm)

The compounds of the following tabulated Examples (Table 15) were prepared from 4-[[2-(4-chloro-3-hydroxy-phenyl)acetyl]amino]pyridine-2-carboxylic acid (Example 92, step 3) analogously to Example 92 step 4 by replacing 4-aminotetrahydropyran-4-carbonitrile with the appropriate commercially available amine.

TABLE 15

| Ex. | Structure and Name | 1H NMR<br>LCMS Retention Time, [M + H]+, |
|---|---|---|
| 92.1 | 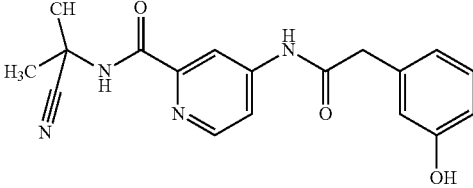<br>4-[[2-(4-Chloro-3-hydroxy-phenyl)acetyl]amino]-N-(1-cyano-1-methyl-ethyl)pyridine-2-carboxamide | 1H NMR (500 MHz, DMSO-d6) δ 10.79 (s, 1H), 10.14 (br s, 1H), 8.83 (s, 1H), 8.51 (d, J = 5.5 Hz, 1H), 8.23 (d, J = 2.0 Hz, 1H), 7.85 (dd, J = 5.5, 2.2 Hz, 1H), 7.26 (d, J = 8.1 Hz, 1H), 6.94 (s, 1H), 6.76 (d, J = 7.5 Hz, 1H), 3.63 (s, 2H), 1.72 (s, 6H).<br>LC-MS (Method A): Rt 2.63 mins; MS m/z 373.1/375.1 = [M + H]+ (95% @ 215 nm) |
| 92.2 | 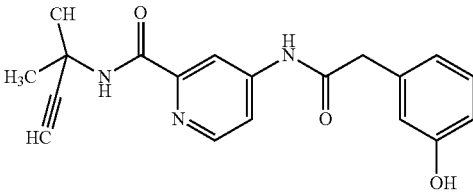<br>4-[[2-(4-Chloro-3-hydroxy-phenyl)acetyl]amino]-N-(1,1-dimethylprop-2-ynyl)pyridine-2-carboxamide | 1H NMR (500 MHz, DMSO-d6) δ 10.76 (s, 1H), 10.12 (s, 1H), 8.47 (d, J = 5.5 Hz, 1H), 8.31 (s, 1H), 8.20 (d, J = 2.0 Hz, 1H), 7.82 (dd, J = 5.5, 2.2 Hz, 1H), 7.26 (d, J = 8.1 Hz, 1H), 6.94 (d, J = 2.0 Hz, 1H), 6.76 (dd, J = 8.2, 2.0 Hz, 1H), 3.63 (s, 2H), 3.21 (s, 1H), 1.64 (s, 6H).<br>LC-MS (Method A): Rt 2.90 mins; MS m/z 372.1/374.1 = [M + H]+ (97% @ 215 nm) |
| 92.3 | 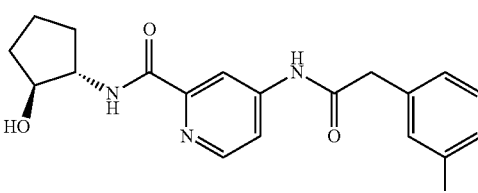<br>4-[[2-(4-Chloro-3-hydroxy-phenyl)acetyl]amino]-N-[(1s,2s)-2-hydroxycyclopentyl]pyridine-2-carboxamide | 1H NMR (500 MHz, DMSO-d6) δ 10.73 (s, 1H), 10.13 (s, 1H), 8.48 (d, J = 5.5 Hz, 1H), 8.44 (d, J = 7.6 Hz, 1H), 8.19 (d, J = 2.1 Hz, 1H), 7.81 (dd, J = 5.5, 2.2 Hz, 1H), 7.26 (d, J = 8.1 Hz, 1H), 6.95 (d, J = 1.9 Hz, 1H), 6.76 (dd, J = 8.2, 1.9 Hz, 1H), 4.80 (d, J = 4.5 Hz, 1H), 3.98 (dq, J = 13.1, 7.2, 6.4 Hz, 2H), 3.62 (s, 2H), 2.05-1.93 (m, 1H), 1.92-1.79 (m, 1H), 1.72-1.57 (m, 2H), 1.57-1.38 (m, 2H).<br>LC-MS (Method A): Rt 2.37 mins; MS m/z 390.1/392.1 = [M + H]+ (99% @ 215 nm) |

Example 93

4-[[2-(4-tert-Butyl-3-hydroxy-phenyl)acetyl]amino]-N-[3-(hydroxymethyl)tetrahydrofuran-3-yl]pyridine-2-carboxamide

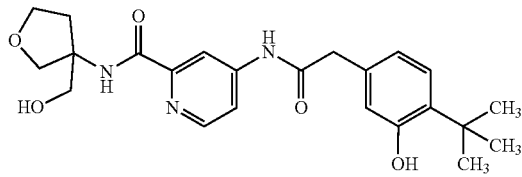 [SMILES: CC(C)(C)c1ccc(CC(=O)Nc2ccnc(C(=O)NC3(CO)CCOC3)c2)cc1O]

To a stirred solution of 4-tert-butyl-3-methoxy-benzoic acid (1.9 g, 9.12 mmol) in THF (20 mL) was added 1M borane-THF (25.55 mL, 25.55 mmol) and the mixture was stirred at 50° C. for 1 hour. After cooling to room temperature, the reaction was quenched with methanol (10 mL) and the volatile solvent removed in vacuo. More methanol (10 mL) was added and the volatiles were removed in vacuo. This process was repeated once more to afford the titled compound as a pale yellow oil.

1H NMR (400 MHz, DMSO-d6) δ 7.14 (d, J=7.9 Hz, 1H), 6.94 (s, 1H), 6.81 (d, J=7.8 Hz, 1H), 5.09 (s, 1H), 4.45 (s, 2H), 3.80 (s, 3H), 1.32 (s, 9H).

Step 1: (4-tert-Butyl-3-methoxy-phenyl)methanol

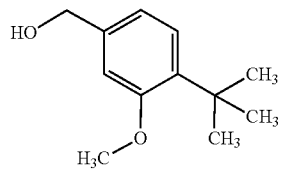

Step 2: 1-tert-Butyl-4-(chloromethyl)-2-methoxy-benzene

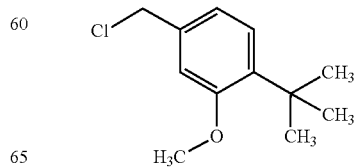

A stirred solution of (4-tert-butyl-3-methoxy-phenyl)methanol (step 1)(1.56 g, 8.03 mmol) and DMF (0.59 mL, 8.03 mmol) in DCM (20 mL) was treated dropwise with thionyl chloride (1.42 mL, 16.06 mmol) and the mixture stirred at room temperature for 1 hour. The resulting mixture was concentrated in vacuo and the residue diluted with EtOAc (10 mL) and washed with saturated NaHCO₃ (10 mL). The organic portion was separated, washed with brine (2 mL), dried over Na₂SO₄, filtered and concentrated in vacuo to afford the titled compound as a yellow oil.

1H NMR (400 MHz, DMSO-d6) δ 7.21 (d, J=7.9 Hz, 1H), 7.05 (d, J=1.4 Hz, 1H), 6.94 (dd, J=7.9, 1.6 Hz, 1H), 4.72 (s, 2H), 3.82 (s, 3H), 1.33 (s, 9H).

Step 3: 2-(4-tert-Butyl-3-methoxy-phenyl)acetonitrile

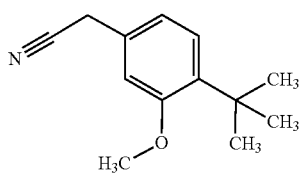

A solution of 1-tert-butyl-4-(chloromethyl)-2-methoxy-benzene (step 2)(1.7 g, 7.99 mmol) in DMF (10 mL) was treated with sodium cyanide (0.78 g, 15.98 mmol) and the resulting mixture stirred at room temperature for 8 hours. The mixture was diluted with EtOAc (30 mL) and washed with sat. sodium carbonate (3×20 mL) and brine (2×20 mL). The organic layer was separated, dried over sodium sulfate and concentrated in vacuo to afford the titled compound as a yellow oil.

1H NMR (500 MHz, DMSO-d6) δ 7.22 (d, J=7.9 Hz, 1H), 6.95 (d, J=1.6 Hz, 1H), 6.86 (dd, J=7.9, 1.7 Hz, 1H), 3.96 (s, 2H), 3.82 (s, 3H), 1.32 (s, 9H).

Step 4: 2-(4-tert-Butyl-3-methoxy-phenyl)acetic acid

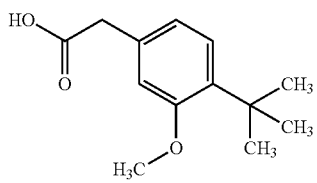

To a solution of 2-(4-tert-butyl-3-methoxy-phenyl)acetonitrile (step 3) (1.52 g, 7.48 mmol) H₂O (5 mL) was added lithium hydroxide hydrate (1.76 mL, 37.39 mmol) and the reaction mixture was heated at reflux for 10 hours. After cooling to room temperature, the mixture was acidified with concentrated HCl solution. The mixture was extracted with DCM (10 mL) and the combined organic extracts were dried over sodium sulphate and concentrated in vacuo to afford the titled compound as a pale yellow solid.

1H NMR (400 MHz, DMSO-d6) δ 12.13 (s, 1H), 7.13 (d, J=7.9 Hz, 1H), 6.87 (d, J=1.6 Hz, 1H), 6.76 (dd, J=7.9, 1.7 Hz, 1H), 3.79 (s, 3H), 3.51 (s, 2H), 1.32 (s, 9H).

LC-MS (Method E): Rt 1.14 mins; MS m/z 220.9=[M+H]+ (99% @ 215 nm)

Step 5: Methyl 4-[[2-(4-tert-butyl-3-methoxy-phenyl)acetyl]amino]pyridine-2-carboxylate

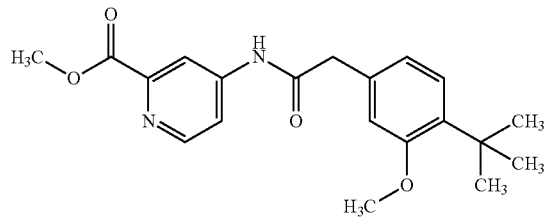 [SMILES: COC(=O)c1cc(NC(=O)Cc2ccc(C(C)(C)C)c(OC)c2)ccn1]

The titled compound was prepared from 2-(4-tert-butyl-3-methoxy-phenyl)acetic acid (step 4) and methyl 4-aminopyridine-2-carboxylate analogously to Example 30 step 1.

1H NMR (500 MHz, DMSO-d6) δ 10.78 (s, 1H), 8.55 (d, J=5.5 Hz, 1H), 8.31 (d, J=2.0 Hz, 1H), 7.80 (dd, J=5.5, 2.1 Hz, 1H), 7.16 (d, J=7.9 Hz, 1H), 6.96 (d, J=1.5 Hz, 1H), 6.84 (dd, J=7.9, 1.6 Hz, 1H), 3.87 (s, 3H), 3.81 (s, 3H), 3.66 (s, 2H), 1.31 (s, 9H).

LC-MS (Method E): Rt 1.19 mins; MS m/z 357.0=[M+H]+ (97% @ 215 nm)

Step 6: 4-[[2-(4-tert-Butyl-3-methoxy-phenyl)acetyl]amino]pyridine-2-carboxylic acid

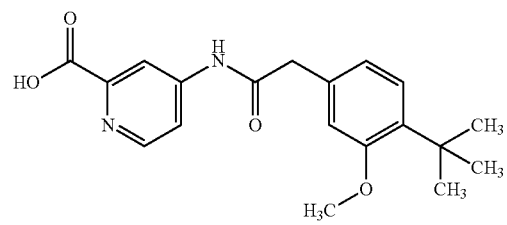 [SMILES: COc1cc(CC(=O)Nc2ccnc(C(=O)O)c2)ccc1C(C)(C)C]

The titled compound was prepared from methyl 4-[[2-(4-tert-butyl-3-methoxy-phenyl)acetyl]amino]pyridine-2-carboxylate (step 5) and lithium hydroxide hydrate analogously to Example 30 step 2.

1H NMR (500 MHz, DMSO-d6) δ 10.87 (s, 1H), 8.54 (d, J=5.6 Hz, 1H), 8.30 (d, J=2.0 Hz, 1H), 7.84 (dd, J=5.6, 2.2 Hz, 1H), 7.16 (d, J=7.9 Hz, 1H), 6.97 (d, J=1.6 Hz, 1H), 6.84 (dd, J=7.9, 1.6 Hz, 1H), 3.81 (s, 3H), 3.68 (s, 2H), 1.31 (s, 9H)

LC-MS (Method E): Rt 1.03 mins; MS m/z 343.1=[M+H]+ (94% @ 215 nm)

Step 7: 4-[[2-(4-tert-Butyl-3-hydroxy-phenyl)acetyl]amino]pyridine-2-carboxylic acid

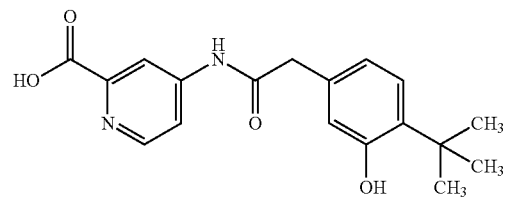 [SMILES: CC(C)(C)c1ccc(CC(=O)Nc2ccnc(C(=O)O)c2)cc1O]

The titled compound was prepared from 4-[[2-(4-tert-butyl-3-methoxy-phenyl)acetyl]amino]pyridine-2-carboxylic acid (step 6) and BBr₃ analogously to Example 31 step 1.

1H NMR (500 MHz, DMSO-d6) δ 11.12 (s, 1H), 9.32 (s, 1H), 8.60 (d, J=6.0 Hz, 1H), 8.38 (d, J=2.0 Hz, 1H), 7.98 (dd, J=5.9, 2.1 Hz, 1H), 7.08 (d, J=7.9 Hz, 1H), 6.76 (d, J=1.7 Hz, 1H), 6.71-6.66 (m, 1H), 3.62 (s, 2H), 1.32 (s, 9H).

LC-MS (Method E): Rt 0.97 mins; MS m/z 329=[M+H]+ (76% @ 215 nm)

Step 8: 4-[[2-(4-tert-butyl-3-hydroxy-phenyl)acetyl]amino]-N-[3-(hydroxymethyl)tetrahydrofuran-3-yl]pyridine-2-carboxamide The titled compound was prepared from 4-[[2-(4-tert-butyl-3-hydroxy-phenyl)acetyl]amino]pyridine-2-carboxylic acid (step 7) and (3-aminotetrahydrofuran-3-yl)methanol analogously to Example 31 step 2.

1H NMR (500 MHz, DMSO-d6) δ 10.72 (s, 1H), 9.30 (s, 1H), 8.48 (d, J=5.5 Hz, 1H), 8.41 (s, 1H), 8.22 (d, J=2.1 Hz, 1H), 7.82 (dd, J=5.5, 2.1 Hz, 1H), 7.08 (d, J=8.0 Hz, 1H), 6.76 (d, J=1.7 Hz, 1H), 6.68 (dd, J=7.9, 1.6 Hz, 1H), 5.17 (t, J=5.6 Hz, 1H), 3.90-3.76 (m, 4H), 3.61 (d, J=5.2 Hz, 2H), 3.56 (s, 2H), 2.32 (ddd, J=12.6, 7.6, 5.0 Hz, 1H), 1.98 (dt, J=12.8, 7.8 Hz, 1H), 1.32 (s, 9H).

LC-MS (Method A): Rt 2.91 mins; MS m/z 428.3=[M+H]+ (96% @ 215 nm)

The compounds of the following tabulated Examples (Table 16) were prepared from 4-[[2-(4-tert-butyl-3-hydroxy-phenyl)acetyl]amino]pyridine-2-carboxylic acid (Example 93, step 7) analogously to Example 93 step 8 by replacing (3-aminotetrahydrofuran-3-yl)methanol with the appropriate commercially available amine.

TABLE 16

| Ex. | Structure and Name | 1H NMR<br>LCMS Retention Time, [M + H]+, |
|---|---|---|
| 93.1 | 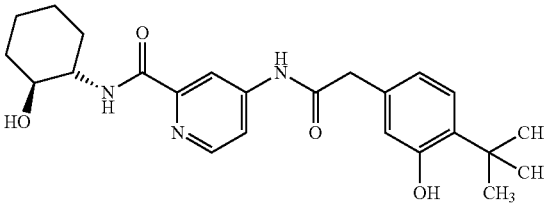<br>4-[2-(4-tert-butyl-3-hydroxyphenyl)acetamido]-N-[(1S,2S)-2-hydroxycyclohexyl]pyridine-2-carboxamide | 1H NMR (500 MHz, DMSO-d6) δ 10.74 (s, 1H), 9.31 (s, 1H), 8.48 (d, J = 5.5 Hz, 1H), 8.34 (d, J = 8.1 Hz, 1H), 8.21 (d, J = 2.0 Hz, 1H), 7.84 (dd, J = 5.5, 2.2 Hz, 1H), 7.07 (d, J = 8.0 Hz, 1H), 6.77 (d, J = 1.6 Hz, 1H), 6.69 (dd, J = 8.0, 1.6 Hz, 1H), 4.69 (d, J = 5.5 Hz, 1H), 3.61-3.52 (m, 3H), 3.48-3.39 (m, 1H), 1.96-1.84 (m, 2H), 1.69-1.58 (m, 2H), 1.32 (s, 9H), 1.32-1.20 (m, 4H).<br>LC-MS (Method A): Rt 3.24 mins; MS m/z 426.3 = [M + H]+ (100% @ 215 nm) |
| 93.2 | 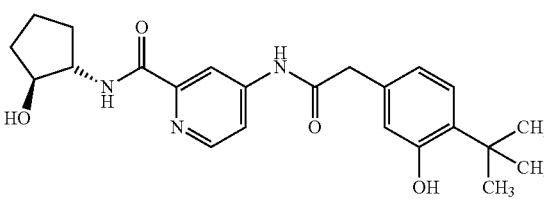<br>4-[2-(4-tert-butyl-3-hydroxyphenyl)acetamido]-N-[(1S,2S)-2-hydroxycyclopentyl]pyridine-2-carboxamide | 1H NMR (500 MHz, DMSO-d6) δ 10.76 (s, 1H), 9.31 (s, 1H), 8.48 (d, J = 5.5 Hz, 1H), 8.44 (d, J = 7.6 Hz, 1H), 8.21 (d, J = 1.9 Hz, 1H), 7.83 (dd, J = 5.5, 2.2 Hz, 1H), 7.07 (d, J = 8.0 Hz, 1H), 6.77 (d, J = 1.6 Hz, 1H), 6.69 (dd, J = 8.0, 1.7 Hz, 1H), 4.81 (d, J = 4.3 Hz, 1H), 4.05-3.93 (m, 2H), 3.56 (s, 2H), 2.05-1.95 (m, 1H), 1.91-1.80 (m, 1H), 1.74-1.58 (m, 2H), 1.56-1.42 (m, 2H), 1.32 (s, 9H).<br>LC-MS (Method A): Rt 3.12 mins; MS m/z 412.3 = [M + H]+ (100% @ 215 nm) |
| 93.3 | 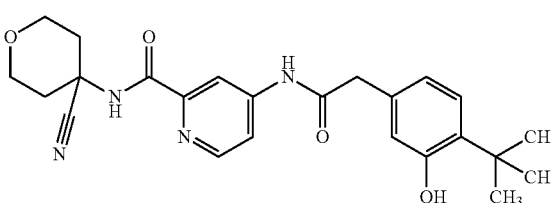<br>4-[[2-(4-tert-Butyl-3-hydroxy-phenyl)acetyl]amino]-N-(4-cyanotetrahydropyran-4-yl)pyridine-2-carboxamide | 1H NMR (500 MHz, DMSO-d6) δ 10.77 (s, 1H), 9.30 (s, 1H), 9.01 (s, 1H), 8.54 (d, J = 5.5 Hz, 1H), 8.25 (d, J = 2.0 Hz, 1H), 7.87 (dd, J = 5.5, 2.2 Hz, 1H), 7.08 (d, J = 8.0 Hz, 1H), 6.77 (d, J = 1.7 Hz, 1H), 6.69 (dd, J = 8.0, 1.7 Hz, 1H), 3.87 (dt, J = 12.2, 3.8 Hz, 2H), 3.64-3.55 (m, 4H), 2.41-2.33 (m, 2H), 2.08 (ddd, J = 13.8, 10.3, 3.9 Hz, 2H), 1.32 (s, 9H).<br>LC-MS (Method A): Rt 3.30 mins; MS m/z 437.2 = [M + H]+ (98% @ 215 nm) |
| 93.4 | 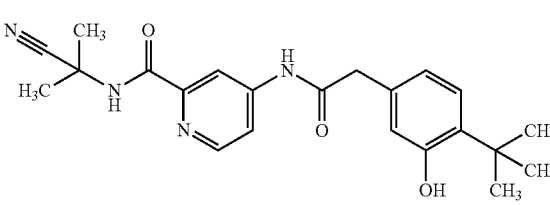<br>4-[[2-(4-tert-Butyl-3-hydroxy-phenyl)acetyl]amino]-N-(1-cyano-1-methyl-ethyl)pyridine-2-carboxamide | 1H NMR (500 MHz, DMSO-d6) δ 10.76 (s, 1H), 9.30 (s, 1H), 8.83 (s, 1H), 8.52 (d, J = 5.5 Hz, 1H), 8.25 (d, J = 2.0 Hz, 1H), 7.86 (dd, J = 5.5, 2.2 Hz, 1H), 7.08 (d, J = 8.0 Hz, 1H), 6.77 (d, J = 1.8 Hz, 1H), 6.69 (dd, J = 7.9, 1.8 Hz, 1H), 3.57 (s, 2H), 1.73 (s, 6H), 1.33 (s, 9H).<br>LC-MS (Method A): Rt 3.41 mins; MS m/z 395.2 = [M + H]+ (99% @ 215 nm) |

TABLE 16-continued

| Ex. | Structure and Name | 1H NMR<br>LCMS Retention Time, [M + H]+, |
|---|---|---|
| 93.5 | 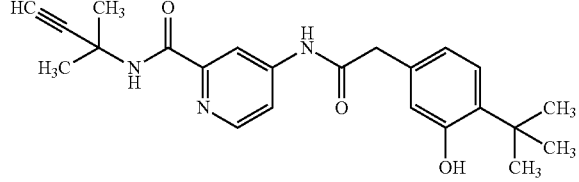<br>4-[[2-(4-tert-Butyl-3-hydroxy-phenyl)acetyl]amino]-N-(1,1-dimethylprop-2-ynyl)pyridine-2-carboxamide | 1H NMR (500 MHz, DMSO-d6) δ 10.74 (s, 1H), 9.30 (s, 1H), 8.48 (d, J = 5.5 Hz, 1H), 8.32 (s, 1H), 8.21 (d, J = 2.0 Hz, 1H), 7.83 (dd, J = 5.5, 2.2 Hz, 1H), 7.08 (d, J = 8.0 Hz, 1H), 6.76 (d, J = 1.8 Hz, 1H), 6.69 (dd, J = 8.0, 1.8 Hz, 1H), 3.56 (s, 2H), 3.21 (s, 1H), 1.65 (s, 6H), 1.32 (s, 9H).<br>LC-MS (Method A): Rt 3.64 mins; MS m/z 394.2 = [M + H]+ (96% @ 215 nm) |

Example 94

4-[[2-(5-Chloro-2-hydroxy-phenyl)acetyl]amino]-N-(1-methyl-1-phenyl-ethyl)pyridine-2-carboxamide

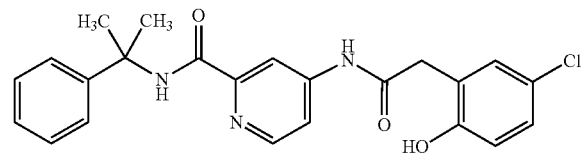 [SMILES: CC(C)(NC(=O)c1cc(NC(=O)Cc2cc(Cl)ccc2O)ccn1)c1ccccc1]

Step 1: 4-[[2-(5-Chloro-2-methoxy-phenyl)acetyl]amino]-N-(1-methyl-1-phenyl-ethyl)pyridine-2-carboxamide

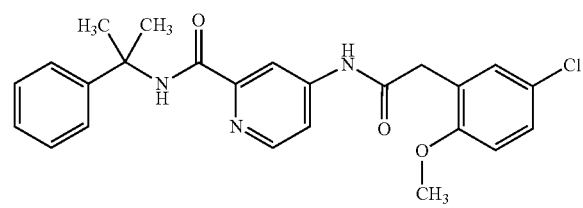 [SMILES: COc1ccc(Cl)cc1CC(=O)Nc1ccnc(C(=O)NC(C)(C)c2ccccc2)c1]

The titled compound was prepared from 4-[[2-(5-chloro-2-methoxy-phenyl)acetyl]amino]pyridine-2-carboxylic acid (Example 8.1 step 2) and 2-phenylpropan-2-amine analogously to Example 86, step 7.

Step 2: 4-[[2-(5-Chloro-2-hydroxy-phenyl)acetyl]amino]-N-(1-methyl-1-phenyl-ethyl)pyridine-2-carboxamide The titled compound was prepared from 4-[[2-(5-chloro-2-methoxy-phenyl)acetyl]amino]-N-(1-methyl-1-phenyl-ethyl)pyridine-2-carboxamide (step 1) and $BBr_3$ analogously to Example 3 step 3.

1H NMR (500 MHz, DMSO-d6) δ 10.77 (s, 1H), 9.80 (s, 1H), 8.56 (s, 1H), 8.49 (d, J=5.5 Hz, 1H), 8.10 (d, J=2.0 Hz, 1H), 7.84 (dd, J=5.6, 2.2 Hz, 1H), 7.41-7.37 (m, 2H), 7.33-7.28 (m, 2H), 7.23-7.18 (m, 2H), 7.11 (dd, J=8.6, 2.7 Hz, 1H), 6.79 (d, J=8.6 Hz, 1H), 3.65 (s, 2H), 1.72 (s, 6H).

LC-MS (Method A): Rt 3.88 mins; MS m/z 424.2/426.2= [M+H]+ (99% @ 215 nm)

Biological Example 95

Automated Whole-Cell Patch Clamp Assay to Detect TMEM16A Activity in Recombinant Cells Cell Culture and Preparation Fisher rat thyroid (FRT) cells stably expressing human TMEM16A (TMEM16Aabc variant; Dr Luis Galietta, Insituto Giannina, Italy) were cultured in T-75 flasks in Hams F-12 media with Coon's modification (Sigma) supplemented with 10% (v/v) foetal bovine serum, penicillin-streptomycin (10,000 U/mL/10000 μg/mL), G-418 (750 μg/mL), L-glutamine (2 mM) and sodium bicarbonate solution (7.5% v/v). At ~90% confluence cells were harvested for experiments by detachment with a 2:1 (v/v) mixture of Detachin (BMS Biotechnology) and 0.25% (w/v) trypsin-EDTA. Cells were diluted to a density of $3.5$-$4.5 \times 10^6$ cells/mL with media consisting of CHO-S-SFM II (Sigma), 25 mM HEPES (Sigma) and Soy bean trypsin inhibitor (Sigma).

Whole-Cell Patch Clamp Recording

FRT-TMEM16A cells were whole-cell patch clamped using an automated planar patch clamp system (Qpatch, Sophion). Briefly, once high resistance (GOhm) seals were established between the cells and the planar recording array the patch was ruptured using suction pulses to establish the whole-cell recording configuration of the patch clamp technique. The assay employed the following solutions (all reagents Sigma):

Intracellular solution (mM): N-methyl-D-glucamine 130, $CaCl_2$ 18.2, $MgCl_2$ 1, HEPES 10, EGTA 10, BAPTA 20, Mg-ATP 2, pH 7.25, 325 mOsm with sucrose.

Extracellular solution (mM): N-methyl-D-glucamine 130, $CaCl_2$ 2, $MgCl_2$ 1, HEPES 10, pH 7.3, 320 mOsm with sucrose.

The intracellular solution buffers intracellular calcium at levels required to give ~20% activation of the maximal TMEM16A mediated current ($EC_{20}$ for calcium ions). Cells were voltage clamped at a holding potential of −70 mV and a combined voltage step (to +70 mV)/ramp (−90 my to +90 mV) was applied at 0.05 Hz. After a period of current stabilisation test compounds, solubilised in 100% (v/v) DMSO and subsequently diluted into extracellular solution, were applied to generate a cumulative concentration response curve. Each concentration of test compound was incubated for 5 minutes before addition of the next concentration. After the final concentration was tested a supramaximal concentration of either a known active positive modulator or the TMEM16A inhibitor, CaCCinhA01 (Del La Fuente et al, 2008) was added to define the upper and lower limits of the assay.

Compound activity was quantified by measuring the increase in current upon compound addition and expressing this as a percentage increase of baseline TMEM16A current level. Percentage increases in current were determined for each concentration and the data plotted as a function of concentration using either the Qpatch software or Graphpad Prism v6.05 providing the concentration which gave 50% of its maximal effect ($EC_{50}$) and maximum efficacy (percentage of baseline increase).

The method of calculating the results is illustrated in FIG. 1, which shows an example trace from the Qpatch TMEM16A assay. In FIG. 1, $I_{BL}$ equals baseline current, $I_{[\#1]}$ equals the peak current during test compound concentration 1 incubation period and so on.

Peak TMEM16A current at +70 mV was plotted as a function of time over the assay period. Baseline current ($I_{BL}$) was measured after a period of stabilisation. The increase in current for each compound addition was determined by taking the peak current during the incubation period and subtracting the current from the previous recording period and then expressing this as a percentage of the baseline current. For test compound concentration 1 in FIG. 1 this is:

$$(I_{[\#1]} - I_{BL}/I_{BL}) \times 100$$

For each additional concentration tested the increase in current was determined by subtracting the current from the previous incubation period and normalising the baseline value—for test concentration 2 in FIG. 1 this is:

$$(I_{[\#2]} - I_{[\#1]}/I_{BL}) \times 100$$

The values for each test concentration were plotted as a cumulative function of concentration eg. for test concentration two this would be the sum of the peak changes measured during concentration one plus concentration two.

The results obtained for the example compounds are shown in Table 8, from which it can be seen that the compounds of the present invention are capable of significantly increasing the TMEM16A current level.

TABLE 17

% Potentiation shown by 3.33 μM solution of Test Compounds and Calculated $EC_{50}$ Values

| Example | % Potentiation @ 3.33 μM Avg | $EC_{50}$ Avg (μM) |
|---|---|---|
| 1 | 203 | 0.21 |
| 1.1 | 182 | 0.56 |
| 1.2 | 170 | 0.54 |
| 1.3 | 233 | 0.24 |
| 1.4 | 195 | 0.40 |
| 1.5 | 149 | 0.34 |
| 1.6 | 255 | 0.06 |
| 1.7 | 239 | 0.15 |
| 1.8 | 300 | 0.41 |
| 1.9 | 79 | 4.20 |
| 1.10 | 200 | 0.08 |
| 2 | 262 | 0.27 |
| 2.1 | 216 | 0.49 |
| 2.2 | 158 | 1.61 |
| 2.3 | 203 | 0.59 |
| 2.4 | 53 | |
| 2.5 | 51 | 1.34 |
| 2.6 | 140 | 2.91 |
| 2.7 | 51 | 8.19 |
| 2.8 | 74 | 4.55 |
| 2.9 | 148 | 0.99 |
| 2.10 | 133 | 0.46 |
| 2.11 | 126 | 0.43 |
| 2.12 | 111 | 0.31 |
| 2.13 | 126 | 0.46 |
| 2.14 | 100 | 1.78 |
| 2.15 | 163 | 0.49 |
| 2.16 | 60 | 4.27 |
| 2.17 | 172 | 0.27 |
| 2.18 | 118 | 1.41 |
| 2.19 | 249 | 0.46 |
| 3 | 287 | 0.11 |
| 3.1a | 128 | 0.18 |
| 3.2a | 116 | 0.16 |
| 3.3a | 91 | 0.07 |
| 3.4a | 206 | 0.14 |
| 3.5a | 311 | 0.50 |
| 3.6a | 546 | 0.37 |
| 3.7a | 135 | 0.28 |
| 3.5b | 150 | 0.20 |
| 3.6b | 205 | 0.12 |
| 3.7b | 160 | 0.18 |
| 3.8b | 203 | 0.30 |
| 3.9b | 144 | 0.96 |
| 3.10b | 159 | 0.46 |
| 3.11b | 168 | 0.41 |
| 3.12b | 143 | 0.34 |
| 3.13b | 179 | 0.25 |
| 3.14b | 251 | 0.04 |
| 3.15b | 127 | |
| 3.16b | 167 | 0.17 |
| 3.17b | 227 | 0.12 |
| 4 | 96 | 1.50 |
| 4.1 | 79 | 2.17 |
| 4.2 | 116 | 0.66 |
| 4.3 | 151 | 1.53 |
| 4.4 | 61 | 4.19 |
| 4.5 | 138 | 0.70 |
| 4.6 | 53 | 3.86 |
| 4.7 | 68 | |
| 4.8 | 55 | 2.07 |
| 4.9 | 60 | 4.66 |
| 5 | 78 | 0.80 |
| 5.1 | 140 | 0.87 |
| 5.2 | 63 | |
| 5.3 | 152 | 0.88 |
| 5.4 | 57 | |
| 5.5 | 132 | 0.72 |
| 5.6 | 101 | 0.15 |
| 5.7 | 131 | 1.23 |
| 5.8 | 116 | 0.46 |
| 5.9 | 126 | 1.13 |
| 5.10 | 78 | 3.77 |
| 5.11 | 89 | 0.17 |
| 5.12 | 100 | 0.76 |
| 5.13 | 94 | 1.14 |
| 5.14 | 128 | 0.76 |
| 5.15 | 87 | |
| 5.16 | 110 | |
| 5.17 | 94 | 0.65 |
| 5.18 | 79 | 0.46 |
| 5.19 | 75 | 1.85 |
| 5.20 | 221 | 0.57 |
| 5.21 | 172 | 0.51 |
| 5.22 | 94 | |
| 5.23 | 144 | 1.20 |
| 5.24 | 189 | 0.14 |
| 5.25 | 67 | |
| 5.26 | 110 | 1.20 |
| 5.27 | 84 | |
| 5.29 | 190 | 0.86 |
| 5.31 | 145 | |
| 5.32 | 285 | |
| 5.33 | 49 | |
| 5.34 | 185 | 0.64 |
| 5.35 | 106 | 0.18 |
| 5.36 | 44 | 0.06 |
| 5.37 | 117 | 0.15 |
| 5.38 | 231 | 0.15 |
| 5.39 | 147 | |

TABLE 17-continued

% Potentiation shown by 3.33 μM solution of Test Compounds and Calculated EC$_{50}$ Values

| Example | % Potentiation @ 3.33 μM Avg | EC$_{50}$ Avg (μM) |
|---|---|---|
| 6 | 162 | 1.14 |
| 7 | 153 | 0.65 |
| 7.1 | 241 | 0.34 |
| 7.2 | 203 | 0.26 |
| 7.3 | 125 | 0.20 |
| 7.4 | 52 | 0.65 |
| 7.5 | 239 | 0.28 |
| 7.6 | 285 | 0.10 |
| 7.7 | 234 | 0.13 |
| 7.8 | 231 | 0.92 |
| 7.9 | 288 | 0.23 |
| 7.10 | 218 | 0.36 |
| 7.11 | 167 | 0.32 |
| 7.12 | 101 | 2.11 |
| 7.13 | 212 | 0.09 |
| 7.14 | 225 | 0.15 |
| 7.15 | 230 | 0.05 |
| 7.16 | 354 | 0.13 |
| 8 | 88 | 3.02 |
| 8.1 | 155 | 0.59 |
| 8.2 | 169 | 1.96 |
| 8.3 | 238 | 0.23 |
| 9 | 149 | 0.23 |
| 9.1 | 77 | 4.62 |
| 9.2 | 196 | 0.19 |
| 10 | 250 | 0.22 |
| 11 | 76 | 0.90 |
| 12 | 112 | 1.76 |
| 13 | 245 | 1.00 |
| 14 | 58 | |
| 15 | 200 | 0.13 |
| 16 | 63 | |
| 17 | 173 | 1.49 |
| 18 | 405 | 0.45 |
| 19 | 57 | |
| 20 | 111 | 0.22 |
| 21a | 99 | 1.57 |
| 21b | 164 | 1.08 |
| 22.1 | 114 | |
| 22.2 | 157 | 0.26 |
| 22.3 | 132 | |
| 23 | 93 | |
| 23.1 | 150 | |
| 23.2 | 87 | |
| 23.3 | 59 | 0.47 |
| 23.4 | 115 | |
| 23.5 | 110 | |
| 23.6 | 108 | |
| 23.7 | 98 | |
| 23.8 | 122 | |
| 23.9 | 47 | |
| 23.11 | 101 | |
| 23.12 | 197 | 0.33 |
| 23.13 | 169 | 0.57 |
| 23.14 | 33 | |
| 23.15 | 147 | 1.19 |
| 23.16 | 68 | 1.40 |
| 24 | 68 | |
| 25 | 330 | 0.37 |
| 25.1 | 393 | 0.14 |
| 26 | 108 | |
| 27 | 90 | |
| 27.1 | 52 | |
| 27.2 | 300 | |
| 27.3 | 166 | 0.29 |
| 28 | 318 | 0.40 |
| 28.1 | 68 | |
| 30 | 113 | 1.22 |
| 30.1 | 245 | 0.14 |
| 30.2 | 221 | 0.18 |
| 30.3 | 100 | 0.25 |
| 30.3a | 221 | |
| 30.4 | 95 | 0.75 |
| 30.5 | 63 | |
| 30.6 | 80 | |
| 30.7 | 124 | 0.34 |
| 30.8 | 121 | 0.70 |
| 30.9 | 100 | 0.47 |
| 30.10 | 265 | |
| 30.11 | 125 | 0.22 |
| 30.12 | 314 | |
| 30.13 | 205 | 0.38 |
| 31 | 223 | 0.12 |
| 31.2 | 110 | 0.01 |
| 31.3 | 205 | 0.21 |
| 31.3a | 238 | 0.55 |
| 31.4 | 186 | 0.02 |
| 32 | 171 | |
| 32.1 | 246 | |
| 32.2 | 183 | 0.34 |
| 32.3 | 288 | 0.29 |
| 32.4 | 187 | 0.71 |
| 32.5 | 177 | 0.59 |
| 32.6 | 153 | 0.82 |
| 32.7 | 111 | 0.20 |
| 32.8 | 79 | |
| 32.9 | 31 | |
| 33 | 245 | 0.24 |
| 34 | 245 | 0.09 |
| 35 | 180 | 0.19 |
| 35a | 137 | 0.10 |
| 35b | 190 | 0.31 |
| 35.1 | 51 | |
| 35.2 | 300 | 0.61 |
| 35.3 | 144 | |
| 35.4 | 138 | |
| 35.6 | 53 | |
| 35.7 | 97 | |
| 35.8 | 250 | 0.18 |
| 35.9 | 455 | 0.54 |
| 35.10 | 223 | 0.28 |
| 35.11 | 107 | |
| 35.12 | 158 | 0.42 |
| 35.13 | 191 | 0.35 |
| 35.14 | 172 | 0.27 |
| 35.15 | 158 | 0.15 |
| 35.16 | 85 | 0.33 |
| 35.17 | 153 | 0.15 |
| 35.18 | 147 | 0.43 |
| 35.19 | 248 | 0.47 |
| 35.20 | 240 | 0.42 |
| 35.21 | 200 | 0.41 |
| 35.22 | 104 | 0.22 |
| 35.24 | 120 | 0.01 |
| 35.25 | 126 | 0.10 |
| 35.26 | 157 | |
| 35.27 | 496 | 0.33 |
| 36 | 199 | 0.02 |
| 37 | 352 | 0.12 |
| 38 | 307 | 0.05 |
| 39 | 262 | 0.06 |
| 40 | 153 | 0.70 |
| 40.1 | 91 | 0.87 |
| 41 | 38 | |
| 42 | 143 | 0.76 |
| 43 | 174 | 0.70 |
| 44 | 377 | 0.05 |
| 45 | 151 | |
| 46 | 275 | 0.25 |
| 46a | 249 | 0.11 |
| 46b | 215 | |
| 47 | 237 | 0.18 |
| 47.1 | 156 | 1.92 |
| 47.2 | 212 | 0.23 |
| 47.3 | 237 | 0.35 |
| 48 | 195 | 0.10 |
| 48.1 | 185 | 0.42 |
| 49 | 226 | 0.68 |

TABLE 17-continued

% Potentiation shown by 3.33 μM solution of Test Compounds and Calculated EC$_{50}$ Values

| Example | % Potentiation @ 3.33 μM Avg | EC$_{50}$ Avg (μM) |
|---|---|---|
| 50 | 65 | |
| 51 | 54 | |
| 53 | 184 | 0.39 |
| 54 | 62 | |
| 55 | 114 | |
| 56 | 76 | |
| 57a | 285 | 0.51 |
| 57b | 162 | 0.67 |
| 58 | 217 | |
| 59 | 175 | |
| 60 | 126 | 0.35 |
| 60.1 | 60 | |
| 60.2 | 169 | 0.20 |
| 61 | 85 | |
| 62 | 99 | |
| 63 | 37 | |
| 64 | 55 | |
| 64.1 | 78 | |
| 64.2 | 61 | |
| 64.3 | 70 | |
| 64.4 | 2 | |
| 64.5 | 143 | 0.45 |
| 64.6 | 0 | |
| 64.7 | 83 | |
| 64.8 | 97 | |
| 65 | 55 | |
| 65.1 | 75 | 0.47 |
| 65.2 | 73 | 0.48 |
| 65.3 | 33 | |
| 65.4 | 10 | |
| 66 | 130 | |
| 67 | 158 | 1.10 |
| 68 | 39 | |
| 69 | 47 | |
| 70 | 138 | |
| 71 | 162 | |
| 71.1 | 256 | 0.25 |
| 72 | 53 | |
| 73 | 196 | 0.31 |
| 73.1 | 389 | 0.28 |
| 74 | 337 | 0.18 |
| 74.1 | 49 | |
| 75 | 34 | |
| 76 | 366 | 0.22 |
| 77 | 139 | 0.41 |
| 77.1 | 151 | 0.54 |
| 78 | 98 | 0.02 |
| 78.1 | 238 | 0.05 |
| 78.2 | 86 | 0.02 |
| 79 | 60 | |
| 79.1 | 45 | |
| 79.2 | 211 | |
| 79.3 | 64 | 0.24 |
| 80 | 130 | |
| 81 | 151 | 0.37 |
| 81.1 | 108 | |
| 81.2 | 103 | 0.42 |
| 81.3 | 129 | 0.04 |
| 81.4 | 122 | 0.04 |
| 81.5 | 74 | |
| 82 | 88 | 0.72 |
| 83 | 6 | |
| 83.1 | 159 | |
| 83.2 | 41 | |
| 83.3 | 16 | |
| 83.4 | 58 | |
| 83.5 | 185 | |
| 83.6 | 248 | |
| 83.7 | 147 | |
| 83.8 | 35 | |
| 83.9 | 18 | |
| 83.10 | 62 | |
| 83.11 | 13 | |
| 83.13 | -1 | |
| 83.14 | 70 | |
| 83.15 | -10 | |
| 83.16 | 60 | |
| 83.17 | 8 | |
| 83.18 | 16 | |
| 83.19 | 28 | |
| 83.20 | 9 | |
| 83.21 | 70 | |
| 83.22 | 85 | |
| 83.23 | -11 | |
| 83.24 | 55 | |
| 83.25 | -8 | |
| 83.26 | 95 | |
| 83.27 | -11 | |
| 83.28 | 20 | |
| 83.29 | -9 | |
| 83.30 | 93 | |
| 83.31 | 78 | |
| 83.32 | -16 | |
| 85 | 155 | 0.35 |
| 86 | 593 | 0.35 |
| 87 | 332 | 0.22 |
| 88 | 270 | 0.24 |
| 89 | 366 | 0.09 |
| 90 | 219 | 0.12 |
| 92 | 133 | 0.11 |
| 92.1 | 151 | 0.14 |
| 92.2 | 71 | 0.01 |
| 93.1 | 207 | 0.05 |
| 93.2 | 220 | 0.04 |
| 93.3 | 130 | 0.06 |
| 93.4 | 476 | 0.07 |
| 93.5 | 136 | 0.02 |
| 94 | 516 | 0.34 |

REFERENCES

Accurso F J, Moss R B, Wilmott R W, Anbar R D, Schaberg A E, Durham T A, Ramsay B W; TIGER-1 Investigator Study Group (2011) Denufosol tetrasodium in patients with cystic fibrosis and normal to mildly impaired lung function. Am J Respir Crit Care Med, 183(5):627-634.

Boucher R C (2007) Evidence for airway surface dehydration as the initiating event in CF airway disease. J Intern Med., 261(1):5-16.

Caputo A, Caci E, Ferrera L, Pedemonte N, Barsanti C, Sondo E, Pfeffer U, Ravazzolo R, Zegarra-Moran O & Galietta L J (2008) TMEM16A, a membrane protein associated with calcium-dependent chloride channel activity. Science, 322(5901):590-594.

Del La Fuente R, Namkung W, Mills A & Verkman A S (2008) Small molecule screen identifies inhibitors of a human intestinal calcium-activated chloride channel. Mol Pharmacol, 73(3):758-768.

Kellerman D, Rossi Mospan A, Engels J, Schaberg A, Gorden J & Smiley L (2008) Denufosol: a review of studies with inhaled P2Y(2) agonists that led to Phase 2. Pulm Pharmacol Ther, 21(4):600-607.

Kunzelmann K & Mall M (2003) Pharmacotherapy of the ion transport defect in cystic fibrosis: role of purinergic receptor agonists and other potential therapeutics. Am J Respir Med, 2(4):299-309.

Matsui H, Grubb B R, Tarran R, Randell S H, Gatzy J T, Davis C W and Boucher R C (1998) Evidence for periciliary liquid layer depletion, not abnormal ion composition, in the pathogenesis of cystic fibrosis airways disease. Cell, 95(7):1005-15.

Moss R B (2013) Pitfalls of drug development: lessons learned from trials of denufosol in cystic fibrosis. J Pediatr, 162(4):676-680.

Pedemonte N & Galietta L J (2014) Structure and function of TMEM16 proteins (anoctamins). Physiol Rev, 94(2): 419-459.

Pezullo A A, Tang X X, Hoegger M J, Abou Alaiwa M H, Ramachandran S, Moninger T O, Karp P H, Wohlford-Lenan C L, Haagsman H P, van Eijk M, Banfi B, Horswill A R, Stoltz D A, McCray P B Jr, Welsh M J & Zabner J (2012) reduced airway surface pH impairs bacterial killing in the porcine cystic fibrosis lung. Nature, 487(7405): 109-113.

Yang Y D, Cho H, Koo J Y, Tak M H, Cho Y, Shim W S, Park S P, Lee J, Lee B, Kim B M, Raouf R, Shin Y K & Oh U (2008) TMEM16 confers receptor-activated calcium-dependent chloride conductance. Nature, 455(7217):1210-1215.

The invention claimed is:

1. A method for the treatment or prophylaxis of diseases and conditions affected by modulation of TMEM16A, the method comprising administering to a patient an effective amount of a compound according to formula (I):

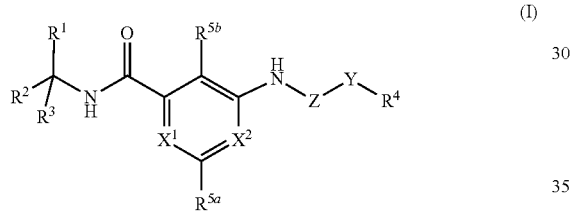

wherein:
$R^1$ is H, CN, C(O)OR$^{12}$, $C_{1-3}$ alkyl, $C_{2-3}$ alkenyl or $C_{2-3}$ alkynyl, any of which alkyl, alkenyl or alkynyl groups are optionally substituted with one or more substituents selected from fluoro, OR$^{12}$, N(R$^{12}$)$_2$, C(O)OR$^{12}$, C(O)N(R$^{12}$)$_2$, C(O)R$^{12}$ and N(R$^{13}$)C(O)R$^{12}$;
wherein each R$^{12}$ and R$^{13}$ is independently selected from H, $C_{1-6}$ alkyl and $C_{1-6}$ fluoroalkyl $R^2$ is H or $C_{1-6}$ alkyl optionally substituted with OR$^{12}$;
$R^3$ is:
$C_{1-10}$ alkyl, $C_{2-10}$ alkenyl or $C_{2-10}$ alkynyl, any of which is optionally substituted with one or more substituents selected from fluoro, CN, R$^{14}$ OR$^{14}$, OR$^{15}$, N(R$^{15}$)$_2$, C(O)OR$^{15}$, C(O)N(R$^{15}$)$_2$, N(R$^{16}$)C(O)R$^{15}$, N(R$^{15}$)S(O)$_2$R$^{14}$, N(R$^{15}$)S(O)$_2$R$^{16}$ and N(R$^{15}$) C(O) OR$^{16}$; or a 3- to 7-membered carbocyclic or heterocyclic ring system or a 6- to 10 membered aryl or 5- to 10-membered heteroaryl ring system, either of which is optionally substituted with one or more substituents selected from halo, CN, $C_{1-4}$ alkyl, $C_{1-4}$ haloalkyl, OR$^{17}$ and N(R$^{17}$)$_2$;
wherein R$^{14}$ is a 6- to 10-membered aryl or 5- to 10-membered heteroaryl ring system or a 3- to 7-membered carbocyclic or heterocyclic ring system, any of which is optionally substituted with one or more substituents selected from halo, $C_{1-4}$ alkyl, $C_{1-4}$ haloalkyl, OR$^{17}$ and N(R$^{17}$)$_2$; wherein each R$^{17}$ is independently H, $C_{1-4}$ alkyl or $C_{1-4}$ haloalkyl;

each R$^{15}$ and R$^{16}$ is independently H, $C_{1-6}$ alkyl or $C_{1-6}$ haloalkyl; or $R^2$ and $R^3$ together with the carbon atom to which they are attached combine to form a 3- to 10-membered carbocyclic or heterocyclic ring system optionally substituted with one or more substituents selected from halo, CN, OR$^9$, N(R$^9$)$_2$, C(O)OR$^9$, C(O)N(R$^9$)$_2$, C(O)R$^9$, N(R$^9$)C(O)R$^9$ and $C_{1-4}$ alkyl optionally substituted with halo, OR$^9$ or N(R$^9$)$_2$; or $R^1$, $R^2$ and $R^3$ together with the carbon atom to which they are attached combine to form a bridged 5- to 10-membered carbocyclic or heterocyclic ring system or phenyl, any of which is optionally substituted with one or more substituents selected from halo, CN, OR$^9$, N(R$^9$)$_2$, C(O)OR$^9$, C(O)N(R$^9$)$_2$, C(O)R$^9$,N(R$^9$)C(O)R$^9$ and $C_{1-4}$ alkyl optionally substituted with halo, OR$^9$ or N(R$^9$)$_2$;

each R$^9$ is independently selected from H, $C_{1-6}$ alkyl or $C_{1-6}$ haloalkyl;

$X^1$ is N;
$X^2$ is CR$^8$
$R^8$ is H, halo, OH, O($C_{1-4}$ alkyl), CN or NH$_2$;
Y is a bond or a straight $C_{1-6}$ alkylene chain which is optionally substituted with one or more substituents R$^{18}$, wherein two substituents R$^{18}$ may be attached to the same or to different carbon atoms;
wherein each R$^{18}$ is independently $C_{1-3}$ alkyl or $C_{1-3}$ haloalkyl in which a —CH$_2$— is optionally replaced with —NH— or —O— and wherein two R$^{18}$ groups may combine with the atom or atoms to which they are attached to form a 3- to 6-membered carbocyclic or heterocyclic ring system;

Z is —C(O)— or —C(O)NH—;
$R^4$ is a 6- to 14-membered aryl, 5- to 14-membered heteroaryl or a 5- to 10-membered carbocyclic ring system, any of which is optionally substituted with one or more substituents selected from: halo, CN, nitro, R$^{19}$, OR$^{19}$, OR$^6$, SR$^6$, NR$^6$R$^7$, C(O)R$^6$, C(O)R$^{19}$, C(O) OR$^6$, C(O)N(R$^6$) (R$^7$), N(R$^7$)C(O)R$^6$;
$C_{1-6}$ alkyl or O($C_{1-6}$ alkyl), either of which is optionally substituted with one or more substituents selected from halo, CN, nitro, R$^{19}$, OR$^6$, SR$^6$, NR$^6$R$^7$, C(O)R$^6$ C(O) OR$^6$, C(O)N(R$^6$) (R$^7$) and N(R$^7$)C(O)R$^6$, and
when R$^4$ is not fully aromatic in character, oxo;
wherein R$^{19}$ is 5- or 6-membered aryl or heteroaryl ring system or a 3- to 7-membered carbocyclic or heterocyclic ring system, any of which is optionally substituted with one or more substituents selected from halo, $C_{1-4}$ alkyl, $C_{1-4}$ haloalkyl, OH, O($C_{1-4}$ alkyl), O($C_{1-4}$ haloalkyl);

$R^6$ is H, $C_{1-6}$ alkyl, $C_{1-6}$ haloalkyl, benzyl, 3- to 7-membered carbocyclyl or 3- to 7-membered heterocyclyl;
$R^7$ is H, $C_{1-6}$ alkyl or $C_{1-6}$ haloalkyl; or
$R^6$ and $R^7$ together with the nitrogen atom to which they are attached may form a 4 to 7-membered heterocyclic ring optionally containing one or more further heteroatoms and optionally substituted with one or more substituents selected from oxo and halo; and each of R$^{5a}$ and R$^{5b}$ is independently H, $C_{1-4}$ alkyl or halo.

2. The method of claim 1, wherein the compound has a structure according to formula (Ia):

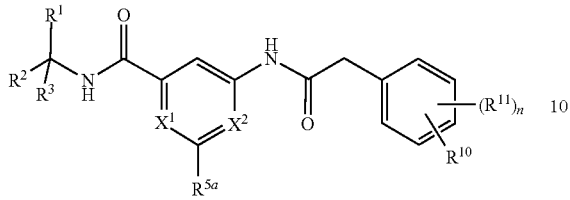

(Ia)

or a stereoisomer, a tautomer, a solvate or a salt thereof, wherein:
$R^1$ is H, CN, C(O)OR$^{12}$, $C_{1-3}$ alkyl, $C_{2-3}$ alkenyl or $C_{2-3}$ alkynyl, any of which alkyl, alkenyl or alkynyl groups are optionally substituted with one or more substituents selected from fluoro, OR$^{12}$, N(R$^{12}$)$_2$, C(O)OR$^{12}$, C(O)N(R$^{12}$)$_2$, C(O)R$^{12}$ and N(R$^{13}$)C(O)R$^{12}$;
wherein each R$^{12}$ and R$^{13}$ is independently selected from H, $C_{1-6}$ alkyl and $C_{1-6}$ fluoroalkyl
$R^2$ is H or $C_{1-6}$ alkyl optionally substituted with OR$^{12}$;
$R^3$ is:
$C_{1-10}$ alkyl, $C_{2-10}$ alkenyl or $C_{2-10}$ alkynyl, any of which is optionally substituted with one or more substituents selected from fluoro, CN, R$^{14}$ OR$^{14}$, OR$^{15}$, N(R$^{15}$)$_2$, C(O)OR$^{15}$, C(O)N(R$^{15}$)$_2$, N(R$^{16}$)C(O)R$^{15}$, N(R$^{15}$)S(O)$_2$R$^{14}$, N(R$^{15}$)S(O)$_2$R$^{16}$ and N(R$^{15}$) C(O)OR$^{16}$; or
a 3- to 7-membered carbocyclic or heterocyclic ring system or a 6- to 10 membered aryl or 5- to 10-membered heteroaryl ring system, either of which is optionally substituted with one or more substituents selected from halo, CN, $C_{1-4}$ alkyl, $C_{1-4}$ haloalkyl, OR$^{17}$ and N(R$^{17}$)$_2$;
wherein R$^{14}$ is a 6- to 10-membered aryl or 5- to 10-membered heteroaryl ring system or a 3- to 7-membered carbocyclic or heterocyclic ring system, any of which is optionally substituted with one or more substituents selected from halo, $C_{1-4}$ alkyl, $C_{1-4}$ haloalkyl, OR$^{17}$ and N(R$^{17}$)$_2$; wherein each R$^{17}$ is independently H, $C_{1-4}$ alkyl or $C_{1-4}$ haloalkyl;
each R$^{15}$ and R$^{16}$ is independently H, $C_{1-6}$ alkyl or $C_{1-6}$ haloalkyl; or
$R^2$ and $R^3$ together with the carbon atom to which they are attached combine to form a 3- to 10-membered carbocyclic or heterocyclic ring system optionally substituted with one or more substituents selected from halo, CN, OR$^9$, N(R$^9$)$_2$, C(O)OR$^9$, C(O)N(R$^9$)$_2$, C(O)R$^9$, N(R$^9$)C(O)R$^9$ and $C_{1-4}$ alkyl optionally substituted with halo, OR$^9$ or N(R$^9$)$_2$; or
$R^1$, $R^2$ and $R^3$ together with the carbon atom to which they are attached combine to form a bridged 5- to 10-membered carbocyclic or heterocyclic ring system or phenyl, any of which is optionally substituted with one or more substituents selected from halo, CN, OR$^9$, N(R$^9$)$_2$, C(O)OR$^9$, C(O)N(R$^9$)$_2$, C(O)R$^9$, N(R$^9$)C(O)R$^9$ and $C_{1-4}$ alkyl optionally substituted with halo, OR$^9$ or N(R$^9$)$_2$;
each R$^9$ is independently selected from H, $C_{1-6}$ alkyl or $C_{1-6}$ haloalkyl;
$X^1$ is N;
$X^2$ is CR$^8$
$R^8$ is H, halo, OH, O($C_{1-4}$ alkyl), CN or NH$_2$;
each of R$^{5a}$ and R$^{5b}$ is independently H, $C_{1-4}$ alkyl or halo;

R$^{10}$ is H, OH, halo, $C_{1-6}$ alkyl, —O($C_{1-6}$ alkyl);
each R$^{11}$ is independently H, halo, OH, CN, $C_{1-6}$ alkyl, $C_{1-6}$ haloalkyl, —O($C_{1-6}$ alkyl) or C(O)O—($C_{1-6}$ alkyl); and
n is 1 or 2.

3. The method of claim 1, wherein the compound has a structure according to formula (Id) or (Ie):

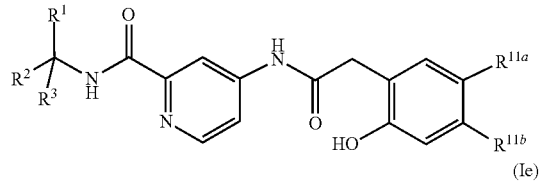

(Id)

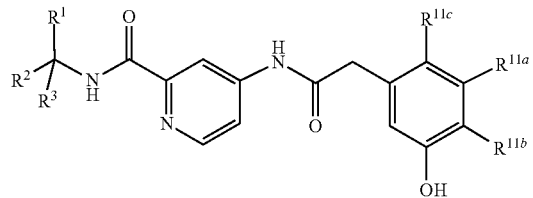

(Ie)

wherein
$R^1$, $R^2$ and $R^3$, are as defined in claim 1;
R$^{11a}$ is H, halo, $C_{1-4}$ alkyl, $C_{1-4}$ haloalkyl or C(O)O($C_{1-4}$ alkyl);
R$^{11b}$ is H, halo, $C_{1-4}$ alkyl or $C_{1-4}$ haloalkyl; and
R$^{11c}$ is H, halo, CN, $C_{1-4}$ alkyl or $C_{1-4}$ haloalkyl.

4. A method for the treatment or prophylaxis of diseases and conditions affected by modulation of TMEM16A, the method comprising administering to a patient an effective amount of a compound selected from the group consisting of:
N-tert-Butyl-4-[[2-(2-hydroxyphenyl)acetyl]amino]pyridine-2-carboxamide (Compound 1);
N-(1,1-Dimethylpropyl)-3-[[2-(2-hydroxyphenyl)acetyl]amino]benzamide (Compound 1.1);
N-(1-Adamantyl)-3-[[2-(5-chloro-2-hydroxy-phenyl)acetyl]amino]benzamide (Compound 1.2);
N-(1-Adamantyl)-4-[[2-(5-chloro-2-hydroxy-phenyl)acetyl]amino]pyridine-2-carboxamide (Compound 1.3);
4-[[2-(5-Chloro-2-hydroxy-phenyl)acetyl]amino]-N-(3-methoxy-1,1-dimethyl-propyl)pyridine-2-carboxamide (Compound 1.4);
3-[[2-(5-Chloro-2-hydroxy-phenyl)acetyl]amino]-N-(1,1-dimethyl propyl)benzamide (Compound 1.5);
4-[[2-(5-Chloro-2-hydroxy-phenyl)acetyl]amino]-N-(1-methylcyclobutyl)pyridine-2-carboxamide (Compound 1.6);
4-[[2-(5-Chloro-2-hydroxy-phenyl)acetyl]amino]-N-(1-methylcyclohexyl)pyridine-2-carboxamide (Compound 1.7);
tert-Butyl N-[3-[[4-[[2-(5-chloro-2-hydroxy-phenyl)acetyl]amino]pyridine-2-carbonyl]amino]-3-methylbutyl]carbamate (Compound 1.8);
4-[[2-(5-Chloro-2-hydroxy-phenyl)acetyl]amino]-N-cyclohexyl-pyridine-2-carboxamide (Compound 1.10);
N-tert-Butyl-3-[[2-(5-chloro-2-hydroxy-phenyl)acetyl]amino]benzamide (Compound 2);
N-tert-Butyl-3-[[2-(5-fluoro-2-hydroxy-phenyl)acetyl]amino]benzamide (Compound 2.1);

N-tert-Butyl-3-[[2-(4-fluoro-2-hydroxy-phenyl)acetyl] amino]benzamide (Compound 2.3);
N-tert-Butyl-3-[[2-(3,5-difluoro-2-hydroxy-phenyl) acetyl]amino]benzamide (Compound 2.9);
3-[[2-(5-Bromo-2-hydroxy-phenyl)acetyl]amino]-N-tert-butyl-benzamide (Compound 2.10);
N-tert-Butyl-3-[[2-(2,3-difluoro-6-hydroxy-phenyl) acetyl]amino]benzamide (Compound 2.11);
N-tert-Butyl-3-[[2-(4,5-difluoro-2-hydroxy-phenyl) acetyl]amino]benzamide (Compound 2.12);
N-(1,1-Dimethylpropyl)-3-[[2-(4-fluoro-2-hydroxy-phenyl)acetyl]amino]benzamide (Compound 2.13);
N-tert-Butyl-3-[[2-(2-fluoro-6-hydroxy-phenyl)acetyl] amino]benzamide (Compound 2.15);
N-tert-Butyl-3-[[2-[2-hydroxy-5-(trifluoro methyl)phenyl]acetyl]amino]benzamide (Compound 2.17);
N-tert-Butyl-3-[[2-[2-hydroxy-4-(trifluoro methyl)phenyl]acetyl]amino]benzamide (Compound 2.19);
N-tert-Butyl-4-[[2-(5-chloro-2-hydroxy-phenyl)acetyl] amino]pyridine-2-carboxamide (Compound 3);
N-(1,1-Dimethylpropyl)-4-[[2-(4-fluoro-2-hydroxy-phenyl)acetyl]amino]pyridine-2-carboxamide (Compound 3.1a);
N-tert-Butyl-4-[[2-(4-fluoro-2-hydroxy-phenyl)acetyl] amino]pyridine-2-carboxamide (Compound 3.2a);
N-tert-Butyl-4-[[2-(2-chloro-6-hydroxy-phenyl)acetyl] amino]pyridine-2-carboxamide (Compound 3.3a);
4-[[2-(4-Bromo-5-chloro-2-hydroxy-phenyl)acetyl] amino]-N-tert-butyl-pyridine-2-carboxamide (Compound 3.4a);
4-[[2-(5-tert-Butyl-2-hydroxy-phenyl)acetyl]amino]-N-(1-cyanocyclobutyl)pyridine-2-carboxamide (Compound 3.5a);
4-[[2-(5-tert-Butyl-2-hydroxy-phenyl)acetyl]amino]-N-(1-methyl cyclobutyl)pyridine-2-carboxamide (Compound 3.6a);
N-tert-butyl-4-[2-(2,5-dibromo-3-fluoro-6-hydroxyphenyl) acetamido]pyridine-2-carboxamide (Compound 3.7a);
N-tert-Butyl-4-[[2-[2-hydroxy-5-(trifluoromethyl)phenyl]acetyl]amino]pyridine-2-carboxamide (Compound 3.5b);
N-tert-Butyl-4-[[2-(4-chloro-2-hydroxy-phenyl)acetyl] amino]pyridine-2-carboxamide (Compound 3.6b);
N-tert-Butyl-4-[[2-[2-hydroxy-4-(trifluoro methyl)phenyl]acetyl]amino]pyridine-2-carboxamide (Compound 3.7b);
N-tert-Butyl-4-[[2-(2-hydroxy-5-methoxy-phenyl)acetyl] amino]pyridine-2-carboxamide (Compound 3.8b);
N-tert-Butyl-4-[[2-(2,5-dibromo-3-chloro-6-hydroxy-phenyl)acetyl]amino]pyridine-2-carboxamide (Compound 3.11b);
N-tert-Butyl-4-[[2-(3-hydroxyphenyl)acetyl]amino]pyridine-2-carboxamide (Compound 3.12b);
N-tert-Butyl-4-[[2-(2-fluoro-5-hydroxy-phenyl)acetyl] amino]pyridine-2-carboxamide (Compound 3.13b);
N-tert-Butyl-4-[[2-(4-chloro-3-hydroxy-phenyl)acetyl] amino]pyridine-2-carboxamide (Compound 3.14b);
N-tert-Butyl-4-[[2-(2-chloro-3-hydroxy-phenyl)acetyl] amino]pyridine-2-carboxamide (Compound 3.15b);
N-tert-Butyl-4-[[2-(2-chloro-5-hydroxy-phenyl)acetyl] amino]pyridine-2-carboxamide (Compound 3.16b);
N-tert-Butyl-4-[[2-(3-chloro-5-hydroxy-phenyl)acetyl] amino]pyridine-2-carboxamide (Compound 3.17b);
N-tert-Butyl-4-[[2-(5-chloro-2-fluoro-phenyl)acetyl] amino]pyridine-2-carboxamide (Compound 5.3);
N-tert-Butyl-4-[[2-(3-chlorophenyl)acetyl]amino]pyridine-2-carboxamide (Compound 5.5);
N-tert-Butyl-4-[[2-(3,4-dichlorophenyl)acetyl]amino] pyridine-2-carboxamide (Compound 5.8);
N-tert-Butyl-4-[[2-(p-tolyl)acetyl]amino]pyridine-2-carboxamide (Compound 5.11);
N-tert-Butyl-4-[[2-(2-fluorophenyl)acetyl]amino]pyridine-2-carboxamide (Compound 5.12);
N-tert-Butyl-4-[[2-(m-tolyl)acetyl]amino]pyridine-2-carboxamide (Compound 5.14);
N-tert-Butyl-4-[[2-(2,6-dichlorophenyl)acetyl]amino] pyridine-2-carboxamide (Compound 5.17);
N-tert-Butyl-4-[[2-(4-chloro-3-fluoro-phenyl)acetyl] amino]pyridine-2-carboxamide (Compound 5.18);
N-tert-Butyl-4-[[2-(2-chlorophenyl)acetyl]amino]pyridine-2-carboxamide (Compound 5.20);
N-tert-Butyl-4-[[2-(3-chloro-4-hydroxy-phenyl)acetyl] amino]pyridine-2-carboxamide (Compound 5.21);
N-tert-butyl-4-[[1-(3-chlorophenyl)cyclopropanecarbonyl]amino]pyridine-2-carboxamide (Compound 5.31);
N-(1,1-Dimethylprop-2-ynyl)-4-[[2-[4-(trifluoromethyl) phenyl]acetyl]amino]pyridine-2-carboxamide (Compound 5.35);
N-(1,1-Dimethylprop-2-ynyl)-4-[[2-[3-(trifluoromethyl) phenyl]acetyl]amino]pyridine-2-carboxamide (Compound 5.37);
N-(1,1-Dimethylprop-2-ynyl)-4-[[2-[2-(trifluoromethyl) phenyl]acetyl]amino]pyridine-2-carboxamide (Compound 5.38);
3-[[2-(5-Chloro-2-hydroxy-phenyl)acetyl]amino]-N-(1,1,2,2-tetramethylpropyl)benzamide (Compound 7);
3-[[2-(5-Chloro-2-hydroxy-phenyl)acetyl]amino]-N-(1,1-dimethylbutyl)benzamide (Compound 7.1)
4-[[2-(5-Chloro-2-hydroxy-phenyl)acetyl]amino]-N-(1,1-dimethylbutyl)pyridine-2-carboxamide (Compound 7.2);
3-[[2-(5-Chloro-2-hydroxy-phenyl)acetyl]amino]-N-cyclohexyl-benzamide (Compound 7.3);
3-[[2-(5-Chloro-2-hydroxy-phenyl)acetyl]amino]-N-tetrahydropyran-4-yl-benzamide (Compound 7.4);
3-[[2-(5-Chloro-2-hydroxy-phenyl)acetyl]amino]-N-(1,1,2-trimethylpropyl)benzamide (Compound 7.5);
4-[[2-(5-Chloro-2-hydroxy-phenyl)acetyl]amino]-N-(1,1,2-trimethylpropyl)pyridine-2-carboxamide (Compound 7.6);
4-[[2-(5-Chloro-2-hydroxy-phenyl)acetyl]amino]-N-isopropyl-pyridine-2-carboxamide (Compound 7.7);
3-[[2-(5-Chloro-2-hydroxy-phenyl)acetyl]amino]-N-(4-methyltetrahydropyran-4-yl)benzamide (Compound 7.8);
4-[[2-(5-Chloro-2-hydroxy-phenyl)acetyl]amino]-N-(4-methyltetrahydropyran-4-yl)pyridine-2-carboxamide (Compound 7.9);
3-[[2-(5-Chloro-2-hydroxy-phenyl)acetyl]amino]-N-(1-methylcyclobutyl)benzamide (Compound 7.10);
4-[[2-(5-Chloro-2-hydroxy-phenyl)acetyl]amino]-N-tetrahydropyran-4-yl-pyridine-2-carboxamide (Compound 7.11);
4-[[2-(5-Chloro-2-hydroxy-phenyl)acetyl]amino]-N-sec-butyl-pyridine-2-carboxamide (Compound 7.13);
4-[[2-(5-Chloro-2-hydroxy-phenyl)acetyl]amino]-N-(2-hydroxy-1,1,2-trimethyl-propyl)pyridine-2-carboxamide (Compound 7.14);
N-(3-Bicyclo[1.1.1]pentanyl)-4-[[2-(5-chloro-2-hydroxy-phenyl)acetyl]amino]pyridine-2-carboxamide (Compound 7.15);

4-[[2-(5-Chloro-2-hydroxy-phenyl)acetyl]amino]-N-(1-cyanocyclobutyl)pyridine-2-carboxamide (Compound 7.16);
tert-Butyl-3-[[4-[[2-(5-chloro-2-hydroxy-phenyl)acetyl]amino]pyridine-2-carbonyl]amino]piperidine-1-carboxylate (Compound 8.1);
tert-Butyl (1r,5s,6s)-6-{4-[2-(5-chloro-2-hydroxyphenyl)acetamido]pyridine-2-amido}-3-azabicyclo[3.1.0]hexane-3-carboxylate (Compound 8.3);
N-tert-Butyl-3-[[2-(5-chloro-2-hydroxy-phenyl)acetyl]amino]-4-fluoro-benzamide (Compound 9);
4-[[2-(5-Chloro-2-hydroxy-phenyl)acetyl]amino]-N-(1,1-dimethylpropyl)pyridine-2-carboxamide (Compound 9.2);
N-tert-Butyl-4-[[2-(5-tert-butyl-2-hydroxy-phenyl)acetyl]amino]pyridine-2-carboxamide (Compound 10);
N-tert-Butyl-5-[[2-(5-chloro-2-hydroxy-phenyl)acetyl]amino]-2-hydroxy-benzamide (Compound 11);
N-tert-Butyl-4-[[2-(2-hydroxy-5-methyl-phenyl)acetyl]amino]pyridine-2-carboxamide (Compound 15);
N-tert-Butyl-3-[[2-(5-chloro-2-hydroxy-phenyl)acetyl]amino]-5-fluoro-benzamide (Compound 18);
N-tert-Butyl-4-[[2-(3-hydroxy-2-pyridyl)acetyl]amino]pyridine-2-carboxamide (Compound 19);
N-tert-Butyl-4-[[2-(5-fluoro-2-hydroxy-phenyl)acetyl]amino]pyridine-2-carboxamide (Compound 20);
N-tert-Butyl-4-[(2-phenylacetyl)amino]pyridine-2-carboxamide (Compound 22);
4-[[2-(4-Chlorophenyl)acetyl]amino]-N-(1-cyanocyclopropyl)pyridine-2-carboxamide (Compound 23);
4-[[2-(3-Chlorophenyl)acetyl]amino]-N-(1-cyanocyclo propyl)pyridine-2-carboxamide (Compound 23.1);
4-[[2-(2-Chloro-5-fluoro-phenyl)acetyl]amino]-N-(1-cyanocyclo propyl)pyridine-2-carboxamide (Compound 23.2);
N-tert-Butyl-4-[[2-[2-(difluoromethoxy)phenyl]acetyl]amino]pyridine-2-carboxamide (Compound 23.4);
N-tert-Butyl-4-[[2-[2-(difluoromethyl)phenyl]acetyl]amino]pyridine-2-carboxamide (Compound 23.5);
N-tert-Butyl-4-[[2-(3,4-difluorophenyl)acetyl]amino]pyridine-2-carboxamide (Compound 23.6);
N-tert-Butyl-4-[[2-(3,5-difluorophenyl)acetyl]amino]pyridine-2-carboxamide (Compound 23.7);
N-tert-Butyl-4-[[2-(2,3-difluorophenyl)acetyl]amino]pyridine-2-carboxamide (Compound 23.8);
4-[[2-(2-Chlorophenyl)acetyl]amino]-N-tetrahydropyran-4-yl-pyridine-2-carboxamide (Compound 23.9);
N-tert-Butyl-4-[[2-[2-(trifluoromethyl)phenyl]acetyl]amino]pyridine-2-carboxamide (Compound 23.12);
4-[[2-(2-Bromophenyl)acetyl]amino]-N-tert-butyl-pyridine-2-carboxamide (Compound 23.13);
N-tert-Butyl-4-[[2-(2-cyanophenyl)acetyl]amino]pyridine-2-carboxamide (Compound 23.14);
4-[[2-(2-Chloro-5-methoxy-phenyl)acetyl]amino]-N-(1-cyanocyclopropyl)pyridine-2-carboxamide (Compound 24);
N-(3-Bicyclo[1.1.1]pentanyl)-4-[[2-(5-tert-butyl-2-hydroxy-phenyl)acetyl]amino]pyridine-2-carboxamide (Compound 25);
-[[2-(5-tert-Butyl-2-hydroxy-phenyl)acetyl]amino]-N-(4-cyanotetrahydropyran-4-yl)pyridine-2-carboxamide (Compound 25.1);
N-tert-Butyl-4-[[2-(2-hydroxy-5-phenyl-phenyl)acetyl]amino]pyridine-2-carboxamide (Compound 26);
N-tert-Butyl-4-[[2-[5-chloro-2-hydroxy-4-(pyrrolidin-1-ylmethyl)phenyl]acetyl]amino]pyridine-2-carboxamide (Compound 27);
N-tert-Butyl-4-[[2-[4-[(tert-butylamino)methyl]-5-chloro-2-hydroxy-phenyl]acetyl]amino]pyridine-2-carboxamide (Compound 27.1);
N-tert-Butyl-4-[[2-[5-chloro-2-hydroxy-4-(morpholinomethyl)phenyl]acetyl]amino]pyridine-2-carboxamide (Compound 27.2);
N-tert-Butyl-4-[[2-[5-chloro-4-[(3,3-difluoropyrrolidin-1-yl)methyl]-2-hydroxy-phenyl]acetyl]amino]pyridine-2-carboxamide (Compound 27.3);
N-tert-butyl-4-[[2-(5-chloro-2-hydroxy-phenyl)acetyl]amino]-5-fluoro-pyridine-2-carboxamide (Compound 28);
N-tert-Butyl-4-[[2-(5-chloro-2-hydroxy-phenyl)acetyl]amino]-3-fluoro-pyridine-2-carboxamide (Compound 28.1);
4-[[2-(2-Chlorophenyl)acetyl]amino]-N-(1,1-dimethylprop-2-ynyl)pyridine-2-carboxamide (Compound 30.1);
4-[[2-(2-Chlorophenyl)acetyl]amino]-N-(4-fluoro-1-bicyclo[2.1.1]hexanyl)pyridine-2-carboxamide (Compound 30.2);
4-[[2-(2-Chlorophenyl)acetyl]amino]-N-(1-cyclopropyl-1-methyl-ethyl)pyridine-2-carboxamide (Compound 30.3);
4-[[2-(2-Chlorophenyl)acetyl]amino]-N-(1-cyano-1-methyl-ethyl)pyridine-2-carboxamide (Compound 30.3a);
4-[[2-(2-Chlorophenyl)acetyl]amino]-N-(1-methyl-3-bicyclo[1.1.1]pentanyl)pyridine-2-carboxamide (Compound 30.4);
4-[[2-(2-Chlorophenyl)acetyl]amino]-N-(1-cyano-3-bicyclo[1.1.1]pentanyl)pyridine-2-carboxamide (Compound 30.5);
4-[[2-(2-Chlorophenyl)acetyl]amino]-N-(2,2-difluorocyclopropyl)pyridine-2-carboxamide (Compound 30.6);
4-[[2-(2-Chlorophenyl)acetyl]amino]-N-(1-cyanocyclopropyl)pyridine-2-carboxamide (Compound 30.7);
4-[[2-(2-Clorophenyl)acetyl]amino]-N-(1-methylcyclopropyl)pyridine-2-carboxamide (Compound 30.8);
4-[[2-(2-Chlorophenyl)acetyl]amino]-N-(3-fluoro-1-bicyclo[1.1.1]pentanyl)pyridine-2-carboxamide (Compound 30.9);
4-[[2-(2-Chlorophenyl)acetyl]amino]-N-(2-fluoro-1,1-dimethyl-ethyl)pyridine-2-carboxamide (Compound 30.10);
4-[[2-(2-Chlorophenyl)acetyl]amino]-N-(4-ethynyltetrahydropyran-4-yl)pyridine-2-carboxamide (Compound 30.11);
4-[[2-(2-Chlorophenyl)acetyl]amino]-N-(1-cyanocyclopentyl)pyridine-2-carboxamide (Compound 30.12);
4-[[2-(2-Chlorophenyl)acetyl]amino]-N-(2,2-difluoro-1,1-dimethyl-ethyl)pyridine-2-carboxamide (Compound 30.13);
4-[[2-(5-Chloro-2-hydroxy-phenyl)acetyl]amino]-N-(4-cyanotetrahydropyran-4-yl)pyridine-2-carboxamide (Compound 31);
4-[[2-(5-Chloro-2-hydroxy-phenyl)acetyl]amino]-N-(1-ethynylcyclopentyl)pyridine-2-carboxamide (Compound 31.2);
4-[2-(5-Chloro-2-hydroxyphenyl) acetamido]-N-[(1s,2s)-2-hydroxycyclohexyl]pyridine-2-carboxamide (Compound 31.3);
4-[[2-(5-Chloro-2-hydroxy-phenyl)acetyl]amino]-N-[(1S,2S)-2-hydroxycyclo hexyl]pyridine-2-carboxamide or 4-[[2-(5-Chloro-2-hydroxy-phenyl)acetyl]amino]-N-[(1R,2R)-2-hydroxycyclohexyl]pyridine-2-carboxamide (Compound 31.3a);

4-[[2-(5-Chloro-2-hydroxy-phenyl)acetyl]amino]-N-(4-ethynyltetrahydropyran-4-yl)pyridine-2-carboxamide (Compound 31.4);

N-[(6-Amino-2-pyridyl)methyl]-4-[[2-(5-chloro-2-hydroxy-phenyl)acetyl]amino]pyridine-2-carboxamide (Compound 32);

12-[[4-[[2-(5-Chloro-2-hydroxy-phenyl)acetyl]amino]pyridine-2-carbonyl]amino]dodecanoic acid (Compound 32.1);

4-[[2-(5-Chloro-2-hydroxy-phenyl)acetyl]amino]-N-(3-pyridylmethyl)pyridine-2-carboxamide (Compound 32.2);

4-[[2-(5-Chloro-2-hydroxy-phenyl)acetyl]amino]-N-(2-pyridylmethyl)pyridine-2-carboxamide (Compound 32.3);

4-[[2-(5-Chloro-2-hydroxy-phenyl)acetyl]amino]-N-(4-pyridylmethyl)pyridine-2-carboxamide (Compound 32.4);

4-[[2-(5-Chloro-2-hydroxy-phenyl)acetyl]amino]-N-[(2-hydroxyphenyl)methyl]pyridine-2-carboxamide (Compound 32.5);

4-[[2-(5-Chloro-2-hydroxy-phenyl)acetyl]amino]-N-(1,1-dimethyl-2-morpholino-ethyl)pyridine-2-carboxamide (Compound 32.6);

4-[[2-(5-Chloro-2-hydroxy-phenyl)acetyl]amino]-N-(2-hydroxy-1,1-dimethyl-ethyl)pyridine-2-carboxamide (Compound 32.7);

4-[[2-(5-Chloro-2-hydroxy-phenyl)acetyl]amino]-N-(3,3-difluoro-4-piperidyl)pyridine-2-carboxamide (Compound 32.8);

4-[[2-(5-Chloro-2-hydroxy-phenyl)acetyl]amino]-N-(1H-imidazol-2-yl)pyridine-2-carboxamide (Compound 32.9);

4-[[2-(5-Chloro-2-hydroxy-phenyl)acetyl]amino]-N-[(1R,2R)-2-hydroxycyclopentyl]pyridine-2-carboxamide (Compound 33);

4-[[2-(5-Chloro-2-hydroxy-phenyl)acetyl]amino]-N-(1-cyano-1-methyl-ethyl)pyridine-2-carboxamide (Compound 34);

4-[[2-(5-Chloro-2-hydroxy-phenyl)acetyl]amino]-N-[3-(hydroxymethyl)tetrahydrofuran-3-yl]pyridine-2-carboxamide (Compound 35);

4-[[2-(5-Chloro-2-hydroxy-phenyl)acetyl]amino]-N-[(3R)-3-(hydroxymethyl)tetrahydrofuran-3-yl]pyridine-2-carboxamide or 4-[[2-(5-chloro-2-hydroxy-phenyl)acetyl]amino]-N-[(3S)-3-(hydroxymethyl)tetrahydrofuran-3-yl]pyridine-2-carboxamide (Compound 35a);

-[[2-(5-Chloro-2-hydroxy-phenyl)acetyl]amino]-N-[(3R)-3-(hydroxymethyl)tetrahydrofuran-3-yl]pyridine-2-carboxamide or 4-[[2-(5-chloro-2-hydroxy-phenyl)acetyl]amino]-N-[(3S)-3-(hydroxymethyl)tetrahydrofuran-3-yl]pyridine-2-carboxamide (Compound 35b);

4-[[2-(5-Chloro-2-hydroxy-phenyl)acetyl]amino]-N-(4-hydroxy-4-methyl-cyclohexyl)pyridine-2-carboxamide as a 6:4 mixture of stereoisomers (Compound 35.1);

4-[[2-(5-Chloro-2-hydroxy-phenyl)acetyl]amino]-N-[(1s,2r)-2-(hydroxy methyl)cyclohexyl]pyridine-2-carboxamide (Compound 35.2);

4-[[2-(5-Chloro-2-hydroxy-phenyl)acetyl]amino]-N-[(1s,3r)-3-hydroxycyclopentyl]pyridine-2-carboxamide (Compound 35.3);

4-[[2-(5-Chloro-2-hydroxy-phenyl)acetyl]amino]-N-[2-hydroxy-1-(hydroxy methyl)-1-methyl-ethyl]pyridine-2-carboxamide (Compound 35.4);

4-[[2-(5-Chloro-2-hydroxy-phenyl)acetyl]amino]-N-(3-hydroxycyclohexyl)pyridine-2-carboxamide as a mixture of stereoisomers (Compound 35.6);

4-[[2-(5-Chloro-2-hydroxy-phenyl)acetyl]amino]-N-(3-phenoxypropyl)pyridine-2-carboxamide (Compound 35.7);

4-[[2-(5-Chloro-2-hydroxy-phenyl)acetyl]amino]-N-(1-methylcyclo propyl)pyridine-2-carboxamide (Compound 35.8);

4-[[2-(5-Chloro-2-hydroxy-phenyl)acetyl]amino]-N-[1-methyl-1-(2-pyridyl)ethyl]pyridine-2-carboxamide (Compound 35.9);

4-[[2-(5-Chloro-2-hydroxy-phenyl)acetyl]amino]-N-(3-phenylpropyl)pyridine-2-carboxamide (Compound 35.10);

4-[[2-(5-Chloro-2-hydroxy-phenyl)acetyl]amino]-N-[2-hydroxy-1-(2-pyridyl)ethyl]pyridine-2-carboxamide (Compound 35.11);

4-[[2-(5-Chloro-2-hydroxy-phenyl)acetyl]amino]-N-[(5-methoxy-2-pyridyl)methyl]pyridine-2-carboxamide (Compound 35.12);

Ethyl 3-[[4-[[2-(5-chloro-2-hydroxy-phenyl)acetyl]amino]pyridine-2-carbonyl]amino]-3-methyl-butanoate (Compound 35.13);

4-[[2-(5-Chloro-2-hydroxy-phenyl)acetyl]amino]-N-(3-hydroxy-1,1-dimethyl-propyl)pyridine-2-carboxamide (Compound 35.14);

N-Benzyl-4-[[2-(5-chloro-2-hydroxy-phenyl)acetyl]amino]pyridine-2-carboxamide (Compound 35.15);

4-[[2-(5-Chloro-2-hydroxy-phenyl)acetyl]amino]-N-phenyl-pyridine-2-carboxamide (Compound 35.16);

4-[[2-(5-Chloro-2-hydroxy-phenyl)acetyl]amino]-N-[(1S,2S)-2-hydroxycyclopentyl]pyridine-2-carboxamide (Compound 35.17);

4-[[2-(5-Chloro-2-hydroxy-phenyl)acetyl]amino]-N-[(1R,2S)-2-hydroxy cyclopentyl]pyridine-2-carboxamide (Compound 35.18);

4-[[2-(5-Chloro-2-hydroxy-phenyl)acetyl]amino]-N-[(1S,2R)-2-hydroxy cyclopentyl]pyridine-2-carboxamide (Compound 35.19);

3-[[2-(5-Fluoro-2-hydroxy-phenyl)acetyl]amino]-N-(1-methylcyclohexyl)benzamide (Compound 35.20);

N-(1,1-Dimethylprop-2-ynyl)-3-[[2-(5-fluoro-2-hydroxy-phenyl)acetyl]amino]benzamide (Compound 35.21);

N-Cyclohexyl-3-[[2-(5-fluoro-2-hydroxy-phenyl)acetyl]amino]benzamide (Compound 35.22);

3-[[2-(5-Fluoro-2-hydroxy-phenyl)acetyl]amino]-N-[3-(hydroxymethyl)tetrahydrofuran-3-yl]benzamide (Compound 35.23);

4-[[2-(5-Chloro-2-hydroxy-phenyl)acetyl]amino]-N-(1-ethynylcyclohexyl)pyridine-2-carboxamide (Compound 35.24);

4-[[2-(5-Chloro-2-hydroxy-phenyl)acetyl]amino]-N-[1-(hydroxymethyl)cyclobutyl]pyridine-2-carboxamide (Compound 35.25);

4-[[2-(5-Chloro-2-hydroxy-phenyl)acetyl]amino]-N-[3-(hydroxymethyl) oxetan-3-yl]pyridine-2-carboxamide (Compound 35.26);

4-[[2-(5-Chloro-2-hydroxy-phenyl)acetyl]amino]-N-(1-cyano-2-methoxy-1-methyl-ethyl)pyridine-2-carboxamide (Compound 35.27);

4-[[2-(5-Chloro-2-hydroxy-phenyl)acetyl]amino]-N-(1,1-dimethylprop-2-ynyl)pyridine-2-carboxamide (Compound 36);

4-[[2-(5-Chloro-2-hydroxy-phenyl)acetyl]amino]-N-(1-cyano-1,2-dimethyl-propyl)pyridine-2-carboxamide (Compound 37);

4-[[2-(5-Chloro-2-hydroxy-phenyl)acetyl]amino]-N-(1-methylcyclopentyl)pyridine-2-carboxamide (Compound 38);

N-(4-tert-Butylcyclohexyl)-4-[[2-(5-chloro-2-hydroxy-phenyl)acetyl]amino]pyridine-2-carboxamide (Compound 39);

N-tert-Butyl-4-[[2-(2-chloro-3-fluoro-phenyl)acetyl]amino]pyridine-2-carboxamide (Compound 40);

N-tert-Butyl-4-[[2-(2-chloro-5-fluoro-phenyl)acetyl]amino]pyridine-2-carboxamide (Compound 40.1);

4-[[2-(5-Chloro-2-hydroxy-phenyl)acetyl]amino]-N-[4-(2-hydroxyethyl)tetrahydropyran-4-yl]pyridine-2-carboxamide (Compound 42);

4-[[2-(5-Chloro-2-hydroxy-phenyl)acetyl]amino]-N-[1,1-dimethyl-3-(2,2,2-trifluoro ethylamino) propyl]pyridine-2-carboxamide (Compound 43);

4-[[2-(5-Chloro-2-hydroxy-phenyl)acetyl]amino]-N-(4-fluoro-1-bicyclo[2.1.1]hexanyl)pyridine-2-carboxamide (Compound 44);

4-[[2-(5-Chloro-2-hydroxy-phenyl)acetyl]amino]-N-[3-(2,2-dimethylpropanoyl amino)-1,1-dimethyl-propyl]pyridine-2-carboxamide (Compound 45);

4-[[2-(5-Chloro-2-hydroxy-phenyl)acetyl]amino]-N-(1-cyano-2-hydroxy-1-methyl-ethyl)pyridine-2-carboxamide (Compound 46);

4-[[2-(5-Chloro-2-hydroxy-phenyl)acetyl]amino]-N-[(1S)-1-cyano-2-hydroxy-1-methyl-ethyl]pyridine-2-carboxamide or 4-[[2-(5-chloro-2-hydroxy-phenyl)acetyl]amino]-N-[(1R)-1-cyano-2-hydroxy-1-methyl-ethyl]pyridine-2-carboxamide (Compound 46a);

4-[[2-(5-Chloro-2-hydroxy-phenyl)acetyl]amino]-N-[(1S)-1-cyano-2-hydroxy-1-methyl-ethyl]pyridine-2-carboxamide or 4-[[2-(5-chloro-2-hydroxy-phenyl)acetyl]amino]-N-[(1R)-1-cyano-2-hydroxy-1-methyl-ethyl]pyridine-2-carboxamide (Compound 46b);

4-[[2-(5-Chloro-2-hydroxy-phenyl)acetyl]amino]-N-(3-cyanotetrahydrofuran-3-yl)pyridine-2-carboxamide (Compound 47);

Methyl 4-[[4-[[2-(5-chloro-2-hydroxy-phenyl)acetyl]amino]pyridine-2-carbonyl]amino]tetrahydropyran-4-carboxylate (Compound 47.2);

4-[[2-(5-Chloro-2-hydroxy-phenyl)acetyl]amino]-N-(3-cyanooxetan-3-yl)pyridine-2-carboxamide (Compound 47.3);

4-[[2-(5-Fluoro-2-hydroxy-phenyl)acetyl]amino]-N-(1-methylcyclobutyl)pyridine-2-carboxamide (Compound 48);

N-(4-Cyanotetrahydropyran-4-yl)-4-[[2-(5-fluoro-2-hydroxy-phenyl)acetyl]amino]pyridine-2-carboxamide (Compound 48.1);

N-[3-(tert-Butylamino)-1,1-dimethyl-3-oxo-propyl]-4-[[2-(5-chloro-2-hydroxy-phenyl) acetyl]amino]pyridine-2-carboxamide (Compound 49);

4-[[2-(5-Chloro-2-hydroxy-phenyl)acetyl]amino]-N-[3-(methanesulfonamido)-1, 1-dimethyl-propyl]pyridine-2-carboxamide (Compound 50);

N-(3-Acetamido-1,1-dimethyl-propyl)-4-[[2-(5-chloro-2-hydroxy-phenyl)acetyl]amino]pyridine-2-carboxamide (Compound 51);

4-[[2-(5-Chloro-2-hydroxy-phenyl)acetyl]amino]-N-[4-(hydroxymethyl)tetrahydro pyran-4-yl]pyridine-2-carboxamide (Compound 53);

N-tert-Butyl-4-[[2-[3-(1-hydroxyethyl)phenyl]acetyl]amino]pyridine-2-carboxamide (Compound 54);

N-tert-Butyl-5-chloro-4-[[2-(5-chloro-2-hydroxy-phenyl)acetyl]amino]pyridine-2-carboxamide (Compound 55);

N-tert-Butyl-4-[[2-[5-chloro-2-[(4-methoxyphenyl)methoxy]phenyl]acetyl]amino]pyridine-2-carboxamide (Compound 56);

N-tert-Butyl-4-[[2-(2-cyclopropylphenyl)acetyl]amino]pyridine-2-carboxamide (Compound 58);

4-[[2-(3-Bromo-5-chloro-2-hydroxy-phenyl)acetyl]amino]-N-tert-butyl-pyridine-2-carboxamide (Compound 59);

N-(4-Fluoro-1-bicyclo[2.1.1]hexanyl)-4-[[2-(2-fluoro-phenyl)acetyl]amino]pyridine-2-carboxamide (Compound 60);

N-(1-Cyano-2-hydroxy-1-methyl-ethyl)-4-[[2-(2-fluoro-phenyl)acetyl]amino]pyridine-2-carboxamide (Compound 60.1);

N-(1,1-Dimethylprop-2-ynyl)-4-[[2-(2-fluorophenyl)acetyl]amino]pyridine-2-carboxamide (Compound 60.2);

N-tert-Butyl-4-[[2-(5-chloro-2-hydroxy-3-isopropyl-phenyl)acetyl]amino]pyridine-2-carboxamide (Compound 61);

N-tert-Butyl-4-[[2-[5-chloro-2-hydroxy-3-(1-methoxyethyl)phenyl]acetyl]amino]pyridine-2-carboxamide (Compound 62);

4-(Benzylcarbamoylamino)-N-tert-butyl-pyridine-2-carboxamide (Compound 64);

N-tert-Butyl-4-[(2-chlorophenyl)methylcarbamoylamino]pyridine-2-carboxamide (Compound 64.5);

N-tert-Butyl-4-[(3-chlorophenyl)methyl carbamoylamino]pyridine-2-carboxamide (Compound 64.7);

N-tert-butyl-4-[(4-chlorophenyl)methyl carbamoylamino]pyridine-2-carboxamide (Compound 64.8);

N-tert-Butyl-4-[(2-hydroxyphenyl) carbamoylamino]pyridine-2-carboxamide (Compound 65);

N-tert-Butyl-4-[(2-methoxyphenyl)methylcarbamoylamino]pyridine-2-carboxamide (Compound 65.1);

N-tert-Butyl-4-[(2-hydroxyphenyl)methylcarbamoylamino]pyridine-2-carboxamide (Compound 65.2);

N-tert-Butyl-4-[(3-hydroxyphenyl)methylcarbamoylamino]pyridine-2-carboxamide (Compound 65.3);

N-tert-Butyl-4-[(4-hydroxyphenyl)methylcarbamoylamino]pyridine-2-carboxamide (Compound 65.4);

N-tert-Butyl-4-[[2-[2-hydroxy-5-(1-hydroxyethyl)phenyl]acetyl]amino]pyridine-2-carboxamide (Compound 66);

N-tert-Butyl-4-[[2-[3-(cyanomethyl)phenyl]acetyl]amino]pyridine-2-carboxamide (Compound 68);

N-tert-Butyl-4-[[2-[3-(methoxymethyl)phenyl]acetyl]amino]pyridine-2-carboxamide (Compound 69);

N-tert-Butyl-4-[[2-[2-hydroxy-5-(morpholinomethyl)phenyl]acetyl]amino]pyridine-2-carboxamide (Compound 70);

3-[[2-(5-Chloro-2-hydroxy-phenyl)acetyl]amino]-N-(1-methylcyclohexyl)benzamide (Compound 71.1);

4-[[2-(5-Fluoro-2-hydroxy-phenyl)acetyl]amino]-N-[3-(hydroxymethyl)tetrahydrofuran-3-yl]pyridine-2-carboxamide (Compound 72);

4-[[2-(5-Chloro-2-hydroxy-phenyl)acetyl]amino]-N-[1-(hydroxymethyl)-2-methoxy-1-methyl-ethyl]pyridine-2-carboxamide (Compound 73);

4-[[2-(5-Chloro-2-hydroxy-phenyl)acetyl]amino]-N-(1,1-dimethylbut-2-ynyl)pyridine-2-carboxamide (Compound 73.1);

3-[[2-(5-Chloro-2-hydroxy-phenyl)acetyl]amino]-N-(1,1-dimethylprop-2-ynyl)benzamide (Compound 74);

N-tert-Butyl-4-[[2-[2-hydroxy-5-(3-hydroxypropyl)phenyl]acetyl]amino]pyridine-2-carboxamide (Compound 75);

4-[[2-(5-Chloro-4-fluoro-2-hydroxy-phenyl)acetyl]amino]-N-(1-methylcyclo butyl)pyridine-2-carboxamide (Compound 76);
4-[[2-(2,5-Difluorophenyl)acetyl]amino]-N-(1,1-dimethylprop-2-ynyl)pyridine-2-carboxamide (Compound 77);
4-[[2-(2,5-Difluorophenyl)acetyl]amino]-N-(4-fluoro-1-bicyclo[2.1.1]hexanyl)pyridine-2-carboxamide (Compound 77.1);
4-[[2-(4-Chloro-2-hydroxy-phenyl)acetyl]amino]-N-(1,1-dimethylprop-2-ynyl)pyridine-2-carboxamide (Compound 78);
N-(1,1-Dimethylprop-2-ynyl)-4-[[2-[2-hydroxy-4-(trifluoromethyl)phenyl]acetyl]amino]pyridine-2-carboxamide (Compound 78.1);
N-(1,1-Dimethylprop-2-ynyl)-4-[[2-[2-hydroxy-5-(trifluoromethyl)phenyl]acetyl]amino]pyridine-2-carboxamide (Compound 78.2);
N-(1-Cyano-1-methyl-ethyl)-4-[[2-(5-fluoro-2-hydroxy-phenyl)acetyl]amino]pyridine-2-carboxamide (Compound 81);
N-(1-Cyano-2-hydroxy-1-methyl-ethyl)-4-[[2-(5-fluoro-2-hydroxy-phenyl)acetyl]amino]pyridine-2-carboxamide (Compound 81.1);
4-[[2-(5-Fluoro-2-hydroxy-phenyl)acetyl]amino]-N-isopropyl-pyridine-2-carboxamide (Compound 81.2);
N-(1,1-Dimethylprop-2-ynyl)-4-[[2-(5-fluoro-2-hydroxy-phenyl)acetyl]amino]pyridine-2-carboxamide (Compound 81.3);
N-(4-Fluoro-1-bicyclo[2.1.1]hexanyl)-4-[[2-(5-fluoro-2-hydroxy-phenyl)acetyl]amino]pyridine-2-carboxamide (Compound 81.4);
4-[[2-(5-Fluoro-2-hydroxy-phenyl)acetyl]amino]-N-[1-(hydroxymethyl)cyclobutyl]pyridine-2-carboxamide (Compound 81.5);
N-tert-Butyl-6-[[2-(5-chloro-2-methoxy-phenyl)acetyl]amino]pyrimidine-4-carboxamide (Compound 82);
4-[(4-Acetamidobenzoyl)amino]-N-(1-cyano-1-methyl-ethyl)pyridine-2-carboxamide (Compound 83.29);
N-tert-Butyl-6-[[2-(5-chloro-2-hydroxy-phenyl)acetyl]amino]pyrimidine-4-carboxamide (Compound 85);
4-[[2-(5-Chloro-2-hydroxy-phenyl)acetyl]amino]-N-[1-cyano-2-methoxy-1-(methoxy methyl)ethyl]pyridine-2-carboxamide (Compound 86);
N-tert-Butyl-4-[[2-(4-tert-butyl-3-hydroxy-phenyl)acetyl]amino]pyridine-2-carboxamide (Compound 89);
N-tert-Butyl-4-[[2-(4-tert-butyl-2-hydroxy-phenyl)acetyl]amino]pyridine-2-carboxamide (Compound 90);
N-tert-Butyl-4-[[2-(4-tert-butyl-2-fluoro-5-hydroxy-phenyl)acetyl]amino]pyridine-2-carboxamide (Compound 91);
4-[[2-(4-Chloro-3-hydroxy-phenyl)acetyl]amino]-N-(4-cyanotetrahydropyran-4-yl)pyridine-2-carboxamide (Compound 92);
4-[[2-(4-Chloro-3-hydroxy-phenyl)acetyl]amino]-N-(1-cyano-1-methyl-ethyl)pyridine-2-carboxamide (Compound 92.1);
4-[[2-(4-Chloro-3-hydroxy-phenyl)acetyl]amino]-N-(1,1-dimethylprop-2-ynyl)pyridine-2-carboxamide (Compound 92.2);
4-[[2-(4-tert-Butyl-3-hydroxy-phenyl)acetyl]amino]-N-[(2S)-2-hydroxycyclohexyl]pyridine-2-carboxamide (Compound 93.1);
4-[[2-(4-tert-Butyl-3-hydroxy-phenyl)acetyl]amino]-N-[(2S)-2-hydroxycyclopentyl]pyridine-2-carboxamide (Compound 93.2);
4-[[2-(4-tert-Butyl-3-hydroxy-phenyl)acetyl]amino]-N-(4-cyanotetrahydropyran-4-yl)pyridine-2-carboxamide (Compound 93.3);
4-[[2-(4-tert-Butyl-3-hydroxy-phenyl)acetyl]amino]-N-(1-cyano-1-methyl-ethyl)pyridine-2-carboxamide (Compound 93.4);
4-[[2-(4-tert-Butyl-3-hydroxy-phenyl)acetyl]amino]-N-(1,1-dimethylprop-2-ynyl)pyridine-2-carboxamide (Compound 93.5); and
4-[[2-(5-Chloro-2-hydroxy-phenyl)acetyl]amino]-N-(1-methyl-1-phenyl-ethyl)pyridine-2-carboxamide (Compound 94);
and salts and solvates of any of the above.

5. The method of claim 1, wherein the compound is 4-[[2-(5-Chloro-2-hydroxy-phenyl)acetyl]amino]-N-[(3R)-3-(hydroxymethyl)tetrahydrofuran-3-yl]pyridine-2-carboxamide or 4-[[2-(5-chloro-2-hydroxy-phenyl)acetyl]amino]-N-[(3S)-3-(hydroxymethyl)tetrahydrofuran-3-yl]pyridine-2-carboxamide (Compound 35a) or a salt or solvate thereof.

6. The method of claim 1, wherein the compound is 4-[[2-(5-Chloro-2-hydroxy-phenyl)acetyl]amino]-N-(1,1-dimethylprop-2-ynyl)pyridine-2-carboxamide (Compound 36) or a salt or solvate thereof.

7. The method of claim 1, wherein the compound is N-(1,1-Dimethylprop-2-ynyl)-4-[[2-[3-(trifluoromethyl)-1H-pyrazol-4-yl]acetyl]amino]pyridine-2-carboxamide (Compound 5.36) or a salt or solvate thereof.

8. The method according to claim 1, wherein the disease or condition affected by modulation of TMEM16A is selected from respiratory diseases and conditions, dry mouth (xerostomia), intestinal hypermobility, cholestasis and ocular conditions.

9. The method according to claim 8, wherein the respiratory diseases and conditions are selected from cystic fibrosis, chronic obstructive pulmonary disease (COPD), chronic bronchitis, emphysema, bronchiectasis, including non-cystic fibrosis bronchiectasis, asthma and primary ciliary dyskinesia.

10. The method according to claim 8, wherein the dry mouth (xerostomia) results from Sjorgens syndrome, radiotherapy treatment or xerogenic drugs.

11. The method according to claim 8, wherein the intestinal hypermobility is associated with gastric dyspepsia, gastroparesis, chronic constipation or irritable bowel syndrome.

12. The method according to claim 8, wherein the ocular disease is dry eye disease.

13. The method according to claim 8, wherein the compound of general formula (I) is used in combination with an additional active agent useful in the treatment or prevention of respiratory conditions.

14. The method of claim 13, wherein the wherein the additional agent useful in the treatment or prevention of respiratory conditions is selected from:
β2 adrenoreceptor agonists selected from metaproterenol, isoproterenol, isoprenaline, albuterol, salbutamol, formoterol, salmeterol, indacaterol, terbutaline, orciprenaline, bitolterol mesylate, pirbuterol, olodaterol, vilanterol and abediterol;
antihistamines selected from histamine H1 receptor antagonists selected from loratadine, cetirizine, desloratadine, levocetirizine, fexofenadine, astemizole, azelastine and chlorpheniramine or H4 receptor antagonists;
dornase alpha;
corticosteroids selected from prednisone, prednisolone, flunisolide, triamcinolone acetonide, beclomethasone dipropionate, budesonide, fluticasone propionate mometasone furoate and fluticasone furoate;

Leukotriene antagonists selected from montelukast and zafirlukast;

anticholinergic compounds, muscarinic antagonists selected from ipratropium, tiotropium, glycopyrrolate, aclidinium and umeclidinium;

CFTR repair therapies selected from CFTR potentiators, correctors or amplifiers, the CFTR potentiators, correctors or amplifiers selected from Ivacaftor, QBW251, VX659, VX445, VX561/CPT-656, VX152, VX440, GLP2737, GLP2222, GLP2451, PTI438, PTI801, PTI808, FDL-169 and FDL-176 and CFTR correctors selected from Lumacaftor and Tezacaftor;

ENaC modulators, ENaC inhibitors selected from:
  amiloride, VX-371, AZD5634, QBW276, SPX-101, BI443651, ETD001 and compounds having a cation selected from:
    2-[({3-amino-5H-pyrrolo[2,3-b]pyrazin-2-yl}formamido)ethyl]-6-(4-{bis[(2S,3R,4R,5R)-2,3,4,5,6-pentahydroxyhexyl]amino}piperidine-1-carbonyl)-1,3-diethyl-1H-1,3-benzodiazol-3-ium;
    2-[({3-amino-5H-pyrrolo[2,3-b]pyrazin-2-yl}formamido)methyl]-6-{[2-(4-{bis[(2S,3R,4R,5R)-2,3,4,5,6-pentahydroxyhexyl]amino}piperidin-1-yl)ethyl]carbamoyl}-1,3-diethyl-1H-1,3-benzodiazol-3-ium;
    2-[({3-amino-5H-pyrrolo[2,3-b]pyrazin-2-yl}formamido)methyl]-5-[4-({bis[(2S,3R,4R,5R)-2,3,4,5,6-pentahydroxyhexyl]amino}methyl)piperidine-1-carbonyl]-1,3-diethyl-1H-1,3-benzodiazol-3-ium;
    2-[({3-amino-5H-pyrrolo[2,3-b]pyrazin-2-yl}formamido)methyl]-6-[(3R)-3-{bis[(2S,3R,4R,5R)-2,3,4,5,6-pentahydroxyhexyl]amino}pyrrolidine-1-carbonyl]-1,3-diethyl-1H-1,3-benzodiazol-3-ium;
    2-[({3-amino-5H-pyrrolo[2,3-b]pyrazin-2-yl}formamido)methyl]-6-[(3S)-3-{bis[(2S,3R,4R,5R)-2,3,4,5,6-pentahydroxyhexyl]amino}pyrrolidine-1-carbonyl]-1,3-diethyl-1H-1,3-benzodiazol-3-ium;
    2-[({3-amino-5H-pyrrolo[2,3-b]pyrazin-2-yl}formamido)methyl]-1,3-diethyl-6-{[(1r,4r)-4-{bis[(2S,3R,4R,5R)-2,3,4,5,6-pentahydroxyhexyl]amino}cyclohexyl]carbamoyl}-1H-1,3-benzodiazol-3-ium;
    2-[({3-amino-5H-pyrrolo[2,3-b]pyrazin-2-yl}formamido)methyl]-1,3-diethyl-6-{[(1s,4s)-4-{bis[(2S,3R,4R,5R)-2,3,4,5,6-pentahydroxyhexyl]amino}cyclohexyl]carbamoyl}-1H-1,3-benzodiazol-3-ium;
  and an anion selected from halide, sulfate, nitrate, phosphate, formate, acetate, trifluoroacetate, fumarate, citrate, tartrate, oxalate, succinate, mandelate, methane sulfonate or p-toluene sulfonate;

antibiotics;

airway hydrating agents (osmoloytes) selected from hypertonic saline and mannitol; and mucolytic agents selected from N-acetyl cysteine.

\* \* \* \* \*